United States Patent
Chen et al.

(10) Patent No.: US 10,421,774 B2
(45) Date of Patent: Sep. 24, 2019

(54) C-3 AND C-17 MODIFIED TRITERPENOIDS AS HIV-1 INHIBITORS

(71) Applicant: ViiV HEALTHCARE UK (NO.5) LIMITED, Brentford, Middlesex (GB)

(72) Inventors: Jie Chen, Wallingford, CT (US); Yan Chen, Wallingford, CT (US); Ira B. Dicker, Wallingford, CT (US); Richard A. Hartz, Wallingford, CT (US); Nicholas A. Meanwell, Wallingford, CT (US); Beata Nowicka-Sans, Wallingford, CT (US); Alicia Regueiro-Ren, Wallingford, CT (US); Sing-Yuen Sit, Wallingford, CT (US); Ny Sin, Wallingford, CT (US); Jacob Swidorski, Wallingford, CT (US); Brian Lee Venables, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 16/071,925

(22) PCT Filed: Feb. 2, 2017

(86) PCT No.: PCT/IB2017/050568
§ 371 (c)(1),
(2) Date: Jul. 23, 2018

(87) PCT Pub. No.: WO2017/134596
PCT Pub. Date: Aug. 10, 2017

(65) Prior Publication Data
US 2019/0031709 A1    Jan. 31, 2019

Related U.S. Application Data

(60) Provisional application No. 62/291,298, filed on Feb. 4, 2016.

(51) Int. Cl.
| | | |
|---|---|---|
| C07J 53/00 | (2006.01) |
| C07J 63/00 | (2006.01) |
| C12N 9/50 | (2006.01) |
| A61P 31/18 | (2006.01) |

(52) U.S. Cl.
CPC ............. *C07J 53/002* (2013.01); *A61P 31/18* (2018.01); *C07J 63/008* (2013.01); *C12N 9/506* (2013.01); *C12N 2740/16222* (2013.01)

(58) Field of Classification Search
CPC ................................ C07J 53/002; A61P 31/18
See application file for complete search history.

(56) References Cited

U.S. PATENT DOCUMENTS 8,846,647 B2 *   9/2014   Regueiro-Ren ........ C07J 63/008
                                                          514/169
8,906,889 B2 * 12/2014   Swidorski .............. C07J 53/002
                                                          514/169

FOREIGN PATENT DOCUMENTS

| WO | WO 2014/123889 A1 | 8/2014 |
| WO | WO 2015/157483 A1 | 10/2015 |

* cited by examiner

*Primary Examiner* — Golam M Shameem
(74) *Attorney, Agent, or Firm* — Robert H. Brink; Kathryn A. Lutomski; Edward R. Gimmi

(57) ABSTRACT

Compounds having drug and bio-affecting properties, their pharmaceutical compositions and methods of use are set forth. In particular, betulinic acid derivatives that possess unique antiviral activity are provided as HIV maturation inhibitors, as represented by compounds of Formula I:

Formula I

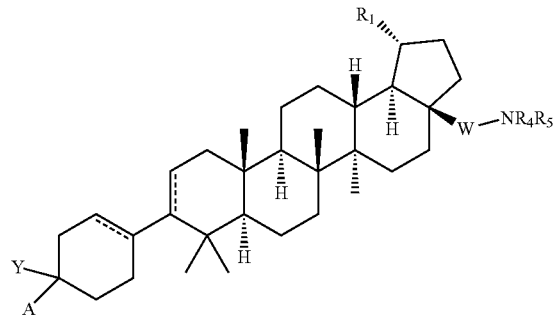

These compounds are useful for the treatment of HIV and AIDS.

4 Claims, No Drawings

C-3 AND C-17 MODIFIED TRITERPENOIDS AS HIV-1 INHIBITORS

This application is a § 371 of International Application No. PCT/IB2017/050568, filed 2 Feb. 2017, which claims the benefit of U.S. Provisional Application No. 62/291,298, filed 4 Feb. 2016.

FIELD OF THE INVENTION

The present invention relates to novel compounds useful against HIV and, more particularly, to compounds derived from betulinic acid and other compounds which are useful as HIV maturation inhibitors, and to pharmaceutical compositions containing same, as well as to methods for their preparation.

BACKGROUND OF THE INVENTION

HIV-1 (human immunodeficiency virus—1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), tenofovir disoproxil fumarate salt (or VIREAD®), emtricitabine (or FTC-EMTRIVA®), COMBIVIR® (contains—3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA® +SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ) and tipranavir (APTIVUS) and cobicistat, and integrase inhibitors such as raltegravir (ISENTRESS), and entry inhibitors such as enfuvirtide (T-20) (FUZEON) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. Nos. 7,354,924 and 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., "Synthesis of derivatives of plant triterpenes and study of their antiviral and immunostimulating activity," Khimiya y Interesakh Ustoichivogo Razvitiya, Vol. 9, No. 3, pp. 485-491 (2001) (English abstract).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (now U.S. Pat. No. 8,754,068) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (now U.S. Pat. No. 8,802,661). Reference is also made to the application entitled "C-28 AMINES OF C-3 MODIFIED BETULINIC ACID DERIVATIVES AS HIV MATURATION INHIBITORS" U.S. Ser. No. 13/359,680, filed on Jan. 27, 2012 (now U.S.

Pat. No. 8,748,415). In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012 (now U.S. Pat. No. 8,846,647). Further reference is also made to the application "C-3 CYCLOALKENYL TRITERPENOIDS WITH HIV MATURATION INHIBITORY ACTIVITY" filed U.S. Ser. No. 13/760,726 on Feb. 6, 2013 (now U.S. Pat. No. 8,906,889), as well as to the application entitled "TRITERPENOIDS WITH HIV MATURATION INHIBITORY ACTIVITY" U.S. Ser. No. 14/682,179 filed on Apr. 9, 2015.

What is now needed in the art are new compounds which are useful as HIV maturation inhibitors, as well as new pharmaceutical compositions containing these compounds. In particular, new compounds are needed that will be effective against emerging genotypic HIV mutants.

SUMMARY OF THE INVENTION

The present invention provides compounds of Formula I below, including pharmaceutically acceptable salts thereof, their pharmaceutical formulations, and their use in patients suffering from or susceptible to a virus such as HIV. The compounds of Formula I are effective antiviral agents, particularly as inhibitors of HIV. They are useful for the treatment of HIV and AIDS.

One embodiment of the present invention is directed to a compound of Formula I, including pharmaceutically acceptable salts thereof:

Formula I

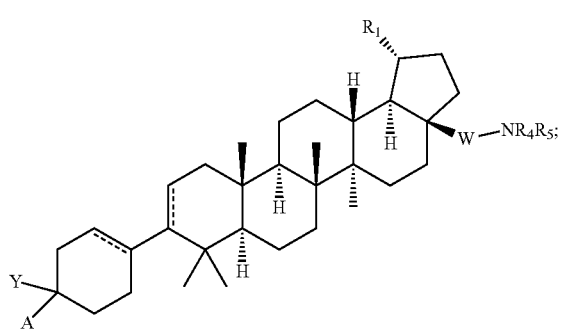

wherein R1 is isopropenyl or isopropyl;

A is —$C_{1-6}$alkyl-OR⁰;

wherein $R_0$ is heteroaryl-$Q_0$;

$Q_0$ is selected from the group of —H, —CN, —$C_{1-6}$alkyl, —COOH, —Ph, —O$C_{1-6}$ alkyl, -halo, —$CF_3$, Y is selected from the group of —$COOR_2$, —$C(O)NR_2SO_2R_3$, —$C(O)NHSO_2NR_2R_2$, —$SO_2NR_2C(O)R_2$, -tetrazole, and —CONHOH;

$R_2$ is —H, —$C_{1-6}$alkyl, -alkyl substituted $C_{1-6}$alkyl or-aryl substituted $C_{1-6}$alkyl;

W is absent, or is —$CH_2$— or —CO—;

$R_3$ is —H, —$C_{1-6}$alkyl or -alkylsubstituted $C_{1-6}$alkyl;

$R_4$ is selected from the group of —H, —$C_{1-6}$alkyl, —$C_{1-6}$alkyl-$C_{3-6}$cycloalkyl, —$C_{1-6}$ substituted —$C_{1-6}$alkyl, —$C_{1-6}$alkyl-$Q_1$, —$C_{1-6}$alkyl-$C_{3-6}$cycloalkyl-$Q_1$, aryl, heteroaryl, substituted heteroaryl, —$COR_6$, —$SO_2R_7$, —$SO_2NR_2R_2$, and

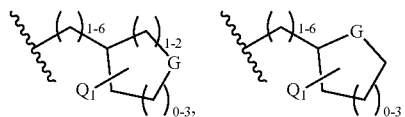

wherein G is selected from the group of —O—, —$SO_2$— and —$NR_{12}$—;

wherein $Q_1$ is selected from the group of —$C_{1-6}$alkyl, —$C_{1-6}$ fluoroalkyl, heteroaryl, substituted heteroaryl, halogen, —$CF_3$, —$OR_2$, —$COOR_2$, —$NR_8R_9$, —$CONR_8R_9$ and —$SO_2R_7$;

$R_5$ is selected from the group of —H, —$C_{1-6}$alkyl, —$C_{3-6}$cycloalkyl, —$C_{1-6}$alkylsubstituted alkyl, —$C_{1-6}$alkyl-$NR_8R_9$, —$COR_3$, —$SO_2R_7$ and —$SO_2NR_2R_2$;

with the proviso that $R_4$ or $R_5$ is not —$COR_3$ when W is —CO—;

with the further proviso that only one of $R_4$ or $R_5$ is selected from the group of —$COR_3$, —$COCOR_6$, —$SO_2R_7$ and —$SO_2NR_2R_2$;

$R_6$ is selected from the group of —H, —$C_{1-6}$alkyl, —$C_{1-6}$alkyl-substituted alkyl, —$C_{3-6}$ cycloalkyl, —$C_{3-6}$ substituted cycloalkyl-$Q_2$, —$C_{1-6}$alkyl-$Q_2$, —$C_{1-6}$alkyl-substituted alkyl-$Q_2$, —$C_{3-6}$cycloalkyl-$Q_2$, aryl-$Q_2$, —$NR_{13}R_{14}$, and —$OR_{15}$;

wherein $Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —H, —$C_{1-6}$alkyl, —$C_{1-6}$ substituted alkyl, —$C_{3-6}$ cycloalkyl, —$CF_3$, aryl, and heteroaryl;

$R_8$ and $R_9$ are independently selected from the group of —H, —$C_{1-6}$alkyl, —$C_{1-6}$ substituted alkyl, aryl, heteroaryl, substituted aryl, substituted heteroaryl, —$C_{1-6}$alkyl-$Q_2$, and —$COOR_3$, or $R_8$ and $R_9$ are taken together with the adjacent N to form a cycle selected from the group of:

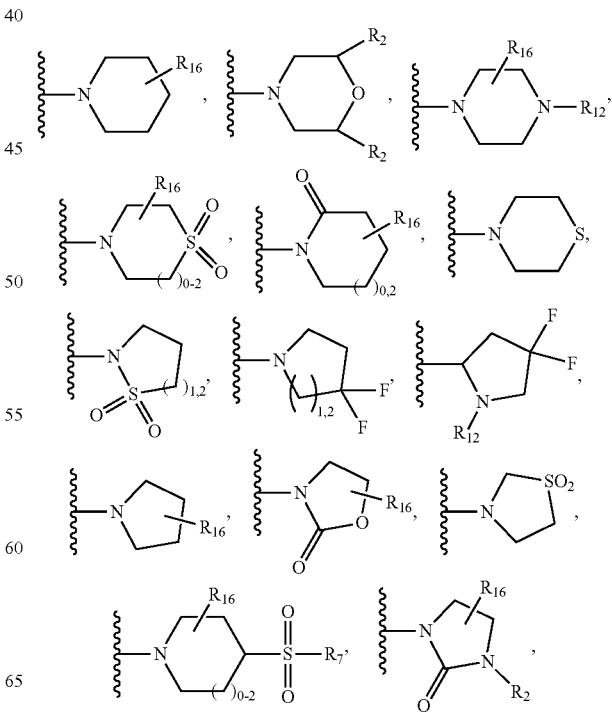

-continued

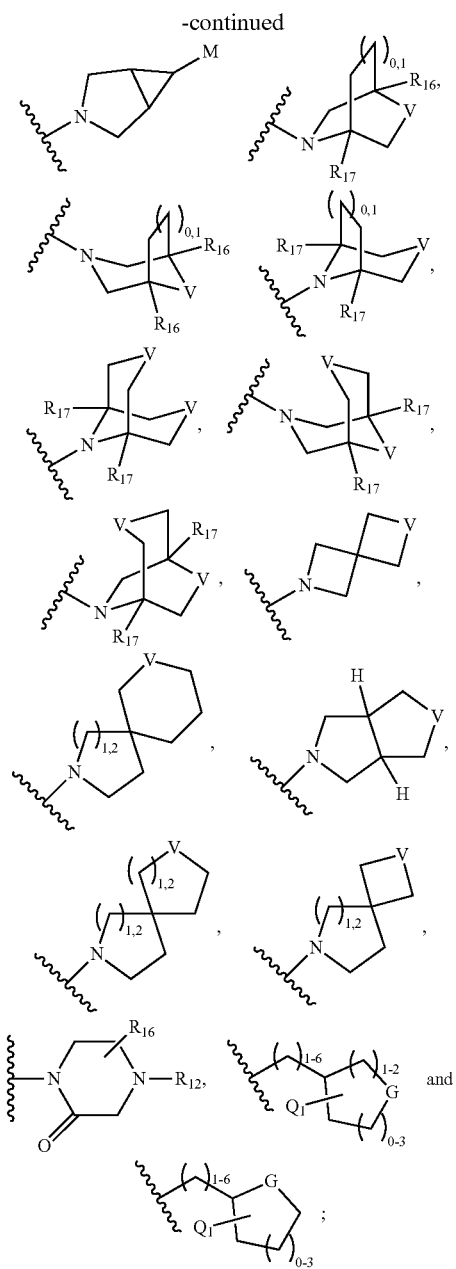

M is selected from the group of —$R_{15}$, —$SO_2R_2$, —$SO_2NR_2R_2$, —OH and —$NR_2R_{12}$;

V is selected from the group of —$CR_{10}R_{11}$—, —$SO_2$—, —O— and $NR_{12}$—;

with the proviso that only one of $R_8$ or $R_9$ can be —$COOR_3$;

$R_{10}$ and $R_{11}$ are independently selected from the group of —H, —$C_{1-6}$alkyl, —$C_{1-6}$ substituted alkyl and —$C_{3-6}$cycloalkyl;

$R_{12}$ is selected from the group of —H, —$C_{1-6}$alkyl, -alkylsubstituted $C_{1-6}$alkyl, —$CONR_2R_2$, —$SO_2R_3$, and —$SO_2NR_2R_2$;

$R_{13}$ and $R_{14}$ are independently selected from the group of —H, —$C_{1-6}$alkyl, —$C_{3-6}$cycloalkyl, —$C_{1-6}$ substituted alkyl, —$C_{1-6}$alkyl-$Q_3$, —$C_{1-6}$alkyl-$C_{3-6}$cycloalkyl-$Q_3$, and $C_{1-6}$substituted alkyl-$Q_3$;

$Q_3$ is selected from the group of heteroaryl, substituted heteroaryl, —$NR_2R_{12}$, —$CONR_2R_2$, —$COOR_2$, —$OR_2$, and —$SO_2R_3$;

$R_{15}$ is selected from the group of —$C_{1-6}$alkyl, —$C_{3-6}$cycloalkyl, —$C_{1-6}$substituted alkyl, —$C_{1-6}$alkyl-$Q_3$, —$C_{1-6}$alkyl-$C_{3-6}$cycloalkyl-$Q_3$ and —$C_{1-6}$ substituted alkyl-$Q_3$;

$R_{16}$ is selected from the group of —H, —$C_{1-6}$alkyl, —$NR_2R_2$, and $COOR_2$; with the proviso that when V is —$NR_{12}$—; $R_{16}$ is not $NR_2R_2$; and $R_{17}$ is selected from the group of —H, —$C_{1-6}$alkyl, —$COOR_3$, and aryl.

In a further embodiment, there is provided a method for treating mammals infected with a virus, especially wherein said virus is HIV, comprising administering to said mammal an antiviral effective amount of a compound which is selected from the group of compounds of Formula I, and one or more pharmaceutically acceptable carriers, excipients or diluents. Optionally, the compound of Formula I can be administered in combination with an antiviral effective amount of another AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising one or more compounds of Formula I, and one or more pharmaceutically acceptable carriers, excipients, and/or diluents; and optionally in combination with another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I herein.

Also provided herein are intermediate compounds useful in making the compounds of Formula I herein.

The present invention is directed to these, as well as other important ends, hereinafter described.

DETAILED DESCRIPTION OF THE EMBODIMENTS

As used herein, the singular forms "a", "an", and "the" include plural reference unless the context clearly dictates otherwise.

Since the compounds of the present invention may possess asymmetric centers and therefore occur as mixtures of diastereomers, the present disclosure includes the individual diastereoisomeric forms of the compounds of Formula I in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$fluoroalkyl" refers to F-substituted $C_1$-$C_4$alkyl wherein at least one H atom is substituted with F atom, and each H atom can be independently substituted by F atom;

"Halogen" or "halo" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group(s) are preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^Y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

A "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

A "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and its S oxides and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo methanesulfonamido, trihalo methanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an OH group.

An "alkoxy" group refers to both an O-alkyl and an O-cycloalkyl group as defined herein.

An "aryloxy" group refers to both an O-aryl and an O-heteroaryl group, as defined herein.

A "heteroaryloxy" group refers to a heteroaryl-O-group with heteroaryl as defined herein.

A "heteroalicycloxy" group refers to a heteroalicyclic-O-group with heteroalicyclic as defined herein.

A "thiohydroxy" group refers to an SH group.

A "thioalkoxy" group refers to both an S-alkyl and an S-cycloalkyl group, as defined herein.

A "thioaryloxy" group refers to both an S-aryl and an S-heteroaryl group, as defined herein.

A "thioheteroaryloxy" group refers to a heteroaryl-S-group with heteroaryl as defined herein.

A "thioheteroalicycloxy" group refers to a heteroalicyclic-S-group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a $CZ_3$, group wherein Z is a halogen group as defined herein.

A "trihalomethanesulfonyl" group refers to a $Z_3CS(=O)_2$-groups with Z as defined above.

A "trihalomethanesulfonamido" group refers to a $Z_3CS(=O)_2NR_x$-group with Z as defined above and $R^x$ being H or $(C_{1-6})$alkyl.

A "sulfinyl" group refers to a S(=O)—R" group, with R" being $(C_{1-6})$alkyl.

A "sulfonyl" group refers to a $S(=O)_2$R" group with R" being $(C_{1-6})$alkyl.

A "S-sulfonamido" group refers to a $S(=O)_2NR^XR^Y$, with $R^X$ and $R^Y$ independently being H or $(C_{1-6})$alkyl.

A "N-sulfonamido" group refers to a $R"S(=O)_2NR_x$-group, with $R_x$ being H or $(C_{1-6})$alkyl.

A "O-carbamyl" group refers to a $OC(=O)NR^xR^y$ group, with $R^x$ and $R^y$ independently being H or $(C_{1-6})$alkyl.

A "N-carbamyl" group refers to a $R^xOC(=O)NR_y$ group, with $R^x$ and $R^y$ independently being H or $(C_{1-6})$alkyl.

A "O-thiocarbamyl" group refers to a —$OC(=S)NR^xR^y$ group, with $R^x$ and $R^y$ independently being H or $(C_{1-6})$alkyl.

A "N-thiocarbamyl" group refers to a $R^xOC(=S)NR^y$-group, with $R^x$ and $R^y$ independently being H or $(C_{1-6})$alkyl.

An "amino" group refers to an —$NH_2$ group.

A "C-amido" group refers to a —$C(=O)NR^xR^y$ group, with $R^x$ and $R_y$ independently being H or $(C_{1-6})$alkyl.

A "C-thioamido" group refers to a —$C(=S)NR^xR^y$ group, with $R^x$ and $R^y$ independently being H or $(C_{1-6})$alkyl.

A "N-amido" group refers to a $R^xC(=O)NR^y$-group, with $R^x$ and $R_y$ independently being H or $(C_{1-6})$alkyl.

An "ureido" group refers to a —$NR^xC(=O)NR_yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "amidino" group refers to a $R^xR^yNC(=N)$-group, with $R^x$ and $R^y$ independently being H or $(C_{1-6})$alkyl.

A "cyano" group refers to a —CN group.

A "silyl" group refers to a —$Si(R")_3$, with R" being $(C_{1-6})$alkyl or phenyl.

A "phosphonyl" group refers to a $P(=O)(OR^x)_2$ with $R^x$ being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

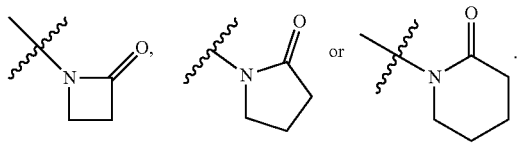 [SMILES: *N1CCC1=O ; *N1CCCC1=O ; *N1CCCCC1=O ; "."]

A "spiro" group is a bicyclic organic group with rings connected through just one atom. The rings can be different in nature or identical. The connecting atom is also called the spiroatom, most often a quaternary carbon ("spiro carbon").

An "oxospiro" or "oxaspiro" group is a spiro group having an oxygen contained within the bicyclic ring structure. A "dioxospiro" or "dioxaspiro" group has two oxygens within the bicyclic ring structure.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound, including pharmaceutically acceptable salts thereof, which is selected from a compound of Formula I:

Formula I

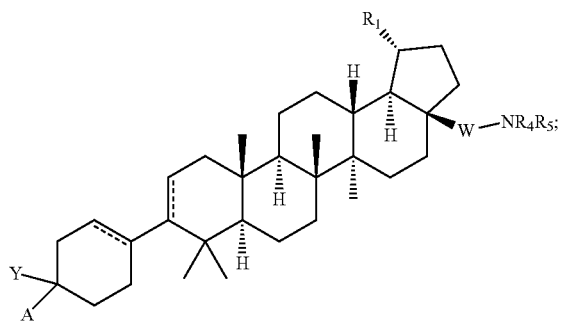

wherein R$_1$ is isopropenyl or isopropyl;

A is —C$_{1-6}$alkyl-OR$_0$;

wherein R$_0$ is heteroaryl-Q$_0$;

Q$_0$ is selected from the group of —H, —CN, —C$_{1-6}$alkyl, —COOH, —Ph, —OC$_{1-6}$alkyl, -halo, —CF$_3$, Y is selected from the group of —COOR$_2$, —C(O)NR$_2$SO$_2$R$_3$, —C(O)NHSO$_2$NR$_2$R$_2$, —SO$_2$NR$_2$C(O)R$_2$, -tetrazole, and —CONHOH;

R$_2$ is —H, —C$_{1-6}$alkyl, -alkylsubstituted C$_{1-6}$alkyl or -aryl substituted C$_{1-6}$alkyl;

W is absent, or is —CH$_2$— or —CO—;

R$_3$ is H, —C$_{1-6}$alkyl or -alkylsubstituted C$_{1-6}$alkyl;

R$_4$ is selected from the group of —H, —C$_{1-6}$alkyl, —C$_{1-6}$alkyl-C$_{3-6}$cycloalkyl, —C$_{1-6}$ substituted —C$_{1-6}$alkyl, —C$_{1-6}$alkyl-Q$_1$, —C$_{1-6}$alkyl-C$_{3-6}$cycloalkyl-Q$_1$, aryl, heteroaryl, substituted heteroaryl, —COR$_6$, —SO$_2$R$_7$, —SO$_2$NR$_2$R$_2$, and

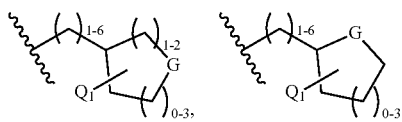

wherein G is selected from the group of —O—, —SO$_2$— and —NR$_{12}$-;

wherein Q$_1$ is selected from the group of —C$_{1-6}$alkyl, —C$_{1-6}$fluoroalkyl, heteroaryl, substituted heteroaryl, halogen, —CF$_3$, —OR$_2$, —COOR$_2$, —NR$_8$R$_9$, —CONR$_8$R$_9$ and —SO$_2$R$_7$;

R$_5$ is selected from the group of —H, —C$_{1-6}$alkyl, —C$_{3-6}$cycloalkyl, —C$_{1-6}$alkylsubstituted alkyl, —C$_{1-6}$ alkyl-NR$_8$R$_9$, —COR$_3$, —SO$_2$R$_7$ and —SO$_2$NR$_2$R$_2$;

with the proviso that R$_4$ or R$_5$ is not —COR$_6$ when W is —CO—;

with the further proviso that only one of R$_4$ or R$_5$ is selected from the group of —COR$_6$, —COCOR$_6$, —SO$_2$R$_7$ and —SO$_2$NR$_2$R$_2$;

R$_6$ is selected from the group of —H, —C$_{1-6}$alkyl, —C$_{1-6}$alkyl-substituted alkyl, —C$_{3-6}$ cycloalkyl, —C$_{3-6}$substituted cycloalkyl-Q$_2$, —C$_{1-6}$alkyl-Q$_2$, —C$_{1-6}$alkyl-substituted alkyl-Q$_2$, —C$_{3-6}$cycloalkyl-Q$_2$, aryl-Q$_2$, —NR$_{13}$R$_{14}$ and —OR$_{15}$;

wherein Q$_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

R$_7$ is selected from the group of —H, —C$_{1-6}$alkyl, —C$_{1-6}$ substituted alkyl, —C$_{3-6}$ cycloalkyl, —CF$_3$, aryl, and heteroaryl;

R$_8$ and R$_9$ are independently selected from the group of —H, —C$_{1-6}$alkyl, —C$_{1-6}$substituted alkyl, aryl, heteroaryl, substituted aryl, substituted heteroaryl, —C$_{1-6}$alkyl-Q$_2$, and —COOR$_3$, or R$_8$ and R$_9$ are taken together with the adjacent N to form a cycle selected from the group of:

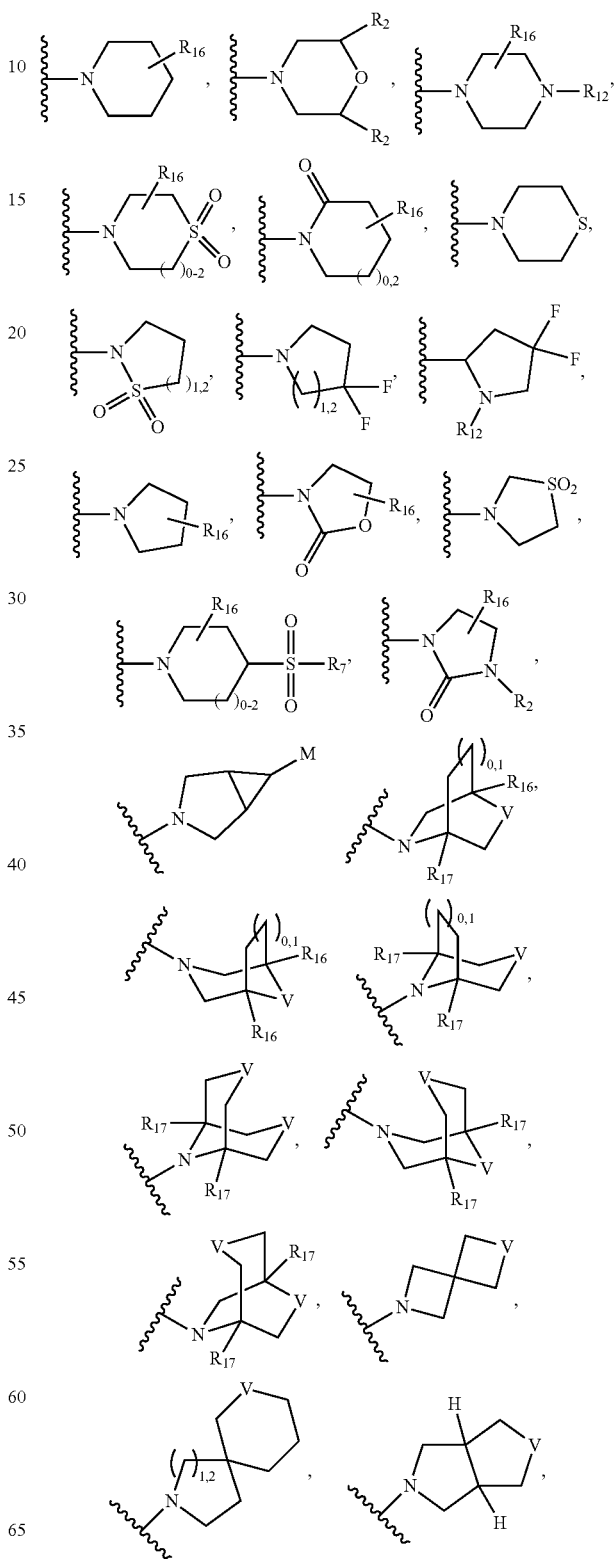

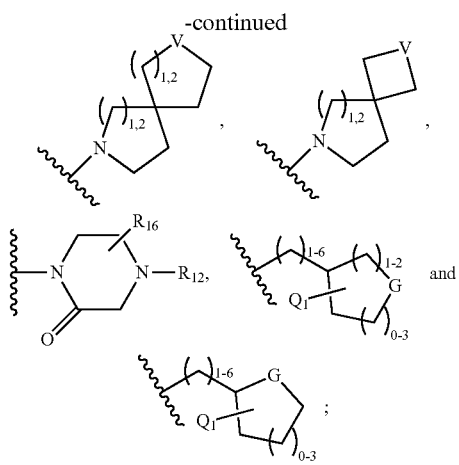

M is selected from the group of —$R_{15}$, —$SO_2R_2$, —$SO_2NR_2R_2$, —OH and —$NR_2R_{12}$;

V is selected from the group of —$CR_{10}R_{11}$—, —$SO_2$—, —O— and —$NR_{12}$—;

with the proviso that only one of $R_8$ or $R_9$ can be —$COOR_3$;

$R_{10}$ and $R_{11}$ are independently selected from the group of —H, —$C_{1-6}$alkyl, —$C_{1-6}$substituted alkyl and —$C_{3-6}$cycloalkyl;

$R_{12}$ is selected from the group of —H, —$C_{1-6}$alkyl, -alkylsubstituted $C_{1-6}$alkyl, —$CONR_2R_2$, —$SO_2R_3$, and —$SO_2NR_2R_2$;

$R_{13}$ and $R_{14}$ are independently selected from the group of —H, —$C_{1-6}$alkyl, —$C_{3-6}$cycloalkyl, —$C_{1-6}$substituted alkyl, —$C_{1-6}$alkyl-$Q_3$, —$C_{1-6}$alkyl-$C_{3-6}$cycloalkyl-$Q_3$, and $C_{1-6}$substituted alkyl-$Q_3$;

$Q_3$ is selected from the group of heteroaryl, substituted heteroaryl, —$NR_2R_{12}$, —$CONR_2R_2$, —$COOR_2$, —$OR_2$, and —$SO_2R_3$;

$R_{15}$ is selected from the group of —$C_{1-6}$alkyl, —$C_{3-6}$cycloalkyl, —$C_{1-6}$substituted alkyl, —$C_{1-6}$alkyl-$Q_3$, —$C_{1-6}$alkyl-$C_{3-6}$cycloalkyl-$Q_3$ and —$C_{1-6}$substituted alkyl-$Q_3$;

$R_{16}$ is selected from the group of —H, —$C_{1-6}$alkyl, —$NR_2R_2$, and $COOR_2$; with the proviso that when V is $NR_{12}$—; $R_{16}$ is not —$NR_2R_2$; and $R_{17}$ is selected from the group of —H, —$C_{1-6}$alkyl, —$COOR_3$, and aryl.

In a preferred embodiment of the invention, $R_1$ is isopropenyl.

It is also preferred that Y is —$COOR_2$. More preferably, $R_2$ in this embodiment is H.

In another preferred embodiment of the invention, in the $R_0$ group the "heteroaryl" moiety is preferably selected from the group of:

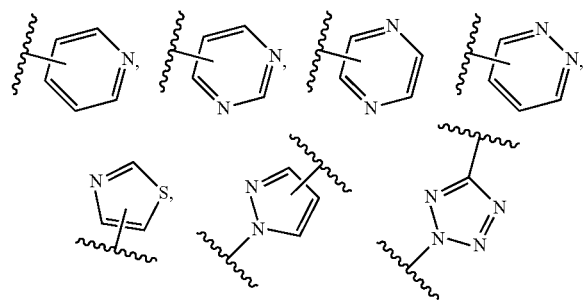

It is also preferred that there is no intervening alkyl group or other substituent group between the —O moiety and the $R_0$ group in substituent A.

It is further preferred that $R_4$ is $C_{1-6}$alkyl-$Q_1$.

Also preferred is the embodiment wherein $Q_1$ is —$NR_8R_9$.

Additionally, when $R_8$ and $R_9$ are taken together with the adjacent —N to form a cycle, the preferred cycle will be selected from the group of:

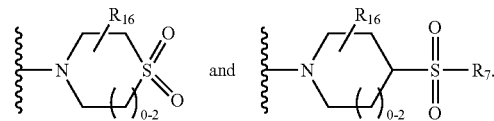

In some embodiments it is also preferred that $Q_0$ is —CN.

In another preferred embodiment, RI is isopropenyl, in the $R_0$ group the "heteroaryl" moiety is selected from the group of:

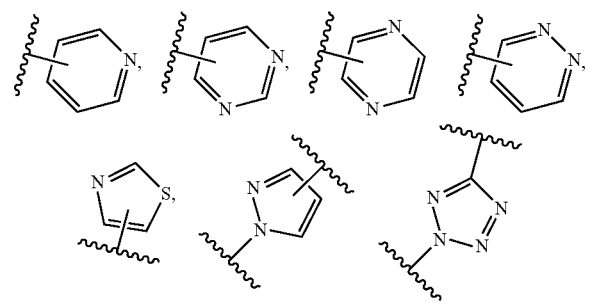

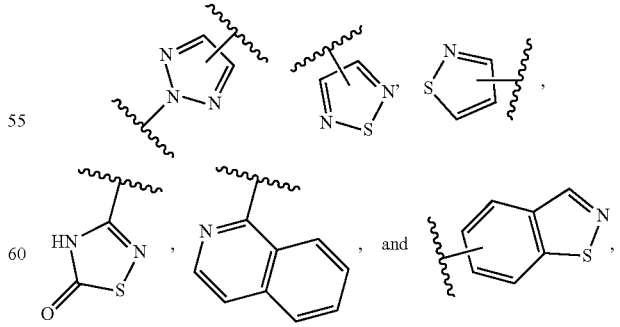

Y is —COOH, $R_4$ is —$C_{1-6}$alkyl-$Q_1$, $Q_1$ is —$NR_8R_9$, and $R_8$ and $R_9$ are taken together with the adjacent —N to form a cycle which is selected from the group of:

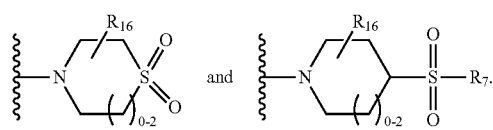
In this embodiment, it is also preferred that $R_7$ and $R_{16}$ are each —H or —$C_{1-6}$alkyl.
Preferred compounds, including pharmaceutically acceptable salts thereof, as part of the invention include the following:
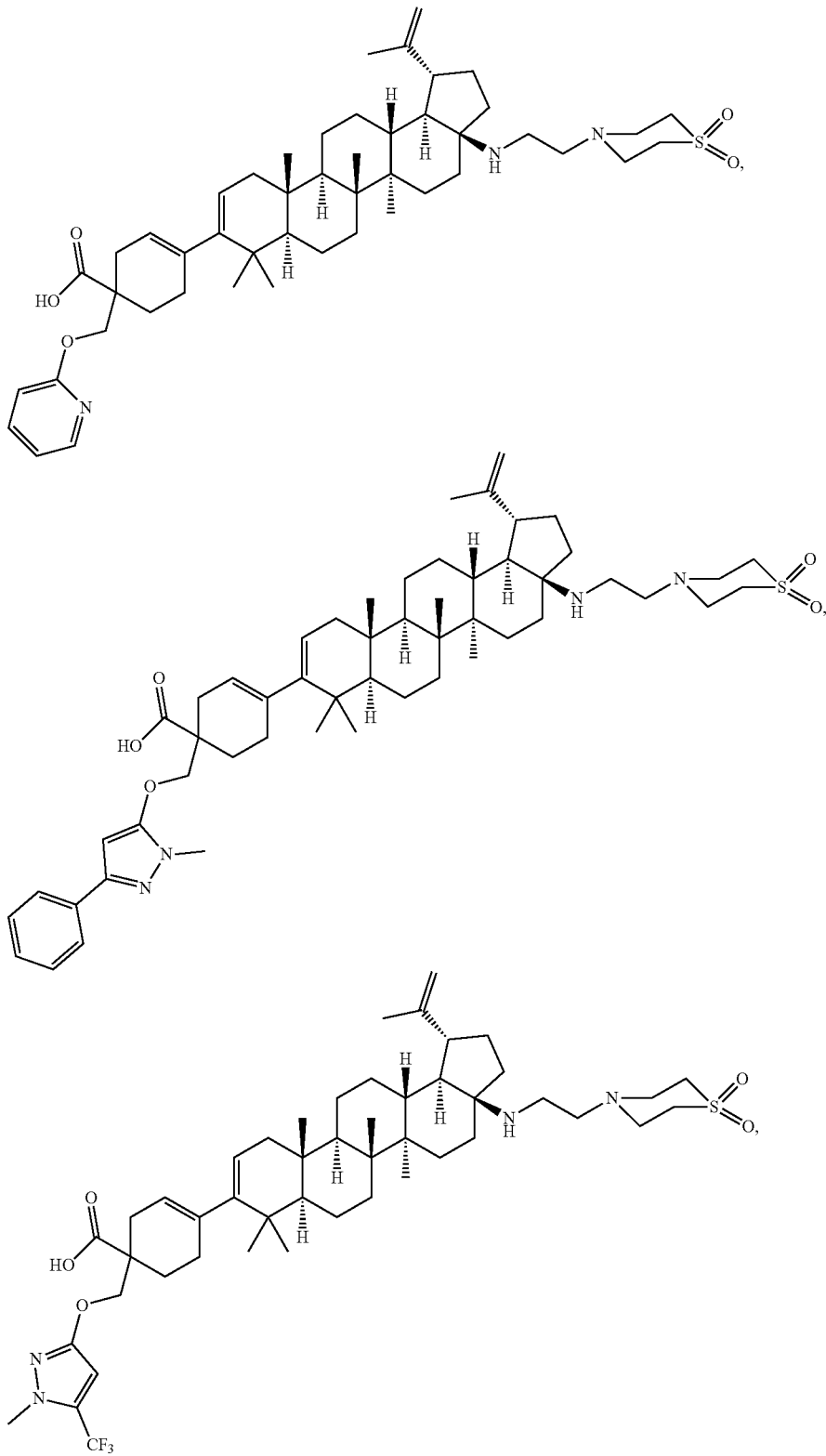

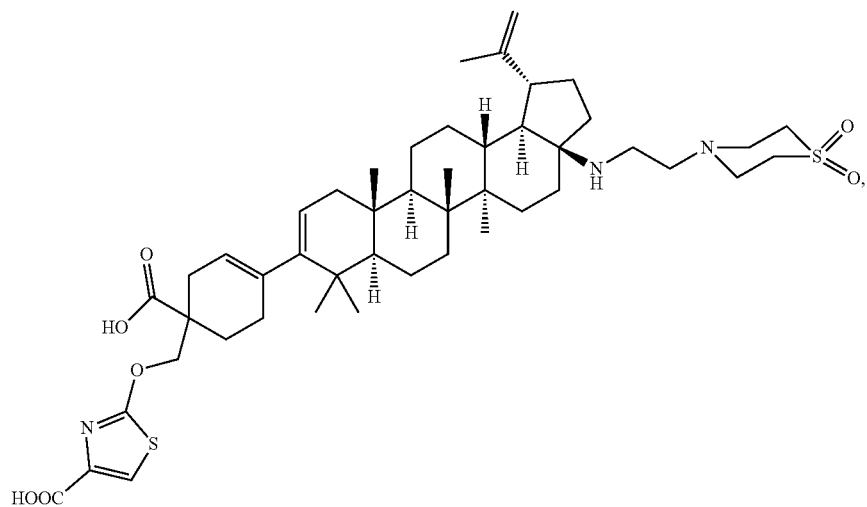
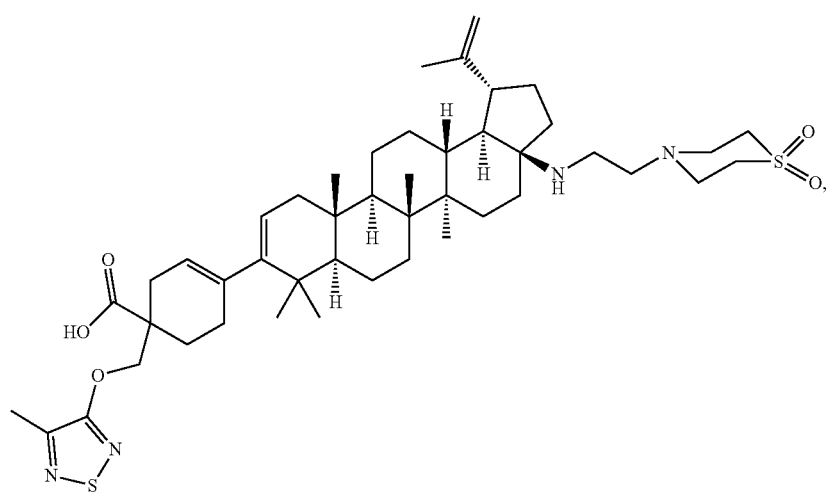
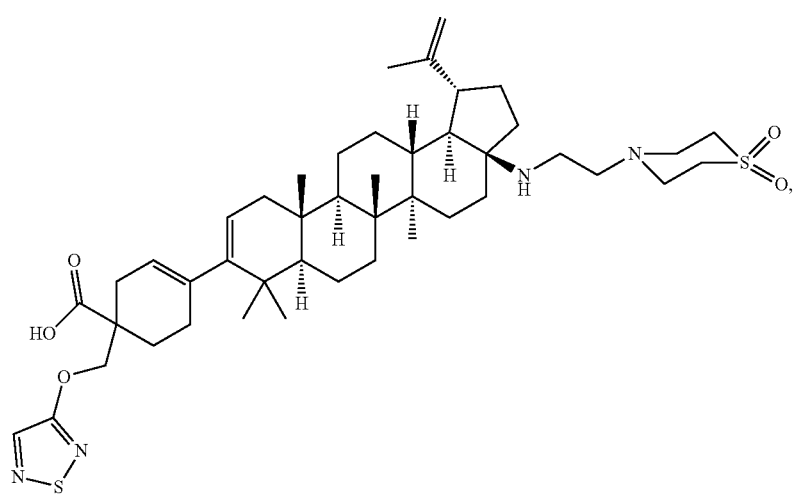

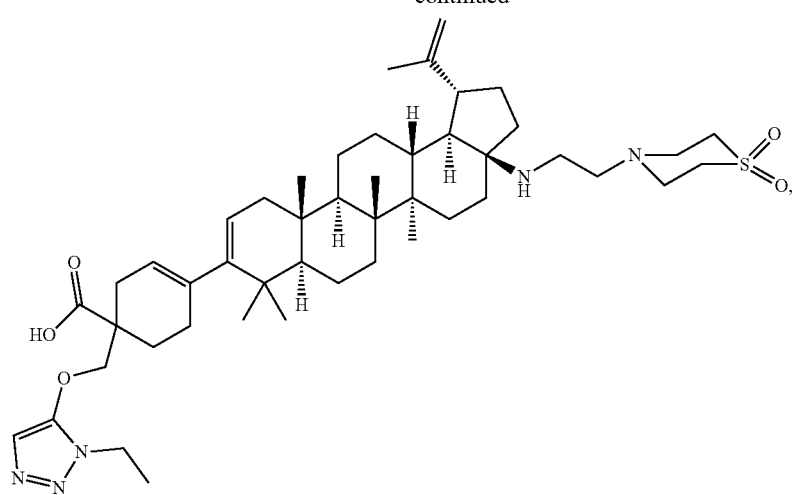
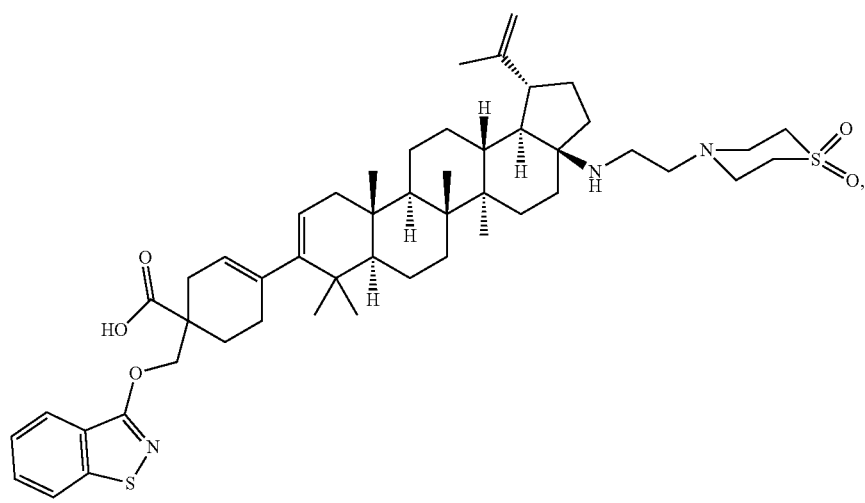
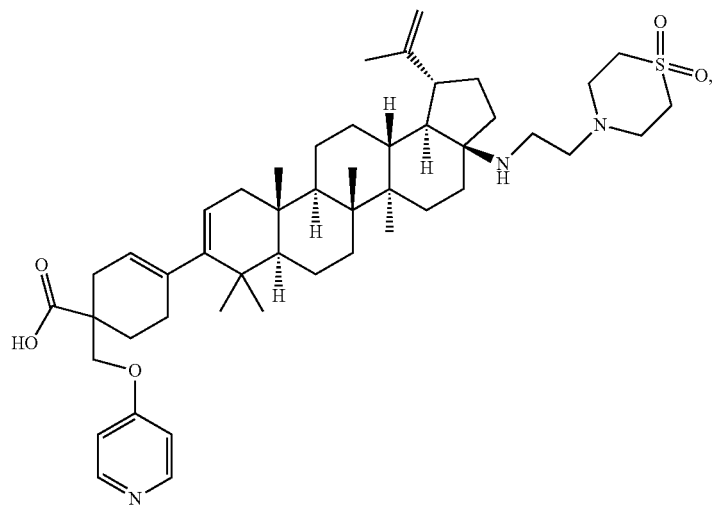

-continued
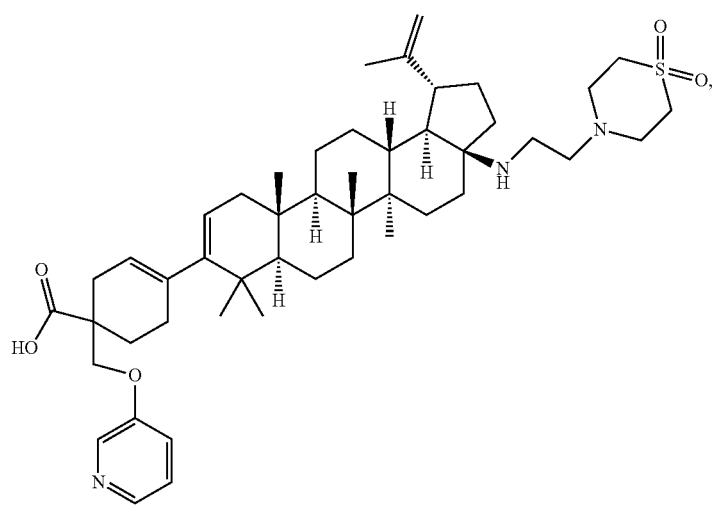
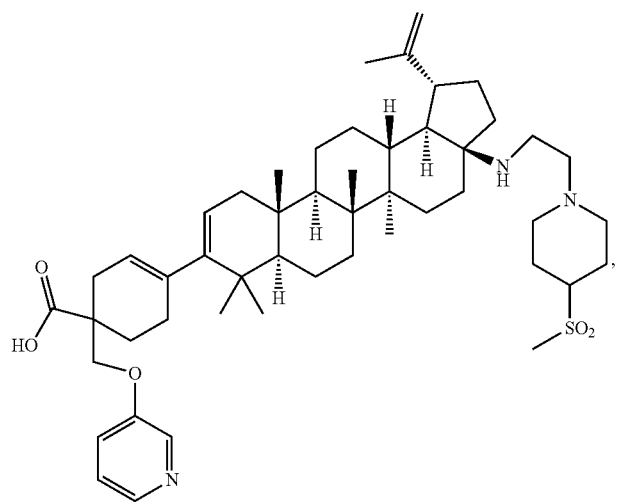
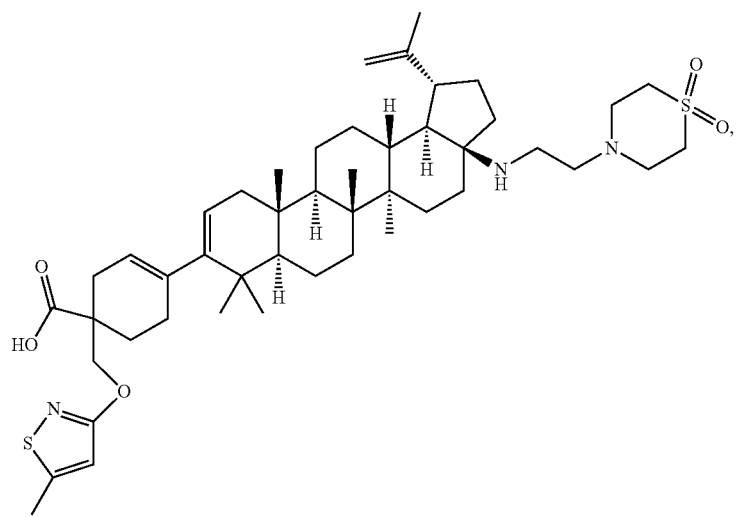

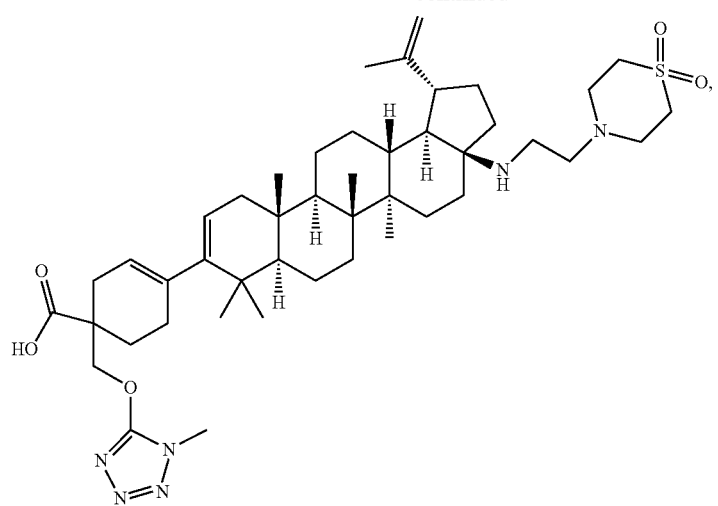
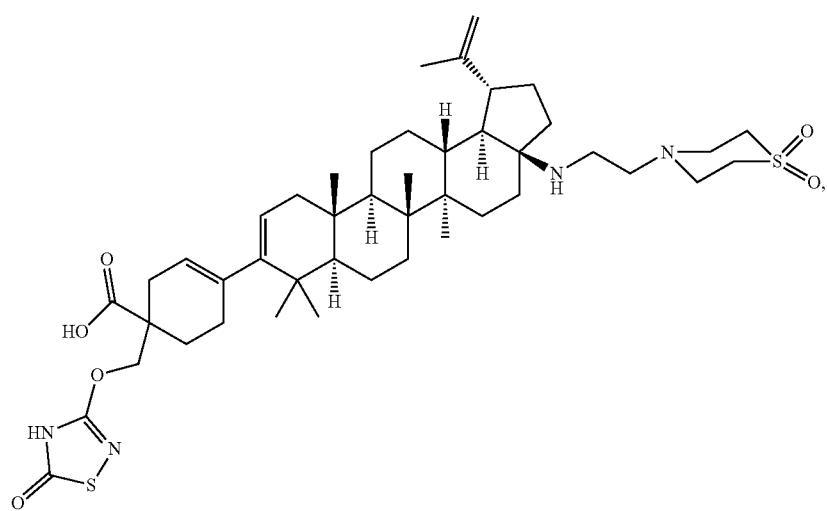
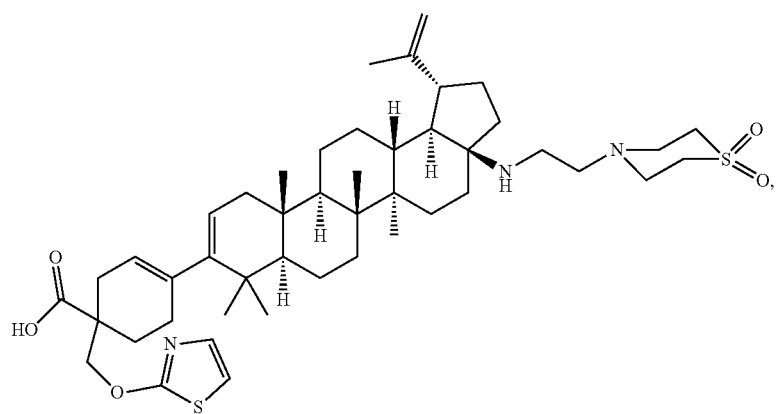

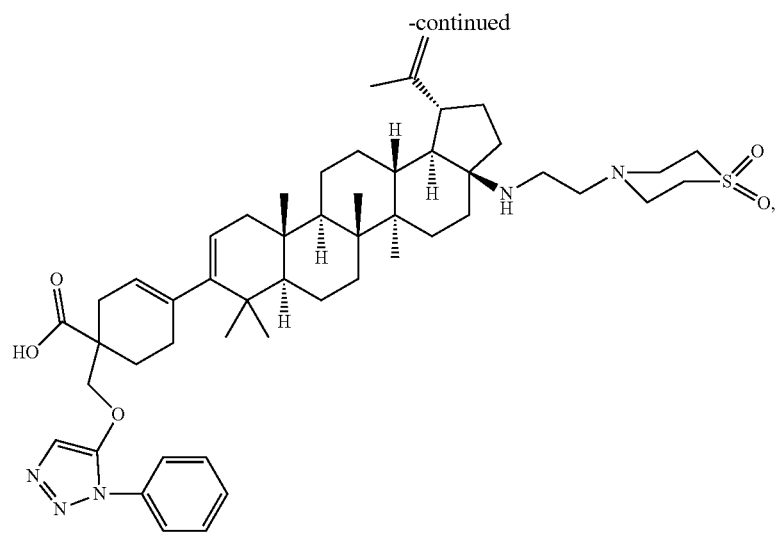
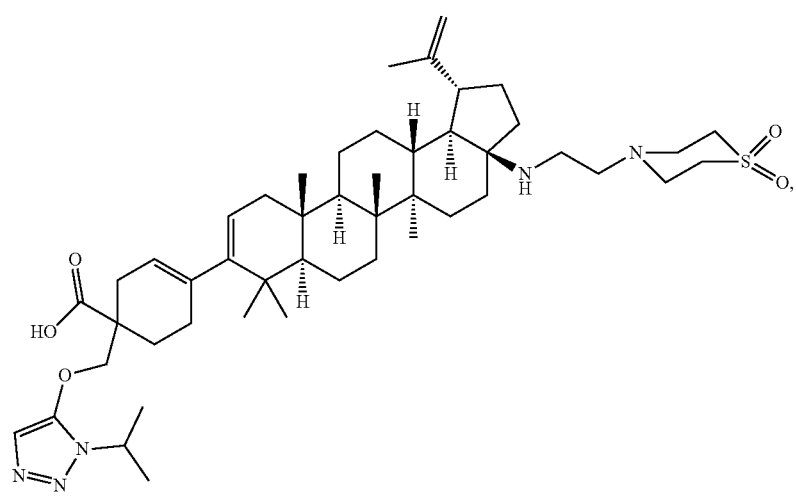
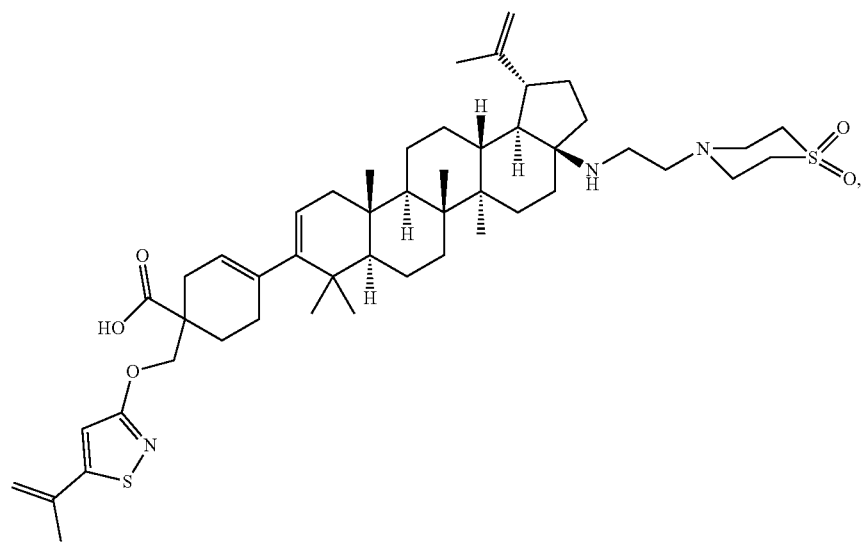

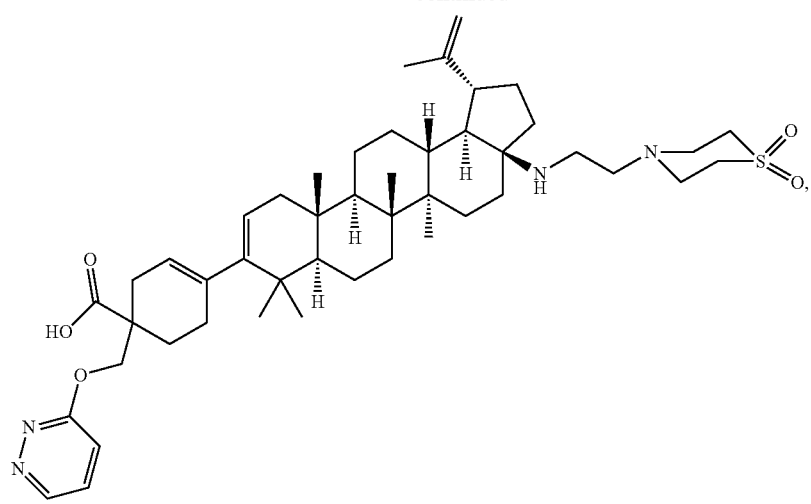
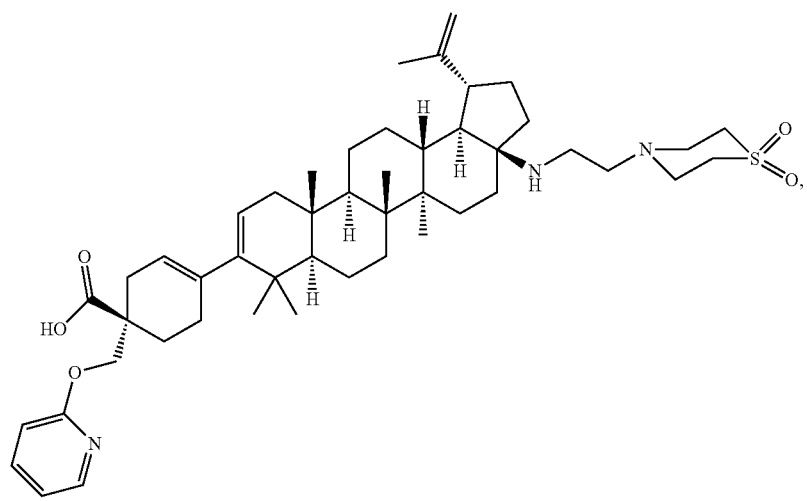
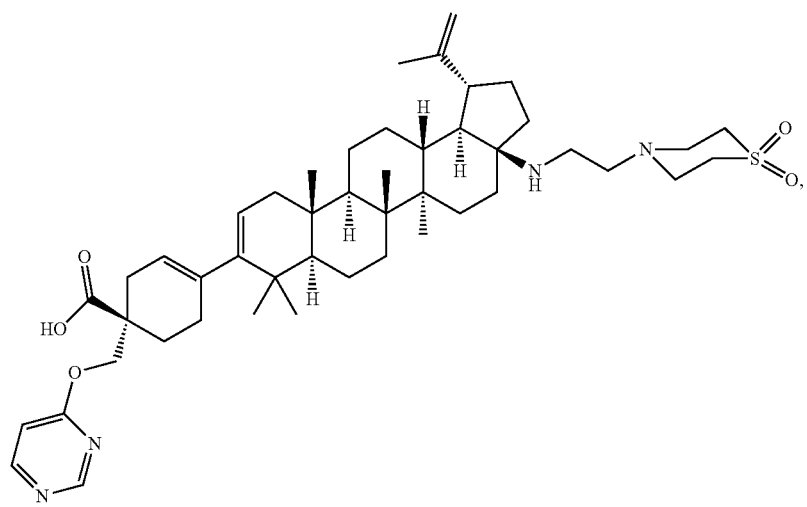

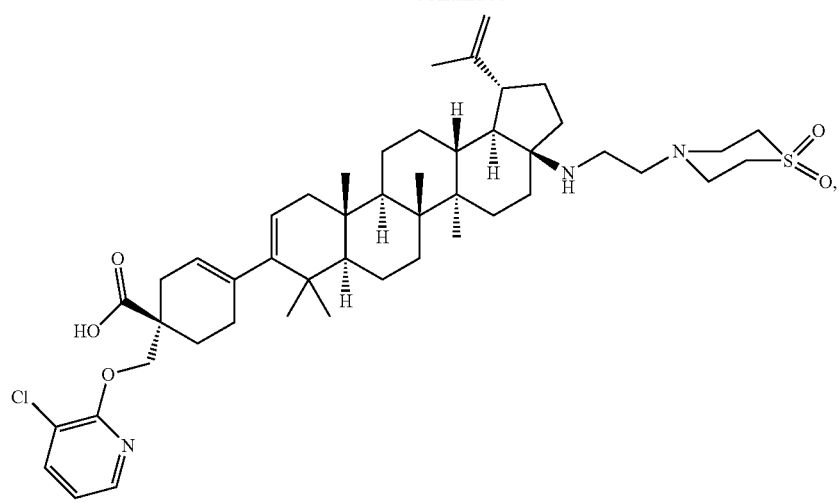
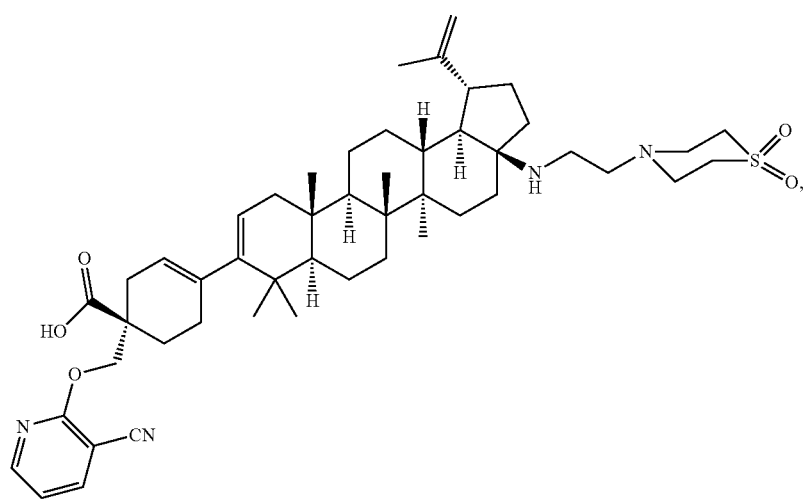
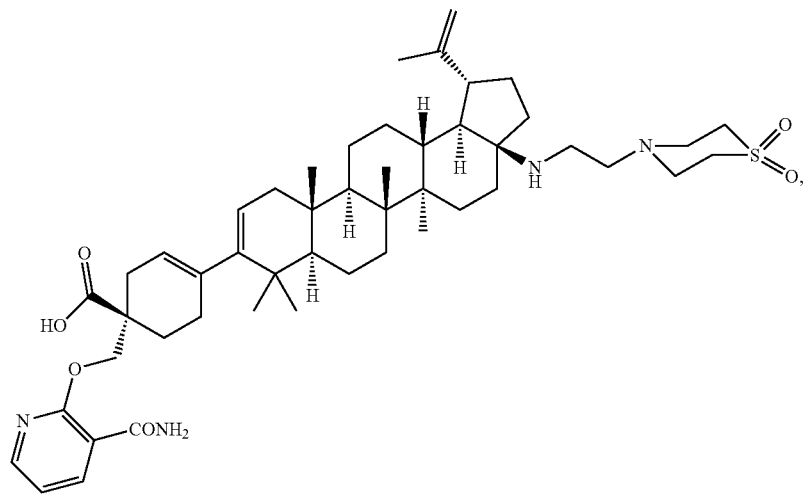

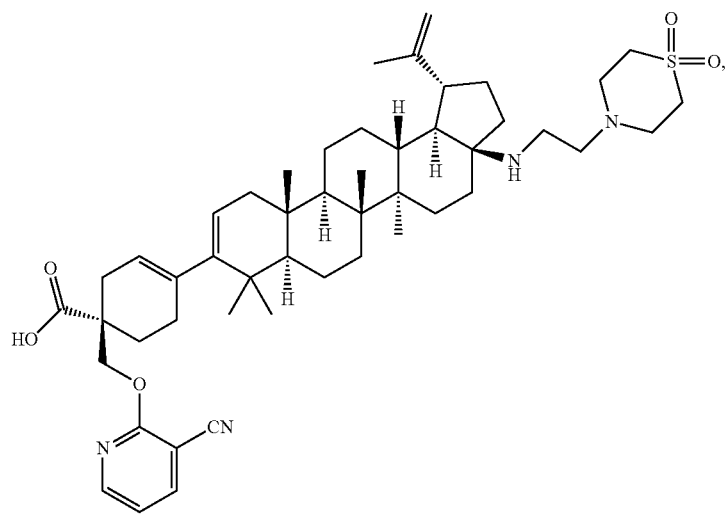
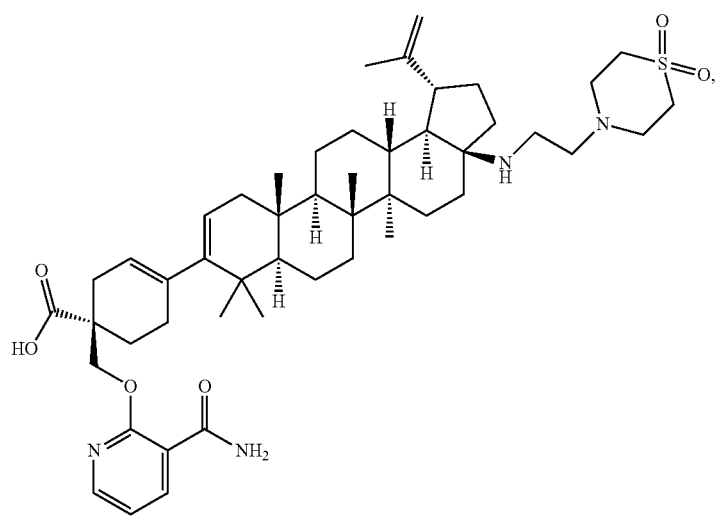
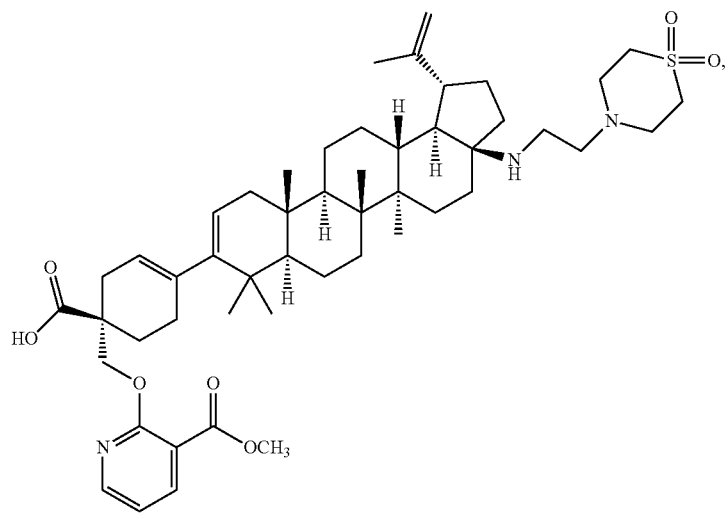

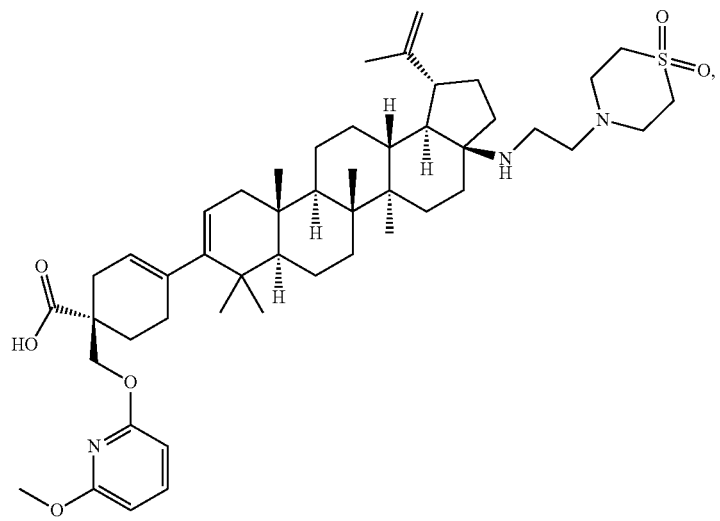
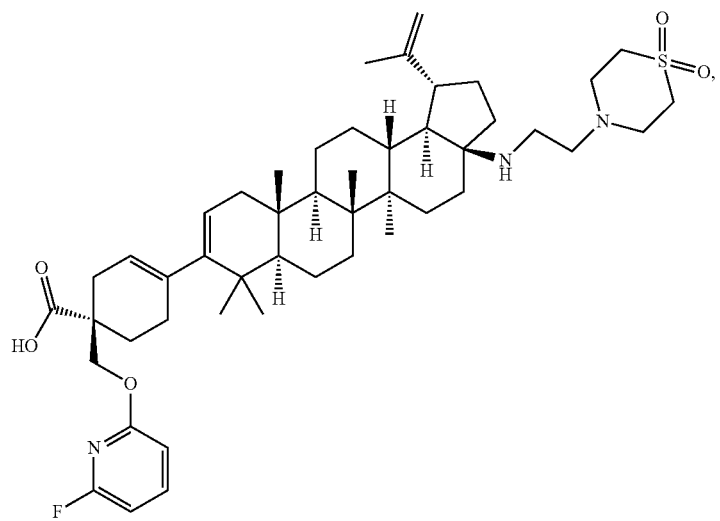
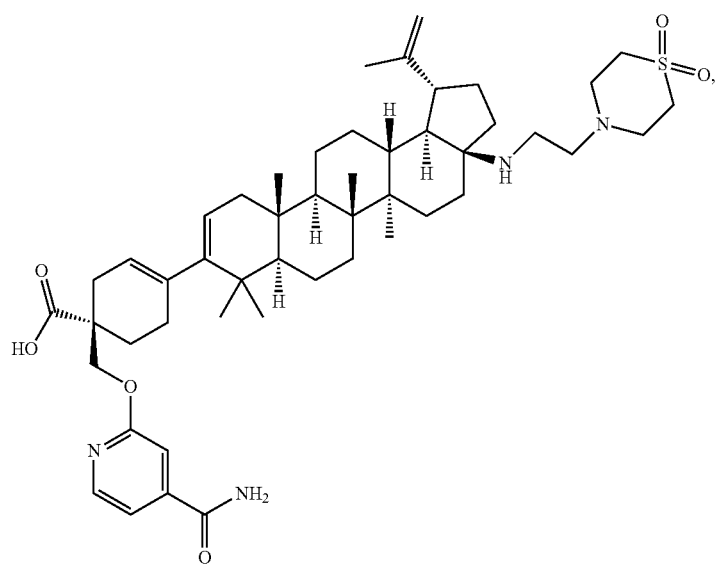

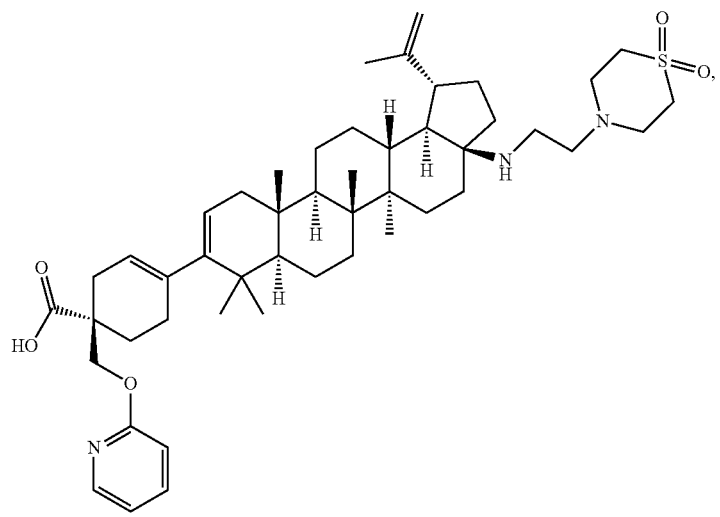
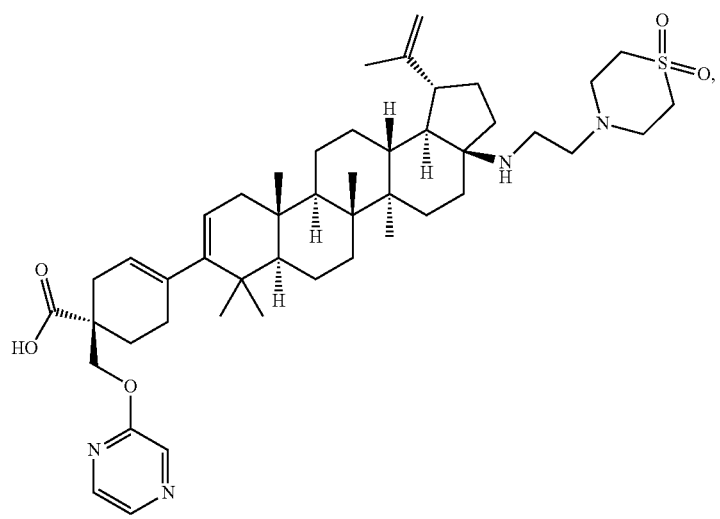
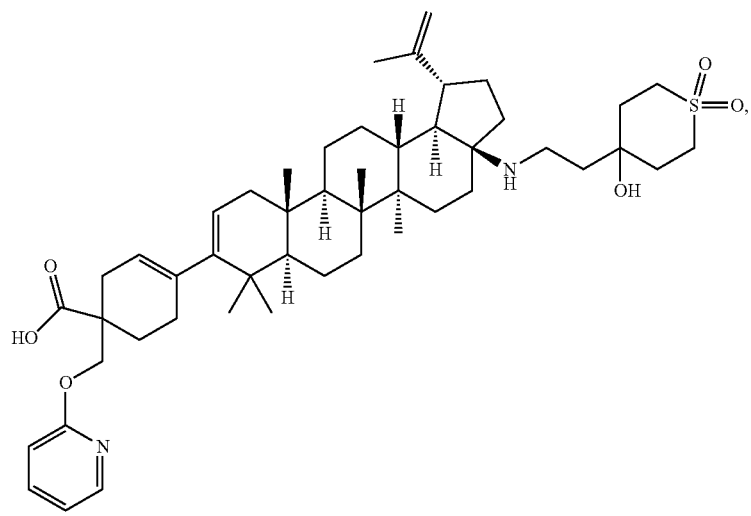

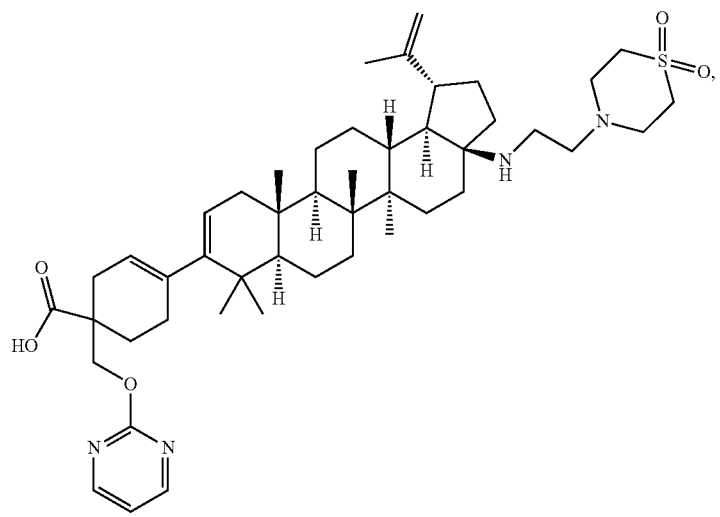
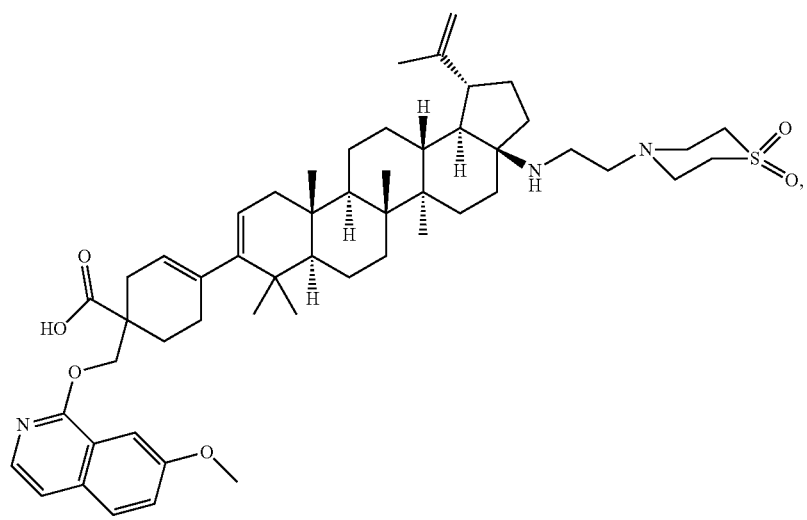
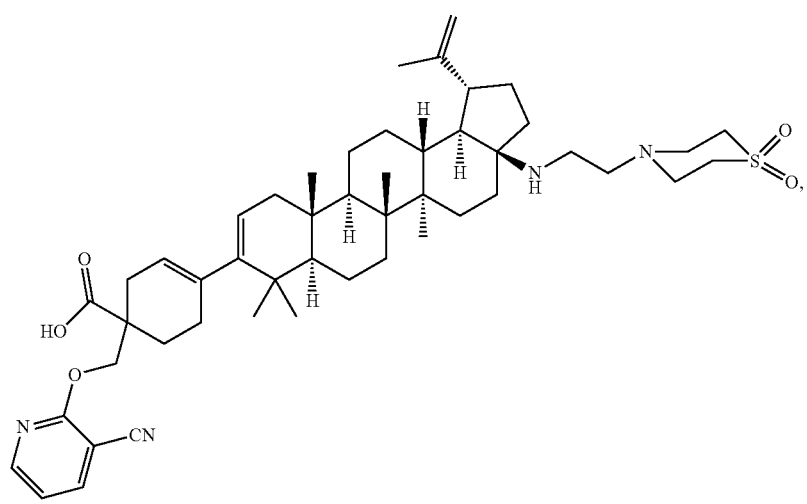

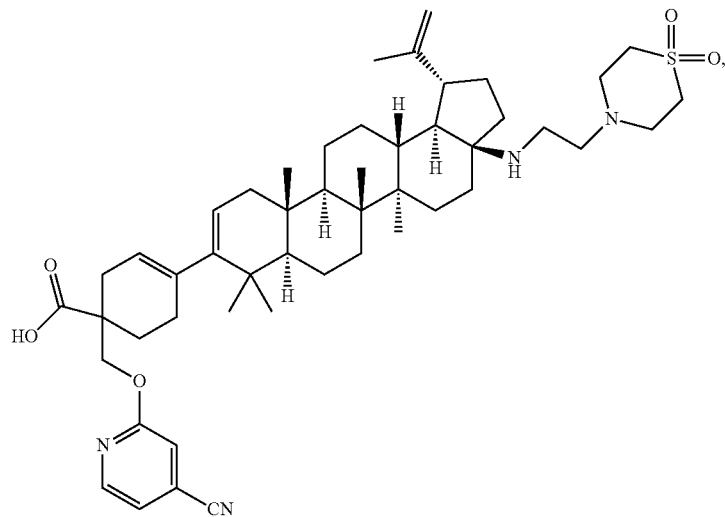
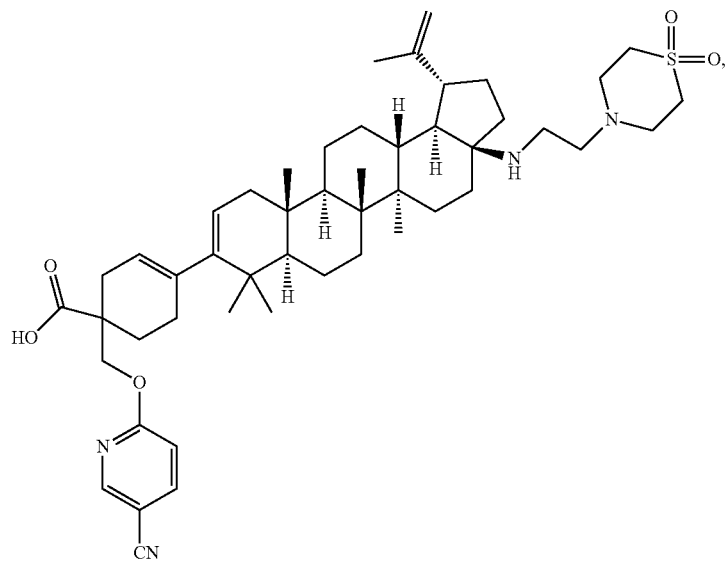
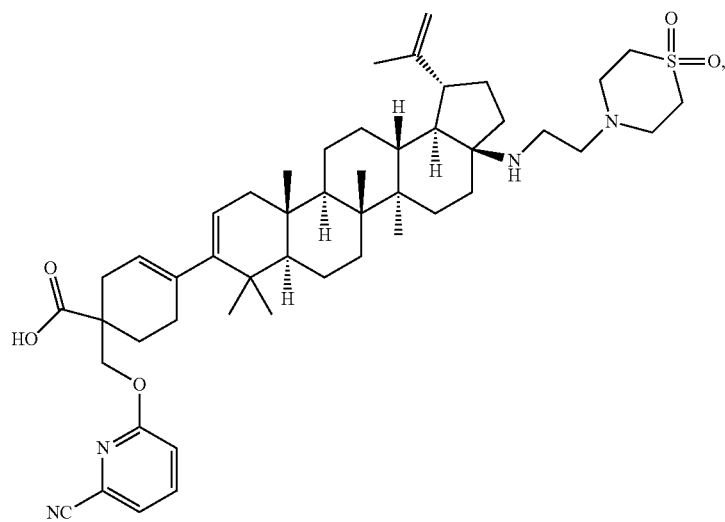

-continued
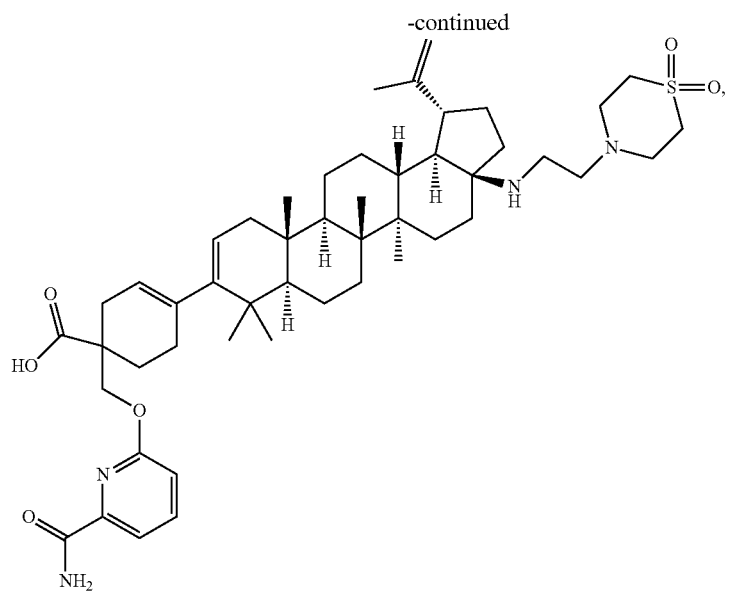
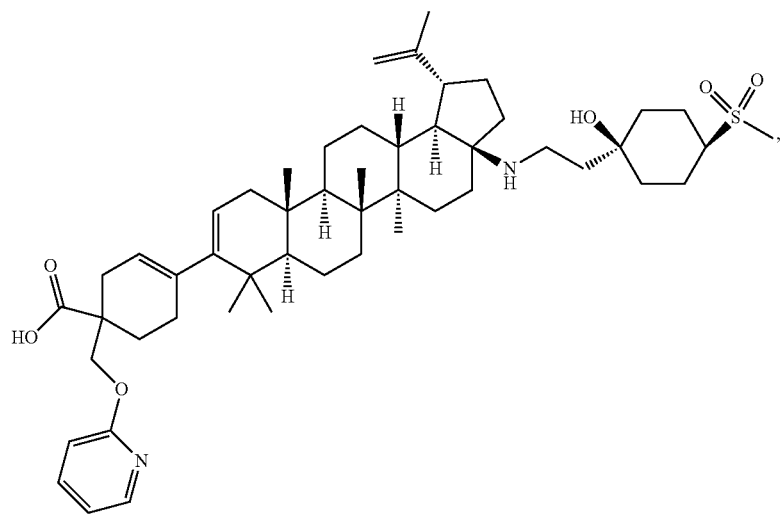
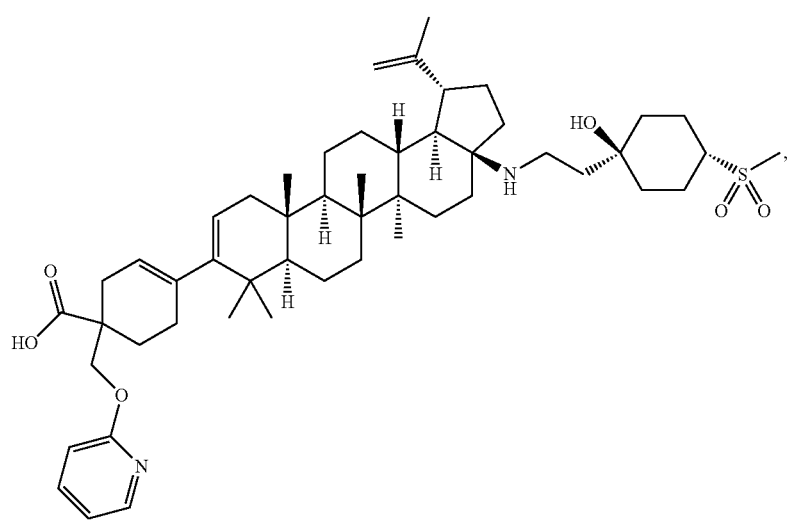

-continued
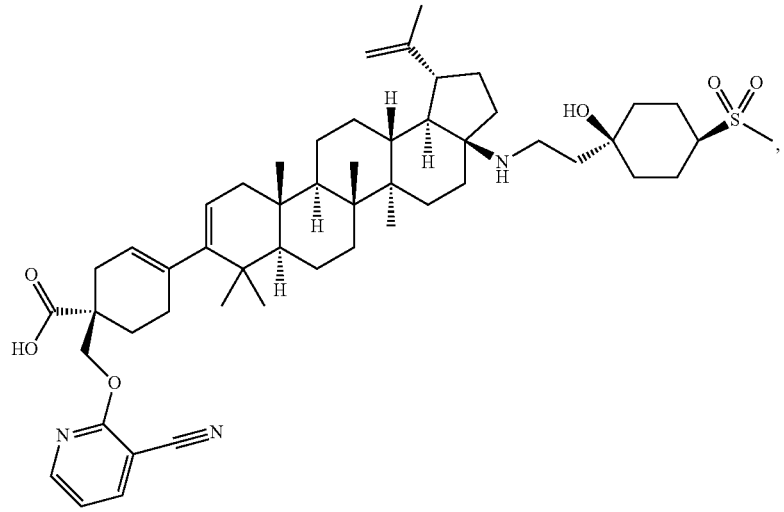
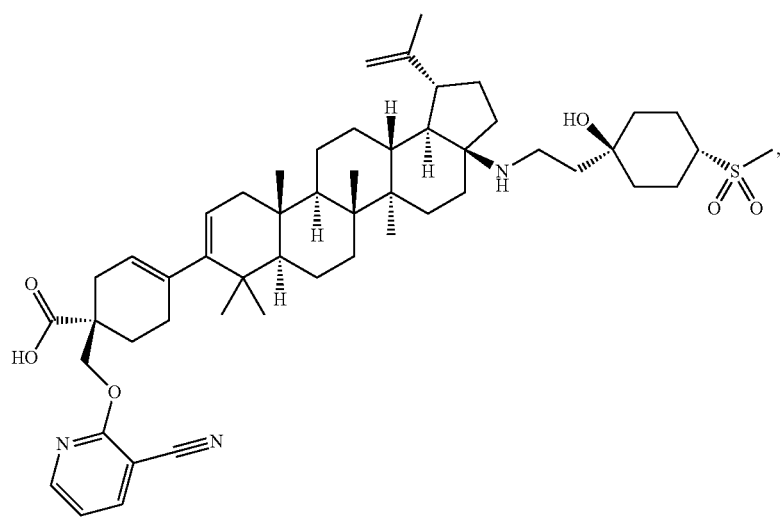
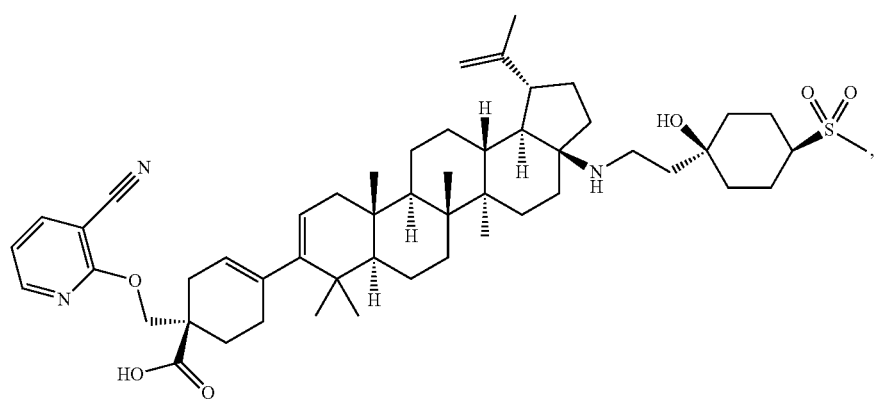

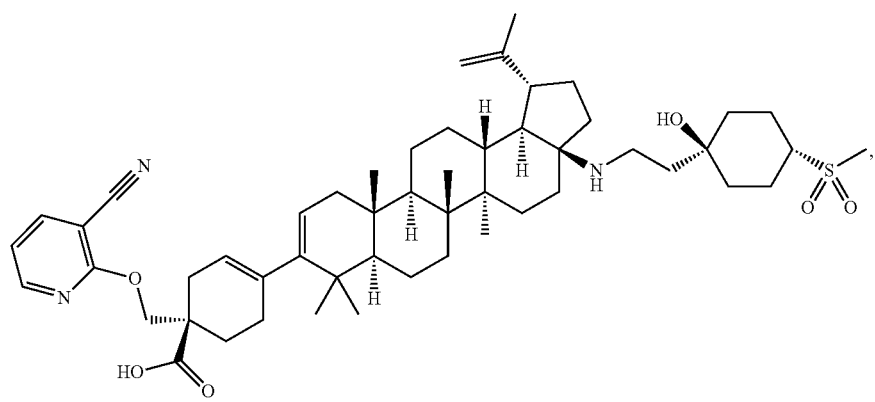
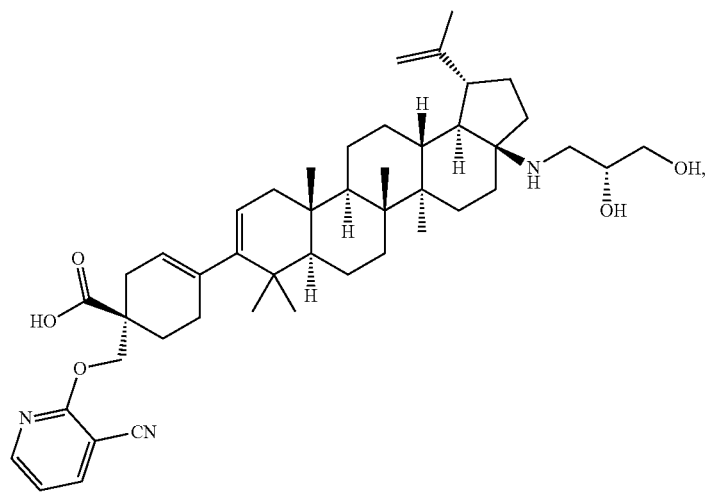
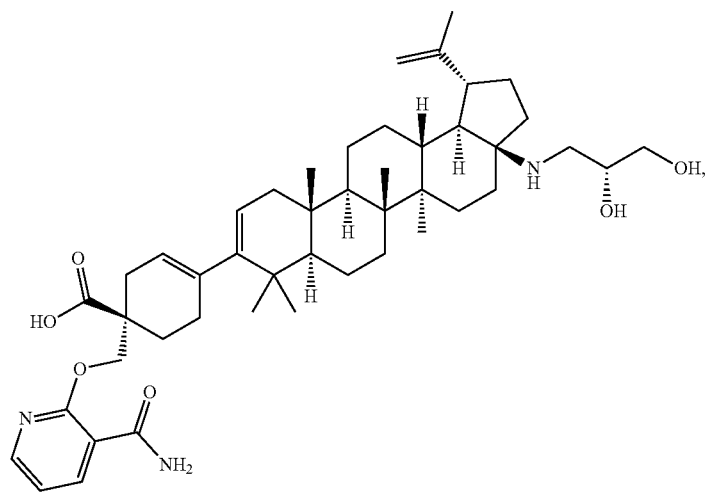

-continued
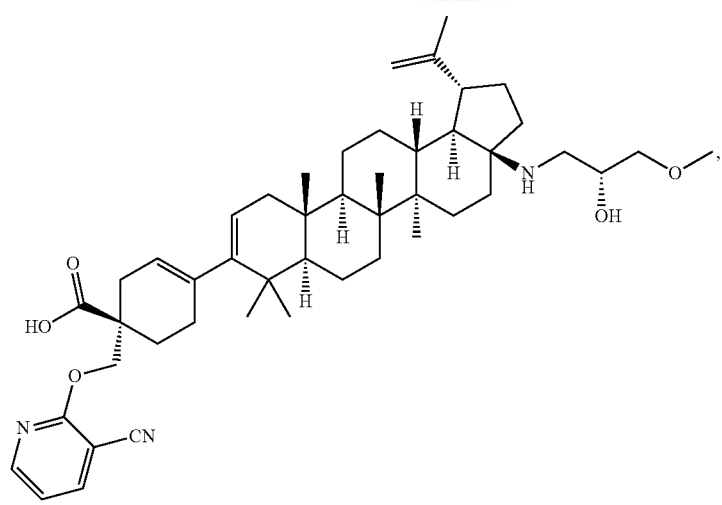
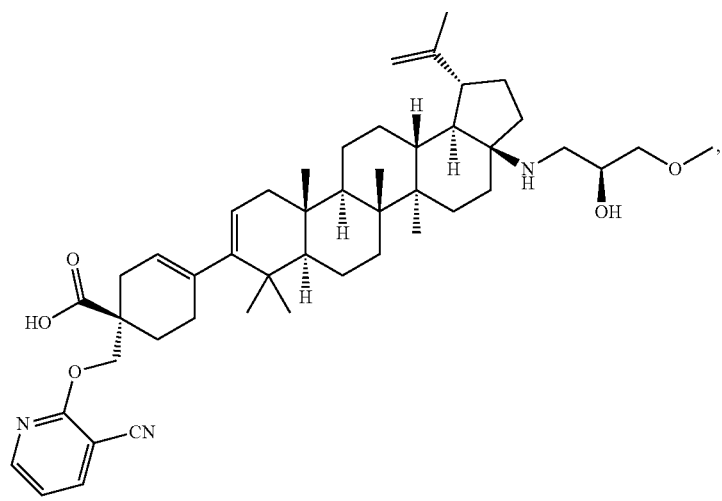
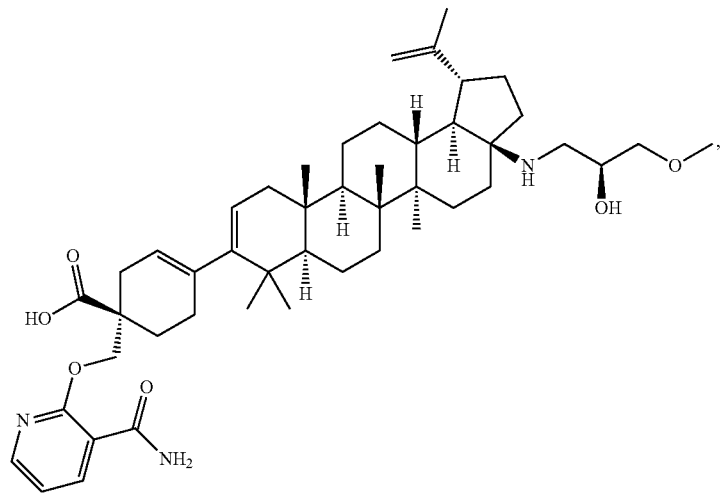

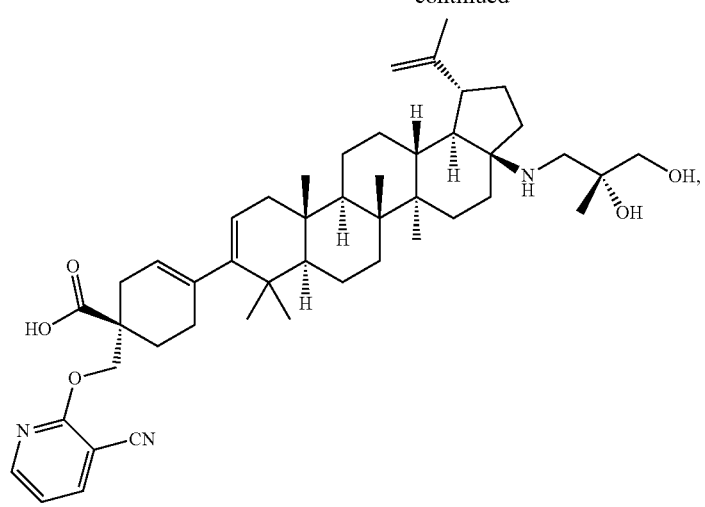
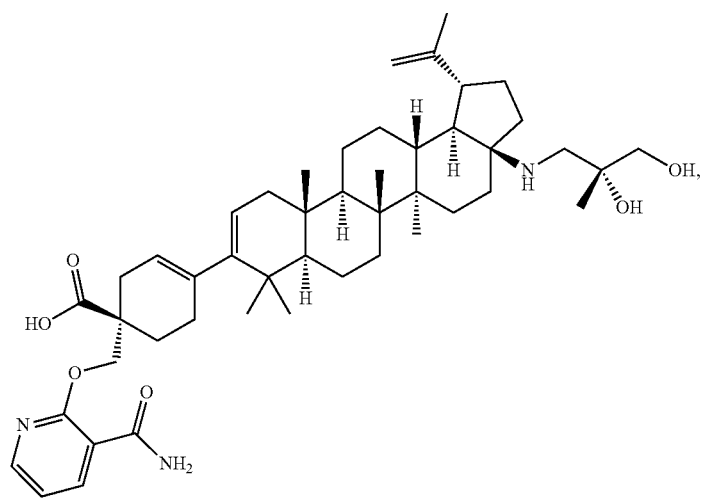
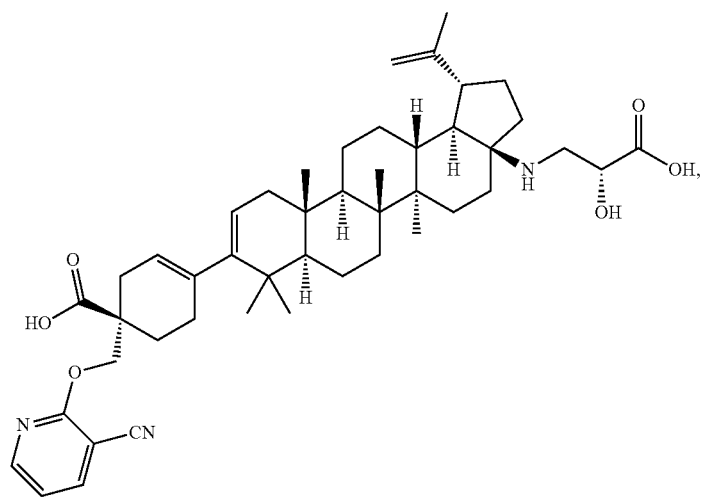

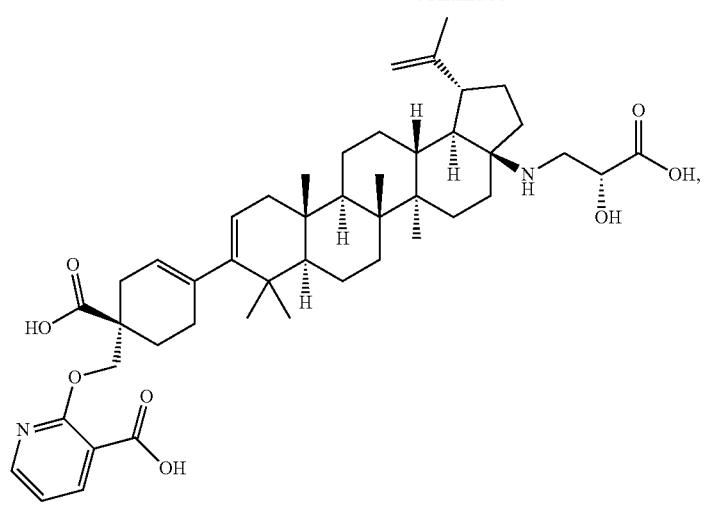
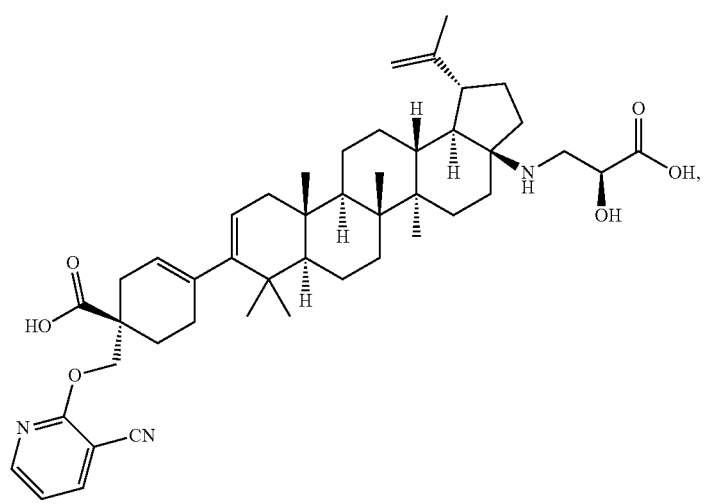
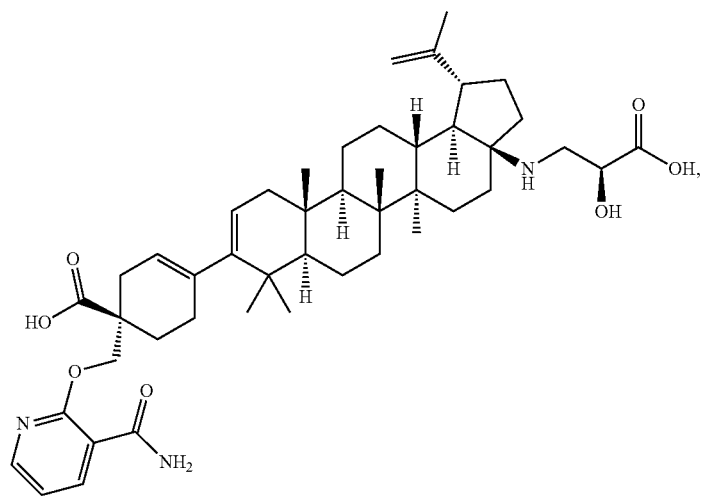

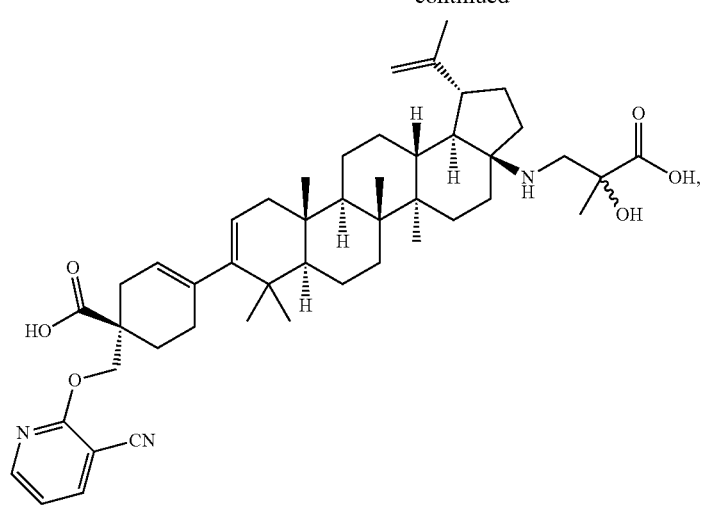
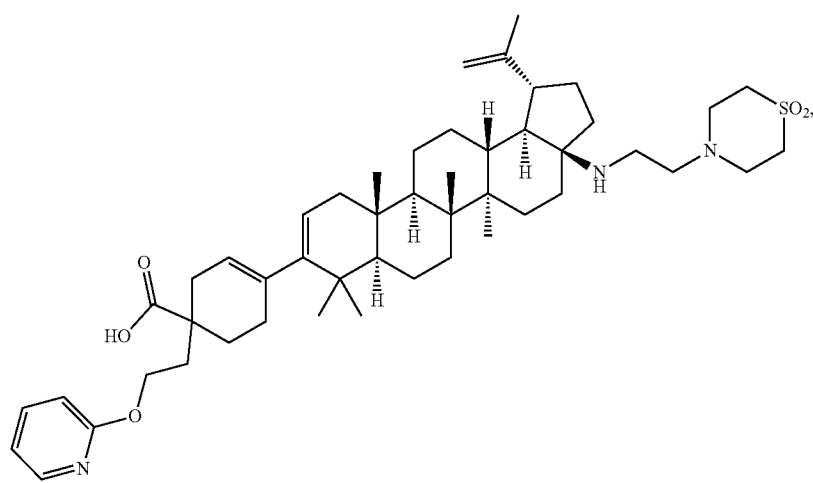
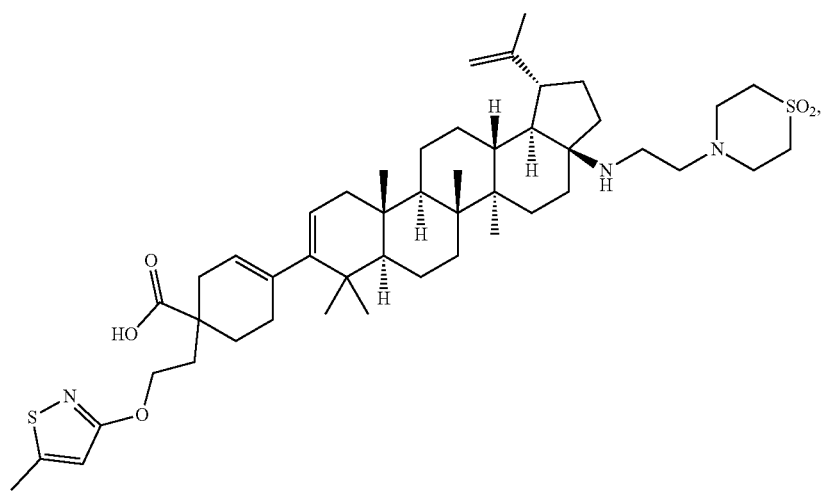

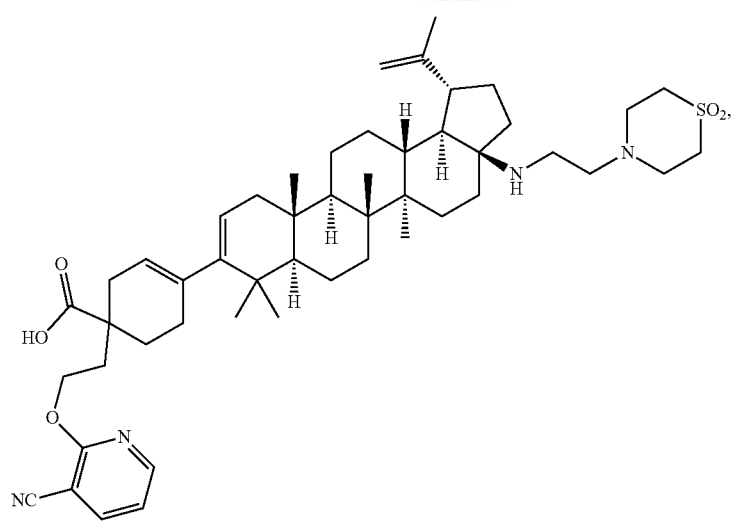
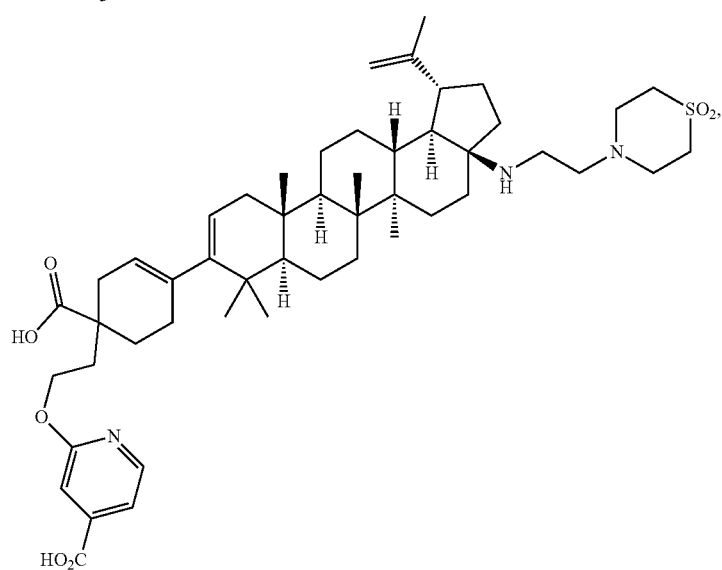
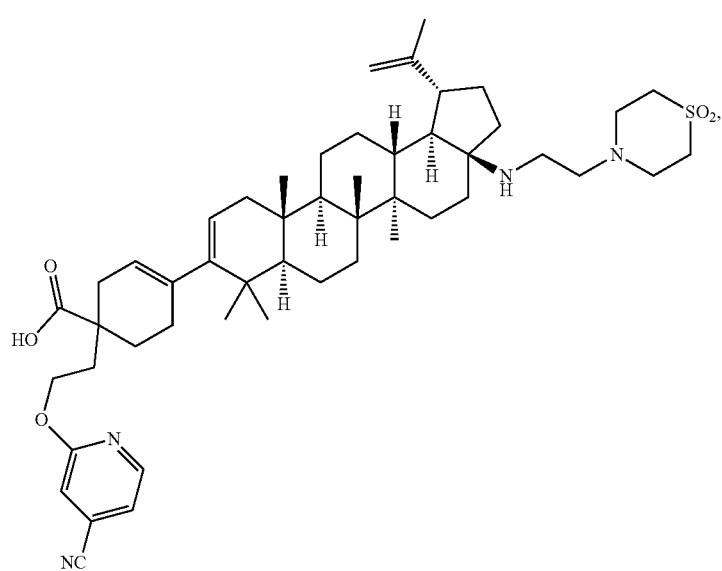

-continued
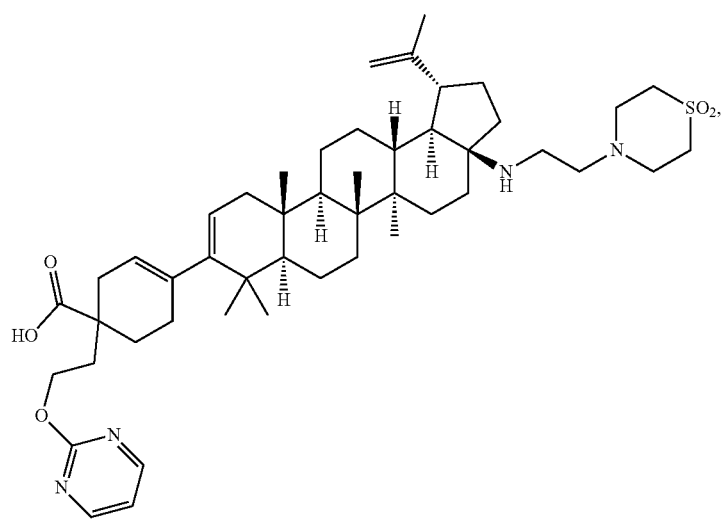
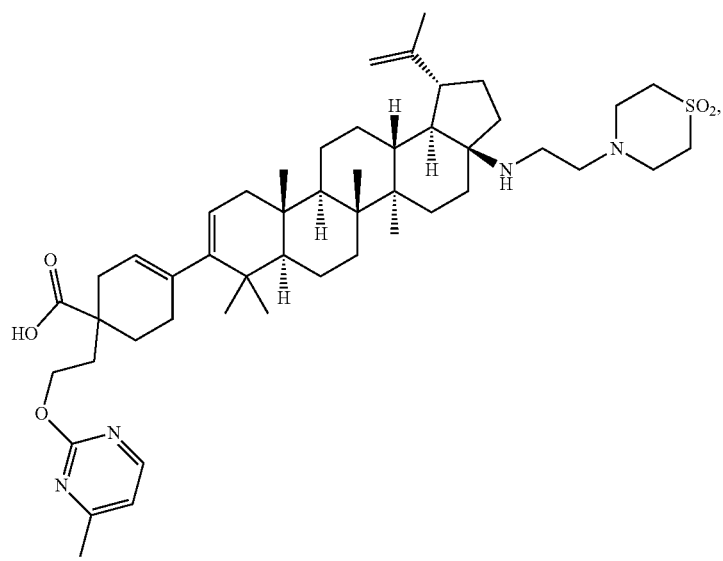
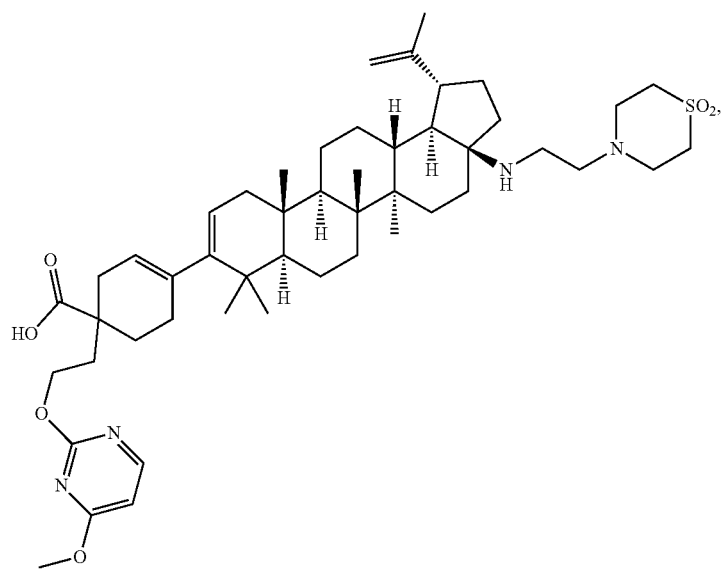

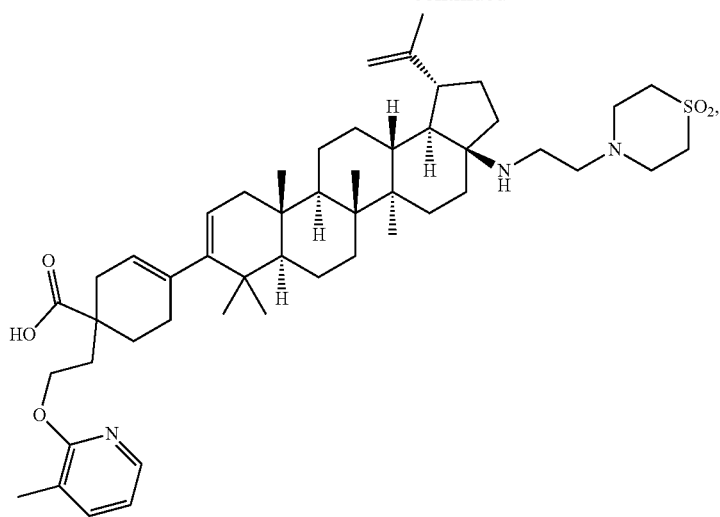
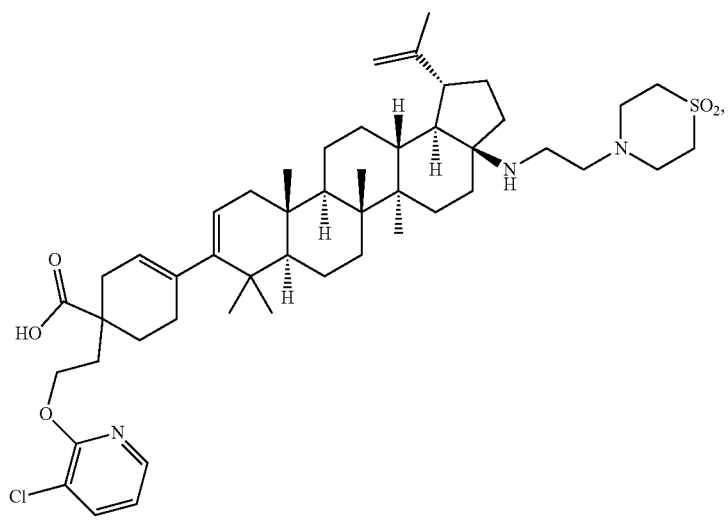
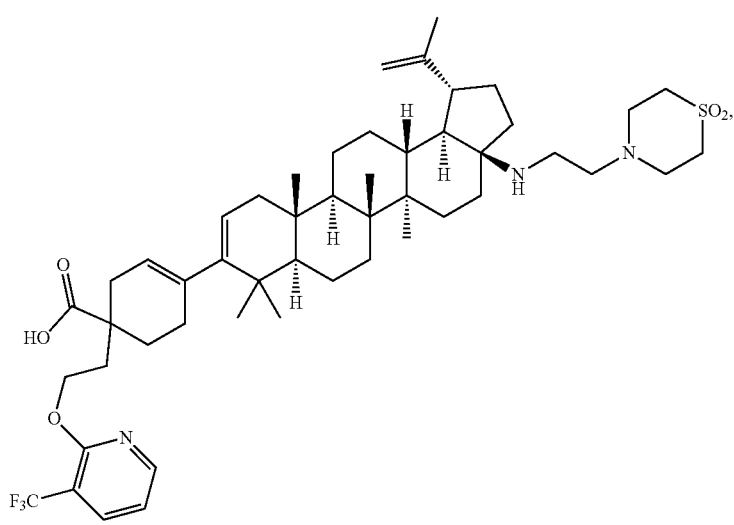

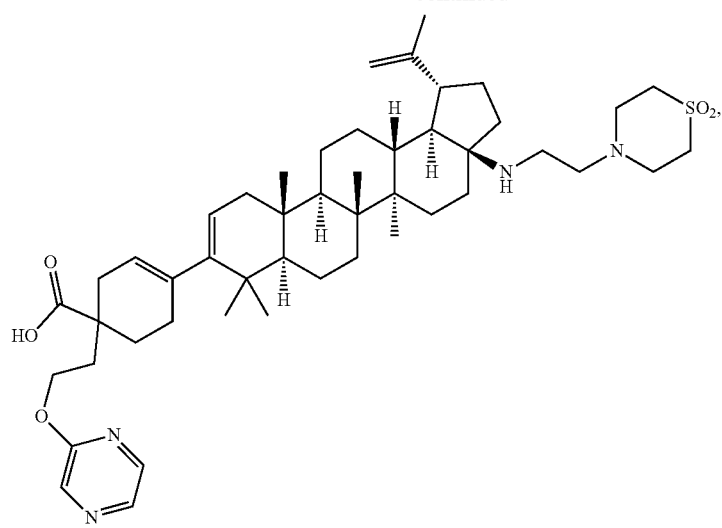
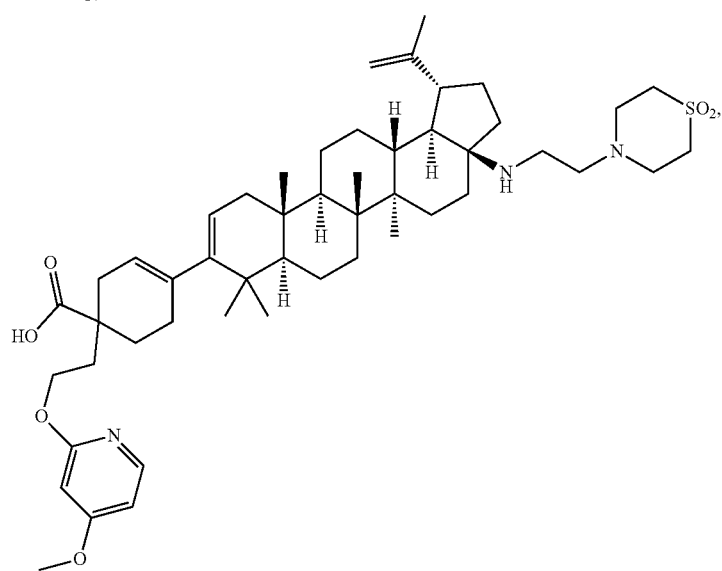
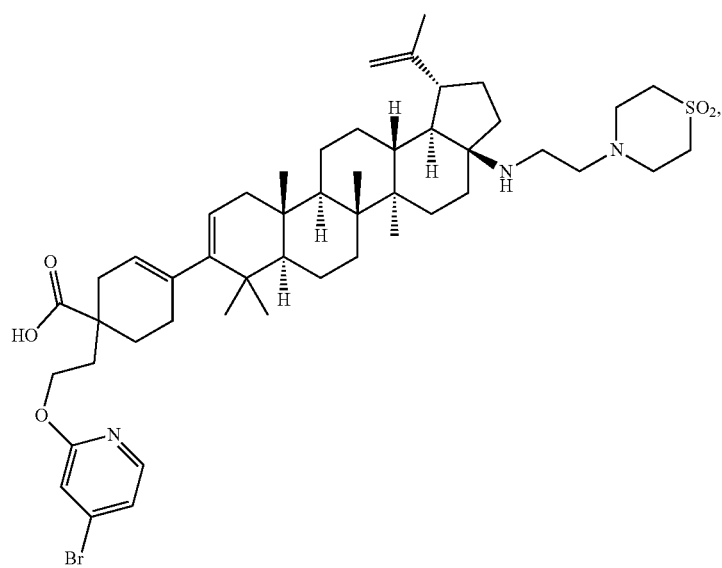

-continued
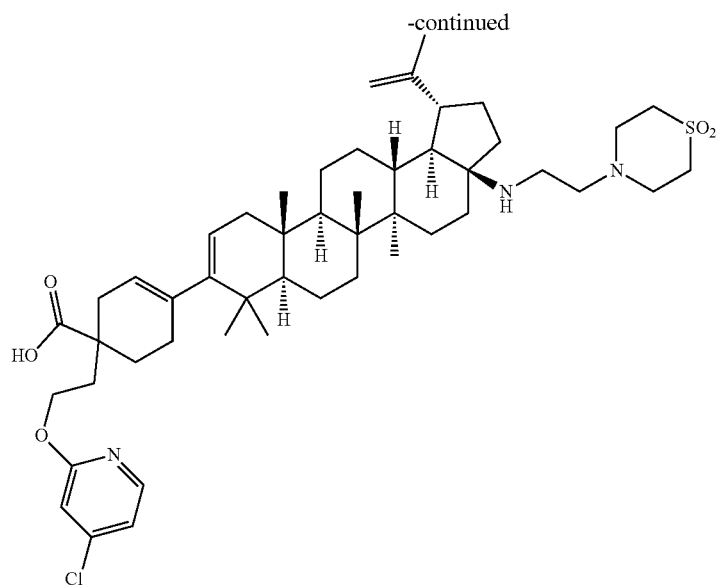
and
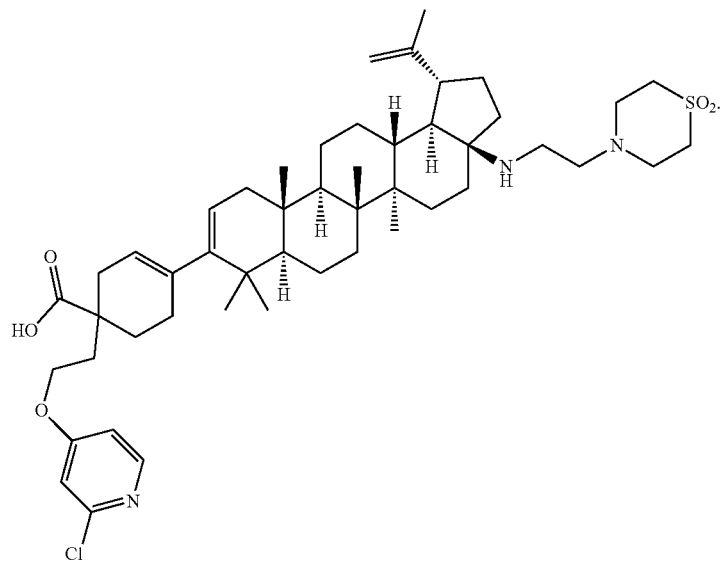
In another embodiment, preferred compounds, including pharmaceutically acceptable salts thereof, will be the following:

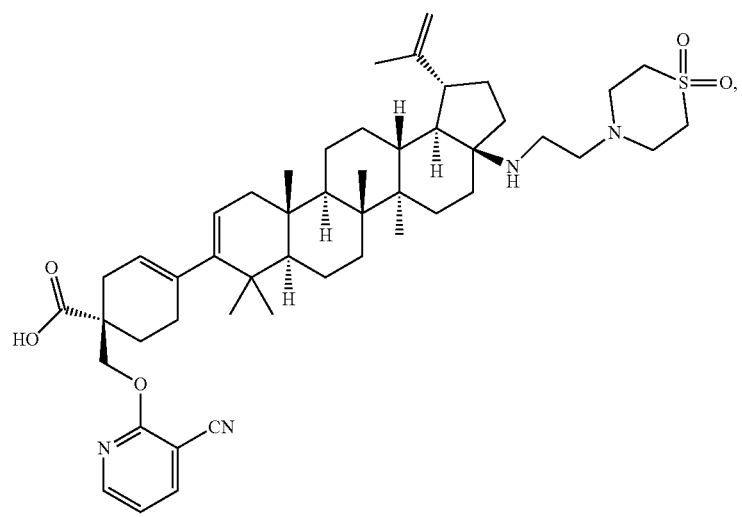
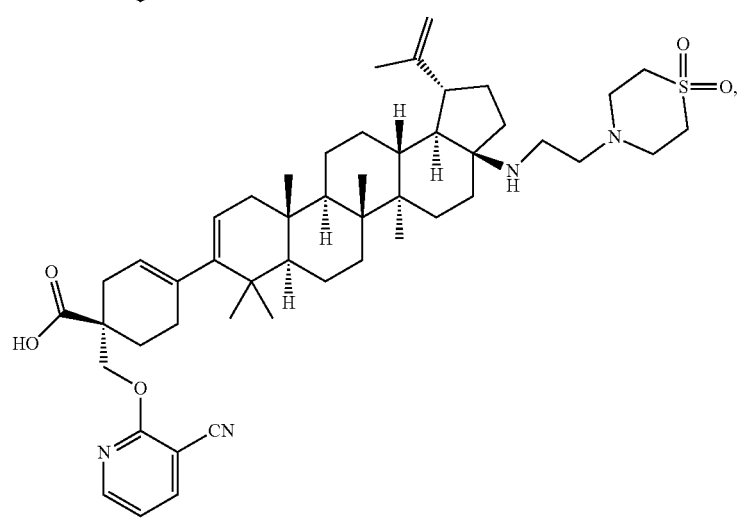
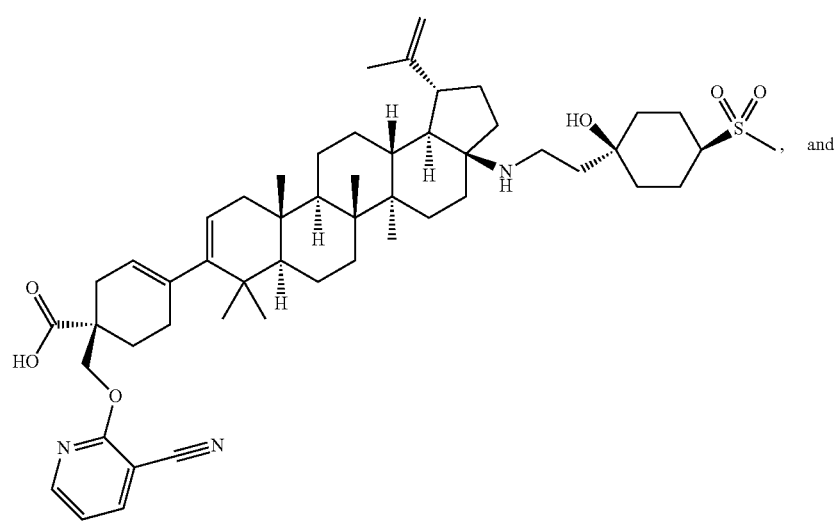, and

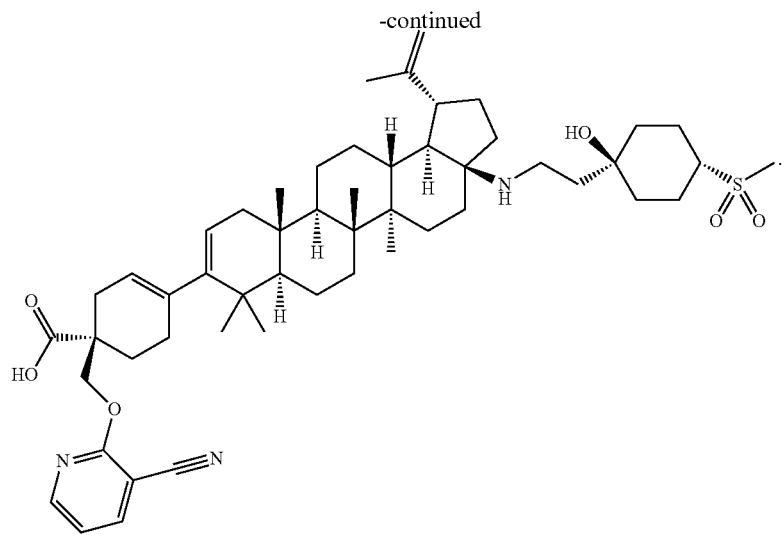

The compounds above represent the mixture of diastereoisomers, and the two individual disastereomers. In certain embodiments, one of the specific diastereomers may be particularly preferred.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, inhibiting, ameliorating and/or healing diseases and conditions associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta Interferon alfa-n3 | Triton Biosciences (Almeda, CA) Interferon Sciences | AIDS, Kaposi's sarcoma, ARC ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Inglehiem | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |

ANTIVIRALS

| Drug Name | Manufacturer | Indication |
|---|---|---|
| REYATAZ® (or atazanavir) | Bristol-Myers Squibb | HIV infection AIDs, protease inhibitor |
| FUZEON® (Enfuvirtide or T-20) | Roche/Trimeris | HIV infection AIDs, viral Fusion inhibitor |
| LEXIVA® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA® | Gilead | Combination of Tenofovir disoproxil fumarate salt (VIREAD®) and EMTRIVA® (Emtricitabine) |
| Integrase Inhibitor GS917/JTK-303 Elvitegravir | Gilead/Japan Tobacco | HIV Infection AIDs in development |
| Triple drug combination ATRIPLA® | Gilead/ Bristol-Myers Squibb | Combination of Tenofovir disoproxil fumarate salt (VIREAD®), EMTRIVA® (Emtricitabine), and SUSTIVA® (Efavirenz) |
| FESTINAVIR® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor dolutegravir | GSK | HIV infection AIDs |
| S/GSK1265744 Integrase inhibitor | GSK | HIV infection AIDs |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine- Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |

ANTI-INFECTIVES -continued

| Drug Name | Manufacturer | Indication |
| --- | --- | --- |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells.* Meanwell, Nicholas A.; Kadow, John F., Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR$_4$ coreceptor. HIV attachment inhibitors are also set forth in U.S. Pat. Nos. 7,354,924 and 7,745,625.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV.

Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound(s) of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formula I, their pharmaceutical formulations, and their use in patients suffering from or susceptible to HIV infection. The compounds of Formula I also include pharmaceutically acceptable salts thereof. Procedures to construct compounds of Formula I and intermediates useful for their synthesis are described after the Abbreviations.

Abbreviations

One or more of the following abbreviations, most of which are conventional abbreviations well known to those skilled in the art, may be used throughout the description of the disclosure and the examples:

RT=room temperature
BHT=2,6-di-tert-butyl-4-hydroxytoluene
CSA=camphorsulfonic acid
LDA=lithium diisopropylamide
KHMDS=potassium bis(trimethylsilyl)amide
SFC=supercritical fluid chromatography
Quant=quantitative
TBDMS=tert-butyldimethylsilane
PTFE=polytetrafluoroethylene
NMO=4-methylmorpholine-N-oxide
THF=tetrahydrofuran
TLC=thin layer chromatography
DCM=dichloromethane
DCE=dichloroethane
TFA=trifluoroacetic acid
LCMS=liquid chromatography mass spectroscopy
Prep=preparative
HPLC=high performance liquid chromatography
DAST=(diethylamino)sulfur trifluoride
TEA=triethylamine
DIPEA=N,N-diisopropylethylamine
HATU=[O-(7-azabenzotriazol-1-yl)-1,1,3,3-tetramethyluronium hexafluorophosphate]
DCC=N,N'-dicyclohexylcarbodiimide
DMAP=dimethylaminopyridine
TMS=trimethylsilyl
NMR=nuclear magnetic resonance
DPPA=diphenyl phosphoryl azide
AIBN=azobisisobutyronitrile
TBAF=tetrabutylammonium fluoride
DMF=dimethylformamide
TBTU=O-(benzotriazol-1-yl)-N,N,N',N'-tetramethyluronium tetrafluoroborate
Min(s)=minute(s)
h=hour(s)
sat.=saturated
TEA=triethylamine EtOAc=ethyl acetate
TFA=trifluoroacetic acid
PCC=pyridinium chlorochromate
TLC=thin layer chromatography
Tf₂NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
μtg=microgram(s)
μl=microliter(s)
μm=micrometer(s)
mm=millimeter(s)
Rpm=revolutions per minute
SM=starting material
TLC=thin layer chromatography
AP=area percentage
Equiv.=equivalent(s)
DMP=Dess-Martin periodinane
TMSCl=trimethylsilyl chloride
TBSCl=tert-Butyldimethylsilyl chloride
TBSOTf=trimethylsilyl trifluoromethanesulfonate
PhMe=toluene
PhNTf₂=N-Phenyl-bis(trifluoromethanesulfonimide)
S-Phos=2-Dicyclohexylphosphino-2',6'-dimethoxybiphenyl
TFDO=methyl(trifluoromethyl)dioxirane
TEMPO=2,2,6,6-tetramethylpiperidinyloxy
DI=deionized water The terms "C-3" and "C-28" refer to certain positions of a triterpene core as numbered in accordance with IUPAC rules (positions depicted below with respect to an illustrative triterpene: betulin):

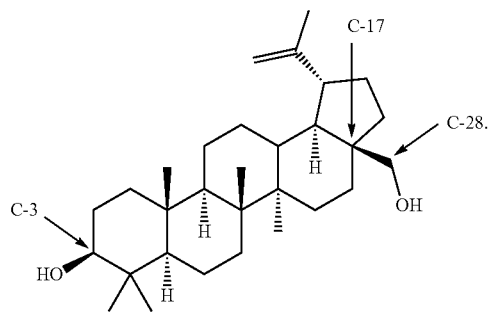

The same numbering is maintained when referring to the compound series in schemes and general descriptions of methods.

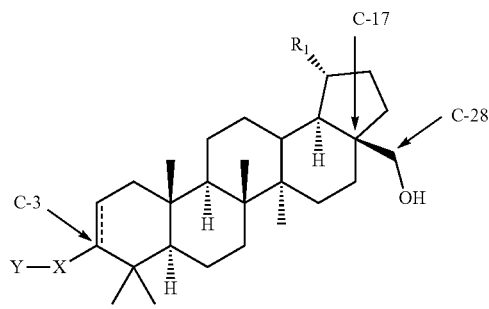

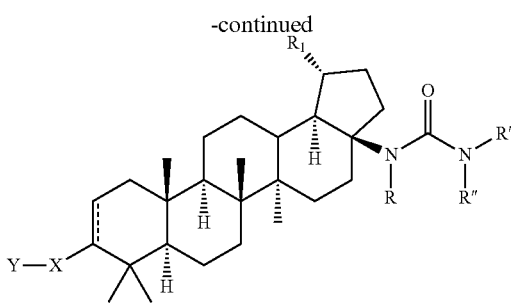

C-17 ureas

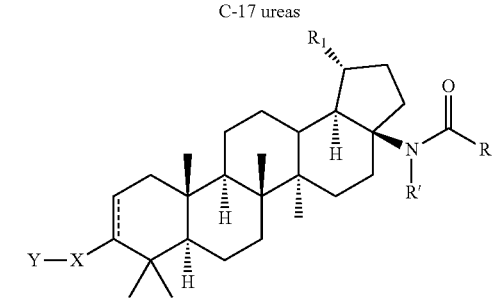

C-17 amides

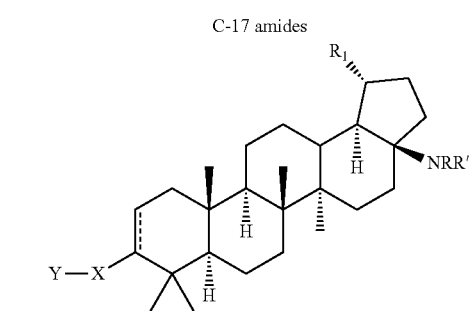

C-17 amines

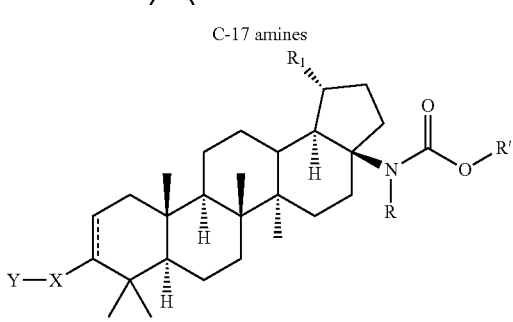

C-17 carbamates

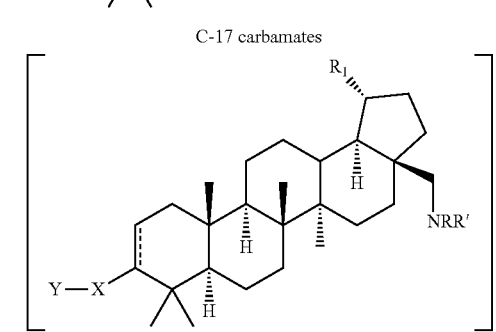

C-28 amines

EXAMPLES

The following examples illustrate typical syntheses of the compounds of Formula I as described generally above.

These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B, or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD (δ3.30), acetic-d4 (Acetic Acid d$_4$) ($\delta_H$ 11.6, 2.07), DMSO mix or DMSO-D6-CDCl$_3$ ($\delta_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LCMS Methods

LCMS Method 1:
Start % B=0
Final % B=100
Gradient Time=2 min
Flow Rate=1 mL/min
Wavelength=220 nm
Solvent A=10% MeOH-90% H$_2$O-0.1% TFA
Solvent B=90% MeOH-10% H$_2$O-0.1% TFA
Column=Phenomenex C18 2.0×30 mm 3 μm LCMS Method 2:
Start % B=20
Final % B=100
Gradient Time=3 min
Flow Rate=0.6 mL/min
Wavelength=220 nm
Solvent A=10% MeOH-90% H$_2$O-0.1% TFA
Solvent B=90% MeOH-10% H$_2$O-0.1% TFA
Column=Xbridge Phenyl 2.1×50 mm 2.5 μm LCMS Method 3:
Start % B=20
Final % B=100
Gradient Time=2 min
Flow Rate=0.6 mL/min
Wavelength=220 nm
Solvent A=10% MeOH-90% H$_2$O-0.1% TFA
Solvent B=90% MeOH-10% H$_2$O-0.1% TFA
Column=Xbridge Phenyl 2.1×50 mm 2.5 μm LCMS Method 4:
Start % B=0
Final % B=100
Gradient Time=4 min
Flow Rate=0.8 mL/min
Wavelength=220 nm
Solvent A=10% MeOH-90% H$_2$O-0.1% TFA
Solvent B=90% MeOH-10% H$_2$O-0.1% TFA
Column=Phenomenex C18 2.0×50 mm 3 μm LCMS Method 5:
Start % B=20
Final % B=100
Gradient Time=3 min
Flow Rate=0.8 mL/min
Wavelength=220 nm
Solvent A=10% MeOH-90% H$_2$O-0.1% TFA
Solvent B=90% MeOH-10% H$_2$O-0.1% TFA
Column=Phenomenex C18 2.0×50 mm 3 μm LCMS Method 6:
Start % B=20
Final % B=100
Gradient Time=2 min
Flow Rate=0.8 mL/min
Wavelength=220 nm
Solvent A=10% MeOH-90% H$_2$O-0.1% TFA
Solvent B=90% MeOH-10% H$_2$O-0.1% TFA
Column=Phenomenex C18 2.0×50 mm 3 μm LCMS Method 7:
Start % B=20
Final % B=100
Gradient Time=2 min
Flow Rate=0.5 mL/min
Wavelength=220 nm
Solvent A=10% MeOH-90% H$_2$O-0.1% TFA
Solvent B=90% MeOH-10% H$_2$O-0.1% TFA
Column=Xbridge Phenyl 2.1×50 mm 2.5 μm LCMS Method 8:
Start % B=20
Final % B=100
Gradient Time=2 min
Flow Rate=0.8 mL/min
Wavelength=220 nm
Solvent A=10% MeOH-90% H$_2$O-0.1% TFA
Solvent B=90% MeOH-10% H$_2$O-0.1% TFA
Column=Xbridge Phenyl 2.1×50 mm 2.5 μm LCMS Method 9:
Start % B=0
Final % B=100
Gradient Time=2 min
Flow Rate=1.0 mL/min
Wavelength=220 nm
Solvent A=5% MeCN-95% H$_2$O-10 mM Ammonium Acetate
Solvent B=95% MeCN-5% H$_2$O-10 mM Ammonium Acetate
Column=PHENOMENEX-LUNA C18 2.0×30 mm 3 μm LCMS Method 10:
Start % B=0
Final % B=100
Gradient Time=4 min
Flow Rate=0.6 mL/min
Wavelength=220 nm
Solvent A=10% MeOH-90% H$_2$O-0.1% TFA
Solvent B=90% MeOH-10% H$_2$O-0.1% TFA
Column=Xbridge Phenyl 2.1×50 mm 2.5 μm LCMS Method 11:
Start % B=0
Final % B=100
Gradient Time=4 min
Flow Rate=0.8 mL/min
Wavelength=220 nm
Solvent A=10% MeOH-90% H$_2$O-0.1% TFA
Solvent B=90% MeOH-10% H$_2$O-0.1% TFA
Column=Phenomenex C18 2.0×50 mm 3 μm LCMS Method 12:
Start % B=40
Final % B=60
Gradient Time=4 min Flow Rate=0.8 mL/min
Wavelength=254 nm
Solvent A=10% MeOH-90% H$_2$O-0.1% TFA
Solvent B=90% MeOH-10% H$_2$O-0.1% TFA
Column=Xbridge Phenyl 2.1×50 mm 2.5 μm
LCMS Method 13:
Start % B=35
Final % B=100
Gradient Time=4 min
Flow Rate=0.8 mL/min
Wavelength=220 nm
Solvent A=10% MeOH-90% H$_2$O-0.1% TFA
Solvent B=90% MeOH-10% H$_2$O-0.1% TFA
Column=Phenomenex C18 2.0×50 mm 3 μm
LCMS Method 14
Conditions: 0% B→100% B over 4 minute gradient; hold at 100% B for 1 min
Solvent A: 90% water, 10% methanol, 0.1% TFA
Solvent B: 10% water, 90% methanol, 0.1% TFA
Column: Phenomenex Luna C18, 3 mm, 2.0×50 mm
Flow Rate: 1 mL/min
Detector Wavelength: 220 nm
LCMS Method 15
Conditions: 0% B→100% B over 2 minute gradient; hold at 100% B for 1 min
Solvent A: 90% water, 10% methanol, 0.1% TFA
Solvent B: 10% water, 90% methanol, 0.1% TFA
Column: Phenomenex Luna C18, 2.0×50 mm, 3
Flow Rate: 1 mL/min
Detector Wavelength: 220 nm
LCMS Method 16
Start % B=2, Final % B=98 over 1.5 minute gradient; hold at 98% B for 0.5 min
Flow Rate=0.8 mL/min
Detector Wavelength=220 nm
Solvent A=100% water, 0.05% TFA
Solvent B=100% acetonitrile, 0.05% TFA
Column=Waters Aquity UPLC BEH C18 2.1×50 mm 1.7 μm
Oven temp=40° C.
LCMS Method 17
Start % B=2, Final % B=98 over 3 minute gradient; hold at 98% B for 1 min
Flow Rate=0.8 mL/min
Detector Wavelength=220 nm
Solvent A=100% water, 0.05% TFA
Solvent B=100% acetonitrile, 0.05% TFA
Column=Waters Aquity UPLC BEH C18, 2.1×50 mm, 1.7 μm
Oven temp=40° C.
LCMS Method 18
Start % B=0, Final % B=100 over 4 minute gradient; hold at 100% B for 1 min
Flow Rate=0.8 mL/min
Detector Wavelength=220 nm
Solvent A=95% water, 5% acetonitrile, 10 mM ammonium acetate
Solvent B=5% water, 95% acetonitrile, 10 mM ammonium acetate
Column=Phenomenex Luna C18, 50×2 mm, 3 μm
Oven temp=40° C.
LCMS Method 19
Start % B=2, Final % B=98 over 4 minute gradient; hold at 98% B for 1 min
Flow Rate=0.8 mL/min
Detector Wavelength=220 nm
Solvent A=100% water, 0.05% TFA
Solvent B=100% acetonitrile, 0.05% TFA
Column=Waters Aquity UPLC BEH C18, 2.1×50 mm, 1.7 μm
Oven temp=40° C.
LCMS Method 20
Start % B=2, Final % B=98 over 2 minute gradient; hold at 98% B for 1 min
Flow Rate=0.8 mL/min
Detector Wavelength=220 nm
Solvent A=100% water, 0.05% TFA
Solvent B=100% acetonitrile, 0.05% TFA
Column=Waters Aquity UPLC BEH C18, 2.1×50 mm, 1.7 μm
Oven temp=40° C.
LCMS Method 21
Start % B=0, Final % B=100 over 2 minute gradient; hold at 100% B for 3 min
Flow Rate=0.8 mL/min
Detector Wavelength=220 nm
Solvent A=95% water, 5% acetonitrile, 10 mM ammonium acetate
Solvent B=5% water, 95% acetonitrile, 10 mM ammonium acetate
Column=Phenomenex Luna C18, 50×2 mm, 3 μm
Oven temp=40° C.
Preparative HPLC Methods
Preparative HPLC Method 1
Conditions: 30% B→100% B over 20 minute gradient; hold at 100% B for 4 min
Solvent A: 5% acetonitrile, 95% water, 0.1% TFA
Solvent B: 95% acetonitrile, 5% water 0.1% TFA
Column: Waters Xbridge 30×100 mm, 5 μm
Flow Rate: 40 mL/min
Detector Wavelength: 220 nm
Preparative HPLC Method 2
Conditions: 10% B→100% B over 25 minute gradient
Solvent A: 5% acetonitrile, 95% water, 0.1% TFA
Solvent B: 95% acetonitrile, 5% water 0.1% TFA
Column: Waters Sunfire 30×150 mm, 5 μm
Flow Rate: 40 mL/min
Detector Wavelength: 220 nm
Preparative HPLC Method 3
Conditions: 10% B→100% B over 20 minute gradient; hold at 100% B for 5 min
Solvent A: 5% acetonitrile, 95% water, 0.1% TFA
Solvent B: 95% acetonitrile, 5% water 0.1% TFA
Column: Waters Sunfire 30×150 mm, 5 μm
Flow Rate: 40 mL/min
Detector Wavelength: 220 nm
Preparative HPLC Method 4
Conditions: 30% B→100% B over 20 minute gradient; hold at 100% B for 5 min
Solvent A: 5% acetonitrile, 95% water, 0.1% TFA
Solvent B: 95% acetonitrile, 5% water 0.1% TFA
Column: Waters Sunfire 30×150 mm, 5 μm
Flow Rate: 40 mL/min
Detector Wavelength: 220 nm
Preparative HPLC Method 5:
Start % B=20, Final % B=100 over 10 min gradient, hold at 100% B for 4 min
Flow Rate=50 ml/min
Wavelength=220
Solvent Pair=Water—acetonitrile—TFA
Solvent A=90% Water—10% acetonitrile—0.1% TFA
Solvent B=10% Water—90% acetonitrile—0.1% TFA
Column=Waters Sunfire C18, 5 μm, 30×150 mm Preparative HPLC Method 6
Conditions: 0% B→100% B over 20 minute gradient
Solvent A: 10% acetonitrile, 90% water, 0.1% TFA
Solvent B: 90% acetonitrile, 10% water 0.1% TFA
Column: Waters Sunfire C18, 30×150 mm, 5 µm
Flow Rate: 50 mL/min
Detector Wavelength: 220 nm
Preparative HPLC Method 7
Conditions: 30% B→100% B over 20 minute gradient
Solvent A: 10% acetonitrile, 90% water, 0.1% TFA
Solvent B: 90% acetonitrile, 10% water 0.1% TFA
Column: Waters Sunfire C18, 30×150 mm, 5 µm
Flow Rate: 50 mL/min
Detector Wavelength: 220 nm
Preparative HPLC Method 8
Conditions: 20% B→100% B over 15 minute gradient
Solvent A: 10% acetonitrile, 90% water, 0.1% TFA
Solvent B: 90% acetonitrile, 10% water 0.1% TFA
Column: Waters Sunfire C18, 30×150 mm, 5 µm
Flow Rate: 50 mL/min
Detector Wavelength: 220 nm
Preparative MPLC Methods
Preparative MPLC Method 1
Conditions: 30% B for 1 column volume, 30% B to 80% B gradient over 7 column volumes, 80% B to 100% B gradient over 0.5 column volumes, 100% B for 2 column volumes
Solvent A=5% acetonitrile, 95% water, 0.1% TFA
Solvent B=95% acetonitrile, 5% water 0.1% TFA
Column=Redi Sep Gold (150 g)
Flow Rate=60 mL/min
Detector Wavelength=220 nm
Preparative MPLC Method 2
Conditions: 30% B for 1 column volume, 30% B to 80% B gradient over 10 column volumes, 100% B for 2 column volumes
Solvent A=5% acetonitrile, 95% water, 0.1% TFA
Solvent B=95% acetonitrile, 5% water 0.1% TFA
Column=Redi Sep Gold (150 g)
Flow Rate=60 mL/min
Detector Wavelength=220 nm
Analytical HPLC Methods
Analytical HPLC Method 1
Conditions: 10% B→100% B over 15 min gradient; hold at 100% B for 10 min
Solvent A: 10% methanol, 90% water, 0.1% TFA
Solvent B: 90% methanol, 10% water, 0.1% TFA
Column: Waters Sunfire C18, 4.6×150 mm, 3.5 mm
Flow Rate: 1 mL/min
Detector Wavelength: 220 nm
Analytical HPLC Method 2
Conditions: 10% B→100% B over 15 min gradient; hold at 100% B for 10 min
Solvent A: 10% methanol, 90% water, 0.1% TFA
Solvent B: 90% methanol, 10% water, 0.1% TFA
Column: Waters Xbridge phenyl, 4.6×150 mm, 3.5 mm
Flow Rate: 1 mL/min
Detector Wavelength: 220 nm
Analytical HPLC Method 3
Conditions: 10% B→100% B over 15 min gradient; hold at 100% B for 10 min
Solvent A: 5% acetonitrile, 95% water, 0.1% TFA
Solvent B: 95% acetonitrile, 5% water, 0.1% TFA
Column: Waters Sunfire C18, 3.0×150 mm, 3.5 um
Flow Rate: 0.5 mL/min
Detector Wavelength: 220 nm Analytical HPLC Method 4
Conditions: 10% B→100% B over 15 min gradient; hold at 100% B for 10 min
Solvent A: 5% acetonitrile, 95% water, 0.1% TFA
Solvent B: 95% acetonitrile, 5% water, 0.1% TFA
Column: Waters Xbridge phenyl, 3.0×150 mm, 3.5 um
Flow Rate: 0.5 mL/min
Detector Wavelength: 220 nm
Preparation of Intermediates

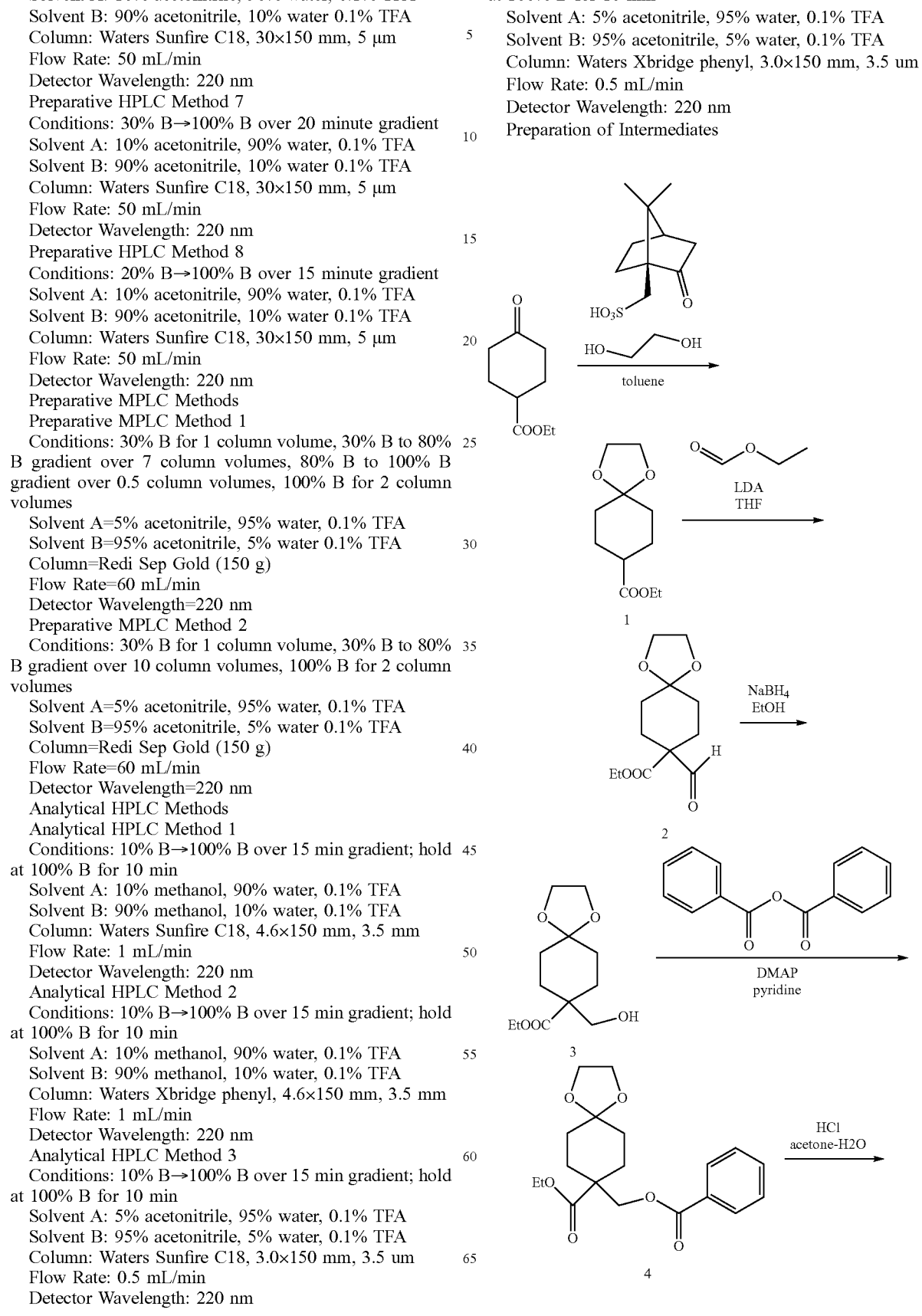

-continued

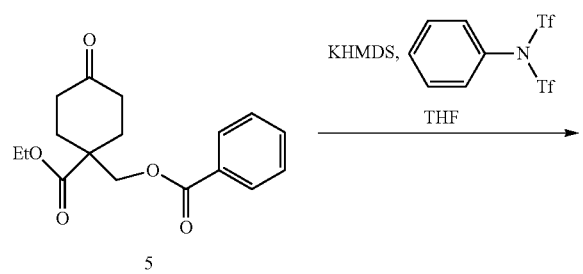

5

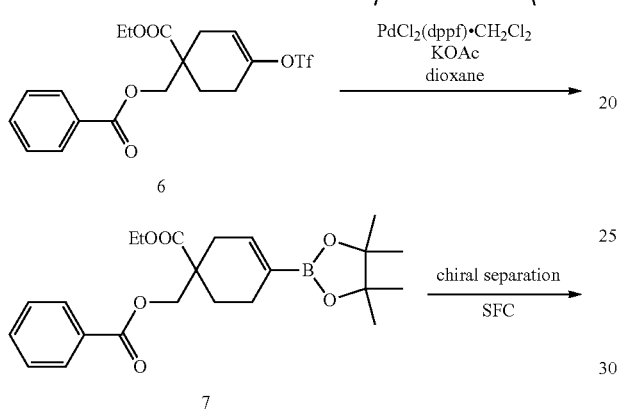

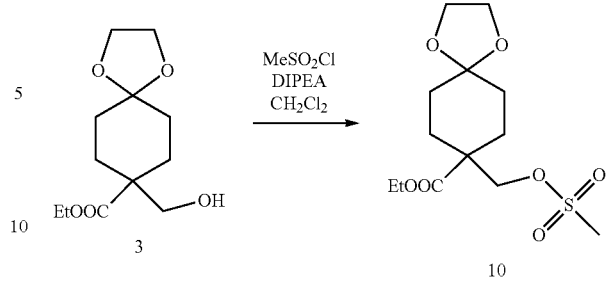

-continued

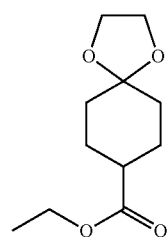

Intermediate 1. Preparation of ethyl 1,4-dioxaspiro[4.5]decane-8-carboxylate

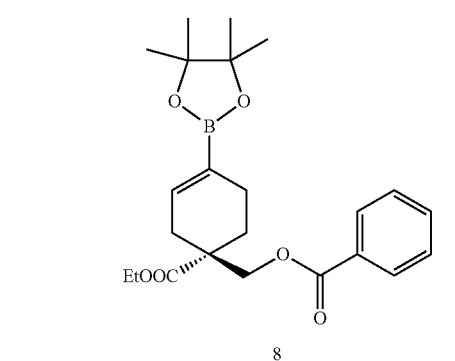

A mixture of ethyl 4-oxocyclohexanecarboxylate (12.7 g, 75 mmol), ethylene glycol (21 ml, 373 mmol), (1S)-(+)-10-camphorsulfonic acid (0.175 g, 0.75 mmol) and anhydrous toluene (300 mL) was refluxed with a Dean-Stark water trap for 8 hours. The mixture was quenched with 100 mL saturated sodium bicarbonate solution and was vigorously stirred. The separated organic phase was washed with water (100 mL), dried over $Na_2SO_4$ and concentrated in vacuo. The crude product was purified by silica gel column eluted with 0-15% ethyl acetate/hexanes to give the desired product as an oil (15.9 g, 99%). $^1$H NMR (400 MHz, CHLOROFORM-d) δ 4.13 (q, J=7.2 Hz, 2H), 3.95 (s, 4H), 2.34 (tt, J=10.4, 4.0 Hz, 1H), 1.98-1.90 (m, 2H), 1.87-1.75 (m, 4H), 1.61-1.51 (m, 2H), 1.25 (t, J=7.2 Hz, 3H).

Intermediate 2. Preparation of ethyl 8-formyl-1,4-dioxaspiro[4.5]decane-8-carboxylate

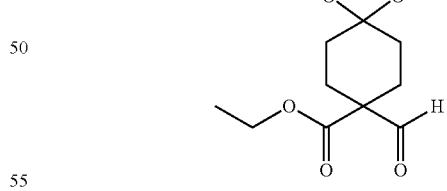

To a solution of ethyl 1,4-dioxaspiro[4.5]decane-8-carboxylate (21 g, 98 mmol) in THF (150 mL) at −78° C. was added 2M LDA (64 mL, 127 mmol) dropwise. The resulting solution was stirred at −78° C. for 1 h, then in an ice bath for 1.5 h. The reaction mixture was chilled back to −78° C. and molecular sieves were added. Dried ethyl formate (12 mL, 147 mmol) was added dropwise slowly over 1 h. The reaction mixture was stirred at −78° C. for 1 h. The cold bath was removed and the reaction was quenched with a saturated solution of $NH_4Cl$ in 0.5 N HCl (250 mL) dropwise. The mixture was extracted with EtOAc (3×200 mL). The combined organic layer was washed with saturated solution of NH$_4$Cl in 0.5 N HCl (200 mL), brine (200 mL), dried over Na$_2$SO$_4$, and concentrated in vacuo. The crude product was purified by silica gel column eluted with 0-20% ethyl acetate/hexanes to give the desired product as an oil (9.3 g, 39%). $^1$H NMR (400 MHz, CHLOROFORM-d) δ 9.54 (s, 1H), 4.21 (q, J=7.1 Hz, 2H), 3.98-3.90 (m, 4H), 2.25-2.16 (m, 2H), 2.10-2.01 (m, 2H), 1.74-1.60 (m, 4H), 1.27 (t, J=7.2 Hz, 3H).

Intermediate 3. Preparation of ethyl 8-(hydroxymethyl)-1,4-dioxaspiro[4.5]decane-8-carboxylate

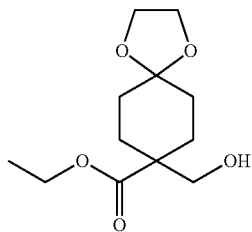 [SMILES: CCOC(=O)C1(CO)CCC2(CC1)OCCO2]

To a solution of the ethyl 8-formyl-1,4-dioxaspiro[4.5]decane-8-carboxylate (1.0 g, 4.13 mmol) in EtOH (10 mL) at 0° C. was added NaBH$_4$ (0.187 g, 4.95 mmol). The mixture was stirred at 0° C. for 1 h. The reaction was quenched with saturated NH$_4$Cl (10 mL) and was then diluted with H$_2$O until dissolved. The mixture was extracted with EtOAc (3×50 mL), washed with brine (50 mL), dried over Na$_2$SO$_4$ and concentrated in vacuo. The crude product was purified by silica gel column eluted with 0-25% ethyl acetate/hexanes to give the desired product as an oil (0.86 g, 85%). $^1$H NMR (400 MHz, CHLOROFORM-d) δ 4.21 (q, J=7.1 Hz, 2H), 3.99-3.91 (m, 4H), 3.65 (d, J=6.5 Hz, 2H), 2.19-2.11 (m, 2H), 1.68 (dd, J=6.8, 5.5 Hz, 4H), 1.63-1.57 (m, 2H), 1.29 (t, J=7.0 Hz, 3H).

Intermediate 4. Preparation of ethyl 8-((benzoyloxy)methyl)-1,4-dioxaspiro[4.5]decane-8-carboxylate

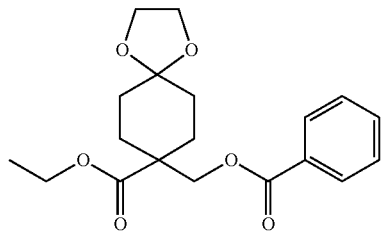 [SMILES: CCOC(=O)C1(COC(=O)c2ccccc2)CCC2(CC1)OCCO2]

To a solution of ethyl 8-(hydroxymethyl)-1,4-dioxaspiro[4.5]decane-8-carboxylate (3.0 g, 12.3 mmol) in pyridine (60 mL) was added DMAP (0.3 g, 2.5 mmol). The mixture was heated to 50° C. and benzoic anhydride (3.1 g, 13.5 mmol) was added. The reaction mixture was stirred at 50° C. for 3 h. The reaction mixture was concentrated in vacuo. The residue was dissolved in EtOAc (50 mL), washed with brine (50 mL), dried over Na$_2$SO$_4$, and concentrated in vacuo. The crude product was purified by silica gel column eluted with 0-20% hexane/EtOAc to give the desired product as an oil (4.3 g, 100%). $^1$H NMR (400 MHz, CHLOROFORM-d) δ 8.01 (dd, J=8.4, 1.4 Hz, 2H), 7.60-7.54 (m, 1H), 7.47-7.40 (m, 2H), 4.35 (s, 2H), 4.20 (q, J=7.2 Hz, 2H), 3.99-3.92 (m, 4H), 2.36-2.23 (m, 2H), 1.76-1.63 (m, 6H), 1.24 (t, J=7.2 Hz, 3H).

Intermediate 5. Preparation of (1-(ethoxycarbonyl)-4-oxocyclohexyl)methyl benzoate

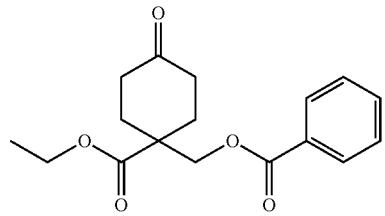 [SMILES: CCOC(=O)C1(COC(=O)c2ccccc2)CCC(=O)CC1]

A solution of ethyl 8-((benzoyloxy)methyl)-1,4-dioxaspiro[4.5]decane-8-carboxylate (4.3 g, 12.4 mmol) in acetone (120 mL) and 0.5N HCl (24.8 mL, 12.4 mmol) was stirred at 50° C. overnight. The reaction mixture was neutralized with saturated aqueous Na$_2$CO$_3$ and partially concentrated in vacuo to remove acetone. The residue was diluted with H$_2$O (50 mL) and extracted with EtOAc (3×100 mL). The combined organic layers were washed brine (50 mL), dried over Na$_2$SO$_4$, and concentrated in vacuo. The crude product was purified by silica gel column eluted with 0-30% hexane/EtOAc to give the desired product as an oil (3.8 g, 100%). $^1$H NMR (400 MHz, CHLOROFORM-d) δ 8.01 (d, J=7.6 Hz, 2H), 7.62-7.55 (m, 1H), 7.49-7.42 (m, 2H), 4.45 (s, 2H), 4.28 (q, J=7.1 Hz, 2H), 2.61-2.48 (m, 4H), 2.47-2.37 (m, 2H), 1.91-1.79 (m, 2H), 1.28 (t, J=7.1 Hz, 3H).

Intermediate 6. Preparation of (1-(ethoxycarbonyl)-4-(((trifluoromethyl)sulfonyl)oxy)cyclohex-3-en-1-yl)methyl benzoate

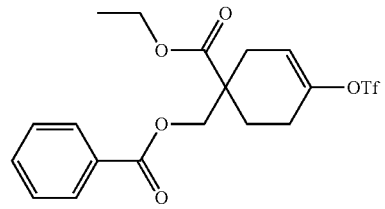 [SMILES: CCOC(=O)C1(COC(=O)c2ccccc2)CC=C(OS(=O)(=O)C(F)(F)F)CC1]

A solution of (1-(ethoxycarbonyl)-4-oxocyclohexyl)methyl benzoate (3.8 g, 12.4 mmol) and 1,1,1-trifluoro-N-phenyl-N-((trifluoromethyl)sulfonyl)methanesulfonamide (4.95 g, 13.8 mmol) in THF (120 mL) was cooled to −78° C. To this solution was added KHMDS (1 M in THF) (16.4 mL, 16.4 mmol). The resulting solution was stirred at −78° C. for 2 h. The reaction was quenched with saturated aqueous NH$_4$Cl (50 mL), extracted with EtOAc (3×100 mL). The combined organic layers were washed with brine (50 mL), dried over Na$_2$SO$_4$, and concentrated in vacuo. The crude product was purified by silica gel column eluted with 0-20% ethyl acetate/hexanes to give the desired product (3.8 g, 69%) as an oil. $^1$H NMR (400 MHz, CHLOROFORM-d) δ 8.00 (dd, J=8.4, 1.1 Hz, 2H), 7.62-7.56 (m, 1H), 7.49-7.44 (m, 2H), 5.80 (td, J=3.2, 1.6 Hz, 1H), 4.46-4.40 (m, 2H), 4.21 (qd, J=7.1, 2.1 Hz, 2H), 2.93-2.83 (m, 1H), 2.59-2.27 (m, 4H), 1.99-1.90 (m, 1H), 1.25 (t, J=7.2 Hz, 3H).

Intermediate 7. (1-(ethoxycarbonyl)-4-(4,4,5,5-tetramethyl-1,3,2-dioxaborolan-2-yl)cyclohex-3-en-1-yl)methyl benzoate

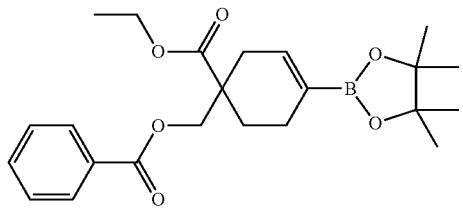 [SMILES: CCOC(=O)C1(COC(=O)c2ccccc2)CC=C(B2OC(C)(C)C(C)(C)O2)CC1]

A mixture of (1-(ethoxycarbonyl)-4-(((trifluoromethyl)sulfonypoxy)cyclohex-3-en-1-yl)methyl benzoate (3.8 g, 8.7 mmol), bis(pinacolato)diboron (2.4 g, 9.5 mmol), potassium acetate (2.6 g, 26.0 mmol) and PdCl$_2$(dppf)-CH$_2$Cl$_2$ adduct (0.2 g, 0.260 mmol) in 1,4-dioxane (80 mL) was cooled to −78° C. Three cycles of evacuating the flask and purging with nitrogen were performed. The mixture was stirred at 70° C. for 3 h. The mixture was diluted with water (50 mL) and extracted with ethyl acetate (3×100 mL). The combined organic layers were washed with brine (50 mL), dried over Na$_2$SO$_4$, and concentrated in vacuo. The crude product was purified by silica gel column eluted with 0-20% ethyl acetate/hexanes to give the desired product (5.8 g, 67%) as an oil. $^1$H NMR (400 MHz, CHLOROFORM-d) δ 8.00 (dd, J=8.4, 1.4 Hz, 2H), 7.59-7.54 (m, 1H), 7.46-7.41 (m, 2H), 6.54 (dt, J=3.6, 1.9 Hz, 1H), 4.44 (d, J=10.8 Hz, 1H), 4.39 (d, J=10.8 Hz, 2H), 4.17 (q, J=7.2 Hz, 2H), 2.77-2.68 (m, 1H), 2.29-2.20 (m, 3H), 2.05-1.97 (m, 1H), 1.92-1.83 (m, 1H), 1.27 (s, 12H), 1.22 (t, J=7.2 Hz, 3H).

Intermediates 8 and 9. Chiral Separation of (S)-(1-(ethoxycarbonyl)-4-(4,4,5,5-tetramethyl-1,3,2-dioxaborolan-2-yl)cyclohex-3-en-1-yl)methyl benzoate and (R)-(1-(ethoxycarbonyl)-4-(4,4,5,5-tetramethyl-1,3,2-dioxaborolan-2-yl)cyclohex-3-en-1-yl)methyl benzoate

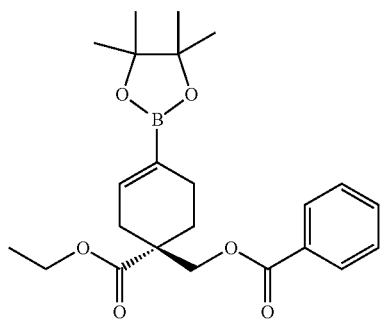

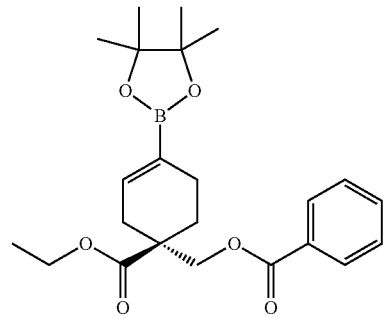

The racemic mixture was separated by supercritical fluid chromatography (SFC) to give (S)-(1-(ethoxycarbonyl)-4-(4,4,5,5-tetramethyl-1,3,2-dioxaborolan-2-yl)cyclohex-3-en-1-yl)methyl benzoate and (R)-(1-(ethoxycarbonyl)-4-(4,4,5,5-tetramethyl-1,3,2-dioxaborolan-2-yl)cyclohex-3-en-1-yl)methyl benzoate.

SFC Experimental Details:

| | |
|---|---|
| Column: | ChiralCel OJ-H, 30 × 250 mm, 5 μm |
| Mobile Phase: | 5% MeOH/95% CO2 |
| Pressure: | 100 bar |
| Temperature: | 40° C. |
| Flow Rate: | 70 mL/min |
| UV: | 225 nm |
| Injection: | 0.50 mL (~100 mg/mL in IPA:ACN:MeOH, 2:2:1) |
| Fraction Collection: | Slope & Level (w/6 mL/min MeOH make-up): |
| | Peak 1 window: 3.00'-4.50' |
| | Peak 2 window: 3.80'-7.00' |

Intermediate 10. Preparation of ethyl 8-(((methylsulfonyl)oxy)methyl)-1,4-dioxaspiro[4.5]decane-8-carboxylate

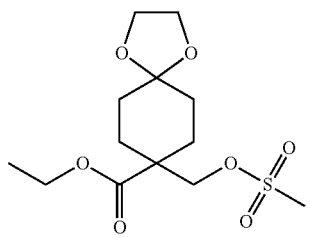 [SMILES: CCOC(=O)C1(COS(C)(=O)=O)CCC2(CC1)OCCO2]

To vacuum dried ethyl 8-(hydroxymethyl)-1,4-dioxaspiro[4.5]decane-8-carboxylate (280 mg, 1.146 mmol) in DCM (2 mL) was added N,N-diisopropylethylamine (0.299 mL, 1.719 mmol) under nitrogen. The clear solution was chilled in an ice bath until cold. To this was added, dropwise, neat methanesulfonyl chloride (0.106 mL, 1.375 mmol) and the resulting solution was stirred in the ice bath and allowed to reach RT overnight. The crude reaction mixture was purified on silica gel column eluted with 50% ethyl acetate/hexanes to give the desired product (304 mg, 82%). $^1$H NMR (400 MHz, CHLOROFORM-d) δ 4.26-4.17 (m, 4H), 3.97-3.93 (m, 4H), 3.00 (s, 3H), 2.24-2.15 (m, 2H), 1.73-1.61 (m, 6H), 1.29 (t, J=7.2 Hz, 3H).

General Procedure A: Preparation of C-3 α-substituted cyclohexenecarboxylic acid derivatives.
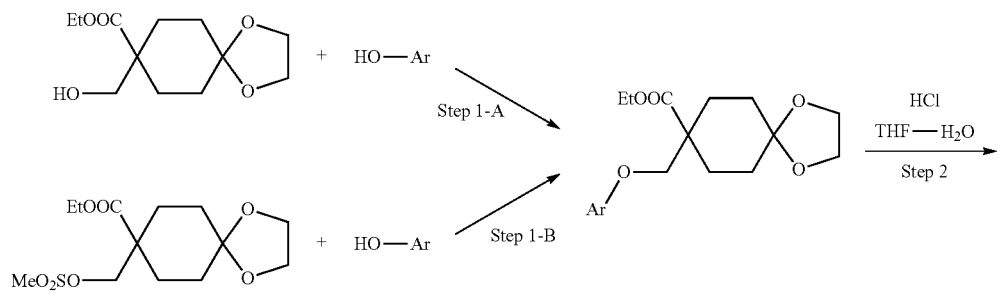
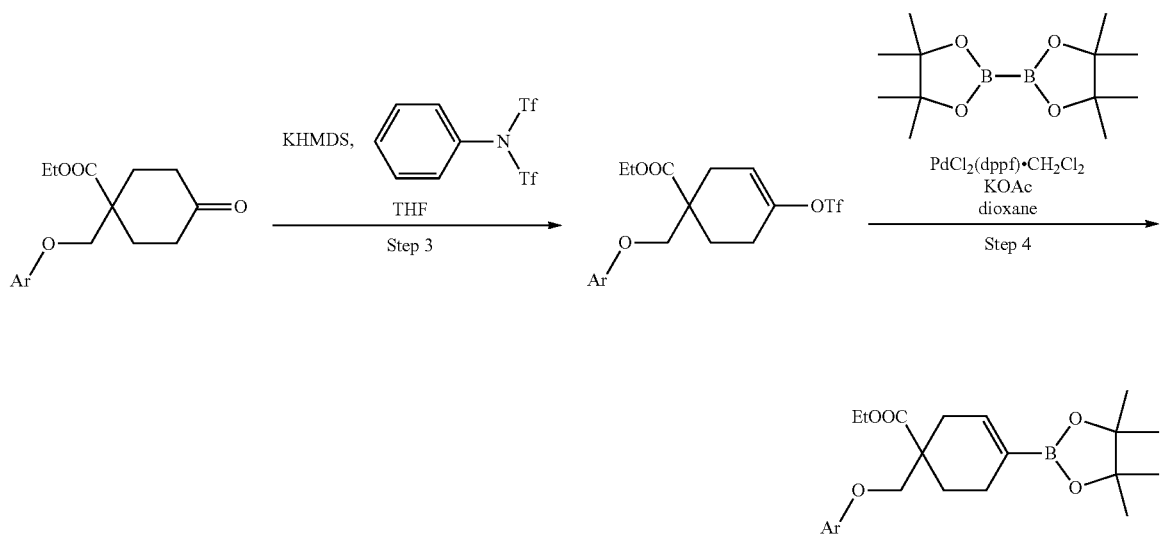
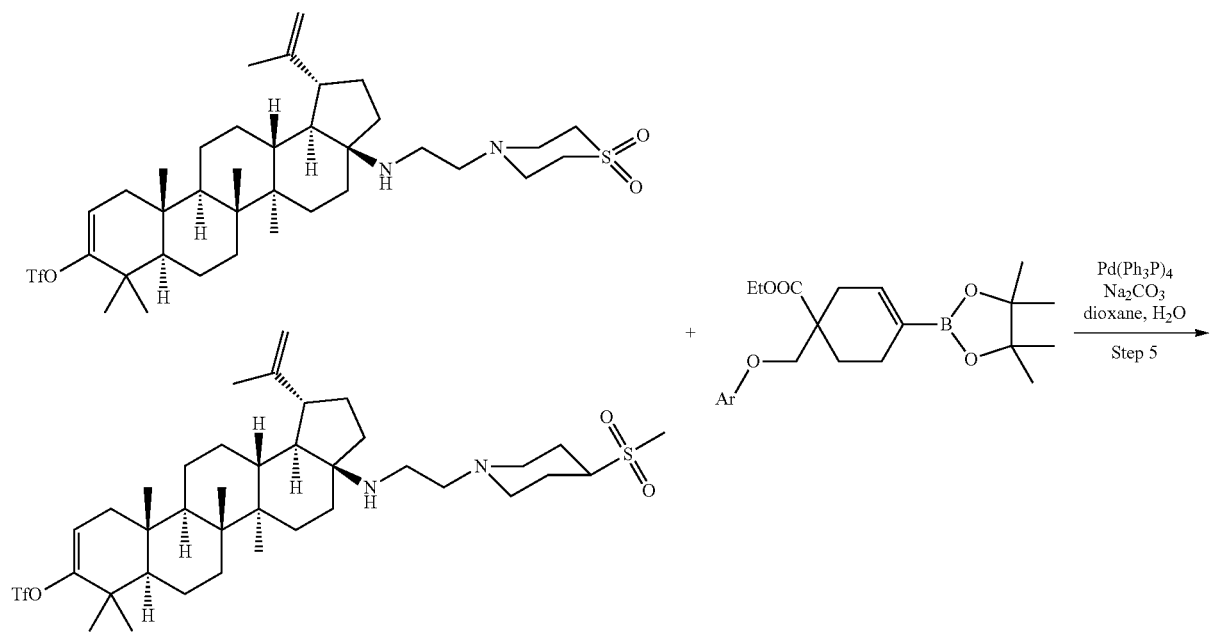

-continued
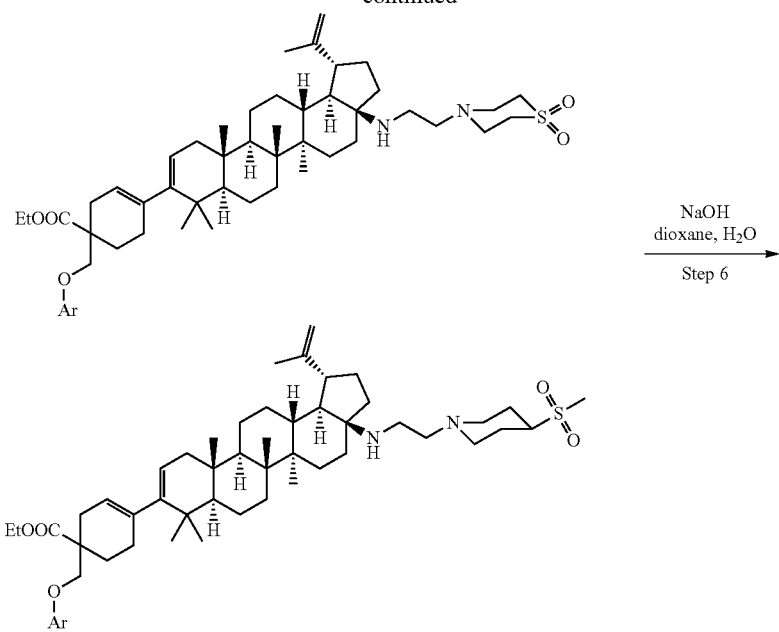
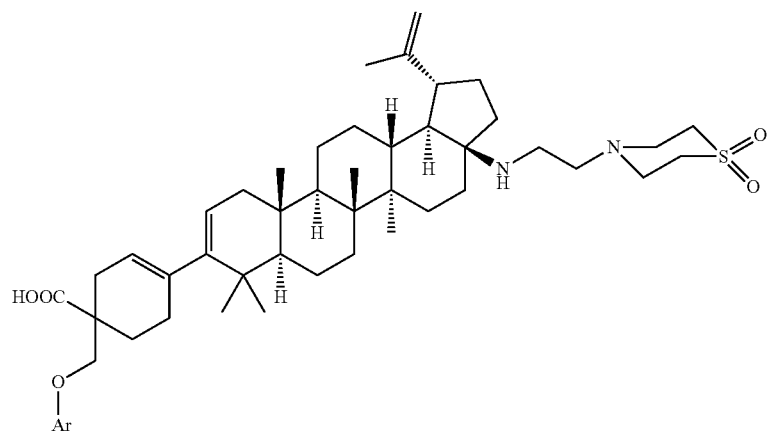
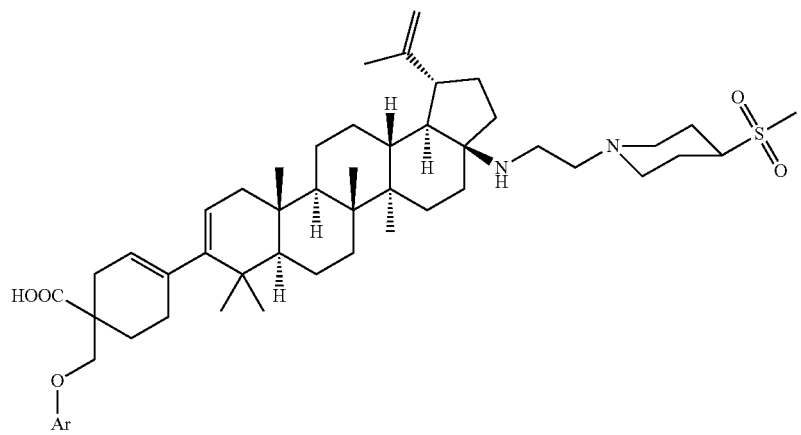

Step 1: Preparation of ether.

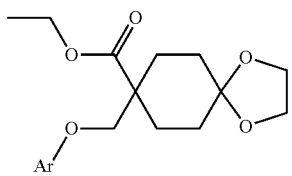

Step 1-A: To a solution of ethyl 8-(hydroxymethyl)-1,4-dioxaspiro[4.5]decane-8-carboxylate (intermediate 3) (1 eq), reactant Ar—OH (1 eq) and triphenylphosphine (1.2 eq) in THF was added diisopropyl diazene-1,2-dicarboxylate (1.2 eq) dropwise under nitrogen. The resulting solution was stirred at RT for 1 h, then at 50° C. for 3 days. The reaction mixture was diluted with saturated $NH_4Cl$, extracted with EtOAc, washed with brine, dried over $Na_2SO_4$, and concentrated in vacuo. The crude product was purified by silica gel column eluted with ethyl acetate/hexanes to give the desired product.

Step 1-B: A mixture of ethyl 8-(((methylsulfonyl)oxy)methyl)-1,4-dioxaspiro[4.5]decane-8-carboxylate (1 eq), cesium carbonate (2.15 eq) and Ar—OH (3.5 eq) in acetonitrile was stirred at 85° C. over 48 hours. The inorganic salts were removed by filtration, and the filtrate was washed with water, extracted with ethyl acetate. The combine organic phase was concentrated in vacuo. The crude product was purified by silica gel column eluted with Ethyl acetate/hexanes to give the desired product.

Step 2: Preparation of Ketone.

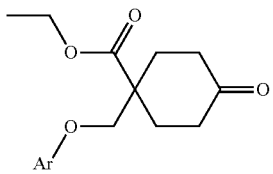

A solution of the product from step 1 (1 eq) and 0.5 N HCl (1 eq) in acetone was stirred at 50° C. for 1-2 days. The reaction mixture was neutralized with saturated aqueous. $Na_2CO_3$ and partially concentrated in vacuo to remove acetone. The residue was diluted with $H_2O$, extracted with EtOAc, washed with brine, dried over $Na_2SO_4$, and concentrated in vacuo. The crude product was purified by silica gel column eluted with ethyl acetate/hexanes to give the desired ketone.

Step 3: Preparation of triflate.

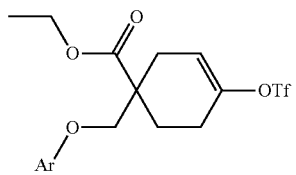

To a solution of ketone from step 2 (1 eq) and 1,1,1-trifluoro-N-phenyl-N-((trifluoromethyl)sulfonyl)-methanesulfonamide (1.1 eq) in THF at −78° C. was added KHMDS (1 M in THF) (1.3 eq). The resulting yellow to orange solution was stirred at −78° C. for 2 h. The reaction was quenched with saturated aqueous $NH_4Cl$. The mixture was extracted with EtOAc, washed with brine, dried over $Na_2SO_4$, and concentrated in vacuo. The crude product was purified by silica gel column eluted with ethyl acetate/hexanes to give the desired triflate.

Step 4: Preparation of boronate.

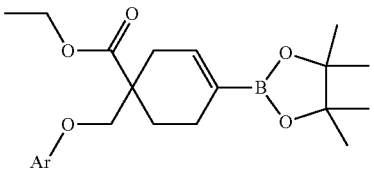

In a pressure vessel, a mixture of triflate from step 3 (1 eq), bis(pinacolato)diboron (1.1 eq), KOAc (2.5 eq) and $PdCl_2(dppf)$-$CH_2Cl_2$ adduct (0.03 eq) in 1,4-dioxane was flushed with nitrogen, sealed and heated at 70° C. for 2 h. The mixture was diluted with water and extracted with EtOAc. The combined organic layers were washed with brine, dried over $Na_2SO_4$, and concentrated in vacuo. The crude product was purified by silica gel column eluted with ethyl acetate/hexanes to give the desired boronate.

Step 5: Preparation of C-3 α-substituted cyclohexenecarboxylic ester.

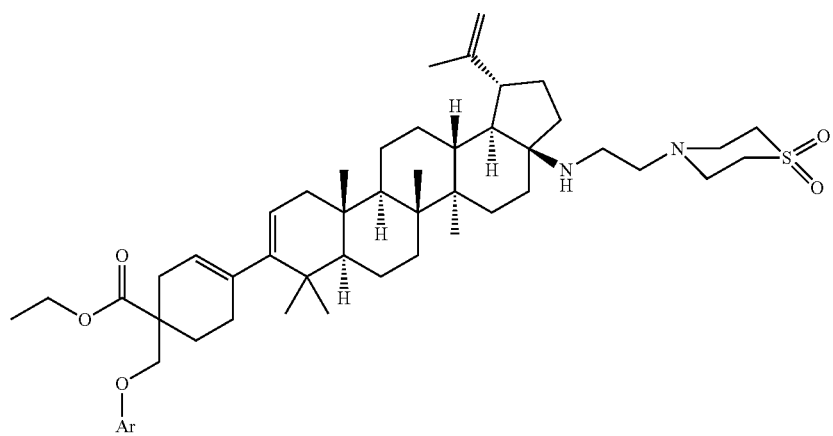

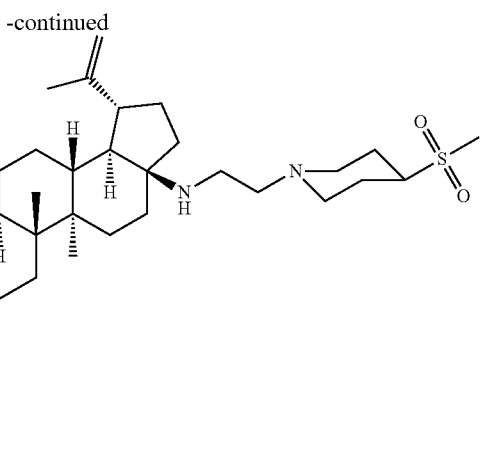

A mixture of C3-triflate (1 eq), boronate from step 4 (1 eq), Na₂CO₃ H₂O (3 eq) and Pd(Ph₃P)₄ (0.06 eq) in dioxane and H₂O (4:1), was flushed with nitrogen, sealed and heated at 70° C. for 2 h. The reaction mixture was concentrated in vacuo, and the residue was partitioned between EtOAc and H₂O. The separated aqueous layer was extracted with EtOAc. The combined organic layers were washed with brine dried over Na₂SO₄, and concentrated in vacuo. The crude product was purified by silica gel column eluted with ethyl acetate/hexanes to give the desired C-3 α-substituted cyclohexenecarboxylic ester.

Step 6: Preparation of carboxylic acid.

A solution of ester from step 5 in 1,4-dioxane, MeOH and 1N NaOH (2:1:1) was stirred at 60-70° C. for 1-2 h. The reaction mixture was purified by reverse phase preparative HPLC to give the final product.

Example 1

Preparation of 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylic acid.

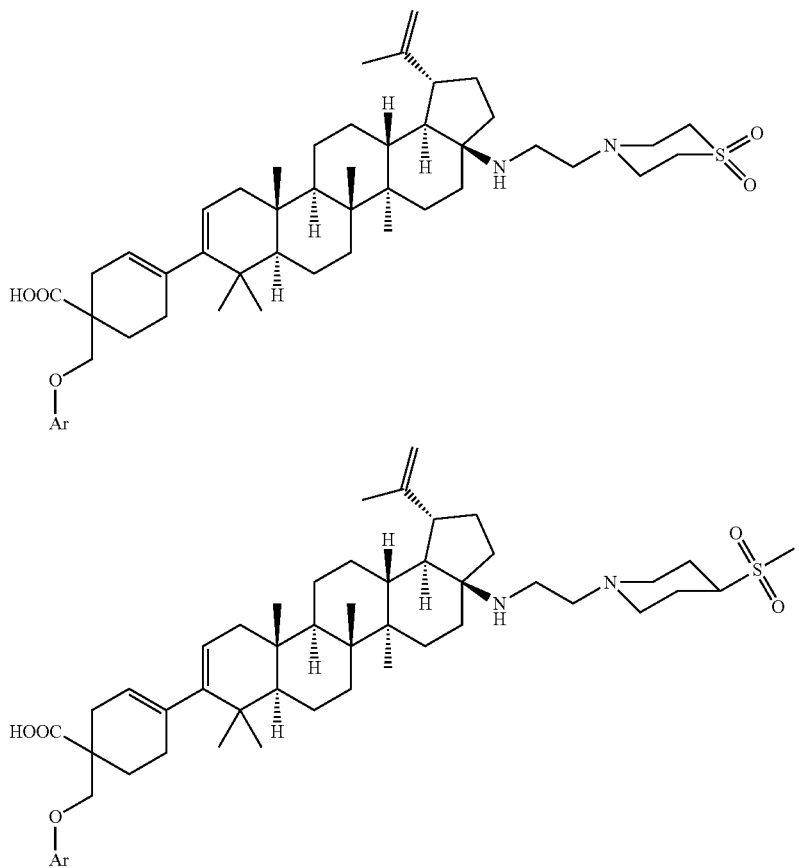

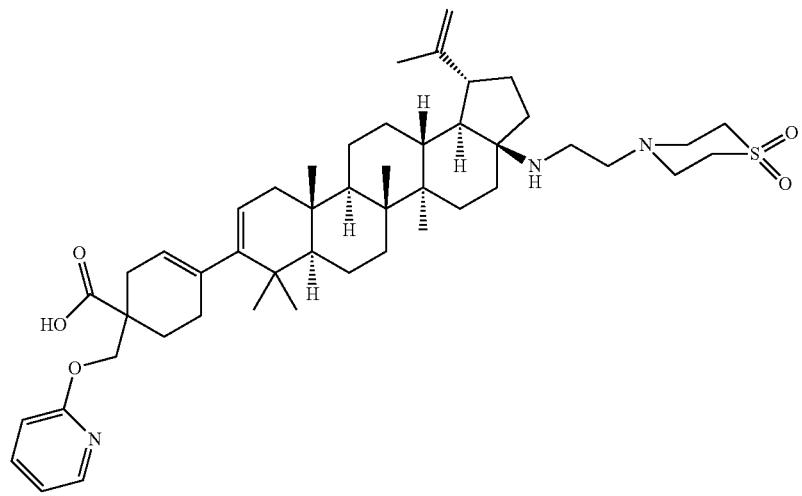

Step 1. Preparation of ethyl 8-((pyridin-2-yloxy)methyl)-1,4-dioxaspiro[4.5]decane-8-carboxylate.

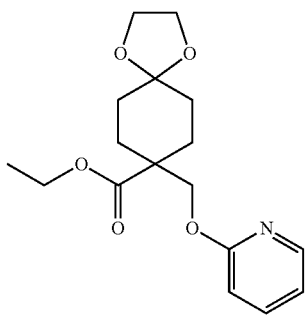 [SMILES: CCOC(=O)C1(COc2ccccn2)CCC2(CC1)OCCO2]

The title compound was prepared in 83% yield as an oil, following the procedure described in general procedure A step 1-A, using pyridin-2-ol as reactant. $^1$H NMR (500 MHz, CHLOROFORM-d) δ 8.14 (ddd, J=5.0, 2.0, 0.8 Hz, 1H), 7.59-7.53 (m, 1H), 6.87 (ddd, J=7.1, 5.1, 0.9 Hz, 1H), 6.73 (dt, J=8.4, 0.8 Hz, 1H), 4.38 (s, 2H), 4.17 (q, J=7.2 Hz, 2H), 4.01-3.93 (m, 4H), 2.35-2.24 (m, 2H), 1.79-1.67 (m, 6H), 1.23 (t, J=7.1 Hz, 3H). LC/MS m/z 322.10 (M+H)$^+$, 1.93 min (LCMS Method 1).

Step 2. Preparation of ethyl 4-oxo-1-((pyridin-2-yloxy)methyl)cyclohexane-1-carboxylate.

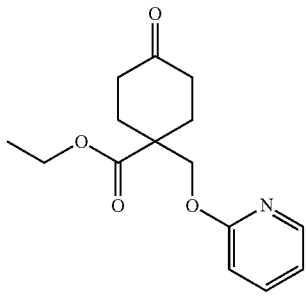 [SMILES: CCOC(=O)C1(COc2ccccn2)CCC(=O)CC1]

The title compound was prepared in 99% yield as an oil, following the procedure described in general procedure A step 2, using ethyl 8-((pyridin-2-yloxy)methyl)-1,4-dioxaspiro[4.5]decane-8-carboxylate as reactant. $^1$H NMR (400 MHz, CHLOROFORM-d) δ 8.14 (ddd, J=5.1, 1.9, 0.8 Hz, 1H), 7.61-7.55 (m, 1H), 6.90 (ddd, J=7.1, 5.1, 0.9 Hz, 1H), 6.74 (dt, J=8.3, 0.8 Hz, 1H), 4.45 (s, 2H), 4.24 (q, J=7.0 Hz, 2H), 2.59-2.48 (m, 4H), 2.46-2.37 (m, 2H), 1.94-1.83 (m, 2H), 1.26 (t, J=7.2 Hz, 3H). LC/MS m/z 278.05 (M+H)$^+$, 1.74 min (LCMS Method 1).

Step 3. Preparation of ethyl 1-((pyridin-2-yloxy)methyl)-4-(((trifluoromethyl)sulfonyl)oxy)cyclohex-3-ene-1-carboxylate.

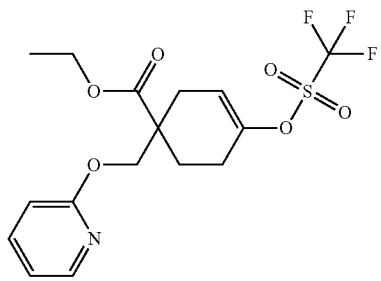 [SMILES: CCOC(=O)C1(COc2ccccn2)CC=C(OS(=O)(=O)C(F)(F)F)CC1]

The title compound was prepared in 110% yield (containing PhNHTf) as an oil, following the procedure described in general procedure A step 3, using ethyl 4-oxo-1-((pyridin-2-yloxy)methyl)cyclohexane-1-carboxylate as reactant. $^1$H NMR (400 MHz, CHLOROFORM-d) δ 8.14 (ddd, J=5.0, 2.0, 0.8 Hz, 1H), 7.62-7.55 (m, 1H), 6.90 (ddd, J=7.1, 5.1, 0.9 Hz, 1H), 6.73 (dt, J=8.3, 0.8 Hz, 1H), 5.80-5.76 (m 1H), 4.45 (d, J=10.3 Hz, 1H), 4.39 (d, J=10.3 Hz, 1H), 4.18 (qd, J=7.1, 1.3 Hz, 2H), 2.88-2.80 (m, 1H), 2.56-2.25 (m, 4H), 2.02-1.93 (m, 1H), 1.22 (t, J=7.2 Hz, 3H). $^{19}$F NMR (376 MHz, CHLOROFORM-d) δ -73.87 (s, 3 F)./LC/MS m/z 410.00 (M+H)$^+$, 2.24 min (LCMS Method 1).

Step 4. Preparation of ethyl 1-((pyridin-2-yloxy)methyl)-4-(4,4,5,5-tetramethyl-1,3,2-dioxaborolan-2-yl)cyclohex-3-ene-1-carboxylate.

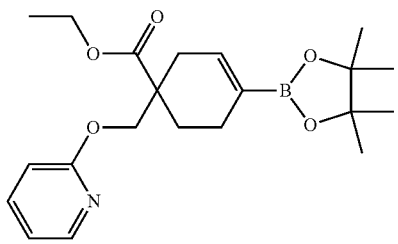 [SMILES: CCOC(=O)C1(COc2ccccn2)CC=C(B2OC(C)(C)C(C)(C)O2)CC1]

The title compound was prepared in 75% yield as an oil, following the procedure described in general procedure A step 4, using ethyl 1-((pyridin-2-yloxy)methyl)-4-(((trifluoromethyl)sulfonyl)oxy)cyclohex-3-ene-1-carboxylate as reactant. $^1$H NMR (400 MHz, CHLOROFORM-d) δ 8.13 (ddd, J=5.0, 2.0, 0.8 Hz, 1H), 7.58-7.51 (m, 1H), 6.86 (ddd, J=7.0, 5.1, 0.9 Hz, 1H), 6.71 (dt, J=8.4, 0.8 Hz, 1H), 6.57-6.53 (m, 1H), 4.42 (d, J=10.0 Hz, 1H), 4.33 (d, J=10.0 Hz, 1H), 4.14 (qd, J=6.7, 1.4 Hz, 2H), 2.73 (dq, J=18.8, 2.8 Hz, 1H), 2.31-2.18 (m, 3H), 2.03-1.95 (m, 1H), 1.91-1.83 (m, 1H), 1.27 (s, 6H), 1.26 (s, 6H), 1.19 (t, J=7.0 Hz, 3H). LC/MS m/z 388.20 (M+H)$^-$, 2.22 min (LCMS Method 1).

Step 5. Preparation of ethyl 4-((1R,3aS,5aR,5bR,7aR,11aS,11bR,13aR,13bR)-3a--((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylate.

The title compound was prepared in 71% yield as a solid, following the procedure described in general procedure A step 5, using ethyl 1-((pyridin-2-yloxy)methyl)-4-(4,4,5,5-tetramethyl-1,3,2-dioxaborolan-2-yl)cyclohex-3-ene-1-carboxylate as reactant. $^1$H NMR (400 MHz, CHLOROFORM-d) δ 8.13 (dd, J=5.1, 1.4 Hz, 1H), 7.55 (ddd, J=8.6, 7.0, 2.0 Hz, 1H), 6.85 (ddd, J=7.0, 5.3, 0.8 Hz, 1H), 6.72 (d, J=8.3 Hz, 1H), 5.35 (br. s, 1H), 5.18 (d, J=5.5 Hz, 1H), 4.71 (s, 1H), 4.59 (s, 1H), 4.47-4.37 (m, 2H), 4.14 ((qd, J=6.7, 1.4 Hz, 2H), 3.12-2.99 (m, 8H), 2.73-2.39 (m, 6H), 2.23-0.84 (m, 27H), 1.69 (s, 3H), 1.20 (t, J=7.2 Hz, 3H), 1.05 (s, 3H), 0.96-0.90 (m, 9H), 0.89 (s, 3H). LC/MS m/z 830.00 (M+H)$^+$, 3.74 min (LCMS Method 2).

Step 6. 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyridin-2-yloxy)methyl)cyclohex-3-ene-1-carboxylic acid was prepared in 32% yield as a solid, following the procedure described in general procedure A step 6, using ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylate as reactant. $^1$H NMR (400 MHz, CHLOROFORM-d) δ 8.14 (d, J=3.8 Hz, 1H), 7.59-7.52 (m, 1H), 6.89-6.84 (m, 1H), 6.73 (d, J=8.3 Hz, 1H), 5.35 (br. s, 1H), 5.21-5.16 (m, 1H), 4.71 (s, 1H), 4.60 (s, 1H), 4.50-4.38 (m, 2H), 3.14-2.99 (m, 8H), 2.86-2.57 (m, 6H), 2.29-0.89 (m, 27H), 1.68 (s, 3H), 1.10 (s, 3H), 0.98 (s, 3H), 0.97-0.91 (m, 6H), 0.85 (s, 3H). LC/MS m/z 802.50 (M+H)$^+$, 3.56 min (LCMS Method 2).

Example 2

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-3-phenyl-1H-pyrazol-5-yl)oxy)methyl)cyclohex-3-ene-1-carboxylic acid.

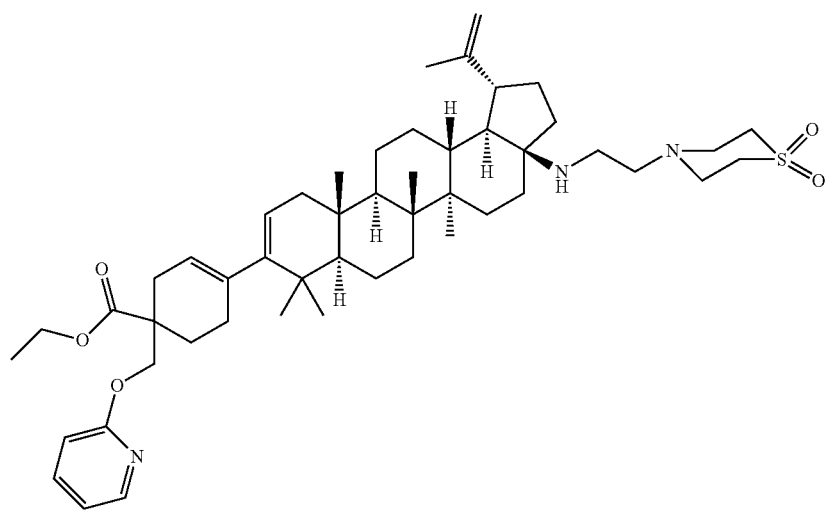

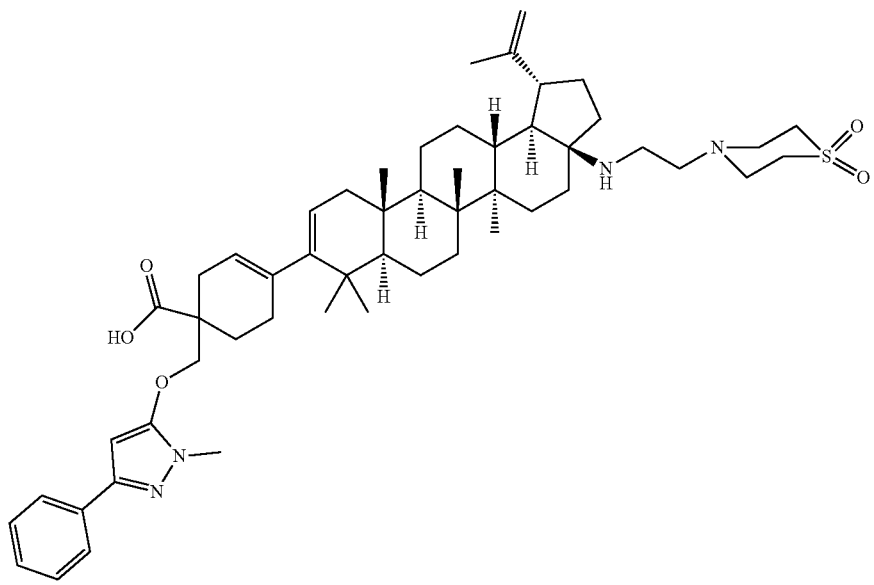

Step 1. Preparation of ethyl 8-(((1-methyl-3-phenyl-1H-pyrazol-5-yl)oxy)methyl)-1,4-dioxaspiro[4.5]decane-8-carboxylate.

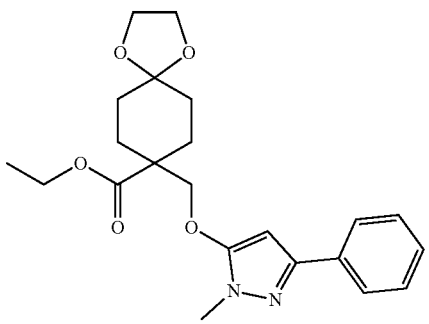 [SMILES: CCOC(=O)C1(COc2cc(-c3ccccc3)nn2C)CCC2(CC1)OCCO2]

The title compound was prepared in 99% yield as an oil, following the procedure described in general procedure A step 1-A, using 1-methyl-3-phenyl-1H-pyrazol-5-ol as reactant. $^1$H NMR (500 MHz, CHLOROFORM-d) δ 7.78-7.70 (m, 2H), 7.39 (t, J=7.6 Hz, 2H), 7.32-7.28 (m, 1H), 5.83 (s, 1H), 4.21 (q, J=7.1 Hz, 2H), 4.12 (s, 2H), 4.01-3.94 (m, 4H), 3.67 (s, 3H), 2.37-2.26 (m, 2H), 1.80-1.65 (m, 6H), 1.31-1.26 (m, 3H). LC/MS m/z 401.10 (M+H)$^+$, 2.17 min (LCMS Method 1).

Step 2. Preparation of ethyl 1-(((1-methyl-3-phenyl-1H-pyrazol-5-yl)oxy)methyl)-4-oxocyclohexane-1-carboxylate.

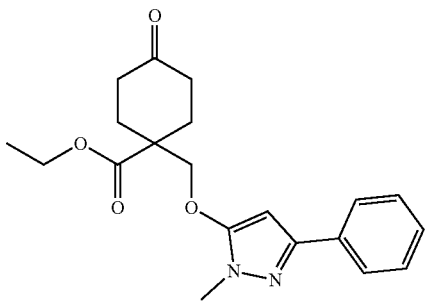 [SMILES: CCOC(=O)C1(COc2cc(-c3ccccc3)nn2C)CCC(=O)CC1]

The title compound was prepared in 81% yield as an oil, following the procedure described in general procedure A step 2, using ethyl 8-(((1-methyl-3-phenyl-1H-pyrazol-5-yl)oxy)methyl)-1,4-dioxaspiro[4.5]decane-8-carboxylate as reactant. $^1$H NMR (400 MHz, CHLOROFORM-d) δ 7.75-7.71 (m, 2H), 7.42-7.35 (m, 2H), 7.32-7.27 (m, 1H), 5.84 (s, 1H), 4.28 (q, J=7.0 Hz, 2H), 4.19 (s, 2H), 3.68 (s, 3H), 2.63-2.51 (m, 4H), 2.48-2.39 (m, 2H), 1.92-1.81 (m, 2H), 1.30 (t, J=7.2 Hz, 3H). LC/MS m/z 357.15 (M+H)$^+$, 1.99 min (LCMS Method 1).

Step 3. Preparation of ethyl 1-(((1-methyl-3-phenyl-1H-pyrazol-5-yl)oxy)methyl)-4-(((trifluoromethyl)sulfonyl)oxy)cyclohex-3-ene-1-carboxylate.

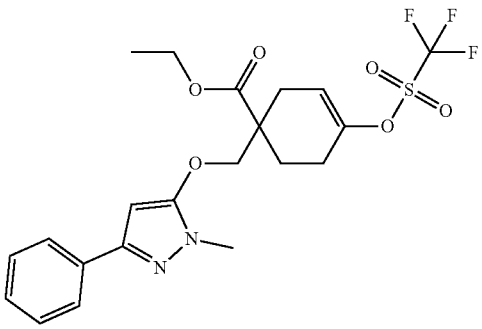 [SMILES: CCOC(=O)C1(COc2cc(-c3ccccc3)nn2C)CC=C(OS(=O)(=O)C(F)(F)F)CC1]

The title compound was prepared in 68% yield as an oil, following the procedure described in general procedure A step 3, using ethyl 1-(((1-methyl-3-phenyl-1H-pyrazol-5-yl)oxy)methyl)-4-oxocyclohexane-1-carboxylate as reactant. $^1$H NMR (400 MHz, CHLOROFORM-d) δ 7.75-7.71 (m, 2H), 7.41-7.35 (m, 2H), 7.32-7.29 (m, 1H), 5.84 (s, 1H), 5.83-5.79 (m, 1H), 4.25-4.10 (m, 4H), 3.67 (s, 3H), 2.92-2.82 (m, 1H), 2.59-2.25 (m, 4H), 2.00 (ddd, J=13.7, 7.8, 6.4 Hz, 1H), 1.27 (t, J=7.2 Hz, 3H). $^{19}$F NMR (376 MHz, CHLOROFORM-d) δ −73.83 (s, 3F). LC/MS m/z 489.20 (M+H)$^+$, 2.30 min (LCMS Method 1).

Step 4. Preparation of ethyl 1-(((1-methyl-3-phenyl-1H-pyrazol-5-yl)oxy)methyl)-4-(4,4,5,5-tetramethyl-1,3,2-dioxaborolan-2-yl)cyclohex-3-ene-1-carboxylate.

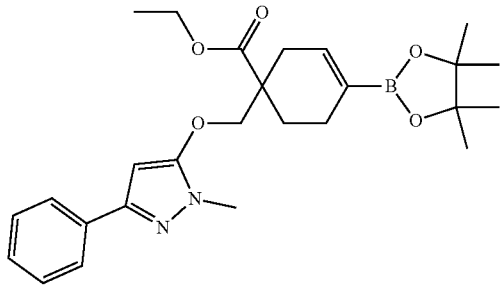 [SMILES: CCOC(=O)C1(COc2cc(-c3ccccc3)nn2C)CC=C(B2OC(C)(C)C(C)(C)O2)CC1]

The title compound was prepared in 68% yield as a wax, following the procedure described in general procedure A step 4, using ethyl 1-(((1-methyl-3-phenyl-1H-pyrazol-5-yl)oxy)methyl)-4-(((trifluoromethyl)sulfonyl)oxy)cyclohex-3-ene-1-carboxylate as reactant. $^1$H NMR (400 MHz, CHLOROFORM-d) δ 7.75-7.71 (m, 2H), 7.41-7.34 (m, 2H), 7.31-7.28 (m, J=7.5 Hz, 1H), 6.57-6.53 (m, 1H), 5.83 (s, 1H), 4.23-4.11 (m, 4H), 3.65 (s, 3H), 2.76-2.67 (m, 1H), 2.32-2.12 (m, 3H), 2.03-1.86 (m, 2H), 1.27 (s, 12H), 1.23 (t, J=7.0 Hz 3H). LC/MS m/z 467.30 (M+H)$^+$, 3.58 min (LCMS Method 2).

Step 5. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-3-phenyl-1H-pyrazol-5-yl)oxy)methyl)cyclohex-3-ene-1-carboxylate.

The title compound was prepared in 59% yield as a solid, following the procedure described in general procedure A step 5, using ethyl 1-(((1-methyl-3-phenyl-1H-pyrazol-5-yl)oxy)methyl)-4-(4,4,5,5-tetramethyl-1,3,2-dioxaborolan-2-yl)cyclohex-3-ene-1-carboxylate as reactant. $^1$H NMR (400 MHz, CHLOROFORM-d) δ 7.74-7.70 (m, 2H), 7.40-7.33 (m, 2H), 7.31-7.25 (m, 1H), 5.83 (s, 1H), 5.36 (br. s., 1H), 5.19 (d, J=4.8 Hz, 1H), 4.71 (d, J=2.0 Hz, 1H), 4.59 (s, 1H), 4.24-4.15 (m, 4H), 3.65 (s, 3H), 3.10-2.98 (m, 8H), 2.74-2.43 (m, 6H), 2.32-1.02 (m, 27H), 1.68 (s, 3H), 1.26 (t, J=7.0 Hz, 3H), 1.06 (s, 3H), 0.97-0.91 (m, 9H), 0.86 (s, 3H). LC/MS m/z 909.60 (M+H)$^+$, 3.89 min (LCMS Method 2).

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-3-phenyl-1H-pyrazol-5-yl)oxy)methyl)cyclohex-3-ene-1-carboxylic acid was prepared in 81% yield as a solid, following the procedure described in general procedure A step 6, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-3-phenyl-1H-pyrazol-5-yl)oxy)methyl)cyclohex-3-ene-1-carboxylate as reactant. $^1$H NMR (400 MHz, METHANOL-d$_4$) δ 7.73-7.68 (m, 2H), 7.40-7.34 (m, 2H), 7.31-7.26 (m, 1H), 6.04 (s, 1H), 5.37 (br. s., 1H), 5.22 (d, J=4.5 Hz, 1H), 4.76 (s, 1H), 4.65 (s, 1H), 4.31-4.23 (m, 2H), 3.64 (s, 3H), 3.20-3.04 (m, 8H), 2.92-2.61 (m, 6H), 2.24-1.10 (m, 27H), 1.73 (s, 3H), 1.16 (s, 3H), 1.06 (s, 3H), 1.00 (s, 3H), 0.97 (s, 3H), 0.92 (s, 3H). LC/MS m/z 881.55 (M+H)$^-$, 3.77 min (LCMS Method 2).

Example 3

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-5-(trifluoromethyl)-1H-pyrazol-3-yl)oxy)methyl)cyclohex-3-ene-1-carboxylic acid.

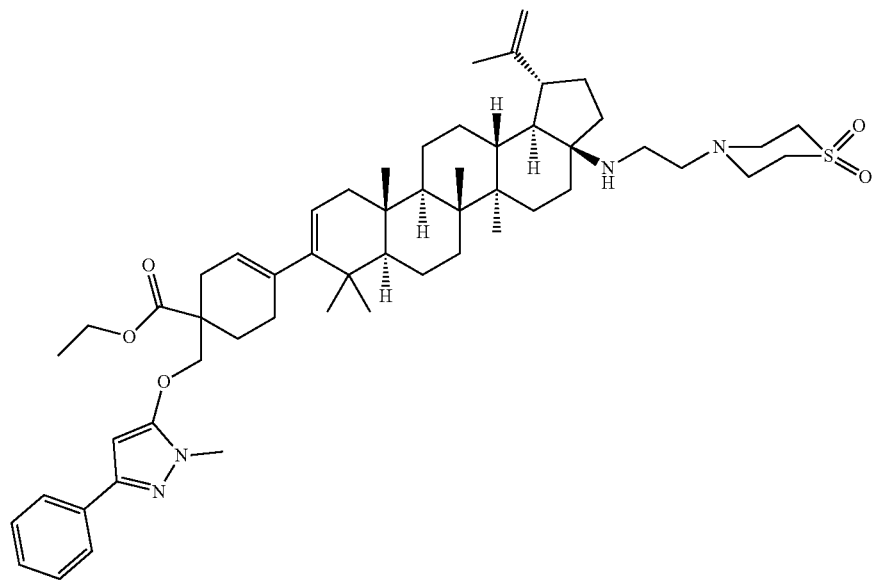

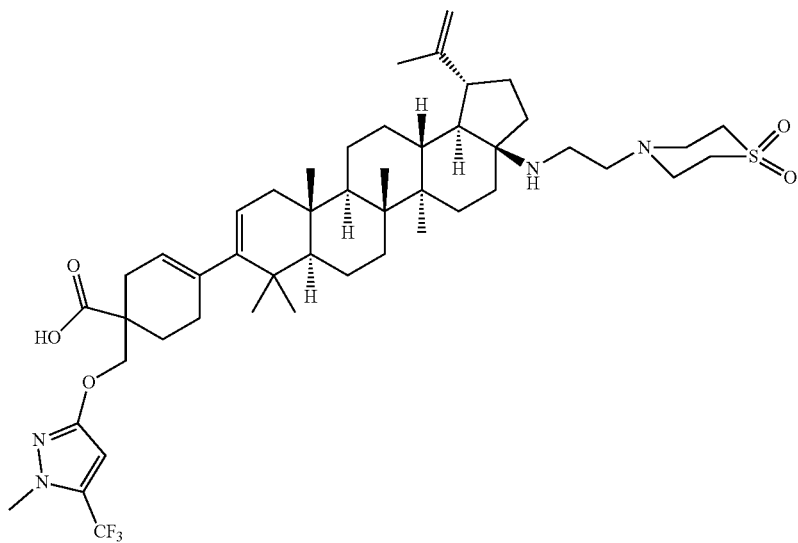

Step 1. Preparation of ethyl 8-(((1-methyl-5-(trifluoromethyl)-1H-pyrazol-3-yl)oxy)methyl)-1,4-dioxaspiro[4.5]decane-8-carboxylate.

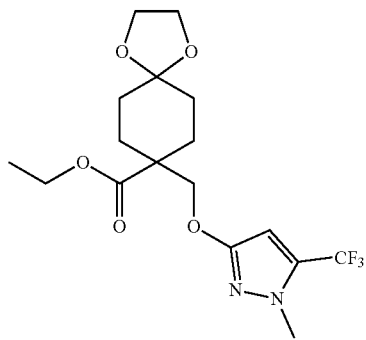 [SMILES: CCOC(=O)C1(COc2cc(C(F)(F)F)n(C)n2)CCC2(CC1)OCCO2]

The title compound was prepared in 86% yield as an oil, following the procedure described in general procedure A step 1-A, using 1-methyl-5-(trifluoromethyl)-1H-pyrazol-3-ol as reactant. $^1$H NMR (500 MHz, CHLOROFORM-d) δ 5.99 (s, 1H), 4.20 (q, J=7.2 Hz, 2H), 4.19 (s, 2H), 3.96 (t, J=3.0 Hz, 4H), 3.82 (s, 3H), 2.31-2.19 (m, 2H), 1.78-1.64 (m, 6H), 1.26 (t, J=7.1 Hz, 3H). LC/MS m/z 393.05 (M+H)$^+$, 2.18 min (LCMS Method 1).

Step 2. Preparation of ethyl 1-(((1-methyl-5-(trifluoromethyl)-1H-pyrazol-3-yl)oxy)methyl)-4-oxocyclohexane-1-carboxylate.

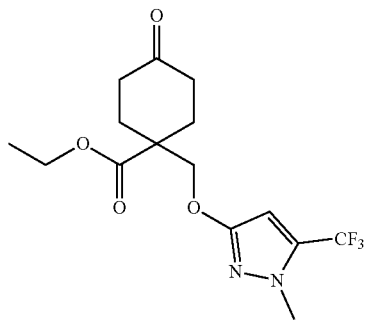 [SMILES: CCOC(=O)C1(COc2cc(C(F)(F)F)n(C)n2)CCC(=O)CC1]

The title compound was prepared in 98% yield as an oil, following the procedure described in general procedure A step 2, using ethyl 8-(((1-methyl-5-(trifluoromethyl)-1H-pyrazol-3-yl)oxy)methyl)-1,4-dioxaspiro[4.5]decane-8-carboxylate as reactant. $^1$H NMR (400 MHz, CHLOROFORM-d) δ 5.99 (s, 1H), 4.26 (s, 2H), 4.26 (q, J=7.1 Hz, 2H), 3.82 (d, J=0.8 Hz, 3H), 2.59-2.34 (m, 6H), 1.92-1.79 (m, 2H), 1.28 (t, J=6.8 Hz, 3H). $^{19}$F NMR (376 MHz, CHLOROFORM-d) δ −60.88 (s, 3F). LC/MS m/z 349.15 (M+H)$^+$, 2.08 min (LCMS Method 1).

Step 3. Preparation of ethyl 1-(((1-methyl-5-(trifluoromethyl)-1H-pyrazol-3-yl)oxy)methyl)-4-(((trifluoromethyl)sulfonyl)oxy)cyclohex-3-ene-1-carboxylate.

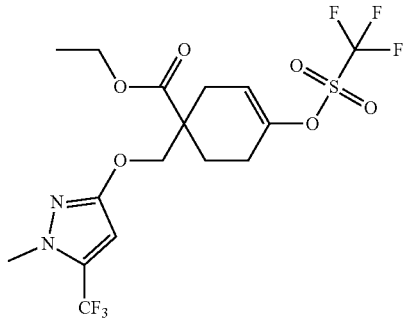 [SMILES: CCOC(=O)C1(COc2cc(C(F)(F)F)n(C)n2)CC=C(OS(=O)(=O)C(F)(F)F)CC1]

The title compound was prepared in 70% yield as an oil, following the procedure described in general procedure A step 3, using ethyl 1-(((1-methyl-5-(trifluoromethyl)-1H-pyrazol-3-yl)oxy)methyl)-4-oxocyclohexane-1-carboxylate as reactant. $^1$H NMR (400 MHz, CHLOROFORM-d) δ 5.99 (s, 1H), 5.79-5.76 (m, 1H), 4.29-4.16 (m, 4H), 3.81 (d, J=0.8 Hz, 3H), 2.85-2.75 (m, 1H), 2.55-2.19 (m, 4H), 2.02-1.93 (m, 1H), 1.25 (t, J=7.2 Hz, 3H). $^{19}$F NMR (376 MHz, CHLOROFORM-d) δ −60.89 (s, 3F), −73.88 (s, 3F). LC/MS m/z 481.10 (M+H)$^+$, 2.32 min (LCMS Method 1).

Step 4. Preparation of ethyl 1-(((1-methyl-5-(trifluoromethyl)-1H-pyrazol-3-yl)oxy)methyl)-4-(4,4,5,5-tetramethyl-1,3,2-dioxaborolan-2-yl)cyclohex-3-ene-1-carboxylate.

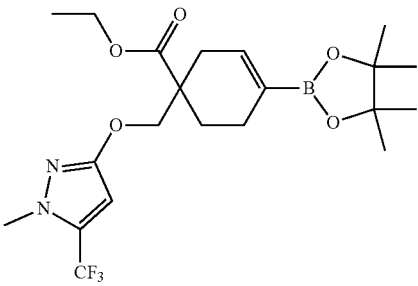

The title compound was prepared in 79% yield as a wax, following the procedure described in general procedure A step 4, using ethyl 1-(((1-methyl-5-(trifluoromethyl)-1H-pyrazol-3-yl)oxy)methyl)-4-4(((trifluoromethyl)sulfonyl)oxy)cyclohex-3-ene-1-carboxylate as reactant. $^1$H NMR (400 MHz, CHLOROFORM-d) δ 6.55-6.51 (m, 1H), 5.97 (s, 1H), 4.25 (d, J=9.3 Hz 1H), 4.19-4.13 (m, 3H), 3.81 (d, J=0.8 Hz, 3H), 2.69 (dq, J=19.1, 2.8 Hz, 1H), 2.27-2.16 (m, 3H), 2.00-1.81 (m, 2H), 1.26 (s, 12H), 1.22 (t, J=7.2 Hz, 3H). $^{19}$F NMR (376 MHz, CHLOROFORM-d) δ −60.84 (s, 3F). LC/MS m/z 481.13 (M+Na)$^+$, 2.41 min (LCMS Method 1).

Step 5. Preparation of ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-5-(trifluoromethyl)-1H-pyrazol-3-yl)oxy)methyl)cyclohex-3-ene-1-carboxylate.

The title compound was prepared in 88% yield as a solid, following the procedure described in general procedure A step 5, using ethyl 1-(((1-methyl-5-(trifluoromethyl)-1H-pyrazol-3-yl)oxy)methyl)-4-(4,4,5,5-tetramethyl-1,3,2-dioxaborolan-2-yl)cyclohex-3-ene-1-carboxylate as reactant. $^1$H NMR (400 MHz, CHLOROFORM-d) δ 5.98 (s, 1H), 5.33 (br. s., 1H), 5.17 (d, J=4.8 Hz, 1H), 4.71 (s, 1H), 4.60 (s, 1H), 4.29-4.09 (m, 4H), 3.80 (s, 3H), 3.12-3.00 (m, 8H), 2.79-2.46 (m, 6H), 2.24-0.88 (m, 27H), 1.69 (s, 3H), 1.22 (t, J=7.0 Hz, 3H), 1.05 (s, 3H), 0.96 (s, 3H), 0.96-0.89 (m, 6H), 0.85 (s, 3H). $^{19}$F NMR (376 MHz, CHLOROFORM-d) δ −60.83 (s, 3F). LC/MS m/z 901.50 (M+H)$^+$, 3.89 min (LCMS Method 2).

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-5-(trifluoromethyl)-1H-pyrazol-3-yl)oxy)methyl)cyclohex-3-ene-1-carboxylic acid was prepared in 56% yield as a solid, following the procedure described in general procedure A step 6, using ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-5-(trifluoromethyl)-1H-pyrazol-3-yl)oxy)methyl)cyclohex-3-ene-1-carboxylate as reactant. $^1$H NMR (400 MHz, CHLOROFORM-d) δ 6.00 (s, 1H), 5.35 (br. s., 1H), 5.19 (d, J=5.8 Hz, 1H), 4.71 (s, 1H), 4.60 (s, 1H), 4.34-4.21 (m, 2H), 3.81 (s, 3H), 3.14-2.99 (m, 8H), 2.76-2.54 (m, 6H), 2.23-1.04 (m, 27H), 1.69 (s, 3H), 1.08 (s, 3H), 0.97 (s, 3H), 0.97-0.92 (m, 6H), 0.86 (s, 3H). $^{19}$F NMR (376 MHz, CHLOROFORM-d) δ −60.81 (s, 3F). LC/MS m/z 873.45 (M+H)$^+$, 3.73 min (LCMS Method 2).

Example 4

Preparation of 2-((1-carboxy-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)cyclohex-3-en-1-yl)methoxy)thiazole-4-carboxylic acid.

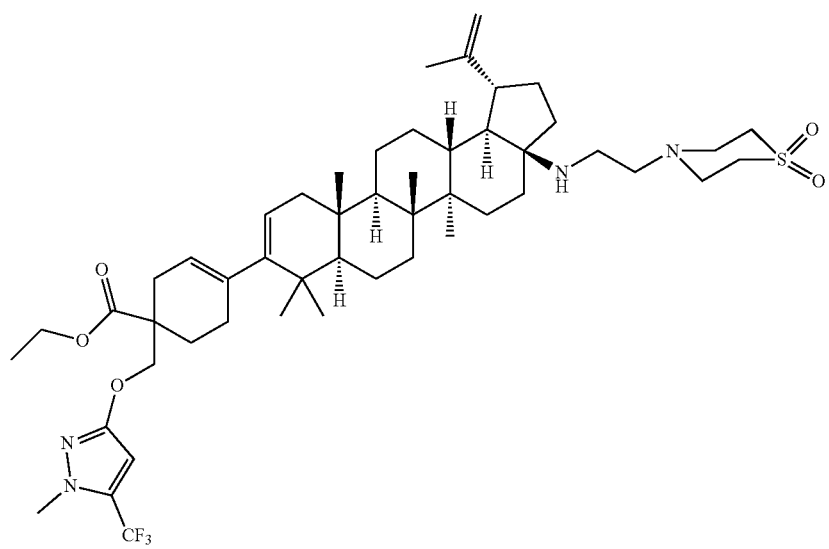

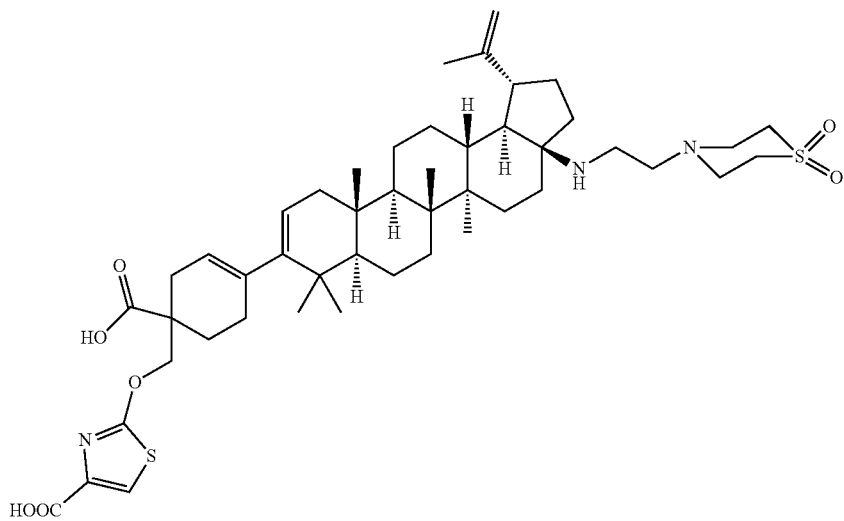

Step 1. Preparation of ethyl 2-((8-(ethoxycarbonyl)-1,4-dioxaspiro[4.5]decan-8-yl)methoxy)thiazole-4-carboxylate.

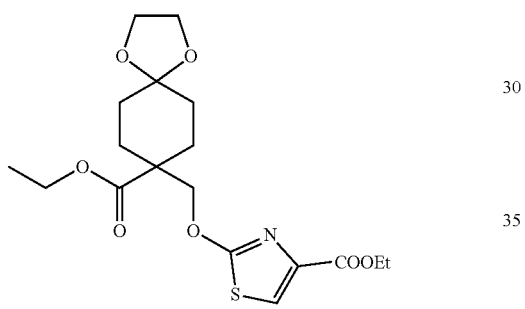

The title compound was prepared as an oil without further purification, following the procedure described in general procedure A step 1-A, using ethyl 2-hydroxythiazole-4-carboxylate as reactant. LC/MS m/z 400.30 (M+H)$^+$, 2.18 min (LCMS Method 1).

Step 2. Preparation of ethyl 2-((1-(ethoxycarbonyl)-4-oxocyclohexyl)methoxy)thiazole-4-carboxylate.

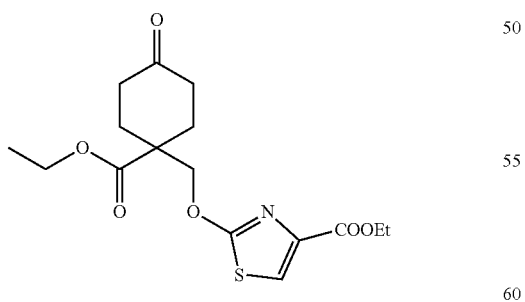

The title compound was prepared in 26% yield (yield calculated over 2 steps) as a solid, following the procedure described in general procedure A step 2, using crude ethyl 2-((8-(ethoxycarbonyl)-1,4-dioxaspiro[4.5]decan-8-yl)methoxy)thiazole-4-carboxylate as reactant. $^1$H NMR (400 MHz, CHLOROFORM-d) δ 7.61 (s, 1H), 4.66 (s, 2H), 4.38 (q, J=7.3 Hz, 2H), 4.26 (q, J=7.2 Hz, 2H), 2.58-2.48 (m, 4H), 2.45-2.36 (m, 2H), 1.92-1.81 (m, 2H), 1.39 (t, J=7.2 Hz, 3H), 1.28 (t, J=7.2 Hz, 3H).

Step 3. Preparation of ethyl 2-((1-(ethoxycarbonyl)-4-(((trifluoromethyl)sulfonyl)oxy)cyclohex-3-en-1-yl)methoxy)thiazole-4-carboxylate.

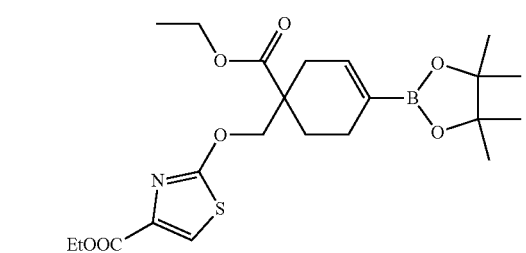 [SMILES: CCOC(=O)c1csc(OCC2(C(=O)OCC)CC=C(B3OC(C)(C)C(C)(C)O3)CC2)n1]

The title compound was prepared in 40% yield as an oil, following the procedure described in general procedure A step 3, using ethyl 2-((1-(ethoxycarbonyl)-4-oxocyclohexyl)methoxy)thiazole-4-carboxylate as reactant. $^1$H NMR (400 MHz, CHLOROFORM-d) δ 7.60 (s, 1H), 5.80-5.76 (m, 1H), 4.66 (d, J=10.0 Hz, 1H), 4.60 (d, J=10.3 Hz, 1H), 4.38 (q, J=7.0 Hz, 2H), 4.19 (qd, J=7.1, 0.8 Hz, 2H), 2.87-2.79 (m, 1H), 2.56-2.23 (m, 4H), 1.99-1.90 (m, 1H), 1.38 (t, J=7.2 Hz, 3H), 1.24 (t, J=7.0 Hz, 3H). $^{19}$F NMR (376 MHz, CHLOROFORM-d) δ −73.84 (s, 3F). LC/MS m/z 488.15 (M+H)+, 2.41 min (LCMS Method 1).

Step 4. Preparation of ethyl 2-((1-(ethoxycarbonyl)-4-(4,4,5,5-tetramethyl-1,3,2-dioxaborolan-2-yl)cyclohex-3-en-1-yl)methoxy)thiazole-4-carboxylate.

The title compound was prepared in 57% yield as an oil, following the procedure described in general procedure A step 4, using ethyl 2-((1-(ethoxycarbonyl)-4-(((trifluoromethyl)sulfonyloxy)cyclohex-3-en-1-yl)methoxy)thiazole-4-carboxylate as reactant. $^1$H NMR (400 MHz, CHLOROFORM-d) δ 7.58 (s, 1H), 6.54-6.49 (m, 1H), 4.64 (d, J=10.0 Hz, 1H), 4.56 (d, J=10.0 Hz, 1H), 4.37 (q, J=7.0 Hz, 2H), 4.16 (q, J=7.2 Hz, 2H), 2.68 (dq, J=19.1, 3.0 Hz, 1H), 2.27-2.16 (m, 3H), 2.00-1.81 (m, 2H), 1.38 (t, J=7.0 Hz, 3H), 1.26 (s, 12H), 1.21 (t, J=7.0 Hz, 3H). LC/MS m/z 466.30 (M+H)$^+$, 2.42 min (LCMS Method 1).

Step 5. Preparation of ethyl 2-((4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methoxy) thiazole-4-carboxylate.

Step 6. 2-((1-carboxy-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)methoxy)thiazole-4-carboxylic acid was prepared in 85% yield as a solid, following the procedure described in general procedure A step 6, using ethyl 2-((4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methoxy)thiazole-4-carboxylate as reactant. $^1$H NMR (500 MHz, METHANOL-d$_4$) δ 7.49 (s, 1H), 5.34 (br. s., 1H), 5.21 (d, J=4.7 Hz, 1H), 4.78 (s, 1H), 4.68 (s, 1H), 4.61-4.53 (m, 2H), 3.27-3.06 (m, 11H), 2.99-2.96 (m, 1H), 2.89-2.80 (m, 1H), 2.67-2.58 (m, 1H), 2.35-1.04 (m, 27H), 1.73 (s, 3H), 1.18 (s, 3H), 1.09 (s,

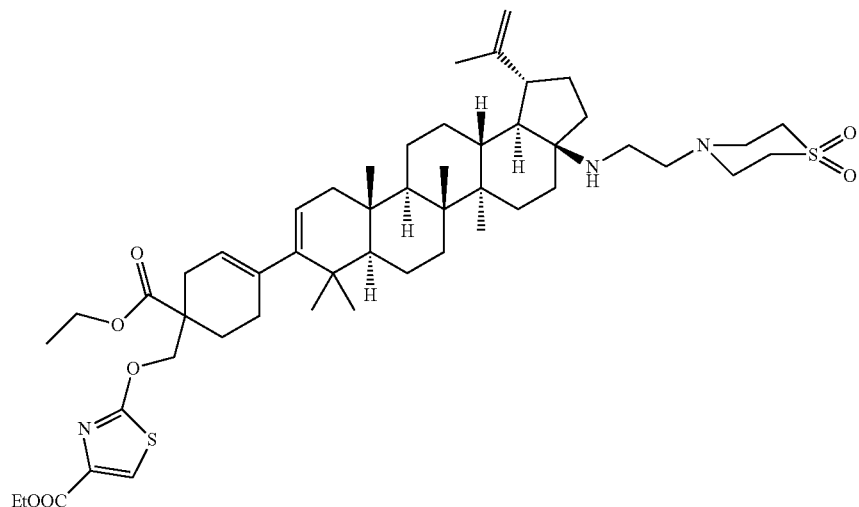

The title compound was prepared in 79% yield as a solid, following the procedure described in general procedure A step 5, using ethyl 2-((1-(ethoxycarbonyl)-4-(4,4,5,5-tetramethyl-1,3,2-dioxaborolan-2-yl)cyclohex-3-en-1-yl)methoxy)thiazole-4-carboxylate as reactant. $^1$H NMR (400 MHz, CHLOROFORM-d) δ 7.58 (s, 1H), 5.33 (br. s., 1H), 5.18 (d, J=6.0 Hz, 1H), 4.71 (d, J=2.0 Hz, 1H), 4.67-4.60 (m, 2H), 4.59 (s, 1H), 4.37 (q, J=7.0 Hz, 2H), 4.20-4.09 (m, 2H), 3.12-2.96 (m, 8H), 2.74-2.41 (m, 6H), 2.21-0.86 (m, 27H), 1.69 (s, 3H), 1.38 (t, J=7.2 Hz, 3H), 1.22 (t, J=7.2 Hz, 3H), 1.05 (s, 3H), 0.96 (s, 3H), 0.96-0.90 (m, 6H), 0.85 (s, 3H). LC/MS m/z 908.60 (M+H)$^+$, 3.05 min (LCMS Method 3).

3H), 1.00-0.96 (m, 6H), 0.92 (s, 3H). LC/MS m/z 852.50 (M+H)$^+$, 2.86 min (LCMS Method 3).

Example 5

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((4-methyl-1,2,5-thiadiazol-3-yl)oxy)methyl)cyclohex-3-ene-1-carboxylic acid.

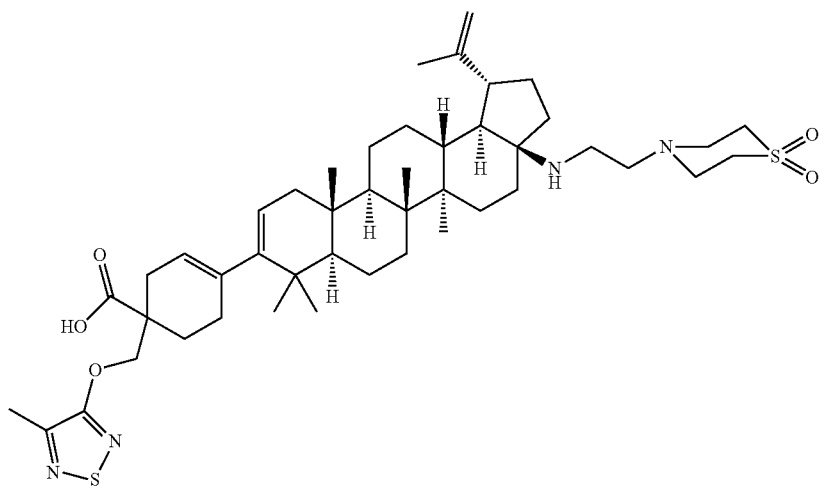

Step 1. Preparation of ethyl 8-(((4-methyl-1,2,5-thiadiazol-3-yl)oxy)methyl)-1,4-dioxaspiro[4.5]decane-8-carboxylate.

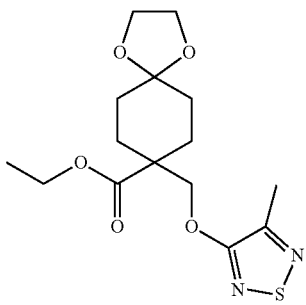 [SMILES: CCOC(=O)C1(COc2nsnc2C)CCC2(CC1)OCCO2]

The title compound was prepared in 64% yield as an oil, following the procedure described in general procedure A step 1-A, using 4-methyl-1,2,5-thiadiazol-3-ol as reactant. $^1$H NMR (400 MHz, CHLOROFORM-d) δ 4.43 (s, 2H), 4.18 (q, J=7.1 Hz, 2H), 3.99-3.92 (m, 4H), 2.36 (s, 3H), 2.31-2.24 (m, 2H), 1.75-1.66 (m, 6H), 1.24 (t, J=7.2 Hz, 3H). LC/MS m/z 343.20 (M+H)$^+$, 2.17 min (LCMS Method 1).

Step 2. Preparation of ethyl 1-(((4-methyl-1,2,5-thiadiazol-3-yl)oxy)methyl)-4-oxocyclohexane-1-carboxylate.

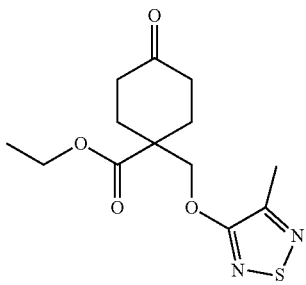 [SMILES: CCOC(=O)C1(COc2nsnc2C)CCC(=O)CC1]

The title compound was prepared in 81% yield as an oil, following the procedure described in general procedure A step 2, using ethyl 8-(((4-methyl-1,2,5-thiadiazol-3-yl)oxy)methyl)-1,4-dioxaspiro[4.5]decane-8-carboxylate as reactant. $^1$H NMR (400 MHz, CHLOROFORM-d) δ 4.51 (s, 2H), 4.26 (q, J=7.1 Hz, 2H), 2.61-2.38 (m, 6H), 2.37 (s, 3H), 1.91-1.82 (m, 2H), 1.28 (t, J=7.2 Hz, 3H). LC/MS m/z 299.20 (M+H)$^+$, 1.94 min (LCMS Method 1).

Step 3. Preparation of ethyl 1-(((4-methyl-1,2,5-thiadiazol-3-yl)oxy)methyl)-4-(((trifluoromethyl)sulfonyl)oxy)cyclohex-3-ene-1-carboxylate.

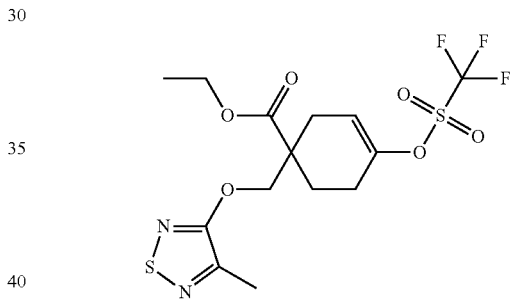

The title compound was prepared in 60% yield as an oil, following the procedure described in general procedure A step 3, using ethyl 1-(((4-methyl-1,2,5-thiadiazol-3-yl)oxy)methyl)-4-oxocyclohexane-1-carboxylate as reactant. $^1$H NMR (400 MHz, CHLOROFORM-d) δ 5.82-5.78 (m, 1H), 4.52 (d, J=10.3 Hz, 1H), 4.47 (d, J=10.3 Hz, 1H), 4.26-4.12 (m, 2H), 2.90-2.82 (m, 1H), 2.59-2.27 (m, 4H), 2.36 (s, 3H), 2.00-1.93 (m, 1H), 1.24 (t, J=7.0 Hz, 3H). $^{19}$F NMR (376 MHz, CHLOROFORM-d) δ −73.83 (s, 3F). LC/MS m/z 431.15 (M+H)$^+$, 2.41 min (LCMS Method 1).

Step 4. Preparation of ethyl 1-(((4-methyl-1,2,5-thiadiazol-3-yl)oxy)methyl)-4-(4,4,5,5-tetramethyl-1,3,2-dioxaborolan-2-yl)cyclohex-3-ene-1-carboxylate.

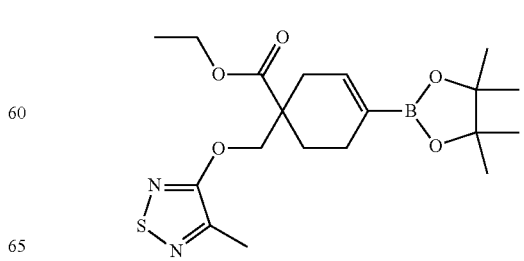

The title compound was prepared in 74% yield as an oil, following the procedure described in general procedure A step 4, using ethyl 1-(((4-methyl-1,2,5-thiadiazol-3-yl)oxy)methyl)-4-(((trifluoromethyl)sulfonyl)oxy)cyclohex-3-ene-1-carboxylate as reactant. $^1$H NMR (400 MHz, CHLOROFORM-d) δ 6.56-6.52 (m, 1H), 4.51 (d, J=10.0 Hz, 1H), 4.44 (d, J=10.0 Hz, 1H), 4.16 (qd, J=7.1, 1.1 Hz, 2H), 2.71 (dq, J=19.1, 3.3 Hz, 1H), 2.35 (s, 3H), 2.31-2.17 (m, 3H), 2.04-1.85 (m, 2H), 1.26 (s 12H), 1.21 (t, J=7.0 Hz, 3H). LC/MS m/z 409.25 (M+H)$^+$, 2.45 min (LCMS Method 1).

Step 5. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((4-methyl-1,2,5-thiadiazol-3-yl)oxy)methyl)cyclohex-3-ene-1-carboxylate.

Step 6. 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((4-methyl-1,2,5-thiadiazol-3-yl)oxy)methyl)cyclohex-3-ene-1-carboxylic acid was prepared in 53% yield as a solid, following the procedure described in general procedure A step 6, using ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((4-methyl-1,2,5-thiadiazol-3-yl)oxy)methyl)cyclohex-3-ene-1-carboxylate as reactant.

$^1$H NMR (400 MHz, CHLOROFORM-d) δ 5.36 (br. s., 1H), 5.18 (br. s., 1H), 4.74 (br. s., 1H), 4.65 (br. s., 1H),

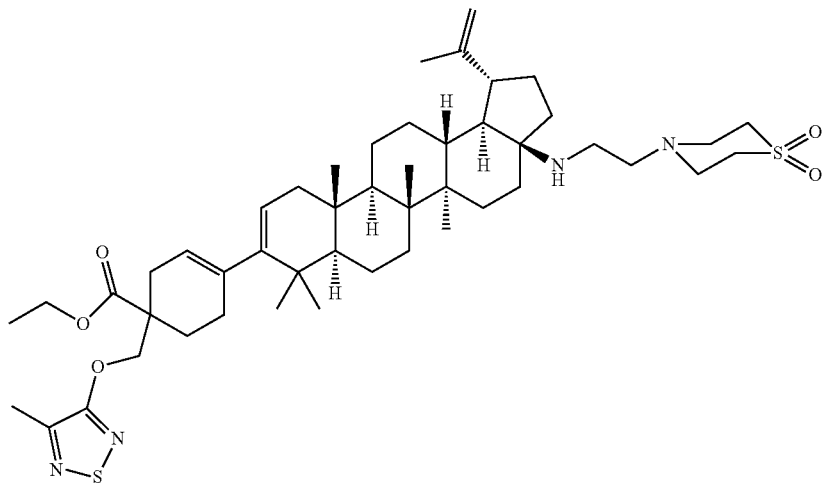

The title compound was prepared in 73% yield as a solid, following the procedure described in general procedure A step 5, using ethyl 1-(((4-methyl-1,2,5-thiadiazol-3-yl)oxy)methyl)-4-(4,4,5,5-tetramethyl-1,3,2-dioxaborolan-2-yl)cyclohex-3-ene-1-carboxylate as reactant. $^1$H NMR (400 MHz, CHLOROFORM-d) δ 5.36 (br. s., 1H), 5.19 (d, J=5.3 Hz, 1H), 4.76 (s, 1H), 4.63 (s, 1H), 4.56-4.44 (m, 2H), 4.21-4.09 (m, 2H), 3.17-3.00 (m, 8H), 2.98-2.59 (m, 6H), 2.23-0.82 (m, 27H), 2.35 (s, 3H), 1.70 (s, 3H), 1.22 (t, J=7.2 Hz, 3H), 1.06 (s, 3H), 0.98 (s, 3H), 0.97-0.91 (m, 6H), 0.85 (s, 3H). LC/MS m/z 851.55 (M+H)$^+$, 3.07 min (LCMS Method 3).

4.59-4.45 (m, 2H), 3.24-2.98 (m, 9H), 2.89-2.51 (m, 5H), 2.34 (s, 3H), 1.68 (s, 3H), 2.22-0.97 (m, 27H), 1.15 (s, 3H), 1.02 (s, 3H), 0.97-0.89 (m, 6H), 0.86 (s, 3H). LC/MS m/z 823.55 (M+H)$^+$, 2.85 min (LCMS Method 3).

Example 6

Preparation of 1-(((1,2,5-thiadiazol-3-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

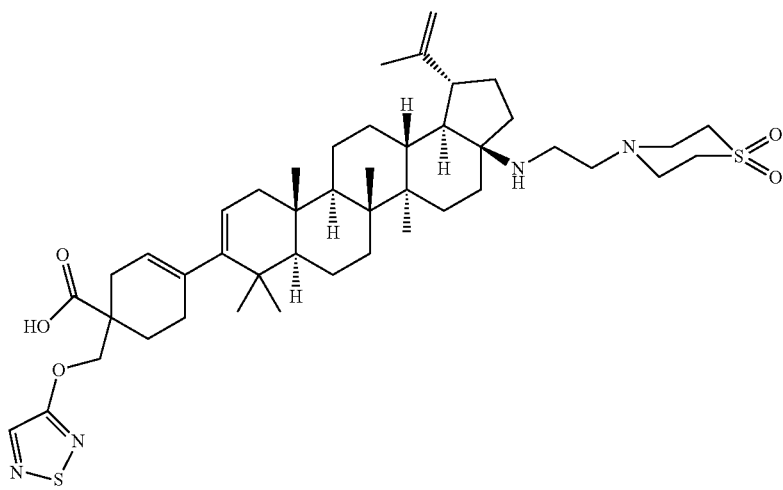

Step 1. Preparation of ethyl 8-(((1,2,5-thiadiazol-3-yl)oxy)methyl)-1,4-dioxaspiro[4.5]decane-8-carboxylate.

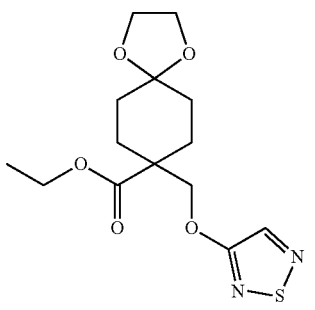 [SMILES: CCOC(=O)C1(COc2cnsn2)CCC2(CC1)OCCO2]

The title compound was prepared in 92% yield as an oil, following the procedure described in general procedure A step 1-A, using 1,2,5-thiadiazol-3-ol as reactant. $^1$H NMR (400 MHz, CHLOROFORM-d) δ 7.97 (s, 1H), 4.46 (s, 2H), 4.18 (q, J=7.1 Hz, 2H), 4.00-3.92 (m, 4H), 2.32-2.21 (m, 2H), 1.76-1.66 (m, 6H), 1.24 (t, J=7.2 Hz, 3H). LC/MS m/z 329.20 (M+H)$^+$, 2.07 min (LCMS Method 1).

Step 2. Preparation of ethyl 1-(((1,2,5-thiadiazol-3-yl)oxy)methyl)-4-oxocyclohexane-1-carboxylate.

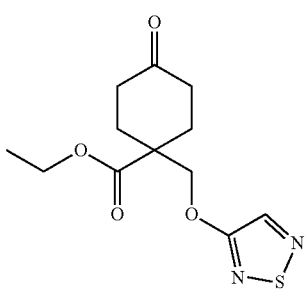 [SMILES: CCOC(=O)C1(COc2cnsn2)CCC(=O)CC1]

The title compound was prepared in 80% yield as an oil, following the procedure described in general procedure A step 2, using ethyl 8-4(1,2,5-thiadiazol-3-yl)oxy)methyl)-1,4-dioxaspiro[4.5]decane-8-carboxylate as reactant. $^1$H NMR (400 MHz, CHLOROFORM-d) δ 7.99 (s, 1H), 4.54 (s, 2H), 4.26 (q, J=7.0 Hz, 2H), 2.60-2.50 (m, 4H), 2.47-2.38 (m, 2H), 1.93-1.82 (m, 2H), 1.28 (t, J=7.0 Hz, 3H). LC/MS m/z 285.15 (M+H)$^-$, 1.85 min (LCMS Method 1).

Step 3. Preparation of ethyl 1-(((1,2,5-thiadiazol-3-yl)oxy)methyl)-4-((((trifluoromethyl)sulfonyl)oxy)cyclohex-3-ene-1-carboxylate.

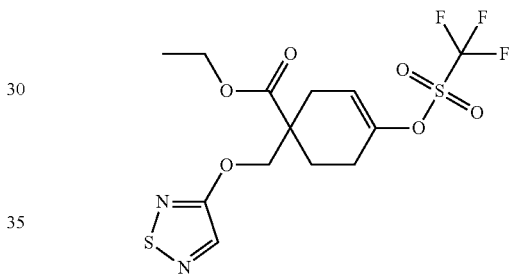

The title compound was prepared in 34% yield as an oil, following the procedure described in general procedure A step 3, using ethyl 1-(((1,2,5-thiadiazol-3-yl)oxy)methyl)-4-oxocyclohexane-1-carboxylate as reactant. $^1$H NMR (400 MHz, CHLOROFORM-d) δ 7.99 (s, 1H), 5.81-5.78 (m, 1H), 4.55 (d, J=10.3 Hz, 1H), 4.50 (d, J=10.3 Hz, 1H), 4.20 (qd, J=7.1, 0.8 Hz, 2H), 2.90-2.81 (m, 1H), 2.57-2.25 (m, 4H), 2.04-1.95 (m, 1H), 1.24 (t, J=7.2 Hz, 3H). $^{19}$F NMR (376 MHz, CHLOROFORM-d) δ −73.83 (s, 3F). LC/MS m/z 417.10 (M+H)$^+$, 2.37 min (LCMS Method 1).

Step 4. Preparation of ethyl 1-(((1,2,5-thiadiazol-3-yl)oxy)methyl)-4-(4,4,5,5-tetramethyl-1,3,2-dioxaborolan-2-yl)cyclohex-3-ene-1-carboxylate.

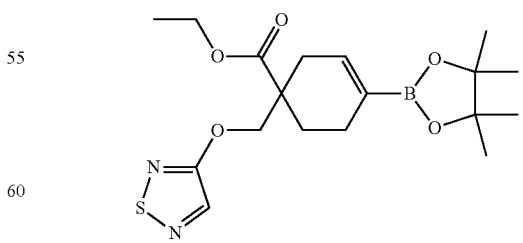

The title compound was prepared in 69% yield as an oil, following the procedure described in general procedure A step 4, using ethyl 1-4(1,2,5-thiadiazol-3-yl)oxy)methyl)-4-((((trifluoromethyl)sulfonyl)oxy)cyclohex-3-ene-1-carboxylate as reactant. ¹H NMR (400 MHz, CHLOROFORM-d) δ 7.96 (s, 1H), 6.56-6.52 (m, 1H), 4.54 (d, J=10.0 Hz, 1H), 4.45 (d, J=10.0 Hz, 1H), 4.16 (q, J=7.0 Hz, 2H), 2.71 (dq, J=18.9, 3.4 Hz, 1H), 2.30-2.17 (m, 3H), 2.03-1.94 (m, 1H), 1.92-1.83 (m, 1H), 1.26 (s, 12H), 1.21 (t, J=7.2 Hz, 3H). LC/MS m/z 395.30 (M+H)⁺, 2.40 min (LCMS Method 1).

Step 5. Preparation of ethyl 1-(((1,2,5-thiadiazol-3-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopentalalchrysen-9-yl)cyclohex-3-ene-1-carboxylate.

ethyl-1-(prop-1-en-2-yl)-2,3,3a,4,5,5a,5b,6,7,7a,8,11,11a,11 b,12,13,13a,13b-octadecahydro-1H-cyclopentalalchrysen-9-yl)cyclohex-3-ene-1-carboxylic acid was prepared in 56% yield as a solid, following the procedure described in general procedure A step 6, using ethyl 1-(((1,2,5-thiadiazol-3-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as reactant. ¹H NMR (400 MHz, CHLOROFORM-d) δ 7.98 (s, 1H), 5.37 (br. s., 1H), 5.19 (br. s., 1H), 4.76 (s, 1H), 4.66 (s,

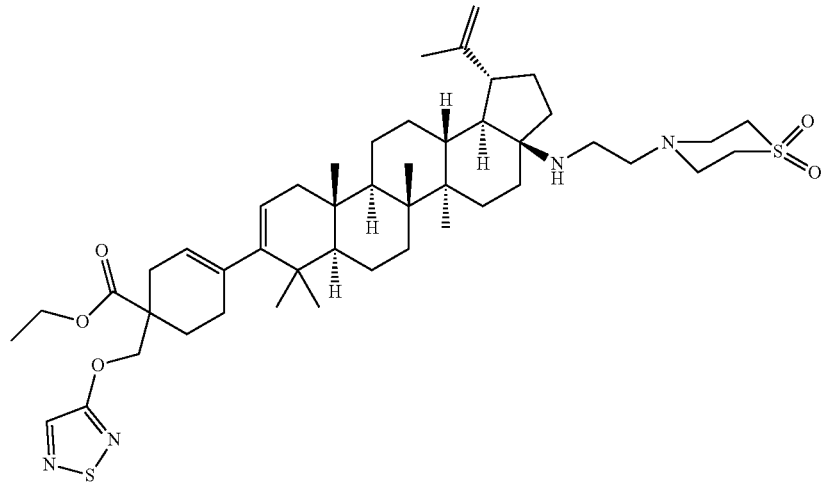

The title compound was prepared in 76% yield as a solid, following the procedure described in general procedure A step 5, using ethyl 1-4(1,2,5-thiadiazol-3-yl)oxy)methyl)-4-(4,4,5,5-tetramethyl-1,3,2-dioxaborolan-2-yl)cyclohex-3-ene-1-carboxylate as reactant. ¹H NMR (400 MHz, CHLOROFORM-d) δ 7.97 (s, 1H), 5.35 (br. s., 1H), 5.18 (d, J=5.0 Hz, 1H), 4.71 (s, 1H), 4.59 (s, 1H), 4.58-4.49 (m, 2H), 4.16 (q, J=7.5 Hz, 2H), 3.13-2.98 (m, 8H), 2.76-2.43 (m, 6H), 2.22-0.82 (m, 27H), 1.69 (s, 3H), 1.22 (t, J=7.2 Hz 3H), 1.06 (s, 3H), 0.97 (s, 3H), 0.96-0.91 (m, 6H), 0.85 (s, 3H). LC/MS m/z 837.55 (M+H)⁺, 3.08 min (LCMS Method 3).

Step 6. 1-(((1,2,5-thiadiazol-3-yl)oxy)methyl)-4-(((1R,3aS,5aR,5bR,7aR,11aS,11bR,13aR,13bR)-3a-((2-(1,1-dioxidothiomorpholino)ethypamino)-5a,5b,8,8,11a-pentam- 1H), 4.62-4.49 (m, 2H), 3.23-3.00 (m, 8H), 2.90-2.53 (m, 6H), 2.28-0.89 (m, 27H), 1.69 (s, 3H), 1.16 (s, 3H), 1.03 (s, 3H), 0.97-0.91 (m, 6H), 0.86 (s, 3H). LC/MS m/z 809.50 (M+H)⁺, 2.90 min (LCMS Method 3).

Example 7

Preparation of 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((1-ethyl-1H-1,2,3-triazol-5-yl)oxy)methyl)cyclohex-3-ene-1-carboxylic acid.

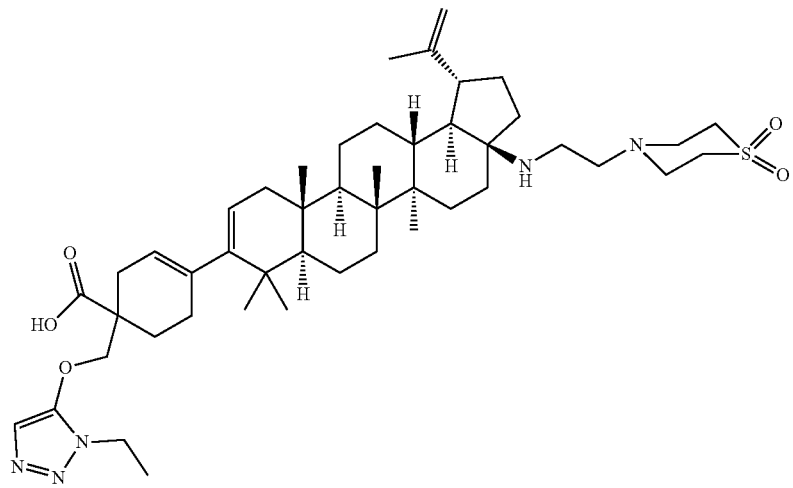

Step 1. Preparation of ethyl 8-(((1-ethyl-1H-1,2,3-triazol-5-yl)oxy)methyl)-1,4-dioxaspiro[4.5]decane-8-carboxylate.

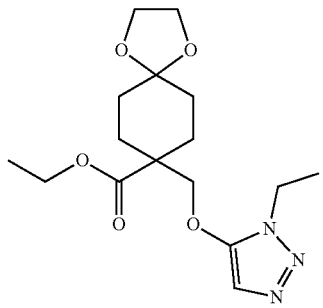 [SMILES: CCOC(=O)C1(COc2cnnn2CC)CCC2(CC1)OCCO2]

The title compound was prepared in 56% yield as an oil, following the procedure described in general procedure A step 1-B, using 1-ethyl-1H-1,2,3-triazol-5-ol as reactant. $^1$H NMR (500 MHz, CHLOROFORM-d) δ 7.07 (s, 1H), 4.19 (q, J=7.1 Hz, 3H), 4.17 (q, J=7.3 Hz, 2H), 4.10 (s, 2H), 4.01-3.92 (m, 4H), 2.33-2.24 (m, 2H), 1.76-1.61 (m, 6H), 1.44 (t, J=7.3 Hz, 3H), 1.25 (t, J=7.2 Hz, 3H). LC/MS m/z 340.25 (M+Na)⁻, 1.91 min (LCMS Method 1).

Step 2. Preparation of ethyl 1-(((1-ethyl-1H-1,2,3-triazol-5-yl)oxy)methyl)-4-oxocyclohexane-1-carboxylate.

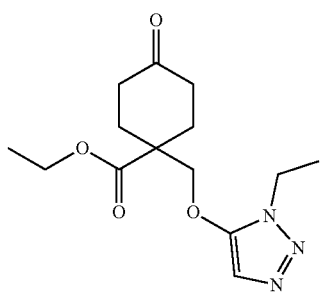 [SMILES: CCOC(=O)C1(COc2cnnn2CC)CCC(=O)CC1]

The title compound was prepared in 86% yield as an oil, following the procedure described in general procedure A step 2, using ethyl 8-(((1-ethyl-1H-1,2,3-triazol-5-yl)oxy)methyl)-1,4-dioxaspiro[4.5]decane-8-carboxylate as reactant. $^1$H NMR (400 MHz, CHLOROFORM-d) δ 7.09 (s, 1H), 4.26 (q, J=7.0 Hz, 2H), 4.18 (q, J=7.5 Hz, 2H), 4.17 (s, 2H), 2.61-2.50 (m, 4H), 2.47-2.38 (m, 2H), 1.89-1.78 (m, 2H), 1.45 (t, J=7.4 Hz, 3H), 1.28 (t, J=7.2 Hz, 3H). LC/MS m/z 296.25 (M+H)⁺, 1.62 min (LCMS Method 1).

Step 3. Preparation of ethyl 1-(((1-ethyl-1H-1,2,3-triazol-5-yl)oxy)methyl)-4-(((trifluoromethyl)sulfonyl)oxy)cyclohex-3-ene-1-carboxylate.

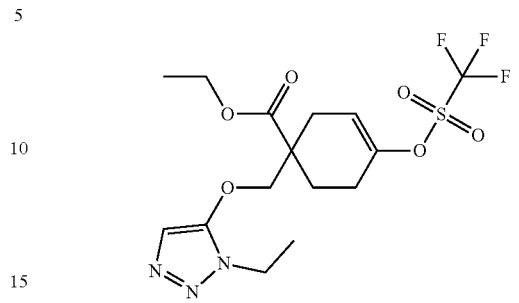

The title compound was prepared in 35% yield as an oil, following the procedure described in general procedure A step 3, using ethyl 1-(((1-ethyl-1H-1,2,3-triazol-5-yl)oxy)methyl)-4-oxocyclohexane-1-carboxylate as reactant. $^1$H NMR (400 MHz, CHLOROFORM-d) δ 7.09 (s, 1H), 5.82-5.78 (m, 1H), 4.24-4.13 (m, 6H), 2.90-2.81 (m, 1H), 2.60-2.24 (m, 4H), 2.00-1.92 (m, 1H), 1.44 (t, J=7.3 Hz, 3H), 1.25 (t, J=7.2 Hz, 3H). $^{19}$F NMR (376 MHz, CHLOROFORM-d) δ −73.82 (s, 3F). LC/MS m/z 428.20 (M+H)⁻, 2.15 min (LCMS Method 1).

Step 4. Preparation of ethyl 1-(((1-ethyl-1H-1,2,3-triazol-5-yl)oxy)methyl)-4-(4,4,5,5-tetramethyl-1,3,2-dioxaborolan-2-yl)cyclohex-3-ene-1-carboxylate.

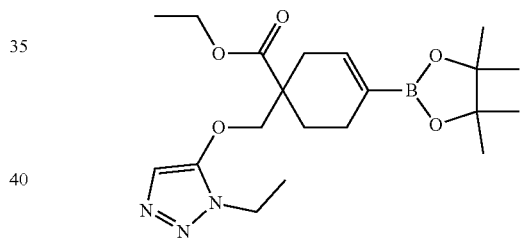

The title compound was prepared in 57% yield as an oil, following the procedure described in general procedure A step 4, using ethyl 1-(((1-ethyl-1H-1,2,3-triazol-5-yl)oxy)methyl)-4-(((trifluoromethyl)sulfonyl)oxy)cyclohex-3-ene-1-carboxylate as reactant. $^1$H NMR (400 MHz, CHLOROFORM-d) δ 7.07 (s, 1H), 6.55-6.50 (m, 1H), 4.21-4.11 (m, 6H), 2.69 (dq, J=19.0, 2.9 Hz, 1H), 2.31-2.09 (m, 3H), 2.02-1.85 (m, 2H), 1.43 (t, J=7.3 Hz, 3H), 1.27 (s, 12H), 1.22 (t, J=7.2 Hz, 3H). LC/MS m/z 406.20 (M+H)⁻, 2.22 min (LCMS Method 1).

Step 5. Preparation of ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-ethyl-1H-1,2,3-triazol-5-yl)oxy)methyl)cyclohex-3-ene-1-carboxylate.

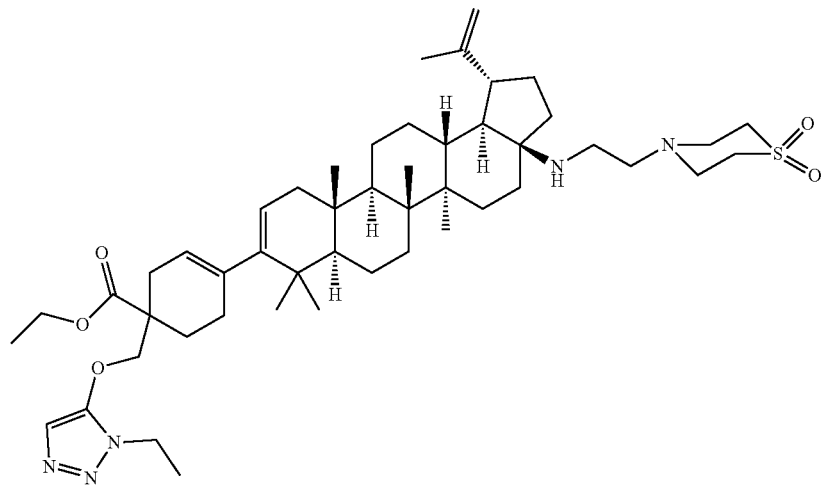

The title compound was prepared in 90% yield as a solid, following the procedure described in general procedure A step 5, using ethyl 1-(((1-ethyl-1H-1,2,3-triazol-5-yl)oxy) methyl)-4-(4,4,5,5-tetramethyl-1,3,2-dioxaborolan-2-yl)cyclohex-3-ene-1-carboxylate as reactant. $^1$H NMR (400 MHz, CHLOROFORM-d) δ 7.07 (s, 1H), 5.35 (br. s., 1H), 5.18 (d, J=6.0 Hz, 1H), 4.70 (s, 1H), 4.59 (s, 1H), 4.23-4.11 (m, 6H), 3.11-2.97 (m, 8H), 2.71-2.42 (m, 6H), 2.24-0.86 (m, 27H), 1.68 (s, 3H), 1.42 (t, J=7.3 Hz, 3H), 1.23 (t, J=7.0 Hz, 3H), 1.05 (s, 3H), 0.96 (s, 3H), 0.95-0.90 (m, 6H), 0.85 (s, 3H). LC/MS m/z 848.60 (M+H)$^+$, 2.74 min (LCMS Method 3).

Step 6. 4-((1R,3aS,5aR,5bR,7aR,11aS,11bR,13aR, 13bR)-3a-((2-(1,1-dioxidothiomorpholino)ethyl)amino)-5a, 5b,8,8,11a-pentamethyl-1-(prop-1-en-2-yl)-2,3,3a,4,5,5a, 5b,6,7,7a,8,11,11a,11 b,12,13,13a,13b-octadecahydro-1H-cyclopenta[a]chrysen-9-yl)-1-(((1-ethyl-1H-1,2,3-triazol-5-yl)oxy)methyl)cyclohex-3-ene-1-carboxylic acid was prepared in 61% yield as a solid, following the procedure described in general procedure A step 6, using ethyl 4-((1R, 3aS,5aR,5bR,7aR,11aS,11bR,13aR,13bR)-3a-((2-(1,1-di-oxidothiomorpholino)ethypamino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)-1-(((1-ethyl-1H-1,2,3-triazol-5-yl)oxy) methyl)cyclohex-3-ene-1-carboxylate as reactant.

$^1$H NMR (400 MHz, CHLOROFORM-d) δ 7.10 (s, 1H), 5.36 (br. s., 1H), 5.18 (br. s., 1H), 4.69 (s, 1H), 4.59 (s, 1H), 4.28-4.20 (m, 2H), 4.16 (q, J=7.3 Hz, 2H), 3.13-2.99 (m, 8H), 2.82-2.55 (m, 6H), 2.24-1.00 (m, 27H), 1.68 (s, 3H), 1.43 (t, J=7.3 Hz, 3H), 1.09 (s, 3H), 0.98 (s, 3H), 0.96-0.91 (m, 6H), 0.85 (s, 3H). LC/MS m/z 820.55 (M+H)$^+$, 2.86 min (LCMS Method 3).

Example 8

Preparation of 1-((benzo[d]isothiazol-3-yloxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-ene-1-carboxylic acid.

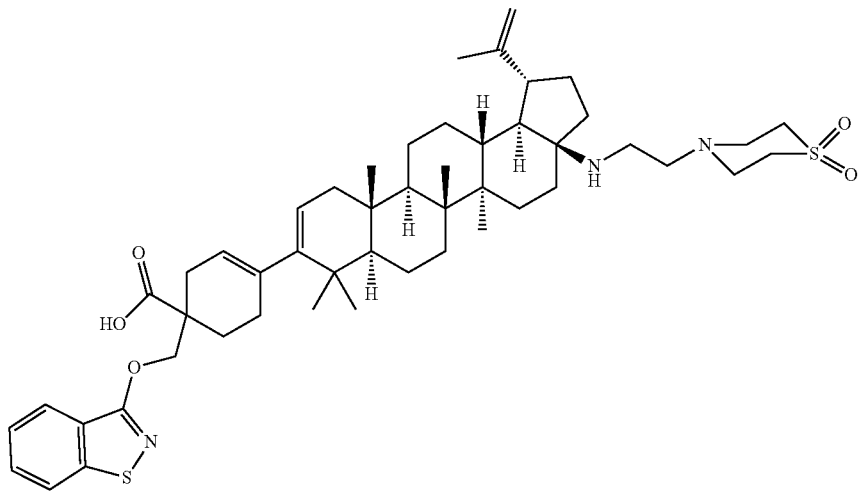

Step 1. Preparation of ethyl 8-((benzo[d]isothiazol-3-yloxy)methyl)-1,4-dioxaspiro[4, 5]decane-8-carboxylate.

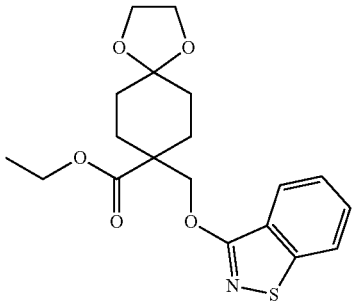 [SMILES: CCOC(=O)C1(COc2nsc3ccccc23)CCC2(CC1)OCCO2]

The title compound was prepared in 26% yield as an oil, following the procedure described in general procedure A step 1-B, using benzo[d]isothiazol-3(2H)-one as reactant. $^1$H NMR (500 MHz, CHLOROFORM-d) δ 7.88 (dd, J=8.1, 0.9 Hz, 1H), 7.78 (d, J=8.1 Hz, 1H), 7.53 (ddd, J=8.2, 7.1, 1.1 Hz, 1H), 7.39 (td, J=7.5, 0.8 Hz, 1H), 4.63-4.59 (m, 2H), 4.20 (q, J=7.1 Hz, 2H), 3.97 (t, J=2.6 Hz, 4H), 2.41-2.31 (m, 2H), 1.82-1.73 (m, 6H), 1.23 (t, J=7.1 Hz, 3H). LC/MS m/z 378.25 (M+H)$^-$, 4.17 min (LCMS Method 4).

Step 2. Preparation of ethyl 1-((benzoldlisothiazol-3-yloxy)methyl)-4-oxocyclohexane-1-carboxylate.

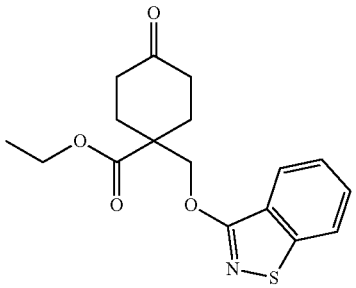 [SMILES: CCOC(=O)C1(COc2nsc3ccccc23)CCC(=O)CC1]

The title compound was prepared in 88% yield as a wax, following the procedure described in general procedure A step 2, using ethyl 8-((benzoldlisothiazol-3-yloxy)methyl)-1,4-dioxaspiro[4.5]clecane-8-carboxylate as reactant. $^1$H NMR (400 MHz, CHLOROFORM-d) δ 7.87 (dt, J=8.0, 1.0 Hz, 1H), 7.79 (dt, J=8.2, 0.8 Hz, 1H), 7.54 (ddd, J=8.2, 7.0, 1.1 Hz, 1H), 7.40 (ddd, J=8.0, 7.0, 1.0 Hz, 1H), 4.68 (s, 2H), 4.26 (q, J=7.3 Hz, 2H), 2.66-2.51 (m, 4H), 2.49-2.40 (m, 2H), 1.99-1.88 (m, 2H), 1.26 (t, J=7.2 Hz, 3H). LC/MS m/z 334.20 (M+H)$^+$, 2.31 min (LCMS Method 1).

Step 3. Preparation of ethyl 1-((benzoldlisothiazol-3-yloxy)methyl)-4-(((trifluoromethyl)sulfonyl)oxy)cyclohex-3-ene-1-carboxylate.

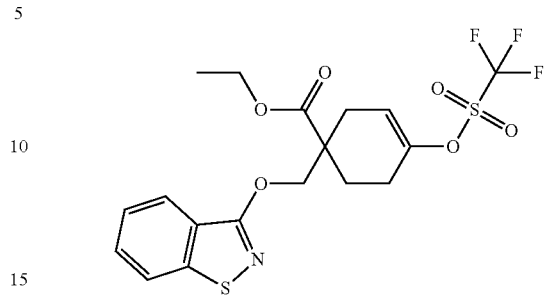

The title compound was prepared in 64% yield as an oil, following the procedure described in general procedure A step 3, using ethyl 1-((benzoldlisothiazol-3-yloxy)methyl)-4-oxocyclohexane-1-carboxylate as reactant. $^1$H NMR (400 MHz, CHLOROFORM-d) δ 7.86 (dt, J=8.0, 1.0 Hz, 1H), 7.79 (dt, J=8.1, 0.8 Hz, 1H), 7.54 (ddd, J=8.2, 7.0, 1.1 Hz, 1H), 7.43-7.39 (m, 1H), 5.83-5.79 (m, 1H), 4.68 (d, J=10.0 Hz, 1H), 4.63 (d, J=10.3 Hz, 1H), 4.20 (qd, J=7.2, 2.1 Hz, 2H), 2.97-2.88 (m, 1H), 2.59-2.32 (m, 4H), 2.07-1.98 (m, 1H), 1.23 (t, J=7.2 Hz, 3H). $^{19}$F NMR (376 MHz, CHLOROFORM-d) δ −73.83 (s, 3F). LC/MS m/z 466.15 (M+H)$^+$, 2.51 min (LCMS Method 1).

Step 4. Preparation of ethyl 1-((benzoldlisothiazol-3-yloxy)methyl)-4-(4,4,5,5-tetramethyl-1,3,2-dioxaborolan-2-yl)cyclohex-3-ene-1-carboxylate.

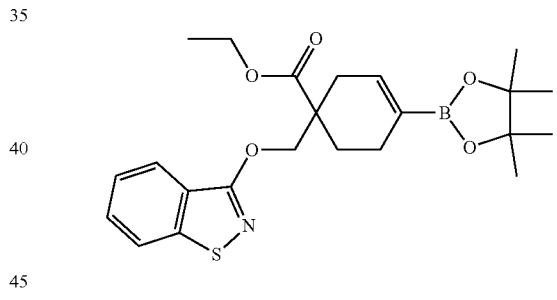

The title compound was prepared in 61% yield as an oil, following the procedure described in general procedure A step 4, using ethyl 1-((benzoldlisothiazol-3-yloxy)methyl)-4-(((trifluoromethyl)sulfonyl)oxy)cyclohex-3-ene-1-carboxylate as reactant. $^1$H NMR (400 MHz, CHLOROFORM-d) δ 7.85 (dt, J=7.9, 0.9 Hz, 1H), 7.76 (dt, J=8.2, 0.8 Hz, 1H), 7.52 (ddd, J=8.2, 7.0, 1.1 Hz, 1H), 7.42-7.37 (m, 1H), 6.58-6.54 (m. 1H), 4.66 (d, J=10.0 Hz, 1H), 4.58 (d, J=10.0 Hz, 1H), 4.16 (qd, J=7.1, 1.0 Hz, 2H), 2.76 (dq, J=18.9, 2.7 Hz, 1H), 2.37-2.28 (m, 1H), 2.27-2.20 (m, 2H), 2.07-1.89 (m, 2H), 1.28-1.25 (m, 12H), 1.19 (t, J=7.2 Hz, 3H). LC/MS m/z 444.25 (M+H)$^+$, 2.58 min (LCMS Method 1).

Step 5. Preparation of ethyl 1-((benzoldlisothiazol-3-yloxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate.

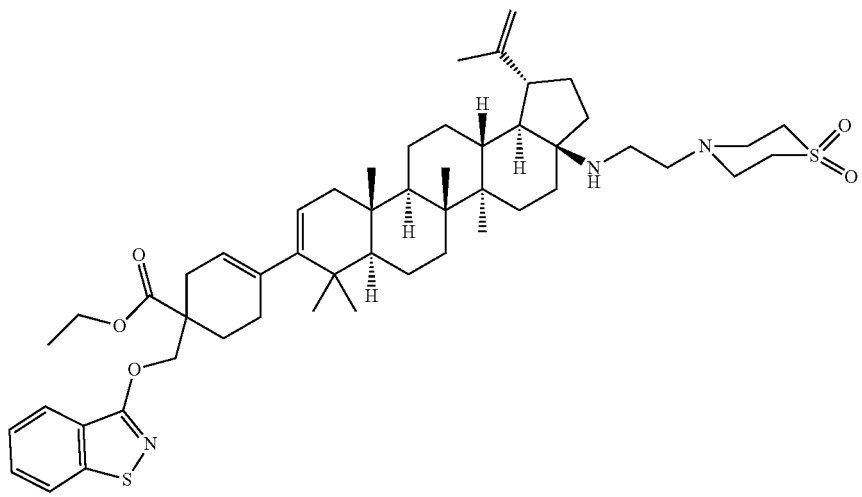

The title compound was prepared in 47% yield as a solid, following the procedure described in general procedure A step 5, using ethyl 1-((benzo[d]isothiazol-3-yloxy)methyl)-4-(4,4,5,5-tetramethyl-1,3,2-dioxaborolan-2-yl)cyclohex-3-ene-1-carboxylate as reactant. $^1$H NMR (400 MHz, CHLOROFORM-d) δ 7.87 (d, J=7.8 Hz, 1H), 7.77 (d, J=8.0 Hz, 1H), 7.52 (td, J=7.6, 1.1 Hz, 1H), 7.37 (td, J=7.5, 1.0 Hz, 1H), 5.37 (br. s., 1H), 5.20 (d, J=6.0 Hz, 1H), 4.76 (s, 1H), 4.64 (s, 1H), 4.19-4.16 (m, 2H), 4.13 (q, J=7.1 Hz, 2H), 3.17-3.03 (m, 8H), 2.79-2.36 (m, 6H), 2.28-0.83 (27H), 1.70 (s, 3H), 1.27 (t, J=7.3 Hz, 3H), 1.08 (s, 3H), 0.99 (s, 3H), 0.99-0.95 (m, 6H), 0.85 (s, 3H). LC/MS m/z 886.55 (M+H)$^+$, 3.07 min (LCMS Method 3).

Step 6. 1-((benzo[d]isothiazol-3-yloxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid was prepared in 21% yield as a solid, following the procedure described in general procedure A step 6, using ethyl 1-((benzo[d]isothiazol-3-yloxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)cyclohex-3-ene-1-carboxylate as reactant. $^1$H NMR (400 MHz, CHLOROFORM-d) δ 7.88 (d, J=8.0 Hz, 1H), 7.77 (d, J=8.3 Hz, 1H), 7.55-7.49 (m, 1H), 7.40-7.33 (m, 1H), 5.39 (br. s., 1H), 5.20 (br. s., 1H), 4.78 (s, 1H), 4.71 (s, 1H), 4.74-4.64 (m, 2H), 3.34-2.52 (m, 14H), 2.33-1.00 (m, 27H), 1.69 (s, 3H), 1.15 (s, 3H), 1.04 (s, 3H), 0.98-0.91 (m, 6H), 0.87 (s, 3H). LC/MS m/z 858.50 (M+H)$^+$, 2.88 min (LCMS Method 3).

Example 9

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-4-yloxy)methyl)cyclohex-3-ene-1-carboxylic acid.

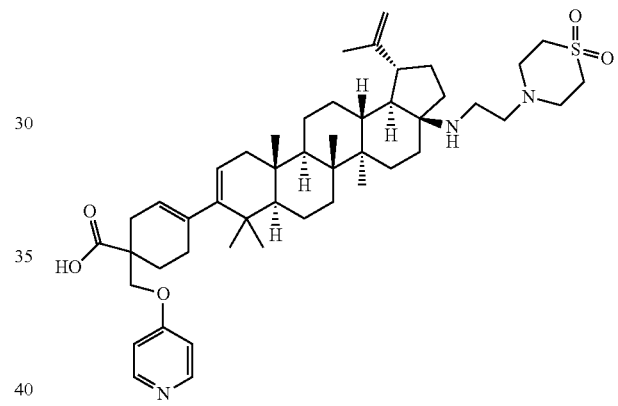

Step 1. Preparation of ethyl 8-((pyridin-4-yloxy)methyl)-1,4-dioxaspiro[4.5]decane-8-carboxylate.

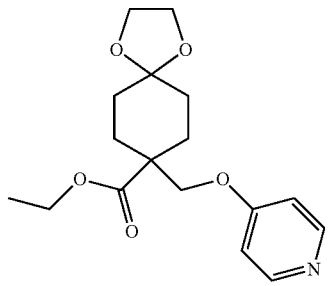 [SMILES: CCOC(=O)C1(COc2ccncc2)CCC2(CC1)OCCO2]

The title compound was prepared in 77% yield, following the procedure described in general procedure A step 1-A, using 4-hydroxypyridine as reactant. $^1$H NMR (500 MHz, CHLOROFORM-d) δ 8.46-8.41 (m, 2H), 6.81-6.77 (m, 2H), 4.20 (q, J=7.2 Hz, 2H), 4.04 (s, 2H), 4.01-3.93 (m, 4H), 2.37-2.25 (m, 2H), 1.80-1.66 (m, 6H), 1.24 (t, J=7.1 Hz, 3H). LC/MS: m/e 322.05 (M+H)$^+$, 2.26 min (LCMS Method 11).

Step 2. Preparation of ethyl 4-oxo-1-((pyridin-4-yloxy)methyl)cyclohexane-1-carboxylate.

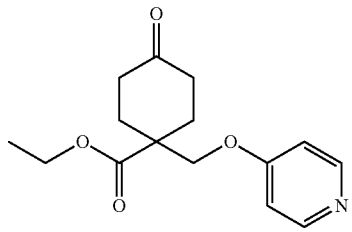 [SMILES: CCOC(=O)C1(COc2ccncc2)CCC(=O)CC1]

The title compound was prepared in 64% yield, following the procedure described in general procedure A step 2, using ethyl 8-((pyridin-4-yloxy)methyl)-1,4-dioxaspiro[4.5]decane-8-carboxylate as reactant. $^1$H NMR (400 MHz, CHLOROFORM-d) δ 8.27-8.23 (m, 2H), 6.67-6.62 (m, 2H), 3.97 (s, 2H), 3.92 (q, J=7.3 Hz, 2H), 2.43-2.31 (m, 4H), 2.27-2.17 (m, 2H), 1.77-1.66 (m, 2H), 1.07 (t, J=7.3 Hz, 3H). LC/MS: m/e 278.05 (M+H)$^+$, 0.81 min (LCMS Method 8).

Step 3. Preparation of ethyl 1-((pyridin-4-yloxy)methyl)-4-(((trifluoromethyl)sulfonyl)oxy)cyclohex-3-ene-1-carboxylate.

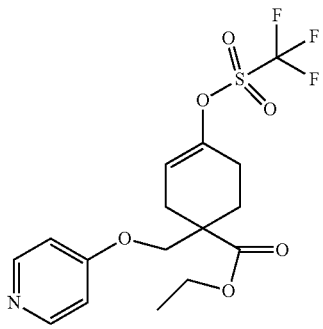 [SMILES: CCOC(=O)C1(COc2ccncc2)CC=C(OS(=O)(=O)C(F)(F)F)CC1]

The title compound was prepared in 66% yield, following the procedure described in general procedure A step 3, using ethyl 4-oxo-1-((pyridin-4-yloxy)methyl)cyclohexanecarboxylate as reactant. $^1$H NMR (400 MHz, CHLOROFORM-d) δ 8.47-8.44 (m, 2H), 6.83-6.79 (m, 2H), 5.82 (t, J=4.1 Hz, 1H), 4.21 (q, J=7.2 Hz, 2H), 4.17-4.07 (m, 2H), 2.91-2.82 (m, 1H), 2.59-2.47 (m, 1H), 2.45-2.25 (m, 4H), 2.09-2.00 (m, 2H), 1.25 (t, J=7.2 Hz, 3H). LC/MS: m/e 410.00 (M+H)$^+$, 1.92 min (LCMS Method 8).

Step 4. Preparation of ethyl 1-((pyridin-4-yloxy)methyl)-4-(4,4,5,5-tetramethyl-1,3,2-dioxaborolan-2-yl)cyclohex-3-ene-1-carboxylate.

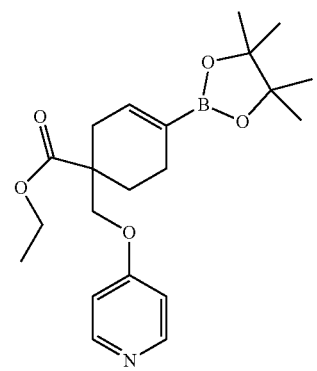 [SMILES: CCOC(=O)C1(COc2ccncc2)CC=C(B2OC(C)(C)C(C)(C)O2)CC1]

The title compound was prepared in 59% yield, following the procedure described in general procedure A step 4, using ethyl 1-((pyridin-4-yloxy)methyl)-4-(((trifluoromethyl)sulfonyl)oxy)cyclohex-3-enecarboxylate as reactant. $^1$H NMR (400 MHz, CHLOROFORM-d) δ 8.33-8.30 (m, 2H), 6.73-6.69 (m, 2H), 6.46 (br. s., 1H), 4.10-4.04 (m, 2H), 4.02-3.95 (m, 2H), 2.63 (dd, J=19.2, 2.9 Hz, 1H), 2.23-2.12 (m, 2H), 2.12-2.01 (m, 1H), 1.94-1.77 (m, 2H), 1.17 (s, 12H), 1.11 (t, J=7.2 Hz, 3H). LC/MS: m/e 388.10 (M+H)$^+$, 1.90 min (LCMS Method 8).

Step 5. Preparation of ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-4-yloxy)methyl)cyclohex-3-ene-1-carboxylate.

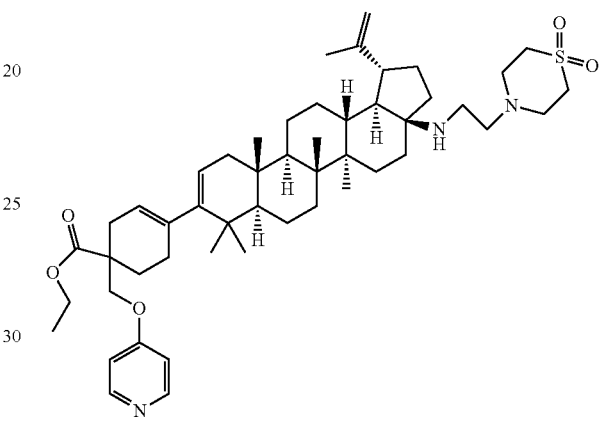

The title compound was prepared in 34% yield, following the procedure described in general procedure A step 5, using ethyl 1-((pyridin-4-yloxy)methyl)-4-(4,4,5,5-tetramethyl-1,3,2-dioxaborolan-2-yl)cyclohex-3-enecarboxylate as reactant. LC/MS: m/e 831.45 (M+H)$^+$, 2.54 min (LCMS Method 3). $^1$H NMR (400 MHz, CHLOROFORM-d) δ 8.42 (d, J=6.0 Hz, 2H), 6.80 (d, J=6.3 Hz, 2H), 5.36 (br. s., 1H), 5.18 (d, J=4.8 Hz, 1H), 4.71 (d, J=1.8 Hz, 1H), 4.59 (s, 1H), 4.20-4.06 (m, 4H), 3.12-2.97 (m, 8H), 2.74-2.51 (m, 4H), 2.51-2.40 (m, 1H), 2.31-2.12 (m, 4H), 2.11-1.98 (m, 3H), 1.98-1.80 (m, 5H), 1.80-1.62 (m, 2H), 1.69 (s, 3H), 1.62-1.37 (m, 10H), 1.37-1.17 (m, 4H), 1.26 (t, J=7.2 Hz, 3H), 1.16-0.99 (m, 3H), 0.99-0.93 (m, 6H), 0.93-0.87 (m, 3H), 0.87-0.81 (m, 3H).

Step 6. 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-4-yloxy)methyl)cyclohex-3-ene-1-carboxylic acid was prepared in 47% yield, following the procedure described in general procedure A step 6, using ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-4-yloxy)methyl)cyclohex-3-enecarboxylate as reactant. $^1$H NMR (400 MHz, METHANOL-d$_4$) δ 8.33 (d, J=6.3 Hz, 2H), 6.98 (d, J=5.5 Hz, 2H), 5.38 (br. s., 1H), 5.21 (d, J=5.0 Hz, 1H), 4.80-4.71 (m, 1H), 4.65 (s, 1H), 4.28-4.12 (m, 2H), 3.24-3.00 (m, 8H), 2.94-2.72 (m, 5H), 2.66 (d, J=18.1 Hz, 1H), 2.37-1.97 (m, 8H), 1.97-1.78 (m, 1H), 1.72 (s, 3H), 1.78-1.69 (m, 3H), 1.66-1.21 (m, 14H), 1.16 (s, 3H), 1.20-1.08 (m, 2H), 1.05 (s, 3H), 0.99 (s, 3H), 0.96 (s, 3H), 0.91 (s, 3H). LC/MS: m/e 802.45 (M+H)$^+$, 2.50 min (LCMS Method 3).

Example 10

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-3-yloxy)methyl)cyclohex-3-enecarboxylic acid.

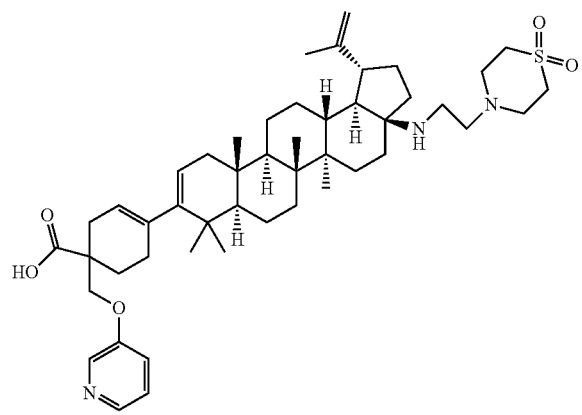

Step 1. Preparation of ethyl 8-((pyridin-3-yloxy)methyl)-1,4-dioxaspiro[4.5]decane-8-carboxylate.

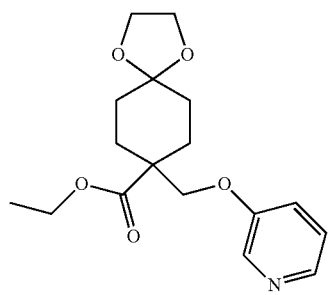 [SMILES: CCOC(=O)C1(COc2cccnc2)CCC2(CC1)OCCO2]

The title compound was prepared in 84% yield, following the procedure described in general procedure A step 1-A, using 3-hydroxypyridine as reactant ¹H NMR (500 MHz, CHLOROFORM-d) δ 8.30 (d, J=2.7 Hz, 1H), 8.24 (dd, J=4.4, 1.4 Hz, 1H), 7.25-7.15 (m, 2H), 4.21 (q, J=7.2 Hz, 2H), 4.05 (s, 2H), 4.00-3.93 (m, 4H), 2.38-2.25 (m, 2H), 1.83-1.66 (m, 6H), 1.32-1.22 (m, 3H). LC/MS: m/e 322.10 (M+H)⁺, 2.534 min (LCMS Method 11).

Step 2. Preparation of ethyl 4-oxo-1-((pyridin-3-yloxy)methyl)cyclohexane-1-carboxylate.

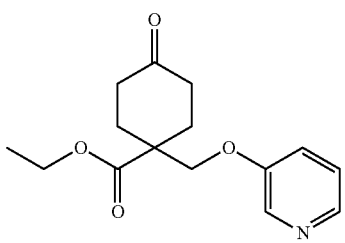 [SMILES: CCOC(=O)C1(COc2cccnc2)CCC(=O)CC1]

The title compound was prepared in 47.8% yield, following the procedure described in general procedure A step 2, using ethyl 8-((pyridin-3-yloxy)methyl)-1,4-dioxaspiro[4.5]decane-8-carboxylate as reactant. LCMS: m/e 279.00 (M+H)⁺, 2.079 min (LCMS Method 8). ¹H NMR (400 MHz, CHLOROFORM-d) δ 8.22 (dd, J=2.6, 0.9 Hz, 1H), 8.16 (dd, J=4.3, 1.8 Hz, 1H), 7.19-7.09 (m, 2H), 4.18 (q, J=7.0 Hz, 2H), 4.07-4.04 (m, 2H), 2.55-2.41 (m, 4H), 2.38-2.28 (m, 2H), 1.88-1.75 (m, 2H), 1.19 (t, J=7.2 Hz, 3H).

Step 3. Preparation of ethyl 1-((pyridin-3-yloxy)methyl)-4-(((trifluoromethyl)sulfonyl)oxy)cyclohex-3-ene-1-carboxylate.

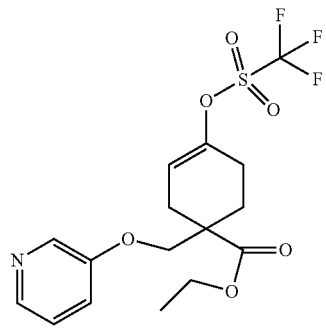 [SMILES: CCOC(=O)C1(COc2cccnc2)CC=C(OS(=O)(=O)C(F)(F)F)CC1]

The title compound was prepared in 51.9% yield, following the procedure described in general procedure A step 3, using ethyl 4-oxo-1-((pyridin-3-yloxy)methyl)cyclohexanecarboxylate as reactant. LCMS: m/e 410.00 (M+H)⁺, 1.983 min (LCMS Method 8). ¹H NMR (400 MHz, CHLOROFORM-d) δ 8.26-8.21 (m, 1H), 8.19-8.13 (m, 1H), 7.20-7.09 (m, 2H), 5.78-5.70 (m, 1H), 4.16-4.10 (m, 2H), 4.09-4.02 (m, 2H), 2.84-2.74 (m, 1H), 2.52-2.40 (m, 1H), 2.38-2.26 (m, 2H), 2.26-2.17 (m, 1H), 2.01-1.92 (m, 1H), 1.21-1.15 (m, 3H).

Step 4. Preparation of ethyl 1-((pyridin-3-yloxy)methyl)-4-(4,4,5,5-tetramethyl-1,3,2-dioxaborolan-2-yl)cyclohex-3-ene-1-carboxylate.

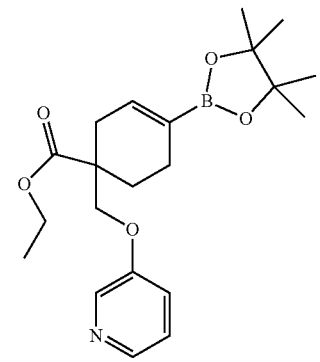 [SMILES: CCOC(=O)C1(COc2cccnc2)CC=C(B2OC(C)(C)C(C)(C)O2)CC1]

The title compound was prepared in 88% yield, following the procedure described in general procedure A step 4, using ethyl 1-((pyridin-3-yloxy)methyl)-4-(((trifluoromethyl)sulfonyl)oxy)cyclohex-3-enecarboxylate as reactant. LCMS: m/e 388.10 (M+H)⁺, 1.986 min (LCMS Method 8). ¹H NMR (400 MHz, CHLOROFORM-d) 8 8.20 (dd, J=2.4, 0.9 Hz, 1H), 8.13 (dd, J=4.0, 2.0 Hz, 1H), 7.18-7.10 (m, 2H), 6.52-6.45 (m, 1H), 4.16-3.95 (m, 4H), 2.71-2.60 (m, 1H), 2.26-2.03 (m, 3H), 1.96-1.79 (m, 2H), 1.20-1.18 (m, 12H), 1.14 (t, J=7.2 Hz, 3H).

Step 5. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-3-yloxy)methyl)cyclohex-3-ene-1-carboxylate and ethyl 4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-3-yloxy)methyl)cyclohex-3-enecarboxylate.

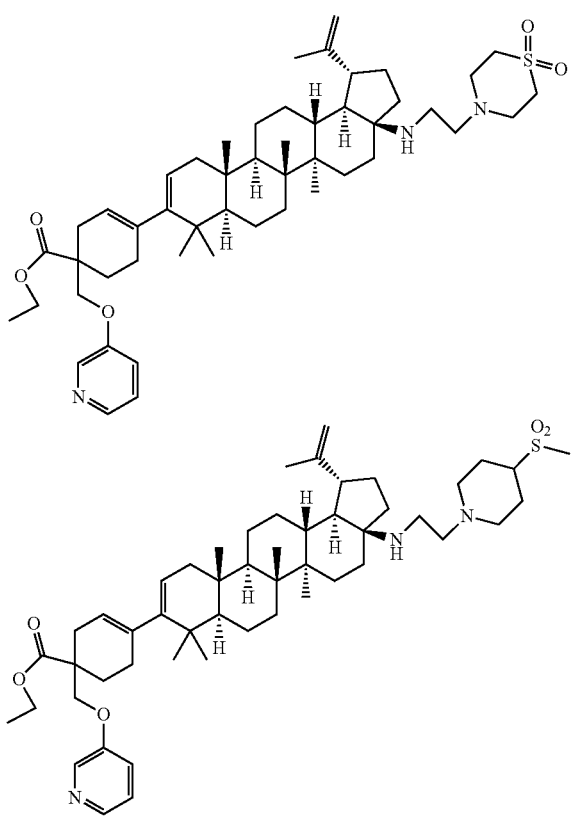

The title compounds were prepared in 26.4% and 28.4 yields respectively, following the procedure described in general procedure A step 5, using ethyl 1-((pyridin-3-yloxy)methyl)-4-(4,4,5,5-tetramethyl-1,3,2-dioxaborolan-2-yl)cyclohex-3-enecarboxylate as reactant.

For ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-3-yloxy)methyl)cyclohex-3-ene-1-carboxylate: LCMS: m/e 830.50 (M+H)$^+$, 2.363 min (LCMS Method 8). $^1$H NMR (400 MHz, CHLOROFORM-d) δ 8.28 (d, J=2.0 Hz, 1H), 8.21 (dd, J=4.0, 2.0 Hz, 1H), 7.23-7.16 (m, 2H), 5.35 (br. s., 1H), 5.17 (d, J=4.8 Hz, 1H), 4.72 (d, J=1.8 Hz, 1H), 4.59 (s, 1H), 4.15-4.09 (m, 4H), 3.14-2.96 (m, 8H), 2.91-2.48 (m, 6H), 1.68 (s, 3H), 1.05 (s, 3H), 2.29-1.00 (m, 30H), 0.97-0.89 (m, 9H), 0.86-0.81 (m, 3H).

For ethyl 4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-3-yloxy)methyl)cyclohex-3-enecarboxylate:
LCMS: m/e 858.55 (M+H)$^+$, 2.454 min (LCMS Method 8). $^1$H NMR (400 MHz, CHLOROFORM-d) δ 8.28 (d, J=1.8 Hz, 1H), 8.21 (dd, J=4.0, 1.8 Hz, 1H), 7.20-7.16 (m, 2H), 5.35 (br. s., 1H), 5.17 (d, J=4.8 Hz, 1H), 4.72 (d, J=1.8 Hz, 1H), 4.58 (s, 1H), 4.20-4.05 (m, 4H), 3.11 (t, J=8.5 Hz, 2H), 2.83 (s, 3H), 2.88-2.76 (m, 1H), 2.2.74-2.38 (m, 7H), 1.68 (s, 3H), 1.06 (s, 3H), 2.27-0.78 (m, 47H).

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-3-yloxy)methyl)cyclohex-3-enecarboxylic acid was prepared in 68.1% yield, following the procedure described in general procedure A step 6, using ethyl 4-41R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11,11b,12,13,13a,13b-octadecahydro-1H-cyclopenta[a]chrysen-9-yl)-1-((pyridin-3-yloxy)methyl)cyclohex-3-enecarboxylate as reactant. $^1$H NMR (400 MHz, CHLOROFORM-d) δ 8.32 (s, 1H), 8.21 (br. s., 1H), 7.23 (br. s., 2H), 5.37 (br. s., 1H), 5.18 (br. s., 1H), 4.71 (s, 1H), 4.60 (s, 1H), 4.23-4.08 (m, 2H), 3.16-2.99 (m, 8H), 2.89-2.57 (m, 6H), 2.33-1.79 (m, 9H), 1.68 (s, 3H), 1.11 (s, 3H), 0.99 (s, 3H), 0.96 (s, 3H), 0.93-0.92 (m, 3H), 0.86 (s, 3H), 1.75-0.81 (m, 18H). LC/MS: m/e 802.45 (M+H)$^+$, 2.346 min (LCMS Method 8).

Example 11

Preparation of 4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-3-yloxy)methyl)cyclohex-3-enecarboxylic acid.

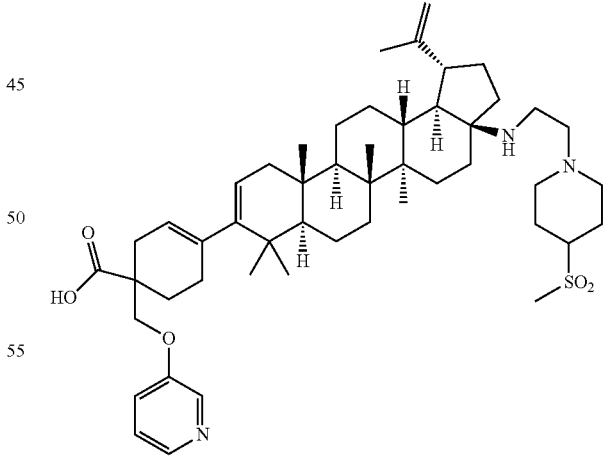

The title compound was prepared in 4.02% yield, following the procedure described in general procedure A step 6, using ethyl 4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin- 3-yloxy)methyl)cyclohex-3-enecarboxylate as reactant. LCMS: m/e 830.50 (M+H)⁺, 2.367 min (LCMS Method 8). ¹H NMR (400 MHz, CHLOROFORM-d) δ 8.31 (s, 1H), 8.20 (t, J=2.9 Hz, 1H), 7.22 (d, J=2.3 Hz, 2H), 5.37 (br. s., 1H), 5.18 (d, J=5.5 Hz, 1H), 4.76-4.67 (m, 1H), 4.59 (s, 1H), 4.16 (br. s., 2H), 3.13 (t, J=10.2 Hz, 2H), 2.92-2.59 (m, 9H), 2.48 (d, J=11.5 Hz, 1H), 2.31-1.78 (m, 15H), 1.68 (s, 3H), 1.12 (s, 3H), 0.98 (s, 3H), 0.96 (s, 3H), 0.93-0.92 (m, 3H), 0.85 (s, 3H), 1.71-0.77 (m, 18H).

Example 12

Preparation of 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((5-methylisothiazol-3-yl)oxy)methyl)cyclohex-3-ene-1-carboxylic acid.

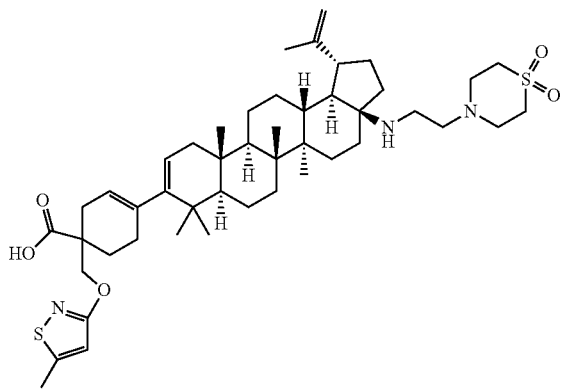

Step 1. Preparation of ethyl 8-((isothiazol-3-yloxy)methyl)-1,4-dioxaspirop.5]decane-8-carboxylate.

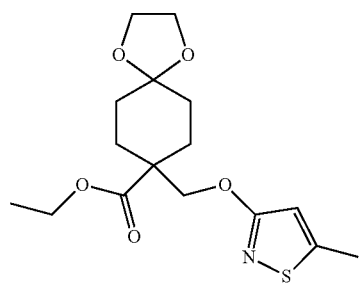 [SMILES: CCOC(=O)C1(COc2cc(C)sn2)CCC2(CC1)OCCO2]

The title compound was prepared in 69% yield, following the procedure described in general procedure A step 1-A, using 5-methylisothiazol-3-ol as reactant. ¹H NMR (400 MHz, CHLOROFORM-d) δ 6.32 (d, J=1.0 Hz, 1H), 4.37 (br. s, 2H), 4.17 (q, J=7.0 Hz, 2H), 3.95 (s, 4H), 2.47 (d, J=1.0 Hz, 3H), 2.28-2.21 (m, 2H), 1.76-1.63 (m, 6H), 1.23 (t, J=7.2 Hz, 3H). LC/MS: m/e 342.10 (M+H)⁺, 3.67 min (LCMS Method 11).

Step 2. Preparation of ethyl 1-(((5-methylisothiazol-3-yl)oxy)methyl)-4-oxocyclohexane-1-carboxylate.

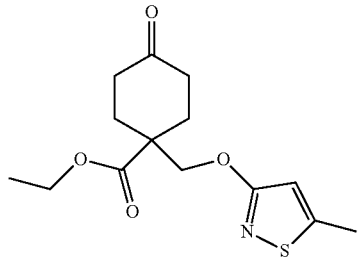 [SMILES: CCOC(=O)C1(COc2cc(C)sn2)CCC(=O)CC1]

The title compound was prepared in 87% yield, following the procedure described in general procedure A step 2, using ethyl 8-(((5-methylisothiazol-3-yl)oxy)methyl)-1,4-dioxaspiro[4.5]decane-8-carboxylate as reactant. ¹H NMR (400 MHz, CHLOROFORM-d) δ 6.34 (s, 1H), 4.48 (s, 2H), 4.26 (q, J=7.1 Hz, 2H), 2.59-2.45 (m, 4H), 2.45-2.36 (m, 2H), 1.94-1.82 (m, 2H), 1.29 (t, J=7.1 Hz, 3H). LC/MS: m/e 298.05 (M+H)⁺, 2.20 min (LCMS Method 8).

Step 3. Preparation of ethyl 1-(((5-methylisothiazol-3-yl)oxy)methyl)-4-(((trifluoromethyl)sulfonyl)oxy)cyclohex-3-ene-1-carboxylate.

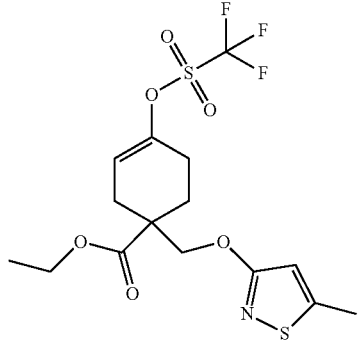 [SMILES: CCOC(=O)C1(COc2cc(C)sn2)CC=C(OS(=O)(=O)C(F)(F)F)CC1]

The title compound was prepared in 87% yield, following the procedure described in general procedure A step 3, using ethyl 1-(((5-methylisothiazol-3-yl)oxy)methyl)-4-oxocyclohexanecarboxylate as reactant. ¹H NMR (400 MHz, CHLOROFORM-d) δ 6.31 (s, 1H), 5.74 (br. s., 1H), 4.43 (d, J=10.3 Hz, 1H), 4.37 (d, J=10.0 Hz, 1H), 4.17 (q, J=7.2 Hz, 2H), 2.79 (dd, J=17.8, 2.8 Hz, 1H), 2.46 (s, 3H), 2.43-2.17 (m, 4H), 1.97-1.86 (m, 1H), 1.22 (t, J=7.3 Hz, 3H). LC/MS: m/e 430.2 (M+H)⁺, 2.20 min.

Step 4. Preparation of ethyl 1-(((5-methylisothiazol-3-yl)oxy)methyl)-4-(4,4,5,5-tetramethyl-1,3,2-dioxaborolan-2-yl)cyclohex-3-ene-1-carboxylate.

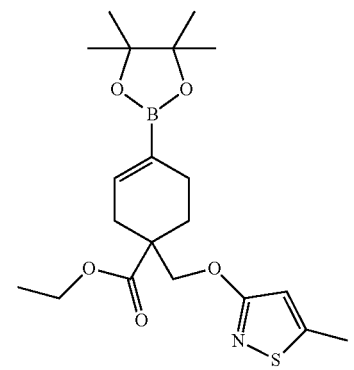 [SMILES: CCOC(=O)C1(COc2cc(C)sn2)CC=C(B2OC(C)(C)C(C)(C)O2)CC1]

The title compound was prepared in 32% yield, following the procedure described in general procedure A step 4, using ethyl 1-(((5-methylisothiazol-3-yl)oxy)methyl)-4-(((trifluoromethy)sulfonypoxy)cyclohex-3-enecarboxylate as reactant. $^1$H NMR (400 MHz, CHLOROFORM-d) δ 6.51-6.45 (m, 1H), 6.26 (d, J=1.0 Hz, 1H), 4.42-4.37 (m, 1H), 4.33-4.26 (m, 1H), 4.11 (q, J=7.0 Hz, 2H), 2.69-2.58 (m, 1H), 2.42 (d, J=1.0 Hz, 3H), 2.22-2.12 (m, 3H), 2.02 (s, 1H), 1.95-1.87 (m, 1H), 1.82-1.74 (m, 1H), 1.22 (d, J=2.0 Hz, 12H), 1.16 (t, J=7.2 Hz, 3H).

Step 5. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((5-methylisothiazol-3-yl)oxy)methyl)cyclohex-3-ene-1-carboxylate.

1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-methylisothiazol-3-yl)oxy)methyl)cyclohex-3-enecarboxylate as reactant. $^1$H NMR (400 MHz, CHLOROFORM-d) δ 6.36 (d, J=0.8 Hz, 1H), 5.37 (br. s., 1H), 5.30-5.10 (m, 1H), 4.79 (s, 1H), 4.72 (s, 1H), 4.51 (d, J=10.0 Hz, 1H), 4.45 (dd, J=10.0, 3.5 Hz, 1H), 3.39 (d, J=12.3 Hz, 1H), 3.28-2.87 (m, 11H), 2.86-2.57 (m, 2H), 2.49 (d, J=0.8 Hz, 3H), 2.31-1.83 (m, 12H), 1.83-1.67 (m, 2H), 1.71 (s, 3H), 1.67-1.23 (m, 13H), 1.16 (s, 3H), 1.13-1.02 (m, 2H), 1.06 (s, 3H), 0.97 (m, 3H), 0.93 (m, 3H), 0.88 (s, 3H). LC/MS: m/e 822.60 (M+H)$^+$, 2.83 min (LCMS Method 3).

Example 13

Preparation of 4-((1R,3aS,5aR,5bR,7aR,11aS,11bR,13aR,13bR)-3a-((2-(1,1-dioxidothiomorpholino)ethy-

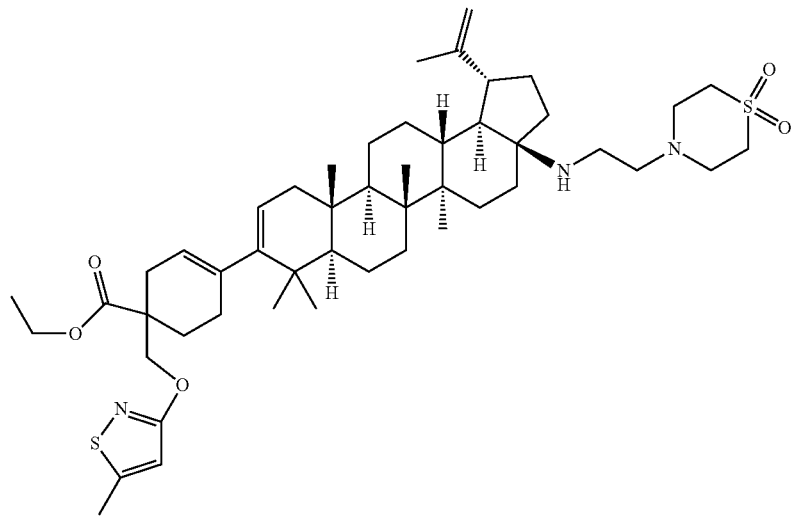

The title compound was prepared in 43% yield, following the procedure described in general procedure A step 5, using ethyl 1-(((5-methylisothiazol-3-yl)oxy)methyl)-4-(4,4,5,5-tetramethyl-1,3,2-dioxaborolan-2-yl)cyclohex-3-enecarboxylate as reactant. $^1$H NMR (400 MHz, CHLOROFORM-d) δ 6.30 (d, J=1.0 Hz, 1H), 5.33 (br. s., 1H), 5.17 (d, J=5.8 Hz, 1H), 4.70 (s, 2H), 4.58 (d, J=1.5 Hz, 2H), 4.49-4.43 (m, 1H), 4.42-4.36 (m, 1H), 4.17-4.12 (m, 2H), 3.13-2.96 (m, 8H), 2.73-2.62 (m, 2H), 2.62-2.52 (m, 2H), 2.50-2.41 (m, 1H), 2.46 (d, J=1.0 Hz, 3H), 2.22-2.10 (m, 8H), 2.10-1.97 (m, 3H), 1.96-1.65 (m, 4H), 1.68 (s, 3H), 1.64-1.37 (m, 7H), 1.37-1.23 (m, 6H), 1.20 (t, J=7.1 Hz, 3H), 1.16-0.98 (m, 5H), 0.98-0.81 (m, 9H). LC/MS: m/e 850.55 (M+H)$^+$, 2.99 min (LCMS Method 3).

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((5-methylisothiazol-3-yl)oxy)methyl)cyclohex-3-ene-1-carboxylic acid was prepared in 36% yield, following the procedure described in general procedure A step 6, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(proppamino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((1-methyl-1H-tetrazol-5-yl)oxy)methyl)cyclohex-3-ene-1-carboxylic acid.

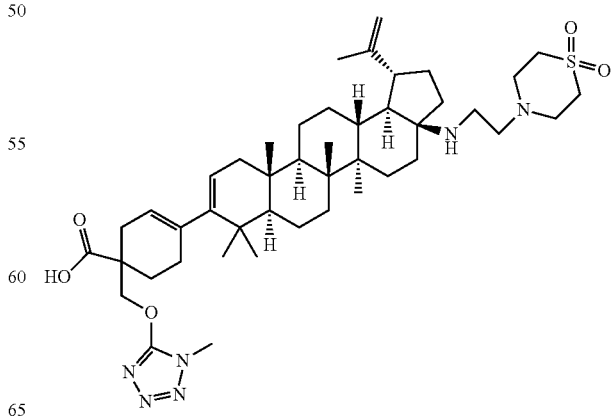

Step 1. Preparation of ethyl 8-(((1-methyl-1H-tetrazol-5-yl)oxy)methyl)-1,4-dioxaspiro[4.5]decane-8-carboxylate.

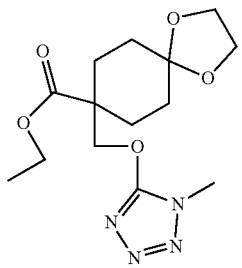 [SMILES: CCOC(=O)C1(COc2nnnn2C)CCC2(CC1)OCCO2]

The title compound was prepared in 82% yield, following the procedure described in general procedure A step 1-A, using 1-methyl-1H-tetrazol-5-ol as reactant. $^1$H NMR (400 MHz, CHLOROFORM-d) δ 4.57 (s, 2H), 4.18 (q, J=7.0 Hz, 2H), 3.97-3.92 (m, 4H), 3.77 (s, 3H), 2.29-2.21 (m, 1H), 2.18-2.10 (m, 1H), 1.76-1.63 (m, 6H), 1.24 (t, J=7.2 Hz, 3H). LC/MS: m/e 327.20 (M+H)$^+$, 2.15 min (LCMS Method 3).

Step 2. Preparation of ethyl 1-(((1-methyl-1H-tetrazol-5-yl)oxy)methyl)-4-oxocyclohexane-1-carboxylate.

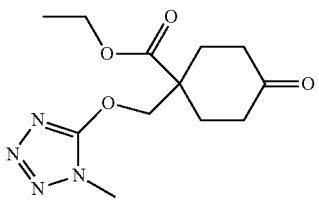 [SMILES: CCOC(=O)C1(COc2nnnn2C)CCC(=O)CC1]

The title compound was prepared in 91% yield, following the procedure described in general procedure A step 2, using ethyl 8-(((1-methyl-1H-tetrazol-5-yl)oxy)methyl)-1,4-dioxaspiro[4.5]decane-8-carboxylate as reactant. $^1$H NMR (400 MHz, CHLOROFORM-d) δ 4.67 (s, 2H), 4.27 (q, J=7.2 Hz, 2H), 3.79 (s, 3H), 2.61-2.36 (m, 6H), 1.92-1.75 (m, 2H), 1.28 (t, J=7.3 Hz, 3H). LC/MS: m/e 283.15 (M+H)$^+$, 3.01 min (LCMS Method 10).

Step 3. Preparation of ethyl 1-(((1-methyl-1H-tetrazol-5-yl)oxy)methyl)-4-(((trifluoromethyl)sulfonyl)oxy)cyclohex-3-ene-1-carboxylate.

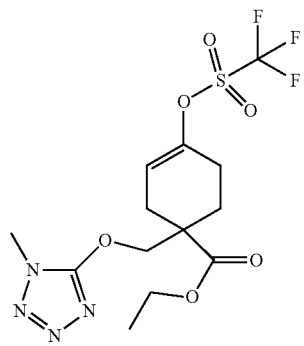 [SMILES: CCOC(=O)C1(COc2nnnn2C)CC=C(OS(=O)(=O)C(F)(F)F)CC1]

The title compound was prepared in 29% yield, following the procedure described in general procedure A step 3, using ethyl 1-(((1-methyl-1H-tetrazol-5-yl)oxy)methyl)-4-oxocyclohexanecarboxylate as reactant. $^1$H NMR (400 MHz, CHLOROFORM-d) δ 5.80-5.72 (m, 1H), 4.70-4.57 (m, 2H), 4.22-4.15 (m, 2H), 3.77 (s, 3H), 2.89-2.81 (m, 1H), 2.50-2.23 (m, 4H), 1.97-1.88 (m, 1H), 1.25 (t, J=7.2 Hz, 3H). LC/MS: m/e 415.25 (M+H)$^+$, 2.51 min (LCMS Method 3).

Step 4. Preparation of ethyl 1-(((1-methyl-1H-tetrazol-5-yl)oxy)methyl)-4-(4,4,5,5-tetramethyl-1,3,2-dioxaborolan-2-yl)cyclohex-3-ene-1-carboxylate.

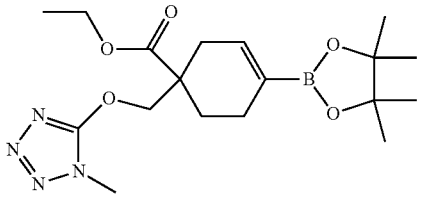 [SMILES: CCOC(=O)C1(COc2nnnn2C)CC=C(B2OC(C)(C)C(C)(C)O2)CC1]

The title compound was prepared in 90% yield, following the procedure described in general procedure A step 4, using ethyl 1-(((1-methyl-1H-tetrazol-5-yl)oxy)methyl)-4-(((trifluoromethyl)sulfonyl)oxy)cyclohex-3-enecarboxylate as reactant. $^1$H NMR (400 MHz, CHLOROFORM-d) δ 6.54-6.40 (m, 1H), 4.64 (d, J=9.8 Hz, 1H), 4.56 (d, J=9.8 Hz, 1H), 4.17-4.10 (m, 2H), 3.74 (s, 3H), 2.72-2.63 (m, 1H), 2.34-2.11 (m, 3H), 2.00-1.92 (m, 1H), 1.88-1.80 (m, 1H), 1.23 (s, 12H), 1.21 (t, J=7.2 Hz 3H). LC/MS: m/e 393.35 (M+H)$^+$, 4.06 min (LCMS Method 10).

Step 5. Preparation of ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-1H-tetrazol-5-yl)oxy)methyl)cyclohex-3-ene-1-carboxylate

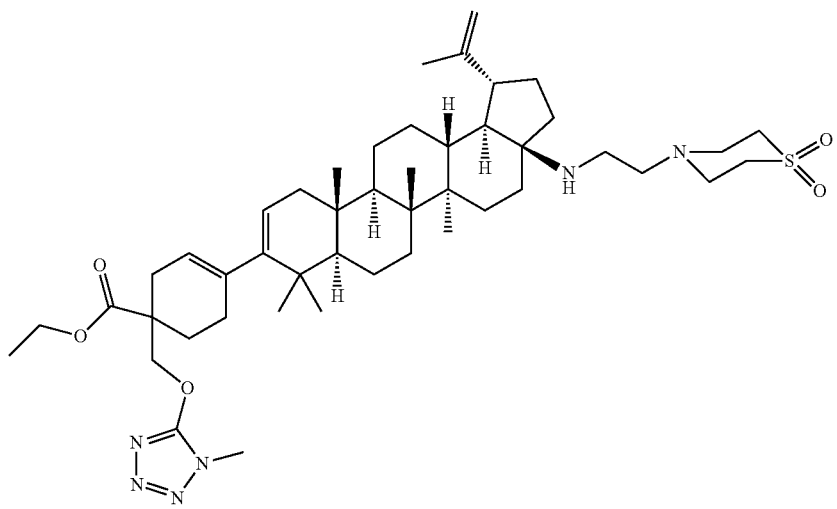

The title compound was prepared in 56% yield, following the procedure described in general procedure A step 5, using ethyl 1-(((1-methyl-1H-tetrazol-5-yl)oxy)methyl)-4-(4,4,5,5-tetramethyl-1,3,2-dioxaborolan-2-yl)cyclohex-3-enecarboxylate as reactant. $^1$H NMR (400 MHz, CHLOROFORM-d) δ 5.33 (br. s., 1H), 5.17 (d, J=5.8 Hz, 1H), 4.70 (d, J=2.0 Hz, 1H), 4.58 (d, J=1.3 Hz, 1H), 4.20-4.10 (m, 4H), 3.75 (s, 3H), 3.12-2.97 (m, 8H), 2.76-2.40 (m, 6H), 2.26-0.87 (m, 27H), 1.68 (s, 3H), 1.21 (t, J=7.2 Hz, 3H), 1.04 (s, 3H), 0.95 (s, 3H), 0.94-0.87 (m, 6H), 0.84 (s, 3H). LC/MS: m/e 835.60 (M+H)$^+$, 2.82 min (LCMS Method 3).

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-1H-tetrazol-5-yl)oxy)methyl)cyclohex-3-ene-1-carboxylic acid was prepared in 74% yield, following the procedure described in general procedure A step 6, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-methyl-1H-tetrazol-5-yl)oxy)methyl)cyclohex-3-enecarboxylate as reactant. $^1$H NMR (400 MHz, CHLOROFORM-d) δ 5.37 (br. s., 1H), 5.20 (t, J=6.4 Hz, 1H), 4.79-4.61 (m, 4H), 3.79 (s, 2H), 3.26-2.98 (m, 10H), 2.82 (d, J=9.3 Hz, 4H), 2.76-2.55 (m, 1H), 2.33-2.11 (m, 1H), 2.08 (s, 3H), 2.11-1.82 (m, 8H), 1.70 (s, 3H), 1.65-1.37 (m, 10H), 1.36-1.22 (m, 4H), 1.16 (s, 3H), 1.11-1.01 (m, 2H), 1.03 (s, 3H), 0.98 (s, 1.5H), 0.97 (s, 1.5H), 0.94 (s, 1.5H), 0.93 (s, 1.5H), 0.87 (s, 3H). LC/MS: m/e 807.60 (M+H)$^+$, 2.90 min (LCMS Method 3).

Example 14

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-oxo-4,5-dihydro-1,2,4-thiadiazol-3-yl)oxy)methyl)cyclohex-3-ene-1-carboxylic acid.

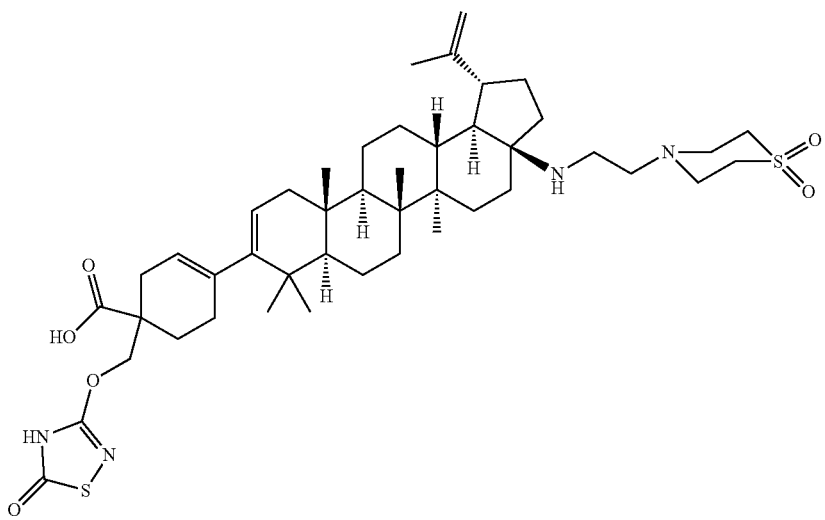

Step 1. Preparation of ethyl 8-(((5-(methylthio)-1,2,4-thiadiazol-3-yl)oxy)methyl)-1,4-dioxaspiro[4.5]decane-8-carboxylate.

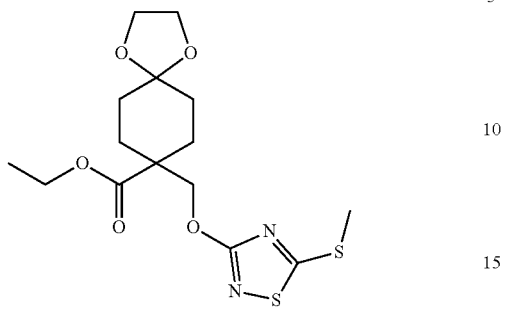

The title compound was prepared in 90% yield, following the procedure described in general procedure A step 1-A, using 5-(methylthio)-1,2,4-thiadiazol-3-ol as reactant. $^1$H NMR (400 MHz, CHLOROFORM-d) δ 4.45 (s, 2H), 4.17 (q, J=7.0 Hz, 2H), 3.98-3.91 (m, 4H), 2.68 (s, 3H), 2.31-2.21 (m, 2H), 1.77-1.66 (m, 6H), 1.24 (t, J=7.2 Hz, 3H). LC/MS: m/e 375.10 (M+H)$^+$, 2.50 min (LCMS Method 3).

Step 2. Preparation of ethyl 1-(((5-(methylthio)-1,2,4-thiadiazol-3-yl)oxy)methyl)-4-oxocyclohexanecarboxylate.

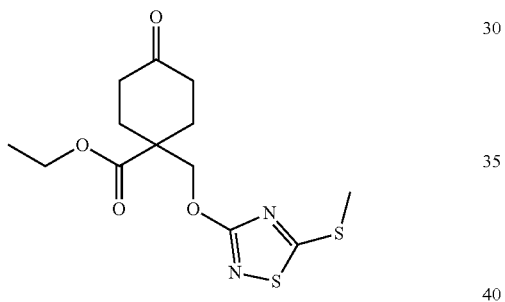

The title compound was prepared in 100% yield, following the procedure described in general procedure A step 2, using ethyl 8-(((5-(methylthio)-1,2,4-thiadiazol-3-yl)oxy)methyl)-1,4-dioxaspiro[4.5]decane-8-carboxylate as reactant. $^1$H NMR (400 MHz, CHLOROFORM-d) δ 4.53 (s, 2H), 4.25 (q, J=7.1 Hz, 2H), 2.69 (s, 3H), 2.58-2.48 (m, 4H), 2.44-2.35 (m, 2H), 1.96-1.86 (m, 2H), 1.28 (t, J=7.2 Hz, 3H). LC/MS: m/e 331.05 (M+H)$^-$, 2.32 min (LCMS Method 3).

Step 3. Preparation of ethyl 1-(((5-(methylthio)-1,2,4-thiadiazol-3-yl)oxy)methyl)-4-(((trifluoromethyl)sulfonyl)oxy)cyclohex-3-ene-1-carboxylate.

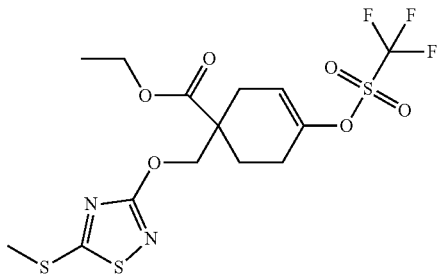 [SMILES: CCOC(=O)C1(COc2nsc(SC)n2)CC=C(OS(=O)(=O)C(F)(F)F)CC1]

The title compound was prepared in 55% yield, following the procedure described in general procedure A step 3, using ethyl 1-(((5-(methylthio)-1,2,4-thiadiazol-3-yl)oxy)methyl)-4-oxocyclohexanecarboxylate as reactant. $^1$H NMR (400 MHz, CHLOROFORM-d) δ 5.74 (td, J=3.1, 1.8 Hz, 1H), 4.50 (d, J=10.3 Hz, 1H), 4.45 (d, J=10.3 Hz, 1H), 4.15 (q, J=7.0 Hz, 2H), 2.84-2.75 (m, 1H), 2.65 (s, 3H), 2.51-2.19 (m, 4H), 2.02-1.94 (m, 1H), 1.21 (t, J=7.2 Hz, 3H).

Step 4. Preparation of ethyl 1-(((5-(methylthio)-1,2,4-thiadiazol-3-yl)oxy)methyl)-4-(4,4,5,5-tetramethyl-1,3,2-dioxaborolan-2-yl)cyclohex-3-enecarboxylate.

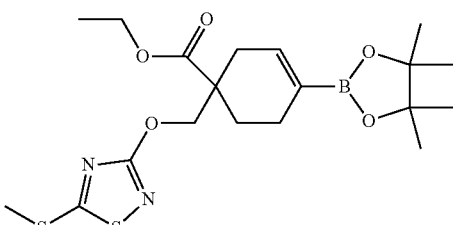

The title compound was prepared in 39% yield, following the procedure described in general procedure A step 4 for 7 h, using ethyl 1-(((5-(methylthio)-1,2,4-thiadiazol-3-yl)oxy)methyl)-4-(((trifluoromethyl)sulfonyl)oxy)cyclohex-3-enecarboxylate as reactant. $^1$H NMR (400 MHz, CHLOROFORM-d) δ 6.50 (dt, J=3.5, 1.8 Hz, 1H), 4.49 (d, J=10.0 Hz, 1H), 4.40 (d, J=10.0 Hz, 1H), 4.11 (q, J=7.0 Hz, 2H), 2.72-2.64 (m, 1H), 2.64 (s, 3H), 2.28-2.16 (m, 3H), 1.98-1.81 (m, 2H), 1.23 (s, 12H), 1.17 (t, J=7.2 Hz, 3H). LC/MS: m/e 441.25 (M+H)$^+$, 2.92 min (LCMS Method 3).

Step 5. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-(methylthio)-1,2,4-thiadiazol-3-yl)oxy)methyl)cyclohex-3-enecarboxylate.

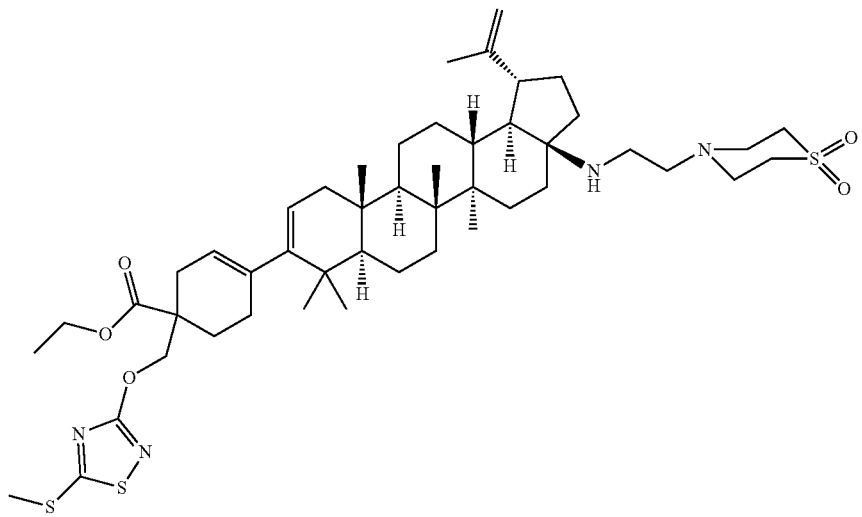

The title compound was prepared, following the procedure described in general procedure A step 5 at 90° C. for 4 h, using ethyl 1-(((5-(methylthio)-1,2,4-thiadiazol-3-yl)oxy)methyl)-4-(4,4,5,5-tetramethyl-1,3,2-dioxaborolan-2-yl)cyclohex-3-enecarboxylate as reactant. LC/MS: m/e 883.55 (M+H)$^+$, 3.11 min (LCMS Method 3).

Step 6. 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-oxo-4,5-dihydro-1,2,4-thiadiazol-3-yl)oxy)methyl)cyclohex-3-ene-1-carboxylic acid was prepared in 10% yield, following the procedure described in general procedure A step 6, using ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-(methylthio)-1,2,4-thiadiazol-3-yl)oxy)methyl)cyclohex-3-enecarboxylate as reactant. $^1$H NMR (400 MHz, CHLOROFORM-d) δ 4.80 (s, 1H), 4.76-4.69 (m, 1H), 4.60-4.50 (m, 2H), 3.35-3.01 (m, 10H), 3.01-2.78 (m, 4H), 2.67-2.51 (m, 4H), 2.51-2.36 (m, 5H), 2.36-2.14 (m, 2H), 1.81-1.75 (m, 2H), 1.72 (s, 3H), 1.75-1.68 (m, 2H), 1.68-1.34 (m, 11H), 1.27 (s, 3H), 1.26 (s, 3H), 1.20 (s, 3H), 1.08 (s, 3H), 1.13-1.03 (m, 4H), 0.94 (s, 3H). LC/MS: m/e 825.50 (M+H)$^+$, 2.78 min (LCMS Method 3).

Example 15

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((thiazol-2-yloxy)methyl)cyclohex-3-ene-1-carboxylic acid.

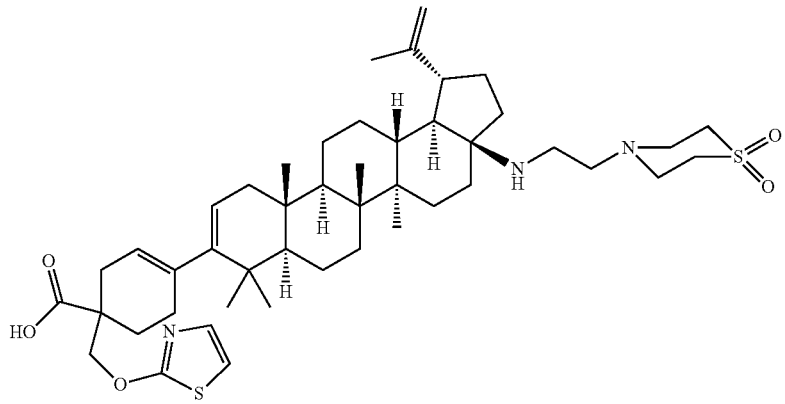

Step 1: Preparation of ethyl 8-((thiazol-2-yloxy)methyl)-1,4-dioxaspiro[4.5]decane-8-carboxylate.

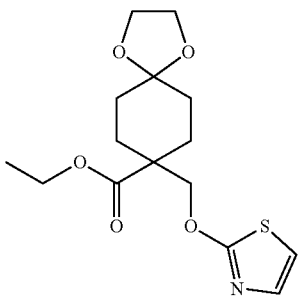 [SMILES: CCOC(=O)C1(COc2nccs2)CCC2(CC1)OCCO2]

The title compound was prepared in 35% yield, following the procedure described in general procedure A step 1-A, using thiazol-2-ol as reactant. $^1$H NMR (400 MHz, CHLOROFORM-d) δ 6.39 (d, J=5.5 Hz, 1H), 6.03 (d, J=5.3 Hz, 1H), 4.09 (q, J=7.3 Hz, 2H), 3.86 (s, 4H), 3.76 (s, 2H), 2.11-2.03 (m, 2H), 1.68-1.46 (m, 6H), 1.20 (t, J=7.2 Hz, 3H). LC/MS m/z 328.10 (M+H)$^+$, 2.09 min (LCMS Method 3).

Step 2. Preparation of ethyl 4-oxo-1-((thiazol-2-yloxy)methyl)cyclohexane-1-carboxylate.

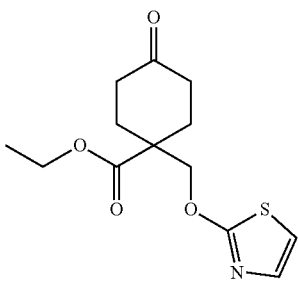 [SMILES: CCOC(=O)C1(COc2nccs2)CCC(=O)CC1]

The title compound was prepared in 80% yield, following the procedure described in general procedure A step 2, using ethyl 8-((thiazol-2-yloxy)methyl)-1,4-dioxaspiro[4.5]decane-8-carboxylate as reactant. $^1$H NMR (400 MHz, CHLOROFORM-d) □ 6.47 (d, J=5.5 Hz, 1H), 6.13 (d, J=5.5 Hz, 1H), 4.28 (q, J=7.0 Hz, 2H), 3.97 (s, 2H), 2.55-2.35 (m, 6H), 1.89-1.77 (m, 2H), 1.34 (t, J=7.2 Hz, 3H). MS m/z 284.20 (M+H)+, 1.72 min (LCMS Method 3).

Step 3. Preparation of ethyl 1-((thiazol-2-yloxy)methyl)-4-(((trifluoromethyl)sulfonyl)oxy)cyclohex-3-ene-1-carboxylate.

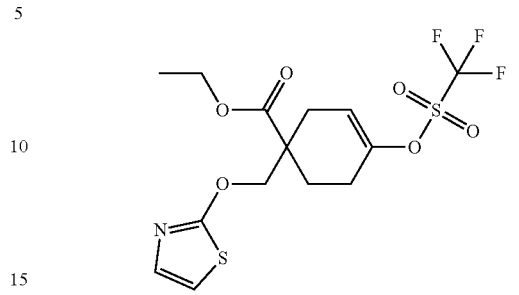

The title compound was prepared in 22% yield as an oil, following the procedure described in general procedure A step 3, using ethyl 4-oxo-1-((thiazol-2-yloxy)methyl)cyclohexane-1-carboxylate as reactant. $^1$H NMR (400 MHz, CHLOROFORM-d) δ 6.43 (d, J=5.5 Hz, 1H), 6.11 (d, J=5.3 Hz, 1H), 5.73 (td, J=3.4, 1.5 Hz, 1H), 4.16 (qd, J=7.2, 2.6 Hz, 2H), 3.90 (s, 2H), 2.74-2.64 (m, 1H), 2.45-2.39 (m, 2H), 2.33-2.20 (m, 2H), 1.85-1.76 (m, 1H), 1.25 (t, J=7.2 Hz, 3H). MS m/z 416.20 (M+H)$^-$, 2.75 min (LCMS Method 3).

Step 4. Preparation of ethyl 4-(4,4,5,5-tetramethyl-1,3,2-dioxaborolan-2-yl)-1-((thiazol-2-yloxy)methyl)cyclohex-3-ene-1-carboxylate.

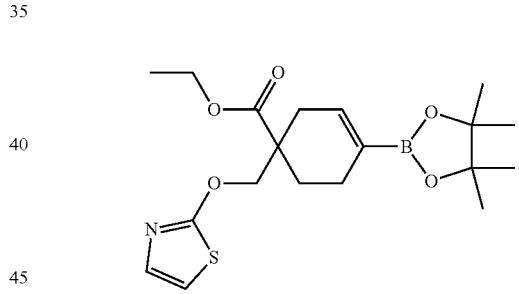

The title compound was prepared in 71% yield, following the procedure described in general procedure A step 4, using ethyl 1-((thiazol-2-yloxy)methyl)-4-(((trifluoromethyl)sulfonyl)oxy)cyclohex-3-enecarboxylate as reactant. $^1$H NMR (400 MHz, CHLOROFORM-d) δ 6.49-6.46 (m, 1H), 6.45 (d, J=5.3 Hz, 1H), 6.06 (d, J=5.3 Hz, 1H), 4.12 (qd, J=7.2, 2.6 Hz, 2H), 3.86 (s, 2H), 2.63-2.54 (m, 1H), 2.31-1.99 (m, 4H), 1.60 (ddd, J=13.0, 9.0, 5.6 Hz, 1H), 1.23 (s, 12H), 1.22 (t, J=7.2 Hz, 3H). MS m/z 394.30 (M+H)$^+$, 2.65 min (LCMS Method 3).

Step 5. Preparation of ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-((thiazol-2-yloxy)methyl)cyclohex-3-enecarboxylate.

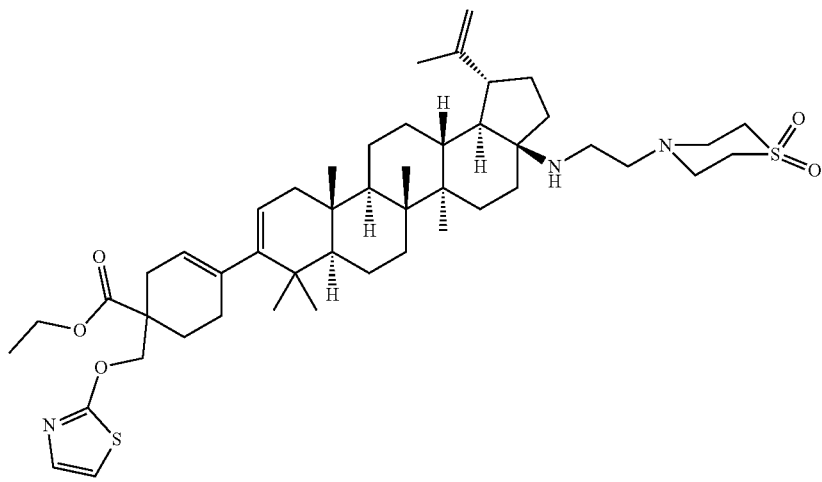

The title compound was prepared in 30% yield as a solid, following the procedure described in general procedure A step 5, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and ethyl 4-(4,4,5,5-tetramethyl-1,3,2-dioxaborolan-2-yl)-1-((thiazol-2-yloxy)methyl)cyclohex-3-enecarboxylate as reactants. $^1$H NMR (400 MHz, CHLOROFORM-d) δ 6.46 (d, J=5.5 Hz, 1H), 6.06 (d, J=5.3 Hz, 1H), 5.30 (br. s., 1H), 5.18-5.13 (m, 1H), 4.70 (d, J=2.0 Hz, 1H), 4.58 (s, 1H), 4.11 (q, J=7.3 Hz, 2H), 3.96-3.84 (m, 2H), 3.11-2.97 (m, 8H), 2.74-2.42 (m, 6H), 2.22-0.85 (m, 27H), 1.67 (s, 3H), 1.25 (t, J=7.2 Hz, 3H), 1.04 (s, 3H), 0.94 (s, 3H), 0.93-0.86 (m, 6H), 0.83 (s, 3H). MS m/z 836.65 (M+H)$^+$, 2.98 min (LCMS Method 3).

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((thiazol-2-yloxy)methyl)cyclohex-3-ene-1-carboxylic acid was prepared in 68% yield as a solid, following the procedure described in general procedure A step 6, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((thiazol-2-yloxy)methyl)cyclohex-3-enecarboxylate as reactant. $^1$H NMR (400 MHz, CHLOROFORM-d) δ 6.70 (d, J=5.5 Hz, 1H), 6.08 (d, J=5.5 Hz, 1H), 5.42-5.28 (m, 1H), 5.20 (dd, J=16.2, 4.9 Hz, 1H), 4.78 (s, 1H), 4.69 (s, 1H), 4.19-4.01 (m, 1H), 4.02-3.85 (m, 1H), 3.29 (d, J=15.8 Hz, 1H), 3.24-2.95 (m, 7H), 2.85 (d, J=10.8 Hz, 2H), 2.61 (d, J=16.6 Hz, 1H), 2.43 (d, J=15.1 Hz, 1H), 2.31-2.12 (m, 8H), 2.12-1.85 (m, 6H), 1.85-1.75 (m, 1H), 1.70 (s, 3H), 1.75-1.60 (m, 2H), 1.59-1.21 (m, 12H), 1.17 (s, 3H), 1.13-1.01 (m, 2H), 1.04 (s, 3H), 0.98 (s, 3H), 0.96 (s, 3H), 0.86 (s, 3H). LC/MS: m/e 808.55 (M+H)$^+$, 1.832 min (LCMS Method 3).

Example 16

Preparation of 4-((1R,3aS,5aR,5bR,7aR,11aS,11bR,13aR,13bR)-3a-((2-(1,1-dioxidothiomorpholino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-phenyl-1H-1,2,3-triazol-5-yl)oxy)methyl)cyclohex-3-ene-1-carboxylic acid.

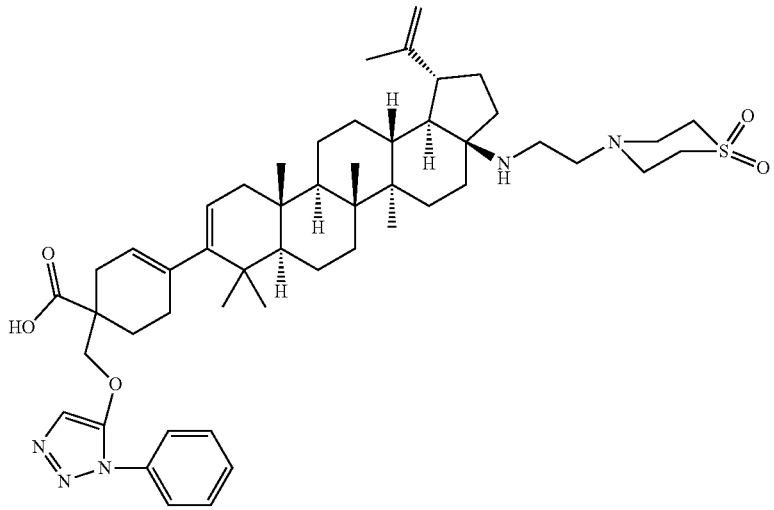

Step 1. Preparation of ethyl 8-(((1-phenyl-1H-1,2,3-triazol-5-yl)oxy)methyl)-1,4-dioxaspiro[4.5]decane-8-carboxylate.

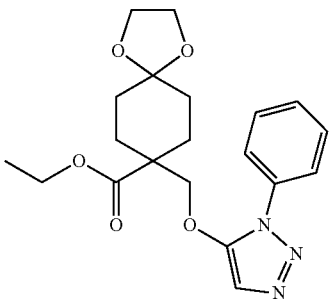 [SMILES: CCOC(=O)C1(COc2cnnn2-c2ccccc2)CCC2(CC1)OCCO2]

The title compound was prepared following the procedure described in general procedure A step 1-A, using 1-phenyl-1H-1,2,3-triazol-5-ol as reactant. This material was carried forward to the next step without purification. LC/MS: m/e 388.20 (M+H)⁺, 2.32 min (LCMS Method 3).

Step 2. Preparation of ethyl 4-oxo-1-(((1-phenyl-1H-1,2,3-triazol-5-yl)oxy)methyl)cyclohexanecarboxylate.

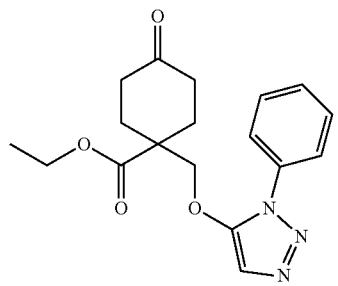 [SMILES: CCOC(=O)C1(COc2cnnn2-c2ccccc2)CCC(=O)CC1]

The title compound was prepared in 9% yield, following the procedure described in general procedure A step 2, using ethyl 8-(((1-phenyl-1H-1,2,3-triazol-5-yl)oxy)methyl)-1,4-dioxaspiro[4.5]decane-8-carboxylate as reactant. ¹H NMR (400 MHz, CHLOROFORM-d) δ 7.66-7.59 (m, 2H), 7.53-7.45 (m, 1H), 7.45-7.36 (m, 2H), 7.20 (s, 1H), 4.22 (s, 2H), 4.15 (q, J=7.1 Hz, 2H), 2.53-2.42 (m, 4H), 2.40-2.30 (m, 2H), 1.83-1.71 (m, 2H), 1.15 (t, J=7.2 Hz, 3H). LC/MS: m/e 388.20 (M+H)⁺, 2.32 min (LCMS Method 3).

Step 3. Preparation of ethyl 1-(((1-phenyl-1H-1,2,3-triazol-5-yl)oxy)methyl)-4-(((trifluoromethyl)sulfonyl)oxy)cyclohex-3-enecarboxylate.

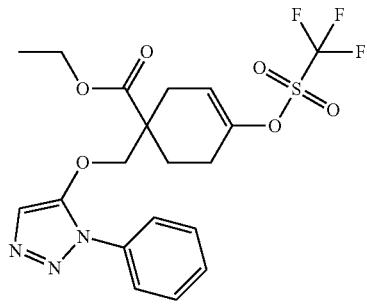 [SMILES: CCOC(=O)C1(COc2cnnn2-c2ccccc2)CC=C(OS(=O)(=O)C(F)(F)F)CC1]

The title compound was prepared in 144% yield, following the procedure described in general procedure A step 3, using ethyl 4-oxo-1-(((1-phenyl-1H-1,2,3-triazol-5-yl)oxy)methyl)cyclohexanecarboxylate as reactant. ¹H NMR (400 MHz, CHLOROFORM-d) δ 7.69-7.63 (m, 2H), 7.54-7.48 (m, 2H), 7.46-7.40 (m, 1H), 7.22 (s, 1H), 5.80-5.75 (m, 1H), 4.29 (d, J=9.0 Hz, 1H), 4.22 (d, J=8.8 Hz, 1H), 4.17-4.11 (m, 2H), 2.87-2.79 (m, 1H), 2.56-2.44 (m, 1H), 2.42-2.22 (m, 3H), 1.97-1.89 (m, 1H), 1.17 (t, J=7.2 Hz, 3H). LC/MS: m/e 476.25 (M+H)⁺, 2.65 min (LCMS Method 3).

Step 4. Preparation of ethyl 1-(((1-phenyl-1H-1,2,3-triazol-5-yl)oxy)methyl)-4-(4,4,5,5-tetramethyl-1,3,2-dioxaborolan-2-yl)cyclohex-3-enecarboxylate.

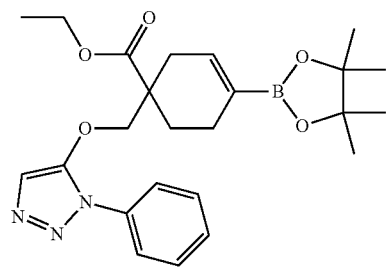 [SMILES: CCOC(=O)C1(COc2cnnn2-c2ccccc2)CC=C(B2OC(C)(C)C(C)(C)O2)CC1]

The title compound was prepared in 91% yield as an oil, following the procedure described in general procedure A step 4, using ethyl 1-(((1-phenyl-1H-1,2,3-triazol-5-yl)oxy)methyl)-4-(((trifluoromethyl)sulfonyl)oxy)cyclohex-3-enecarboxylate as reactant. ¹H NMR (400 MHz, CHLOROFORM-d) δ 7.68-7.63 (m, 2H), 7.50-7.43 (m, 2H), 7.41-7.35 (m, 1H), 7.19 (s, 1H), 6.49 (dt, J=3.5, 1.8 Hz, 1H), 4.25 (d, J=8.8 Hz, 1H), 4.19 (d, J=8.8 Hz, 1H), 4.08 (qd, J=7.1, 1.0 Hz, 2H), 2.69-2.60 (m, 1H), 2.28-2.05 (m, 3H), 1.98-1.90 (m, 1H), 1.88-1.81 (m, 1H), 1.23 (s, 12H), 1.12 (t, J=7.2 Hz, 3H). LC/MS: m/e 454.35 (M+H)⁺, 2.63 min (LCMS Method 3).

Step 4. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-phenyl-1H-1,2,3-triazol-5-yl)oxy)methyl)cyclohex-3-enecarboxylate.

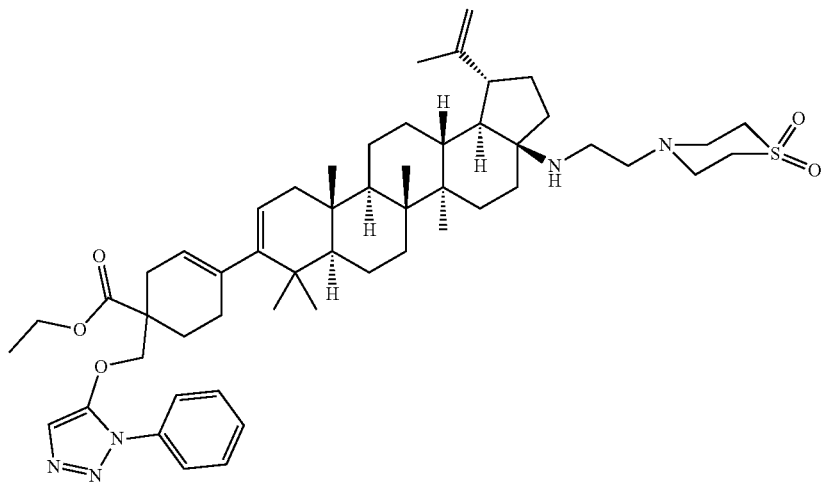

4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((1-phenyl-1H-1,2,3-triazol-5-yl)oxy)methyl)cyclohex-3-ene-1-carboxylic acid was prepared in 58% yield as a solid, following the procedure described in general procedure A step 5, using ethyl 1-(((1-phenyl-1H-1,2,3-triazol-5-yl)oxy)methyl)-4-(4,4,5,5-tetramethyl-1,3,2-dioxaborolan-2-yl)cyclohex-3-enecarboxylate as reactant. $^1$H NMR (400 MHz, CHLOROFORM-d) δ 7.71-7.65 (m, 2H), 7.51-7.44 (m, 2H), 7.41-7.35 (m, 1H), 7.19 (s, 1H), 5.32 (br. s., 1H), 5.15 (d, J=4.8 Hz, 1H), 4.68 (d, J=2.0 Hz, 1H), 4.57 (s, 1H), 4.30-4.20 (m, 2H), 4.09 (q, J=7.3 Hz, 2H), 3.09-2.96 (m, 8H), 2.71-2.38 (m, 6H), 2.25-0.86 (m, 27H), 1.66 (s, 3H), 1.14 (t, J=7.2 Hz, 3H), 1.03 (s, 3H), 0.94 (s, 3H), 0.93-0.87 (m, 6H), 0.83 (s, 3H).

Step 6. The title compound was prepared in 20% yield as a solid, following the procedure described in general procedure A step 5, using ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((1-phenyl-1H-1,2,3-triazol-5-yl)oxy)methyl)cyclohex-3-enecarboxylate as reactant. $^1$H NMR (400 MHz, CHLOROFORM-d) δ 7.79-7.70 (m, 2H), 7.53-7.46 (m, 2H), 7.43-7.37 (m, 1H), 7.26-7.22 (m, 1H), 5.36 (br. s., 1H), 5.18 (t, J=5.5 Hz, 1H), 4.70 (s, 1H), 4.61 (s, 1H), 4.38-4.23 (m, 2H), 3.09-2.92 (m, 8H), 2.90-2.80 (m, 2H), 2.78-2.54 (m, 4H), 2.31-2.10 (m, 4H), 2.04-1.80 (m, 6H), 1.73 (d, J=11.3 Hz, 1H), 1.67 (s, 3H), 1.54 (d, J=17.8 Hz, 3H), 1.49-1.35 (m, 6H), 1.35-1.15 (m, 5H), 1.11 (s, 3H), 1.14-1.02 (m, 2H), 1.00 (s, 3H), 0.97-0.94 (m, 1H), 0.96 (s, 3H), 0.93-0.92 (m, 3H), 0.85 (s, 3H). LC/MS: m/e 868.65 (M+H)$^+$, 2.83 min (LCMS Method 3).

Example 17

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-isopropyl-1H-1,2,3-triazol-5-yl)oxy)methyl)cyclohex-3-ene-1-carboxylic acid.

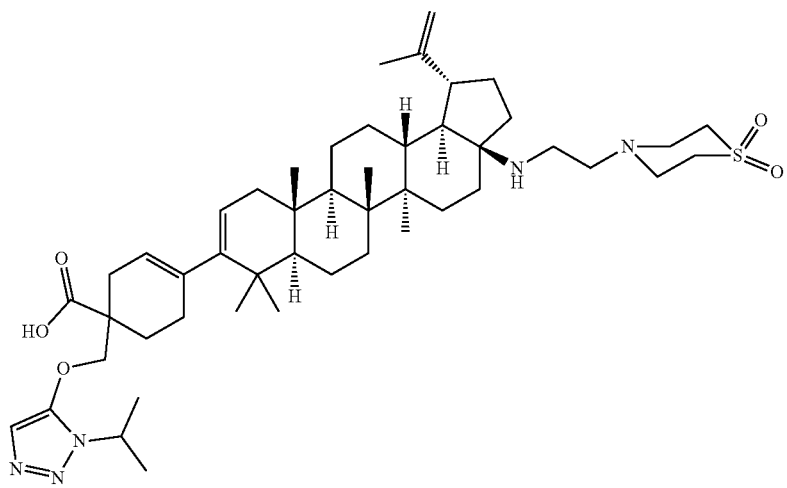

Step 1. Preparation of ethyl 8-(((1-isopropyl-1H-1,2,3-triazol-5-yl)oxy)methyl)-1,4-dioxaspiro[4.5]decane-8-carboxylate.

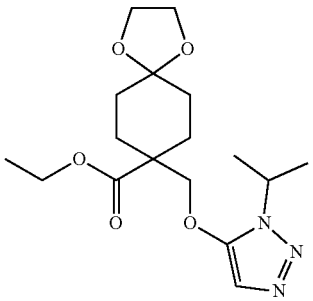 [SMILES: CCOC(=O)C1(COc2cnnn2C(C)C)CCC2(CC1)OCCO2]

The title compound was prepared in 43% yield as a semi-solid, following the procedure described in general procedure A step 1-B at 105° C., using 1-isopropyl-1H-1,2,3-triazol-5-ol as reactant. $^1$H NMR (400 MHz, CHLOROFORM-d) δ 7.06 (s, 1H), 4.59 (spt, J=6.8 Hz, 1H), 4.18 (q, J=7.2 Hz, 2H), 4.08 (s, 2H), 4.00-3.91 (m, 4H), 2.33-2.24 (m, 2H), 1.76-1.65 (m, 6H), 1.51 (d, J=6.8 Hz, 6H), 1.24 (t, J=7.2 Hz, 3H). LC/MS: m/e 354.30 (M+H)$^+$, 3.33 min (LCMS Method 11).

Step 2. Preparation of ethyl 1-(((1-isopropyl-1H-1,2,3-triazol-5-yl)oxy)methyl)-4-oxocyclohexane-1-carboxylate.

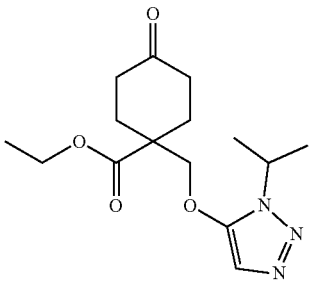 [SMILES: CCOC(=O)C1(COc2cnnn2C(C)C)CCC(=O)CC1]

The title compound was prepared in 91% yield as an oil, following the procedure described in general procedure A step 2, using ethyl 8-(((1-isopropyl-1H-1,2,3-triazol-5-yl)oxy)methyl)-1,4-dioxaspiro[4.5]decane-8-carboxylate as reactant. $^1$H NMR (400 MHz, CHLOROFORM-d) δ 7.02 (s, 1H), 4.50 (spt, J=6.8 Hz, 1H), 4.17 (q, J=7.0 Hz, 2H), 4.11 (s, 2H), 2.52-2.40 (m, 4H), 2.38-2.28 (m, 2H), 1.82-1.71 (m, 2H), 1.43 (d, J=7.0 Hz, 6H), 1.19 (t, J=7.2 Hz, 3H). LC/MS: m/e 354.30 (M+H)$^+$, 1.96 min (LCMS Method 3).

Step 3. Preparation of ethyl 1-(((1-isopropyl-1H-1,2,3-triazol-5-yl)oxy)methyl)-4-((((trifluoromethyl)sulfonyl)oxy)cyclohex-3-enecarboxylate.

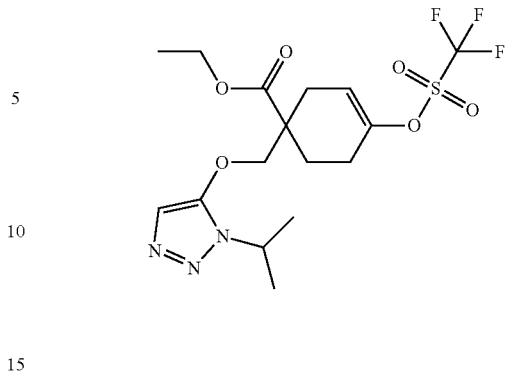

The title compound was prepared in 97% yield as an oil, following the procedure described in general procedure A step 3, using ethyl 1-(((1-isopropyl-1H-1,2,3-triazol-5-yl)oxy)methyl)-4-oxocyclohexanecarboxylate as reactant. $^1$H NMR (400 MHz, CHLOROFORM-d) δ 7.04 (s, 1H), 5.79-5.73 (m, 1H), 4.53 (spt, J=6.8 Hz, 1H), 4.19-4.04 (m, 4H), 2.88-2.76 (m, 1H), 2.55-2.21 (m, 4H), 1.92 (ddd, J=13.7, 7.9, 6.3 Hz, 1H), 1.47 (d, J=6.8 Hz, 6H), 1.20 (t, J=7.2 Hz, 3H). $^{19}$F NMR (376 MHz, CHLOROFORM-d) □-73.94 (s, 3F). LC/MS: m/e 442.20 (M+H)$^+$, 2.64 min (LCMS Method 3).

Step 4. Preparation of ethyl 1-(((1-isopropyl-1H-1,2,3-triazol-5-yl)oxy)methyl)-4-(4,4,5,5-tetramethyl-1,3,2-dioxaborolan-2-yl)cyclohex-3-enecarboxylate.

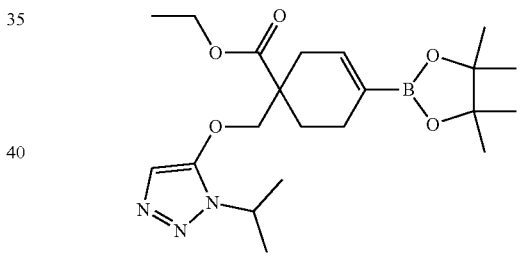

The title compound was prepared in 100% yield, following the procedure described in general procedure A step 4, using ethyl 1-(((1-isopropyl-1H-1,2,3-triazol-5-yl)oxy)methyl)-4-(((trifluoromethypsulfonypoxy)cyclohex-3-enecarboxylate as reactant. $^1$H NMR (400 MHz, CHLOROFORM-d) δ 7.02 (s, 1H), 6.48 (dt, J=3.3, 1.7 Hz, 1H), 4.53 (spt, J=6.8 Hz, 1H), 4.16-4.06 (m, 4H), 2.69-2.60 (m, 1H), 2.28-2.05 (m, 3H), 1.98-1.81 (m, 2H), 1.46 (dd, J=6.8, 2.3 Hz, 6H), 1.22 (s, 12H), 1.17 (t, J=7.2 Hz, 3H). LC/MS: m/e 420.30 (M+H)$^+$, 2.65 min (LCMS Method 3).

Step 5. Preparation of ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-isopropyl-1H-1,2,3-triazol-5-yl)oxy)methyl)cyclohex-3-enecarboxylate.

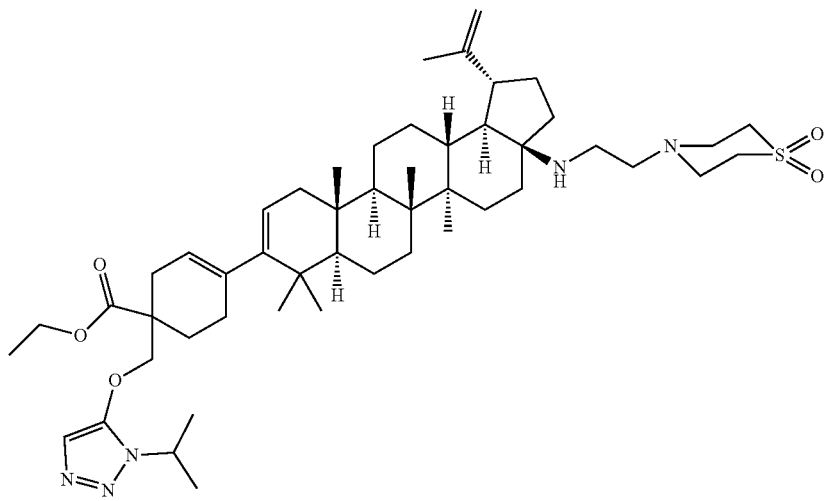

The title compound was prepared in 100% yield, following the procedure described in general procedure A step 5, using ethyl 1-(((1-isopropyl-1H-1,2,3-triazol-5-yl)oxy)methyl)-4-(4,4,5,5-tetramethyl-1,3,2-dioxaborolan-2-yl)cyclohex-3-enecarboxylate as reactant. $^1$H NMR (400 MHz, CHLOROFORM-d) δ 7.05 (s, 1H), 5.33 (br. s., 1H), 5.16 (d, J=4.8 Hz, 1H), 4.68 (s, 1H), 4.56 (s, 1H), 4.56 (spt, J=6.7 Hz, 1H), 4.20-4.09 (m, 4H), 3.11-2.93 (m, 8H), 2.71-2.36 (m, 6H), 2.30-0.86 (m, 27H), 1.66 (s, 3H), 1.49 (d, J=6.3 Hz, 6H), 1.21 (t, J=7.2 Hz, 3H), 1.04 (s, 3H), 0.94 (s, 3H), 0.93-0.87 (m, 6H), 0.83 (s, 3H). LC/MS: m/e 862.73 (M+H)$^+$, 2.35 min (LCMS Method 1).

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-isopropyl-1H-1,2,3-triazol-5-yl)oxy)methyl)cyclohex-3-ene-1-carboxylic acid was prepared in 45% yield, following the procedure described in general procedure A step 6, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((1-isopropyl-1H-1,2,3-triazol-5-yl)oxy)methyl)cyclohex-3-enecarboxylate as reactant. $^1$H NMR (400 MHz, CHLOROFORM-d) δ 7.12 (d, J=2.3 Hz, 1H), 5.36 (br. s., 1H), 5.19 (d, J=4.3 Hz, 1H), 4.72 (s, 1H), 4.63 (s, 1H), 4.67-4.52 (h, J=6.8 Hz, 1H), 4.32-4.10 (m, 2H), 3.20-2.89 (m, 8H), 2.87-2.68 (m, 3H), 2.68-2.53 (m, 1H), 2.34-2.21 (m, 1H), 2.21-1.85 (m, 11H), 1.85-1.73 (m, 1H), 1.71-1.65 (m, 1H), 1.68 (s, 3H), 1.51 (d, J=6.5 Hz, 6H), 1.64-1.36 (m, 9H), 1.36-1.19 (m, 4H), 1.14 (s, 3H), 1.07 (br. s., 2H), 1.01 (s, 3H), 0.97-0.96 (m, 4H), 0.94-0.89 (m, 3H), 0.87 (s, 3H). LC/MS: m/e 834.69 (M+H)$^+$, 2.32 min (LCMS Method 1).

Example 18

Preparation of 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-(prop-1-en-2-yl)isothiazol-3-yl)oxy)methyl)cyclohex-3-ene-1-carboxylic acid.

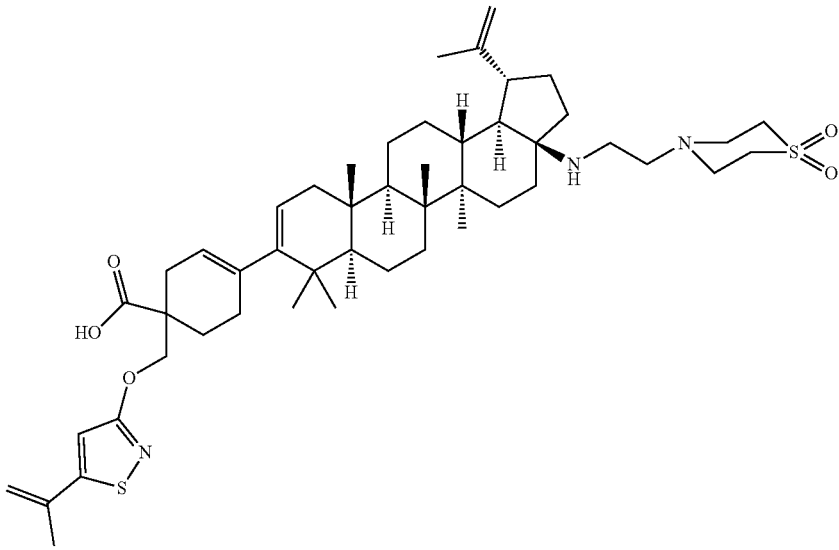

Step 1. Preparation of ethyl 8-((isothiazol-3-yloxy)methyl)-1,4-dioxaspiro[4.5]decane-8-carboxylate.

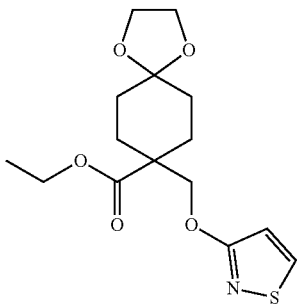 [SMILES: CCOC(=O)C1(COc2ccsn2)CCC2(CC1)OCCO2]

The title compound was prepared in 36% yield, following the procedure described in general procedure A step 1-A, using isothiazol-3(2H)-one as reactant. $^1$H NMR (400 MHz, CHLOROFORM-d) δ 8.42 (d, J=4.8 Hz, 1H), 6.57 (d, J=4.8 Hz, 1H), 4.42 (s, 2H), 4.17 (q, J=7.0 Hz, 2H), 3.99-3.93 (m, 4H), 2.31-2.20 (m, 2H), 1.75-1.65 (m, 6H), 1.23 (t, J=7.2 Hz, 3H). LC/MS: m/e 328.20 (M+H)$^+$, 3.59 min (LCMS Method 12).

Step 2. Preparation of ethyl 8-(((5-(2-hydroxypropan-2-yl)isothiazol-3-yl)oxy)methyl)-1,4-dioxaspiro[4.5]decane-8-carboxylate.

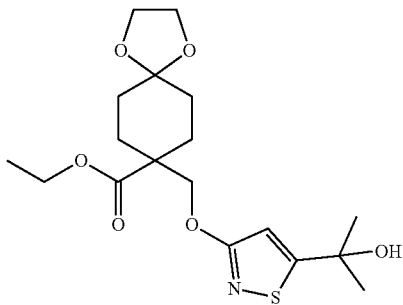 [SMILES: CCOC(=O)C1(COc2cc(C(C)(C)O)sn2)CCC2(CC1)OCCO2]

To a solution of ethyl 8-((isothiazol-3-yloxy)methyl)-1,4-dioxaspiro[4.5]decane-8-carboxylate (100 mg, 0305 mmol) in THF (2 mL) under nitrogen at −78° C. was added a 2M solution of LDA (0.305 mL, 0.611 mmol). It was stirred at −78° C. for 20 minutes before it was added neat propan-2-one (0.045 mL, 0.611 mmol). Stirring continued for another 30 minutes at −78° C. The reaction was quenched with a half-saturated ammonium chloride in 0.5M HCl, extracted with ethyl acetate and concentrated in vacuo. The crude mixture was purified by silica gel column eluted with 0-45% EtOAc/hexanes to give the desired product as an oil (83 mg, 70%). $^1$H NMR (400 MHz, CHLOROFORM-d) δ 6.35 (s, 1H), 4.32 (s, 2H), 4.13 (q, J=7.1 Hz, 2H), 3.91 (s, 4H), 2.84 (s, 1H), 2.26-2.12 (m, 2H), 1.72-1.61 (m, 6H), 1.58 (s, 6H), 1.19 (t, J=7.2 Hz, 3H). LC/MS: m/e 386.20 (M+H)$^+$, 2.75 min (LCMS Method 13).

Step 3. Preparation of ethyl 1-(((5-(2-hydroxypropan-2-yl)isothiazol-3-yl)oxy)methyl)-4-oxocyclohexanecarboxylate.

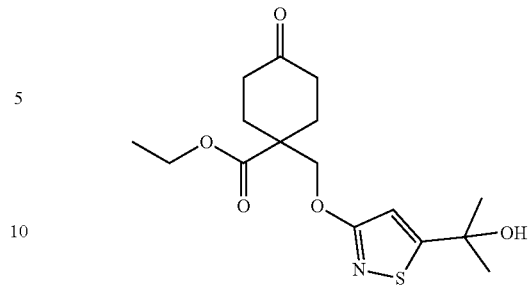

The title compound was prepared in 100% yield, following the procedure described in general procedure A step 2 using ethyl 8-(((5-(2-hydroxypropan-2-yl)isothiazol-3-yl)oxy)methyl)-1,4-dioxaspiro[4.5]decane-8-carboxylate as reactant. $^1$H NMR (400 MHz, CHLOROFORM-d) δ 6.36 (s, 1H), 4.41 (s, 2H), 4.20 (q, J=7.2 Hz, 2H), 2.99 (s, 1H), 2.52-2.41 (m, 4H), 2.39-2.29 (m, 2H), 1.88-1.75 (m, 2H), 1.59 (s, 6H), 1.23 (t, J=7.0 Hz, 3H). LC/MS: m/e 342.15 (M+H)$^+$, 2.03 min (LCMS Method 3).

Step 4. Preparation of ethyl 1-(((5-(prop-1-en-2-yl)isothiazol-3-yl)oxy)methyl)-4-((((trifluoromethyl)sulfonyl)oxy)cyclohex-3-ene-1-carboxylate.

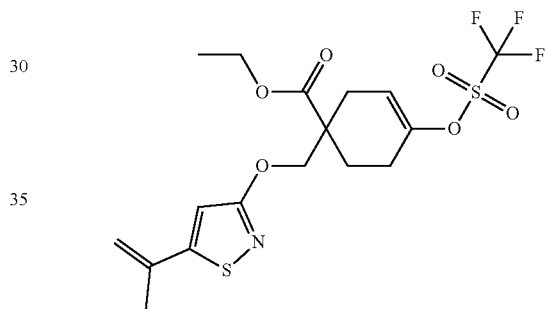

The title compound was prepared in 22% yield, following the procedure described in general procedure A step 3 using ethyl 1-(((5-(2-hydroxypropan-2-yl)isothiazol-3-yl)oxy)methyl)-4-oxocyclohexanecarboxylate as reactant. $^1$H NMR (400 MHz, CHLOROFORM-d) δ 6.50 (s, 1H), 5.76 (td, J=3.3, 1.8 Hz, 1H), 5.45 (s, 1H), 5.18 (s, 1H), 4.47 (d, J=10.0 Hz, 1H), 4.41 (d, J=10.0 Hz, 1H), 4.19 (qd, J=7.1, 0.8 Hz, 2H), 2.85-2.77 (m, 1H), 2.53-2.22 (m, 4H), 2.09 (s, 3H), 1.98-1.90 (m, 1H), 1.24 (t, J=7.2 Hz, 3H). LC/MS: m/e 456.10 (M+H)$^+$, 2.76 min (LCMS Method 3).

Step 5. Preparation of ethyl 1-(((5-(prop-1-en-2-yl)isothiazol-3-yl)oxy)methyl)-4-(4,4,5,5-tetramethyl-1,3,2-dioxaborolan-2-yl)cyclohex-3-ene-1-carboxylate.

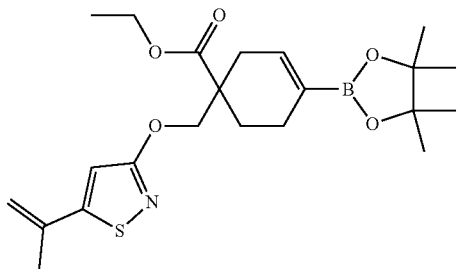 [SMILES: C=C(C)c1cc(OCC2(C(=O)OCC)CC=C(B3OC(C)(C)C(C)(C)O3)CC2)ns1]

The title compound was prepared in 78% yield, following the procedure described in general procedure A step 4 using ethyl 1-(((5-(prop-1-en-2-yl)isothiazol-3-yl)oxy)methyl)-4-(((trifluoromethyl)sulfonyl)oxy)cyclohex-3-enecarboxylate as reactant. ¹H NMR (400 MHz, CHLOROFORM-d) δ 6.55-6.50 (m, 1H), 6.49 (s, 1H), 5.43 (s, 1H), 5.14 (s, 1H), 4.46 (d, J=10.0 Hz, 1H), 4.37 (d, J=10.0 Hz, 1H), 4.15 (q, J=7.0 Hz, 2H), 2.74-2.64 (m, 1H), 2.28-2.16 (m, 3H), 2.09 (s, 3H), 2.01-1.80 (m, 2H), 1.26 (s, 12H), 1.21 (t, J=7.2 Hz, 3H). LC/MS: m/e 434.20 (M+H)⁺, 2.79 min (LCMS Method 3).

Step 6. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((5-(prop-1-en-2-yl)isothiazol-3-yl)oxy)methyl)cyclohex-3-enecarboxylate.

5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-(prop-1-en-2-yl)isothiazol-3-yl)oxy)methyl)cyclohex-3-ene-1-carboxylic acid was prepared in 56% yield, following the procedure described in general procedure A step 6 using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((5-(prop-1-en-2-yl)isothiazol-3-yl)oxy)methyl)cyclohex-3-enecarboxylate as reactant. ¹H NMR (400 MHz, CHLOROFORM-d) δ 6.55 (s, 1H), 5.47 (s, 1H), 5.37 (br. s., 1H), 5.21 (d, J=5.3 Hz, 1H), 5.19 (s, 1H), 4.79 (s, 1H), 4.73 (s, 1H), 4.56-4.50 (m, 1H), 4.50-4.43 (m, 1H), 3.40 (d, J=11.8 Hz, 1H), 3.29-2.91 (m, 10H), 2.80-2.72 (m, 1H), 2.72-2.62 (m, 1H), 2.34-2.09 (m, 6H), 2.11 (s, 3H), 2.09-1.97 (m, 4H), 1.97-1.83 (m, 2H), 1.83-1.68 (m, 2H),

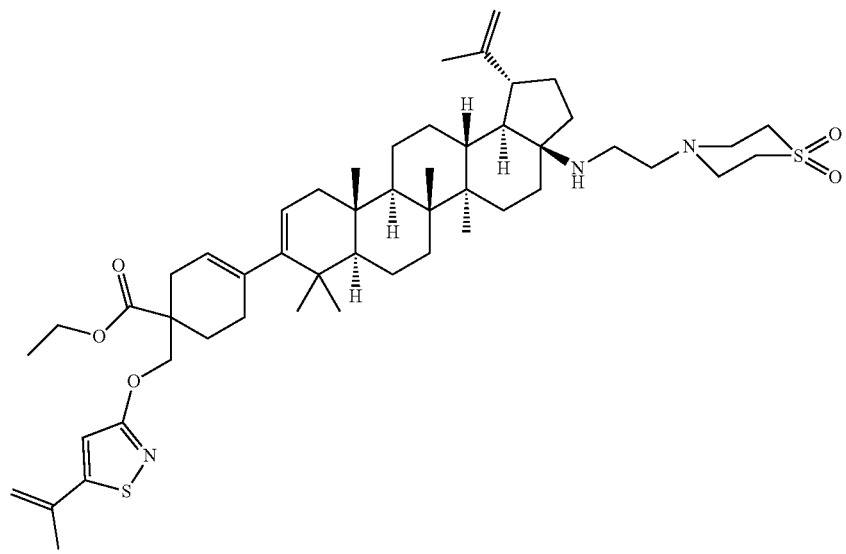

1.71 (s, 3H), 1.67-1.37 (m, 12H), 1.37-1.23 (m, 1H), 1.15 (s, 3H), 1.13-1.03 (m, 2H), 1.06 (s, 3H), 0.98-0.97 (m, 3H), 0.95-0.93 (m, 3H), 0.89 (s, 3H). LC/MS: m/e 848.50 (M+H)⁺, 3.05 min (LCMS Method 3).

Example 19

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridazin-3-yloxy)methyl)cyclohex-3-ene-1-carboxylic acid.

The title compound was prepared in 42% yield, following the procedure described in general procedure A step 5 using ethyl 1-(((5-(prop-1-en-2-yl)isothiazol-3-yl)oxy)methyl)-4-(4,4,5,5-tetramethyl-1,3,2-dioxaborolan-2-yl)cyclohex-3-enecarboxylate as reactant. ¹H NMR (400 MHz, CHLOROFORM-d) δ 6.51 (s, 1H), 5.44 (s, 1H), 5.35 (br. s., 1H), 5.19 (br. s., 1H), 5.17 (s, 1H), 4.76 (s, 1H), 4.71 (s, 1H), 4.51-4.38 (m, 2H), 4.21-4.12 (m, 2H), 3.41-2.92 (m, 11H), 2.78-2.54 (m, 3H), 2.22-0.89 (m, 27H), 2.09 (s, 3H), 1.69 (s, 3H), 1.23 (t, J=7.2 Hz, 3H), 1.13 (s, 3H), 1.04 (s, 3H), 0.96-0.91 (m, 6H), 0.87 (s, 3H). LC/MS: m/e 876.60 (M+H)⁺, 3.01 min (LCMS Method 3).

Step 7. 4-((1R,3aS,5aR,5bR,7aR,11aS,11bR,13aR,13bR)-3a-((2-(1,1-dioxidothiomorpholino)ethyl)amino)-5a,

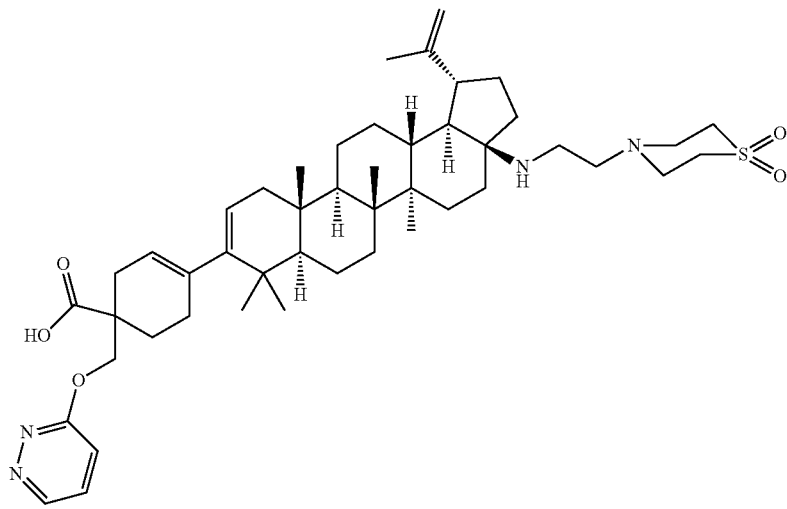

Step 1. Preparation of ethyl 8-((pyridazin-3-yloxy)methyl)-1,4-dioxaspiro[4.5]decane-8-carboxylate

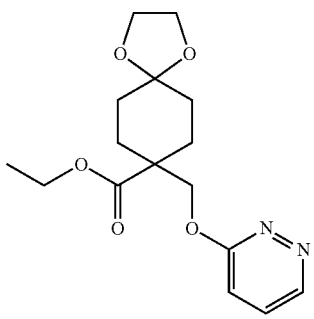 [SMILES: CCOC(=O)C1(COc2cccnn2)CCC2(CC1)OCCO2]

To the solution of ethyl 8-(hydroxymethyl)-1,4-dioxaspiro[4.5]decane-8-carboxylate (300 mg, 1.23 mmol) in DMF (6 mL) at 0° C. was added potassium tert-butoxide (1.84 mL, 1.84 mmol) followed by 3-chloropyridazine (211 mg, 1.84 mmol). The resulting suspension was stirred at 0° C. then warmed to RT overnight. The reaction mixture was diluted with ethyl acetate (10 mL), washed with water, dried over sodium sulfate, and concentrated in vacuo to give crude product. LC/MS: m/e 323.20 (M+H)+, 2.09 min (LCMS Method 7).

Step 2. Preparation of ethyl 4-oxo-1-((pyridazin-3-yloxy)methyl)cyclohexanecarboxylate

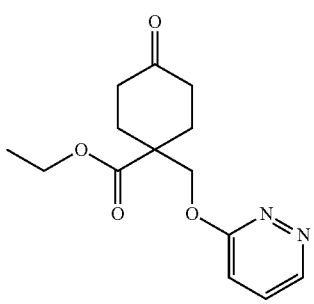 [SMILES: CCOC(=O)C1(COc2cccnn2)CCC(=O)CC1]

The title compound was prepared in 70% yield, following the procedure described in general procedure A step 2 using ethyl 8-((pyridazin-3-yloxy)methyl)-1,4-dioxaspiro[4.5]decane-8-carboxylate as reactant. $^1$H NMR (400 MHz, CHLO-ROFORM-d) δ 8.82 (dd, J=4.5, 1.3 Hz, 1H), 7.37 (dd, J=9.0, 4.5 Hz, 1H), 6.96 (dd, J=8.9, 1.4 Hz, 1H), 4.64 (s, 2H), 4.21 (q, J=7.1 Hz, 2H), 2.57-2.28 (m, 6H), 1.92-1.82 (m, 2H), 1.28 (t, J=7.2 Hz, 3H). LC/MS: m/e 279.15 (M+H)+, 1.71 min (LCMS Method 7).

Step 3. Preparation of ethyl 1-((pyridazin-3-yloxy)methyl)-4-(((trifluoromethyl)sulfonyl)oxy)cyclohex-3-en-ecarboxylate

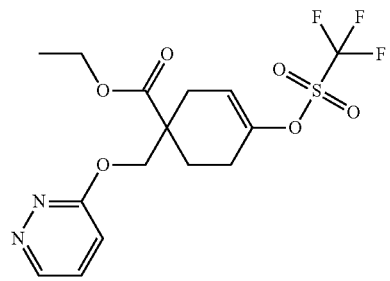 [SMILES: CCOC(=O)C1(COc2cccnn2)CC=C(OS(=O)(=O)C(F)(F)F)CC1]

The title compound was prepared in 39% yield, following the procedure described in general procedure A step 3 using ethyl 4-oxo-1-((pyridazin-3-yloxy)methyl)cyclohexanecarboxylate as reactant. $^1$H NMR (400 MHz, CHLOROFORM-d) δ 8.82 (dd, J=4.5, 1.3 Hz, 1H), 7.36 (dd, J=9.0, 4.5 Hz, 1H), 6.94 (dd, J=9.0, 1.3 Hz, 1H), 5.75 (td, J=3.1, 1.8 Hz, 1H), 4.62 (d, J=10.5 Hz, 1H), 4.59 (d, J=10.5 Hz, 1H), 4.18-4.11 (m, 2H), 2.88-2.79 (m, 1H), 2.53-2.23 (m, 4H), 1.97-1.90 (m, 1H), 1.21 (t, J=7.2 Hz, 3H). LC/MS: m/e 411.15 (M+H)+, 2.66 min (LCMS Method 7).

Step 4. Preparation of ethyl 1-((pyridazin-3-yloxy)methyl)-4-(4,4,5,5-tetramethyl-1,3,2-dioxaborolan-2-yl)cyclohex-3-enecarboxylate

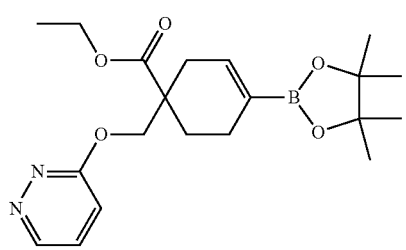 [SMILES: CCOC(=O)C1(COc2cccnn2)CC=C(B2OC(C)(C)C(C)(C)O2)CC1]

The title compound was prepared in 43% yield, following the procedure described in general procedure A step 4 using ethyl 1-((pyridazin-3-yloxy)methyl)-4-(((trifluoromethyl)sulfonyl)oxy)cyclohex-3-enecarboxylate as reactant. $^1$H NMR (400 MHz, CHLOROFORM-d) δ 8.78 (dd, J=4.5, 1.3 Hz, 1H), 7.32 (dd, J=8.9, 4.4 Hz, 1H), 6.91 (dd, J=8.9, 1.4 Hz, 1H), 6.49 (dt, J=3.7, 1.8 Hz, 1H), 4.62 (d, J=10.3 Hz, 1H), 4.53 (d, J=10.5 Hz, 1H), 4.07 (q, J=7.0 Hz, 2H), 2.72-2.64 (m, 1H), 2.27-2.08 (m, 3H), 1.98-1.80 (m, 2H), 1.21 (s, 12H), 1.21 (t, J=7.3 Hz, 3H). LC/MS: m/e 389.25 (M+H)+, 2.74 min (LCMS Method 7).

Step 5. Preparation of ethyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyridazin-3-yloxy)methyl)cyclohex-3-enecarboxylate

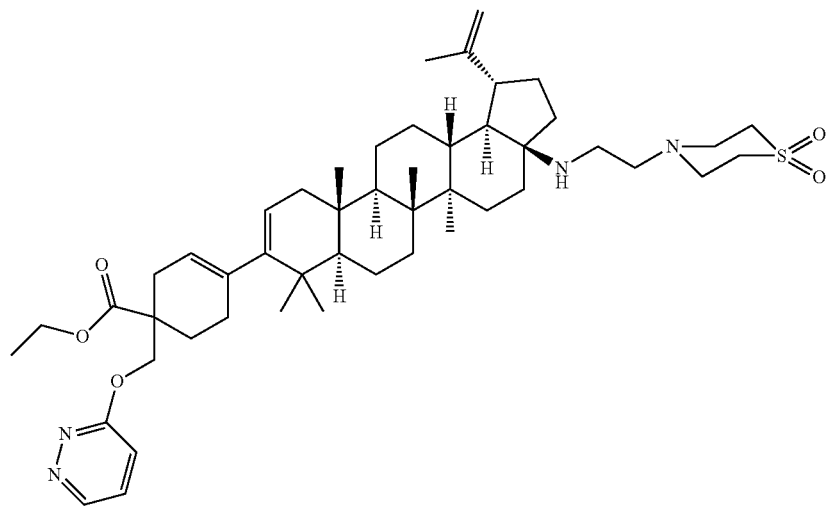

The title compound was prepared following the procedure described in general procedure A step 5 using ethyl 1-((pyridazin-3-yloxy)methyl)-4-(4,4,5,5-tetramethyl-1,3,2-dioxaborolan-2-yl)cyclohex-3-enecarboxylate as reactant. The crude material was taken directly into the next step without purification.

Step 6. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridazin-3-yloxy)methyl)cyclohex-3-ene-1-carboxylic acid was prepared in 22% yield as a solid, following the procedure described in general procedure A step 6 using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyridazin-3-yloxy)methyl)cyclohex-3-enecarboxylate as reactant. $^1$H NMR (400 MHz, CHLOROFORM-d) δ 9.09 (d, J=4.5 Hz, 1H), 7.74 (dd, J=9.0, 4.5 Hz, 1H), 7.35 (d, J=8.8 Hz, 1H), 5.38 (br. s., 1H), 5.21 (t, J=5.6 Hz, 1H), 4.79 (s, 1H), 4.72 (s, 1H), 4.76-4.64 (m, 2H), 3.39 (d, J=12.5 Hz, 1H), 3.25-3.02 (m, 9H), 3.02-2.86 (m, 2H), 2.86-2.62 (m, 2H), 2.32-2.06 (m, 5H), 2.06-1.84 (m, 6H), 1.82-1.67 (m, 2H), 1.71 (s, 3H), 1.66-1.35 (m, 10H), 1.35-1.20 (m, 4H), 1.17 (s, 3H), 1.14-1.04 (m, 2H), 1.05 (s, 3H), 0.97-0.95 (m, 3H), 0.92-0.91 (m, 3H), 0.87 (s, 3H).

LC/MS: m/e 803.48 (M+H)$^+$, 2.27 min (LCMS Method 1).

General Procedure B: Preparation of (R) α-substituted cyclohexenecarboxylic acid derivatives.
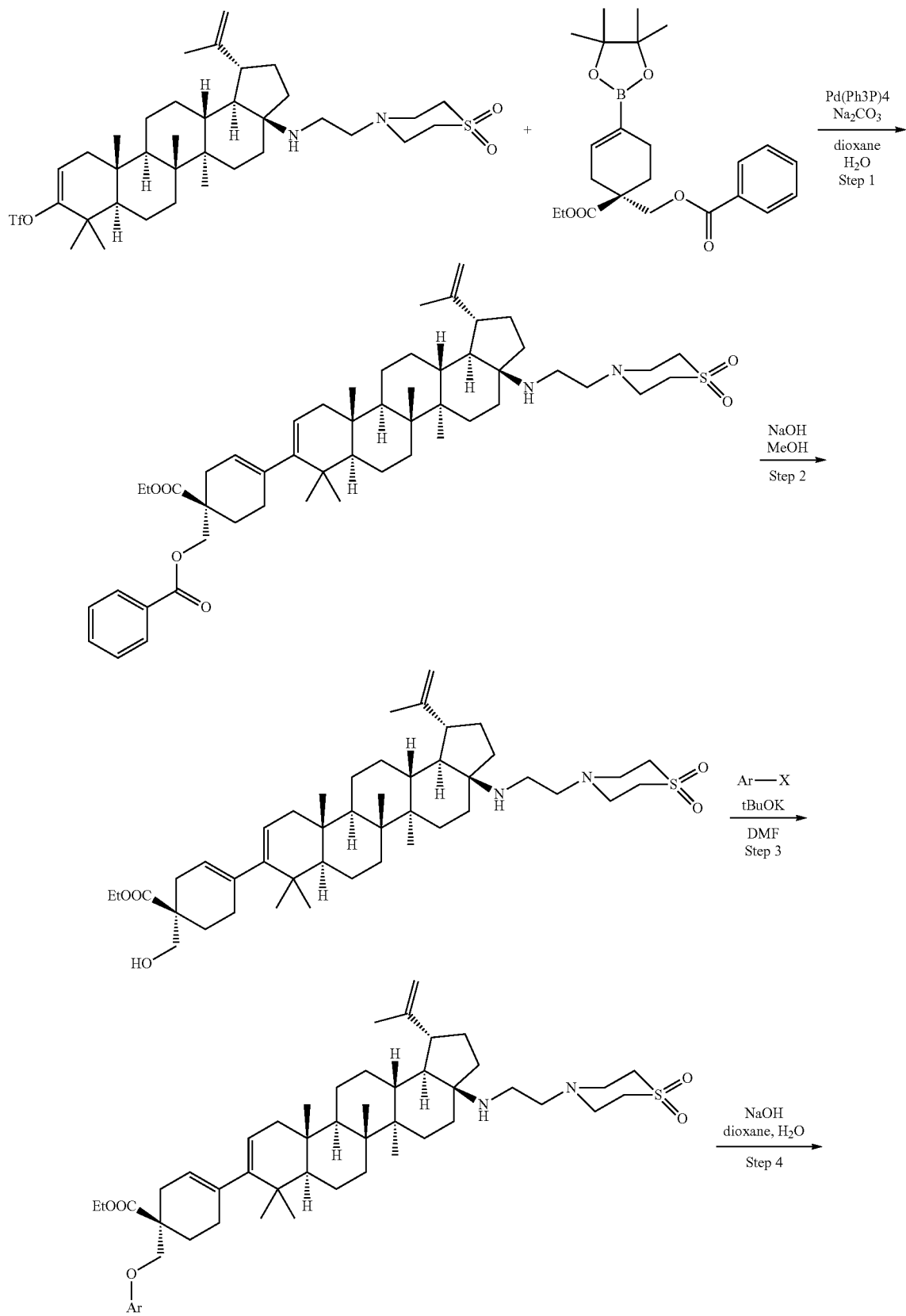

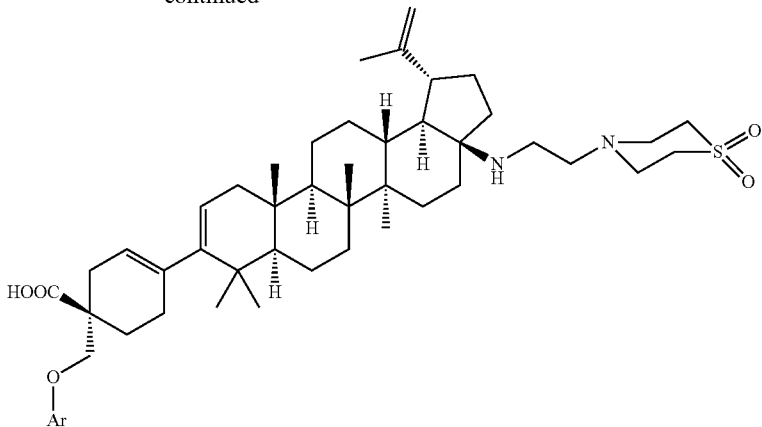

Step 1. Preparation of ((R)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)-1-(ethoxycarbonyl)cyclohex-3-en-1-yl)methyl benzoate.

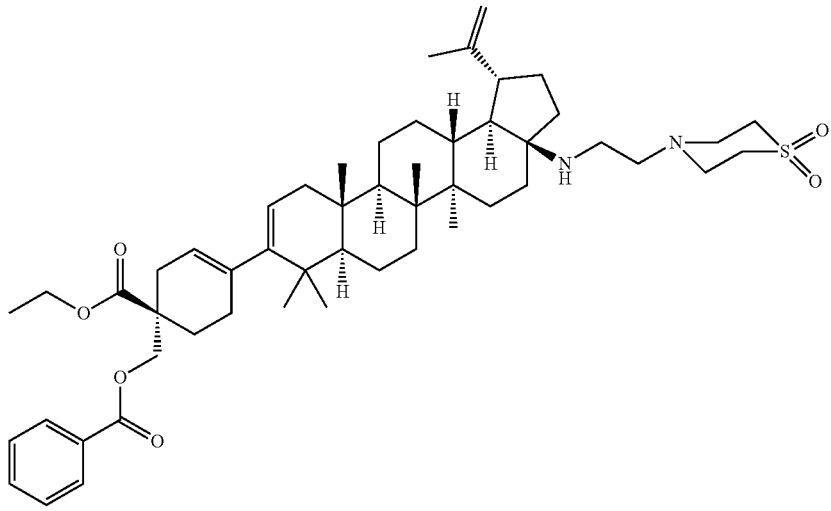

A mixture of (1R,3aS,5aR,5bR,7aR,11aR,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (1 eq), (R)-(1-(ethoxycarbonyl)-4-(4,4,5,5-tetramethyl-1,3,2-dioxaborolan-2-yl)cyclohex-3-en-1-yl)methyl benzoate (1.2 eq), $Na_2CO_3$ (3 eq) and $Pd(Ph_3P)_4$ (0.06 eq) in 1,4-dioxane and $H_2O$ (4:1) was flushed with nitrogen, sealed and heated at 70° C. for 2 h. The reaction mixture was diluted with EtOAc, washed with brine, dried over $Na_2SO_4$, and concentrated in vacuo. The crude product was purified by silica gel column eluted with 0-35% Ethyl acetate/hexanes to give the desired product (68% yield) as a solid. $^1$H NMR (400 MHz, CHLOROFORM-d) δ 8.01 (dd, J=8.4, 1.4 Hz, 2H), 7.60-7.53 (m, 1H), 7.47-7.40 (m, 2H), 5.36 (br. s., 1H), 5.20 (dd, J=6.0, 1.8 Hz, 1H), 4.71 (d, J=2.0 Hz, 1H), 4.60 (s, 1H), 4.49-4.39 (m, 2H), 4.18 (qd, J=7.2, 1.4 Hz, 2H), 3.13-2.98 (m, 8H), 2.73-2.43 (m, 6H), 2.27-0.89 (m, 27H), 1.69 (s, 3H), 1.25-1.20 (m, 3H), 1.07 (s, 3H), 0.97 (br. s., 3H), 0.96 (br. s., 3H), 0.94 (s, 3H), 0.87 (s, 3H). LC/MS m/z 857.65 $(M+H)^+$, 2.43 min (LCMS Method 1).

Step 2. Preparation of ethyl (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate.

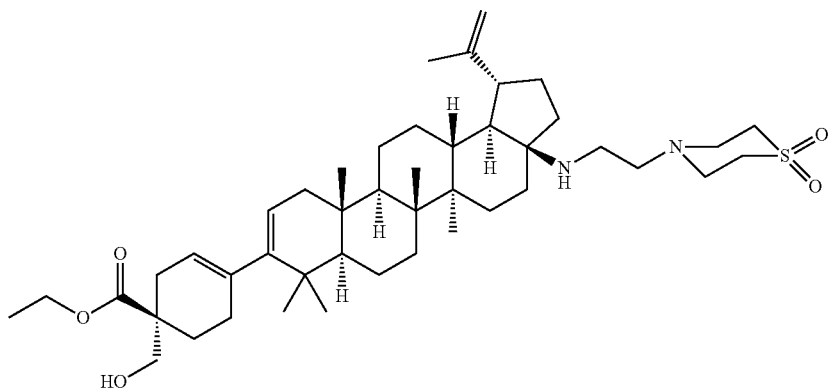

A suspension of ((R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (1 eq) and 1N NaOH (1 eq) in MeOH and THF was stirred at RT for 2 days. The mixture was neutralized with 1N HCl and the solvent was removed in vacuo. The residue was taken into $CH_2Cl_2$, washed with $H_2O$ followed by brine, dried over $Na_2SO_4$, and concentrated in vacuo. The crude product was purified on silica gel eluted with ethyl acetate/hexanes to give the desired product (85% yield) as a solid. $^1H$ NMR (400 MHz, CHLOROFORM-d) δ 5.32 (br. s., 1H), 5.18 (d, J=4.8 Hz, 1H), 4.71 (d, J=2.0 Hz, 1H), 4.60 (s, 1H), 4.19 (q, J=7.2 Hz, 2H), 3.69 (br. s., 2H), 3.12-2.98 (m, 8H), 2.72-2.43 (m, 6H), 2.28-0.89 (m, 27H), 1.70 (s, 3H), 1.28 (t, J=7.2 Hz, 3H), 1.07 (s, 3H), 0.97 (s, 3H), 0.96 (s, 3H), 0.93 (s, 3H), 0.86 (s, 3H). LC/MS m/z 753.65 (M+H)$^-$, 3.79 min (LCMS Method 2).

Step 3. Preparation of (R) α-methyl ether.

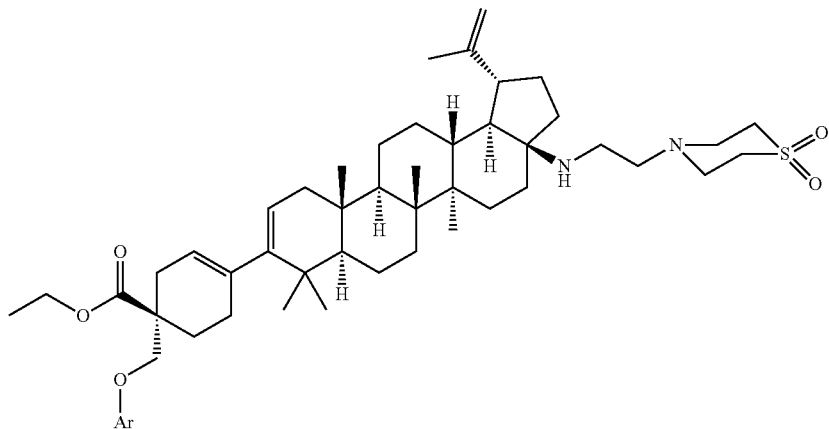

To a solution of ethyl (R)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate (1 eq) and Ar—X (2 eq) in DMF was added KOtBu (2 eq) at 0° C. The resulted mixture was warmed to RT and stirred overnight. The reaction mixture was diluted with EtAOc, washed with water, dried over $Na_2SO_4$, and concentrated in vacuo to give crude product which was used in the next step without further purification.

Step 4: Preparation of (R) α-substituted cyclohexenecarboxylic acid.

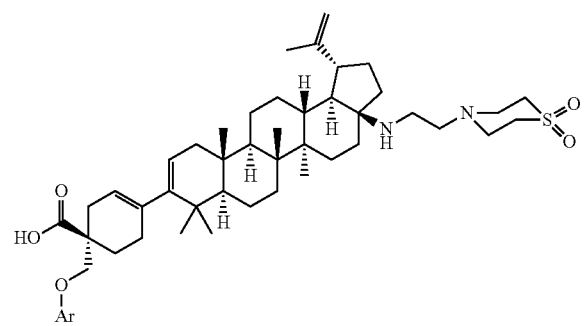

A solution of (R) α-methyl ether from Step 3 in 1,4-dioxane, MeOH and 1N NaOH (2:1:1) was stirred at 50° C. The reaction mixture was purified by reverse phase preparative HPLC to give the final product.

Example 20

Preparation of (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylic acid.

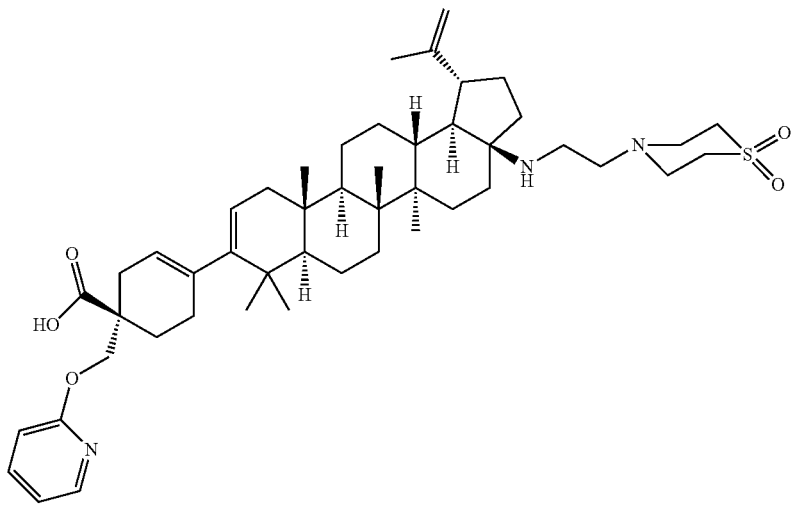

Step 1-2: General procedure B.

Step 3. Preparation of ethyl (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-2-yloxy)methyl)cyclohex-3-ene-1-carboxylate.

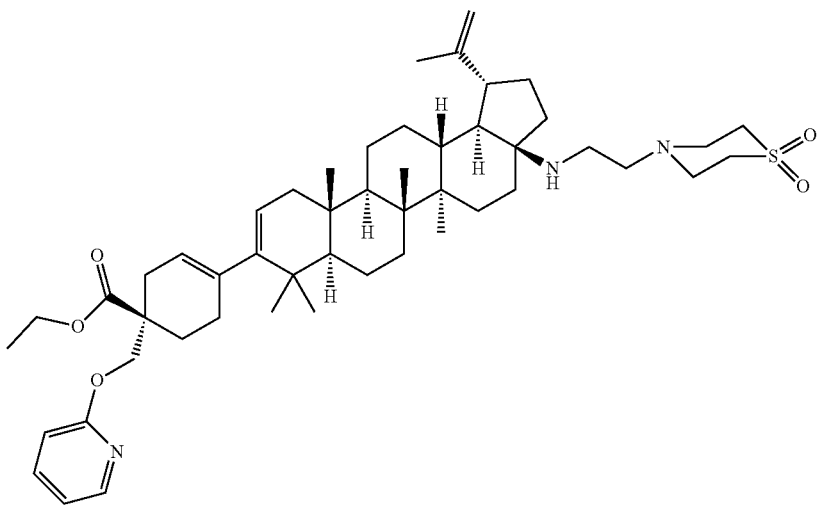

The title compound was prepared as a solid, following the procedure described in General procedure B step 3, using 2-chloropyridine as reactant. LC/MS m/z 830.55 (M+H)+, 3.56 min (LCMS Method 5).

Step 4. (R)-4-((1R,3aS,5aR,5bR,7aR,11aS,11bR,13aR, 13bR)-3a-((2-(1,1-dioxidothiomorpholino)ethyl)amino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-((pyridin-2-yloxy)methyl) cyclohex-3-ene-1-carboxylic acid was prepared in 41% yield (2 steps) as a solid, following the procedure described in General procedure B step 4 for 6 h, using ethyl (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylate as reactant. ¹H NMR (500 MHz, CHLOROFORM-d) δ 8.21 (dd, J=5.3, 1.4 Hz, 1H), 7.70 (ddd, J=8.6, 7.0, 2.0 Hz, 1H), 6.98 (ddd, 5.3, 0.8 Hz, 1H), 6.84 (d, J=8.4 Hz, 1H), 5.37 (br. s., 1H), 5.20 (dd, J=6.1, 1.7 Hz, 1H), 4.78 (s, 1H), 4.71 (s, 1H), 4.49 (d, J=9.9 Hz, 1H), 4.45 (d, J=9.9 Hz, 1H), 3.38-3.31 (m, 1H), 3.25-3.00 (m, 9H), 2.98-2.85 (m, 2H), 2.79 (dt, J=10.9, 5.6 Hz, 1H), 2.70-2.62 (m, 1H), 2.28-1.86 (m, 11H), 1.76-1.07 (m, 16H), 1.70 (s, 3H), 1.16 (s, 3H), 1.04 (s, 3H), 0.96 (s, 3H), 0.93 (s, 3H), 0.87 (s, 3H). LC/MS m/z 802.45 (M+H)+, 3.34 min (LCMS Method 5).

Example 21

Preparation of (R)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrimidin-4-yloxy)methyl)cyclohex-3-ene-1-carboxylic acid.

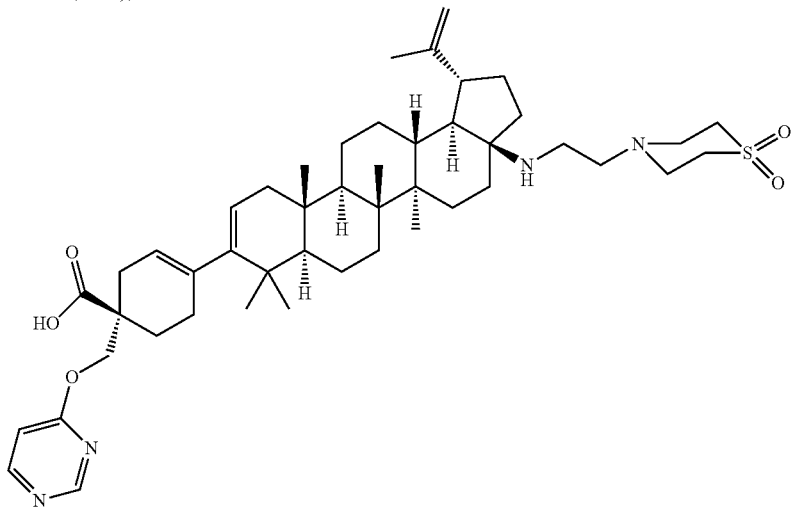

Step 1-2: General procedure B.
Step 3. Preparation of ethyl (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopentatalchrysen-9-yl)-1-((pyrimidin-4-yloxy)methyl)cyclohex-3-ene-1-carboxylate.

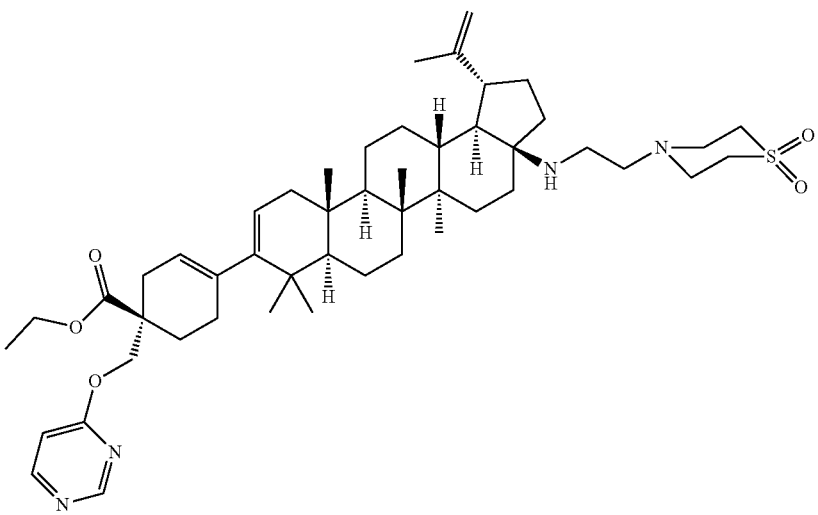

The title compound was prepared as a solid, following the procedure described in General procedure B step 3, using 4-chloropyrimidine as reactant. LC/MS m/z 831.55 (M+H)+, 3.45 min (LCMS Method 5).

Step 4. (R)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrimidin-4-yloxy)methyl)cyclohex-3-ene-1-carboxylic acid was prepared in 31% yield (2 steps) as a solid, following the procedure described in General procedure B step 4 for 4 h, using ethyl (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrimidin-4-yloxy)methyl)cyclohex-3-ene-1-carboxylate as reactant. $^1$H NMR (500 MHz, CHLOROFORM-d) δ 8.95 (s, 1H), 8.57 (d, J=6.4 Hz, 1H), 6.96 (dd, J=6.3, 0.9 Hz, 1H), 5.38 (br. s., 1H), 5.21 (d, J=4.6 Hz, 1H), 4.78 (s, 1H), 4.70 (s, 1H), 4.66 (s, 2H), 3.37-3.31 (m, 1H), 3.23-3.01 (m, 9H), 2.97-2.86 (m, 2H), 2.80 (dt, J=10.6, 5.6 Hz, 1H), 2.69-2.62 (m, 1H), 2.30-1.87 (m, 11H), 1.76-1.01 (m, 16H), 1.70 (s, 3H), 1.16 (s, 3H), 1.04 (s, 3H), 0.95 (s, 3H), 0.93 (s, 3H), 0.87 (s, 3H). LC/MS m/z 725.50 (M+H)$^+$, 3.23 min (LCMS Method 5).

Example 22

Preparation of (R)-1-(((3-chloropyridin-2-yl)oxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

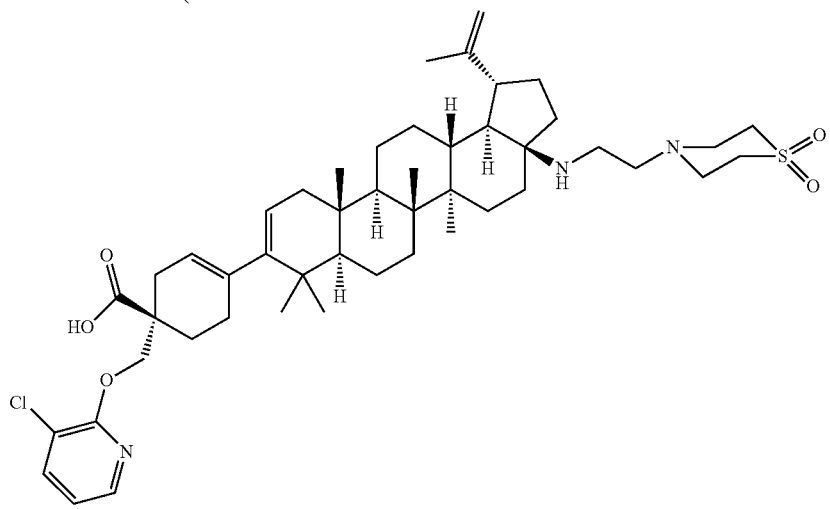

Step 1-2: General procedure B.

Step 3. Preparation of ethyl (R)-1-(((3-chloropyridin-2-yl)oxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate.

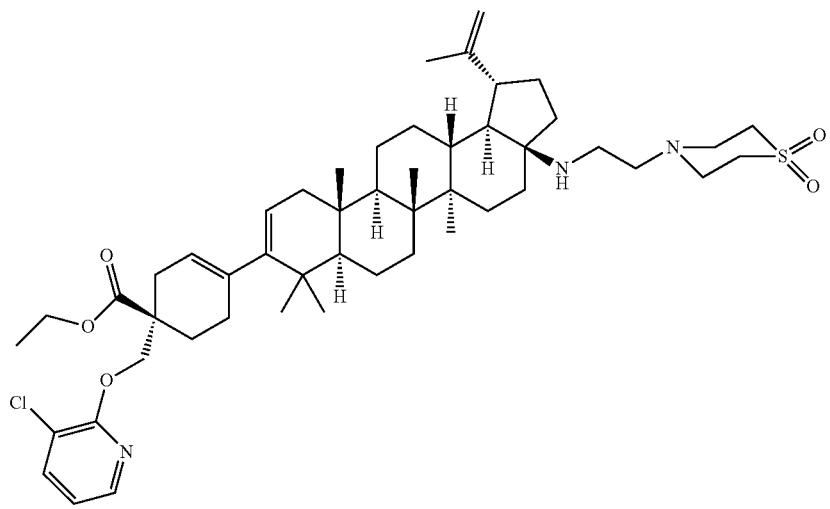

The title compound was prepared as a solid, following the procedure described in General procedure B step 3, using 2,3-dichloropyridine as reactant. LC/MS m/z 864.45 (M+H)+, 3.83 min (LCMS Method 5).

Step 4. (R)-1-(((3-chloropyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid was prepared in 69% yield (2 steps) as a solid, following the procedure described in General procedure B step 4 for 6 h, using ethyl (R)-1-(((3-chloropyridin-2-yl)oxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as reactant. $^1$H NMR (500 MHz, CHLOROFORM-d) δ 8.04 (dd, J=4.9, 1.7 Hz, 1H), 7.64 (dd, 1.5 Hz, 1H), 6.87 (dd, 5.0 Hz, 1H), 5.38 (br. s., 1H), 5.21 (d, J=4.6 Hz, 1H), 4.77 (s, 1H), 4.71 (s, 1H), 4.54 (d, J=10.4 Hz, 1H), 4.51 (d, J=10.2 Hz, 1H), 3.43-3.36 (m, 1H), 3.25-3.01 (m, 9H), 2.99-2.87 (m, 2H), 2.75 (td, J=10.9, 5.7 Hz, 1H), 2.69-2.62 (m, 1H), 2.30-1.85 (m, 11H), 1.76-1.07 (m, 16H), 1.69 (s, 3H), 1.16 (s, 3H), 1.04 (s, 3H), 0.95 (s, 3H), 0.93 (s, 3H), 0.87 (s, 3H). LC/MS m/z 836.45 (M+H)$^+$, 3.48 min (LCMS Method 5).

Example 23

Preparation of (R)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

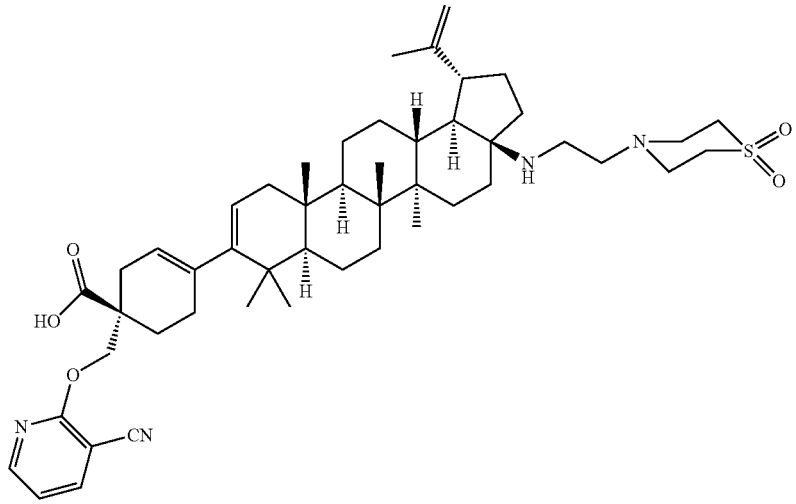

Step 1-2: General procedure B.

Step 3. Preparation of ethyl (R)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate.

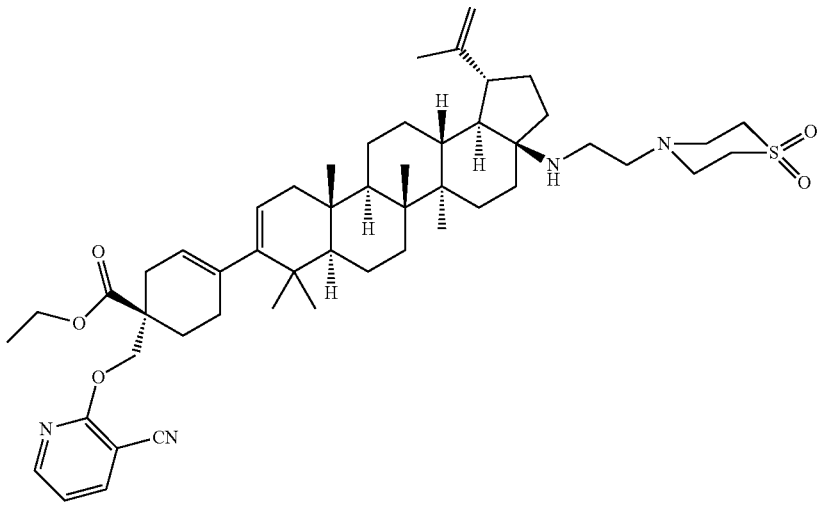

The title compound was prepared in 97% yield as a solid, following the procedure described in General procedure B step 3, using 2-fluoronicotinonitrile as reactant. $^1$H NMR (400 MHz, CHLOROFORM-d) δ 8.33 (dd, J=5.0, 2.0 Hz, 1H), 7.87 (dd, J=7.4, 1.9 Hz, 1H), 7.00-6.95 (m, 1H), 5.37 (br. s., 1H), 5.19 (d, J=4.8 Hz, 1H), 4.71 (d, J=2.0 Hz, 1H), 4.60 (s, 1H), 4.57-4.53 (m, 2H), 4.18 (qd, J=7.2, 2.6 Hz, 2H), 3.12-2.99 (m, 8H), 2.76-2.41 (m, 6H), 2.28-0.90 (m, 27H), 1.69 (s, 3H), 1.27 (t, J=7.2 Hz, 3H), 1.06 (s, 3H), 0.97 (s, 3H), 0.96 (s, 3H), 0.93 (s, 3H), 0.86 (s, 3H). LC/MS m/z 855.60 (M+H)+, 4.03 min (LCMS Method 2).

Step 4. (R)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid was prepared in 67% yield as a solid, following the procedure described in General procedure B step 3 at RT for 2 days, using ethyl (R)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate as reactant. $^1$H NMR (400 MHz, METHANOL-d$_4$) δ 8.37 (dd, J=5.0, 2.0 Hz, 1H), 8.06 (dd, J=7.5, 1.8 Hz, 1H), 7.10 (dd, J=7.5, 5.0 Hz, 1H), 5.37 (br. s., 1H), 5.22 (dd, 1.5 Hz, 1H), 4.85 (s, 1H), 4.76 (t, J=1.5 Hz, 1H), 4.63-4.55 (m, 2H), 3.27-3.07 (m, 11H), 2.91 (ddd, J=14.4, 10.0, 4.6 Hz, 1H), 2.79-2.61 (m, 2H), 2.32-1.09 (m, 27H), 1.77 (s, 3H), 1.17 (s, 3H), 1.12 (s, 3H), 1.00 (s, 3H), 0.97 (s, 3H), 0.93 (s, 3H). LC/MS m/z 827.60 (M+H)$^+$, 3.70 min (LCMS Method 2).

Example 24

Preparation of (R)-1-(((3-carbamoylpyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

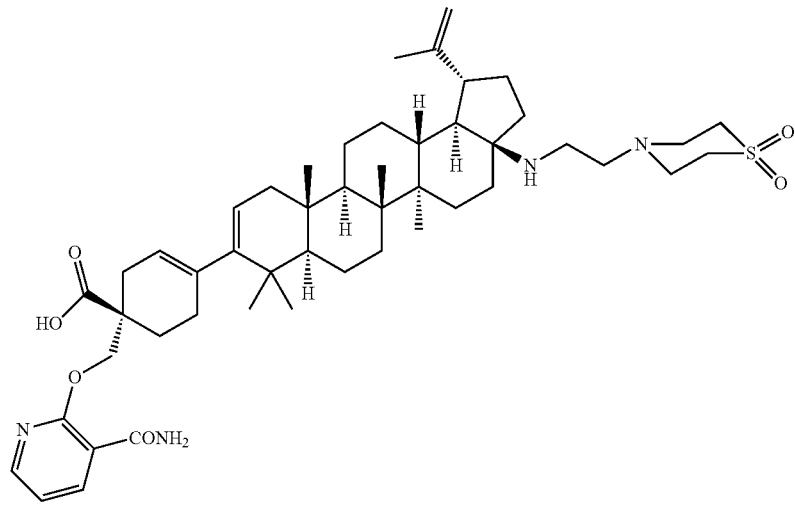

The title compound was a side product formed during Step 4 of the preparation of ethyl (R)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate. The material was isolated in 14% yield as a solid. $^1$H NMR (400 MHz, METHANOL-$d_4$) δ 8.40 (dd, J=7.8, 2.0 Hz, 1H), 8.29 (dd, J=5.0, 2.0 Hz, 1H), 7.13 (dd, J=7.7, 4.9 Hz, 1H), 5.37 (br. s., 1H), 5.21 (d, J=4.5 Hz, 1H), 4.83 (s, 1H), 4.72 (s, 1H), 4.64 (d, J=10.3 Hz, 1H), 4.53 (d, J=10.5 Hz, 1H), 3.28-3.03 (m, 11H), 3.01-2.90 (m, 1H), 2.84-2.68 (m, 2H), 2.37-1.06 (m, 27H), 1.75 (s, 3H), 1.18 (s, 3H), 1.10 (s, 3H), 0.99 (s, 3H), 0.96 (s, 3H), 0.92 (s, 3H). LC/MS m/z 845.60 (M+H)$^-$, 3.66 min (LCMS Method 2).

General Procedure C: Preparation of (S) a-substituted cyclohexenecarboxylic acid derivatives.

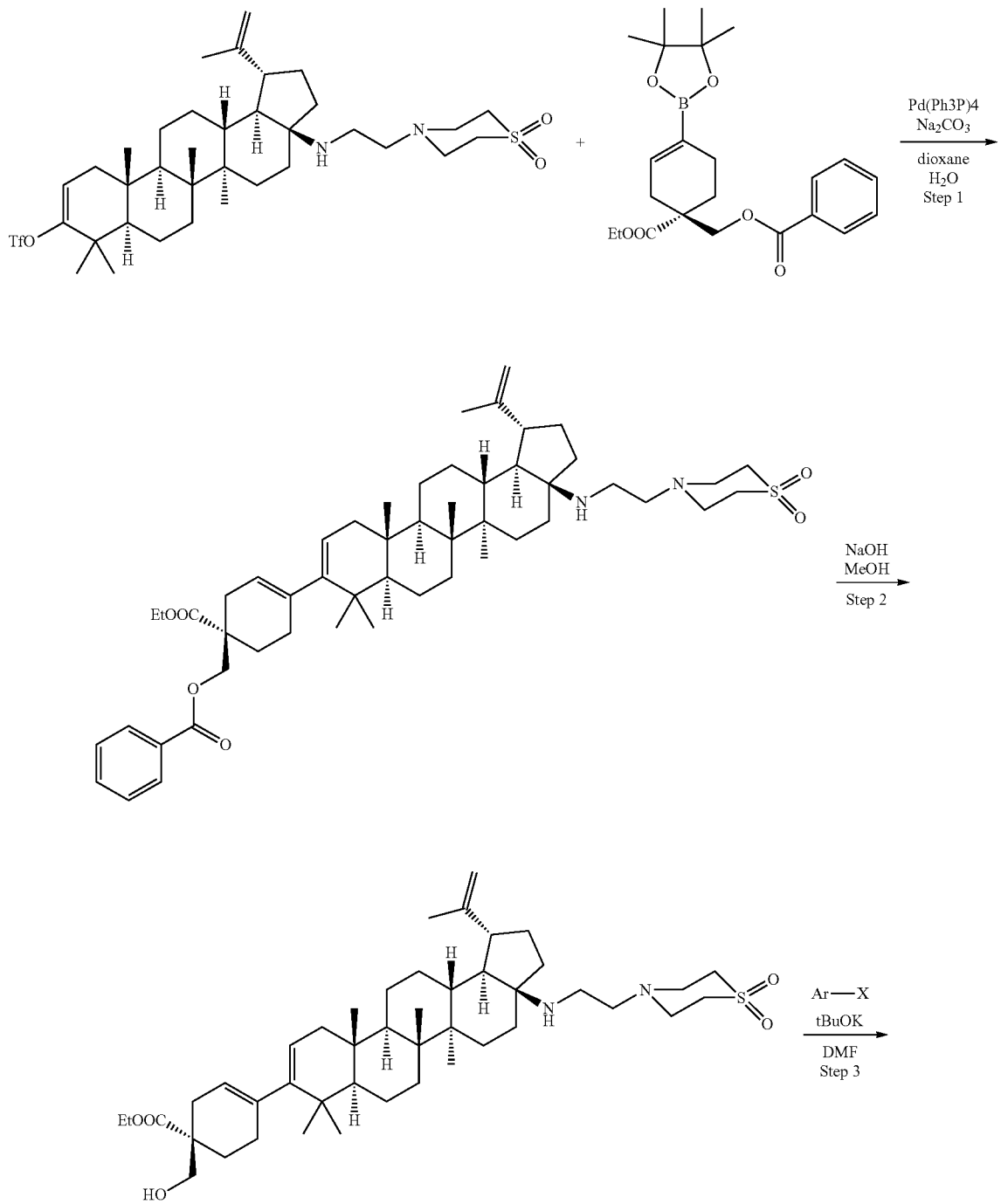

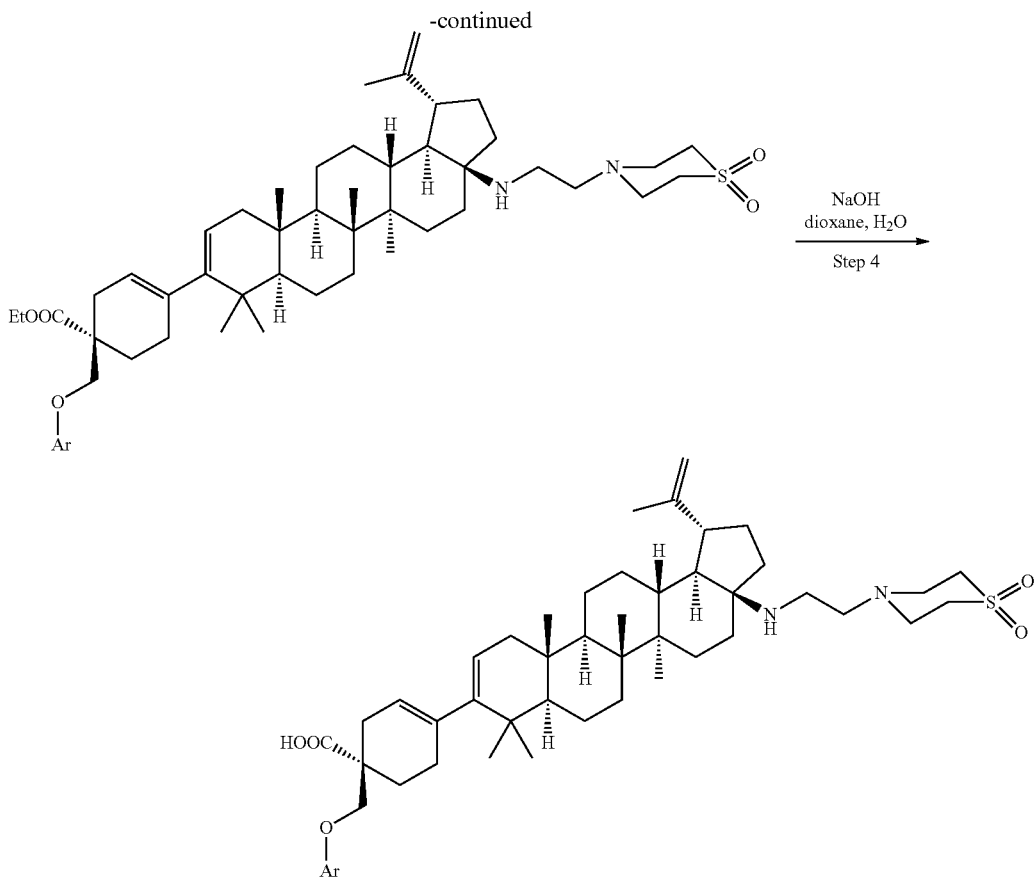

Step 1. Preparation of ((S)-4-((1R,3aS,5aR,5bR,7aR, 11aS, 11bR, 13aR, 13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a, 13b-octadecahydro-1H-cyclopenta[a]chrysen-9-yl)-1-(ethoxycarbonyl)cyclohex-3-en-1-yl)methyl benzoate.

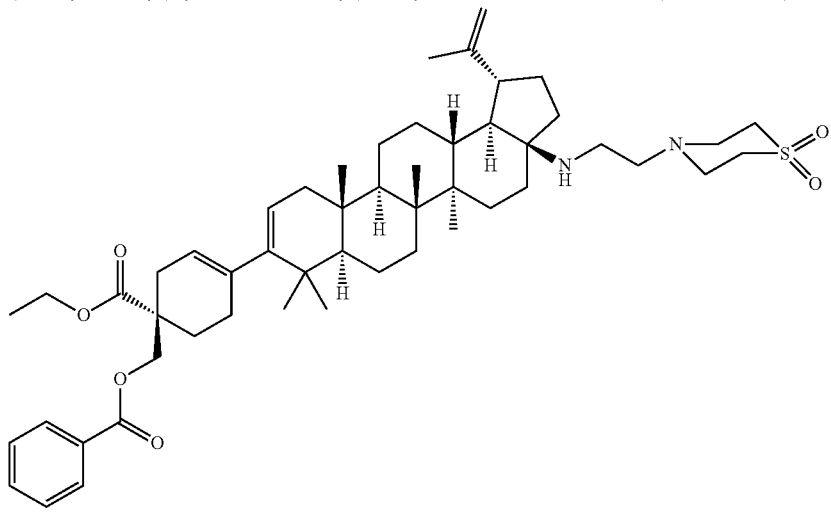

The title compound was prepared in 86% of yield as a solid, following the procedure described in General procedure B step 1, using (S)-(1-(ethoxycarbonyl)-4-(4,4,5,5-tetramethyl-1,3,2-dioxaborolan-2-yl)cyclohex-3-en-1-yl) methyl benzoate instead of (R)-(1-(ethoxycarbonyl)-4-(4,4, 5,5-tetramethyl-1,3,2-dioxaborolan-2-yl)cyclohex-3-en-1-yl)methyl benzoate as the reactant. LC/MS m/z 857.50 $(M+H)^+$, 3.055 min (LCMS Method 3). $^1$H NMR (400 MHz, CHLOROFORM-d) δ 8.07-7.90 (m, 2H), 7.64-7.52 (m, 1H), 7.49-7.37 (m, 2H), 5.37 (br. s., 1H), 5.21 (dd, J=6.0, 1.8 Hz, 1H), 4.72 (d, J=1.8 Hz, 1H), 4.61 (d, J=1.3 Hz, 1H), 4.52-4.37 (m, 2H), 4.25-4.16 (m, 2H), 3.15-3.00 (m, 8H), 2.78-2.53 (m, 5H), 2.51-2.42 (m, 1H), 2.34-2.23 (m, 1H), 1.70 (s, 3H), 1.07 (s, 3H), 0.99 (s, 3H), 0.97 (s, 3H), 0.93 (s, 3H), 0.87 (s, 3H), 2.22-0.80 (m, 29H).

Step 2. Preparation of ethyl (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate.

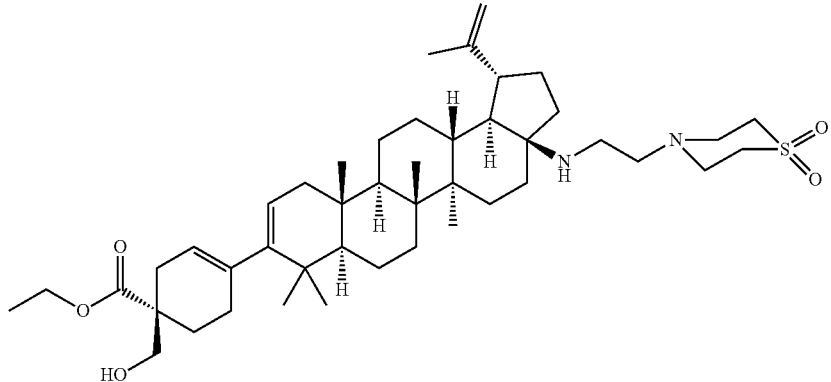

The title compound was prepared in 94% of yield as a solid, following the procedure described in General procedure B step 2, using ((S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)-1-(ethoxycarbonyl)cyclohex-3-en-1-yl)methyl benzoate instead of ((R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)-1-(ethoxycarbonyl)cyclohex-3-en-1-yl)methyl benzoate as the reactant. LC/MS m/z 753.55 (M+H)⁻, 2.754 min (LCMS Method 3). ¹H NMR (400 MHz, CHLOROFORM-d) δ 5.30 (s, 1H), 5.16 (d, J=5.0 Hz, 1H), 4.72 (s, 1H), 4.61 (s, 1H), 4.23-4.12 (m, 2H), 3.67 (s, 2H), 3.28-2.65 (m, 13H), 2.54 (d, J=16.1 Hz, 1H), 1.68 (s, 3H), 1.09 (s, 3H), 0.98 (s, 3H), 0.96 (s, 3H), 0.89 (s, 3H), 0.85 (s, 3H), 2.23-0.78 (m, 30H).

Step 3. Preparation of ethyl (S)-1-((aryloxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate.

To a solution of ethyl (S)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate (1 eq) in DMF at −78° C. was added KOtBu (2 eq). The resulted mixture was stirred for 20 minutes before the addition of Ar—X (2 eq). Then the reaction was warmed to RT and stirred overnight. The reaction mixture was diluted with EtAOc, washed with water, dried over Na₂SO₄, and concentrated in vacuo to give crude product which was either used in next step without further purification or purified by silica gel chromatography using ethyl acetate/hexanes as eluents.

Step 4. Preparation of (S)-1-((aryloxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

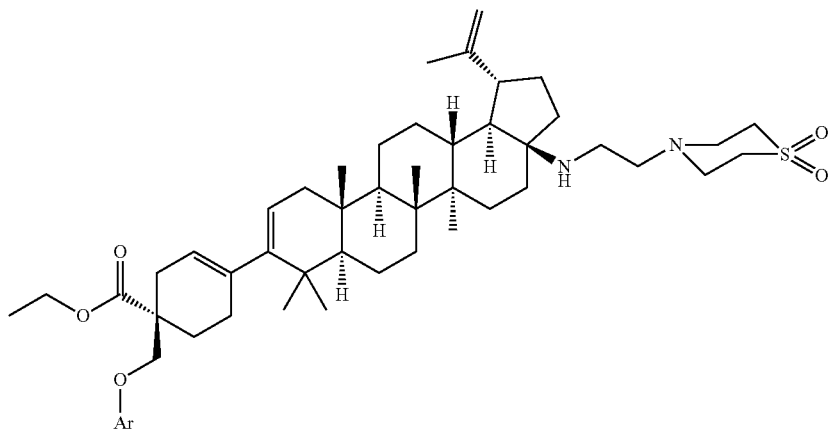

189

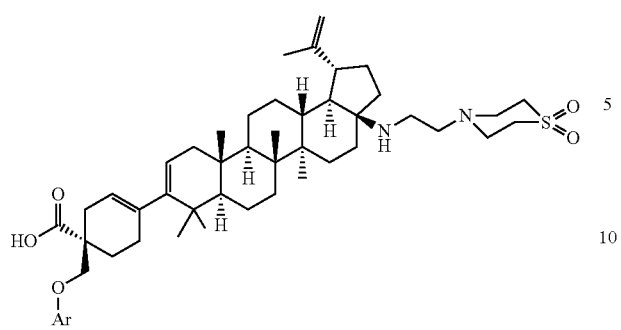

A solution of ethyl (S)-1-((aryloxy)methyl)-4-((1R,3aS,5aR,5bR,7aR,11aS,11bR,13aR,13bR)-3a-((2-(1,1-dioxido-thiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate from Step 3 in 1,4-dioxane, MeOH and 1N NaOH (2:1:1) was stirred at 50° C. for 2-18 hours. The reaction mixture was then purified by reverse phase preparative HPLC to give the final product.

Example 25

Preparation of (S)-1-(((3-cyanopyridin-2-yl)oxy)methyl)-4-((1R,3aS,5aR,5bR,7aR,11aS,11bR,13aR,13bR)-3a-((2-(1,

190

1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

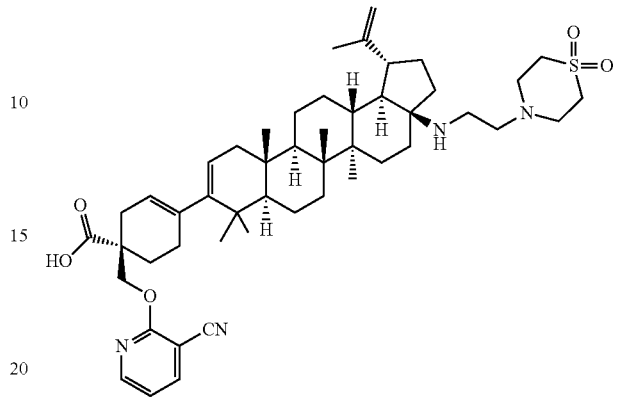

Step 1-2: General procedure C step 1-2.
Step 3. Preparation of ethyl (S)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate.

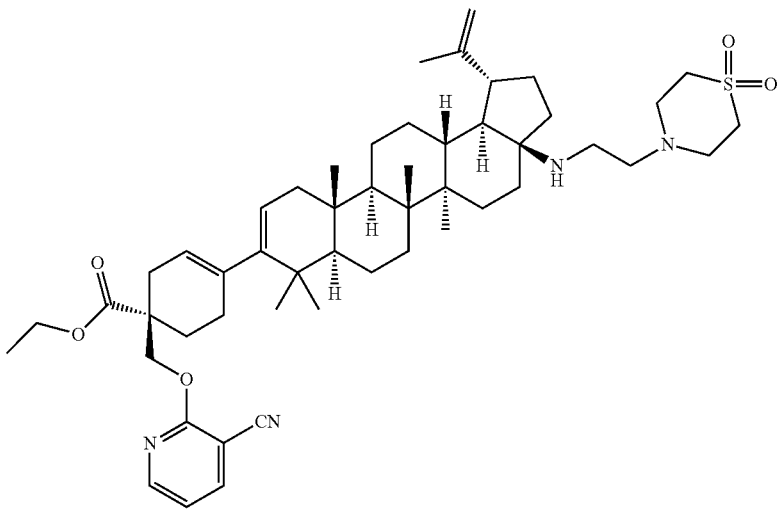

The title compound was prepared as a solid, following the procedure described in General procedure C step 3, using 2-chloronicotinonitrile as the reactant. LC/MS m/z 855.50 (M+H)⁻, 3.004 min (LCMS Method 3).

Step 4. (S)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid was prepared in 29% yield (over 2 steps) as a solid, following the procedure described in General procedure C step 4 for 7 h, using ethyl (S)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS: m/e 827.50 (M+H)⁺, 3.393 min (LCMS Method 7). ¹H NMR (400 MHz, METHANOL-d₄) δ 8.40 (dd, J=5.1, 1.9 Hz, 1H), 8.08 (dd, J=7.5, 2.0 Hz, 1H), 7.12 (dd, J=7.5, 5.0 Hz, 1H), 5.39 (br. s., 1H), 5.25-5.21 (m, 1H), 4.85 (s, 1H), 4.76 (s, 1H), 4.62 (d, J=10.3 Hz, 1H), 4.58 (d, J=10.3 Hz, 1H), 3.31-3.18 (m, 8H), 3.16-3.12 (m, 2H), 3.12-3.07 (m, 1H), 3.02-2.87 (m, 1H), 2.80 (td, J=11.0, 5.5 Hz, 1H), 2.73-2.63 (m, 2H), 2.37-2.27 (m, 1H), 2.26-2.01 (m, 8H), 1.97-1.91 (m, 1H), 1.88-1.75 (m, 2H), 1.78 (s, 3H), 1.72-1.44 (m, 10H), 1.42-1.31 (m, 1H), 1.20 (s, 3H), 1.27-1.09 (m, 3H), 1.13 (s, 3H), 1.02 (s, 3H), 0.98 (s, 3H), 0.95 (s, 3H).

Alternatively, Example 28 can be prepared using the following procedure:

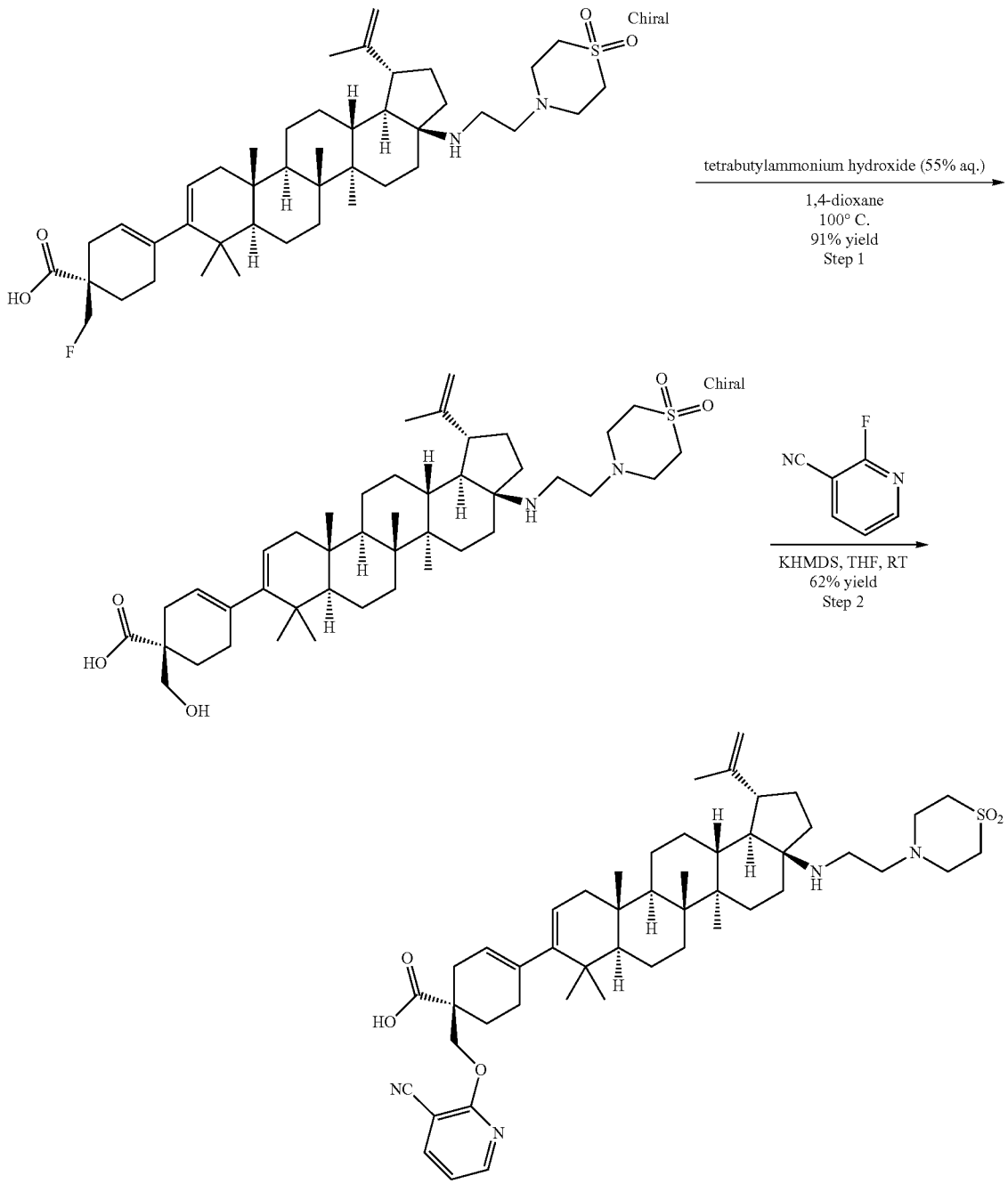

Step 1: Preparation of (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylic acid, HCl. To a flask containing a suspension of (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (4.08 g, 5.61 mmol) prepared as described in WO 2015157483 in 1,4-dioxane (50.0 mL) was added tetrabutylammonium hydroxide (55% in water) (26.5 g, 56.1 mmol). The flask was attached to reflux condensor and was heated in an oil bath at 100° C. After 8.5 days of heating, LC/MS showed the reaction was complete. The mixture was cooled to rt and was transferred to a graduated addition funnel. Upon standing in the addition funnel, two distinct layers formed. The bottom layer containing the product was split in half based on the graduation of the funnel. Half of the material was made acidic by adding 1N HCl. The solids that formed were collected by filtration and were washed with water. The solids were then triturated with ether and collected by filtration. The solids were washed with ether then allowed to dry on the filter paper. The title product was isolated as a white solid (1.95 g, 2.56 mmol, 45.6% yield, 91% if calculated as half of the mixture). LCMS: m/e 725.4 (M+H)+, 1.15 min (method 16).

Step 2. To a suspension of (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylic acid, HCl (1.95 g, 2.56 mmol) in THF (30 mL) was added KHMDS (0.91M in THF) (9.0 mL, 8.19 mmol). The mixture was stirred for 5 minutes, then 2-fluoronicotinonitrile (1.0 g, 8.19 mmol) was added. After 2.5 h an aliquot was removed. LC/MS showed the reaction was complete. The reaction mixture was diluted with 1N HCl (30 mL) then was extracted with ethyl acetate (3×75 mL). The organic layers were washed with sat. aq. NaCl, and dried over magnesium sulfate. The drying agent was removed by filtration. The drying agent did not filter well, so it is likely that solid precipitated while standing at rt, so the solid filter cake was stirred with ethyl acetate, then with dichloromethane, then filtered again. The combined filtrates were concentrated under reduced pressure. The residue was triturated with ether and the solids that formed were collected by filtration and washed with ether. The residue was dissolved in methanol and was purified by reverse phase chromatography using a 275 g Isco Redisep gold C18 column and a 20% B-80% A to 100% B gradient where A was 90% water, 10% acetonitrile with 0.1% TFA buffer and B was 10% water, 90% acetonitrile with 0.1% TFA buffer. The fractions containing the product were combined and concentrated under reduced pressure to give (S)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (1.50 g, 1.59 mmol, 62%) as a white solid. LCMS: m/e 827.4 (M+H)+, 1.32 min (method 16).

Example 26

Preparation of (S)-1-(((3-carbamoylpyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.


The title compound was prepared as a side product in 7% yield (over 2 steps) as a solid, following the procedure described in General procedure C Step 4 for 7 h, using ethyl (S)-1-(((3-cyanopyridin-2-yl)oxy)methyl)-4-41R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopentalalchrysen-9-yl)cyclohex-3-ene-1-carboxylate as the reactant. LC/MS: m/e 845.55 (M+H—H$_2$O)+, 3.349 min (LCMS Method 7). $^1$H NMR (400 MHz, METHANOL-d$_4$) δ 8.42 (dd, J=7.5, 2.0 Hz, 1H), 8.31 (dd, J=4.8, 2.0 Hz, 1H), 7.16 (dd, J=7.5, 5.0 Hz, 1H), 5.40 (br. s., 1H), 5.24 (d, J=4.5 Hz, 1H), 4.86 (br. s., 1H), 4.76 (s, 1H), 4.66-4.62 (d, J=10.5 Hz, 1H), 4.57-4.53 (d, J=10.5 Hz, 1H), 3.30-3.17 (m, 7H), 3.12 (d, J=17.3 Hz, 3H), 2.96-2.92 (m, 1H), 2.81-2.71 (m, 2H), 2.45-2.30 (m, 1H), 2.25-2.12 (m, 5H), 2.12-2.00 (m, 3H), 1.92-1.67 (m, 6H), 1.78 (s, 3H), 1.67-1.41 (m, 10H), 1.26-1.06 (m, 3H), 1.20 (s, 3H), 1.13 (s, 3H), 1.02 (s, 3H), 0.99 (s, 3H), 0.95 (s, 3H).

Example 27

Preparation of (R)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-(methoxycarbonyl)pyridin-2-yl)oxy)methyl)cyclohex-3-ene-1-carboxylic acid.

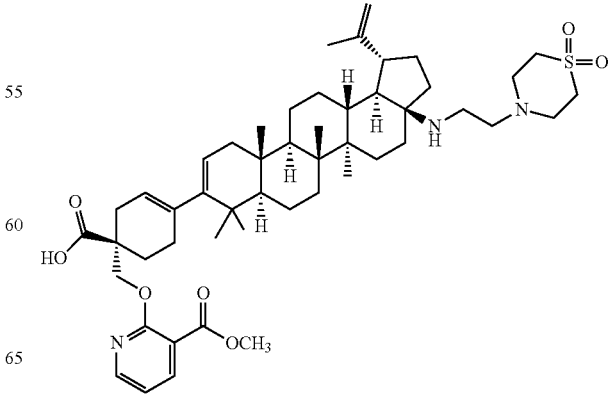

The title compound was prepared as a side product in 0.6% yield (over 2 steps) as a solid, following the procedure described in General procedure B step 4 for 15 h, using ethyl (R)-1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)cyclohex-3-ene-1-carboxylate as the reactant. LC/MS: m/e 860.65 (M+H)⁺, 2.93 min (LCMS Method 7). ¹H NMR (400 MHz, METHANOL-d₄) δ 8.30 (dd, J=5.0, 2.0 Hz, 1H), 8.17 (dd, J=7.5, 2.0 Hz, 1H), 7.06 (dd, J=7.5, 5.0 Hz, 1H), 5.39 (br. s., 1H), 5.25-5.21 (m, 1H), 4.85 (s, 1H), 4.75 (s, 1H), 4.57-4.47 (m, 2H), 3.89 (s, 3H), 3.30-3.17 (m, 8H), 3.16-3.07 (m, 3H), 3.02-2.90 (m, 1H), 2.81 (td, J=11.0, 5.4 Hz, 1H), 2.73-2.63 (m, 1H), 2.36-2.00 (m, 9H), 2.00-1.90 (m, 1H), 1.90-1.75 (m, 3H), 1.77 (s, 3H), 1.75-1.34 (m, 12H), 1.26-1.09 (m, 2H), 1.20 (s, 3H), 1.12 (s, 3H), 1.01 (s, 3H), 0.98 (s, 3H), 0.95 (s, 3H).

Example 28

Preparation of (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((6-methoxypyridin-2-yl)oxy)methyl)cyclohex-3-ene-1-carboxylic acid.

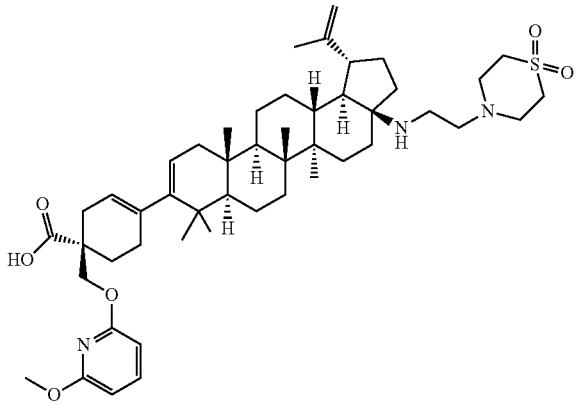

Step 1-2: General procedure C step 1-2.
Step 3. Preparation of ethyl (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((6-fluoropyridin-2-yl)oxy)methyl)cyclohex-3-ene-1-carboxylate.

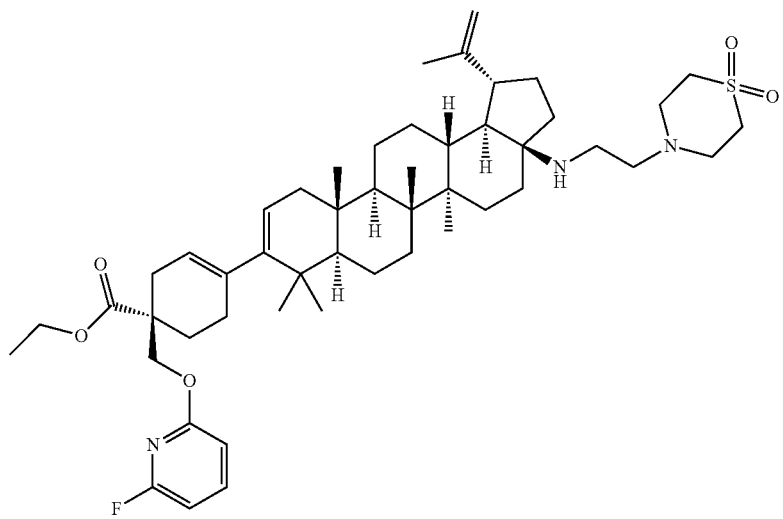

The title compound was prepared as a solid, following the procedure described in General procedure C step 3, using 2,6-difluoropyridine as the reactant. LC/MS m/z 848.50 (M+H)⁻, 3.031 min (LCMS Method 3).

Step 4. (S)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((6-methoxypyridin-2-yl)oxy)methyl)cyclohex-3-ene-1-carboxylic acid was prepared in 3.7% yield (over 2 steps) as a solid, following the procedure described in General procedure C step 4 for 15 h, using ethyl (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((6-fluoropyridin-2-yl)oxy)methyl)cyclohex-3-ene-1-carboxylate as the reactant. LC/MS: m/e 832.50 (M+H)⁺, 3.267 min (LCMS Method 7). ¹H NMR (500 MHz, METHANOL-d₄) δ 7.54 (t, J=7.9 Hz, 1H), 6.32 (d, J=2.9 Hz, 1H), 6.30 (d, J=2.9 Hz, 1H), 5.38 (br. s., 1H), 5.29-5.15 (m, 1H), 4.85 (s, 1H), 4.76 (s, 1H), 4.485-4.345 (m, 2H), 3.89 (s, 3H), 3.30-3.17 (m, 8H), 3.17-3.07 (m, 3H), 2.94 (ddd, J=14.5, 10.2, 4.7 Hz, 1H), 2.78 (td, J=11.0, 5.4 Hz, 1H), 2.67-2.60 (m, 1H), 2.30 (d, J=18.2 Hz, 1H), 2.22-2.09 (m, 3H), 2.09-2.00 (m, 2H), 1.96-1.66 (m, 8H), 1.78 (s, 3H), 1.66-1.43 (m, 10H), 1.43-1.29 (m, 2H), 1.29-1.09 (m, 1H), 1.19 (s, 3H), 1.13 (s, 3H), 1.01 (s, 3H), 0.98 (s, 3H), 0.95 (s, 3H).

Example 29

Preparation of (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-(((6-fluoropyridin-2-yl)oxy)methyl)cyclohex-3-ene-1-carboxylic acid.

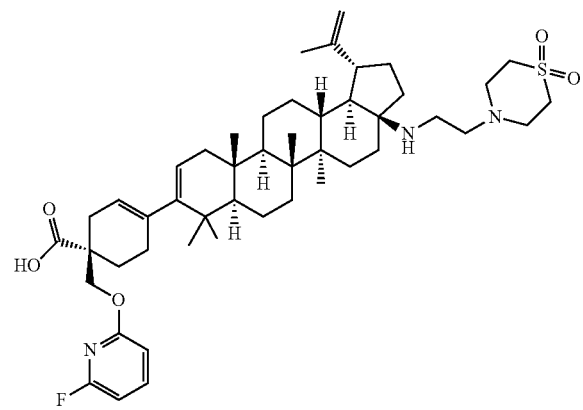

The title compound was prepared in 69.8% of yield (2 steps) as a solid, following the procedure described in General procedure C step 4 for 7 h, using ethyl (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((6-fluoropyridin-2-yl)oxy)methyl)cyclohex-3-ene-1-carboxylate as the reactant. LC/MS: m/e 820.45 (M+H)⁺, 3.136 min (LCMS Method 7). ¹H NMR (500 MHz, ACETONE-d₆) δ 7.85 (q, J=8.1 Hz, 1H), 6.71 (dd, J=8.0, 1.3 Hz, 1H), 6.61 (dd, J=7.8, 2.3 Hz, 1H), 5.42-5.35 (m, 1H), 5.23 (dd, J=6.2, 1.8 Hz, 1H), 4.79 (d, J=1.2 Hz, 1H), 4.68 (d, J=1.4 Hz, 1H), 4.46 (d, J=10.2 Hz, 1H), 4.41 (d, J=10.2 Hz, 1H), 3.43-3.24 (m, 8H), 3.23-3.12 (m, 5H), 3.12-3.05 (m, 3H), 3.02 (td, J=10.8, 5.7 Hz, 1H), 2.70-2.61 (m, 1H), 2.38-2.16 (m, 4H), 2.17-2.01 (m, 3H), 1.95-1.84 (m, 2H), 1.84-1.68 (m, 2H), 1.74 (s, 3H), 1.64 (d, J=16.8 Hz, 1H), 1.61-1.42 (m, 8H), 1.40-1.22 (m, 1H), 1.26 (s, 3H), 1.23-1.11 (m, 2H), 1.13 (s, 3H), 1.02 (s, 3H), 0.97 (s, 3H), 0.94 (s, 3H).

Example 30

Preparation of (S)-1-(((4-carbamoylpyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

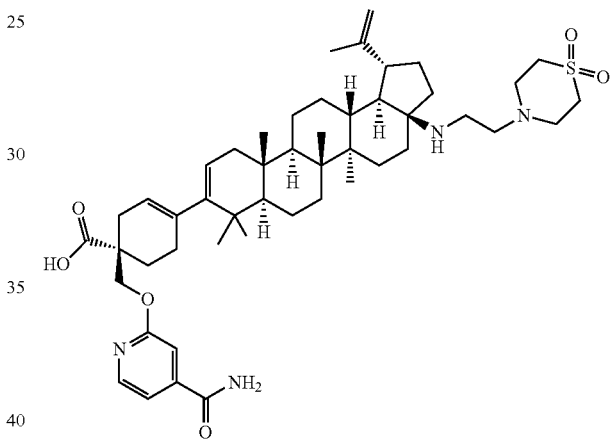

Step 1-2: General procedure C step 1-2.
Step 3. Preparation of ethyl (S)-1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate.

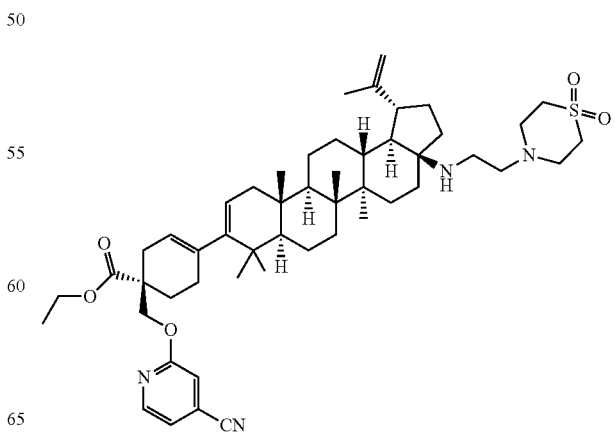

The title compound was prepared as a solid, following the procedure described in General procedure C step 3, using 2-fluoroisonicotinonitrile as the reactant. LC/MS m/z 855.50 (M+H)⁻, 3.048 min (LCMS Method 3).

Step 4. (S)-1-(((4-carbamoylpyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid was prepared in 30.5% yield (over 2 steps) as a solid, following the procedure described in General procedure C step 4 for 7 h, using ethyl (S)-1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS: m/e 845.55 (M+H)⁺, 3.048 min (LCMS Method 7). ¹H NMR (400 MHz, CHLOROFORM-d) δ 8.02 (d, J=5.3 Hz, 1H), 7.12 (d, J=5.3 Hz, 1H), 6.97 (s, 1H), 5.16 (br. s., 1H), 5.00 (d, J=5.5 Hz, 1H), 4.58 (br. s., 1H), 4.48 (br. s., 1H), 4.35-4.18 (m, 2H), 3.25-2.65 (m, 18H), 2.47 (d, J=17.1 Hz, 1H), 2.14-1.64 (m, 10H), 1.52-1.48 (m, 2H), 1.50 (s, 3H), 1.45-1.03 (m, 10H), 0.98 (s, 3H), 0.88-0.84 (m, 2H), 0.86 (s, 3H), 0.78 (s, 3H), 0.73 (s, 3H), 0.68 (s, 3H).

Example 31

Preparation of (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylic acid.

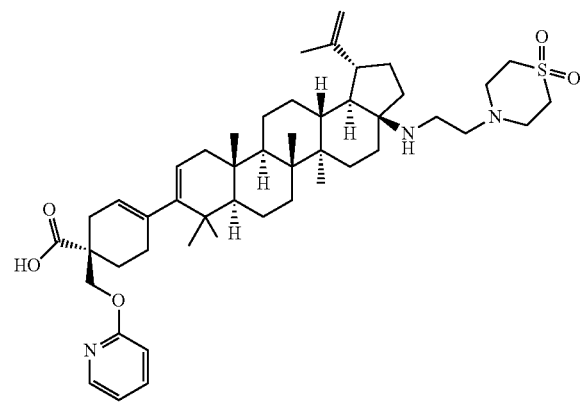

Step 1-2: General procedure C step 1-2.

Step 3. Preparation of ethyl (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylate.

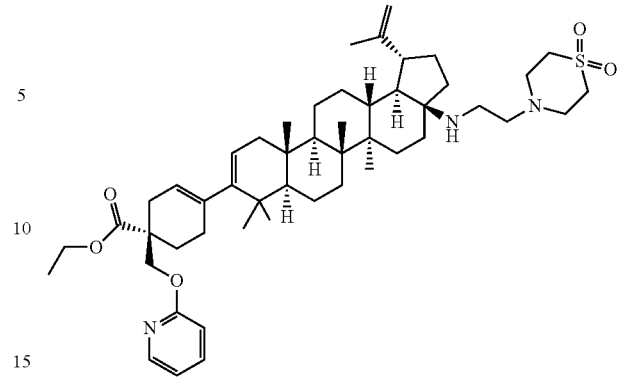

The title compound was prepared as a solid, following the procedure described in General procedure C step 3, using 2-bromopyridine as the reactant. LC/MS m/z M+1=830.55. 2.822 min (LCMS Method 3).

Step 4. (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylic acid was prepared in 22.9% yield (over 2 steps) as a solid, following the procedure described in General procedure C step 4 for 7 h, using ethyl (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylate as the reactant. LC/MS: m/e 802.45 (M+H)⁺, 2.824 min (LCMS Method 3). ¹H NMR (400 MHz, CHLOROFORM-d) δ 8.21 (dd, J=5.1, 1.4 Hz, 1H), 7.69 (ddd, J=8.6, 7.0, 1.8 Hz, 1H), 6.97 (td, J=6.2, 0.9 Hz, 1H), 6.83 (d, J=8.5 Hz, 1H), 5.38 (br. s., 1H), 5.21 (d, J=4.5 Hz, 1H), 4.80 (s, 1H), 4.72 (s, 1H), 4.51 (d, J=10.0 Hz 1H), 4.46 (d, J=10.0 Hz 1H), 3.37-3.34 (m, 1H), 3.25-3.10 (m, 7H), 3.10-3.01 (m, 2H), 3.00-2.87 (m, 2H), 2.82 (dt, J=10.9, 5.6 Hz, 1H), 2.73 (d, J=15.3 Hz, 1H), 2.35-2.13 (m, 4H), 2.13-1.88 (m, 7H), 1.81-1.67 (m, 2H), 1.71 (s, 3H), 1.66-1.26 (m, 13H), 1.18 (s, 3H), 1.13-1.03 (m, 1H), 1.06 (s, 3H), 0.99 (s, 3H), 0.94 (s, 3H), 0.89 (s, 3H).

Example 32

Preparation of (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrazin-2-yloxy)methyl)cyclohex-3-ene-1-carboxylic acid.

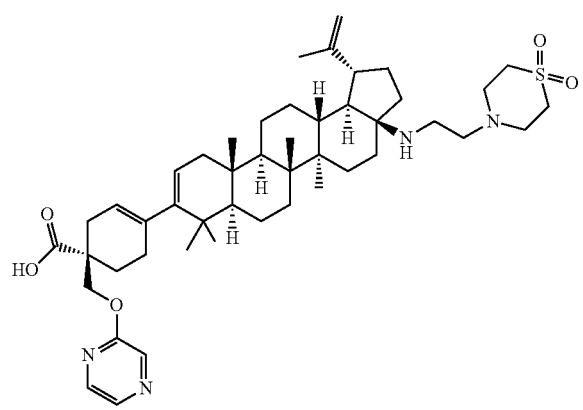

Step 1-2: General procedure C step 1-2.

Step 3. Preparation of ethyl (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrazin-2-yloxy)methyl)cyclohex-3-ene-1-carboxylate.

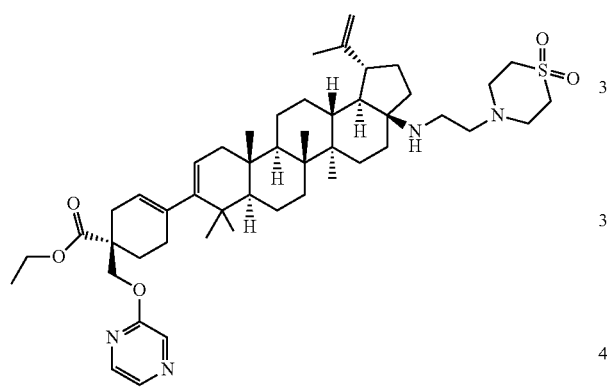

The title compound was prepared as a solid, following the procedure described in General procedure C step 3, using 2-fluoropyrazine as the reactant. LC/MS m/z M+1=831.55. 2.922 min (LCMS Method 3).

Step 4. (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopentatalchrysen-9-yl)-1-((pyrazin-2-yloxy)methyl)cyclohex-3-ene-1-carboxylic acid was prepared in 77.0% yield (over 2 steps) as a solid, following the procedure described in General procedure C step 4 for 9 h, using ethyl (S)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrazin-2-yloxy)methyl)cyclohex-3-ene-1-carboxylate as the reactant. LC/MS: m/e 803.42 (M+H)+, 2.38 min (LCMS Method 1). $^1$H NMR (400 MHz, CHLOROFORM-d) δ 8.27 (br. s., 2H), 8.17 (br. s., 1H), 5.39 (br. s., 1H), 5.22 (d, J=4.8 Hz, 1H), 4.79 (s, 1H), 4.73 (s, 1H), 4.62-4.48 (dd, J=10.5, 17.3 Hz, 2H), 3.44-3.32 (m, 1H), 3.30-2.89 (m, 11H), 2.84-2.64 (m, 2H), 2.38-1.83 (m, 11H), 1.83-1.67 (m, 2H), 1.71 (s, 3H), 1.68-1.37 (m, 10H), 1.38-1.22 (m, 2H), 1.16 (s, 3H), 1.13-1.03 (m, 2H), 1.06 (s, 3H), 0.98 (s, 3H), 0.93 (s, 3H), 0.89 (s, 3H).

General Procedure D: Preparation of a-pyridin-2-yloxy cyclohexenecarboxylic acid derivatives.

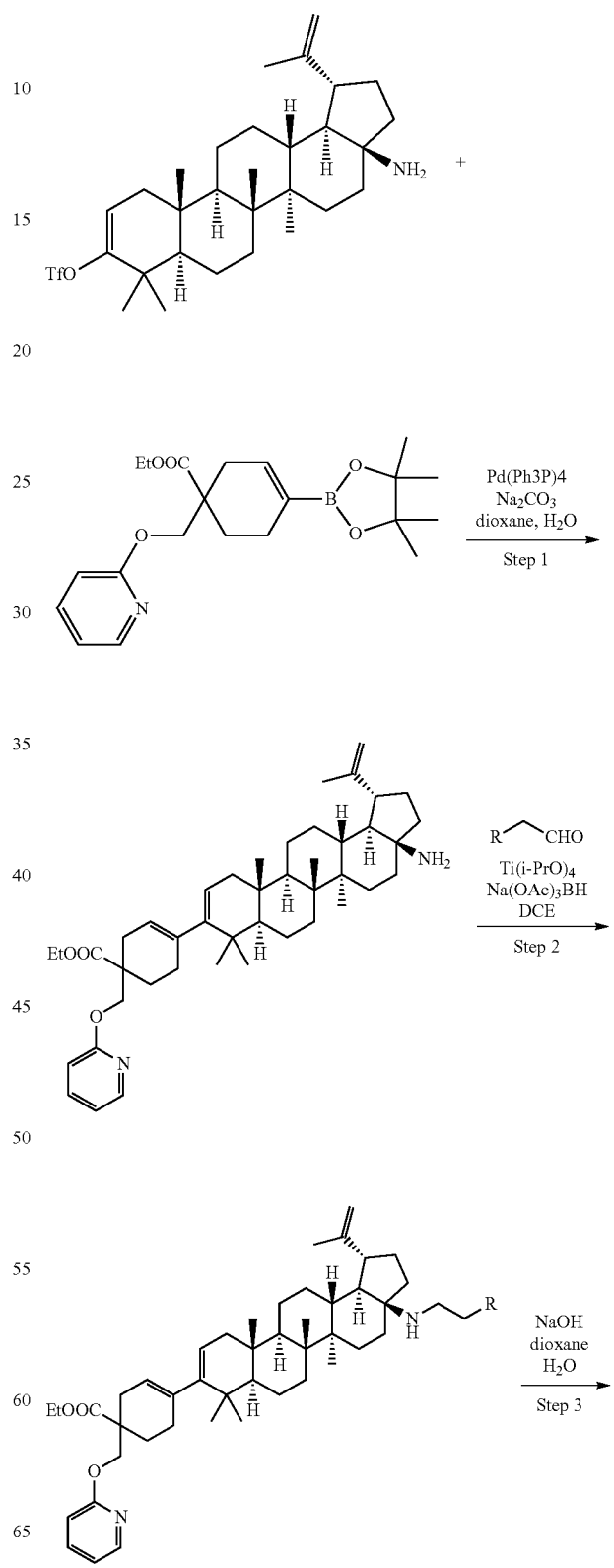

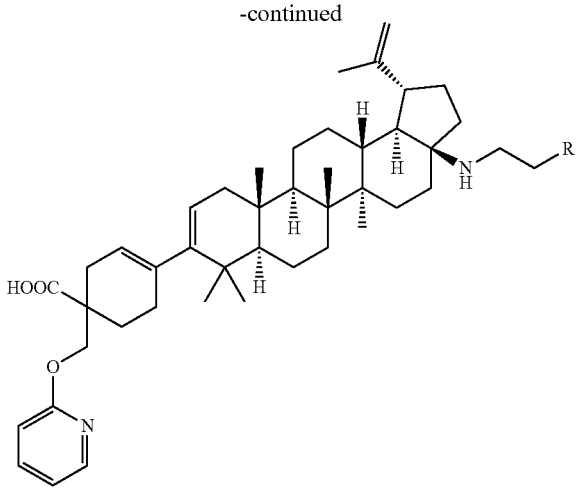

Step 1. Preparation of ethyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-1-((pyridin-2-yloxy)methyl)cyclohex-3-ene-1-carboxylate.

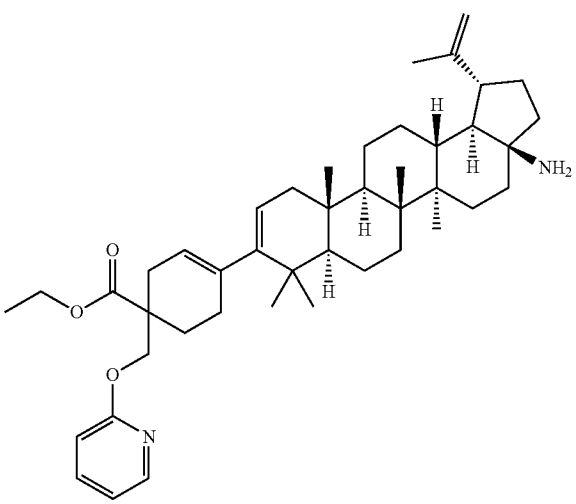

A mixture of (1R,3aS,5aR,5bR,7aR,11aR,11bR,13aR, 13bR)-3a-amino-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl trifluoromethanesulfonate (1 eq), ethyl 1-((pyridin-2-yloxy) methyl)-4-(4,4,5,5-tetramethyl-1,3,2-dioxaborolan-2-yl)cyclohex-3-ene-1-carboxylate (1 eq), $Na_2CO_3$ (3 eq) and $Pd(Ph_3P)_4$ (0.06 eq) in 1,4-dioxane and $H_2O$ (4:1), was flushed with nitrogen, sealed and heated at 70° C. for 2 h. The reaction mixture was diluted with EtOAc, washed with brine, dried over $Na_2SO_4$, and concentrated in vacuo. The crude product was purified by silica gel column eluted with 0-55% ethyl acetate/hexanes to give the desired product (57% yield) as a solid. $^1$H NMR (400 MHz, CHLOROFORM-d) δ 8.13 (dd, J=5.0, 1.5 Hz, 1H), 7.58-7.52 (m, 1H), 6.86 (ddd, J=7.2, 5.1, 0.8 Hz, 1H), 6.72 (d, J=8.5 Hz, 1H), 5.35 (br. s., 1H), 5.19 (d, J=5.8 Hz, 1H), 4.73 (d, J=2.3 Hz, 1H), 4.60 (dd, J=2.3, 1.3 Hz, 1H), 4.48-4.37 (m, 2H), 4.18-4.11 (m, 2H), 2.70-2.62 (m, 1H), 2.54 (td, J=10.9, 5.3 Hz, 1H), 2.29-0.84 (m, 27H), 1.69 (s, 3H), 1.20 (t, J=7.2 Hz, 3H), 1.07 (s, 3H), 0.96 (s, 3H), 0.97-0.91 (m, 6H), 0.86 (s, 3H). LC/MS m/z 669.60 (M+H)$^+$, 2.82 min (LCMS Method 3).

Step 2: Preparation of C-17 amine derivative.

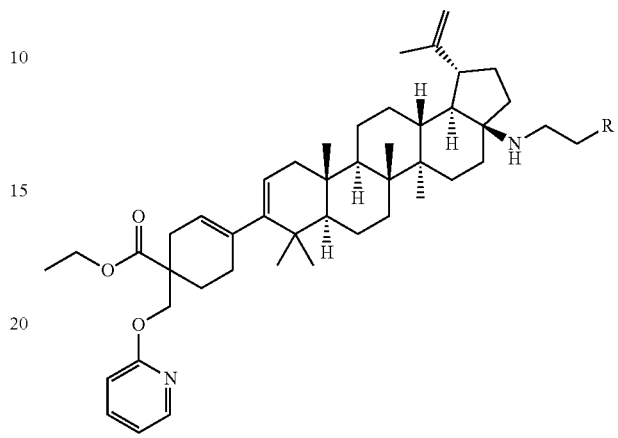

To a solution of ethyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-((pyridin-2-yloxy)methyl)cyclohex-3-ene-1-carboxylate (1 eq) and aldehyde (2 eq) in DCE was added titanium (IV) isopropoxide (2 eq). The mixture was stirred at RT for 1 h. Sodium triacetoxyborohydride (2 eq) was added and the mixture was stirred at RT overnight. The reaction was quenched with saturated aqueous $Na_2CO_3$. The resulting slurry was extracted with dichloromethane, washed with brine, dried over $Na_2SO_4$, and concentrated in vacuo. The crude product was purified by silica gel column eluted with ethyl acetate/hexanes to give the desired product.

Step 3: Preparation of carboxylic acid.

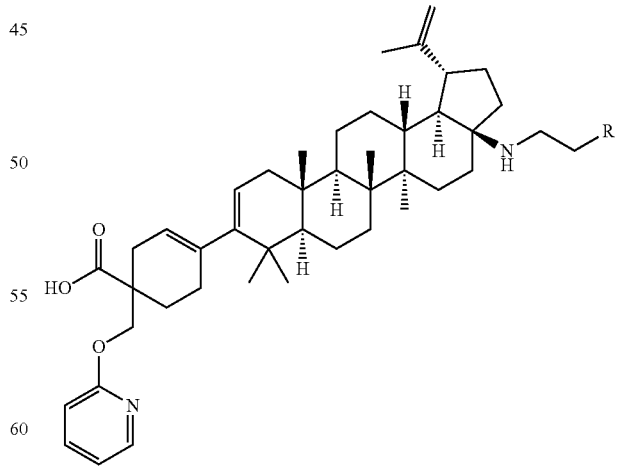

A solution of the ester from step 2 in 1,4-dioxane, MeOH and 1N NaOH (2:1:1) was stirred at 60-70° C. The reaction mixture was purified by reverse phase preparative HPLC to give the final product.

Example 33

Preparation of 4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylic acid.

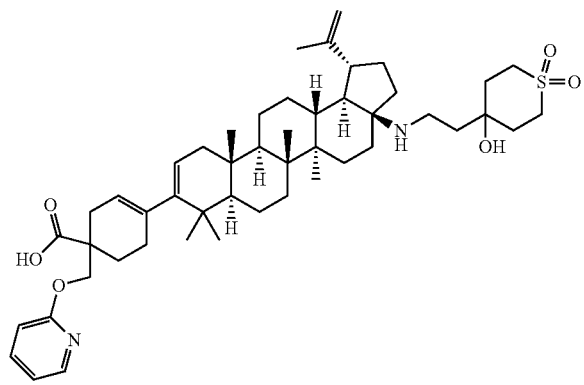

Step 1: General procedure D step 1.

Step 2. Preparation of ethyl 4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylate.

The title compound was prepared in 78% yield as a solid, following the procedure described in general procedure D step 2, using 2-(4-hydroxy-1,1-dioxidotetrahydro-2H-thiopyran-4-yl)acetaldehyde as reactant. $^1$H NMR (400 MHz, CHLOROFORM-d) δ 8.12 (dd, 1.5 Hz, 1H), 7.57-7.52 (m, 1H), 6.85 (ddd, 5.1, 0.9 Hz, 1H), 6.72 (d, J=8.5 Hz, 1H), 5.34 (br. s., 1H), 5.18 (d, J=5.8 Hz, 1H), 4.73 (d, J=1.8 Hz, 1H), 4.61 (s, 1H), 4.48-4.36 (m, 2H), 4.18-4.08 (m, 4H), 3.57-3.43 (m, 2H), 2.91-2.61 (m, 5H), 2.50 (td, J=10.7, 5.5 Hz, 1H), 2.24-0.88 (31H), 1.68 (s, 3H), 1.19 (t, J=7.2 Hz, 3H), 1.03 (s, 3H), 0.96 (s, 3H), 0.95-0.90 (m, 6H), 0.85 (s, 3H). LC/MS m/z 845.60 (M+H)$^+$, 3.59 min (LCMS Method 4).

Step 3. 4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylic acid was prepared in 76% yield as a solid, following the procedure described in general procedure D step 3 at 60° C. for 12 h, using ethyl 4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-ene-1-carboxylate as reactant. $^1$H NMR (400 MHz, CHLOROFORM-d) δ 8.29 (br. s., 1H), 7.96 (t, J=7.0 Hz, 1H), 7.17 (br. s., 1H), 7.04 (d, J=8.3 Hz, 1H), 5.35 (br. s., 1H), 5.18 (d, J=5.3 Hz, 1H), 4.75 (s, 1H), 4.69 (s, 1H), 4.53-4.39 (m, 2H), 3.58-3.35 (m, 2H), 3.21 (br. s., 2H), 2.97-2.84 (m, 2H), 2.76-2.62 (m, 2H), 2.58-2.44 (m, 1H), 2.34-1.04 (m, 32H), 1.68 (s, 3H), 1.07 (s, 3H), 1.02 (s, 3H), 0.95-0.91 (m, 6H), 0.87 (s, 3H). LC/MS m/z 817.55 (M+H)+, 5.51 min (LCMS Method 4).

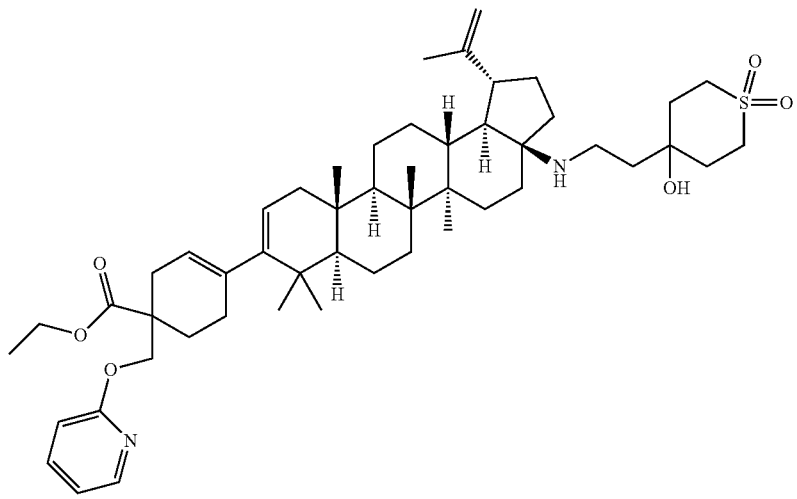

General Procedure E. Preparation of a-substituted cyclohexenecarboxylic acid derivatives via alkylation of α-methyl alcohol.
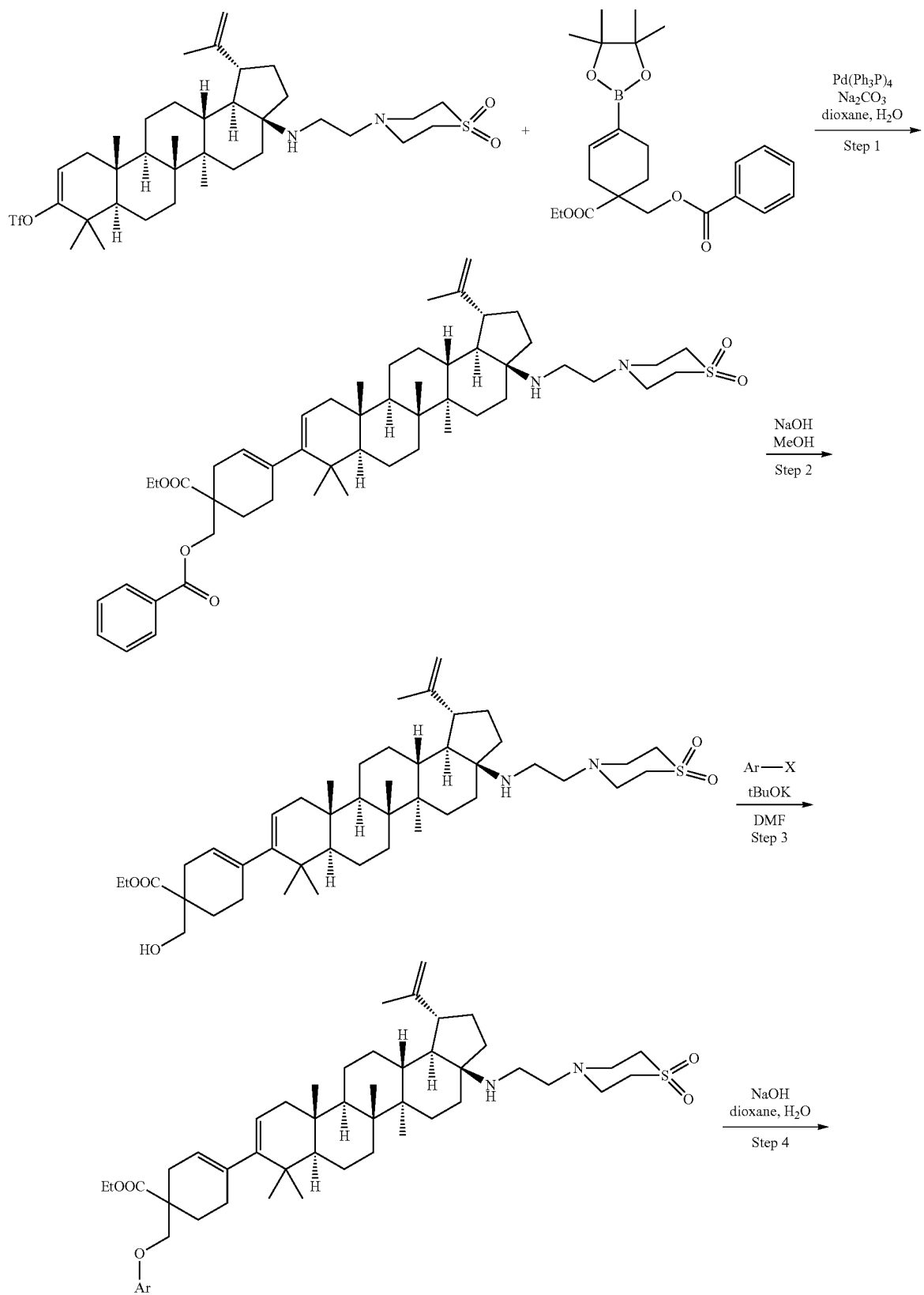

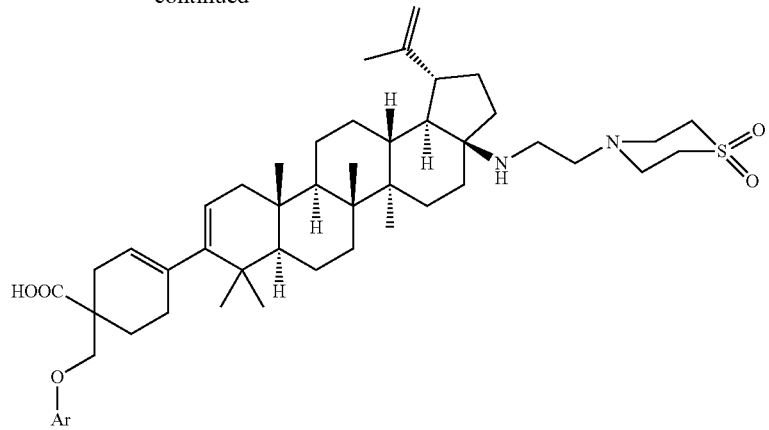

Step 1. Preparation of (4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)-1-(ethoxycarbonyl)cyclohex-3-en-1-yl)methyl benzoate.

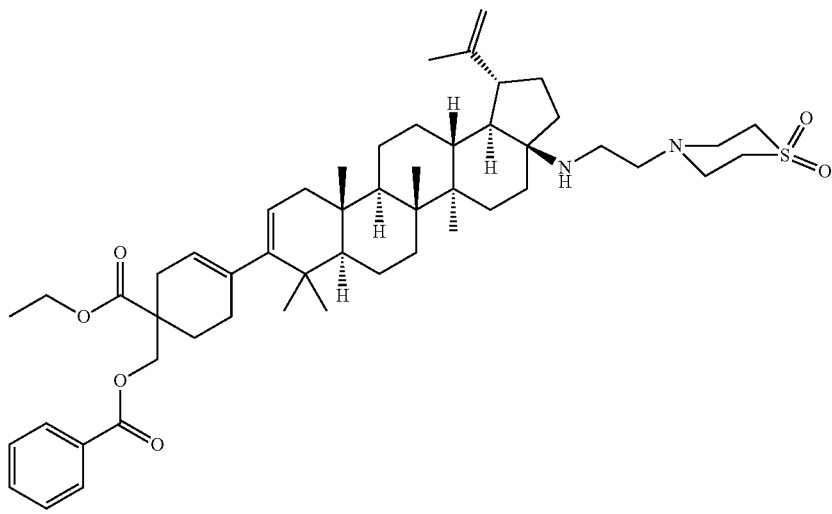

A mixture of (1R,3aS,5aR,5bR,7aR,11aR,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl trifluoromethanesulfonate (1 eq), (1-(ethoxycarbonyl)-4-(4,4,5,5-tetramethyl-1,3,2-dioxaborolan-2-yl)cyclohex-3-en-1-yl)methyl benzoate (1.05 eq), $Na_2CO_3$ $H_2O$ (3 eq) and $Pd(Ph_3P)_4$ (0.06 eq) in 1,4-dioxane and $H_2O$ (4:1) was flushed with nitrogen, sealed and heated at 70° C. for 2 h. The reaction mixture was concentrated in vacuo, and the residue was partitioned between EtOAc and $H_2O$. The separated aqueous layer was extracted with EtOAc. The combined organic layers were washed with brine dried over $Na_2SO_4$, and concentrated in vacuo. The crude product was purified by silica gel column eluted with 0-60% ethyl acetate/hexanes to give the desired product as a solid (67% yield). $^1H$ NMR (400 MHz, CHLOROFORM-d) δ 8.01 (dd, J=8.2, 1.1 Hz, 2H), 7.59-7.53 (m, 1H), 7.46-7.40 (m, 2H), 5.36 (br. s., 1H), 5.20 (d, J=5.5 Hz, 1H), 4.71 (d, J=2.0 Hz, 1H), 4.59 (s, 1H), 4.48-4.39 (m, 2H), 4.21-4.14 (m, 2H), 3.12-2.98 (m, 8H), 2.73-2.53 (m, 5H), 2.50-2.42 (m, 1H), 2.31-0.81 (m, 27H), 1.69 (s, 3H), 1.22 (t, J=7.2 Hz, 3H), 1.06 (s, 3H), 0.96 (s, 3H), 0.98-0.92 (m, 6H), 0.86 (s, 3H). LC/MS: m/e 857.50 (M+H)$^+$, 2.91 min (LCMS Method 3).

Step 2:. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate.

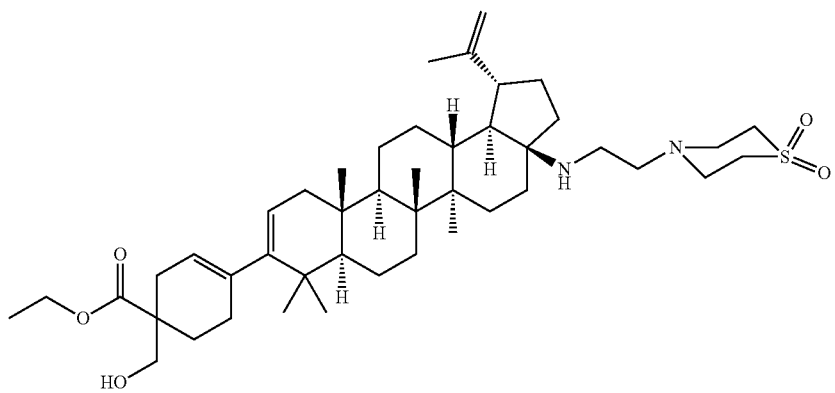

A suspension of 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (1 eq) and 1N NaOH (1 eq) in MeOH and THF was stirred at RT for 1 day. The mixture was neutralized with saturated aqueous citric acid and the solvent was removed in vacuo. The residue was taken into EtOAc, washed with brine, dried over Na$_2$SO$_4$, and concentrated in vacuo to give the desired product (99% yield) as a solid without further purification. LC/MS m/z 753.70 (M+H)$^+$, 2.85 min (LCMS Method 3).

Step 3. Preparation of a-substituted cyclohexenecarboxylic ester.

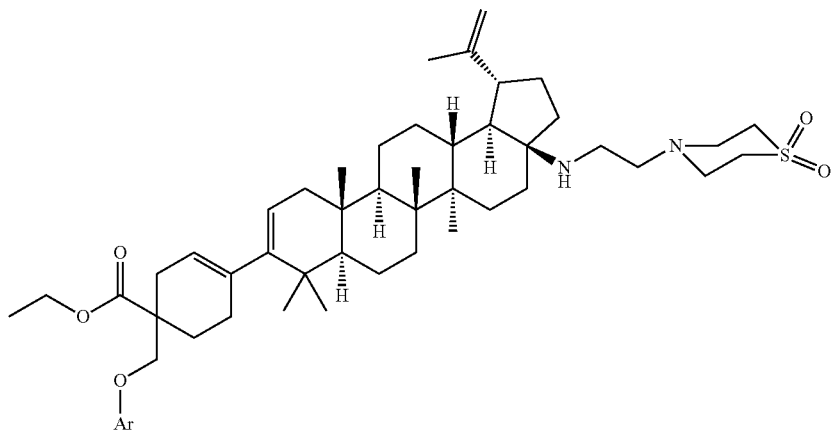

To a solution of ethyl-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate (1 eq) and Ar—X (2 eq) in DMF was added KOtBu (2 eq). The resulting mixture was warmed to RT and stirred overnight. The reaction mixture was diluted with EtAOc, washed with water, dried over Na$_2$SO$_4$, and concentrated in vacuo to give crude product which was used in next step without further purification.

Step 4. Preparation of a-substituted cyclohexenecarboxylic acid.

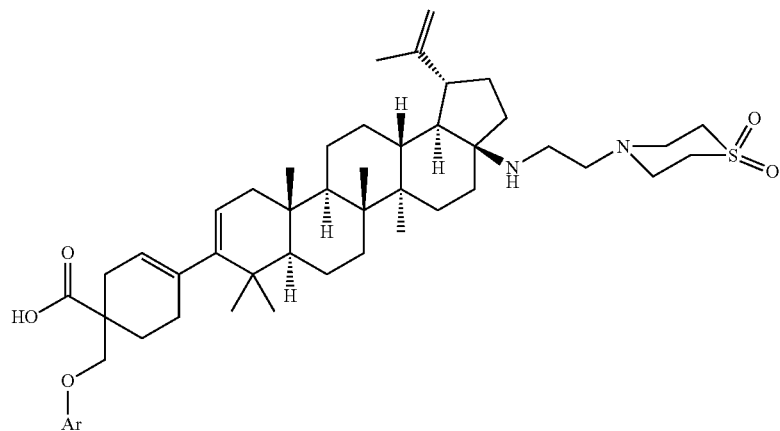

A solution of a-methyl ether from step 4 in 1,4-dioxane, MeOH and 1N NaOH (2:1:1) was stirred at 50° C. The reaction mixture was purified by reverse phase preparative HPLC to give the final product.

Example 34

Preparation of 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrimidin-2-yloxy)methyl)cyclohex-3-ene-1-carboxylic acid.

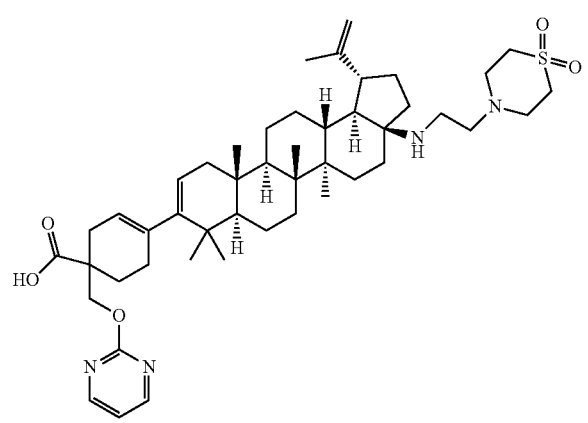

Step 1-2: General procedure E.

Step 3. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrimidin-2-yloxy)methyl)cyclohex-3-ene-1-carboxylate.

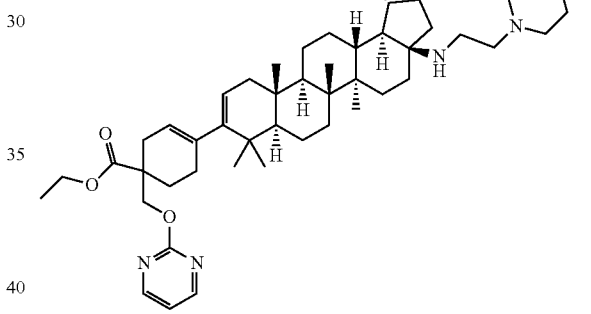

The title compound was prepared as crude product, following the procedure described in general procedure E step 3, using 2-bromopyrimidine as reactant. LC/MS m/z 831.60 (M+H)⁻, 2.76 min (LCMS Method 3).

Step 4. 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrimidin-2-yloxy)methyl)cyclohex-3-ene-1-carboxylic acid was prepared in 11% yield as a solid, following the procedure described in general procedure E step 4, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-((pyrimidin-2-yloxy)methyl)cyclohex-3-enecarboxylate as reactant. ¹H NMR (400 MHz, CHLOROFORM-d) δ 8.62 (d, J=4.8 Hz, 2H), 7.10 (t, J=4.9 Hz, 1H), 5.39 (br. s., 1H), 5.21 (d, J=4.5 Hz, 1H), 4.78 (s, 1H), 4.72 (s, 1H), 4.64-4.54 (m, 2H), 3.39 (br. d, J=13.1 Hz, 1H), 3.27-3.03 (m, 9H), 3.03-2.89 (m, 2H), 2.80-2.70 (m, 1H), 2.33-2.06 (m, 4H), 2.06-2.02 (m, 6H), 2.02-1.85 (m, 4H), 1.81-1.67 (m, 2H), 1.71 (s, 3H), 1.67-1.37 (m, 10H), 1.37-1.25 (m, 2H), 1.16 (s, 3H), 1.12-1.03 (m, 1H), 1.06 (s, 3H), 0.98-0.97 (m, 3H), 0.95-0.94 (m, 3H), 0.89 (s, 3H). LC/MS: m/e 803.50 (M+H)⁺, 2.80 min (LCMS Method 3).

Example 35

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((7-methoxyisoquinolin-1-yl)oxy)methyl)cyclohex-3-ene-1-carboxylic acid.

The title compound was prepared as crude product, following the procedure described in general procedure E step 3, using 1-chloro-7-methoxyisoquinoline as reactant. LC/MS:

m/e 910.65 (M+H)+, 2.98 min (LCMS Method 3).

Step 4: 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-

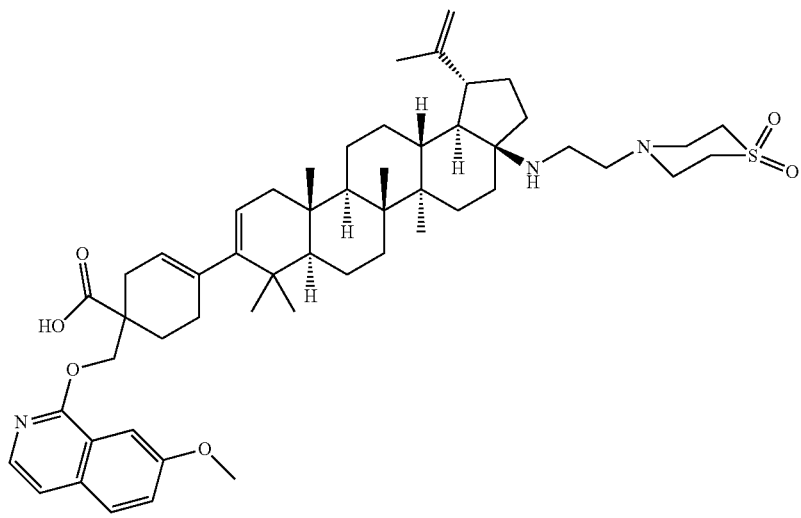

Step 1-2: General procedure E.

Step 3. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((7-methoxyisoquinolin-1-yl)oxy)methyl)cyclohex-3-enecarboxylate.

cyclopenta[a]chrysen-9-yl)-1-(((7-methoxyisoquinolin-1-yl)oxy)methyl)cyclohex-3-ene-1-carboxylic acid was prepared in 39% yield as a solid, following the procedure described in general procedure E step 4, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]

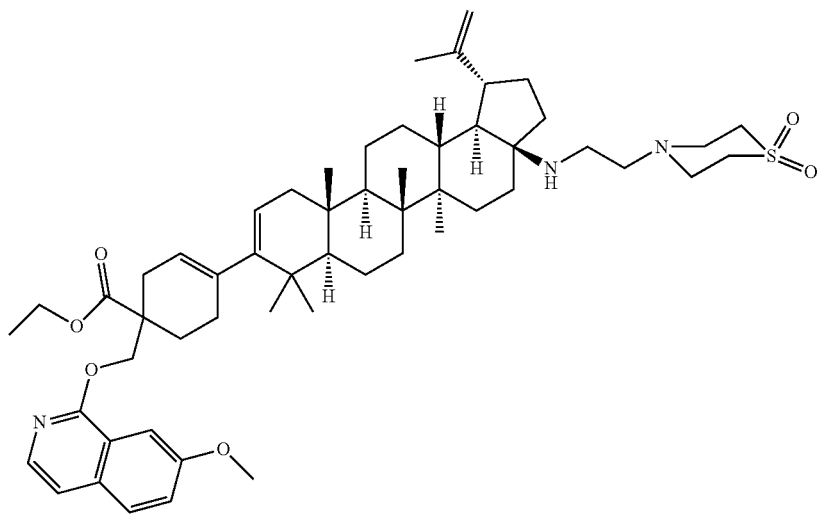

chrysen-9-yl)-1-(((7-methoxyisoquinolin-1-yl)oxy)methyl)cyclohex-3-enecarboxylate as reactant. LC/MS: m/e 882.60 (M+H)+, 2.83 min (LCMS Method 3).

Example 36

Preparation of 1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

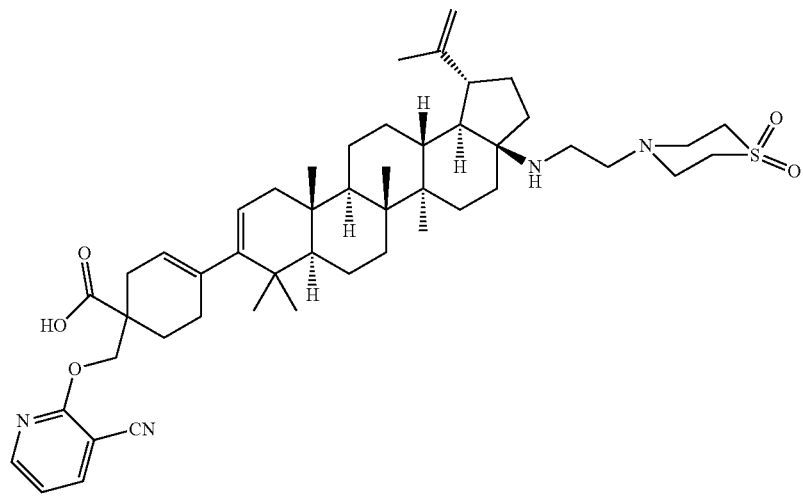

Step 1-2: General procedure E.
Step 3. Preparation of ethyl 1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate.

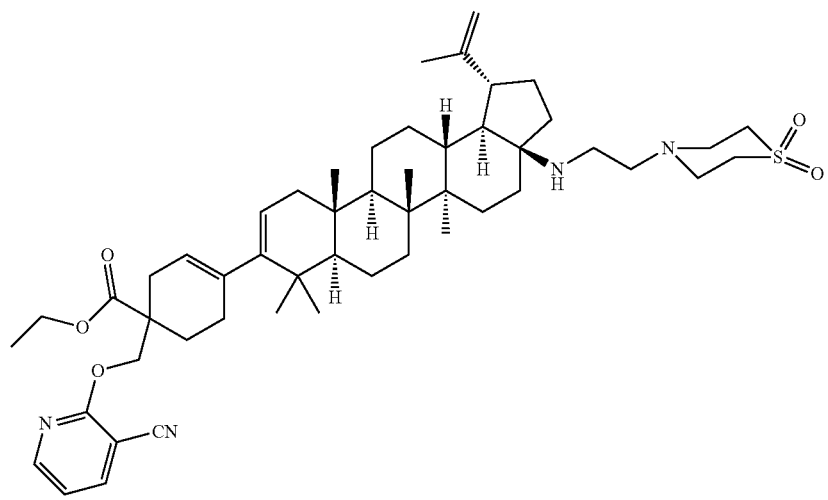

The title compound was prepared in 41% yield, following the procedure described in general procedure E step 3, using 2-chloronicotinonitrile as reactant. $^1$H NMR (400 MHz, CHLOROFORM-d) δ 8.31 (dd, J=5.0, 1.8 Hz, 1H), 7.86 (dd, J=7.5, 2.0 Hz, 1H), 6.97 (dd, 5.1 Hz, 1H), 5.34 (br. s., 1H), 5.17 (d, J=5.0 Hz, 1H), 4.69 (d, J=1.8 Hz, 1H), 4.57 (br. s., 1H), 4.53 (s, 2H), 4.21-4.12 (m, 2H), 3.10-2.97 (m, 8H), 2.74-2.40 (m, 6H), 2.28-0.82 (m, 27H), 1.67 (s, 3H), 1.25 (t, J=7.2 Hz, 3H), 1.04 (s, 3H), 0.94 (s, 3H), 0.93-0.88 (m, 6H), 0.84 (s, 3H). LC/MS: m/e 855.60 (M+H)+, 3.08 min (LCMS Method 7).

Step 4. 1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid was prepared in 33% yield, following the procedure described in general procedure E step 3 at RT, using ethyl 1-(((3-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylate as reactant. $^1$H NMR (400 MHz, METHANOL-$d_4$) 8.41-8.38 (m, 1H), 8.08 (dd, J=7.5, 1.8 Hz, 1H), 7.12 (dd, J=7.7, 5.1 Hz, 1H), 5.39 (br. s., 1H), 5.23 (d, J=4.8 Hz, 1H), 4.85 (s, 1H), 4.75 (s, 1H), 4.63 (dd, J=3.8, 10.5 Hz, 1H), 4.58 (d, J=10.3 Hz, 1H), 3.30-3.17 (m, 8H), 3.17-3.07 (m, 3H), 2.99-2.89 (m, 1H), 2.80 (td, J=11.0, 5.4 Hz, 1H), 2.72-2.64 (m, 1H), 2.40-2.23 (m, 1H), 2.23-2.15 (m, 2H), 2.15-2.01 (m, 7H), 1.99-1.90 (m, 1H), 1.90-1.76 (m, 3H), 1.78 (s, 3H), 1.76-1.64 (m, 2H), 1.63-1.41 (m, 9H), 1.41-1.29 (m, 1H), 1.24-1.18 (m, 1H), 1.20 (s, 3H), 1.18-1.10 (m, 1H), 1.13 (s, 3H), 1.025-1.015 (m, 3H), 0.98 (s, 3H), 0.95 (s, 3H). LC/MS: m/e 827.65 (M+H)$^+$, 3.12 min (LCMS Method 7).
General procedure F. Preparation of a-substituted cyclohexenecarboxylic acid derivatives via silyl carboxylate.
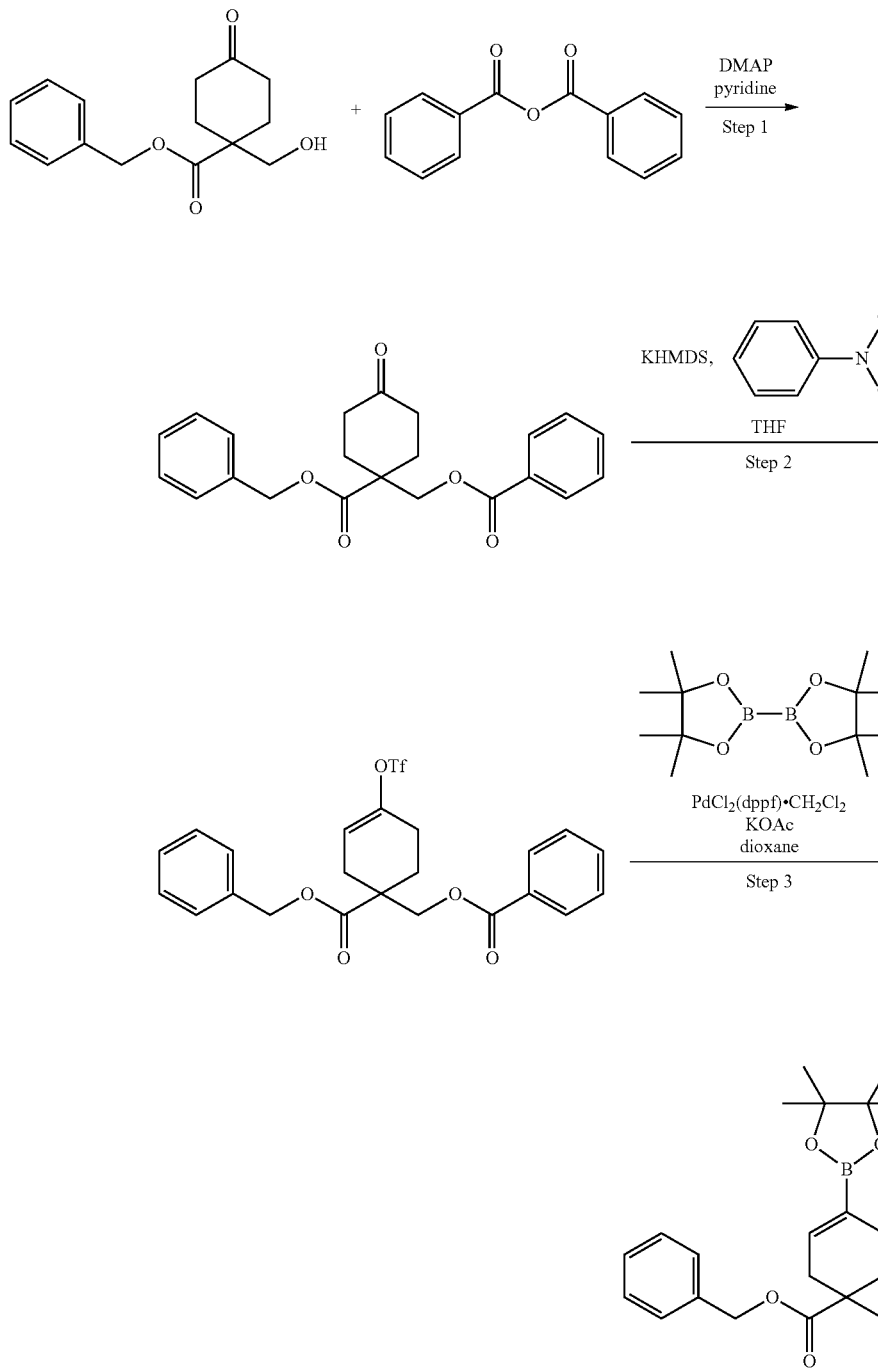

221
222
-continued
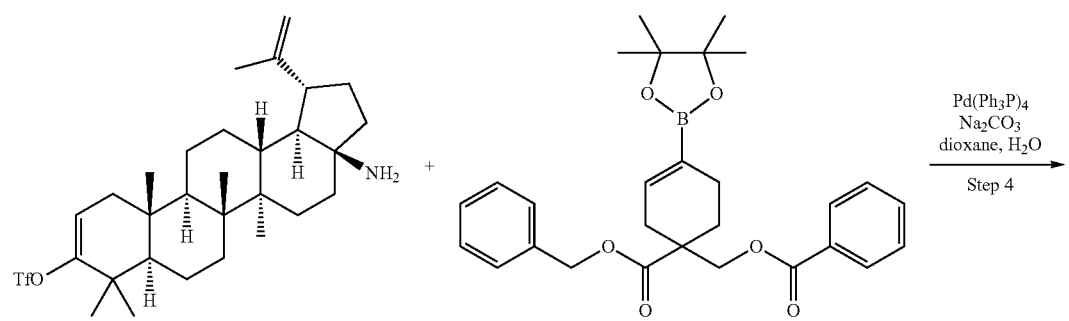
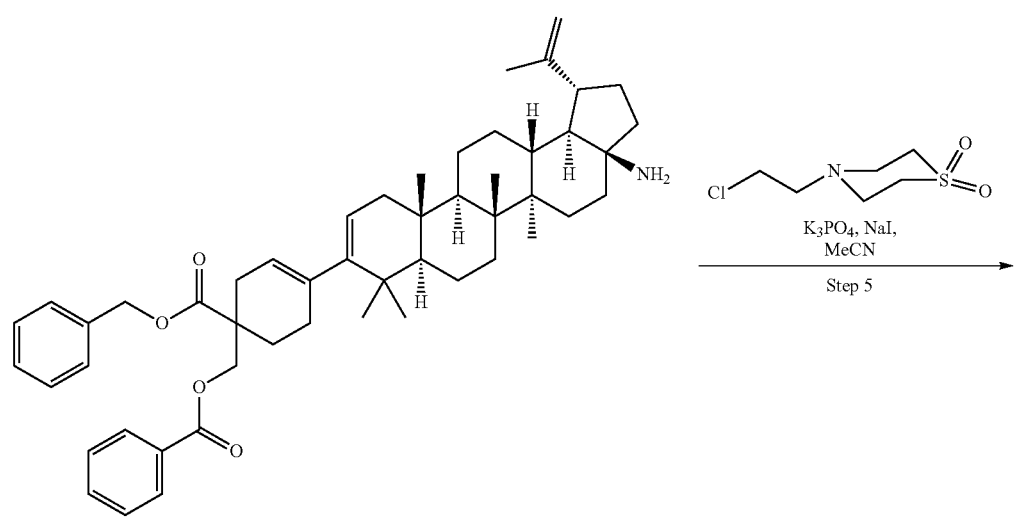
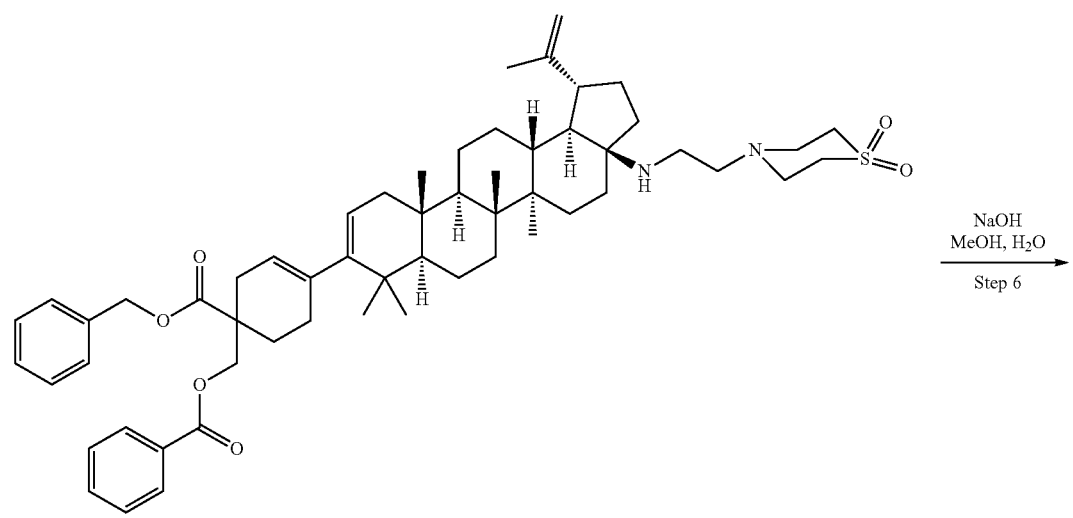

-continued
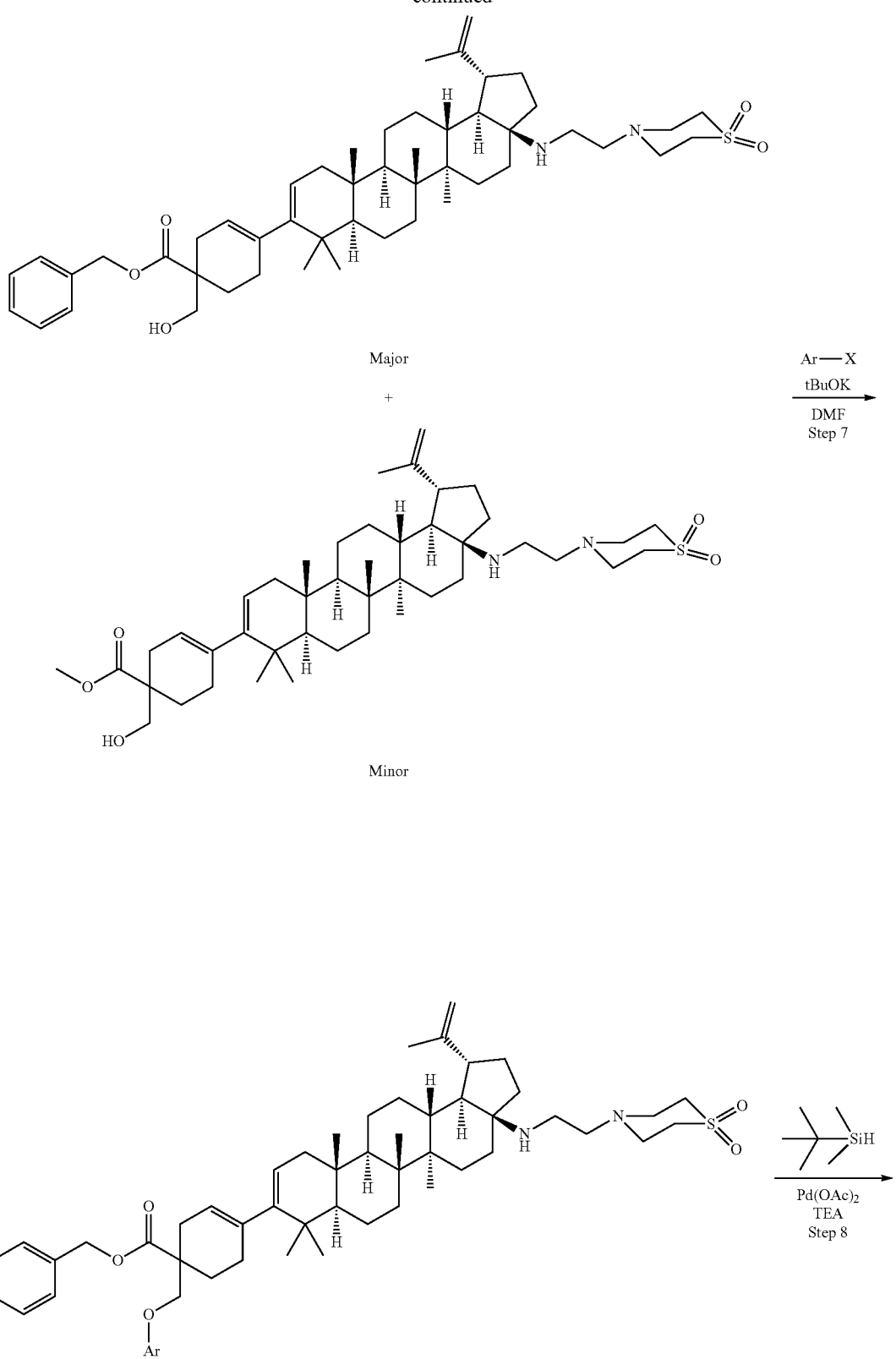
Major
+
Minor
Ar—X
tBuOK
DMF
Step 7
→
tBuMe$_2$SiH
Pd(OAc)$_2$
TEA
Step 8
→

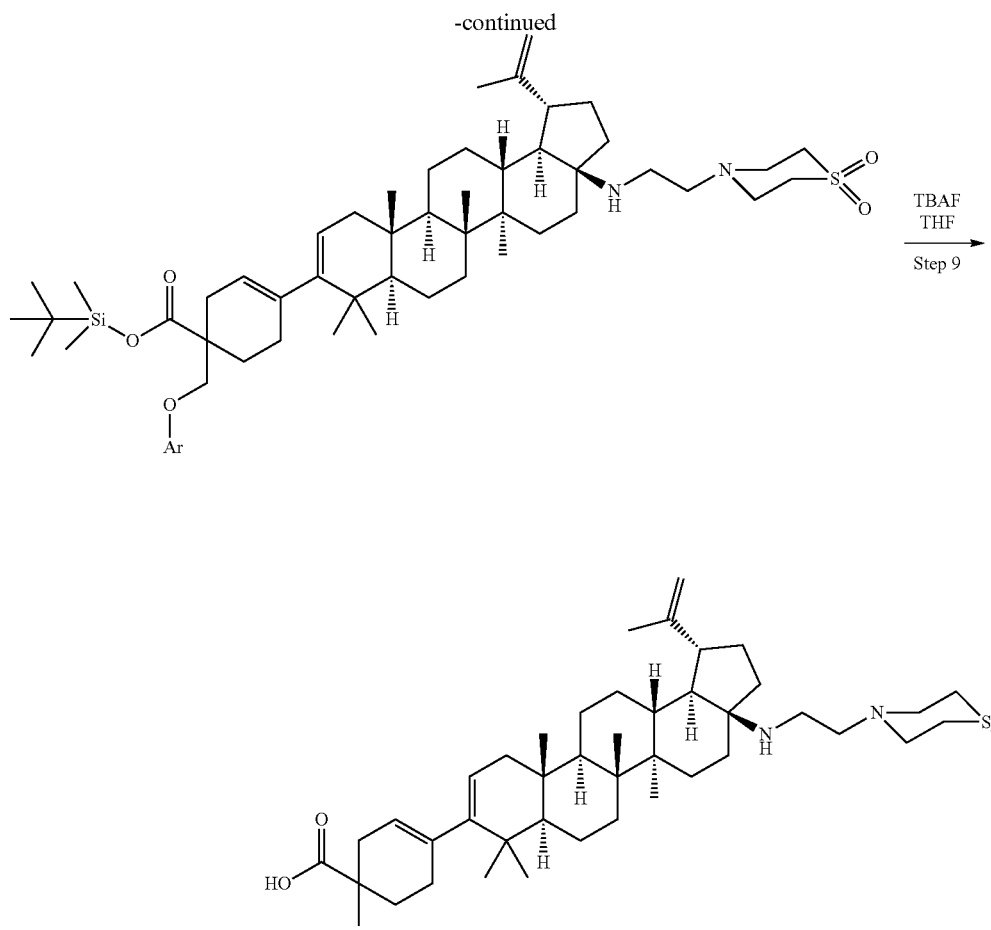

TBAF
THF
→
Step 9

Step 1. Preparation of (1-((benzyloxy)carbonyl)-4-oxocyclohexyl)methyl benzoate.

Step 2. Preparation of (1-((benzyloxy)carbonyl)-4-(((trifluoromethyl)sulfonyl)oxy)cyclohex-3-en-1-yl)methyl benzoate.

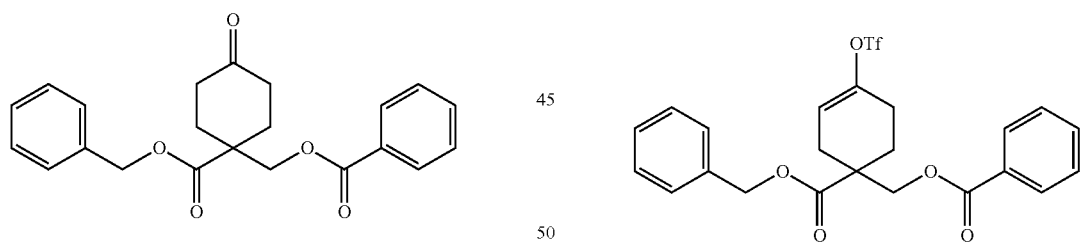

To a solution of benzyl 1-(hydroxymethyl)-4-oxocyclohexanecarboxylate (4.3 g, 16.4 mmol) in pyridine (20 mL) was added benzoic anhydride (4.45 g, 19.7 mmol) followed by DMAP (2.00 g, 16.4 mmol). The resulting solution was stirred at 55° C. for 2 hours. The reaction mixture was diluted with 50 mL of ethyl acetate and was washed with 0.5 N HCl to pH=4. The organic layer was dried over $Na_2SO_4$ and concentrated in vacuo. The crude product was purified by silica gel column eluted with 0-50% ethyl acetate/hexanes to give the desired product as an oil (3.3 g, 49%).

$^1$H NMR (400 MHz, CHLOROFORM-d) δ 7.92 (d, J=7.8 Hz, 2H), 7.65-7.54 (m, 1H), 7.44-7.37 (m, 2H), 7.35-7.27 (m, 5H), 5.25 (s, 2H), 4.46 (s, 2H), 2.63-2.35 (m, 6H), 1.86 (td, J=12.4, 5.0 Hz, 2H).

To a solution of (1-((benzyloxy)carbonyl)-4-oxocyclohexyl)methyl benzoate (4.2 g, 11.5 mmol) and 1,1,1-trifluoro-N-phenyl-N-((trifluoromethyl)sulfonyl)-methane sulfonamide (4.5 g, 12.6 mmol) in THF (50 mL) at −78° C. was added KHMDS (1 M in THF) (14.9 mL, 14.9 mmol). The resulting yellow solution was stirred at −78° C. for 2 h. The reaction was quenched with saturated aqueous $NH_4C_1$. The mixture was extracted with EtOAc, washed with brine, dried over $Na_2SO_4$, and concentrated in vacuo. The crude product was purified by silica gel column eluted with 0-15% ethyl acetate/hexanes to give the desired triflate as an oil (3.6 g, 63%). $^1$H NMR (400 MHz, CHLOROFORM-d) δ 7.92 (d, J=7.8 Hz, 2H), 7.62-7.55 (m, 1H), 7.42 (t, J=7.5 Hz, 2H), 7.35-7.27 (m, 5H), 5.80 (br. s., 1H), 5.26-5.14 (m, 2H), 4.50-4.41 (m, 2H), 2.90 (dd, J=17.9, 2.4 Hz, 1H), 2.57-2.28 (m, 4H), 2.02-1.91 (m, 1H).

Step 3. Preparation of (1-((benzyloxy)carbonyl)-4-(4,4,5,5-tetramethyl-1,3,2-dioxaborolan-2-yl)cyclohex-3-en-1-yl)methyl benzoate.

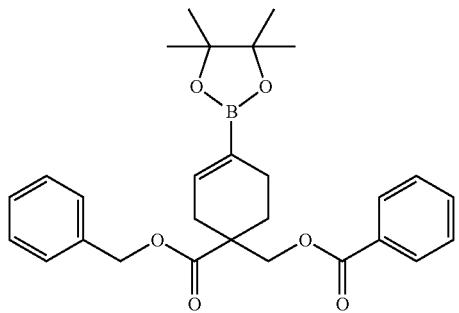 [SMILES: CC1(C)OB(C2=CCC(COC(=O)c3ccccc3)(C(=O)OCc3ccccc3)CC2)OC1(C)C]

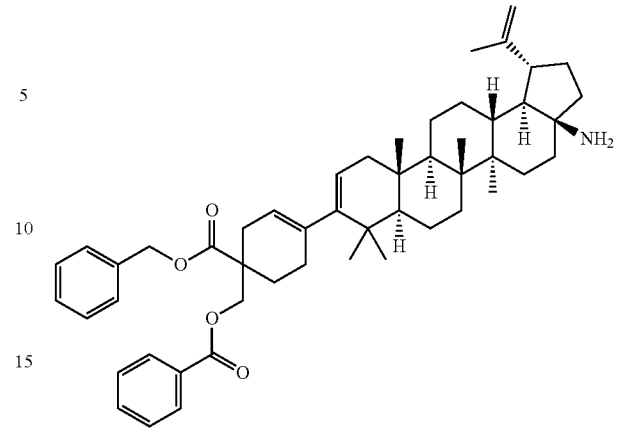

A mixture of (1-((benzyloxy)carbonyl)-4-(((trifluoromethyl)sulfonyloxy)cyclohex-3-en-1-yl)methyl benzoate (3.32 g, 6.66 mmol), bis(pinacolato)diboron (1.71 g, 6.73 mmol), KOAc (1.64 g, 16.7 mmol)) and PdCl2(dppf)-CH2Cl2 adduct (0.16 g, 0.2 mmol) in 1,4-dioxane (30 mL) was flushed with nitrogen, sealed and heated at 70° C. for 20 h. The mixture was diluted with water (150 mL) and extracted with EtOAc (3×125 mL). The combined organic layers were washed with brine, dried over Na2SO4, and concentrated in vacuo. The crude product was purified by silica gel column eluted with 0-20% ethyl acetate/hexanes to give the desired boronate as an oil (2.2 g, 69%). $^1$H NMR (400 MHz, CHLOROFORM-d) δ 7.90 (d, J=8.1 Hz, 2H), 7.58-7.51 (m, 1H), 7.42-7.36 (m, 2H), 7.32-7.22 (m, 5H), 6.54 (br. s., 1H), 5.16 (s, 2H), 4.48-4.36 (m, 2H), 2.75 (d, J=17.6 Hz, 1H), 2.32-2.19 (m, 3H), 2.07-2.00 (m, 1H), 1.92-1.86 (m, 1H), 1.27 (s, 12H). LC/MS: m/e 499.20 (M+Na)$^+$, 3.10 min (LCMS Method 7).

Step 4. Preparation of (4-((1R,3aS,5aR,5bR,7aR,11aS,11bR,13aR,13bR)-3a-amino-1-(buta-2,3-dien-2-yl)-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-((benzyloxy)carbonyl)cyclohex-3-en-1-yl)methyl benzoate.

A mixture of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (2.4 g, 4.3 mmol), (1-((benzyloxy)carbonyl)-4-(4,4,5,5-tetramethyl-1,3,2-dioxaborolan-2-yl)cyclohex-3-en-1-yl)methyl benzoate (2.05 g, 4.3 mmol), Na2CO3·H2O (1.60 g, 12.9 mmol) and Pd(Ph3P)4 (0.3 g, 0.26 mmol) in 1,4-dioxane (100 mL) and H2O (25 mL) was flushed with nitrogen, sealed and heated at 70° C. for 2 h. The reaction mixture was diluted with EtOAc, washed with brine, dried over Na2SO4, and concentrated in vacuo. The crude product was purified by silica gel column eluted with 0-55% ethyl acetate/hexanes to give the desired C-3 α-substituted cyclohexenecarboxylic ester (1.8 g, 55%). $^1$H NMR (400 MHz, CHLOROFORM-d) δ 7.91 (d, J=7.0 Hz, 2H), 7.58-7.51 (m, 1H), 7.42-7.35 (m, 2H), 7.33-7.28 (m, 2H), 7.26-7.22 (m, 3H), 5.34 (br. s., 1H), 5.21-5.11 (m, 3H), 4.73 (s, 1H), 4.60 (br. s., 1H), 4.51-4.39 (m, 2H), 2.71 (d, J=17.3 Hz, 1H), 2.54 (td, J=10.9, 5.1 Hz, 1H), 2.25-0.92 (m, 27H), 1.69 (s, 3H), 1.13-0.85 (m, 15H). LC/MS: m/e 758.70 (M+H)$^-$, 3.24 min (LCMS Method 7).

Step 5. Preparation of (1-((benzyloxy)carbonyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)methyl benzoate.

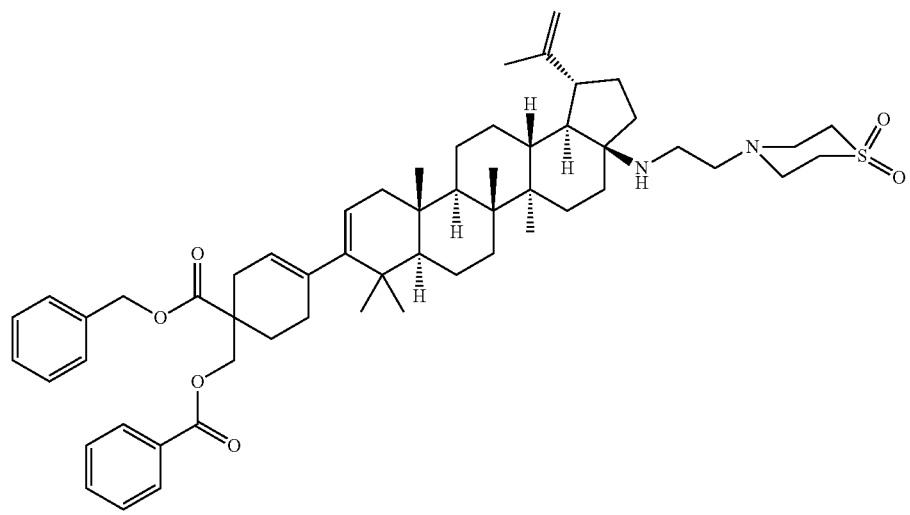

A suspension of (4-((1R,3aS,5aR,5bR,7aR,11aS,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-((benzyloxy)carbonyl)cyclohex-3-en-1-yl)methyl benzoate (1.6 g, 2.11 mmol), 4-(2-chloroethyl)thiomorpholine 1,1-dioxide hydrochloride (1.5 g, 6.33 mmol), sodium iodide (0.35 g, 2.32 mmol) and $K_3PO_4$ (2.24 g, 10.55 mmol) in acetonitrile (20 mL) was flushed with $N_2$, sealed and heated at 100° C. for 15 h. The reaction mixture was diluted with EtOAc (100 mL), washed with water (100 mL), dried over $Na_2SO_4$, and concentrated in vacuo. The crude product was purified on silica gel column eluted with 25-60% EtOAc/hexane to give the desired product (1.3 g, 67% yield). $^1$H NMR (400 MHz, CHLOROFORM-d) δ 7.92 (d, J=7.8 Hz, 2H), 7.58-7.51 (m, 1H), 7.43-7.36 (m, 2H), 7.31 (d, J=4.6 Hz, 2H), 7.25 (d, J=4.4 Hz, 3H), 5.35 (br. s., 1H), 5.22-5.12 (m, 3H), 4.71 (s, 1H), 4.60 (br. s., 1H), 4.45 (q, J=10.7 Hz, 2H), 3.15-2.99 (m, 8H), 2.78-2.42 (m, 6H), 2.23-0.81 (m, 27H), 1.69 (s, 3H), 1.07-0.79 (m, 15H). LC/MS: m/e 919.60 (M+H)$^+$, 3.27 min (LCMS Method 7).

Step 6. Preparation of benzyl 4-((1R,3aS,5aR,5bR,7aR, 11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11 b,12,13,13a, 13b-octadecahydro-1H-cyclopenta[a] chrysen-9-yl)-1-(hydroxymethyl)cyclohex-3-ene-1-carboxylate.

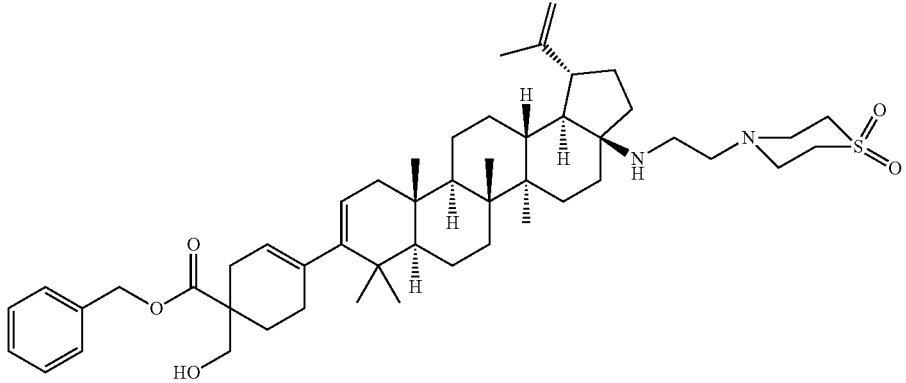

To a solution of (1-((benzyloxy)carbonyl)-4-((1R,3aS, 5aR,5bR,7aR,11aS,11bR,13aR,13bR)-3a-((2-(1,1-dioxido-thiomorpholino)ethypamino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopentalalchrysen-9-yl) cyclohex-3-en-1-yl)methyl benzoate (1.0 g, 1.09 mmol) in MeOH (15 mL) was added 1N NaOH (1.09 mL, 1.09 mmol). The mixture was stirred at RT for 12 h, neutralized with saturated aqueous citric acid and the solvent was removed in vacuo. The residue was dissolved in EtOAc, washed with brine, dried over $Na_2SO_4$, and concentrated in vacuo to give the desired product (56% yield with trace amount methyl ester by product) without further purification. LC/MS: m/e 815 (M+H)$^+$, 4.803 min (LCMS Method 7). For methyl ester: LC/MS: m/e 739.55 (M+H)$^+$, 4.615 min (LCMS Method 7).

Step 7. Preparation of benzyl 1-((aryloxy)methyl)-4-((1R, 3aS,5aR,5bR,7aR,11aS,11bR,13aR,13bR)-3a-((2-(1,1-di-oxidothiomorpholino)ethypamino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)cyclohex-3-ene-1-carboxylate.

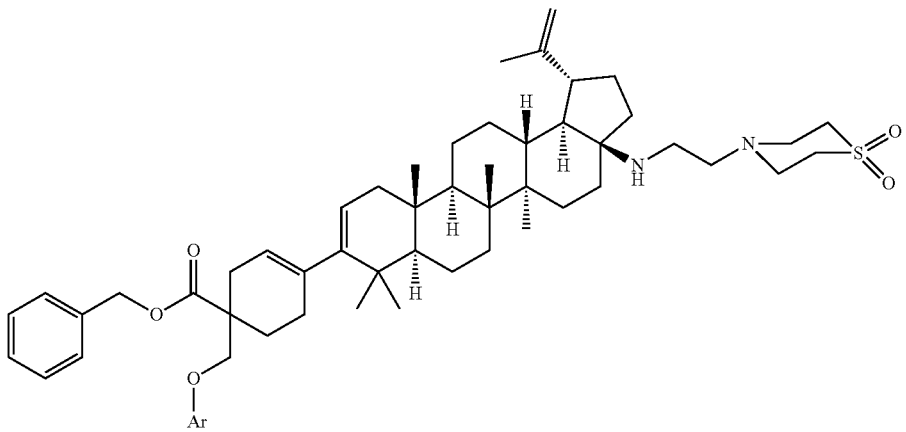

To a solution of benzyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate (1 eq) in DMF at −78° C. was added KOtBu (2 eq). The resulted mixture was stirred for 20 minutes before the addition of Ar—X (2 eq). Then the reaction was warmed to RT and stirred overnight. The reaction mixture was diluted with EtOAc, washed with water, dried over $Na_2SO_4$, and concentrated in vacuo to give crude product which was either used in next step without further purification or purified by silica gel chromatography with ethyl acetate/hexanes as eluents.

Step 8. Preparation of tert-butyldimethylsilyl 1-((aryloxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate.

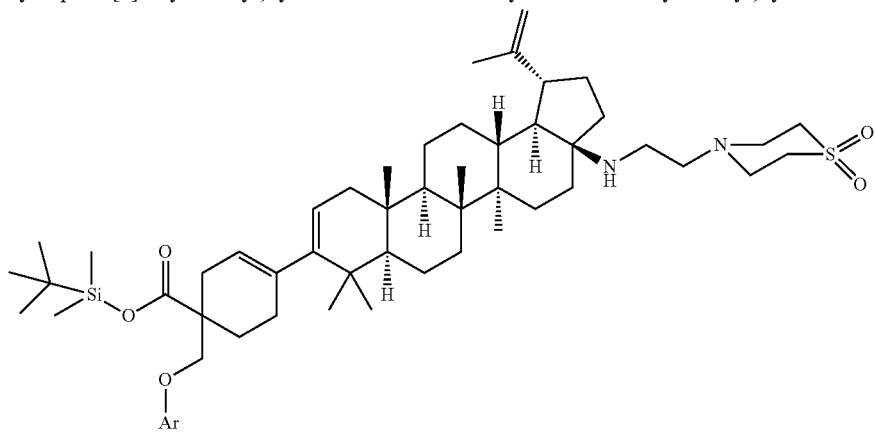

To a solution of the crude product (1 eq) from general procedure F, step 7 in DCE (3 mL) was added TEA (1.6 eq), t-Butyldimethylsilane (2.0 eq), and palladium acetate (0.25 eq). The mixture was flushed with $N_2$ for 5 minutes and then heated at 60° C. for 2-6 hours. The reaction mixture was cooled to room temperature and was filtered through a pad of celite and silica gel and washed with 50% EtOAc in hexanes, then with dichloromethane. The filtrate was concentrated under reduced pressure and the crude product obtained was used in the next step without additional purification.

Step 9. Preparation of 1-((aryloxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid.

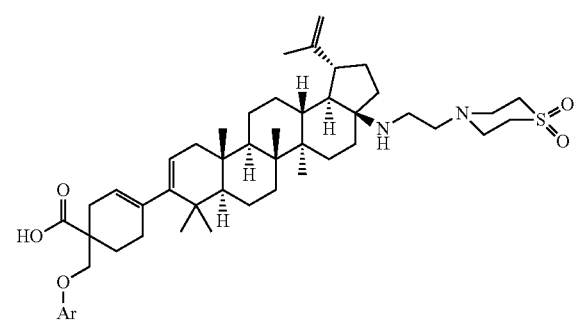

To a solution of the crude product (1 eq) from general procedure F, step 8 in THF (3 mL) was added a solution of TBAF (1.6 eq) in THF. The resulting mixture was stirred for 2 hours. The solution was purified by reverse phase preparative HPLC. Fractions containing the desired product were collected and dried to afford the desired 1-((aryloxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

Example 37

Preparation of 1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

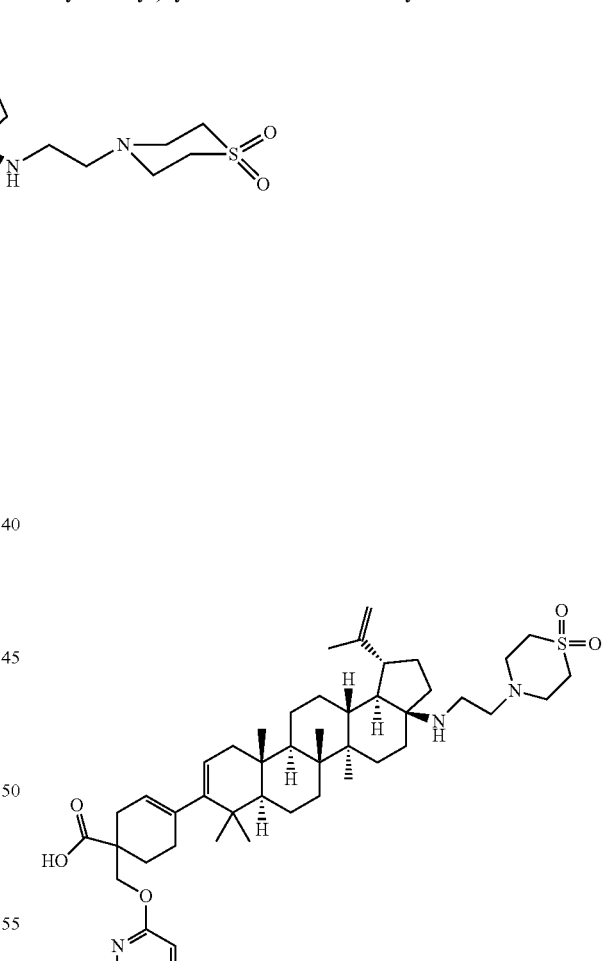

Step 1-6: General procedure F steps 1-6

Step 7. Preparation of benzyl 1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate.

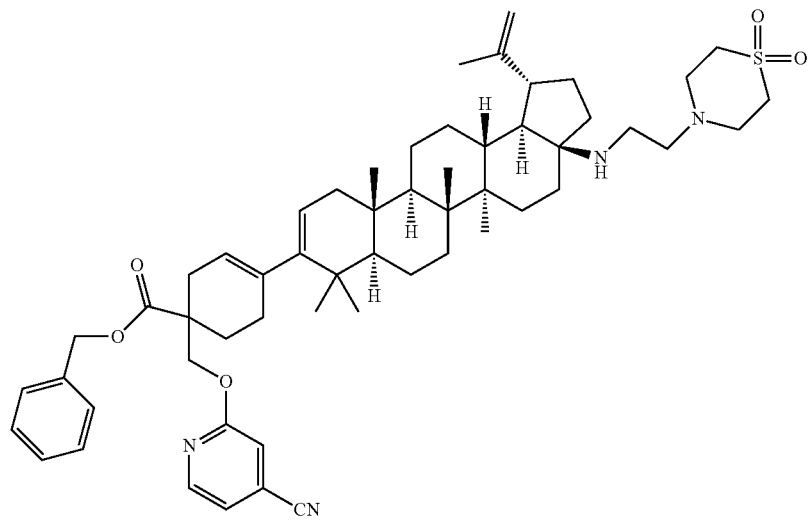

The title compound was prepared in 22% yield as a solid, following the procedure described in general procedure F, step 7, using 2-fluoroisonicotinonitrile as the reactant. LC/MS m/z M+1=917.65, 4.765 min (LCMS Method 7).

Step 8. Preparation of tert-butyldimethylsilyl 1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate.

Step 9. 1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid was prepared in 10.7% yield as a solid, following the procedure described in general procedure F, step 9, using tert-butyldimethylsilyl 1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-

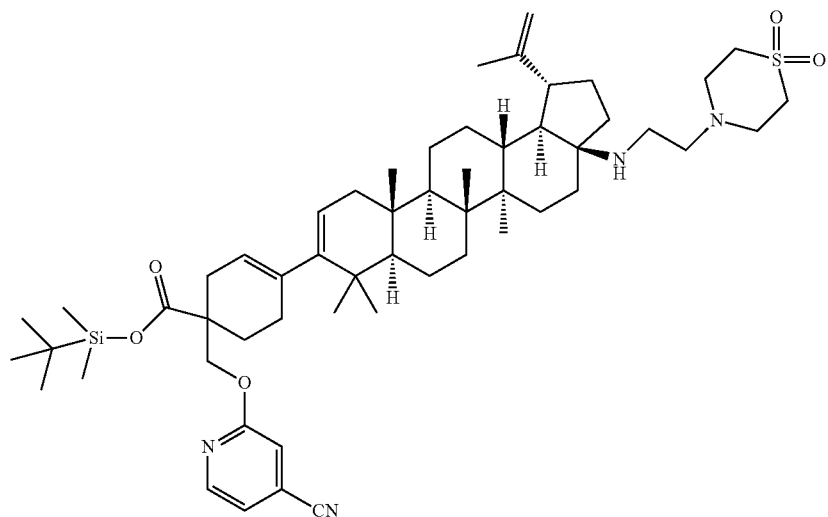

The title compound was prepared as a solid, following the procedure described in general procedure F, step 8, using benzyl 1-(((4-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS m/z M+1=941.75, 3.467 min (LCMS Method 7).

pentamethyl-1-(prop-1-en-2-yl)-2,3,3a,4,5,5a,5b,6,7,7a,8,11,11a,11 b,12,13,13a,13b-octadecahydro-1H-cyclopentalalchrysen-9-yl)cyclohex-3-ene-1-carboxylate as the reactant. LC/MS: m/e 827.60 (M+H)$^+$, 3.00 min (LCMS Method 7). $^1$H NMR (400 MHz, CHLOROFORM-d) δ 8.31 (d, J=5.0 Hz, 1H), 7.21 (dd, J=5.1, 1.1 Hz, 1H), 7.14 (s, 1H), 5.36 (br. s., 1H), 5.21 (d, J=4.8 Hz, 1H), 4.84 (s, 1H), 4.75 (s, 1H), 4.52 (dd, J=4.3, 10.3 Hz, 1H), 4.45 (dd, J=1.8, 10.3 Hz, 1H), 3.28-3.15 (m, 8H),3.14-3.06 (m, 4H), 2.98-2.87 (m, 1H), 2.76 (td, J=11.1, 5.4 Hz, 1H), 2.45-2.58 (m, 1H), 2.35-2.21 (d, J=8.5 Hz, 1H), 2.21-1.98 (m, 8H), 1.92-1.73 (m, 2H), 1.77 (s, 3H), 1.73-1.41 (m, 11H), 1.40-1.28 (m, 2H), 1.27-1.08 (m, 2H), 1.18 (s, 3H), 1.11 (s, 3H), 1.00-0.99 (m, 3H), 0.96 (s, 3H), 0.93 (s, 3H).

Example 38

Preparation of 1-(((5-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

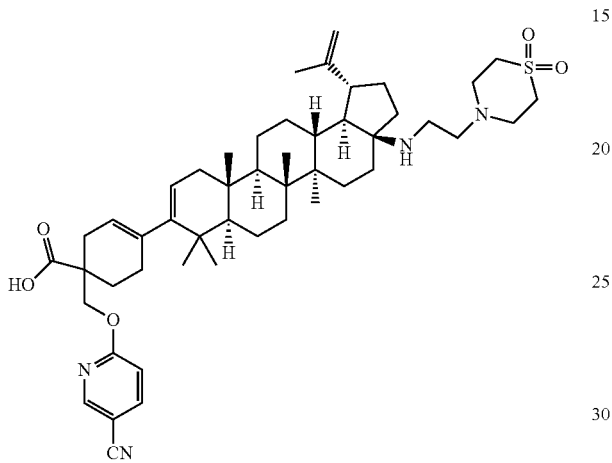

Step 1-6: General procedure F steps 1-6

Step 7. Preparation of benzyl 1-(((5-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate.

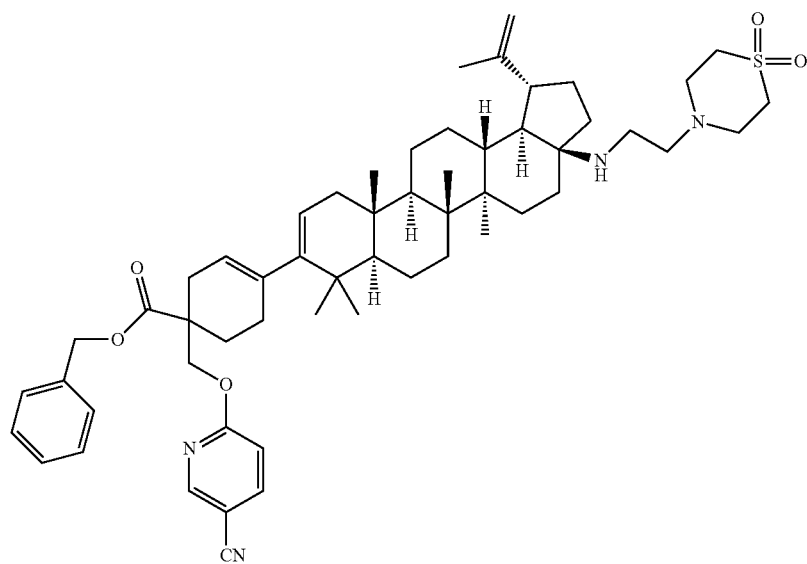

The title compound was prepared in 35.5% yield as a solid, following the procedure described in general procedure F, step 7, using 6-fluoronicotinonitrile as the reactant. LC/MS m/z M+1=917.65, 3.136 min (LCMS Method 7).

Step 8: Preparation of tert-butyldimethylsilyl 1-(((5-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate.

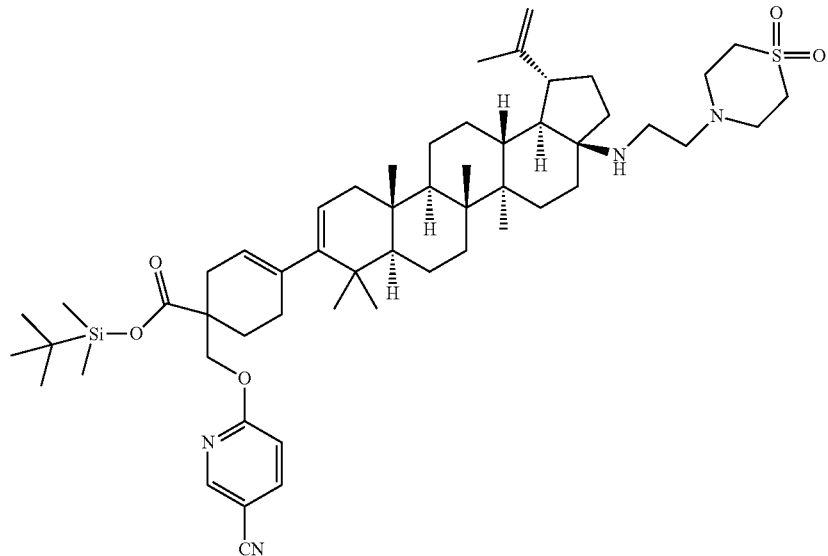

The title compound was prepared as a solid, following the procedure described in general procedure F, step 8, using benzyl 1-(((5-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS m/z M+1=941.70, 3.311 min (LCMS Method 7).

Step 9. 1-(((5-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid was prepared in 10.5% of yield as a solid, following the procedure described in general procedure F, step 9, using tert-butyldimethylsilyl 1-(((5-cyanopyridin-2-yl)oxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS: m/e 827.55 (M+H)$^+$, 3.049 min (LCMS Method 7). $^1$H NMR (400 MHz, METHANOL-d$_4$) δ 8.52 (d, J=2.3 Hz, 1H), 7.96 (dd, J=8.8, 2.3 Hz, 1H), 6.92 (d, J=8.8 Hz, 1H), 5.35 (br. s., 1H), 5.21 (d, J=4.5 Hz, 1H), 4.84 (s, 1H), 4.75 (s, 1H), 4.56 (dd, J=2.8, 10.5 Hz, 1H), 4.49 (d, J=10.5 Hz, 1H), 3.28-3.15 (m, 8H), 3.14-3.06 (m, 3H), 2.93 (dt, J=14.2, 5.2 Hz, 1H), 2.81-2.71 (m, 1H), 2.67-2.57 (m, 1H), 2.35-2.21 (m, 1H), 2.21-1.97 (m, 10H), 1.92-1.72 (m, 5H), 1.77 (s, 3H), 1.72-1.39 (m, 11H), 1.39-1.20 (m, 1H), 1.20-1.07 (m, 1H), 1.18 (s, 3H), 1.11 (s, 3H), 1.02-0.98 (m, 1H), 0.96 (s, 3H), 0.93 (s, 3H).

Example 39

Preparation of 1-(((6-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

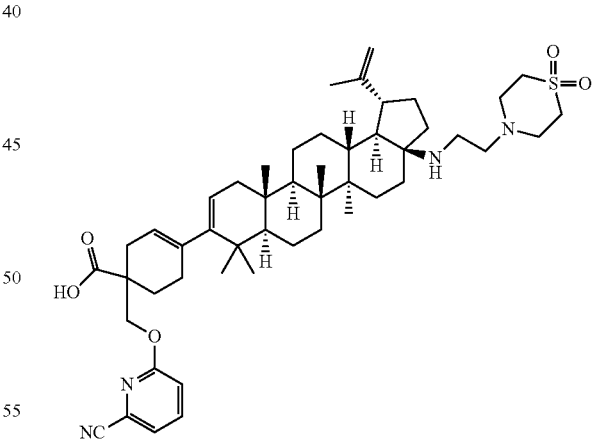

Step 1-6: General procedure F steps 1-6
Step 7. Preparation of benzyl 1-(((6-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate.

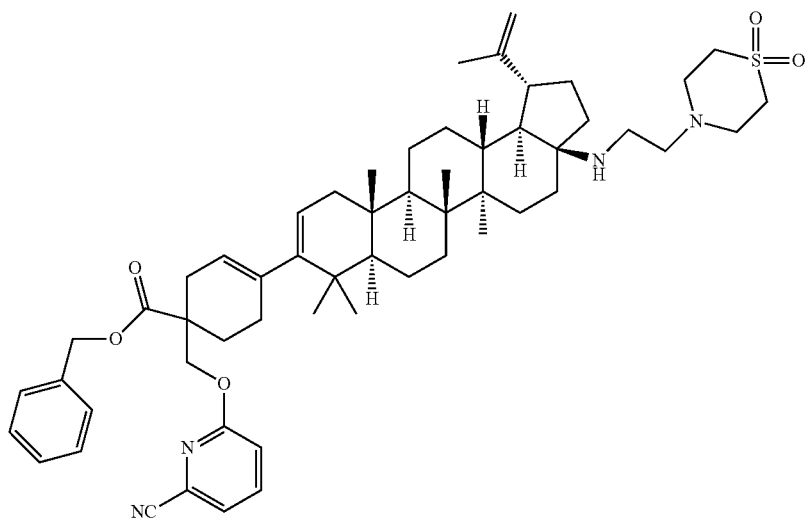

The title compound was prepared as a solid, following the procedure described in general procedure F, step 7, using 6-chloronicotinonitrile as the reactant. LC/MS m/z M+1=917.65, 3.083 min (LCMS Method 7).

Step 8. Preparation of tert-butyldimethylsilyl 1-(((6-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate.

Step 9. 1-(((6-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid was prepared in 17.6% of yield as a solid, following the procedure described in general procedure F, step 9, using tert-butyldimethylsilyl 1-(((6-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,

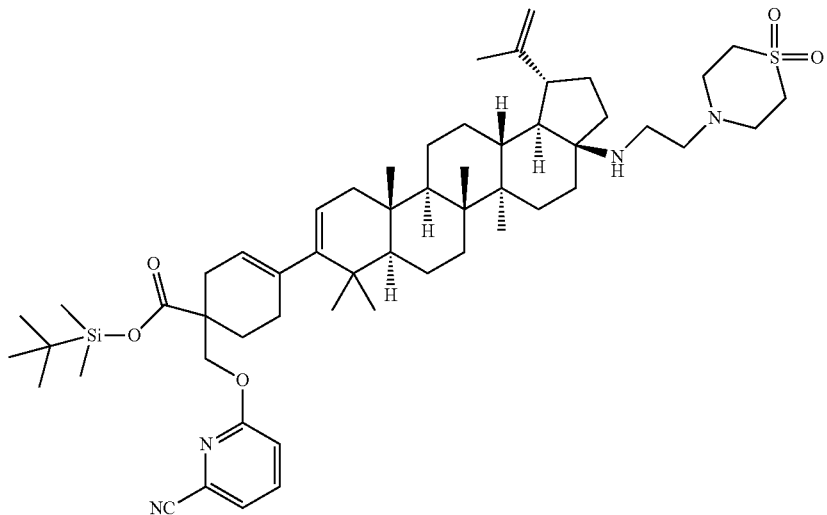

The title compound was prepared as a solid, following the procedure described in general procedure F, step 8, using benzyl 1-(((6-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS m/z M+1=941.70, 3.516 min (LCMS Method 7).

11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS: m/e 827.55 (M+H)$^+$, 3.003 min (LCMS Method 7). $^1$H NMR (400 MHz, METHANOL-d$_4$) δ 7.84 (dd, J=8.5, 7.3 Hz, 1H), 7.47 (d, J=7.3 Hz, 1H), 7.09 (d, J=8.5 Hz, 1H), 5.38 (br. s., 1H), 5.24 (d, J=6.0 Hz, 1H), 4.86 (s, 1H), 4.76 (s, 1H), 4.59-4.53 (m, 1H), 4.48-4.43 (m, 1H), 3.30-3.17 (m, 8H), 3.09-3.17 (m, 3H), 2.98-2.89 (m, 1H), 2.78 (td, J=10.9, 5.5 Hz, 1H), 2.65 (br. d, J=15.8 Hz, 1H), 2.37-2.00 (m, 9H), 1.94-1.74 (m, 5H), 1.79 (s, 3H), 1.74-1.44 (m, 11H), 1.44-1.29 (m, 2H), 1.26-1.10 (m, 2H), 1.20 (s, 3H), 1.13 (s, 3H), 1.03-1.02 (m, 3H), 1.00-0.99 (m, 3H), 0.95 (s, 3H).

Example 40

Preparation of 1-(((6-carbamoylpyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

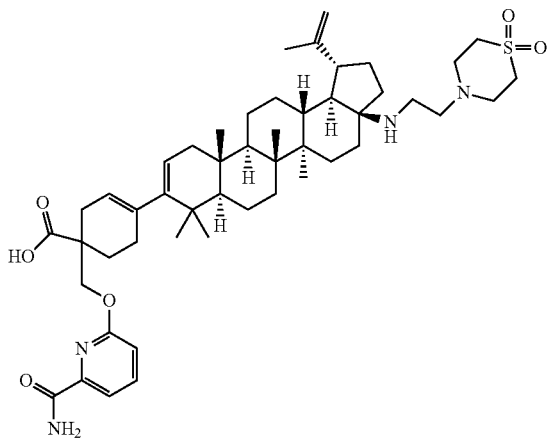

Step 1. Preparation of methyl 1-(((6-cyanopyridin-2-yl)oxy)methyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylate.

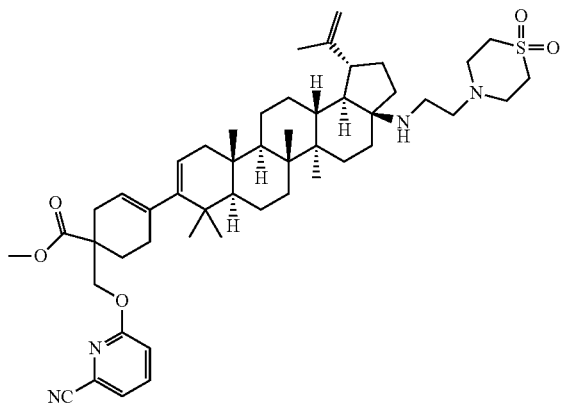

The title compound was prepared as a solid, following the procedure described in general procedure F, step 7, using 6-chloronicotinonitrile and methyl 4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-ene-1-carboxylate instead of benzyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)-1-(hydroxymethyl)cyclohex-3-ene-1-carboxylateas the reactants. LC/MS m/z M+1=841.60, 3.164 min (LCMS Method 7).

Step 2. 1-(((6-carbamoylpyridin-2-yl)oxy)methyl)-4-((1R,3aS,5aR,5bR,7aR,11aS,11bR,13aR,13bR)-3a-((2-(1,1-dioxidothiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylic acid was prepared in a yield of 19.9% as a solid, following the procedure described in general procedure E, step 4, using methyl 1-(((6-cyanopyridin-2-yl)oxy)methyl)-4-((1R,3aS,5aR,5bR,7aR,11aS,11bR,13aR,13bR)-3a-((2-(1,1-dioxido-thiomorpholino)ethypamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-ene-1-carboxylate as the reactant. LC/MS: m/e 845.60 (M+H)⁺, 2.931 min (LCMS Method 7). ¹H NMR (400 MHz, METHANOL-d₄) δ 7.84 (dd, J=8.3, 7.3 Hz, 1H), 7.72 (dd, J=7.3, 0.8 Hz, 1H), 6.99 (d, J=7.8 Hz, 1H), 5.39 (br. s., 1H), 5.23 (d, J=4.3 Hz, 1H), 4.87 (s, 1H), 4.77 (s, 1H), 4.61-4.56 (m, 1H), 4.55-4.50 (m, 1H), 3.25 (d, J=8.8 Hz, 5H), 3.20 (br. s., 2H), 3.17-3.09 (m, 3H), 2.97-2.87 (m, 1H), 2.77 (d, J=5.3 Hz, 1H), 2.68 (d, J=13.6 Hz, 1H), 2.41-1.99 (m, 9H), 1.94-1.68 (m, 6H), 1.79 (s, 3H), 1.68-1.44 (m, 9H), 1.43-1.30 (m, 3H), 1.29-1.11 (m, 2H), 1.19 (s, 3H), 1.13 (s, 3H), 1.01 (s, 3H), 0.98 (s, 3H), 0.95 (s, 3H).

Preparation of 4-(methylsulfonyl)cyclohexanone.

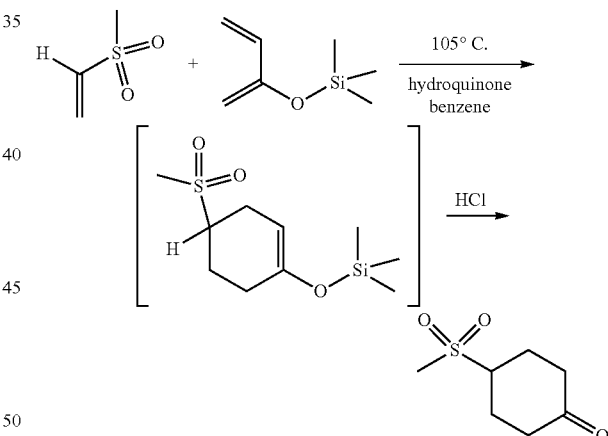

To a solution of (methylsulfonyl)ethene (10.0 g, 94 mmol) in benzene (50 mL) was added (buta-1,3-dien-2-yloxy)trimethylsilane (14.07 g, 99 mmol) and hydroquinone (20 mg, 0.182 mmol). The mixture was degassed several times at −78° C. prior to heating. The contents were sealed and heated at 105° C. for 48 hours. The reaction was analyzed by NMR in CDCl₃ that showed about 10% of the vinyl sulfone residue. Additional (buta-1,3-dien-2-yloxy)trimethylsilane (4 mL) was added and heating resumed for another 48 hours. NMR analysis again at 72 hrs time point showed further reduction of the amount of vinyl sulfone (~3%). The sample from the NMR tube was combined the reaction mixture and evaporated to a thick gum under vacuum at room temperature (~19° C.). The mixture was rediluted with acetone (250 mL) resulting in the formation of a clear solution. The mixture was chilled in an ice bath until cold. 4 mL of 0.25 N HCl (pre-chilled in the same ice-bath) was added resulting in the formation a cloudy mixture, which became clear after 15 minutes of stirring at 0° C., and then returned to a cloudy state in another 10 minutes, it remained turbid for the rest of stirring period. A 50 ut aliquot was removed, flash dried into a film, and was analyzed by NMR in CDCl$_3$. NMR showed ~7% of vinyl sulfone relative to the desired product. The acetone solution was filtered through a short bed of silica gel type-H after a total reaction time of about one hour, and was then washed with more acetone. The filtrate was concentrated on the rotovapor at 19° C. bath temperature. The crude product was sub-divided into two parts, 7.75 gm each, for purification. The product was purified by column chromatography on silica gel (30% ethyl acetate→100% ethyl acetate in hexanes; two 330 g columns) to afford 4-(methylsulfonyl)cyclohexanone (16.7 g, 100% yield) as a white solid: $^1$H NMR (400 MHz, CHLOROFORM-d) δ 3.29 (tt, J=11.0, 3.9 Hz, 1H), 2.94 (s, 3H), 2.73-2.62 (m, 2H), 2.58-2.37 (m, 4H), 2.15 (qd, J=11.9, 4.5 Hz, 2H).

Preparation of 2-(cis-1-hydroxy-4-(methylsulfonyl)cyclohexyl)acetaldehyde and 2-(trans-1-hydroxy-4-(methylsulfonyl)cyclohexyl)acetaldehyde.

tography on silica gel (70% ethyl acetate with 1% methanol/30% hexanes→100% ethyl acetate with 1% methanol; 40 g column) to afford (cis)-1-allyl-4-(methylsulfonyl)cyclohexanol (374 mg, 1.713 mmol, 29% yield) as a white solid and (trans)-1-allyl-4-(methylsulfonyl)cyclohexanol (551 mg, 2.52 mmol, 43% yield) as a colorless oil.

(cis)-1-allyl-4-(methylsulfonyl)cyclohexanol:
$^1$H NMR (400 MHz, CDCl$_3$) δ 5.96-5.79 (m, 1H), 5.26-5.21 (m, 1H), 5.18 (ddt, J=17.1, 2.1, 1.2 Hz, 1H), 2.85 (s, 3H), 2.80 (tt, J=12.5, 3.6 Hz, 1H), 2.25 (d, J=7.5 Hz, 2H), 2.15-2.07 (m, 2H), 1.97 (qd, J=13.0, 3.8 Hz, 2H), 1.88-1.81 (m, 2H), 1.52-1.42 (m, 2H); $^{13}$C NMR (100 MHz, CDCl$_3$) δ 132.50, 120.02, 69.06, 62.26, 47.86, 36.85, 35.67, 21.13. The structure of (cis)-1-allyl-4-(methylsulfonyl)cyclohexanol was confirmed by X-ray crystallography.

(trans)-1-allyl-4-(methylsulfonyl)cyclohexanol:
$^1$H NMR (400 MHz, CDCl$_3$) δ 5.88 (ddt, J=17.2, 10.1, 7.4 Hz, 1H), 5.28-5.16 (m, 2H), 2.98-2.91 (m, 1H), 2.90 (s, 3H), 2.35 (d, J=7.5 Hz, 2H), 2.23-2.14 (m, 2H), 2.02-1.93 (m, 2H), 1.90-1.78 (m, 2H), 1.57-1.46 (m, 2H); $^{13}$C NMR (100 MHz, CDCl$_3$) δ 132.62, 120.19, 69.20, 62.41, 48.00, 36.98, 35.83, 21.29.

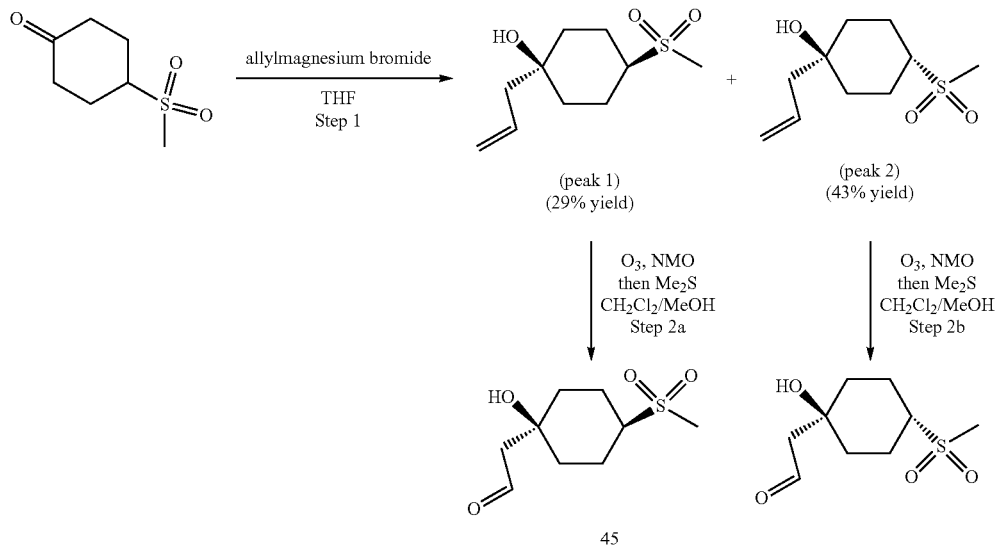

Step 1. Preparation of (cis)-1-allyl-4-(methylsulfonyl)cyclohexanol and (trans)-1-allyl-4-(methylsulfonyl)cyclohexanol.

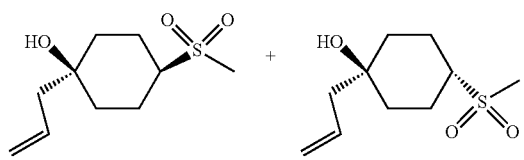

To a solution of 4-(methylsulfonyl)cyclohexanone (1.03 g, 5.84 mmol) in THF (40 mL) at 0° C. was added via cannula allylmagnesium bromide (7.60 mL, 7.60 mmol). The reaction mixture was stirred at 0° C. for 30 min. The reaction was quenched by the addition of saturated NH$_4$Cl solution (25 mL). The mixture was transferred to a separatory funnel and the aqueous layer was extracted with ethyl acetate (5×50 mL). The combined organic layers were washed with brine (20 mL), dried over MgSO$_4$, filtered, and concentrated. The product was purified by column chroma- Step 2a. Preparation of 2-((c)-1-hydroxy-4-(methylsulfonyl)cyclohexyl)acetaldehyde.

(trans)-1-Allyl-4-(methylsulfonyl)cyclohexanol (3.4 g, 15.57 mmol) was dissolved in CH$_2$Cl$_2$ (160 mL) and MeOH (32.0 mL) in a 500 mL round bottom flask. N-Methylmorpholine-N-oxide (NMO) (2.189 g, 18.69 mmol) was added and the mixture was cooled to −78° C. [Schwartz, C., Raible, J., Mott, K., Dussault, P. H. Org. Lett. 2006, 8, 3199-3201]. Ozone was bubbled through the reaction mixture until the solution was saturated with ozone (turned into a blue color) and several minutes thereafter (total time 25 min). Nitrogen was then bubbled through the reaction mixture until the disappearance of the blue color. Dimethyl sulfide (11.52 mL, 156 mmol) was then added and the reaction mixture was stirred at 0° C. for 16 h. The mixture was concentrated under vacuum. The product was purified by column chromatography on silica gel (50% ethyl acetate with 1% methanol/50% hexanes→95% ethyl acetate with 1% methanol/5% hexanes; 330 g column) to afford 2-41s,4s)-1-hydroxy-4-(methylsulfonyl)cyclohexypacetaldehyde (3.31 g, 15.03 mmol, 96% yield) as a white solid: $^1$H NMR (400 MHz, CHLOROFORM-d) δ 9.87 (t, J=1.1 Hz, 1H), 2.85 (s, 3H), 2.82-2.76 (m, 1H), 2.67 (d, J=1.3 Hz, 2H), 2.13-1.98 (m, 6H), 1.50-1.38 (m, 2H); $^{13}$C NMR (101 MHz, CHLOROFORM-d) δ 202.5, 68.9, 61.9, 54.9, 36.8, 35.9, 20.8.

Step 2b. Preparation of 2-((trans)-1-hydroxy-4-(methylsulfonyl)cyclohexyl)acetaldehyde.

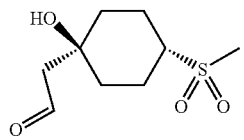

(1r,4r)-1-Allyl-4-(methylsulfonyl)cyclohexanol (2 g, 9.16 mmol) was dissolved in CH$_2$Cl$_2$ (80 mL) and MeOH (16.00 mL) in a 500 mL round bottom flask. N-Methylmorpholine-N-oxide (NMO) (1.288 g, 10.99 mmol) was added and the mixture was cooled to −78° C. [Schwartz, C., Raible, J., Mott, K., Dussault, P. H. Org. Lett. 2006, 8, 3199-3201].

Ozone (excess) was bubbled through the reaction mixture until the solution was saturated with ozone (turned into a blue color) and several minutes thereafter (total time 25 min). Nitrogen was then bubbled through the reaction mixture until the disappearance of the blue color. Dimethyl sulfide (6.78 mL, 92 mmol) was then added and the reaction mixture was stirred at 0° C. for 16 h. The mixture was concentrated under vacuum. The product was purified by column chromatography on silica gel (70% ethyl acetate with 5% methanol/30% hexanes→100% ethyl acetate with 5% methanol; 220 g column) to afford 2-((1r,4r)-1-hydroxy-4-(methylsulfonyl)cyclohexyl)acetaldehyde (1.58 g, 7.17 mmol, 78% yield) as a white solid: $^1$H NMR (400 MHz, CHLOROFORM-d) δ 9.82 (t, J=1.8 Hz, 1H), 2.99-2.88 (m, 1H), 2.85 (s, 3H), 2.67 (d, J=1.8 Hz, 2H), 2.20-2.10 (m, 2H), 2.06-1.98 (m, 2H), 1.74 (dtd, J=14.0, 10.6, 3.5 Hz, 2H), 1.61-1.50 (m, 2H); $^{13}$C NMR (101 MHz, CHLOROFORM-d) δ 202.4, 70.0, 59.3, 50.3, 38.2, 34.9, 21.1.

Example A1

Preparation of 4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-2-yloxy)methyl)cyclohex-3-enecarboxylic acid.

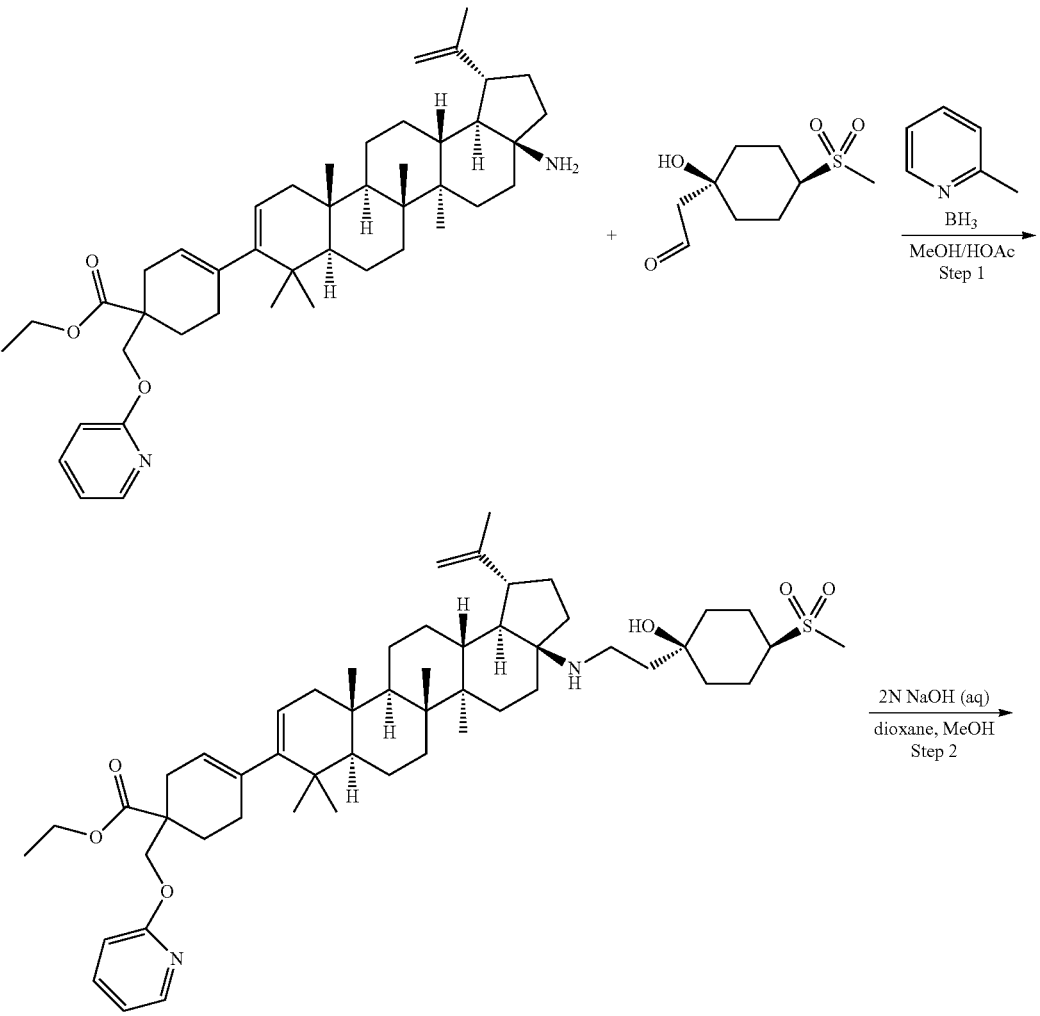

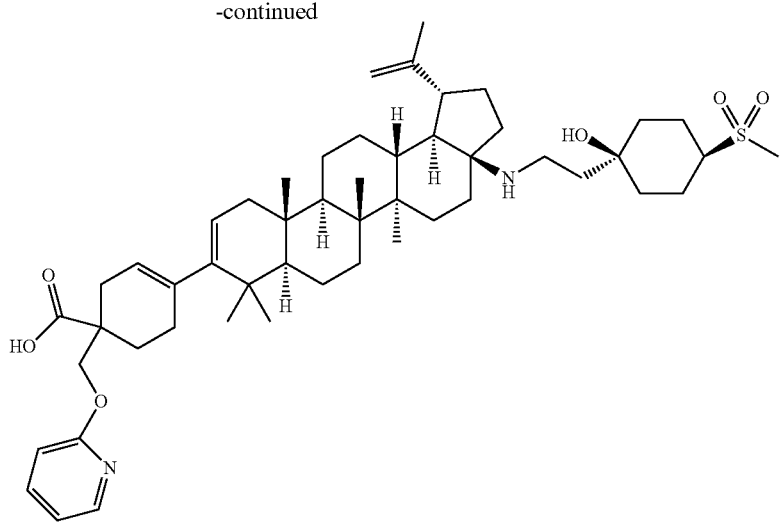

Example A1

Step 1. Preparation of ethyl 4-((1R,3aS,5aR,5bR,7aR, 11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-enecarboxylate.

with dichloromethane (4×20 mL). The combined organic layers were washed with brine (10 mL), dried over MgSO₄, filtered, and concentrated. The product was purified by column chromatography on silica gel (10% 9:1 acetone:methanol/90% hexanes→65% 9:1 acetone:methanol/35% hexanes; 24 g column, λ=220 nm) to afford ethyl 4-((1R,3aS,5aR,5bR,7aR,11aS,11bR,13aR,13bR)-3a-((2-((1s,4R)-

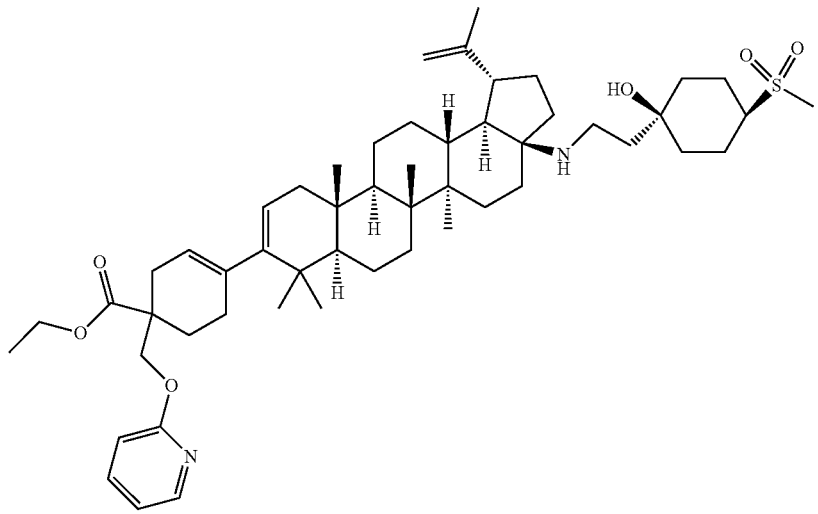

A mixture of ethyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-enecarboxylate (65 mg, 0.097 mmol), 2-((1s,4s)-1-hydroxy-4-(methylsulfonyl)cyclohexypacetaldehyde (47.1 mg, 0.214 mmol), and borane-2-picoline complex (22.86 mg, 0.214 mmol) in MeOH (1 mL) and acetic acid (0.2 mL) was stirred at room temperature for 16 h. The mixture was transferred to a separatory funnel containing saturated aqueous sodium bicarbonate solution (10 mL) and saturated aqueous sodium carbonate solution (2 mL). The aqueous layer was extracted 1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-enecarboxylate (69 mg, 81% yield) as a colorless solid: $^1$H NMR (500 MHz, CHLOROFORM-d) δ 8.15 (dd, J=5.0, 1.8 Hz, 1H), 7.56 (ddd, J=8.5, 6.9, 2.0 Hz, 1H), 6.87 (td, J=6.1, 0.7 Hz, 1H), 6.73 (d, J=8.4 Hz, 1H), 5.37 (br. s., 1H), 5.20 (d, J=6.1 Hz, 1H), 4.75 (d, J=1.5 Hz, 1H), 4.62 (s, 1H), 4.50-4.44 (m, 1H), 4.43-4.37 (m, 1H), 4.21-4.10 (m, 2H), 2.85 (s, 3H), 2.84-2.67 (m, 4H), 2.55 (td, J=10.8, 5.5 Hz, 1H), 2.22-0.88 (m, 43H), 1.70 (s, 3H), 1.21 (t, J=7.1 Hz, 3H), 1.06 (s, 3H), 0.98 (s, 3H), 0.87 (s, 3H);

LC/MS m/e 873.7 [(M+H)+, calcd for $C_{53}H_{81}N_2O_6S$ 873.6], $t_R$=4.67 min (LCMS Method 14).

Step 2. A solution of ethyl 4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-2-yloxy)methyl)cyclohex-3-enecarboxylate (65 mg, 0.074 mmol) in dioxane (1 mL) and MeOH (0.5 mL) was treated with sodium hydroxide (0.372 mL, 0.744 mmol, 2M aq). The reaction mixture was heated at 50° C. for 3 h and then at 60° C. for 6 h. The mixture was cooled to room temperature, and was partially neutralized by the addition of 2 N HCl (200 uL). The mixture was filtered through a syringe filter, and was purified by reverse phase HPLC (Preparative HPLC Method 1). The product (61.7 mg) contained an impurity (ca. 6%). The product was repurified by reverse phase HPLC (Preparative HPLC Method 2). The organic solvent was evaporated on the rotovapor and the aqueous mixture was lyophilized to afford 4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-enecarboxylic acid, TFA (48.4 mg, 67% yield) as a white amorphous solid: $^1$H NMR (500 MHz, Acetic Acid-$d_4$) δ 8.29 (dd, J=5.3, 1.7 Hz, 1H), 7.90-7.82 (m, 1H), 7.13-7.08 (m, 1H), 6.99 (d, J=8.4 Hz, 1H), 5.41 (br. s., 1H), 5.26 (d, J=5.8 Hz, 1H), 4.83 (s, 1H), 4.73 (s, 1H), 4.56-4.50 (m, 1H), 4.49-4.44 (m, 1H), 3.48-3.34 (m, 2H), 3.09-2.99 (m, 1H), 2.96 (s, 3H), 2.89-2.79 (m, 1H), 2.72 (d, J=16.0 Hz, 1H), 2.32-1.32 (m, 35H), 1.75 (s, 3H), 1.17 (s, 3H), 1.13 (d, J=7.5 Hz, 2H), 1.09 (s, 3H), 1.02 (d, J=3.7 Hz, 3H), 0.99 (d, J=3.7 Hz, 3H), 0.95 (s, 3H); LC/MS m/e 845.6 [(M+H)$^+$, calcd for $C_{51}H_{77}N_2O_6S$ 845.6], $t_R$=4.36 min (LCMS Method 14); HPLC (Analytical HPLC Method 1): $t_R$=18.86 min; HPLC (Analytical HPLC Method 2): $t_R$=20.24 min.

Example A2

Preparation of 4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-2-yloxy)methyl)cyclohex-3-enecarboxylic acid.

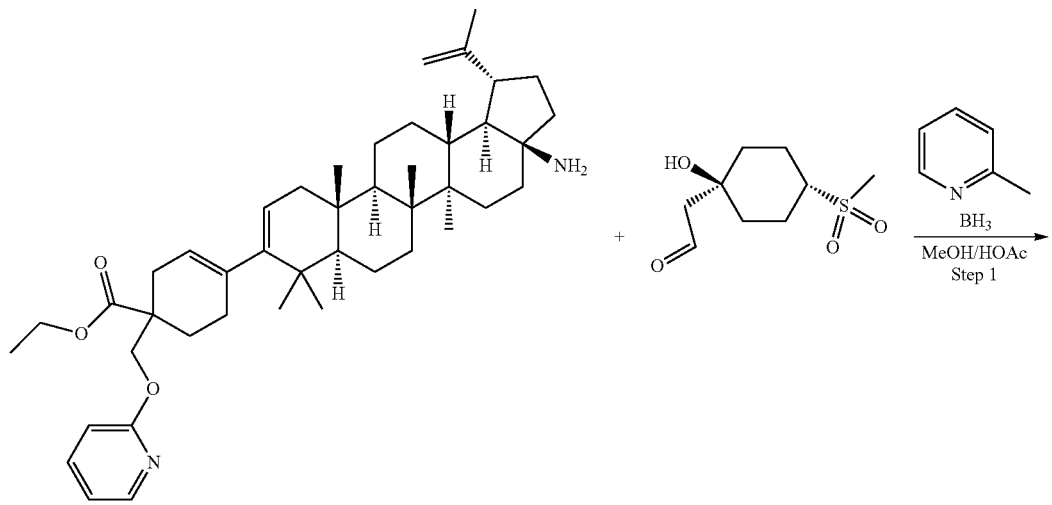

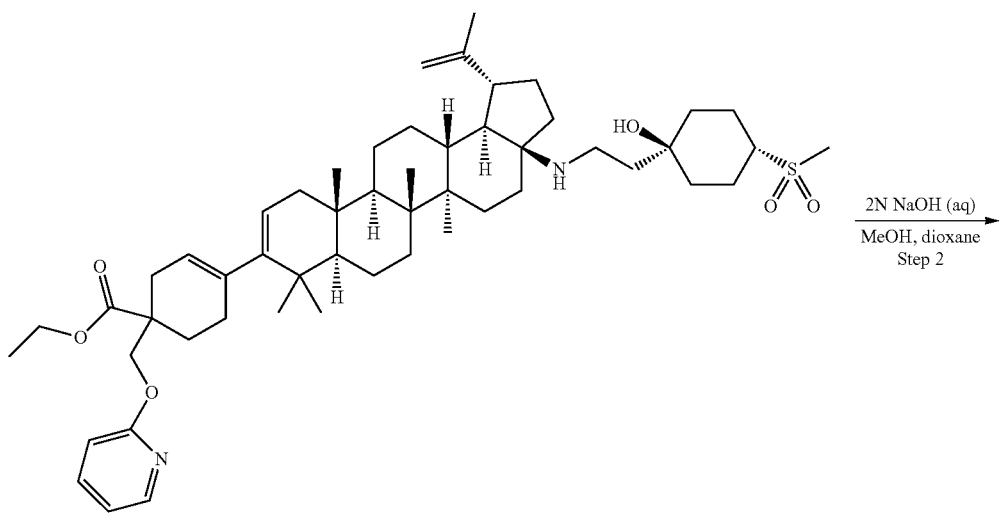

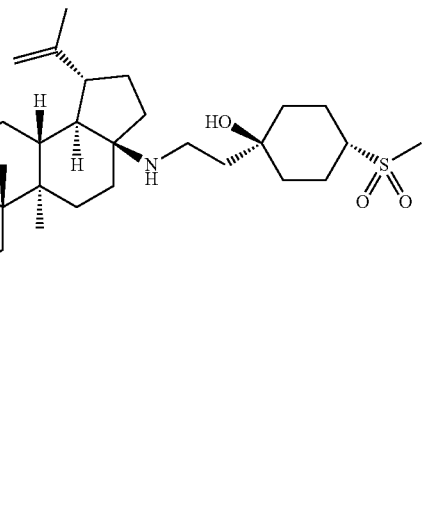

Example A2

Step 1. Preparation of ethyl 4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-enecarboxylate.

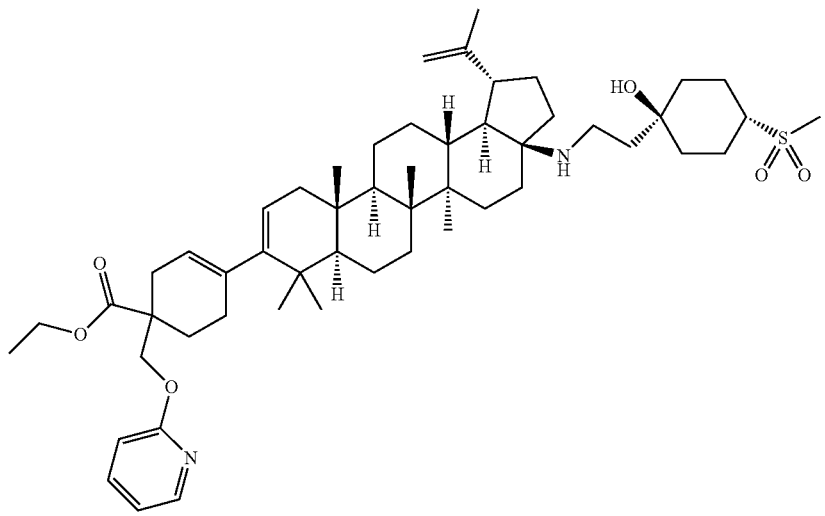

A mixture of ethyl 4-((1R,3aS,5aR,5bR,7aR,11aS, 11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-((pyridin-2-yloxy)methyl)cyclohex-3-enecarboxylate (65 mg, 0.097 mmol), 2-((1r,4r)-1-hydroxy-4-(methylsulfonyl)cyclohexypacetaldehyde (47.1 mg, 0.214 mmol), and borane-2-picoline complex (22.86 mg, 0.214 mmol) in MeOH (1 mL) and acetic acid (0.2 mL) was stirred at room temperature for 16 h. The reaction was not complete. Additional 2-((1r,4r)-1-hydroxy-4-(methylsulfonyl)cyclohexyl)acetaldehyde (21 mg, 0.097 mmol, 1 eq) was then added and 1 h later borane-2-picoline complex (10 mg, 0.097 mmol, 1 eq) was added to the reaction mixture and the mixture was stirred at room temperature for 3 h. The mixture was transferred to a separatory funnel containing saturated aqueous sodium bicarbonate solution (10 mL) and saturated aqueous sodium carbonate solution (2 mL). The aqueous layer was extracted with dichloromethane (4×20 mL). The combined organic layers were washed with brine (10 mL), dried over MgSO$_4$, filtered, and concentrated. The product was purified by column chromatography on silica gel (10% 9:1 acetone:methanol/90% hexanes→65% 9:1 acetone:methanol/35% hexanes; 24 g column, λ=220 nm) to afford ethyl 4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-((pyridin-2-yloxy)methyl)cyclohex-3-enecarboxylate (42.4 mg, 50% yield) as a colorless foam: $^1$H NMR (500 MHz, CHLOROFORM-d) δ 8.14 (dd, J=5.0, 1.8 Hz, 1H), 7.61-7.54 (m, 1H), 6.87 (ddd, 5.1, 0.8 Hz, 1H), 6.73 (d, J=8.4 Hz, 1H), 5.36 (br.

s., 1H), 5.20 (d, J=6.0 Hz, 1H), 4.72 (d, J=1.4 Hz, 1H), 4.60 (s, 1H), 4.51-4.44 (m, 1H), 4.43-4.36 (m, 1H), 4.21-4.10 (m, 2H), 2.99-2.91 (m, 1H), 2.89 (s, 3H), 2.83-2.76 (m, J=12.1 Hz, 1H), 2.72-2.62 (m, 2H), 2.59-2.51 (m, 1H), 2.21-0.88 (m, 43H), 1.69 (s, 3H), 1.21 (t, J=7.1 Hz, 3H), 1.06 (s, 3H), 0.98 (s, 3H), 0.87 (s, 3H); LC/MS m/e 873.7 [(M+H)+, calcd for $C_{53}H_{81}N_2O_6S$ 873.6], $t_R$=4.62 min (LCMS Method 14).

Step 2. A solution of ethyl 4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-2-yloxy)methyl)cyclohex-3-enecarboxylate (42 mg, 0.048 mmol) in dioxane (1 mL) and MeOH (0.5 mL) was treated with sodium hydroxide (0.361 mL, 0.721 mmol, 2 M aq). The reaction mixture was heated at 60° C. for 24 h. Additional sodium hydroxide (0.120 mL, 0.240 mmol, 5 eq, 2 M aq) was added and the reaction mixture was heated at 70° C. for 8 h. The reaction was complete. The mixture was cooled to room temperature, and was partially neutralized by the addition of 2 N HCl (400 uL). The mixture was filtered through a syringe filter, and was purified by reverse phase HPLC (Preparative HPLC Method 3). The organic solvent was evaporated on the rotovapor and the aqueous mixture was lyophilized to afford 4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopenta[a]chrysen-9-yl)-1-((pyridin-2-yloxy)methyl)cyclohex-3-enecarboxylic acid, TFA (31.3 mg, 67% yield) as a white amorphous solid. $^1$H NMR (500 MHz, Acetic Acid-$d_4$) δ 8.30-8.25 (m, 1H), 7.85-7.78 (m, 1H), 7.10-7.04 (m, 1H), 6.95 (dd, J=8.5, 0.6 Hz, 1H), 5.41 (br. s., 1H), 5.26 (d, J=6.0 Hz, 1H), 4.83 (s, 1H), 4.72 (s, 1H), 4.55-4.49 (m, 1H), 4.48-4.43 (m, 1H), 3.46-3.37 (m, 1H), 3.36-3.28 (m, 1H), 3.18-3.10 (m, 1H), 2.98 (s, 3H), 2.91-2.81 (m, 1H), 2.71 (d, J=16.3 Hz, 1H), 2.32-1.32 (m, 35H), 1.75 (s, 3H), 1.16-1.12 (m, 2H), 1.14 (s, 3H), 1.09 (s, 3H), 1.02 (d, J=3.7 Hz, 3H), 0.99 (d, J=3.2 Hz, 3H), 0.94 (s, 3H); LC/MS m/e 845.6 [(M+H)+, calcd for $C_{51}H_{77}N_2O_6S$ 845.6], $t_R$=4.33 min (LCMS Method 14); HPLC (Analytical HPLC Method 1): $t_R$=18.86 min; HPLC (Analytical HPLC Method 2): $t_R$=20.48 min.

Example A3

Preparation of (S)-1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid.

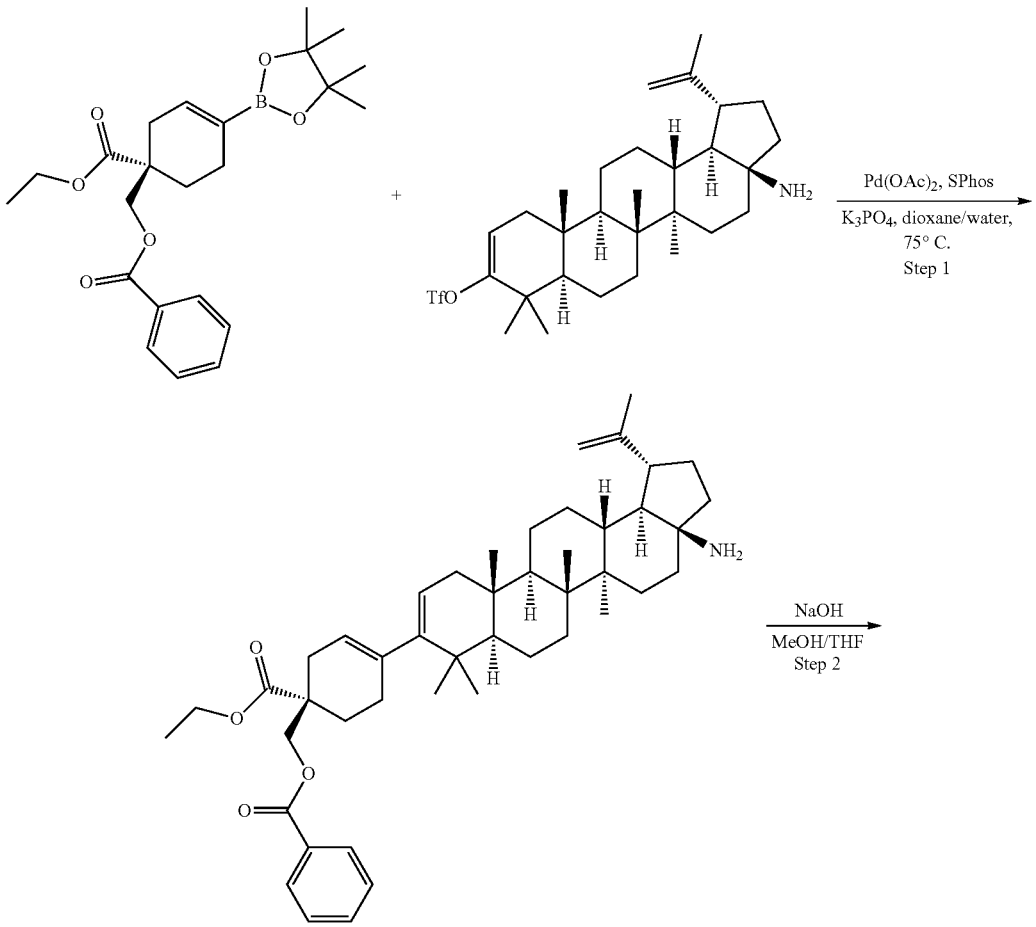

-continued
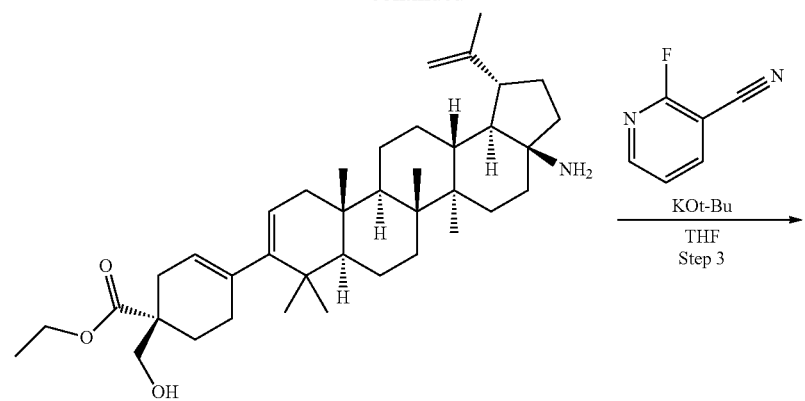
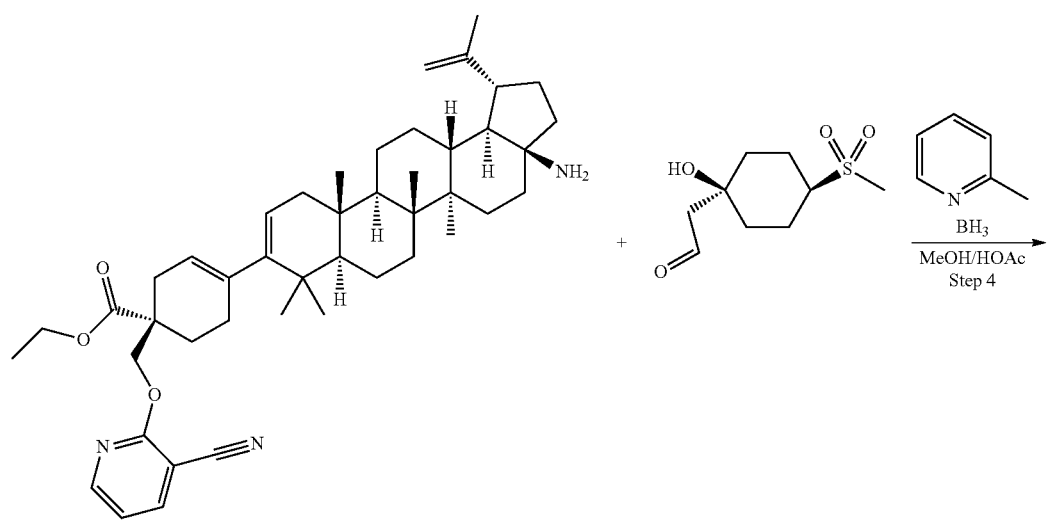
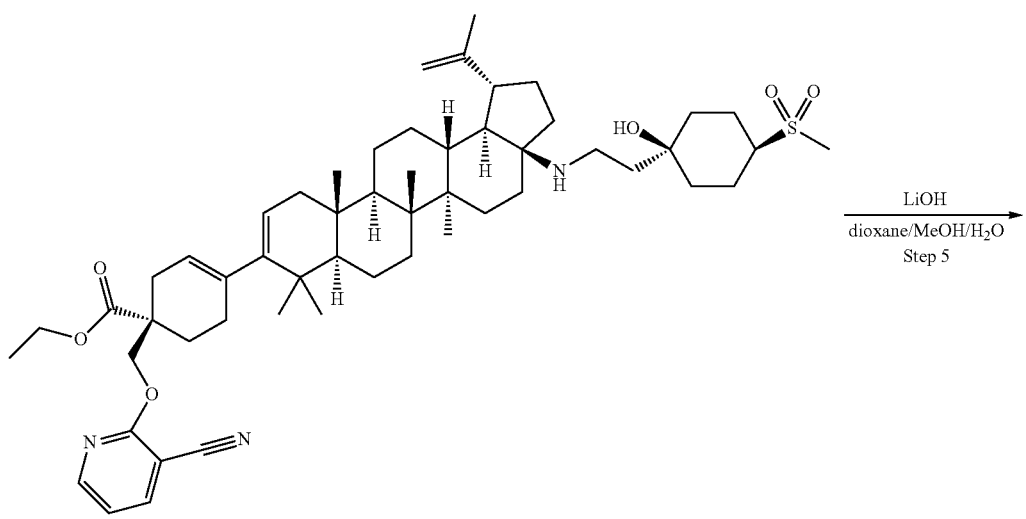

-continued

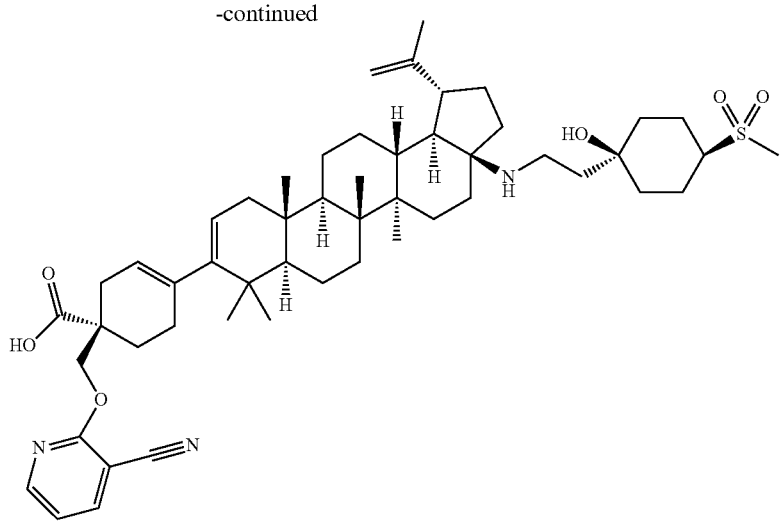

Example A3

Step 1. Preparation of ((S)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,1b,12,13,13a,13b-octadecahydro-1H-cyclopenta[a]chrysen-9-yl)-1-(ethoxycarbonyl)cyclohex-3-en-1-yl)methyl benzoate.

To a flask containing (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (1.00 g, 1.79 mmol) was added (R)-(1-(ethoxycarbonyl)-4-(4,4,5,5-tetramethyl-1,3,2-dioxaborolan-2-yl)cyclohex-3-en-1-yl)methyl benzoate (1.337 g, 3.23 mmol), potassium phosphate tribasic (1.52 g, 7.17 mmol), 2-dicyclohexylphosphino-2',6'-dimethoxybiphenyl (S-Phos) (0.055 g, 0.134 mmol) and palladium(II) acetate (0.020 g, 0.090 mmol). The mixture was diluted with 1,4-dioxane (25 mL) and water (6.25 mL), then was flushed with $N_2$ and heated at 75° C. for 16 h. The mixture was cooled to rt. The mixture was diluted with water (100 mL) and extracted with ethyl acetate (3×75 mL). The organic layers were washed with brine (150 mL), dried over magnesium sulfate, filtered and concentrated under reduced pressure. The residue was purified by column chromatography on silica gel (50% ethyl acetate with 4% MeOH and 0.8% ammonium hydroxide/50% hexanes→70% ethyl acetate with 4% MeOH and 0.8% ammonium hydroxide/30% hexanes, 120 g column) to afford ((S)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (1.15 g, 92% yield) as an off-white solid: $^1$H NMR (400 MHz, CHLOROFORM-d) δ 8.06-8.00 (m, 2H), 7.62-7.55 (m, 1H), 7.49-7.41 (m, 2H), 5.38 (br. s., 1H), 5.22 (dd, J=6.3, 1.8 Hz, 1H), 4.75 (d, J=2.0 Hz, 1H), 4.62 (dd, J=2.3, 1.3 Hz, 1H), 4.52-4.40 (m, 2H), 4.20 (qd, J=7.2, 2.1 Hz, 2H), 2.70 (d, J=18.3 Hz, 1H), 2.56 (td, J=10.9, 5.3 Hz, 1H), 2.35-1.95 (m, 6H), 1.91-1.81 (m, 1H), 1.78-1.13 (m, 20H), 1.71 (s, 3H), 1.24 (t, J=7.3 Hz, 3H), 1.09 (s, 3H), 1.00 (s, 3H), 0.98 (s, 3H), 0.93 (s, 3H), 0.88 (s, 3H); LC/MS m/e 696.7 [(M+H)$^+$, calcd for $C_{46}H_{65}NO_4$ 696.5], $t_R$=2.60 min (LCMS Method 15).

Step 2. Preparation of (S)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate.

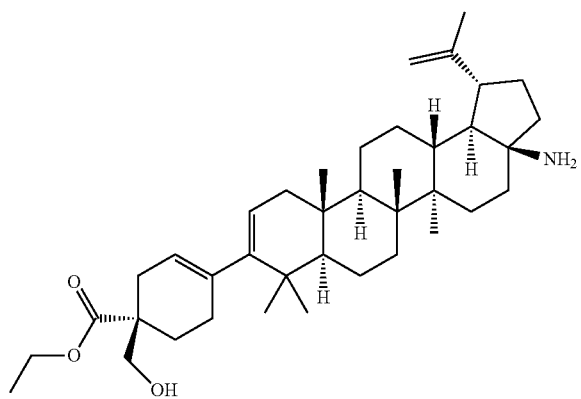

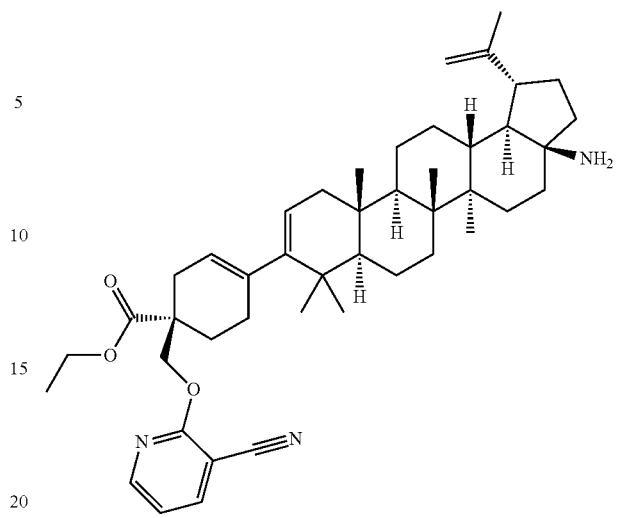

To a solution of ((S)-4-(((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (1.07 g, 1.537 mmol) in THF (10 mL) and MeOH (1 mL) was added sodium hydroxide (1.691 mL, 1.691 mmol). The reaction mixture was stirred at r.t. for 14 h. The solid was removed by filtration. The mixture was transferred to a separatory funnel containing saturated aqueous $NaHCO_3$ solution (10 mL)/water (10 mL). The aqueous layer was extracted with 5% methanol in ethyl acetate (5×25 mL). The combined organic layers were washed with brine (10 mL). The brine wash was reextracted with 5% methanol in ethyl acetate. The combined organic layers were dried over $MgSO_4$, filtered, and concentrated to afford (S)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate (0.535 g, 59% yield) as a white solid. The crude product was used directly in the next step. $^1$H NMR (400 MHz, CHLOROFORM-d) δ 8 5.34 (t, J=3.8 Hz, 1H), 5.20 (dd, J=6.1, 1.9 Hz, 1H), 4.75 (d, J=2.0 Hz, 1H), 4.63 (d, J=1.3 Hz, 1H), 4.21 (q, J=7.0 Hz, 2H), 3.70 (s, 2H), 2.62-2.51 (m, 2H), 2.23-2.15 (m, 2H), 2.09-1.92 (m, 4H), 1.83-1.12 (m, 21H), 1.72 (s, 3H), 1.30 (t, J=7.2 Hz, 3H), 1.09 (s, 3H), 0.99 (s, 3H), 0.98 (s, 3H), 0.93 (s, 3H), 0.88 (s, 3H); LC/MS (ESI) mle 614.6 [(M+H)+, calcd for $C_{39}H_{61}NO_3Na$ 614.5], $t_R$=4.28 min (LCMS Method 14).

Step 3. Preparation of (S)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate.

To a solution of (S)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate (495 mg, 0.836 mmol) and 2-fluoronicotinonitrile (204 mg, 1.673 mmol) in THF (7 mL) and DMF (1 mL) at 0° C. was added potassium tert-butoxide (1.004 mL, 1.004 mmol). The cooling bath was removed and the reaction mixture was stirred at 20° C. for 1.5 h. The mixture was transferred to a separatory funnel containing saturated aqueous $NaHCO_3$ solution (15 mL). The aqueous layer was extracted with ethyl acetate (4×25 mL). The combined organic layers were washed with brine (15 mL), dried over $MgSO_4$, filtered, and concentrated.

The product was purified by column chromatography on silica gel (50% of a 5% methanol in ethyl acetate solution/50% hexanes→100% of a 5% methanol in ethyl acetate solution; 40 g column) to afford (S)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (344 mg, 59% yield) as an off-white solid: $^1$H NMR (400 MHz, CHLOROFORM-d) δ 8.34 (dd, J=5.0, 2.0 Hz, 1H), 7.88 (dd, J=7.5, 2.0 Hz, 1H), 6.99 (dd, J=7.5, 5.0 Hz, 1H), 5.38 (br. s., 1H), 5.21 (dd, J=6.1, 1.6 Hz, 1H), 4.75 (d, J=2.3 Hz, 1H), 4.62 (dd, J=2.1, 1.4 Hz, 1H), 4.57 (s, 2H), 4.25-4.15 (m, 2H), 2.78-2.68 (m, 1H), 2.56 (td, J=10.9, 5.1 Hz, 1H), 2.35-1.89 (m, 6H), 1.79-1.11 (m, 21H), 1.71 (s, 3H), 1.27 (t, J=6.8 Hz, 3H), 1.09 (s, 3H), 0.99 (s, 3H), 0.98 (s, 3H), 0.93 (s, 3H), 0.88 (s, 3H); LC/MS (ESI) mle 694.7 [(M+H)$^+$, calcd for $C_{45}H_{64}N_3O_3$ 694.5], $t_R$=4.52 min (LCMS Method 14).

Step 4. Preparation of (S)-ethyl 1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate.

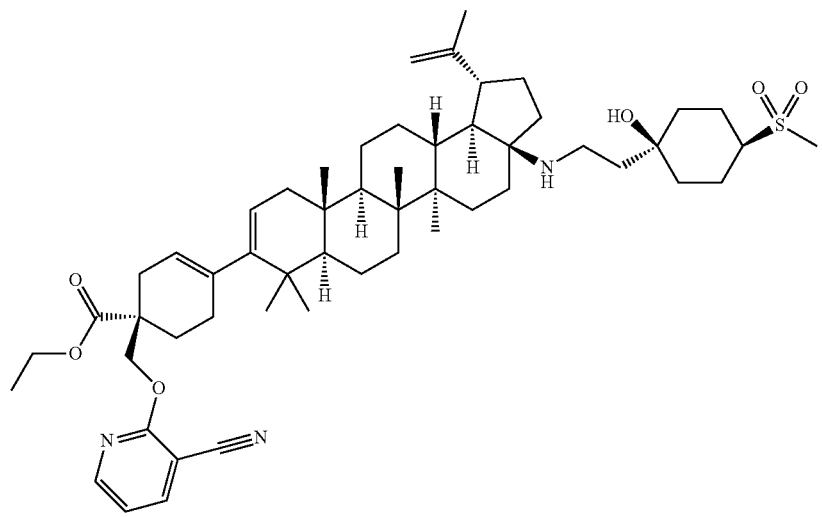

(S)-Ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (150 mg, 0.216 mmol) and 2-((1s,4s)-1-hydroxy-4-(methylsulfonyl)cyclohexyl)acetaldehyde (76 mg, 0.346 mmol) were dissolved in MeOH (1.6 mL) and acetic acid (0.32 mL). Borane-2-picoline complex (37.0 mg, 0.346 mmol) was added and the mixture was stirred at room temperature for 14 h. The mixture was transferred to a separatory funnel containing saturated aqueous sodium bicarbonate solution (3 mL) and sodium carbonate solution (2 mL). The aqueous layer was extracted with ethyl acetate (5×10 mL). The combined organic layers were washed with brine (5 mL), dried over MgSO$_4$, filtered, and concentrated. The product was purified by column chromatography on silica gel (30% ethyl acetate with 5% methanol/70% hexanes→100% ethyl acetate with 5% methanol; 24 g column, 25 min gradient) to afford (S)-ethyl 1-(((3-cyanopyridin-2-yl)oxy)methyl)-4-41R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (134.6 mg, 69% yield) as a white foam: $^1$H NMR (500 MHz, CHLOROFORM-d) δ 8.34 (dd, J=5.0, 2.0 Hz, 1H), 7.88 (dd, J=7.6, 1.9 Hz, 1H), 6.99 (dd, J=7.5, 5.0 Hz, 1H), 5.37 (br. s., 1H), 5.20 (dd, J=6.2, 1.6 Hz, 1H), 4.74 (d, J=1.5 Hz, 1H), 4.61 (s, 1H), 4.56 (s, 2H), 4.24-4.15 (m, 2H), 2.85 (s, 3H), 2.83-2.67 (m, 4H), 2.55 (td, J=10.9, 5.6 Hz, 1H), 2.31-0.88 (m, 37H), 1.70 (s, 3H), 1.26 (t, J=7.1 Hz, 3H), 1.05 (s, 3H), 0.98 (s, 3H), 0.98 (s, 3H), 0.93 (s, 3H), 0.87 (s, 3H); LC/MS (ESI) m/e 898.7 [(M+H)$^+$, calcd for C$_{54}$H$_{80}$N$_3$O$_6$S 898.6], t$_R$=4.44 min (LCMS Method 14).

Step 5. To a solution of (S)-ethyl 1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (123 mg, 0.137 mmol) in dioxane (4 mL) and MeOH (2 mL) was added lithium hydroxide (2 mL, 2.00 mmol, 1 M aq). The mixture was heated at 60° C. for 12.5 h. Only a small amount of starting material was detected by LC/MS (LCMS Method 16). The reaction was stopped at this point due to competing hydrolysis of the nitrile group to the corresponding amide. The mixture was cooled to room temperature and was partially neutralized by the addition of 6 N HCl (250 µL). The mixture was then filtered through a syringe filter, and was purified by reverse phase HPLC (5 injections) (Preparative HPLC Method 4). The organic solvent was evaporated on the rotovapor and the aqueous mixture was lyophilized to afford (S)-1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (51.6 mg, 38% yield) as a white amorphous solid: $^1$H NMR (500 MHz, Acetic Acid-d$_4$) δ 8.42 (dd, J=5.1, 1.9 Hz, 1H), 8.05 (dd, J=7.6, 1.9 Hz, 1H), 7.11 (dd, J=7.6, 5.1 Hz, 1H), 5.43 (s, 1H), 5.27 (d, J=4.7 Hz, 1H), 4.83 (s, 1H), 4.72 (s, 1H), 4.68-4.61 (m, 2H), 3.47-3.33 (m, 2H), 3.08-2.99 (m, 1H), 2.96 (s, 3H), 2.90-2.81 (m, 1H), 2.74 (d, J=15.6 Hz, 1H), 2.38-1.13 (m, 37H), 1.75 (s, 3H), 1.18 (s, 3H), 1.09 (s, 3H), 1.03 (s, 3H), 0.99 (s, 3H), 0.95 (s, 3H); LC/MS (ESI) m/e 870.6 [(M+H)$^+$, calcd for C$_{52}$H$_{76}$N$_3$O$_6$S 870.5], t$_R$=1.31 min (LCMS Method 16); HPLC (Analytical HPLC Method 3): t$_R$=12.19 min; HPLC (Analytical HPLC Method 4): t$_R$=11.64 min.

Alternate route for the preparation of Example A3

Preparation of (S)-1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid.

263 264
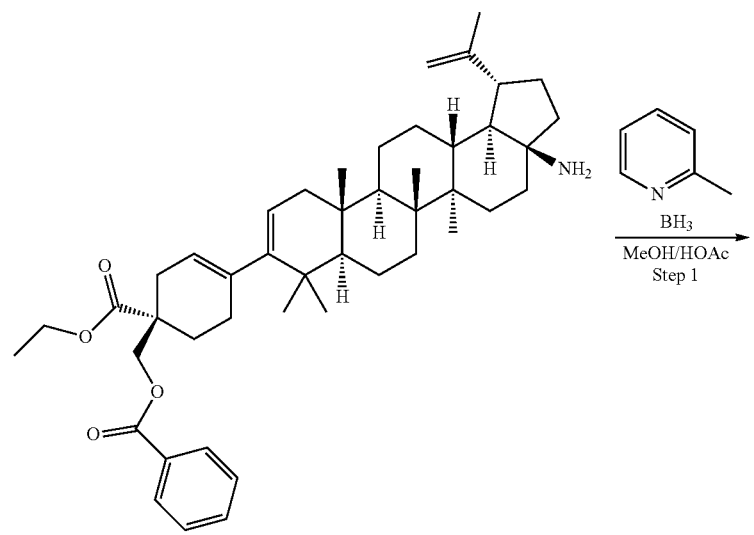
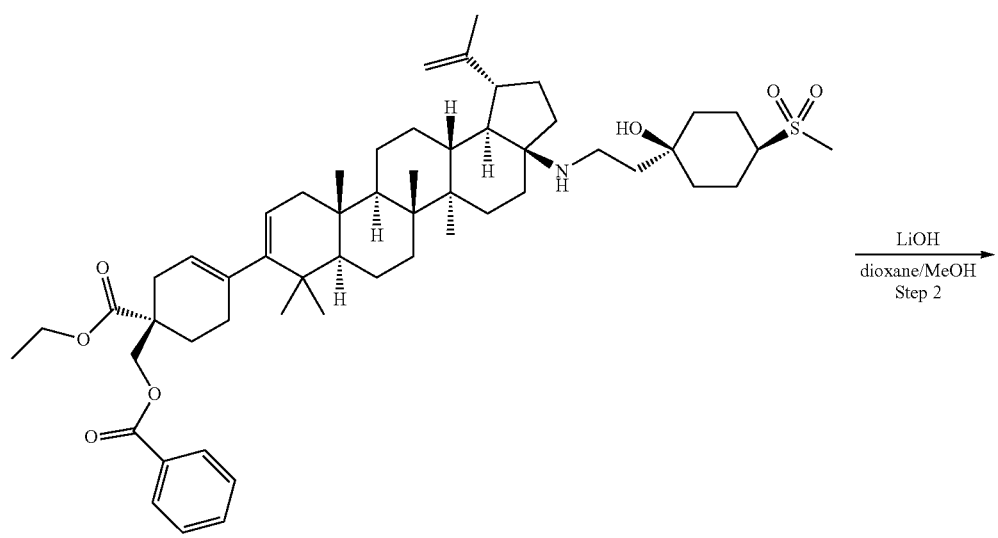
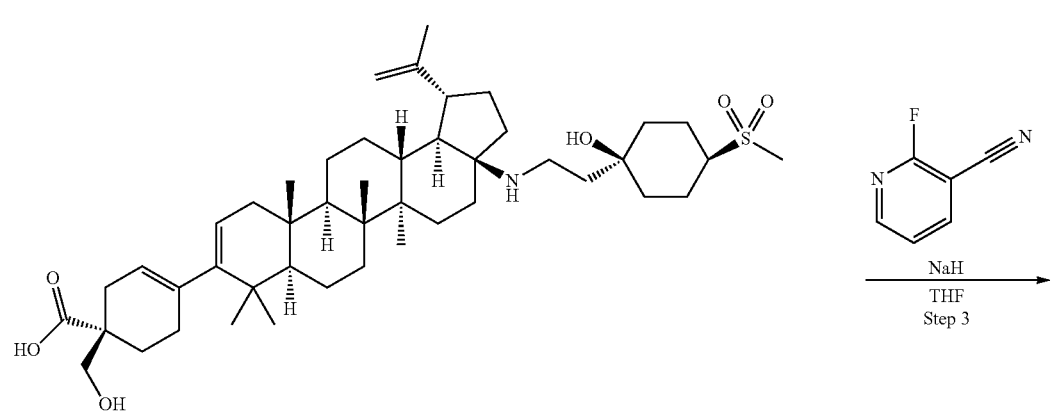

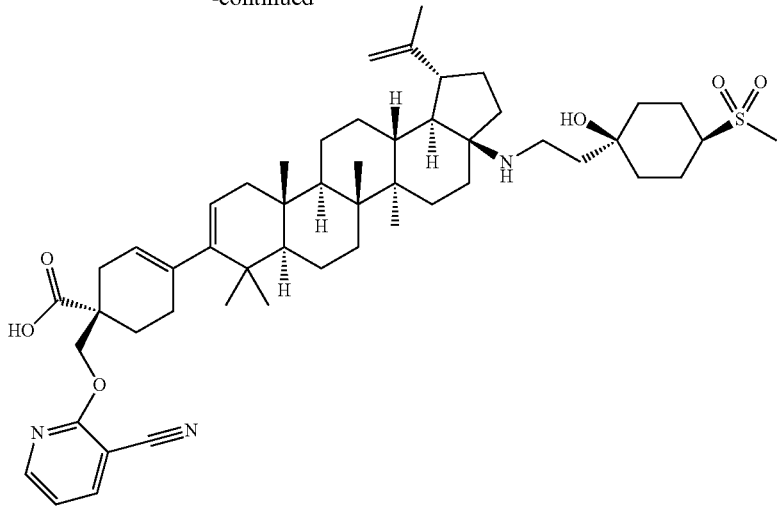

Example A3

Step 1. Preparation of ((S)-1-(ethoxycarbonyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)methyl benzoate.

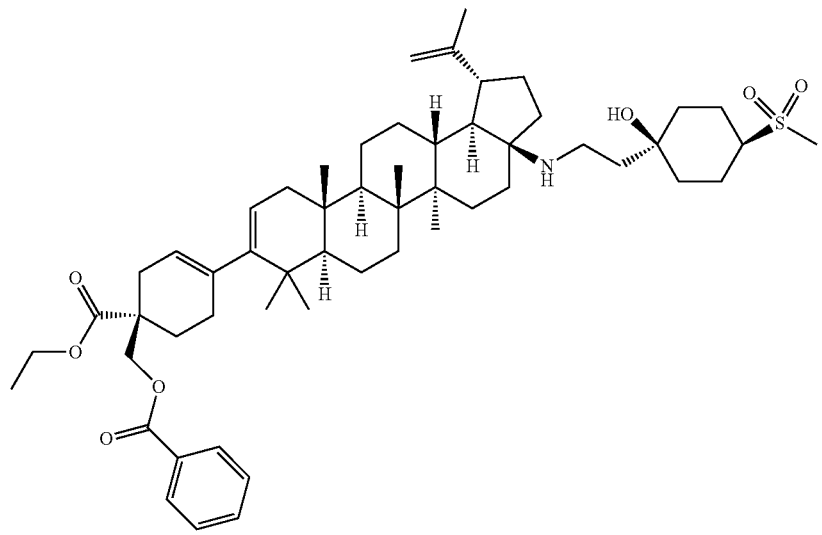

((S)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentata[a]chrysen-9-yl)-1-(ethoxycarbonyl)cyclohex-3-en-1-yl)methyl benzoate (7.63 g, 10.96 mmol), and 2-((1s,4s)-1-hydroxy-4-(methylsulfonyl)cyclohexyl)acetaldehyde (3.86 g, 17.54 mmol) were dissolved in MeOH (30 mL) and acetic acid (6 mL). Borane-2-picoline complex (1.876 g, 17.54 mmol) was added and the mixture was stirred at room temperature for 14 h. The mixture was transferred to a separatory funnel containing saturated aqueous sodium bicarbonate solution (50 mL) and sodium carbonate solution (50 mL). The aqueous layer was extracted with ethyl acetate (7×100 mL). The combined organic layers were washed with brine (25 mL), dried over MgSO$_4$, filtered, and concentrated. The product was purified by column chromatography on silica gel (30% ethyl acetate with 5% methanol/70% hexanes→100% ethyl acetate with 5% methanol; 330 g column, 30 min gradient) to afford ((S)-1-(ethoxycarbonyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11 b,12,13,13a,13b-octadecahydro-1H-cyclopentala[chrysen-9-yl)cyclohex-3-en-1-yl)methyl benzoate (8.81 g, 89% yield) as a white solid: $^1$H NMR (500 MHz, CHLOROFORM-d) δ 8.06-8.00 (m, 2H), 7.61-7.54 (m, 1H), 7.50-7.42 (m, 2H), 5.37 (br. s., 1H), 5.21 (dd, J=6.2, 1.6 Hz, 1H), 4.75 (d, J=1.8 Hz, 1H), 4.62 (s, 1H), 4.47-4.41 (m, 2H), 4.24-4.16 (m, 2H), 2.85 (s, 3H), 2.83-2.65 (m, 4H), 2.55 (td, J=10.9, 5.6 Hz, 1H), 2.33-2.23 (m, 1H), 2.20-1.03 (m, 36H), 1.70 (s, 3H), 1.24 (t, J=7.1 Hz, 3H), 1.05 (s, 3H), 0.99-0.87 (m, 12H); LC/MS (ESI) m/e 900.4 [(M+H)+, calcd for $C_{55}H_{82}NO_7S$ 900.6], $t_R$=4.55 min (LCMS Method 14).

Step 2. Preparation of (S)-4-41R,3aS,5aR,5bR,7aR,11aS, 11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopentatalchrysen-9-yl)-1-(hydroxymethyl)cyclohex-3-enecarboxylic acid.

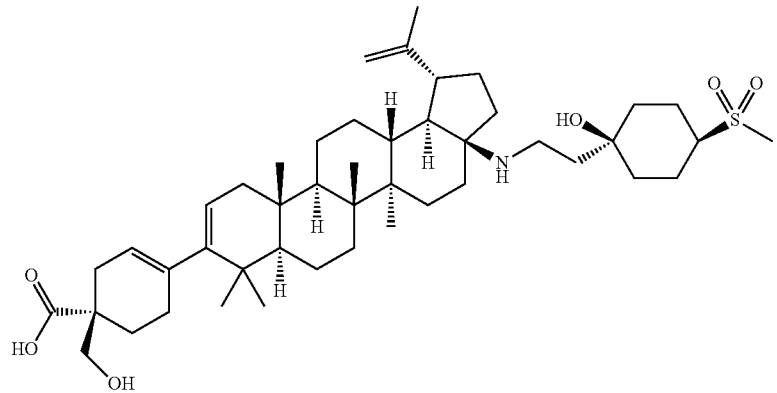

To a solution of ((S)-1-(ethoxycarbonyl)-4-((1R,3aS,5aR, 5bR,7aR,11aS,11bR,13aR,13bR)-3a-((2-((1s,4R)-1-hydroxy-4-(methylsulfonyl)cyclohexyl)ethyl)amino)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-en-1-yl)methyl benzoate (8.00 g, 8.89 mmol) in 1,4-dioxane (160 mL) and methanol (80 mL) in a pressure vessel was added lithium hydroxide (89 mL, 89 mmol). The vessel was sealed and the mixture was heated at 65° C. (internal temperature) for 16 h. The reaction mixture was cooled to room temperature and was partially neutralized by the addition of 4 N HCl (15.5 mL, 7 eq). The mixture was then concentrated. The crude product was taken up in dioxane (40 mL)/methanol (20 mL)/water (5 mL) and was made acidic by the addition of TFA (dropwise until acidic). The suspension became a solution. The solution contained some suspended solid matter. It was passed through a short plug of sand followed by filtration through a syringe filter. The product was then purified by reverse phase MPLC on a C18 Redi Sep Gold column (150 g) on the biotage (Preparative MPLC Method 1, 6 injections). The organic solvent was evaporated on the rotovapor and the aqueous mixture was lyophilized to afford (S)-4-((1R,3aS,5aR,5bR,7aR,11aS,11bR,13aR,13bR)-3a-((2-((1s,4R)-1-hydroxy-4-(methylsulfonyl)cyclohexyl) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylic acid, TFA (6.57 g, 84% yield) as a white amorphous solid. The product was then dried further under vacuum in a vacuum dessicator with dryrite. $^1$H NMR (500 MHz, CHLOROFORM-d) δ 8.54 (br. s., 1H), 8.02 (br. s., 1H), 5.34 (br. s., 1H), 5.23-5.16 (m, 1H), 4.78 (s, 1H), 4.70 (s, 1H), 3.76 (s, 2H), 3.22 (d, J=3.1 Hz, 2H), 2.86 (s, 3H), 2.83-2.68 (m, 2H), 2.59 (d, J=15.3 Hz, 1H), 2.47-2.34 (m, 1H), 2.26-1.06 (m, 36H), 1.71 (s, 3H), 1.09 (s, 3H), 1.03 (s, 3H), 0.98 (s, 3H), 0.93 (s, 3H), 0.88 (s, 3H); LC/MS (ESI) m/e 768.4 [(M+H)+, calcd for C46H74NO6S 768.5], $t_R$=3.85 min. (LCMS Method 14).

Step 3. To a solution of (S)-4-((1R,3aS,5aR,5bR,7aR, 11aS,11bR,13aR,13bR)-3a-((2-((1,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopentatalchrysen-9-yl)-1-(hydroxymethyl)cyclohex-3-enecarboxylic acid, TFA (5.92 g, 6.71 mmol) in THF (80 mL) at 0° C. was added sodium hydride (2.147 g, 53.7 mmol). The cooling bath was removed and the reaction mixture was stirred at room temperature for 15 min. The mixture was cooled to 0° C. and 2-fluoronicotinonitrile (3.28 g, 26.8 mmol) in THF (10 mL) was added via cannula. The reaction mixture was stirred at 0° C. for 1.5 h. The reaction was quenched by the addition of acetic acid (3.84 mL, 67.1 mmol, 10 eq). The solution was directly injected on a column and was purified by column chromatography on silica gel (5% methanol in $CH_2Cl_2$ to elute the high $R_f$ material and then 12% methanol in $CH_2Cl_2$ to elute the product. 6.70 g of product was obtained. The product was then purified further by reverse phase MPLC on a C18 Redi Sep Gold column (150 g) on the biotage (Preparative MPLC Method 2, 5 injections). The organic solvent was evaporated on the rotovapor and the aqueous mixture was lyophilized to afford (S)-1-(((3-cyanopyridin-2-yl)oxy)methyl)-4-((1R, 3aS,5aR,5bR,7aR,11aS,11bR,13aR,13bR)-3a-((2-((1s,4R)-1-hydroxy-4-(methyl sulfonyl)cyclohexyl)ethyl)amino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopentalalchrysen-9-yl)cyclohex-3-enecarboxylic acid, TFA (5.06 g, 5.14 mmol) as a white amorphous solid.

The product (TFA salt) was then dissolved in MeCN/H20 (60/40) and was slowly passed through an AG 1-x2 ion exchange resin chloride form (Bio-Rad 100-200 mesh cat # 140-1241, prewashed with 90% acetonitrile/10% water). 140 grams of resin was used. The fractions containing product were combined and the organic solvent was removed on the rotovapor and water was frozen and placed on the lyophilizer to afford (S)-1-(((3-cyanopyridin-2-yl) oxy)methyl)-4-((1R,3aS,5aR,5bR,7aR,11aS,11bR,13aR, 13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylic acid, HCl (4.26 g, 66% yield) as a white amorphous solid: $^1$H NMR (500 MHz, Acetic Acid-d4) δ 8.42 (dd, J=5.1, 1.9 Hz, 1H), 8.05 (dd, J=7.6, 1.9 Hz, 1H), 7.11 (dd, J=7.6, 5.1 Hz, 1H), 5.43 (br. s., 1H), 5.27 (d, J=4.6 Hz, 1H), 4.89 (s, 1H), 4.73 (s, 1H), 4.69-4.60 (m, 2H), 3.45-3.33 (m, 2H), 3.13 (td, J=10.8, 5.1 Hz, 1H), 3.08-3.00 (m, 1H), 2.97 (s, 3H), 2.74 (d, J=15.1 Hz, 1H), 2.61-2.53 (m, 1H), 2.38-1.13 (m, 36H), 1.76 (s, 3H), 1.20 (s, 3H), 1.10 (s, 3H), 1.03 (s, 3H), 0.99 (s, 3H), 0.95 (s, 3H); LC/MS (ESI) m/e 870.3 [(M+H)+, calcd for C52H76N3O6S 870.5], $t_R$=4.56 min (LCMS Method 14); HPLC (HPLC Method 3): $t_R$=13.13 min; HPLC (HPLC Method 4): $t_R$=12.46 min.

Example A4

Preparation of (S)-1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid.

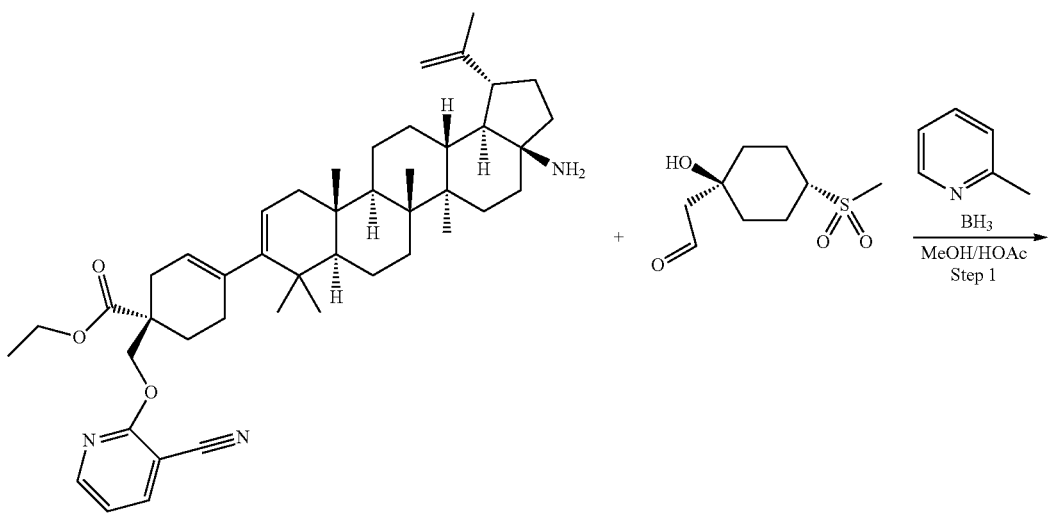

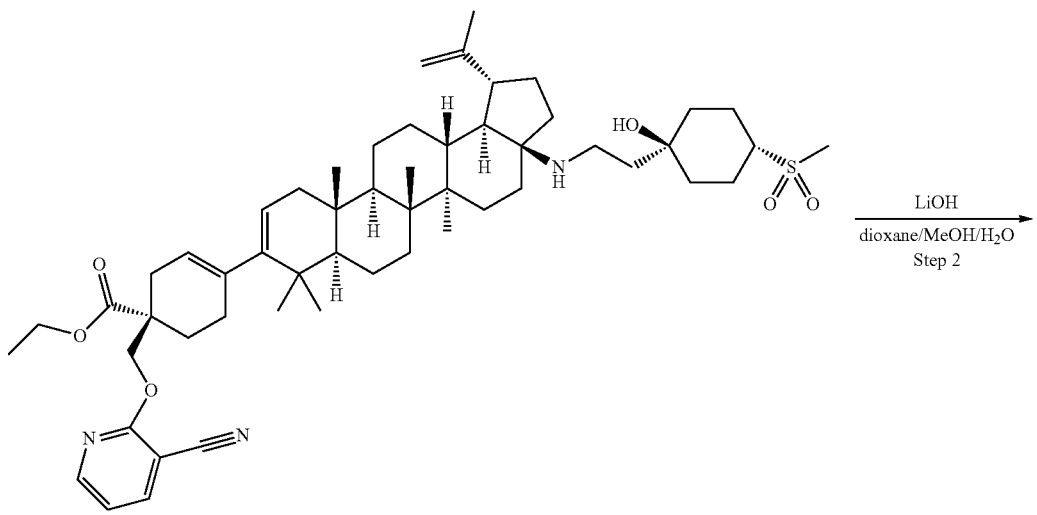

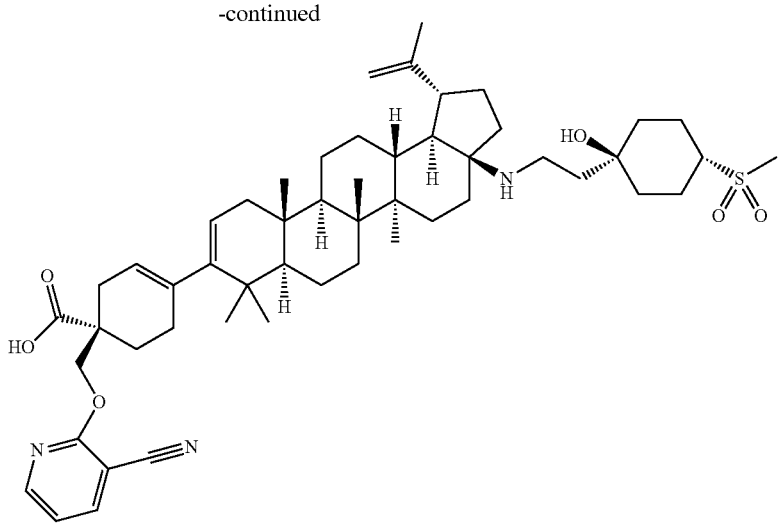

Example A4

Step 1. Preparation of (S)-ethyl 1-(((3-cyanopyridin-2-yl)oxy)methyl)-4-((1R,3aS,5aR,5bR,7aR,11aS,11bR,13aR,13bR)-3a-((2-((br,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate.

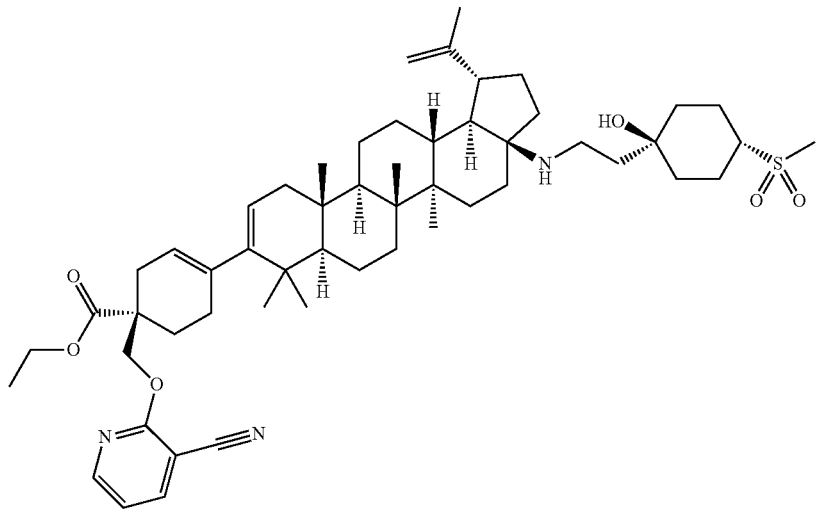

(S)-Ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (150 mg, 0.216 mmol) and 2-((1r,4r)-1-hydroxy-4-(methylsulfonyl)cyclohexyl)acetaldehyde (76 mg, 0.346 mmol) were dissolved in MeOH (1.6 mL) and acetic acid (0.32 mL). Borane-2-picoline complex (37.0 mg, 0.346 mmol) was added and the mixture was stirred at room temperature for 16 h. The mixture was transferred to a separatory funnel containing saturated aqueous sodium bicarbonate solution (20 mL). The aqueous layer was extracted with ethyl acetate (5×20 mL). The combined organic layers were washed with brine (50 mL), dried over MgSO$_4$, filtered, and concentrated. The product was purified by column chromatography on silica gel (30% ethyl acetate with 5% methanol/70% hexanes→100% ethyl acetate with 5% methanol; 24 g column) to afford (S)-ethyl 1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylate (131 mg, 68% yield) as a white foam: $^1$H NMR (400 MHz, CHLOROFORM-d) δ 8.33 (dd, J=5.0, 2.0 Hz, 1H), 7.87 (dd, J=7.5, 2.0 Hz, 1H), 6.98 (dd, 5.1 Hz, 1H), 5.37 (br. s., 1H), 5.20 (d, J=4.5 Hz, 1H), 4.72 (d, J=1.8 Hz, 1H), 4.60 (s, 1H), 4.56 (s, 2H), 4.24-4.15 (m, 2H), 2.99-2.89 (m, 1H), 2.88 (s, 3H), 2.83-2.61 (m, 3H), 2.55 (td, J=10.8, 5.5 Hz, 1H), 2.31-1.02 (m, 37H), 1.69 (s, 3H), 1.27 (q, J=7.2 Hz, 3H), 1.06 (s, 3H), 0.98 (s, 6H), 0.92 (s, 3H), 0.87 (s, 3H);

LC/MS m/e 898.7 [(M+H)+, calcd for $C_{54}H_{79}N_3O_6S$ 898.6], $t_R$=4.44 min (LCMS Method 14).

Step 2. To a solution of (S)-ethyl 1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylate (131 mg, 0.146 mmol) in dioxane (4 mL) and MeOH (2 mL) was added lithium hydroxide (2 mL, 2.00 mmol, 1 M aq). The mixture was heated at 60° C. for 10.5 h. Only a small amount of starting material was detected by LC/MS (LCMS Method 16). The reaction was stopped at this point. The mixture was cooled to room temperature and was partially neutralized by the addition of 6 N HCl (250 µL). The mixture was then filtered through a syringe filter, and was purified by reverse phase HPLC (5 injections) (Preparative HPLC Method 4). The organic solvent was evaporated on the rotovapor and the aqueous mixture was lyophilized to afford (S)-1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (69 mg, 48% yield) as a white amorphous solid: $^1$H NMR (400 MHz, Acetic Acid-$d_4$) δ 8.43 (dd, J=5.0, 2.0 Hz, 1H), 8.06 (dd, J=7.5, 2.0 Hz, 1H), 7.12 (dd, J=7.5, 5.3 Hz, 1H), 5.44 (br. s., 1H), 5.27 (d, J=4.8 Hz, 1H), 4.83 (s, 1H), 4.73 (s, 1H), 4.69-4.61 (m, 2H), 3.43-3.29 (m, 2H), 3.20-3.10 (m, 1H), 2.99 (s, 3H), 2.91-2.81 (m, J=9.0 Hz, 1H), 2.74 (d, J=17.6 Hz, 1H), 2.40-1.33 (m, 37H), 1.76 (s, 3H), 1.15 (s, 3H), 1.10 (s, 3H), 1.04 (s, 3H), 1.00 (s, 3H), 0.95 (s, 3H); LC/MS (ESI) m/e 870.7 [(M+H)$^+$, calcd for $C_{52}H_{75}N_3O_6S$ 870.5], $t_R$=2.37 min (LCMS Method 15); HPLC (Analytical HPLC Method 3): $t_R$=16.00 min; HPLC (Analytical HPLC Method 4): $t_R$=13.90 min.

Example A5

Preparation of (R)-1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid.

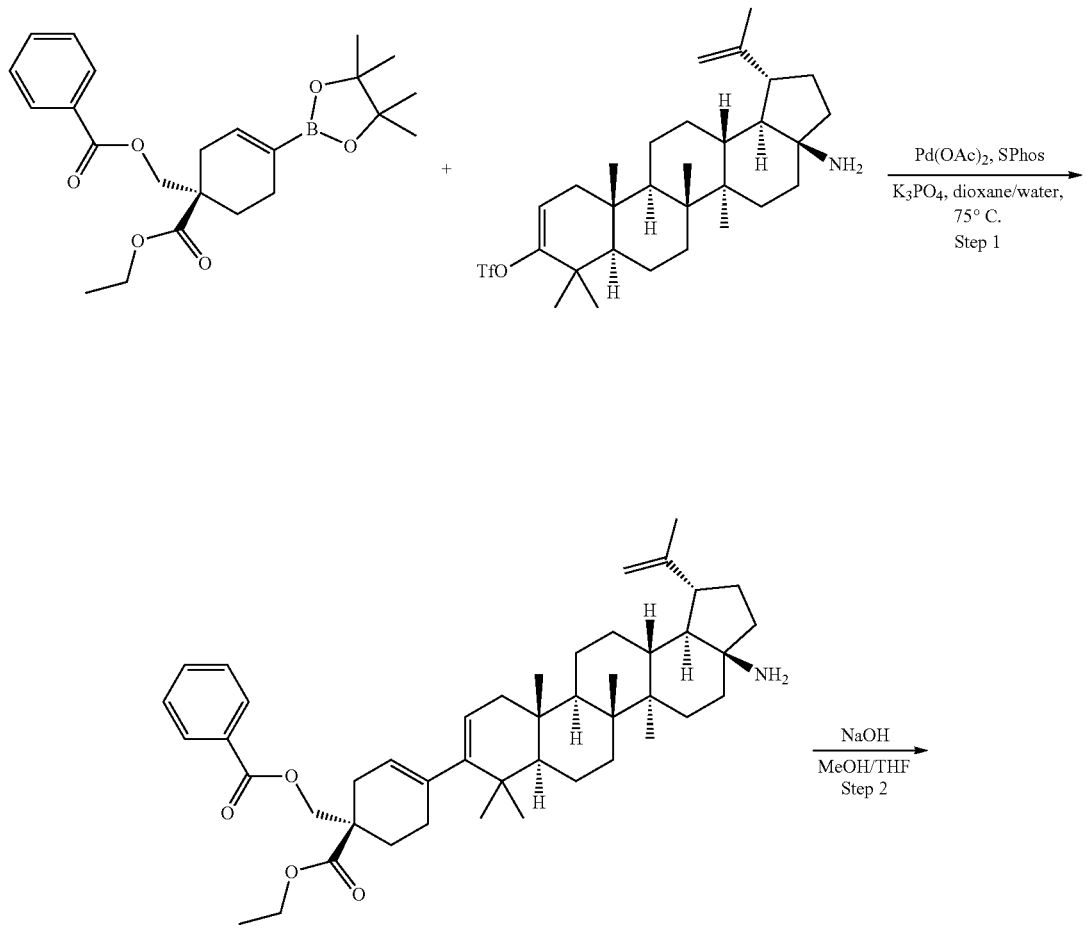

-continued
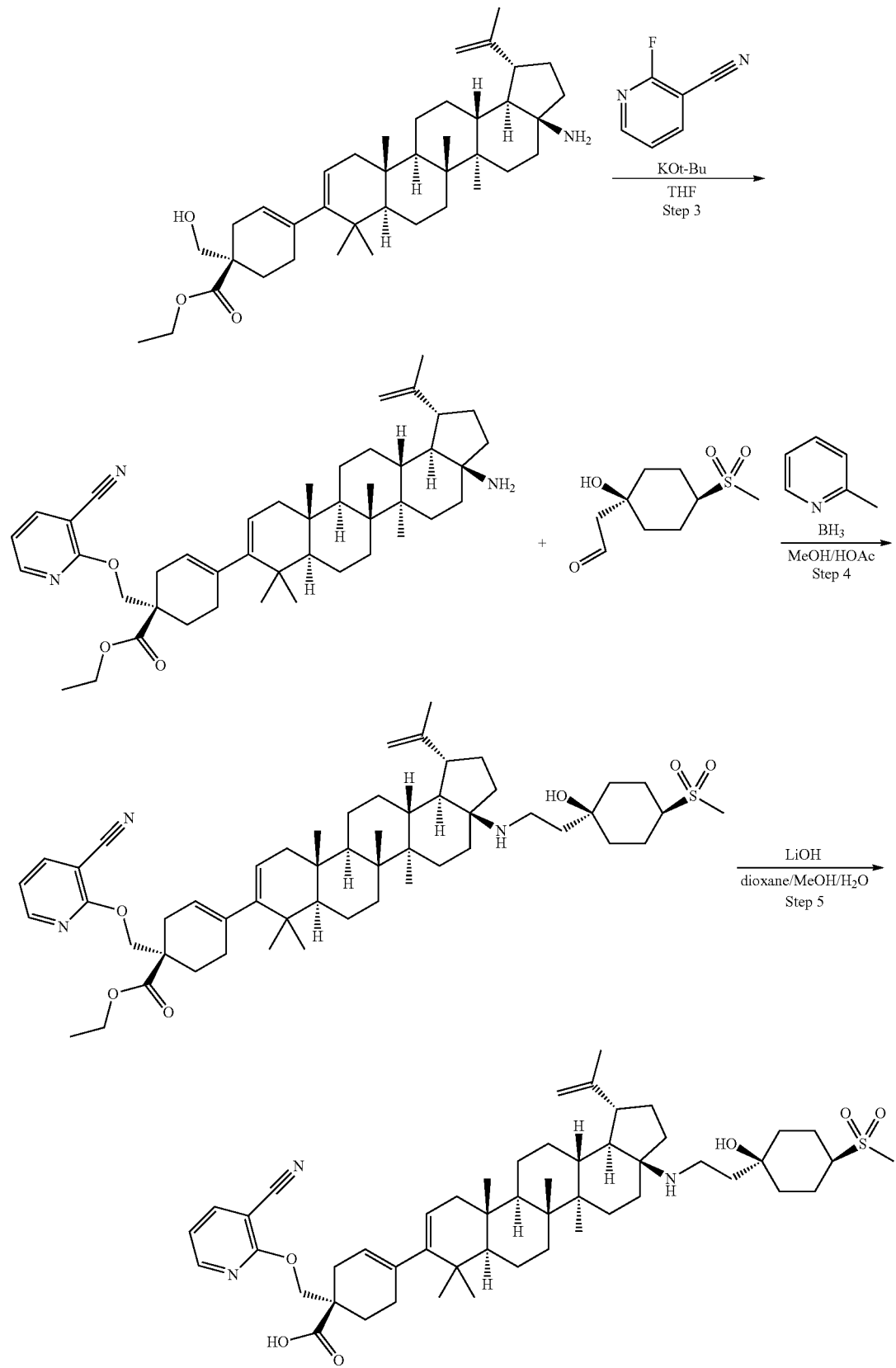
Example A5

Step 1. Preparation of ((R)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate.

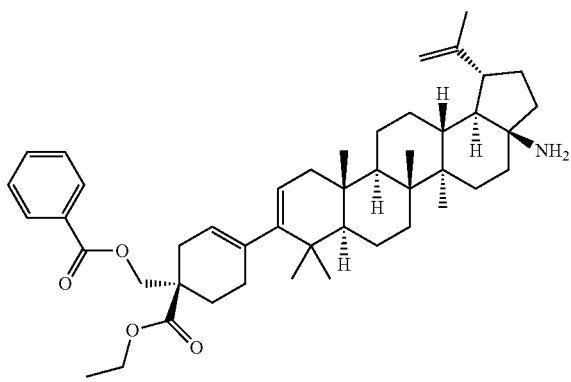

To a flask containing (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (2.2 g, 3.94 mmol) was added (S)-(1-(ethoxycarbonyl)-4-(4,4,5,5-tetramethyl-1,3,2-dioxab orolan-2-yl)cyclohex-3-en-1-yl)methyl benzoate (2.94 g, 7.10 mmol), potassium phosphate tribasic (3.35 g, 15.78 mmol), 2-dicyclohexylphosphino-2',6'-dimethoxybiphenyl (S-Phos) (0.121 g, 0.296 mmol) and palladium(II) acetate (0.044 g, 0.197 mmol). The mixture was diluted with 1,4-dioxane (60 mL) and water (15 mL) and was flushed with $N_2$ and heated at 75° C. for 16 h. The mixture was cooled to rt. The mixture was diluted with water (150 mL) and extracted with ethyl acetate (3×100 mL). The organic layers were washed with brine (200 mL), dried over magnesium sulfate, filtered, and concentrated under reduced pressure. The residue was purified by column chromatography on silica gel The residue was purified by column chromatography on silica gel (50% ethyl acetate with 4% MeOH and 0.8% ammonium hydroxide/50% hexanes→70% ethyl acetate with 4% MeOH and 0.8% ammonium hydroxide/30% hexanes, 220 g column) to afford ((R)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (2.47 g, 90% yield) as an off-white solid: $^1$H NMR (400 MHz, CHLOROFORM-d) δ 8.05-8.00 (m, 2H), 7.61-7.55 (m, 1H), 7.45 (t, J=7.7 Hz, 2H), 5.38 (br. s., 1H), 5.25-5.19 (m, 1H), 4.75 (s, 1H), 4.62 (s, 1H), 4.46 (q, J=10.8 Hz, 2H), 4.19 (q, J=7.0 Hz, 2H), 2.74-2.66 (m, 1H), 2.56 (td, J=10.9, 5.1 Hz, 1H), 2.29-1.96 (m, 6H), 1.87 (dt, J=12.9, 6.2 Hz, 1H), 1.78-1.11 (m, 20H), 1.71 (s, 3H), 1.24 (t, J=7.3 Hz, 3H), 1.09 (s, 3H), 0.98 (br. s., 3H), 0.97 (br. s., 3H), 0.95 (s, 3H), 0.89 (s, 3H); LC/MS m/e 696.7 [(M+H)$^+$, calcd for $C_{46}H_{65}NO_4$ 696.5], $t_R$=2.55 min (LCMS Method 15).

Step 2. Preparation of (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate.

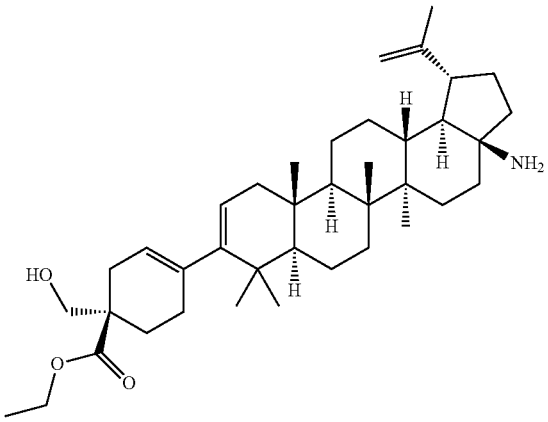

To a solution of ((R)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (1.20 g, 1.724 mmol in THF (10 mL) and MeOH (1 mL) was added sodium hydroxide (1.897 mL, 1.897 mmol). The reaction mixture was stirred at r.t. for 14 h. The solid was removed by filtration. The mixture was transferred to a separatory funnel containing saturated aqueous $NaHCO_3$ solution (10 mL)/water (10 mL). The aqueous layer was extracted with 5% methanol in ethyl acetate (5×25 mL). The combined organic layers were washed with brine (10 mL). The brine wash was reextracted with 5% methanol in ethyl acetate. The combined organic layers were dried over $MgSO_4$, filtered, and concentrated to afford (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate (450 mg, 44% yield) as a white solid. The crude product was used directly in the next step. $^1$H NMR (400 MHz, CHLOROFORM-d) δ 5.34 (br. s., 1H), 5.20 (dd, J=6.0, 1.8 Hz, 1H), 4.75 (d, J=2.0 Hz, 1H), 4.62 (s, 1H), 4.20 (q, J=7.2 Hz, 2H), 3.70 (s, 2H), 2.62-2.51 (m, 2H), 2.21-2.14 (m, 2H), 2.10-1.94 (m, 4H), 1.82-1.12 (m, 21H), 1.71 (s, 3H), 1.29 (t, J=7.2 Hz, 3H), 1.09 (s, 3H), 0.98 (s, 3H), 0.97 (s, 3H), 0.95 (s, 3H), 0.89 (s, 3H); LC/MS (ESI) m/e 614.6 [(M+H)$^+$, calcd for $C_{39}H_{61}NO_3Na$ 614.5], $t_R$=4.27 min (LCMS Method 14).

Step 3. Preparation of (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate.

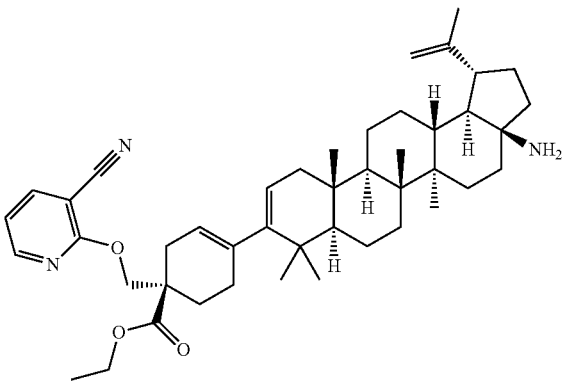

To a solution of (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate (412 mg, 0.696 mmol) and 2-fluoronicotinonitrile (170 mg, 1.392 mmol) in THF (7 mL) and DMF (1 mL) at 0° C. was added potassium tert-butoxide (0.835 mL, 0.835 mmol). The cooling bath was removed and the reaction mixture was stirred at 20° C. for 1.5 h. The mixture was transferred to a separatory funnel containing saturated aqueous NaHCO$_3$ solution (15 mL). The aqueous layer was extracted with ethyl acetate (4×25 mL). The combined organic layers were washed with brine (15 mL), dried over MgSO$_4$, filtered, and concentrated. The product was purified by column chromatography on silica gel (50% of a 5% methanol in ethyl acetate solution/50% hexanes→100% of a 5% methanol in ethyl acetate solution; 40 g column) to afford (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (365 mg, 0.526 mmol, 76% yield) as an off-white solid: $^1$H NMR (400 MHz, CHLOROFORM-d) δ 8.34 (dd, J=5.0, 2.0 Hz, 1H), 7.88 (dd, J=7.4, 1.9 Hz, 1H), 6.99 (dd, J=7.5, 5.0 Hz, 1H), 5.38 (br. s., 1H), 5.21 (dd, J=6.3, 1.8 Hz, 1H), 4.74 (d, J=2.0 Hz, 1H), 4.62 (dd, J=2.1, 1.4 Hz, 1H), 4.60-4.52 (m, 2H), 4.19 (qd, J=7.1, 2.5 Hz, 2H), 2.73 (d, J=17.1 Hz, 1H), 2.56 (td, J=10.9, 5.4 Hz, 1H), 1.78-1.13 (m, 21H), 2.27-1.87 (m, 6H), 1.71 (s, 3H), 1.26 (t, J=6.8 Hz, 3H), 1.09 (s, 3H), 0.98 (s, 3H), 0.97 (s, 3H), 0.94 (s, 3H), 0.88 (s, 3H); LC/MS (ESI) m/e 694.7 [(M+H)$^+$, calcd for C$_{45}$H$_{64}$N$_3$O$_3$ 694.5], t$_R$=4.51 min (LCMS Method 14).

Step 4. Preparation of (R)-ethyl 1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate.

sulfonyl)cyclohexyl)acetaldehyde (76 mg, 0.346 mmol) were dissolved in MeOH (1.4 mL) and acetic acid (0.28 mL). Borane-2-picoline complex (37.0 mg, 0.346 mmol) was added and the mixture was stirred at room temperature for 14 h. The mixture was transferred to a separatory funnel containing saturated aqueous sodium bicarbonate solution (3 mL) and sodium carbonate solution (2 mL). The aqueous layer was extracted with ethyl acetate (5×10 mL). The combined organic layers were washed with brine (5 mL), dried over MgSO$_4$, filtered, and concentrated. The product was purified by column chromatography on silica gel (30% ethyl acetate with 5% methanol/70% hexanes→100% ethyl acetate with 5% methanol; 24 g column, 25 min gradient) to afford (R)-ethyl 1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (130 mg, 67% yield) as a white foam: $^1$H NMR (500 MHz, CHLOROFORM-d) δ 8.34 (dd, J=5.0, 2.0 Hz, 1H), 7.88 (dd, J=7.5, 2.0 Hz, 1H), 6.99 (dd, J=7.5, 5.0 Hz, 1H), 5.38 (br. s., 1H), 5.23-5.19 (m, 1H), 4.75 (d, J=1.7 Hz, 1H), 4.62 (s, 1H), 4.59-4.52 (m, 2H), 4.19 (dtt, J=10.8, 7.2, 3.8 Hz, 2H), 2.85 (s, 3H), 2.83-2.70 (m, 4H), 2.55 (td, J=10.9, 5.6 Hz, 1H), 2.28-0.89 (m, 37H), 1.70 (s, 3H), 1.26 (t, J=7.1 Hz, 3H), 1.06 (s, 3H), 0.98 (s, 3H), 0.96 (s, 3H), 0.95 (s, 3H), 0.87 (s, 3H); LC/MS (ESI) m/e 898.7 [(M+H)$^-$, calcd for C$_{54}$H$_{80}$N$_3$O$_6$S 898.6], t$_R$=4.43 min (LCMS Method 14).

Step 5. To a solution of (R)-ethyl 1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (124 mg, 0.138 mmol) in dioxane (4 mL) and MeOH (2 mL) was added lithium hydroxide (2 mL, 2.00 mmol, 1 M aq). The mixture was heated at 60° C. for 10 h. Some starting material starting was detected by LC/MS (LCMS Method 16) along with forma-

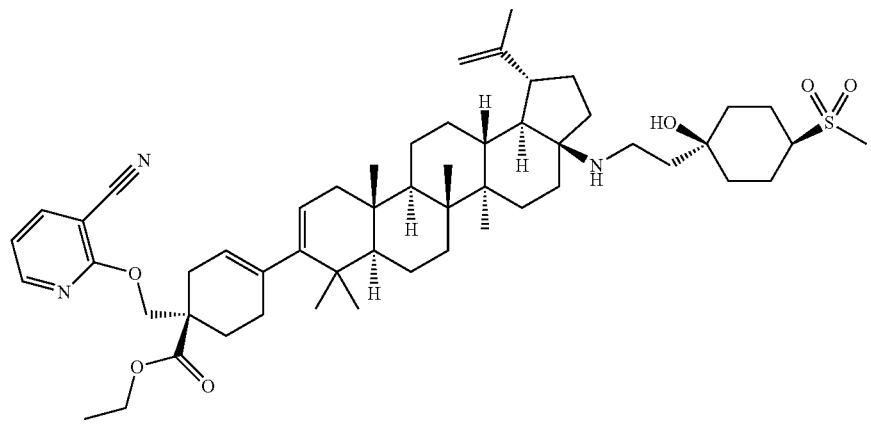

(R)-Ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (150 mg, 0.216 mmol) and 2-((1s,4s)-1-hydroxy-4-(methyltion of an amide by-product due to hydrolysis of the nitrile. The reaction was stopped at this point. The mixture was cooled to room temperature and was partially neutralized by the addition of 6 N HCl (250 μL). The mixture was then filtered through a syringe filter, and was purified by reverse phase HPLC (5 injections) (Preparative HPLC Method 4).

The organic solvent was evaporated on the rotovapor and the aqueous mixture was lyophilized to afford (R)-1-(((3-cyanopyridin-2-yl)oxy)methyl)-4-((1R,3aS,5aR,5bR,7aR,11aS,11bR,13aR,13bR)-3a-((2-((1s,4R)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (48.1 mg, 34% yield) as a white amorphous solid: $^1$H NMR (500 MHz, Acetic Acid-$d_4$) δ 8.42 (dd, J=5.1, 1.9 Hz, 1H), 8.05 (dd, J=7.6, 1.9 Hz, 1H), 7.11 (dd, J=7.5, 5.2 Hz, 1H), 5.43 (br. s., 1H), 5.27 (d, J=4.6 Hz, 1H), 4.83 (s, 1H), 4.72 (s, 1H), 4.68-4.59 (m, 2H), 3.46-3.33 (m, 2H), 3.09-2.99 (m, 1H), 2.96 (s, 3H), 2.89-2.81 (m, 1H), 2.74 (d, J=16.5 Hz, 1H), 2.34-1.13 (m, 37H), 1.75 (s, 3H), 1.17 (s, 3H), 1.09 (s, 3H), 1.02 (s, 3H), 1.00 (s, 3H), 0.95 (s, 3H); LC/MS (ESI) m/e 870.7 [(M+H)$^+$, calcd for $C_{52}H_{76}N_3O_6S$ 870.5], $t_R$=1.24 min (LCMS Method 16); HPLC (Analytical HPLC Method 3): $t_R$=12.24 min; HPLC (Analytical HPLC Method 4): $t_R$=11.77 min.

Example A6

Preparation of (R)-1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid.

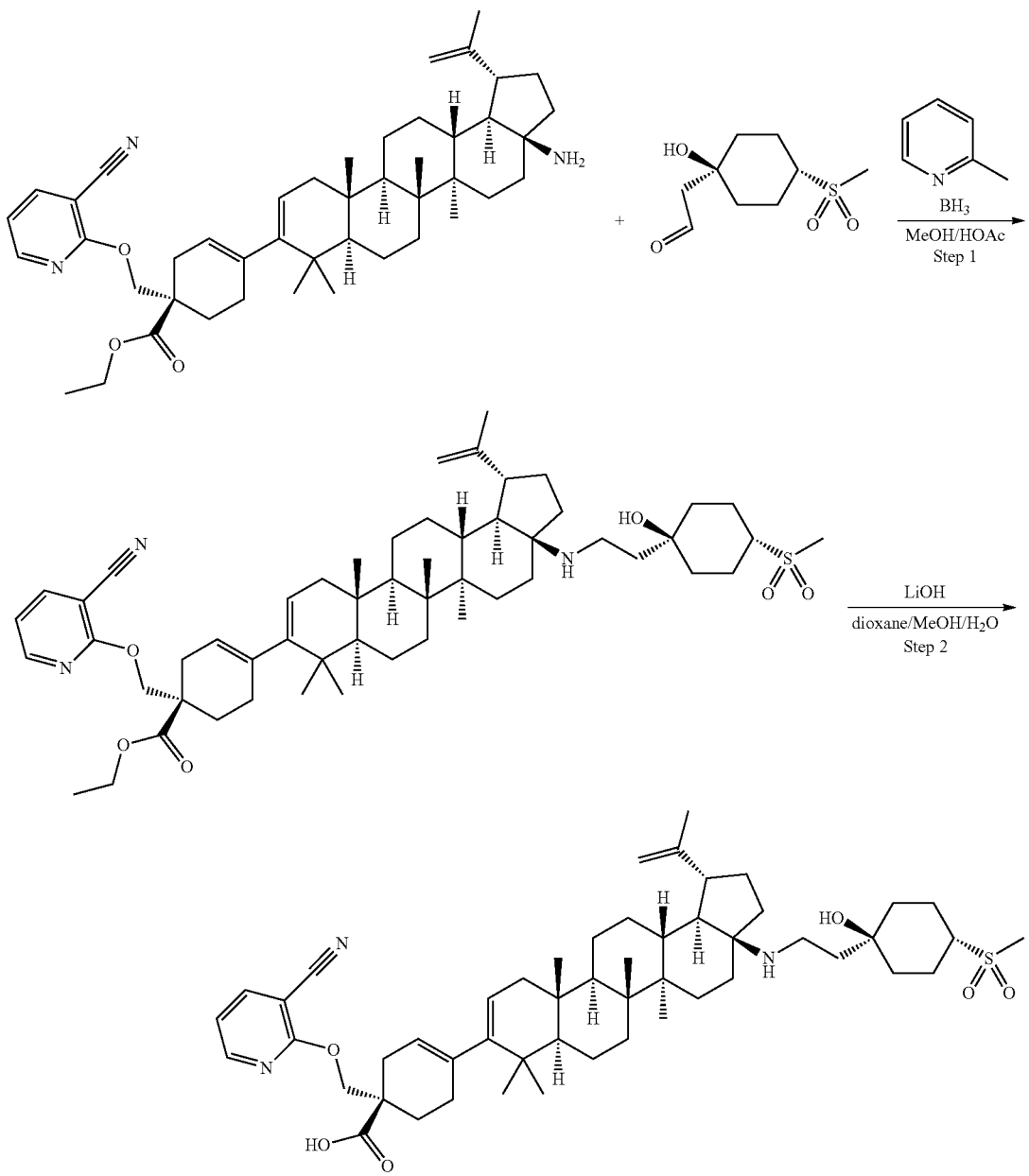

Example A6

Step 1. Preparation of (R)-ethyl 1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate.

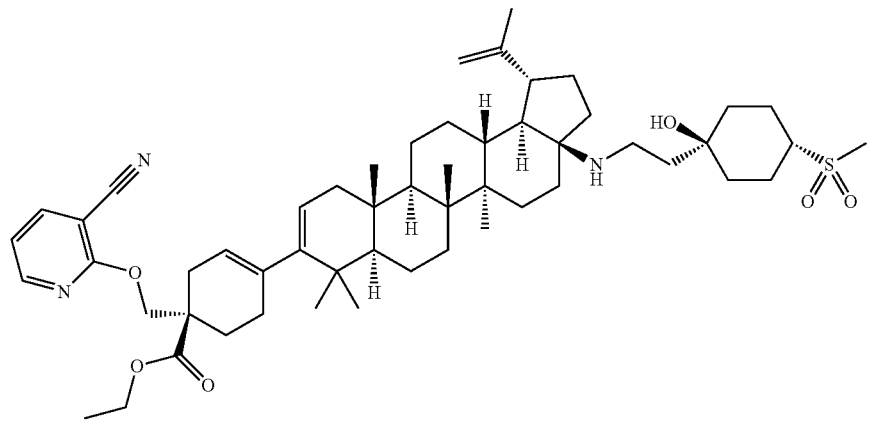

(R)-Ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (150 mg, 0.216 mmol) and 2-((1br,4r)-1-hydroxy-4-(methylsulfonyl)cyclohexyl)acetaldehyde (76 mg, 0.346 mmol) were dissolved in MeOH (1.6 mL) and acetic acid (0.32 mL). Borane-2-picoline complex (37.0 mg, 0.346 mmol) was added and the mixture was stirred at room temperature for 14 h. The mixture was transferred to a separatory funnel containing saturated aqueous sodium bicarbonate solution (20 mL). The aqueous layer was extracted with ethyl acetate (5×20 mL). The combined organic layers were washed with brine (50 mL), dried over MgSO$_4$, filtered, and concentrated. The product was purified by column chromatography on silica gel (30% ethyl acetate with 5% methanol/70% hexanes→100% ethyl acetate with 5% methanol; 24 g column) to afford (R)-ethyl 1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (131 mg, 68% yield) as a white foam: $^1$HNMR (400 MHz, CHLOROFORM-d) δ 8.33 (dd, J=5.1, 1.9 Hz, 1H), 7.87 (dd, J=7.4, 1.9 Hz, 1H), 6.98 (dd, J=7.4, 5.1 Hz, 1H), 5.37 (br. s., 1H), 5.22-5.17 (m, 1H), 4.71 (d, J=1.8 Hz, 1H), 4.61-4.51 (m, 3H), 4.23-4.14 (m, 2H), 2.99-2.90 (m, 1H), 2.87 (s, 3H), 2.82-2.61 (m, 3H), 2.54 (td, J=10.8, 5.5 Hz, 1H), 2.23-1.02 (m, 37H), 1.68 (s, 3H), 1.26 (q, J=7.3 Hz, 3H), 1.06 (s, 3H), 0.97 (s, 3H), 0.95 (s, 3H), 0.93 (s, 3H), 0.86 (s, 3H); LC/MS mle 898.7 [(M+H)$^+$, calcd for C$_{54}$H$_{79}$N$_3$O$_6$S 898.6], t$_R$=4.43 min (LCMS Method 14).

Step 2. To a solution of (R)-ethyl 1-(((3-cyanopyridin-2-yl)oxy)methyl)-4-((1R,3aS,5aR,5bR,7aR,11aS,11bR,13aR,13bR)-3a-((2-((br,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylate (107 mg, 0.119 mmol) in dioxane (4 mL) and MeOH (2 mL) was added lithium hydroxide (2 mL, 2.00 mmol, 1 M aq). The mixture was heated at 60° C. for 10.5 h. Only a small amount of starting material was detected by LC/MS (LCMS Method 16). The reaction was stopped at this point. The mixture was cooled to room temperature and was partially neutralized by the addition of 6 N HCl (250 µL). The mixture was then filtered through a syringe filter, and was purified by reverse phase HPLC (5 injections) (Preparative HPLC Method 4). The organic solvent was evaporated on the rotovapor and the aqueous mixture was lyophilized to afford (R)-1-(((3-cyanopyridin-2-yl)oxy)methyl)-4-((1R,3aS,5aR,5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (58 mg, 49% yield) as a white amorphous solid: $^1$H NMR (400 MHz, Acetic Acid-d$_4$) δ 8.43 (dd, J=5.1, 1.9 Hz, 1H), 8.06 (dd, J=7.5, 1.8 Hz, 1H), 7.12 (dd, J=7.5, 5.0 Hz, 1H), 5.44 (br. s., 1H), 5.27 (d, J=4.8 Hz, 1H), 4.83 (s, 1H), 4.73 (s, 1H), 4.69-4.60 (m, 2H), 3.43-3.29 (m, 2H), 3.20-3.09 (m, 1H), 2.99 (s, 3H), 2.91-2.81 (m, 1H), 2.75 (d, J=15.3 Hz, 1H), 2.32-1.33 (m, 37H), 1.76 (s, 3H), 1.15 (s, 3H), 1.10 (s, 3H), 1.03 (s, 3H), 1.00 (s, 3H), 0.95 (s, 3H); LC/MS (ESI) m/e 870.6 [(M+H)$^+$, calcd for C$_{52}$H$_{75}$N$_3$O$_6$S 870.5], t$_R$=2.30 min (LCMS Method 15); HPLC (Analytical HPLC Method 3): t$_R$=14.96 min; HPLC (Analytical HPLC Method 4): t$_R$=14.64 min.

Example A7 and Example A8

Preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (Example A7) and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (Example A8).

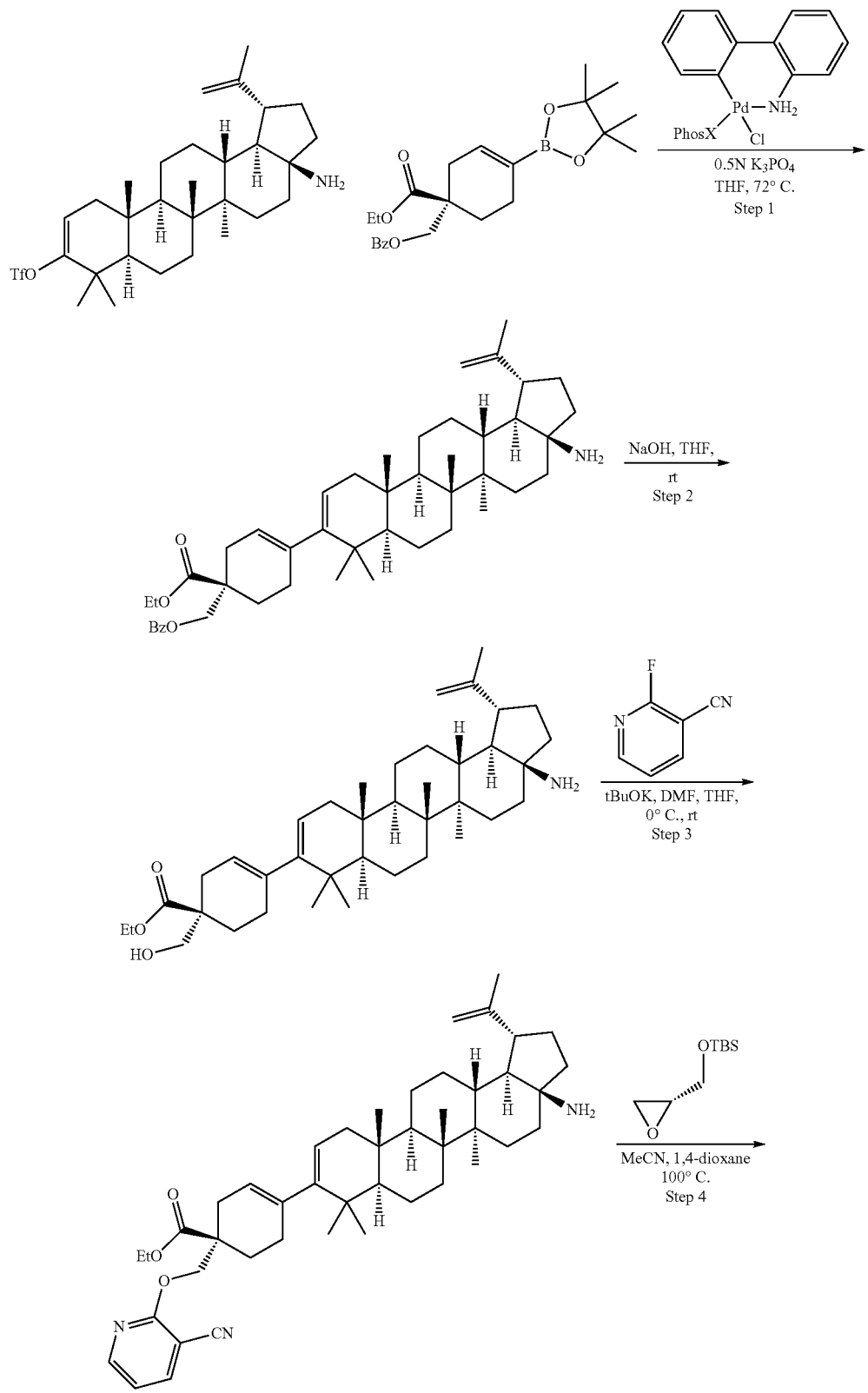

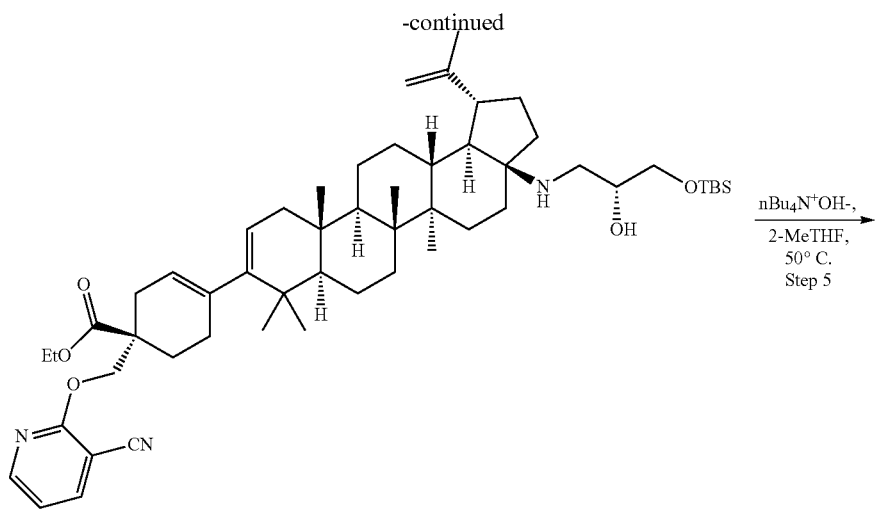
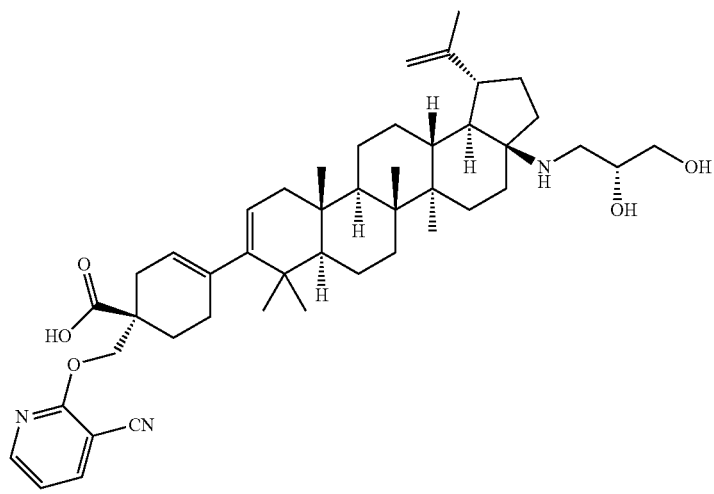
Example A7
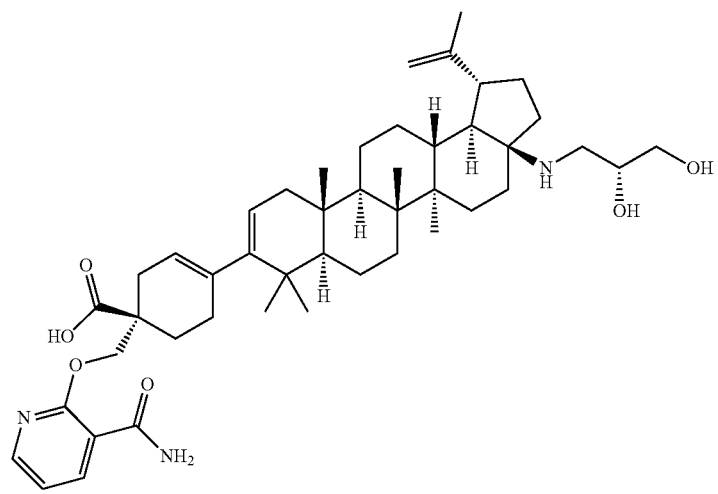
Example A8

Step 1. Preparation of ((R)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate.

Step 2. Preparation of (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate.

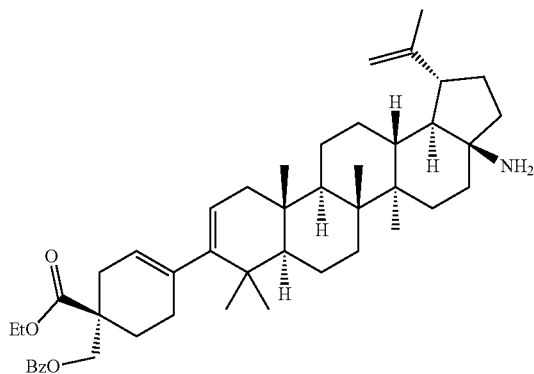

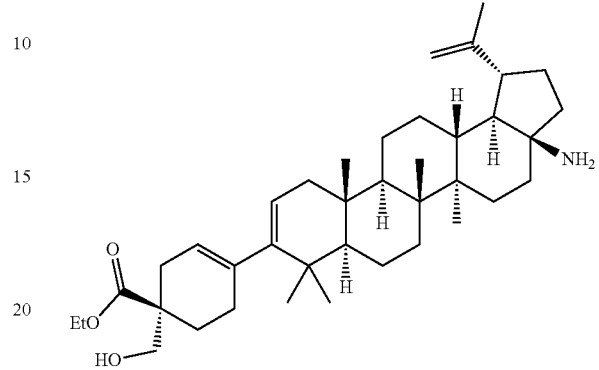

In a 150 mL medium pressure flask was combined (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl trifluoromethanesulfonate (1.5 g, 2.69 mmol), (R)-(1-(ethoxycarbonyl)-4-(4,4,5,5-tetramethyl-1,3,2-dioxab orolan-2-yl)cyclohex-3-en-1-yl)methyl benzoate (1.259 g, 3.04 mmol) and Buchwald pre-catalyst (0.127 g, 0.161 mmol) in THF (25 mL). To the reaction mixture was added a solution of aqueous 0.5 M $K_3PO_4$ (13.45 mL, 6.72 mmol). The resulting brown solution was sparged with $N_2(g)$, stirred at 72° C. overnight. After 16 h, the reaction was allowed to cool to rt, diluted with EtOAc (50 mL) and washed with 1.5M $K_3PO_4$ (50 mL). The aqueous layer was extracted with 2×50 mL EtOAc. The combined organic layer was washed with brine, dried over $MgSO_4$, filtered and concentrated to grey foam. Crude material was dissolved in DCM and loaded onto a silica gel column ($SiO_2$, 80 g Isco cartridge, eluted with 0% B to 50% B over 4 column volumes, and hold at 50% B until all product eluted, solvent A=DCM, solvent B=90:10 DCM:MeOH) and dried in vacuo to give ((R)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (1.8 g, 2.59 mmol, 96% yield) as brown solid. LCMS: m/z 696.6 (M+H$^+$), retention time 1.589 min (LCMS Method 16). $^1$H NMR (400 MHz, CHLOROFORM-d) δ 8.06-7.96 (m, 2H), 7.63-7.53 (m, 1H), 7.48-7.39 (m, 2H), 5.36 (br. s., 1H), 5.20 (dd, J=6.1, 1.7 Hz, 1H), 4.73 (d, J=2.0 Hz, 1H), 4.61 (s, 1H), 4.44 (q, J=10.8 Hz, 2H), 4.18 (qd, J=7.1, 1.0 Hz, 2H), 2.77-2.64 (m, 1H), 2.55 (td, J=10.9, 5.3 Hz, 1H), 2.26-2.13 (m, 3H), 2.08 (td, J=12.7, 5.7 Hz, 2H), 2.00 (dd, J=17.0, 6.5 Hz, 1H), 1.85 (dt, J=13.1, 6.4 Hz, 1H), 1.78-1.71 (m, 2H), 1.70 (s, 3H), 1.67-1.56 (m, 6H), 1.55-1.49 (m, 4H), 1.48-1.38 (m, 6H), 1.37-1.26 (m, 3H), 1.24-1.19 (m, 3H), 1.08 (s, 3H), 0.97 (s, 3H), 0.96 (br. s., 3H), 0.94 (s, 3H), 0.87 (s, 3H).

To a solution of ((R)-4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate (0.692 g, 0.994 mmol) in THF (10 mL) and MeOH (1 mL) was added sodium hydroxide (0.994 mL, 0.994 mmol) and the resulting mixture was stirred at rt. After 3 h, the reaction was concentrated to dryness and the material was dissolved in DCM:MeOH and purified by flash column chromatography ($SiO_2$, 40 g Isco cartridge, eluted with 95:5 DCM:MeOH) and dried in vacuo to give (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate (427 mg, 0.721 mmol, 72.6% yield) as light yellow solid. LCMS: m/z 592.5 (M+H$^+$), retention time 1.705 min (LCMS Method 16). $^1$H NMR (400 MHz, 1:1 CDCl$_3$:METHANOL-d$_4$) δ 5.30 (br. s., 1H), 5.14 (d, J=4.6 Hz, 1H), 4.72 (br. s., 1H), 4.60 (br. s., 1H), 4.22-4.00 (m, 2H), 3.74-3.53 (m, 2H), 2.60-2.42 (m, 2H), 2.13 (br. s., 2H), 2.06-1.87 (m, 4H), 1.78-1.70 (m, 1H), 1.67 (br. s., 5H), 1.63-1.51 (m, 6H), 1.43 (br. s., 7H), 1.32 (br. s., 1H), 1.24 (t, J=7.0 Hz, 4H), 1.06 (br. s., 4H), 0.97 (br. s., 3H), 0.92 (br. s., 3H), 0.90 (br. s., 3H), 0.85 (br. s., 3H).

Step 3. Preparation of (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate.

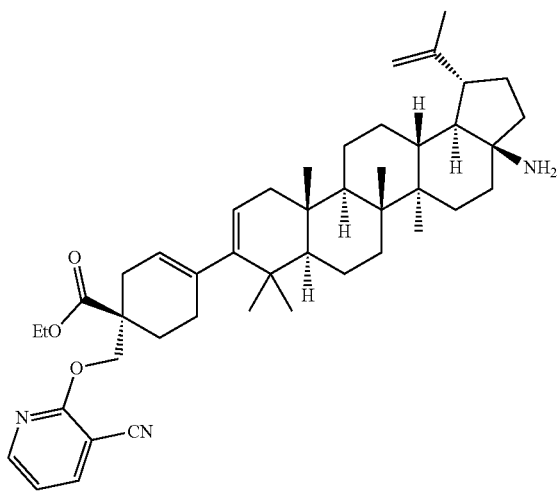

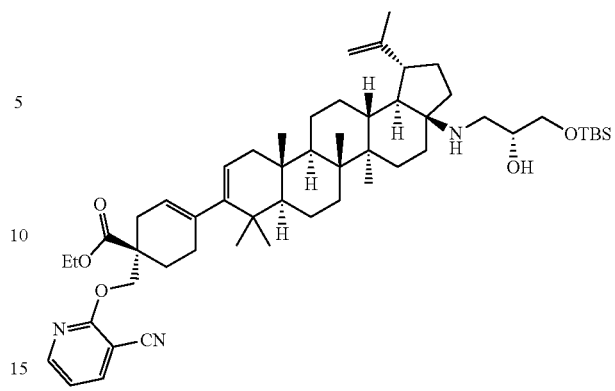

(R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(hydroxymethyl)cyclohex-3-enecarboxylate (420 mg, 0.710 mmol) and 3-cyano-2-fluoropyridine (130 mg, 1.064 mmol) were combined in DMF (3 mL) and THF (3 mL) chilled to 0° C. To the yellow slurry was treated with a solution of potassium tert-butoxide (0.781 mL, 0.781 mmol) in THF. The reaction became almost totally homogeneous; the cold bath was removed and the reaction was stirred to rt. After 3.5 h, there was still a small amount of starting material left; thus to the reaction was added more 3-cyano-2-fluoropyridine (43.3 mg, 0.355 mmol) and potassium tert-butoxide (0.142 mL, 0.142 mmol) and stirred at RT for an additional 1 h. The reaction was diluted with EtOAc and washed with 0.5N HCl 25 mL. The aqueous layer was extracted with 2×50 mL EtOAc. The combined organic layer was washed with saturated NaHCO$_3$, brine, dried over MgSO$_4$, filtered and concentrated to brown paste. Crude material was purified by flash column chromatography (SiO$_2$, 40 g Isco cartridge, eluted with 95:5 DCM:MeOH) and dried under vacuo to give (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (426 mg, 0.614 mmol, 87% yield) as light brown solid. LCMS: m/z 694.9 (M+H$^+$), retention time 1.517 min (LCMS Method 16).

Step 4. Preparation of (R)-ethyl 4-((1R,3aS,5aR,5bR,7aR,11aS,11bR,13aR,13bR)-3a-(((R)-3-((tert-butyldimethylsilyl)oxy)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate, TFA.

To a solution of (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate (48.5 mg, 0.070 mmol) in acetonitrile (0.5 mL) and 1,4-dioxane (0.5 mL) was added tert-butyldimethylsilyl (R)-(−)-glycidyl ether (0.094 mL, 0.489 mmol) and the mixture was stirred at 100° C. overnight. After 19 h, the reaction was allowed to cool to RT and was purified by reverse phase preparative HPLC using preparative HPLC method 8 and dried under vacuo to give (R)-ethyl 4-((1R,3aS,5aR,5bR,7aR,11aS,11bR,13aR,13bR)-3a-(((R)-3-((tert-butyldimethylsilyl)oxy)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate, TFA (22.8 mg, 0.023 mmol, 32.7% yield, 53.5% yield based on recovered starting material) and recovered starting material (21.9 mg), both as clear glass solid. LCMS: m/z 882.4 (M+H$^+$), retention time 1.849 min (LCMS Method 16).

Step 5. To a solution of (R)-ethyl 4-((1R,3aS,5aR,5bR,7aR,11aS,11bR,13aR,13bR)-3a-(((R)-3-((tert-butyldimethylsilyl)oxy)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-(((3-cyanopyridin-2-yl)oxy)methyl)cyclohex-3-enecarboxylate, TFA (22.8 mg, 0.023 mmol) in 2-Me-THF (1 mL) and H$_2$O (0.3 mL) was added a solution of tetrabutylammonium hydroxide (0.105 mL, 0.160 mmol) and the mixture was stirred at RT for 4 h but LC/MS showed no reaction. The reaction was then stirred at 50° C. After 14 h, LC/MS showed approximately 60% of starting material remained; thus the mixture was stirred at 50° C. for another night. After 40 h, the reaction mixture was purified by reverse phase preparative HPLC using preparative HPLC method 8 and product fractions were dried in vacuo to give two products, both as glass solids.

Example A8 was the first of the two isolated products to elute from the preparative HPLC column: (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (4.0 mg, 4.36 µmol, 19.04% yield). LCMS: m/z 758.7 (M+H$^{3o}$), retention time 1.219 min (LCMS Method 16). $^1$H NMR (400 MHz, 1:1 CDCl$_3$: METHANOL-d$_4$) δ 8.47-8.36 (m, 1H), 8.25 (d, J=3.2 Hz, 1H), 7.08 (dd, J=7.6, 4.9 Hz, 1H), 5.34 (br. s., 1H), 5.19 (d, J=4.9 Hz, 1H), 4.79 (s, 1H), 4.71 (br. s., 1H), 4.06-3.90 (m, 1H), 3.66 (d, J=4.2 Hz, 2H), 3.23-3.11 (m, 1H), 3.03-2.92 (m, 1H), 2.80-2.61 (m, 2H), 2.48-1.90 (m, 10H), 1.84 (d, J=6.6 Hz, 1H), 1.71 (s, 4H), 1.69-1.21 (m, 15H), 1.15 (d, J=12.7 Hz, 1H), 1.08 (s, 3H), 1.05 (s, 3H), 0.96 (s, 3H), 0.92 (s, 3H), 0.86 (s, 3H).

Example A7 was the second of the two isolated products to elute from the preparative HPLC column: (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (6.5 mg, 7.46 μmol, 32.6% yield). LCMS: m/z 740.6 (M+H$^+$), retention time 1.289 min (LCMS Method 16). $^1$H NMR (400 MHz, 1:1 CDCl$_3$: METHANOL-d$_4$) δ 8.33 (dd, J=5.0, 1.8 Hz, 1H), 7.94 (dd, J=7.6, 1.7 Hz, 1H), 7.03 (dd, J=7.6, 5.1 Hz, 1H), 5.34 (br. s., 1H), 5.18 (d, J=4.9 Hz, 1H), 4.79 (s, 1H), 4.71 (s, 1H), 3.99 (dd, J=8.6, 3.9 Hz, 1H), 3.66 (d, J=4.2 Hz, 2H), 3.18 (dd, J=12.1, 3.5 Hz, 1H), 2.98 (dd, J=11.9, 8.9 Hz, 1H), 2.78-2.56 (m, 2H), 2.35-2.08 (m, 4H), 2.08-1.87 (m, 6H), 1.75 (br. s., 1H), 1.72 (s, 3H), 1.70-1.53 (m, 6H), 1.51-1.22 (m, 8H), 1.21-1.12 (m, 1H), 1.08 (s, 3H), 1.05 (s, 3H), 0.96 (s, 3H), 0.91 (s, 3H), 0.86 (s, 3H).

Example A9 and Example A10

Preparation of (R)-1-(((3-cyanopyridin-2-yl)oxy)methyl)-4-((1R,3aS,5aR,5bR,7aR,11aS,11bR,13aR,13bR)-3a-(((R)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (Example A9) and (R)-1-(((3-carbamoylpyridin-2-yl)oxy)methyl)-4-((1R,3aS,5aR,5bR,7aR,11aS,11bR,13aR,13bR)-3a-(((R)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (Example A10).

Example A9

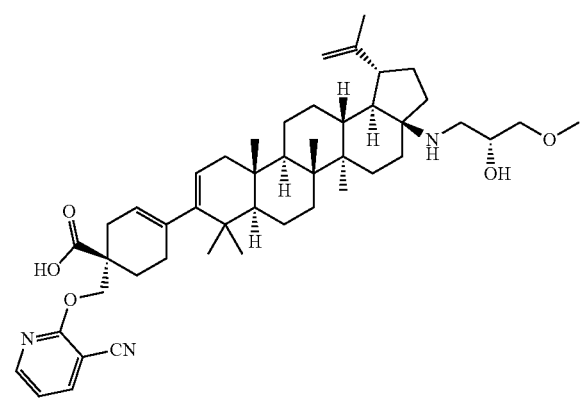

Example A10

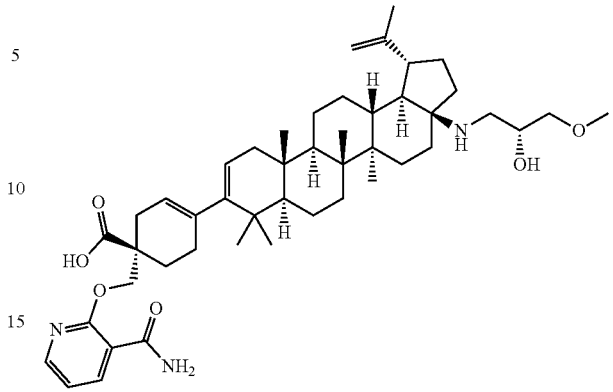

The title compounds were prepared in 7.1% and 16.1% yield, respectively, from (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-(((3-cyanopyridin-2-yl)oxy)methyl)cyclohex-3-enecarboxylate following the same procedure as described for the preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, except (R)-(−)-methyl glycidyl ether was used instead of tert-butyldimethylsilyl (R)-(−)-glycidyl ether in Step 4.

Example A10 was the first of the two isolated products to elute from the preparative HPLC column: (R)-1-(((3-carbamoylpyridin-2-yl)oxy)methyl)-4-((1R,3aS,5aR,5bR,7aR,11aS,11bR,13aR,13bR)-3a-(((R)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (5.6 mg, 7.25 μmol, 16.13% yield). LCMS: m/e 772.6 (M+H$^+$), 1.284 min (LCMS Method 16).

Example A9 was the second of the two isolated products to elute from the preparative HPLC column: (R)-1-(((3-cyanopyridin-2-yl)oxy)methyl)-4-((1R,3aS,5aR,5bR,7aR,11aS,11bR,13aR,13bR)-3a-(((R)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (2.9 mg, 3.17 μmol, 7.06% yield). LCMS: m/z 754.6 (M+H$^+$), retention time 1.345 min (LCMS Method 16). $^1$H NMR (400 MHz, 1:1 CDCl$_3$: METHANOL-d$_4$) δ 8.33 (dd, J=5.0, 1.8 Hz, 1H), 7.94 (dd, J=7.5, 1.8 Hz, 1H), 7.03 (dd, 5.0 Hz, 1H), 5.34 (br. s., 1H), 5.18 (d, J=4.4 Hz, 1H), 4.79 (s, 1H), 4.71 (s, 1H), 4.07 (dd, J=9.9, 4.0 Hz, 1H), 3.54-3.44 (m, 2H), 3.39 (s, 3H), 3.15 (dd, J=11.9, 3.3 Hz, 1H), 2.93 (t, J=11.1 Hz, 1H), 2.75-2.59 (m, 2H), 2.31-2.08 (m, 4H), 2.07-1.89 (m, 6H), 1.79-1.73 (m, 1H), 1.71 (s, 3H), 1.67 (br. s., 1H), 1.65-1.57 (m, 3H), 1.56-1.39 (m, 6H), 1.37-1.22 (m, 4H), 1.21-1.13 (m, 1H), 1.08 (s, 3H), 1.05 (s, 3H), 0.96 (s, 3H), 0.91 (s, 3H), 0.86 (s, 3H).

Example A11 and Example A12

Preparation of (R)-1-(((3-cyanopyridin-2-yl)oxy)methyl)-4-((1R,3aS,5aR,5bR,7aR,11aS,11bR,13aR,13bR)-3a-(((S)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (Example A11) and (R)-1-(((3-carbamoylpyridin-2-yl)oxy)methyl)-4-((1R,3aS,5aR,5bR,7aR,11aS,11bR,13aR,13bR)-3a-(((S)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (Example A12).

Example A11

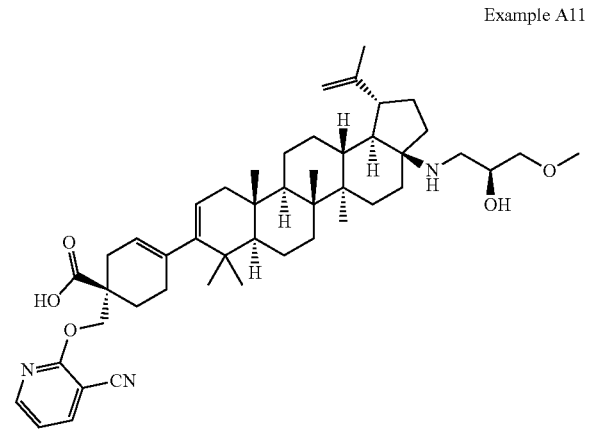

Example A12

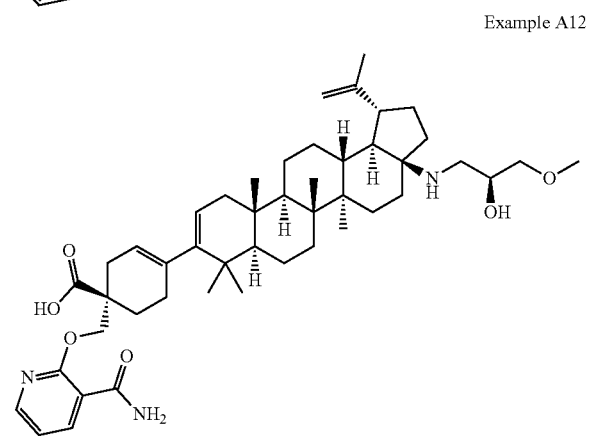

The title compounds were prepared in 26.9% and 6.1% yield, respectively, from (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)-1-(((3-cyanopyridin-2-yl)oxy)methyl)cyclohex-3-enecarboxylate following the same procedure as described for the preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA, except (S)-(+)-methyl glycidyl ether was used instead of tert-butyldimethylsilyl (R)-(−)-glycidyl ether in Step 4.

Example A12 was the first of the two isolated products to elute from the preparative HPLC column: (R)-1-(((3-carbamoylpyridin-2-yl)oxy)methyl)-4-((1R,3aS,5aR,5bR,7aR,11aS,11bR,13aR,13bR)-3a-(((S)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (2.2 mg, 2.359 µl, 6.11% yield). LCMS: m/z 772.6 (M+H$^+$), retention time 1.279 min (LCMS Method 16). $^1$H NMR (400 MHz, 1:1 CDCl$_3$:METHANOL-d$_4$) δ 8.41 (dd, J=7.6, 2.0 Hz, 1H), 8.25 (dd, J=4.8, 2.1 Hz, 1H), 7.08 (dd, J=7.6, 4.9 Hz, 1H), 5.35 (br. s., 1H), 5.19 (d, J=4.6 Hz, 1H), 4.80 (s, 1H), 4.73 (s, 1H), 4.11 (t, J=4.0 Hz, 1H), 3.69-3.63 (m, 1H), 3.61-3.55 (m, 1H), 3.44 (s, 3H), 3.27-3.20 (m, 1H), 3.19-3.12 (m, 1H), 2.72 (d, J=15.9 Hz, 1H), 2.63-2.52 (m, 1H), 2.26 (br. s., 1H), 2.22-2.08 (m, 4H), 2.07-1.95 (m, 4H), 1.88-1.74 (m, 3H), 1.72 (s, 3H), 1.70-1.62 (m, 2H), 1.62-1.41 (m, 8H), 1.41-1.22 (m, 4H), 1.16 (br. s., 1H), 1.09 (s, 3H), 1.05 (s, 3H), 0.96 (s, 3H), 0.92 (s, 3H), 0.87 (s, 3H).

Example A11 was the second of the two isolated products to elute from the preparative HPLC column: (R)-1-(((3-cyanopyridin-2-yl)oxy)methyl)-4-((1R,3aS,5aR,5bR,7aR,11aS,11bR,13aR,13bR)-3a-(((S)-2-hydroxy-3-methoxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (9.5 mg, 10.40 µmol, 26.9% yield). LCMS: m/z 754.6 (M+H$^+$), retention time 1.347 min (LCMS Method 16). $^1$H NMR (400 MHz, 1:1 CDCl$_3$:METHANOL-d$_4$) δ 8.33 (dd, J=5.1, 2.0 Hz, 1H), 7.94 (dd, J=7.6, 2.0 Hz, 1H), 7.03 (dd, J=7.6, 4.9 Hz, 1H), 5.34 (br. s., 1H), 5.18 (d, J=4.4 Hz, 1H), 4.80 (s, 1H), 4.73 (s, 1H), 4.11 (t, J=4.0 Hz, 1H), 3.70-3.54 (m, 2H), 3.44 (s, 3H), 3.27-3.20 (m, 1H), 3.19-3.12 (m, 1H), 2.64 (d, J=15.9 Hz, 1H), 2.60-2.51 (m, 1H), 2.20 (d, J=16.6 Hz, 3H), 2.11-1.89 (m, 7H), 1.82-1.74 (m, 2H), 1.72 (s, 3H), 1.70-1.63 (m, 2H), 1.63-1.22 (m, 12H), 1.20-1.11 (m, 1H), 1.09 (s, 3H), 1.05 (s, 2H), 0.96 (s, 3H), 0.92 (s, 3H), 0.87 (s, 3H). $^{13}$C NMR (101 MHz, 1:1 CDCl$_3$:METHANOL-d$_4$) δ 178.3, 164.5, 152.27-152.01, 148.9, 147.7, 144.1, 139.7, 122.7, 121.9, 117.7, 112.5, 97.5, 78.5, 76.6, 72.6, 71.5, 65.1, 60.2, 53.8, 50.0, 46.8, 46.6, 45.3, 42.8, 41.4, 38.6, 38.3, 36.9, 34.2, 32.6, 31.1, 30.2, 30.1, 28.1, 27.4, 26.8, 25.9, 22.0, 21.7, 20.3, 19.2, 17.0, 16.0, 15.0.

Example A13 and Example A14

Preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxy-2-methylpropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (Example A13) and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxy-2-methylpropyl)amino)-5a,5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)cyclohex-3-enecarboxylic acid, TFA (Example A14).

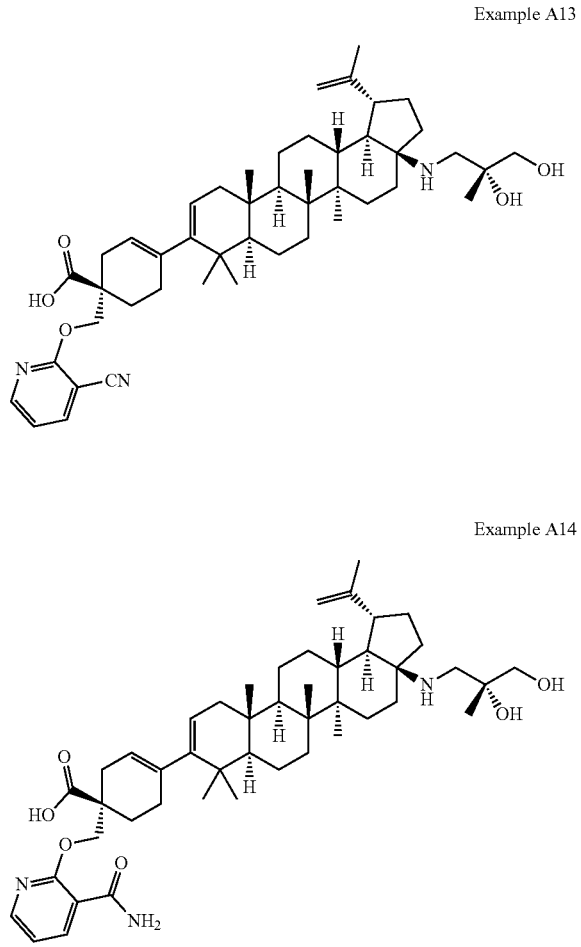

Example A13

Example A14

The title compounds were prepared in 26.0% and 13.6% yield, respectively, from (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-(((3-cyanopyridin-2-yl)oxy)methyl)cyclohex-3-enecarboxylate following the same procedure as described for the preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA, except (2R)-(−)-2-methylglycidyl 4-notrobenzoate was used instead of tert-butyldimethylsilyl (R)-(−)-glycidyl ether in Step 4.

Example A14 was the first of the two isolated products to elute from the preparative HPLC column: (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxy-2-methylpropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (4.8 mg, 5.91 µmol, 13.57% yield). LCMS: m/z 772.6 (M+H$^+$), retention time 1.242 min (LCMS Method 16). $^1$H NMR (400 MHz, 1:1 CDCl$_3$:METHANOL-d$_4$) δ 8.41 (dd, J=7.6, 2.0 Hz, 1H), 8.25 (dd, J=4.9, 2.0 Hz, 1H), 7.08 (dd, J=7.6, 4.9 Hz, 1H), 5.34 (br. s., 1H), 5.19 (d, J=4.6 Hz, 1H), 4.81 (s, 1H), 4.73 (s, 1H), 3.69 (s, 2H), 2.97 (d, J=12.2 Hz, 1H), 2.79-2.68 (m, 1H), 2.68-2.59 (m, 1H), 2.34-2.23 (m, 1H), 2.22-2.08 (m, 3H), 2.08-1.95 (m, 4H), 1.90-1.80 (m, 1H), 1.79-1.74 (m, 1H), 1.73 (s, 3H), 1.71-1.66 (m, 1H), 1.66-1.53 (m, 4H), 1.52-1.33 (m, 6H), 1.30 (br. s., 2H), 1.23 (s, 3H), 1.20-1.09 (m, 2H), 1.06 (s, 3H), 1.04 (s, 3H), 0.96 (s, 3H), 0.92 (s, 3H), 0.86 (s, 3H).

Example A13 was the second of the two isolated products to elute from the preparative HPLC column: (R)-1-(((3-cyanopyridin-2-yl)oxy)methyl)-4-((1R,3aS,5aR,5bR,7aR,11aS,11bR,13aR,13bR)-3a-(((R)-2,3-dihydroxy-2-methylpropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, TFA (8.7 mg, 0.011 mmol, 26.0% yield). LCMS: m/z 754.6 (M+H$^+$), retention time 1.309 min (LCMS Method 16).

$^1$H NMR (400 MHz, 1:1 CDCl$_3$:METHANOL-d$_4$) δ 8.33 (dd, J=5.0, 1.8 Hz, 1H), 7.94 (dd, J=7.6, 2.0 Hz, 1H), 7.03 (dd, J=7.6, 5.1 Hz, 1H), 5.34 (br. s., 1H), 5.18 (d, J=4.4 Hz, 1H), 4.81 (s, 1H), 4.73 (s, 1H), 3.69 (s, 2H), 2.97 (d, J=12.0 Hz, 1H), 2.72-2.59 (m, 2H), 2.30-2.15 (m, 3H), 2.12-1.99 (m, 5H), 1.98-1.88 (m, 2H), 1.81-1.74 (m, 1H), 1.73 (s, 3H), 1.71-1.66 (m, 1H), 1.66-1.53 (m, 5H), 1.52-1.33 (m, 7H), 1.31-1.25 (m, 1H), 1.23 (s, 3H), 1.19-1.09 (m, 2H), 1.06 (s, 3H), 1.04 (s, 2H), 0.96 (s, 3H), 0.91 (s, 3H), 0.86 (s, 3H). $^{13}$C NMR (101 MHz, 1:1 CDCl$_3$:METHANOL-d$_4$) δ 178.3, 164.5, 152.2, 148.9, 147.8, 144.1, 139.7, 122.7, 121.9, 117.7, 112.4, 97.5, 78.6, 72.2, 71.6, 71.5, 69.6, 53.8, 50.0, 46.3, 45.3, 42.9, 42.6, 41.4, 38.6, 38.3, 36.9, 34.2, 32.1, 31.1, 30.2, 30.08-30.04, 28.5, 28.1, 27.7, 26.9, 26.0, 23.5, 22.0, 21.7, 20.3, 19.4, 17.0, 16.0, 15.0.

Example A15 and Example A16

Preparation of (R)-4-((1R,3aS,5aR,5bR,7aR,11aS,11bR,13aR,13bR)-3a-(((R)-2-carboxy-2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylic acid, TFA (Example A15) and 2-(((R)-1-carboxy-4-((1R,3aS,5aR,5bR,7aR,11aS,11bR,13aR,13bR)-3a-(((R)-2-carboxy-2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)methoxy)nicotinic acid, TFA (Example A16).

Example A15

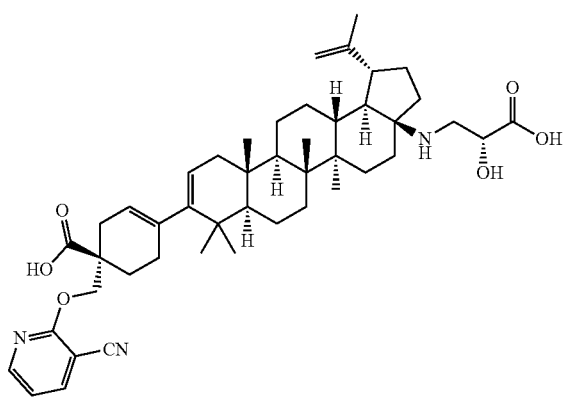

Example A16

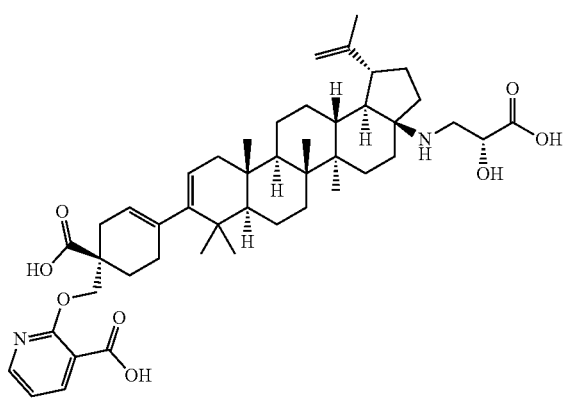

The title compounds were prepared in 19.5% and 17.9% yield, respectively, from (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)-1-(((3-cyanopyridin-2-yl)oxy)methyl)cyclohex-3-enecarboxylate following the same procedure as described for the preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except (R)-methylglycidate was used instead of tert-butyldimethylsilyl (R)-(−)-glycidyl ether in Step 4.

Example A16 was the first of the two isolated products to elute from the preparative HPLC column: 2-(((R)-1-carboxy-4-((1R,3aS,5aR,5bR,7aR,11aS,11bR,13aR,13bR)-3a-(((R)-2-carboxy-2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)methoxy)nicotinic acid (6.0 mg, 7.37 μmol, 17.94% yield). LCMS: m/z 773.5 (M+H$^+$), retention time 1.224 min (LCMS Method 16).

$^1$H NMR (400 MHz, 1:1 CDCl$_3$:METHANOL-d$_4$) δ 8.41 (dd, J=7.6, 2.0 Hz, 1H), 8.25 (dd, J=4.9, 2.0 Hz, 1H), 7.08 (dd, J=7.6, 4.9 Hz, 1H), 5.35 (br. s., 1H), 5.19 (d, J=4.6 Hz, 1H), 4.80 (s, 1H), 4.71 (s, 1H), 4.44 (dd, J=10.0, 4.2 Hz, 1H), 3.40-3.34 (m, 1H), 3.06 (t, J=11.0 Hz, 1H), 2.77-2.62 (m, 2H), 2.26 (br. s., 1H), 2.22-2.05 (m, 5H), 2.04-1.94 (m, 3H), 1.89-1.74 (m, 3H), 1.72 (s, 3H), 1.69-1.57 (m, 4H), 1.57-1.40 (m, 5H), 1.39-1.22 (m, 4H), 1.22-1.12 (m, 1H), 1.10 (s, 3H), 1.05 (s, 3H), 0.96 (s, 3H), 0.92 (s, 3H), 0.87 (s, 3H).

Example A15 was the second of the two isolated products to elute from the preparative HPLC column: (R)-4-((1R,3aS,5aR,5bR,7aR,11aS,11bR,13aR,13bR)-3a-(((R)-2-carboxy-2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylic acid (6.3 mg, 8.02 μmol, 19.52% yield). LCMS: m/z 754.6 (M+H$^+$), retention time 1.289 min (LCMS Method 16). $^1$H NMR (400 MHz, 1:1 CDCl$_3$:METHANOL-d$_4$) δ 8.33 (dd, J=5.0, 1.8 Hz, 1H), 7.94 (dd, J=7.6, 2.0 Hz, 1H), 7.03 (dd, J=7.5, 5.0 Hz, 1H), 5.34 (br. s., 1H), 5.18 (d, J=4.4 Hz, 1H), 4.80 (s, 1H), 4.71 (s, 1H), 4.41 (d, J=5.4 Hz, 1H), 3.06 (t, J=10.8 Hz, 1H), 2.65 (d, J=19.1 Hz, 2H), 2.20 (d, J=15.9 Hz, 3H), 2.14-2.05 (m, 2H), 2.05-1.87 (m, 5H), 1.82-1.69 (m, 5H), 1.68-1.57 (m, 4H), 1.56-1.41 (m, 5H), 1.39-1.22 (m, 4H), 1.21-1.12 (m, 1H), 1.10 (s, 3H), 1.05 (s, 3H), 0.96 (s, 3H), 0.92 (s, 3H), 0.87 (s, 3H).

Example A17 and Example A18

Preparation of (R)-4-((1R,3aS,5aR,5bR,7aR,11aS,11bR,13aR,13bR)-3a-(((S)-2-carboxy-2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylic acid, TFA (Example A17) and (R)-3-(((1R,3aS,5aR,5bR,7aR,11aS,11bR,13aR,13bR)-9-((S)-4-(((3-carbamoylpyridin-2-yl)oxy)methyl)-4-(ethoxycarbonyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)-2-hydroxypropanoic acid, TFA (Example A18).

Example A17

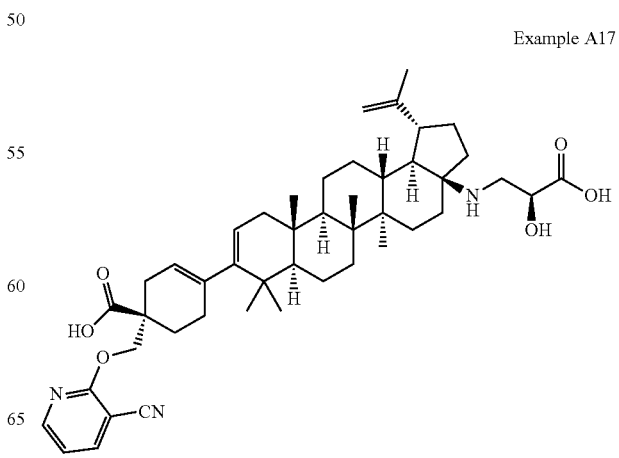

Example A18

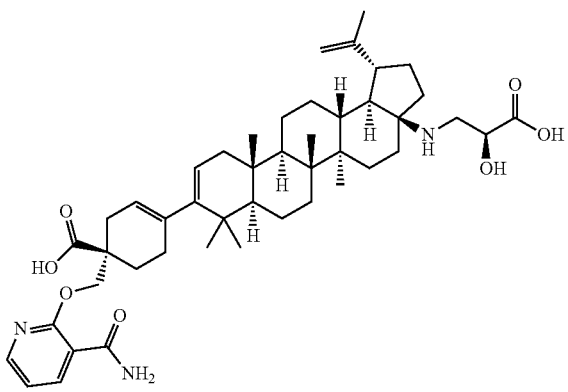

The title compounds were prepared in 19.5% and 16.0% yield, respectively, from (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate following the same procedure as described for the preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-9-yl)cyclohex-3-enecarboxylic acid, except (S)-methylglycidate was used instead of tert-butyldimethylsilyl (R)-(−)-glycidyl ether in Step 4.

Example A18 was the first of the two isolated products to elute from the preparative HPLC column: (R)-3-(((1R,3aS,5aR,5bR,7aR,11aS,11bR,13aR,13bR)-9-((S)-4-(((3-carbamoylpyridin-2-yl)oxy)methyl)-4-(ethoxycarbonyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentalalchrysen-3a-yl)amino)-2-hydroxypropanoic acid, TFA (5.7 mg, 6.11 µmol, 15.98% yield). LCMS: m/z 772.7 (M+H⁺), retention time 1.222 min (LCMS Method 16). ¹H NMR (400 MHz, 1:1 CDCl₃:METHANOL-d₄) δ 8.41 (dd, J=7.6, 2.0 Hz, 1H), 8.25 (dd, J=4.9, 2.0 Hz, 1H), 7.08 (dd, J=7.6, 4.9 Hz, 1H), 5.35 (br. s., 1H), 5.19 (d, J=4.6 Hz, 1H), 4.79 (s, 1H), 4.71 (s, 1H), 4.41 (t, J=6.6 Hz, 1H), 3.20 (d, J=6.4 Hz, 2H), 2.71 (d, J=13.4 Hz, 2H), 2.36-2.23 (m, 1H), 2.16 (d, J=14.9 Hz, 2H), 2.13-2.06 (m, 2H), 2.05-1.95 (m, 4H), 1.89-1.80 (m, 1H), 1.79-1.74 (m, 1H), 1.72 (s, 3H), 1.68 (br. s., 2H), 1.65-1.57 (m, 2H), 1.57-1.50 (m, 2H), 1.49-1.39 (m, 4H), 1.39-1.22 (m, 4H), 1.12 (s, 3H), 1.08 (d, J=9.5 Hz, 3H), 1.04 (s, 3H), 0.96 (s, 3H), 0.92 (s, 3H), 0.87 (s, 3H).

Example A17 was the second of the two isolated products to elute from the preparative HPLC column: (R)-4-((1R,3aS,5aR,5bR,7aR,11aS,11bR,13aR,13bR)-3a-(((S)-2-carboxy-2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylic acid, TFA (6.8 mg, 7.44 µmol, 19.46% yield). LCMS: m/z 754.6(M+H⁺), retention time 1.284 min (LCMS Method 16). ¹H NMR (400 MHz, 1:1 CDCl₃:METHANOL-d₄) δ 8.33 (dd, J=5.0, 1.8 Hz, 1H), 7.94 (dd, J=7.6, 2.0 Hz, 1H), 7.03 (dd, J=7.6, 5.1 Hz, 1H), 5.34 (br. s., 1H), 5.18 (d, J=4.6 Hz, 1H), 4.79 (br. s., 1H), 4.71 (br. s., 1H), 4.41 (br. s., 1H), 3.20 (d, J=5.1 Hz, 2H), 2.70 (br. s., 1H), 2.64 (d, J=18.8 Hz, 1H), 2.20 (d, J=16.1 Hz, 3H), 2.12-1.89 (m, 7H), 1.75 (br. s., 2H), 1.72 (s, 3H), 1.70-1.51 (m, 6H), 1.51-1.39 (m, 4H), 1.38-1.22 (m, 4H), 1.12 (s, 3H), 1.08 (d, J=9.0 Hz, 1H), 1.04 (s, 3H), 0.96 (s, 3H), 0.92 (s, 3H), 0.87 (s, 3H).

Example A19

Preparation of (1R)-4-((1R,3aS,5aR,5bR,7aR,11aS,11bR,13aR,13bR)-3a-((2-carboxy-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylic acid.

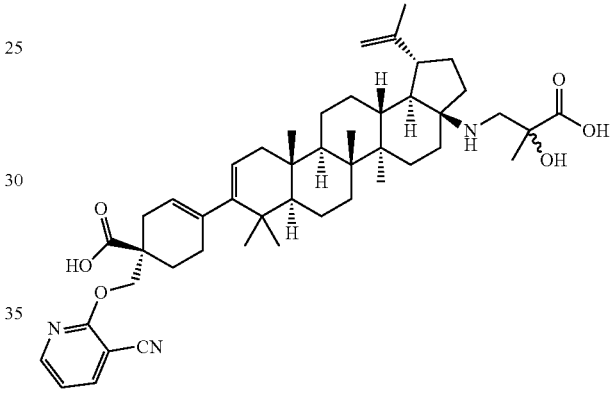

The title compound was prepared in 19.4% yield from (R)-ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(((3-cyanopyridin-2-yl)oxy)methyl)cyclohex-3-enecarboxylate following the same procedure as described for the preparation of (R)-1-(((3-cyanopyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (R)-1-(((3-carbamoylpyridin-2-yl)oxy)methyl)-4-((1R,3aS,5aR,5bR,7aR,11aS,11bR,13aR,13bR)-3a-(((R)-2,3-dihydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopentatalchrysen-9-yl)cyclohex-3-enecarboxylic acid; except methyl 2-methylglycidate was used instead of tert-butyldimethylsilyl (R)-(−)-glycidyl ether in Step 4. LCMS: m/z 768.5 (M+H⁺), retention time 1.295 min (LCMS Method 16). ¹H NMR (400 MHz, 1:1 CDCl₃:METHANOL-d₄) δ .33 (dd, J=5.0, 1.8 Hz, 1H), 7.94 (dd, J=7.6, 2.0 Hz, 1H), 7.03 (dd, J=7.5, 5.0 Hz, 1H), 5.34 (br. s., 1H), 5.18 (d, J=4.6 Hz, 1H), 4.79 (br. s., 1H), 4.71 (br. s., 1H), 3.08-2.89 (m, 1H), 2.80-2.57 (m, 2H), 2.33-2.09 (m, 4H), 2.08-1.87 (m, 6H), 1.82-1.74 (m, 1H), 1.72 (s, 3H), 1.70-1.57 (m, 4H), 1.56-1.41 (m, 8H), 1.40-1.22 (m, 4H), 1.12 (s, 1H), 1.09 (br.

s., 1.5H), 1.07 (br. s., 1.5H), 1.05 (s, 3H), 1.01 (s, 1H), 0.96 (s, 3H), 0.92 (s, 3H), 0.86 (br. s., 3H).

Preparation of 8-(4,4,5,5-tetramethyl-1,3,2-dioxaborolan-2-yl)-2-oxaspiro[4.5]dec-7-en-1-one.

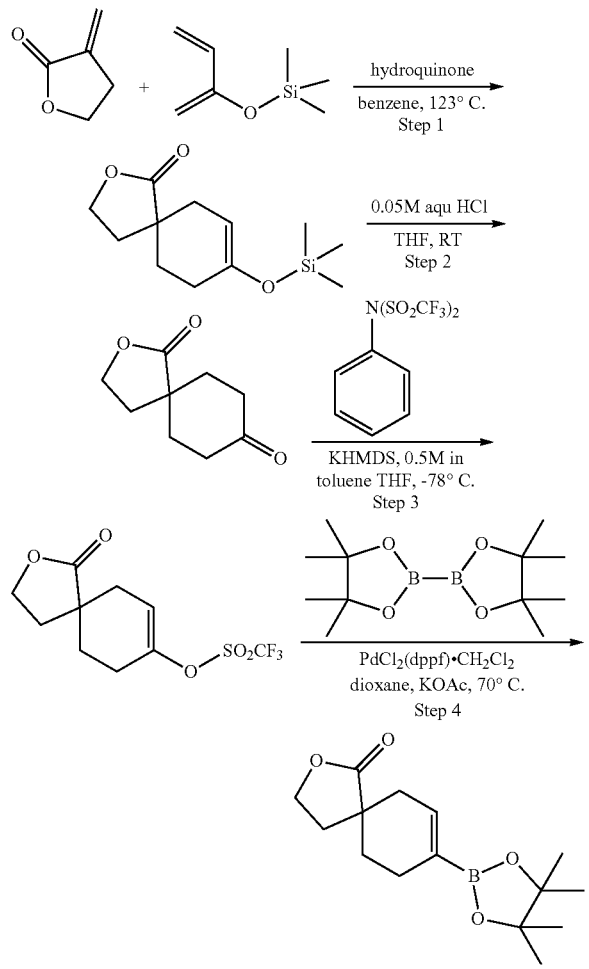

Step 1: Preparation of 8-((trimethylsilyl)oxy)-2-oxaspiro[4.5]dec-7-en-1-one.

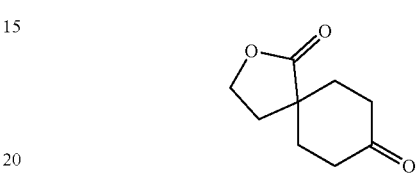

To a 350 mL Chemglass pressure vessel with threaded stopper was added 3-methylenedihydrofuran-2(3H)-one (4.31 g, 43.9 mmol) and (buta-1,3-dien-2-yloxy)trimethylsilane (7.50 g, 52.7 mmol) and benzene (100 mL). Hydroquinone (0.726 g, 6.59 mmol) was added, then the solution was flushed with nitrogen, sealed and heated to 123° C. for 20 h. An additional 2.4 equivalents of (buta-1,3-dien-2-yloxy)trimethylsilane (15.0 g, 105.4 mmol) was then added to the vessel, and the mixture was heated to 123° C. for an additional 60 h. The mixture was concentrated in vacuo to give approximately 19 g of yellow oil. The crude mixture was loaded with minimum DCM and hexanes onto a hexanes preequilibrated Isco 330 g silica cartridge. Elution gradient 100% hexanes to 11:1 hexanes:EtOAc over 2 column volumes, then hold 11:1 hex:EtOAc for 3 column volumes, then gradient to 5:1 hex:EtAc over 2 column volumes, then hold 5:1 hex:EtOAc for 6 column volumes. Concentration of combined fractions containing the desired material provided the product as a white solid: 7.50 g (71.0% yield). $^1$H NMR (400 MHz, CHLOROFORM-d) δ 4.85 (d, J=5.6 Hz, 1H), 4.40-4.23 (m, 2H), 2.47 (dd, J=16.6, 2.2 Hz, 1H), 2.19-2.10 (m, 4H), 2.06 (d, J=3.4 Hz, 1H), 2.04-1.99 (m, 1H), 1.75-1.65 (m, 1H), 0.22 (s, 9H).

Step 2. Preparation of 2-oxaspiro[4.5]decane-1,8-dione.

8-((trimethylsilyl)oxy)-2-oxaspiro[4.5]dec-7-en-1-one (7.50 g, 31.2 mmol) was combined with THF (100 mL) and hydrochloric acid, 0.05M aqueous (3.12 mL, 0.156 mmol). The mixture was stirred for 18 h at RT. The reaction mixture was then concentrated in vacuo to a residue. The residue was taken up in EtOAc (200 mL) and washed with saturated NaHCO$_3$ (50 mL) and with brine (50 mL). The organic phase was dried over anhydrous magnesium sulfate, filtered and concentrated in vacuo. The crude mixture was loaded in minimum DCM onto a hexanes preequilibrated Isco 330 g silica cartridge. Elution gradient 100% hexanes to 1:1 hexanes:EtOAc over 10 column volumes, hold 1:1 hexanes:EtOAc for 6 column volumes. Partial separation of the two materials was achieved. Like fractions were combined and set aside, and mixed fractions were rechromatographed in a similar manner. The desired material was the major product from the reaction and was the second of the two materials to elute from the silica column. The desired material was recovered as a white solid: 4.14 g (79.0% yield). $^1$H NMR (400 MHz, CHLOROFORM-d) δ 4.40 (t, J=7.1 Hz, 2H), 2.87-2.70 (m, 2H), 2.44-2.29 (m, 4H), 2.24 (ddd, J=13.6, 8.3, 5.5 Hz, 2H), 1.96 (dt, J=13.6, 6.5 Hz, 2H).

Step 3. Preparation of 1-oxo-2-oxaspiro[4.5]dec-7-en-8-yl trifluoromethanesulfonate.

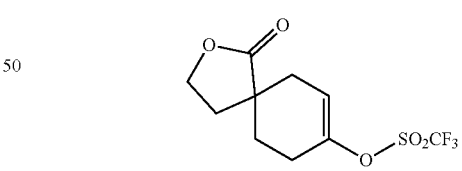

In a 250 mL round bottom flask fitted with magnetic stirrer and rubber septum were combined 2-oxaspiro[4.5]decane-1,8-dione (4.13 g, 24.6 mmol) and N,N-bis(trifluoromethylsulfonyl)aniline (10.1 g, 28.2 mmol) in anhydrous tetrahydrofuran (100 mL). The solution was cooled to −78° C. in a dry ice/acetone bath. To the cold solution was added dropwise potassium hexamethyldisilazide, 0.5M in toluene (56.5 mL, 28.2 mmol) over 15 min. The mixture was stirred at −78° C. for a total of 4 h when it was treated slowly with 100 mL of saturated aqueous ammonium chloride. The mixture was stirred at RT for 15 min and was concentrated in vacuo to remove most of the THF, then to the residue was added ethyl acetate (300 mL). The resulting mixture was shaken and phases were separated. The organic was washed with water (2×100 mL) and with brine (50 mL). The organic was dried over anhydrous magnesium sulfate, filtered and concentrated in vacuo to give a crude yellow oil. The crude residue was loaded as an oil onto a hexanes preequilibrated Isco 220 g silica cartridge and the flask was rinsed with minimum DCM and this was added to the column as well. Elution gradient 100% hexanes to 3:1 hexanes:EtOAc over 3 column volumes, then hold 3:1 hex:EtOAc for 3 column volumes, then 2:1 hex:EtOAc for 3 column volumes. Like product fractions were combined and concentrated in vacuo to give the desired material as a slightly yellow oil: 6.44 g (87.0% yield). $^1$H NMR (400 MHz, CHLOROFORM-d) δ 5.86-5.76 (m, 1H), 4.44-4.29 (m, 2H), 2.63 (dd, J=17.7, 2.8 Hz, 1H), 2.59-2.38 (m, 2H), 2.30-2.16 (m, 3H), 2.16-2.04 (m, 1H), 1.86 (dt, J=13.7, 2.9 Hz, 1H).

Step 4. In a 250 mL round bottom flask fitted with a reflux condenser were combined 1-oxo-2-oxaspiro[4.5]dec-7-en-8-yl trifluoromethanesulfonate (6.43 g, 21.4 mmol), potassium acetate (5.25 g, 53.5 mmol), 4,4,4',4',5,5,5',5'-octamethyl-2,2'-bi(1,3,2-dioxaborolane) (5.71 g, 22.5 mmol) and PdCl$_2$(dppf).CH$_2$Cl$_2$ (0.529 g, 0.642 mmol) in dry 1,4-dioxane (100 mL). The mixture was flushed with nitrogen and heated to 70° C. for 5 h. The reaction mixture was concentrated in vacuo to approx. 25 mL total volume and was diluted with ethyl acetate (300 mL) and water (150 mL). The mixture was shaken and phases were separated. The organic was again washed with water (100 mL) and then with brine (100 mL). The organic phase was dried over anhydrous magnesium sulfate, filtered and concentrated in vacuo to a deep red residue. The crude mixture was dissolved in minimum DCM and loaded onto a hexanes pre-equilibrated Isco 220 g silica cartridge. Elution gradient 100% hexanes to 20% ethyl acetate in hexanes over 10 column volumes, then hold 20% ethyl acetate in hexanes for 6 column volumes, then gradient to 15% ethyl acetate in hexanes over 2 column volumes, then hold 25% ethyl acetate in hexanes for 6 column volumes. Product fractions were combined and concentrated in vacuo to give the desired material as a white foam solid=4.94 g (83.0% yield). $^1$H NMR (400 MHz, CHLOROFORM-d) δ 6.60-6.49 (m, 1H), 4.39-4.22 (m, 2H), 2.50 (d, J=17.6 Hz, 1H), 2.40 (dd, J=18.1, 3.9 Hz, 1H), 2.21-2.01 (m, 4H), 1.85 (td, J=12.3, 5.5 Hz, 1H), 1.73-1.62 (m, 1H), 1.29 (s, 12H).

Example A20

Preparation of 4-((1R,3aS,5aR,5bR,7aR,11aS,11bR,13aR,13bR)-3a-((2-(1,1-dioxidothiomorpholino)ethyl) amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-(pyridin-2-yloxy)ethyl)cyclohex-3-ene-1-carboxylic acid.

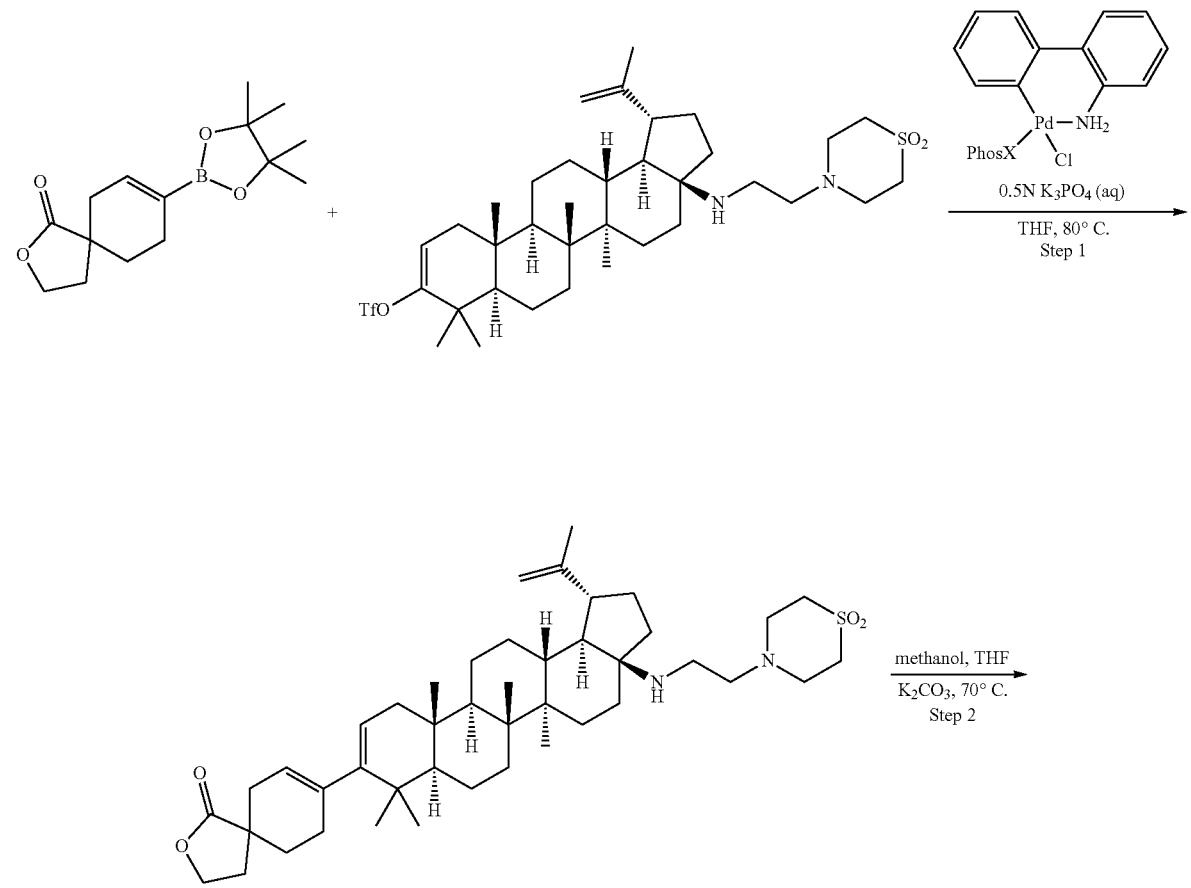

-continued
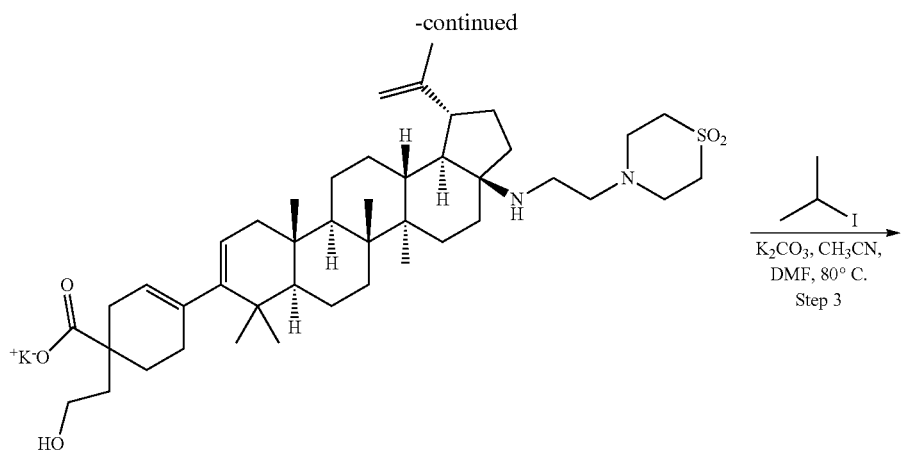
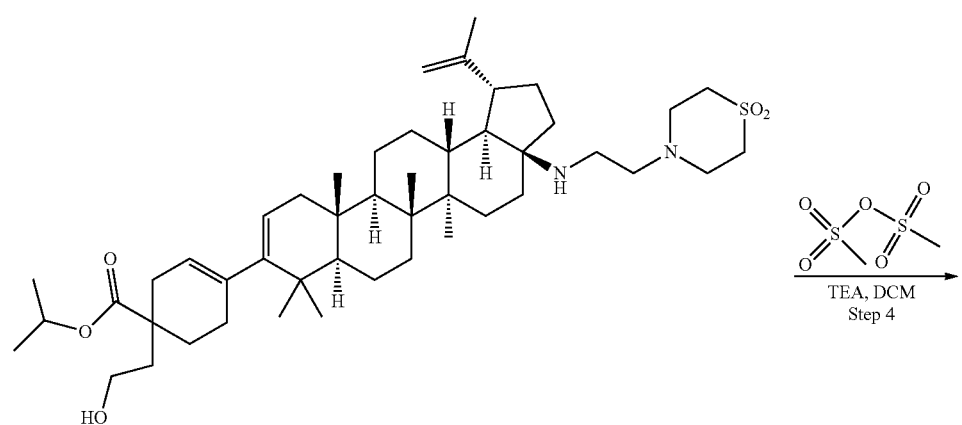
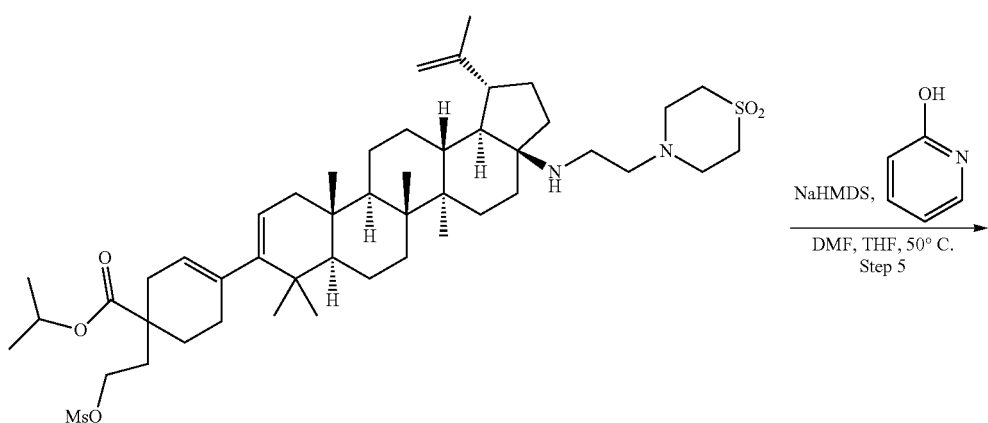

-continued

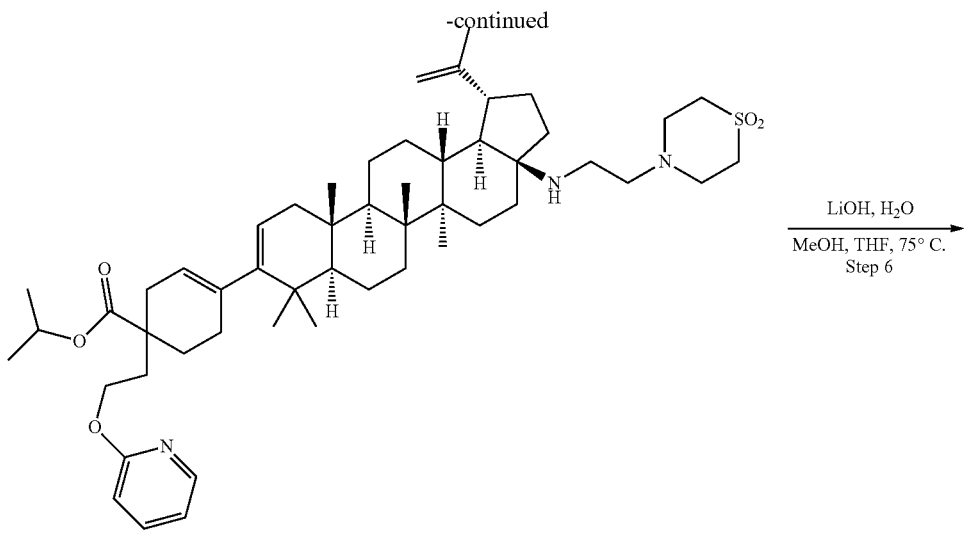

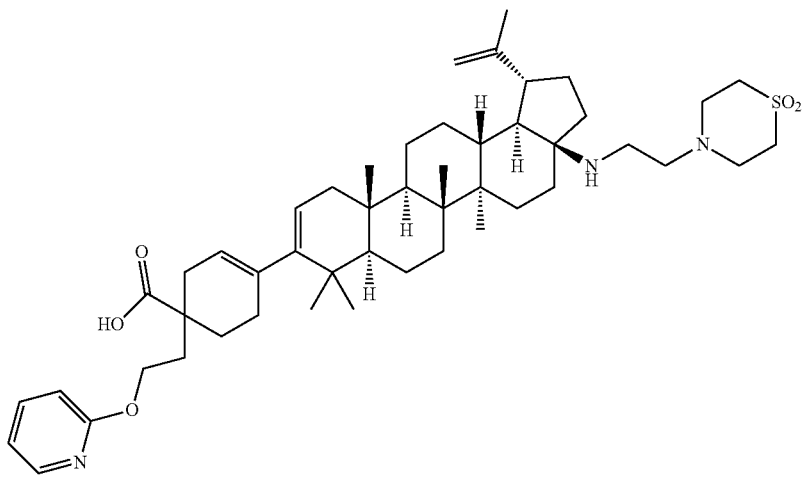

Example A20

Step 1. Preparation of 8-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-oxaspiro[4.5]dec-7-en-1-one.

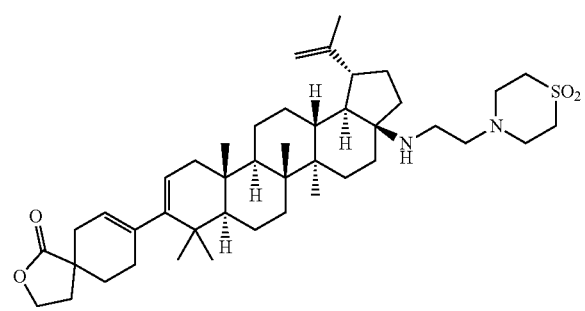

In a 150 mL Chemglass pressure vessel with magnetic stir bar were combined (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (2.00 g, 2.78 mmol) with 8-(4,4,5,5-tetramethyl-1,3,2-dioxaborolan-2-yl)-2-oxaspiro[4.5]dec-7-en-1-one (0.851 g, 3.06 mmol) and Buchwald precatalyst 13 (0.131 g, 0.167 mmol). The vessel was sealed with a rubber septum. A needle was inserted into the septum and the vessel was iteratively evacuated and then purged with nitrogen in a vacuum oven at RT four times over a 15 min period. To the nitrogen purged reaction flask was added anhydrous THF (40 mL) and freshly prepared, nitrogen sparged aqueous 0.5 M $K_3PO_4$ (13.9 mL, 6.95 mmol) was added. The vessel was sealed and the resulting yellow solution was stirred at 80° C. for 20.5 h. The mixture darkened to a very deep green color after 30 min of heating, and after 20.5 h of heating a nearly colorless biphasic mixture was present. The mixture was diluted with EtOAc (150 mL) and washed with saturated aqueous sodium bicarbonate (50 mL×2) and then with brine (50 mL). The combined aqueous layer was extracted with 2×100 mL of chloroform and the organic phases were combined, dried over anhydrous magnesium sulfate, filtered and concentrated to a slightly yellow foam solid. The crude yellow material was loaded in minimum DCM onto a hexanes preequilibrated Isco 80 g silica cartridge. Elution gradient 100% hexanes to 1:1 hexanes:EtOAc over 2 column volumes, hold 1:1 hexanes:EtOAc for 3 column volumes, then gradient 1:1 hexanes:EtOAc to 1:4 hex:EtOAc over 8 column volumes, then hold 1:4 hexanes:EtOAc for 10 column volumes. Product fractions were combined and concentrated in vacuo to give an off-white glassy solid: 1.63 g (81.0% yield). LCMS m/z=721.6 (M+H±), retention time 2.404 min (LCMS Method 17). $^1$H NMR (400 MHz, 1:1 mixture of CDCl$_3$ and CD3OD, CD3OD lock) δ 5.41-5.30 (m, 1H), 5.22 (d, J=5.6 Hz, 1H), 4.70 (br. s., 1H), 4.42-4.27 (m, 2H), 3.19-2.97 (m, 8H), 2.78-2.53 (m, 4H), 2.52-2.32 (m, 2H), 2.29-2.10 (m, 4H), 2.04-1.75 (m, 6H), 1.69 (s, 4H), 1.66-1.54 (m, 4H), 1.53 (br. s., 1H), 1.45 (br. s., 4H), 1.40-1.32 (m, 2H), 1.32-1.13 (m, 5H), 1.10 (s, 6H), 1.04 (br. s., 1H), 0.99 (br. s., 5H), 0.95 (d, J=7.3 Hz, 3H), 0.88 (s, 3H).

Step 2. Preparation of potassium 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-ene-1-carboxylate.

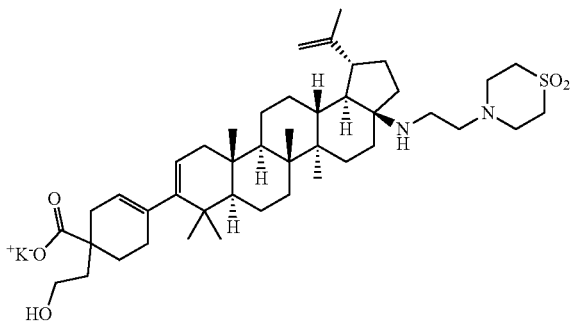

In a 250 mL round bottom flask fitted with a reflux condenser were combined 8-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-oxaspiro[4.5]dec-7-en-1-one (1.61 g, 2.23 mmol) with potassium carbonate (1.54 g, 11.2 mmol) in a mixture of MeOH (20 mL) and THF (20 mL). The result was heated to 70° C. in an oil bath for 2.5 h. Solvent was removed in vacuo to leave a solid brown residue which was carried into the next step without further manipulation. LCMS m/z=739.5 (M+H$^+$), retention time 1.852 min (LCMS Method 18).

Step 3. Preparation of isopropyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-ene-1-carboxylate.

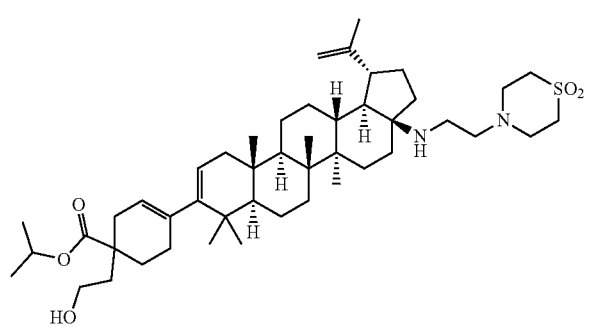

In a 250 mL round bottom flask fitted with a reflux condenser were combined the crude reaction mixture from Step 2 containing potassium 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-enecarboxylate (1.73 g, 2.23 mmol) with potassium carbonate (1.543 g, 11.17 mmol) in a mixture of acetonitrile (20 mL) and DMF (20 mL). To the mixture was added 2-iodopropane (4.46 mL, 44.7 mmol).

The resulting suspension was stirred at 80° C. for 2.5 h. The mixture was concentrated in vacuo to a residue. Ethyl acetate (120 mL) and water (100 mL) were added and the mixture was shaken and phases were separated. The organic phase was washed twice more with water (2×50 mL) and then with brine (20 mL). The slightly yellow organic was dried over anhydrous magnesium sulfate, filtered and concentrated in vacuo to a residue. The material was loaded in DCM onto an Isco 120 g silica gel cartridge which was preequilibrated with DCM. Elution gradient 100% DCM to 19:1 DCM:MeOH over 6 column volumes, hold 19:1 DCM:MeOH for 8 column volumes. The combined product fractions were concentrated in vacuo to a beige foam: 1.55 g (89% yield over 2 steps). LCMS m/z=781.5 (M+H$^+$), retention time 2.873 min (LCMS Method 19). $^1$H NMR (400 MHz, CHLOROFORM-d) δ 5.34 (br. s., 1H), 5.18 (d, J=5.6 Hz, 1H), 5.04 (dt, J=12.4, 6.1 Hz, 1H), 4.73 (s, 1H), 4.61 (s, 1H), 3.73 (d, J=4.9 Hz, 1H), 3.16-2.97 (m, 7H), 2.75-2.54 (m, 4H), 2.54-2.42 (m, 1H), 2.28-2.16 (m, 1H), 2.13 (dd, J=12.1, 6.5 Hz, 1H), 2.07-1.91 (m, 4H), 1.89-1.75 (m, 4H), 1.71 (s, 3H), 1.70-1.62 (m, 2H), 1.62-1.49 (m, 5H), 1.49-1.39 (m, 4H), 1.39-1.29 (m, 3H), 1.29-1.22 (m, 7H), 1.22-1.11 (m, 2H), 1.08 (s, 6H), 1.01-0.95 (m, 6H), 0.94-0.90 (m, 3H), 0.88 (s, 3H).

Step 4. Preparation of isopropyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-((methylsulfonyl)oxy)ethyl)cyclohex-3-ene-1-carboxylate.

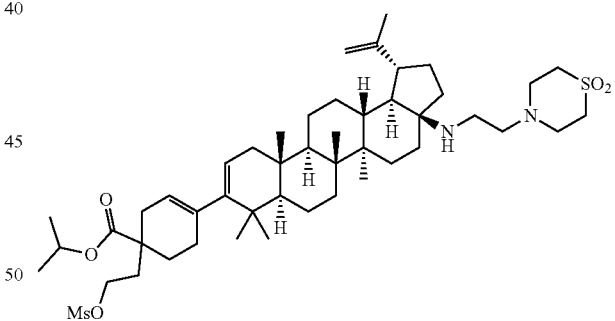

Isopropyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-enecarboxylate (0.800 g, 1.02 mmol) was dissolved in a mixture of triethylamine (5 mL) and DCM (5 mL). The clear mixture was chilled in an ice bath and to it was slowly added a solution of methanesulfonic anhydride (0.446 g, 2.56 mmol) in DCM (3 mL). The colorless solution took on a slightly yellow color turning to deep orange and finally to brown over the course of the reaction. The brown mixture was stirred at 0° C. for 4 h and was then concentrated in vacuo to a residue without warming. The crude residue was diluted with EtOAc (100 mL) and washed with 5% aqueous NaHCO$_3$ (2×20 mL), water (20 mL) and brine (20 mL). The organic was dried over anhydrous magnesium sulfate, filtered and concentrated in vacuo to give a reddish/brown foam. The crude material was loaded in minimum DCM onto an 80 g Isco silica cartridge which was preequilibrated with hexanes. Elution gradient 100% hexanes to 3:2 hexanes:acetone over 3 column volumes, hold 3:2 hexanes:acetone for 10 column volumes. Desired product fractions were combined and concentrated in vacuo to give a yellow foam: 667 mg (76.0% yield). LCMS m/z=859.6 (M+H$^+$), retention time 3.160 min (LCMS Method 19). $^1$H NMR (400 MHz, CHLOROFORM-d) δ 5.33 (br. s., 1H), 5.18 (d, J=5.4 Hz, 1H), 5.04 (dt, J=12.2, 6.3 Hz, 1H), 4.75 (br. s., 1H), 4.63 (br. s., 1H), 4.29 (t, J=7.0 Hz, 1H), 3.72 (t, J=6.5 Hz, 1H), 3.25 (s, 1H), 3.16 (s, 1H), 3.08 (br. s., 6H), 3.01 (s, 2H), 2.83 (s, 1H), 2.77-2.54 (m, 4H), 2.49 (br. s., 1H), 2.30-2.09 (m, 3H), 2.09-1.95 (m, 4H), 1.95-1.76 (m, 4H), 1.72 (br. s., 3H), 1.66 (dd, J=14.3, 7.2 Hz, 3H), 1.61-1.50 (m, 5H), 1.50-1.38 (m, 5H), 1.33 (t, J=13.1 Hz, 3H), 1.29-1.21 (m, 7H), 1.18-1.03 (m, 6H), 1.00 (br. s., 3H), 0.97 (d, J=7.3 Hz, 3H), 0.93 (d, J=5.4 Hz, 3H), 0.88 (s, 3H).

Step 5. Preparation of isopropyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-(pyridin-2-yloxy)ethyl)cyclohex-3-ene-1-carboxylate.

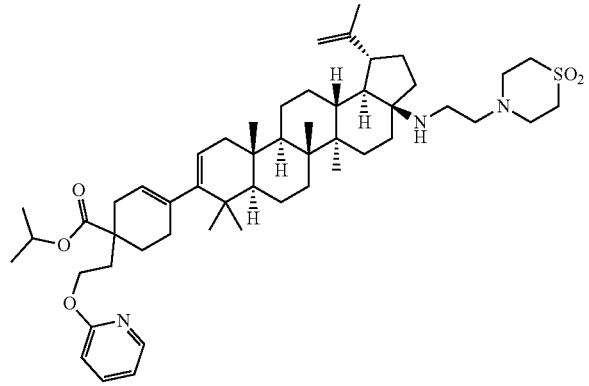

In a 1 dram vial with PTFE screwcap were combined pyridin-2-ol (0.0190 g, 0.204 mmol) and isopropyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-((methylsulfonyl)oxy)ethyl)cyclohex-3-enecarboxylate (0.0250 g, 0.0290 mmol) in anhydrous DMF (0.5 mL). To the mixture was added NaHMDS, 1.0M in THF (0.175 mL, 0.175 mmol) with stirring. The resulting slightly yellow mixture was heated to 50° C. and stirred for 3 d. The crude mixture was purified by reverse phase preparative HPLC (Preparative HPLC Method 6). Thus was isolated the desired material (0.00940 g, 29.7% yield) as a white solid TFA salt. LCMS m/z=858.6 (M+H$^+$), retention time 1.627 min (LCMS Method 16).

Step 6. In a 1 dram vial with PTFE screwcap were combined isopropyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-(pyridin-2-yloxy)ethyl)cyclohex-3-enecarboxylate, TFA salt (0.00940 g, 8.65 μmol) with lithium hydroxide, 1.0M aqueous (0.087 mL, 0.087 mmol) and a mixture of THF (0.3 mL) and MeOH (0.3 mL). The resulting mixture was stirred at 75° C. for 48 h. The crude mixture was purified by reverse phase preparative HPLC (Preparative HPLC Method 6). The fraction containing the desired material was concentrated in vacuo to give the title compound as a white glassy solid (0.0035 g 33% yield). LCMS m/z=816.5 (M+H±), retention time 2.182 min (LCMS Method 17). $^1$H NMR (400 MHz, 1:1 mixture of CDCl$_3$ and CD3OD, CD3OD lock) δ 8.07 (d, J=5.1 Hz, 1H), 7.65-7.59 (m, 1H), 6.90 (t, J=6.1 Hz, 1H), 6.74 (d, J=8.3 Hz, 1H), 5.33 (br. s., 1H), 5.18 (d, J=5.6 Hz, 1H), 4.80 (s, 1H), 4.72 (s, 1H), 4.34 (t, J=6.6 Hz, 2H), 3.24 (br. s., 3H), 3.21-3.13 (m, 3H), 3.12-2.96 (m, 4H), 2.84-2.72 (m, 1H), 2.60 (d, J=15.4 Hz, 1H), 2.26-1.96 (m, 10H), 1.87-1.70 (m, 6H), 1.69-1.59 (m, 3H), 1.57 (br. s., 2H), 1.53-1.43 (m, 5H), 1.40 (br. s., 1H), 1.39-1.22 (m, 2H), 1.15 (s, 3H), 1.11 (br. s., 1H), 1.08 (s, 3H), 1.04-0.99 (m, 1H), 0.97 (br. s., 3H), 0.93 (s, 3H), 0.90 (s, 3H).

Example A21

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-((5-methylisothiazol-3-yl)oxy)ethyl)cyclohex-3-ene-1-carboxylic acid.

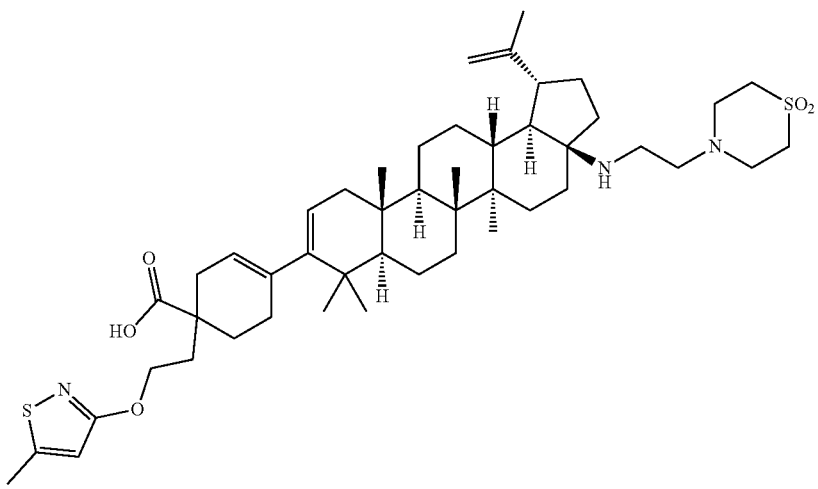

The title compound was obtained by the same procedures used in the preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-(pyridin-2-yloxy)ethyl)cyclohex-3-ene-1-carboxylic acid, except 5-methylisothiazol-3-ol (0.023 g, 0.204 mmol) was used in place of pyridin-2-ol in Step 5. Thus was obtained the title compound as a white glassy solid (0.0027 g, 8.3% combined yield for Steps 5 and 6). LCMS m/z=836.5 (M+H$^+$), retention time 2.394 min (LCMS Method 17). $^1$H NMR (400 MHz, 1:1 mixture of CDCl$_3$ and CD3OD, CD3OD lock) δ 5.32 (br. s., 1H), 5.18 (d, J=5.4 Hz, 1H), 4.80 (s, 1H), 4.73 (s, 1H), 4.36 (t, J=6.6 Hz, 2H), 3.75 (t, J=6.0 Hz, 2H), 3.27-3.12 (m, 8H), 3.12-2.94 (m, 5H), 2.78 (td, J=10.8, 4.4 Hz, 1H), 2.58 (d, J=16.1 Hz, 1H), 2.25-1.95 (m, 11H), 1.92-1.70 (m, 8H), 1.70-1.59 (m, 3H), 1.59-1.39 (m, 9H), 1.39-1.24 (m, 3H), 1.22 (s, 1H), 1.18-1.04 (m, 7H), 0.97 (d, J=2.7 Hz, 3H), 0.92 (br. s., 3H), 0.90 (s, 3H).

Example A22

Preparation of 1-(2-((3-cyanopyridin-2-yl)oxy)ethyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

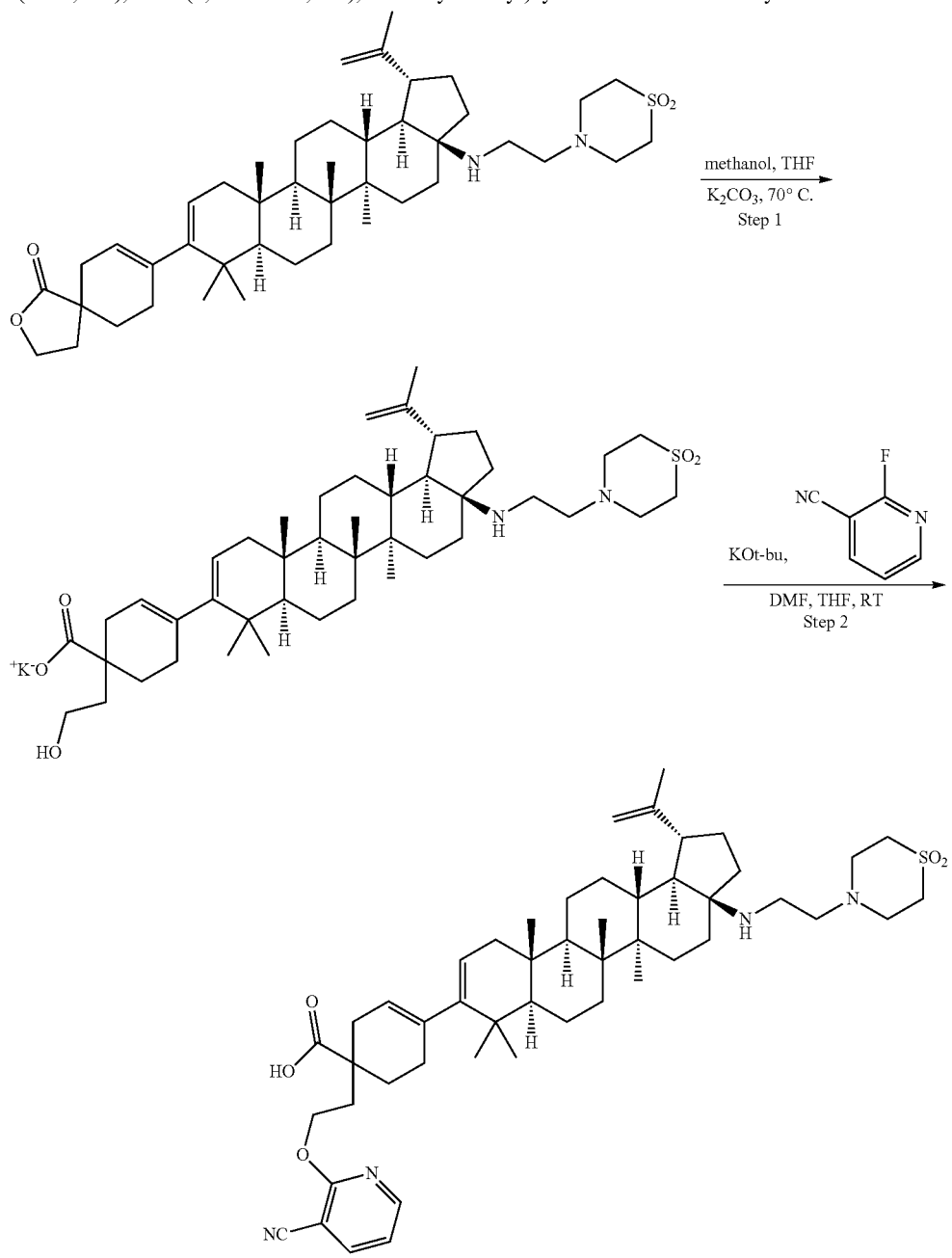

Example A22

Step 1. Preparation of potassium 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-ene-1-carboxylate.

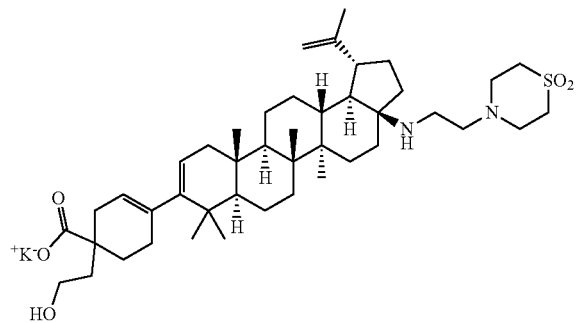

In a 50 mL round bottom flask fitted with a reflux condenser were combined 8-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-oxaspiro[4.5]dec-7-en-1-one (0.700 g, 0.971 mmol) with potassium carbonate (1.34 g, 9.71 mmol) in a mixture of MeOH (10 mL) and THF (15 mL). The result was heated to reflux in an 85° C. oil bath for 24 h. The mixture was allowed to cool to RT, then DCM was added and the result was filtered to remove white solids. Solvent was removed in vacuo and the residue was dried in a vacuum oven at 50° C. overnight to afford the desired material as a white powder (0.940 g, 125% yield). Mass recovery indicated that the material was approximately 80% pure with the remainder as excess potassium salts. This material was used directly in the next step without further purification. LCMS m/z=739.5 (M+H+), retention time 1.852 min (LCMS Method 17).

Step 2. To the crude powder product from Step 1 containing approx. 80% by weight potassium 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-enecarboxylate (0.025 g, 0.026 mmol) was added 2-fluoronicotinonitrile (0.016 g, 0.129 mmol), anhydrous DMF (0.4 mL) and anhydrous THF (0.3 mL) to give a slightly cloudy yellow mixture. To the mixture was added potassium tert-butoxide, 1.0M in THF (0.103 mL, 0.103 mmol). The mixture was stirred at RT for 2 h, and then additional 6-fluoropicolinonitrile (0.032 g, 0.258 mmol) and potassium tert-butoxide, 1.0M in THF (0.206 mL, 0.206 mmol) and more DMF (0.2 mL) were added and the mixture was stirred for another 1 h. The crude mixture was purified by reverse phase preparative HPLC (Preparative HPLC Method 7). The title compound was thus obtained as a slightly yellow powder (0.0086 g, 25% yield) as a TFA salt. LCMS m/z=841.6 (M+H+), retention time 2.289 min (LCMS Method 17). $^1$H NMR (400 MHz, 1:1 mixture of CDCl$_3$ and CD3OD, CD3OD lock) δ 8.34 (dd, J=4.2, 1.0 Hz, 1H), 7.94 (dd, J=8.1, 1.7 Hz, 1H), 7.03 (dd, J=7.1, 5.1 Hz, 1H), 5.40-5.28 (m, 1H), 5.17 (d, J=4.6 Hz, 1H), 4.80 (br. s., 1H), 4.71 (br. s., 1H), 4.39-4.31 (m, 1H), 3.28-3.12 (m, 7H), 3.09 (br. s., 2H), 3.01 (br. s., 2H), 2.82 (br. s., 1H), 2.61 (d, J=17.4 Hz, 1H), 2.25-1.96 (m, 10H), 1.86 (d, J=10.5 Hz, 1H), 1.78-1.68 (m, 5H), 1.67-1.53 (m, 5H), 1.53-1.38 (m, 6H), 1.38-1.24 (m, 3H), 1.19-1.03 (m, 8H), 1.03-0.82 (m, 9H).

Example A23

Preparation of 2-(2-(1-carboxy-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid.

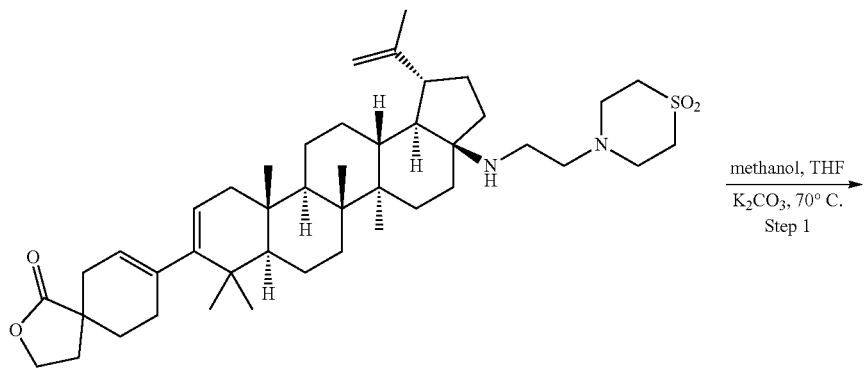

-continued

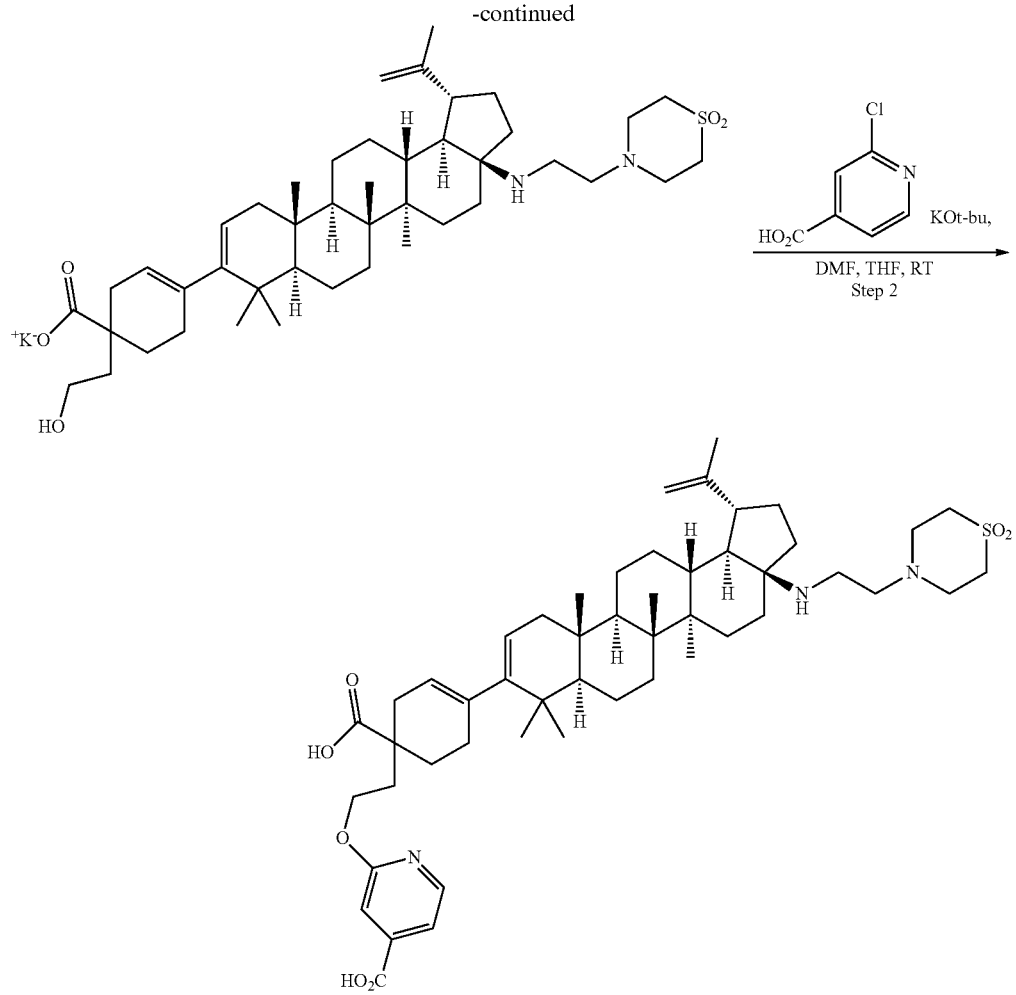

Example A23

Step 1. Preparation of potassium 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-ene-1-carboxylate.

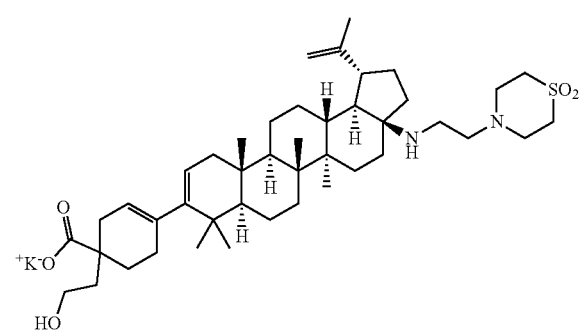

In a 50 mL round bottom flask fitted with a reflux condenser were combined 8-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-oxaspiro[4.5]dec-7-en-1-one (0.700 g, 0.971 mmol) with potassium carbonate (1.34 g, 9.71 mmol) in a mixture of MeOH (10 mL) and THF (15 mL). The result was heated to reflux in an 85° C. oil bath for 24 h. The mixture was allowed to cool to RT, then DCM was added and the result was filtered to remove white solids. Solvent was removed in vacuo and the residue was dried in a vacuum oven at 50° C. overnight to afford the desired material as a white powder (0.940 g, 125% yield). 0.9155 g of this material was dissolved with stirring in 10 mL of 9:1 DCM:MeOH and this suspension (salts did not dissolve) was loaded onto a short 40 mL silica gel plug in a 60 mL glass frit suction funnel. The material was eluted with 400 mL of 9:1 DCM:MeOH.

Much of the orange color associated with the impure product was left behind on the silica. Concentration in vacuo afforded a pinkish/white solid which was placed in a vacuum oven at 45° C. for several hours. The desired material was thus obtained as a white powder (0.5082 g, 69.4% yield). LCMS m/z=739.6 (M+H$^+$), retention time 1.978 min (LCMS Method 21).

Step 2. To the purified Step 1 product potassium 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-hydroxyethyl)cyclohex-3-enecarboxylate (0.025 g, 0.032 mmol) was added 2-chloroisonicotinic acid (0.025 g, 0.161 mmol) followed by anhydrous DMF (0.35 mL). To the mixture was added potassium tert-butoxide, 1.0M in THF (0.322 mL, 0.322 mmol). The mixture became slightly yellow and cloudy with suspended solid upon addition of the base. The mixture was stirred at RT for 70 h. The reaction mixture was quenched by addition of 3 drops of acetic acid. 0.5 mL MeOH was then added and the mixture was filtered. The crude mixture was purified by reverse phase preparative HPLC in a single injection (Preparative HPLC Method 8). Thus was obtained the title compound as a white solid (0.0069 g, 18% yield) TFA salt. LCMS m/z=860.6 (M+H$^+$), retention time 1.559 min (LCMS Method 20).

Example A24

Preparation of 1-(2-((4-cyanopyridin-2-yl)oxy)ethyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

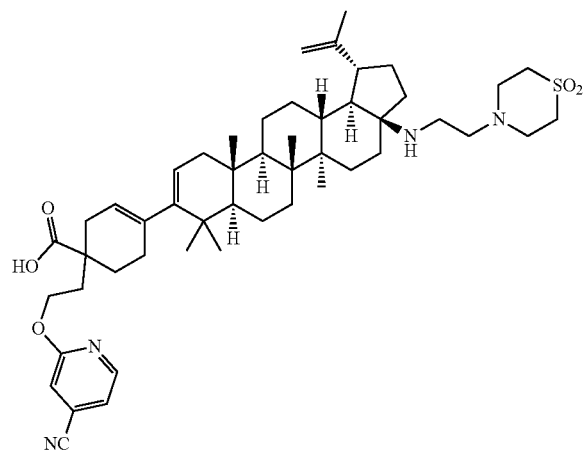

The title compound was prepared following the procedure described for the preparation of 2-(2-(1-carboxy-4-((1R,3aS,5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2-fluoroisonicotinonitrile (0.020 g, 0.161 mmol) was used instead of 2-chloroisonicotinic acid, and there was also less potassium tert-butoxide, 1.0M in THF used in the present case (0.129 mL, 0.129 mmol). The title compound was isolated as a slightly yellow solid (0.0133 g, 36.0% yield) TFA salt. LCMS m/z=841.6 (M+H$^+$), retention time 1.689 min (LCMS Method 20). $^1$H NMR (400 MHz, 1:1 mixture of CDCl$_3$ and CD3OD, CD3OD lock) δ 8.28 (d, J=5.4 Hz, 1H), 7.11 (dd, J=5.1, 1.2 Hz, 1H), 7.00 (s, 1H), 5.33 (br. s., 1H), 5.17 (d, J=4.4 Hz, 1H), 4.79 (s, 1H), 4.71 (s, 1H), 4.47-4.39 (m, 2H), 3.28-3.04 (m, 9H), 3.04-2.96 (m, 2H), 2.86-2.74 (m, 1H), 2.59 (d, J=16.4 Hz, 1H), 2.24-1.95 (m, 11H), 1.89-1.74 (m, 3H), 1.73 (s, 4H), 1.68-1.42 (m, 10H), 1.42-1.29 (m, 3H), 1.15 (s, 3H), 1.11 (br. s., 2H), 1.08 (s, 4H), 0.96 (d, J=2.4 Hz, 3H), 0.92 (d, J=2.9 Hz, 3H), 0.90 (s, 3H).

Example A25

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-(pyrimidin-2-yloxy)ethyl)cyclohex-3-ene-1-carboxylic acid.

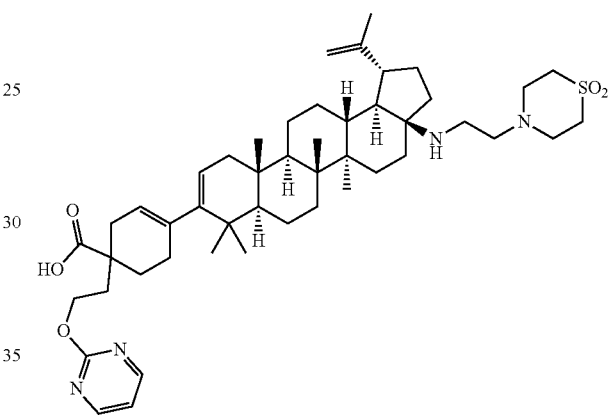

The title compound was prepared following the procedure described for the preparation of 2-(2-(1-carboxy-4-((1R,3aS,5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2-bromopyrimidine (0.026 g, 0.161 mmol) was used instead of 2-chloroisonicotinic acid, and there was also less potassium tert-butoxide, 1.0M in THF used in the present case (0.129 mL, 0.129 mmol). The title compound was isolated as a white solid (0.0056 g, 14.2% yield) TFA salt. LCMS m/z=817.6 (M+H$^+$), retention time 1.547 min (LCMS Method 20). $^1$H NMR (400 MHz, 1:1 mixture of CDCl$_3$ and CD3OD, CD3OD lock) δ 8.50 (d, J=4.9 Hz, 1H), 7.02 (t, J=4.8 Hz, 1H), 5.35 (dd, J=14.7, 2.9 Hz, 1H), 5.25-5.14 (m, 1H), 4.80 (s, 1H), 4.72 (s, 1H), 4.50-4.44 (m, 1H), 4.38-4.31 (m, 1H), 3.27-2.98 (m, 10H), 2.84-2.75 (m, 1H), 2.64-2.58 (m, 1H), 2.25-1.96 (m, 10H), 1.89-1.75 (m, 3H), 1.73 (s, 3H), 1.69-1.53 (m, 5H), 1.53-1.25 (m, 8H), 1.15 (d, J=2.9 Hz, 3H), 1.11 (br. s., 2H), 1.08 (s, 3H), 1.03-0.84 (m, 9H).

Example A26

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-((4-methylpyrimidin-2-yl)oxy)ethyl)cyclohex-3-ene-1-carboxylic acid.

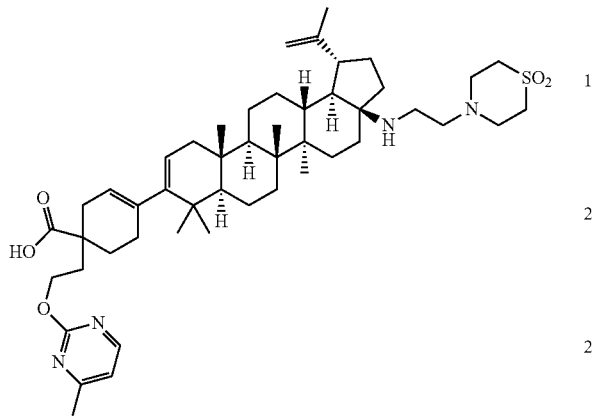

The title compound was prepared following the procedure described for the preparation of 2-(2-(1-carboxy-4-((1R,3aS,5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2-chloro-4-methylpyrimidine (0.021 g, 0.161 mmol) was used instead of 2-chloroisonicotinic acid, and there was also less potassium tert-butoxide, 1.0M in THF used in the present case (0.129 mL, 0.129 mmol). The title compound was isolated as a white solid (0.0056 g, 14.2% yield) TFA salt. LCMS m/z=831.7 (M+H⁺), retention time 1.550 min (LCMS Method 20). ¹H NMR (400 MHz, 1:1 mixture of CDCl₃ and CD3OD, CD3OD lock) δ 8.21 (d, J=6.1 Hz, 1H), 6.52 (d, J=5.9 Hz, 1H), 5.40-5.34 (m, 1H), 5.23 (d, J=4.6 Hz, 1H), 4.79 (s, 1H), 4.71 (s, 1H), 4.41-4.27 (m, 2H), 3.30-3.05 (m, 10H), 3.01 (d, J=3.4 Hz, 2H), 2.81 (td, J=11.2, 4.9 Hz, 1H), 2.49-2.33 (m, 2H), 2.27-1.98 (m, 10H), 1.93-1.81 (m, 2H), 1.81-1.74 (m, 2H), 1.72 (s, 4H), 1.69-1.40 (m, 12H), 1.38-1.34 (m, 1H), 1.21-1.03 (m, 9H), 1.02-0.86 (m, 8H).

Example A27

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-((4-methoxypyrimidin-2-yl)oxy)ethyl)cyclohex-3-ene-1-carboxylic acid.

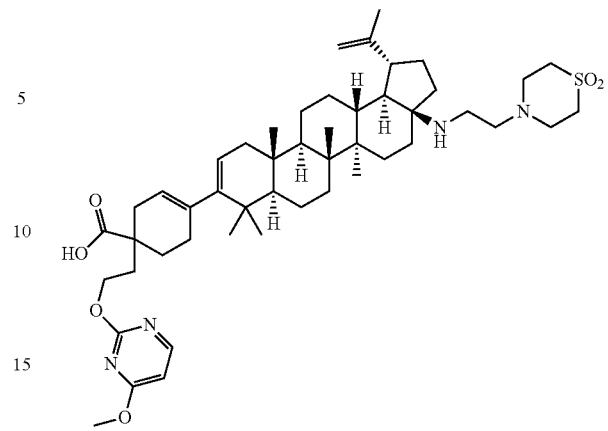

The title compound was prepared following the procedure described for the preparation of 2-(2-(1-carboxy-4-((1R,3aS,5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2-chloro-4-methoxypyrimidine (0.023 g, 0.161 mmol) was used instead of 2-chloroisonicotinic acid, and there was also less potassium tert-butoxide, 1.0M in THF used in the present case (0.129 mL, 0.129 mmol). The title compound was isolated as a white solid (0.0116 g, 28.8% yield) TFA salt. LCMS m/z=847.7 (M+H⁺), retention time 1.525 min (LCMS Method 20). ¹H NMR (400 MHz, 1:1 mixture of CDCl₃ and CD3OD, CD3OD lock) δ 7.28 (d, J=7.6 Hz, 1H), 5.62 (d, J=7.6 Hz, 1H), 5.40-5.33 (m, 1H), 5.23 (d, J=4.9 Hz, 1H), 4.79 (s, 1H), 4.71 (s, 1H), 4.41-4.29 (m, 2H), 3.27-2.97 (m, 12H), 2.81 (td, J=11.2, 4.9 Hz, 1H), 2.43-2.33 (m, 1H), 2.28-1.98 (m, 10H), 1.92-1.81 (m, 2H), 1.80-1.73 (m, 2H), 1.73 (s, 3H), 1.70-1.40 (m, 12H), 1.38-1.34 (m, 1H), 1.16 (s, 3H), 1.15-1.09 (m, 2H), 1.08 (s, 3H), 1.00 (d, J=3.2 Hz, 3H), 0.96 (d, J=7.6 Hz, 3H), 0.91 (s, 3H).

Example A28

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-((3-methylpyridin-2-yl)oxy)ethyl)cyclohex-3-ene-1-carboxylic acid.

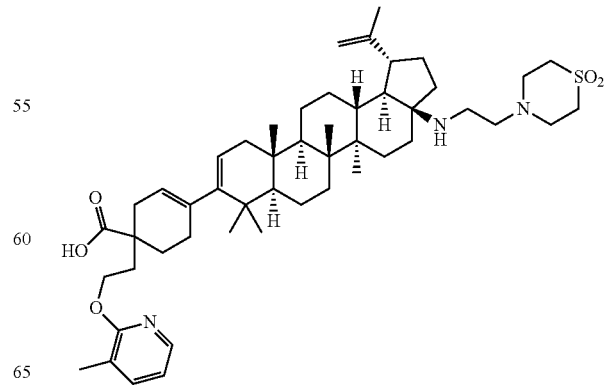

The title compound was prepared following the procedure described for the preparation of 2-(2-(1-carboxy-4-((1R,3aS, 5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-en-1-yl)ethoxy)isonicotinic acid, except in the present case 2-fluoro-3-methylpyridine (0.018 g, 0.161 mmol) was used instead of 2-chloroisonicotinic acid, and there was also less potassium tert-butoxide, 1.0M in THF used in the present case (0.129 mL, 0.129 mmol). The title compound was isolated as a white solid (0.0262 g, 74.7% yield) TFA salt. LCMS m/z=830.7 (M+H$^+$), retention time 1.707 min (LCMS Method 20). $^1$H NMR (400 MHz, 1:1 mixture of CDCl$_3$ and CD3OD, CD3OD lock) δ 7.89 (dd, J=5.1, 1.2 Hz, 0.35H), 7.44 (dd, J=7.1, 1.0 Hz, 0.35H), 7.42-7.37 (m, 0.65H), 7.22 (dd, J=6.5, 1.3 Hz, 0.65H), 6.81 (dd, J=7.0, 5.3 Hz, 0.35H), 6.29 (t, J=6.7 Hz, 0.65H), 5.39-5.30 (m, 1H), 5.23 (d, J=4.9 Hz, 0.65H), 5.18 (d, J=4.6 Hz, 0.35H), 4.79 (s, 1H), 4.71 (s, 1H), 4.41-4.29 (m, 2H), 3.27-2.98 (m, 12H), 2.81 (td, J=11.1, 4.6 Hz, 1H), 2.43-2.33 (m, 1H), 2.30-2.07 (m, 10H), 2.07-1.94 (m, 4H), 1.92-1.73 (m, 4H), 1.72 (s, 3H), 1.69-1.40 (m, 12H), 1.38-1.34 (m, 1H), 1.20-1.05 (m, 9H), 1.02-0.86 (m, 9H).

Example A29

Preparation of 1-(2-((3-chloropyridin-2-yl)oxy)ethyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)cyclohex-3-ene-1-carboxylic acid.

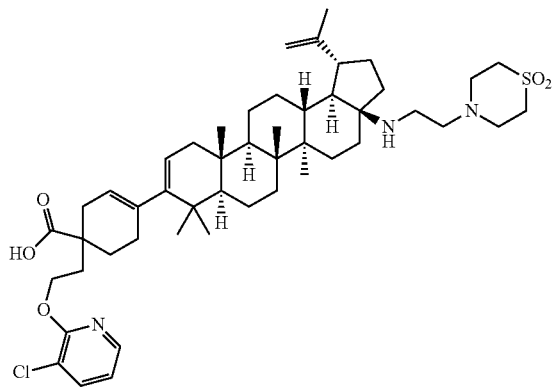

The title compound was prepared following the procedure described for the preparation of 2-(2-(1-carboxy-4-((1R,3aS, 5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-en-1-yl)ethoxy)isonicotinic acid, except in the present case 3-chloro-2-fluoropyridine (0.021 g, 0.161 mmol) was used instead of 2-chloroisonicotinic acid, and there was also less potassium tert-butoxide, 1.0M in THF used in the present case (0.129 mL, 0.129 mmol). The title compound was isolated as a white solid (0.0156 g, 42.7% yield) TFA salt. LCMS m/z=850.6 (M+H$^+$), retention time 1.770 min (LCMS Method 20). $^1$H NMR (400 MHz, 1:1 mixture of CDCl$_3$ and CD3OD, CD3OD lock) δ 7.99 (dd, J=4.9, 1.7 Hz, 1H), 7.65 (dd, J=7.7, 1.6 Hz, 1H), 6.86 (dd, J=7.6, 4.9 Hz, 1H), 5.33 (br. s., 1H), 5.17 (d, J=4.6 Hz, 1H), 4.79 (s, 1H), 4.72 (s, 1H), 4.45 (t, J=6.6 Hz, 2H), 3.27-2.98 (m, 12H), 2.80 (td, J=11.1, 4.8 Hz, 1H), 2.60 (d, J=15.7 Hz, 1H), 2.25-1.95 (m, 10H), 1.90-1.74 (m, 3H), 1.73 (s, 3H), 1.68-1.42 (m, 10H), 1.40 (br. s., 1H), 1.38-1.29 (m, 2H), 1.29-1.23 (m, 1H), 1.15 (s, 3H), 1.12 (d, J=5.4 Hz, 1H), 1.08 (s, 3H), 0.99-0.84 (m, 9H).

Example A30

Preparation of 4-((1R,3aS,5aR,5bR,7aR,11aS,11bR, 13aR,13bR)-3a-((2-(1,1-dioxidothiomorpholino)ethyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)-1-(2-((3-(trifluoromethyl)pyridin-2-yl)oxy)ethyl)cyclohex-3-ene-1-carboxylic acid.

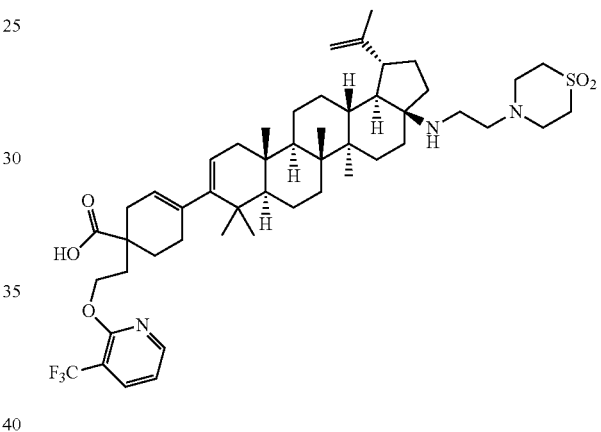

The title compound was prepared following the procedure described for the preparation of 2-(2-(1-carboxy-4-((1R,3aS, 5aR,5bR,7aR,11aS,11bR,13aR,13bR)-3a-((2-(1,1-dioxido-thiomorpholino)ethypamino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-en-1-yl)ethoxy)isonicotinic acid, except in the present case 2-chloro-3-(trifluoromethyl)pyridine (0.029 g, 0.161 mmol) was used instead of 2-chloroisonicotinic acid, and there was also less potassium tert-butoxide, 1.0M in THF used in the present case (0.129 mL, 0.129 mmol). The title compound was isolated as a white solid (0.0020 g, 4.9% yield) TFA salt. LCMS m/z=884.6 (M+H$^+$), retention time 1.810 min (LCMS Method 20).

Example A31

Preparation of 4-((1R,3aS,5aR,5bR,7aR,11aS,11bR, 13aR,13bR)-3a-((2-(1,1-dioxidothiomorpholino)ethyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)-1-(2-(pyrazin-2-yloxy)ethyl)cyclohex-3-ene-1-carboxylic acid.

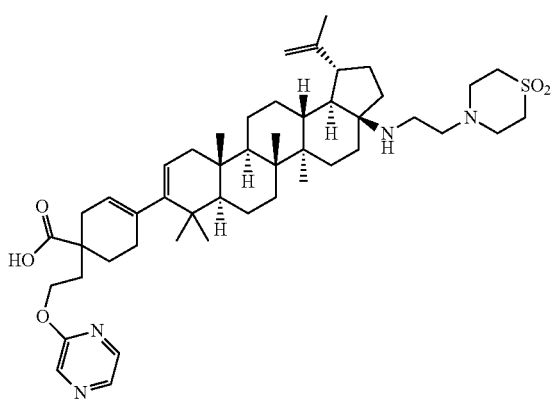

The title compound was prepared following the procedure described for the preparation of 2-(2-(1-carboxy-4-((1R,3aS,5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2-chloropyrazine (0.018 g, 0.161 mmol) was used instead of 2-chloroisonicotinic acid, and there was also less potassium tert-butoxide, 1.0M in THF used in the present case (0.129 mL, 0.129 mmol). The title compound was isolated as a white solid (0.0102 g, 28.2% yield) TFA salt. LCMS m/z=817.6 (M+H$^+$), retention time 1.592 min (LCMS Method 20). $^1$H NMR (400 MHz, 1:1 mixture of CDCl$_3$ and CD3OD, CD3OD lock) δ 8.16-8.08 (m, 2H), 8.05 (d, J=2.4 Hz, 1H), 5.33 (br. s., 1H), 5.18 (d, J=5.4 Hz, 1H), 4.79 (s, 1H), 4.71 (br. s., 1H), 4.44 (t, J=6.2 Hz, 2H), 3.27-3.13 (m, 7H), 3.13-3.05 (m, 3H), 3.05-2.95 (m, 2H), 2.86-2.74 (m, 1H), 2.60 (d, J=17.4 Hz, 1H), 2.25-1.96 (m, 10H), 1.89-1.81 (m, 1H), 1.81-1.74 (m, 2H), 1.73 (s, 4H), 1.65-1.42 (m, 10H), 1.40 (br. s., 1H), 1.38-1.24 (m, 3H), 1.15 (s, 3H), 1.11 (br. s., 2H), 1.08 (s, 3H), 1.01-0.86 (m, 9H).

Example A32

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(2-((4-methoxypyridin-2-yl)oxy)ethyl)cyclohex-3-ene-1-carboxylic acid.

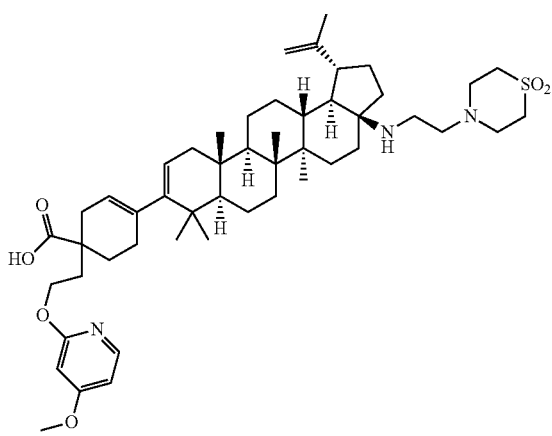

The title compound was prepared following the procedure described for the preparation of 2-(2-(1-carboxy-4-((1R,3aS,5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2-bromo-4-methoxypyridine (0.030 g, 0.161 mmol) was used instead of 2-chloroisonicotinic acid, and there was also less potassium tert-butoxide, 1.0M in THF used in the present case (0.129 mL, 0.129 mmol). The title compound was one of two compounds isolated from this reaction. The material was obtained as a white solid (0.0068 g, 18.3% yield) TFA salt. LCMS m/z=846.7 (M+H$^+$), retention time 1.335 min (LCMS Method 20). $^1$H NMR (400 MHz, 1:1 mixture of CDCl$_3$ and CD3OD, CD3OD lock) δ 7.97 (d, J=6.6 Hz, 1H), 6.76 (dd, J=6.6, 2.2 Hz, 1H), 6.59 (d, J=2.0 Hz, 1H), 5.34 (br. s., 1H), 5.18 (d, J=4.6 Hz, 1H), 4.79 (s, 1H), 4.71 (s, 1H), 4.42 (t, J=6.7 Hz, 2H), 3.98 (s, 3H), 3.27-3.04 (m, 10H), 3.01 (d, J=3.4 Hz, 2H), 2.86-2.76 (m, 1H), 2.67-2.57 (m, 1H), 2.27-2.15 (m, 3H), 2.15-1.96 (m, 8H), 1.85 (td, J=12.2, 3.3 Hz, 1H), 1.81-1.73 (m, 2H), 1.72 (s, 4H), 1.66-1.38 (m, 10H), 1.38-1.28 (m, 2H), 1.15 (s, 3H), 1.12 (br. s., 2H), 1.07 (s, 3H), 1.01-0.85 (m, 9H).

Example A33

Preparation of 1-(2-((4-bromopyridin-2-yl)oxy)ethyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

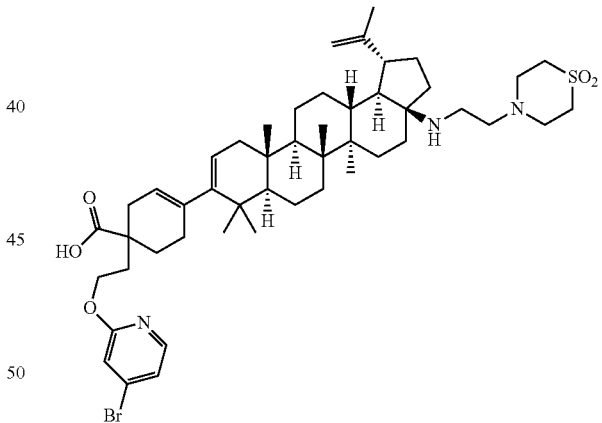

The title compound was prepared following the procedure described for the preparation of 2-(2-(1-carboxy-4-((1R,3aS,5aR,5bR,7aR,11aS,11bR,13aR,13bR)-3a-((2-(1,1-dioxido-thiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2-bromo-4-methoxypyridine (0.030 g, 0.161 mmol) was used instead of 2-chloroisonicotinic acid, and there was also less potassium tert-butoxide, 1.0M in THF used in the present case (0.129 mL, 0.129 mmol). The title compound was one of two compounds isolated from this reaction. The material was obtained as a white solid (0.0045 g, 12.2% yield) TFA salt. LCMS m/z=894.5 (M+H$^+$), retention time 1.672 min (LCMS Method 20). ¹H NMR (400 MHz, 1:1 mixture of CDCl₃ and CD3OD, CD3OD lock) δ 8.09 (d, J=5.9 Hz, 1H), 7.06 (d, J=2.2 Hz, 1H), 6.86 (dd, J=5.9, 2.2 Hz, 1H), 5.33 (br. s., 1H), 5.21-5.15 (m, 1H), 4.80 (s, 1H), 4.72 (s, 1H), 4.16 (t, J=6.6 Hz, 2H), 3.27-2.98 (m, 12H), 2.84-2.74 (m, 1H), 2.60 (dd, J=18.7, 2.8 Hz, 1H), 2.24-1.96 (m, 11H), 1.87-1.74 (m, 3H), 1.73 (s, 4H), 1.68-1.55 (m, 4H), 1.55-1.38 (m, 7H), 1.38-1.25 (m, 2H), 1.15 (s, 3H), 1.14-1.10 (m, 1H), 1.08 (s, 3H), 1.01-0.96 (m, 3H), 0.96-0.91 (m, 3H), 0.90 (s, 3H).

Example A34

Preparation of 1-(2-((4-chloropyridin-2-yl)oxy)ethyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

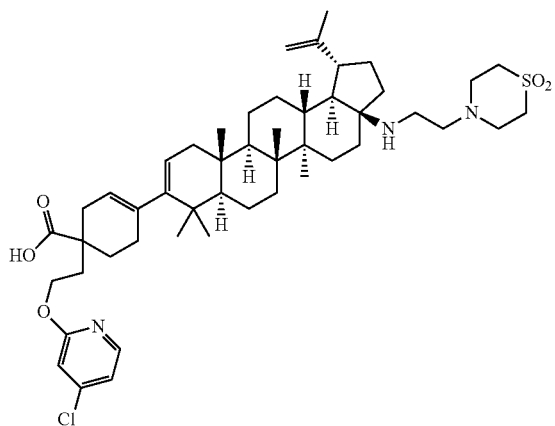

The title compound was prepared following the procedure described for the preparation of 2-(2-(1-carboxy-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2,4-dichloropyridine (0.024 g, 0.161 mmol) was used instead of 2-chloroisonicotinic acid, and there was also less potassium tert-butoxide, 1.0M in THF used in the present case (0.129 mL, 0.129 mmol). The title compound was one of two compounds isolated from this reaction. The material was obtained as a slightly yellow solid (0.0143 g, 38.7% yield) TFA salt. LCMS m/z=850.6 (M+H⁺), retention time 1.637 min (LCMS Method 20). ¹H NMR (400 MHz, 1:1 mixture of CDCl₃ and CD3OD, CD3OD lock) δ 8.11 (d, J=5.9 Hz, 1H), 6.91 (d, J=2.2 Hz, 1H), 6.83 (dd, J=5.9, 2.2 Hz, 1H), 5.33 (br. s., 1H), 5.18 (d, J=4.6 Hz, 1H), 4.79 (s, 1H), 4.71 (s, 1H), 4.17 (t, J=6.6 Hz, 2H), 3.27-2.98 (m, 12H), 2.80 (td, J=11.2, 4.8 Hz, 1H), 2.60 (d, J=16.6 Hz, 1H), 2.26-1.97 (m, 11H), 1.89-1.74 (m, 3H), 1.72 (s, 4H), 1.67-1.38 (m, 11H), 1.38-1.27 (m, 2H), 1.15 (s, 3H), 1.10 (d, J=11.0 Hz, 1H), 1.07 (s, 3H), 0.99-0.86 (m, 9H).

Example A35

Preparation of 1-(2-((2-chloropyridin-4-yl)oxy)ethyl)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1-carboxylic acid.

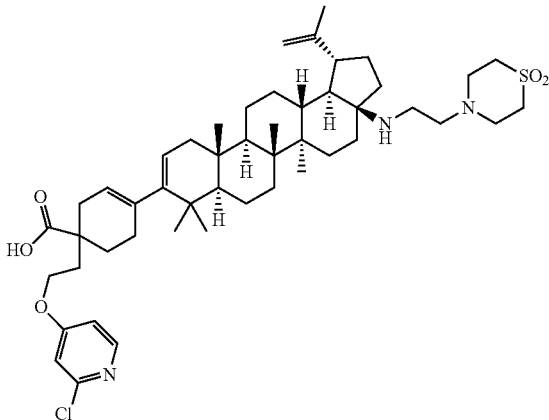

The title compound was prepared following the procedure described for the preparation of 2-(2-(1-carboxy-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)ethoxy)isonicotinic acid, except in the present case 2,4-dichloropyridine (0.024 g, 0.161 mmol) was used instead of 2-chloroisonicotinic acid, and there was also less potassium tert-butoxide, 1.0M in THF used in the present case (0.129 mL, 0.129 mmol). The title compound was one of two compounds isolated from this reaction. The material was obtained as a slightly yellow solid (0.0168 g, 41.2% yield) TFA salt. LCMS m/z=850.6 (M+H⁺), retention time 1.809 min (LCMS Method 20). ¹H NMR (400 MHz, 1:1 mixture of CDCl₃ and CD3OD, CD3OD lock) δ 8.00 (d, J=5.6 Hz, 1H), 6.90 (dd, J=5.6, 1.7 Hz, 1H), 6.76 (d, J=1.7 Hz, 1H), 5.32 (br. s., 1H), 5.17 (d, J=4.9 Hz, 1H), 4.79 (s, 1H), 4.71 (s, 1H), 4.41-4.33 (m, 2H), 3.28-2.98 (m, 12H), 2.80 (td, J=11.0, 4.6 Hz, 1H), 2.58 (d, J=15.4 Hz, 1H), 2.26-1.96 (m, 11H), 1.89-1.73 (m, 2H), 1.72 (s, 4H), 1.67-1.38 (m, 11H), 1.38-1.26 (m, 2H), 1.18-1.04 (m, 8H), 1.01-0.86 (m, 9H).

HIV Cell Culture Assay

Cells. MT-2 cells and 293T cells were obtained from the NIH AIDS Research and Reference Reagent Program. Cell lines were sub-cultured twice a week in either RPMI 1640 (MT-2) or DMEM (293T, HeLa) media supplemented with 10% heat inactivated fetal bovine serum (FBS), 100 units/mL of penicillin G and 100 μg/mL of streptomycin. The DMEM medium was additionally supplemented with 10 mM HEPES buffer, pH 7.55, 2 mM L-glutamine and 0.25 μg/mL of amphotericin B.

Viruses. NLRepRluc virus contains the *Renilla luciferase marker in place of the viral nef gene. The proviral plasmid pNLRepRluc was constructed at Bristol*-Myers Squibb, starting from a proviral NL4-3 clone (B subtype) that was obtained from the NIH AIDS Research and Reference Reagent Program. The parental recombinant wild type (WT) virus (NLRepRlucP373S) was derived from NLRepRluc and contains the additional substitution of P373 for serine in Gag (within the SP1 spacer), the most common 373 variation in subtype B. Other recombinant viruses (A364V, V370A/ΔT371 and the "T3325 triple" (T332S/V362I+ HIV-1 protease $R_{41}G$)) were generated by site-directed mutagenesis of plasmid pNLRepRlucP373S to introduce those amino acid substitutions in Gag and protease. Recombinant virus DNA was then used to generate virus stocks by transfection of 293T cells (Lipofectamine PLUS kit, Invitrogen). Titers of virus stocks were determined using a luciferase assay (Dual-Luciferase® Reporter Assay System, Promega, Milwaukee, Wis., USA) endpoint.

Multiple cycle drug susceptibility assay. Pellets of MT-2 cells were infected with NLRepRlucP373S Gag site-directed viruses, where initial inocula of the reporter strains were normalized using equivalent endpoint luciferase activity signals. Such cell-virus mixtures were resuspended in medium, incubated for 1-hour at 37° C./$CO_2$, and added to compound containing 96-well plates at a final cell density of 10,000 cells per well. The test compounds were 3-fold serially diluted in 100% DMSO, and assayed at a final DMSO concentration of 1%. After 4-5 day incubation at 37° C./$CO_2$, virus yields were determined by *Renilla* luciferase activity (Dual-Luciferase® Reporter Assay System, Promega). The endpoint luminescence was detected on a Wallac Trilux (PerkinElmer).

The 50% inhibitory concentrations ($EC_{50S}$) were calculated by using the exponential form of the median effect equation where Percent Inhibition=$1/[1+(EC_{50}/drug\ conc.)^m]$, where m is a parameter that reflects the slope of the concentration-response curve. Background was taken as the residual signal observed upon inhibition at the highest concentration of a control protease inhibitor, NFV (3 µM).

The 90% inhibitory concentrations ($EC_{90S}$) were calculated by using the exponential form of the median effect equation where $EC_F=[(F/(100-F)]^{1/H} \cdot EC_{50}$, where H is a parameter that reflects the slope of the concentration-response curve. Background was taken as the residual signal observed upon inhibition at the highest concentration of a control protease inhibitor, NFV (3 µM).

HIV Cell Culture Assay

HIV-1 $NL_{4-3}$ expressing *Renilla* luciferase gene was converted to the gag V370A/ΔT371 virus by site directed mutagenesis. A364V is a site directed mutant.

T332sN362I/Pr $R_{41}G$ (N14.3, B Clade) virus' was obtained as follows: Selection for resistance of HIV-1 strain NL4-4 virus with the HIV maturation inhibitor (MI) compound

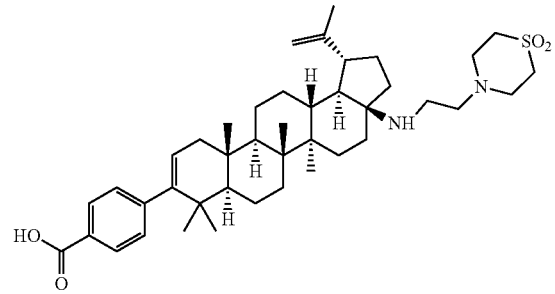

was started at the $EC_{50}$ for this virus (2 nM), with a two-fold increase in the maturation inhibitor compound concentration applied at each passage. At passage 8 virus was harvested and sequenced. The selected virus population contained Gag amino acid substitutions T332S and V362I and the $R_{41}G$ substitution in protease. These substitutions were subsequently introduced into NLRepRlucP373, a derivative of HIV-1 clone NL4-3 modified to contain P373S, the most common polymorphic substitution in subtype B at position 373, and the *Renilla* luciferase gene inserted into the nef locus.

The emergence of selected substitutions in the wt genotypic background is discussed herein:

Starting from wt virus, the HIV protease $R_{41}G$ substitution was detected in one of three in vitro selections for resistance to the MI compound above along with Gag V362I and Gag T332S. $R_{41}G$ is not a primary PI resistance substitution[i] and is not present in the LANL database (2010). There is a single report of $R_{41}G$ associated with in vitro selection for resistance to an investigational PI[ii]. However, in that case, $R_{41}G$ did not itself convey PI resistance. A related change, $R_{41}K$, is a common subtype B polymorph (27% of LANL database), and $R_{41}K$ may be involved in the emergence of protease resistance to an investigational protease inhibitor.[iii] R41 is located in a loop proximal to the HIV-1 protease substrate binding site, and this change might act allosterically to facilitate closing the protease active site pocket over the substrate, thereby allowing catalysis. It might be that $R_{41}G$ alters the dynamics of the loop motion and the final positioning of the loop, which could cause the active site to better recognize the primary MI compound (above)-selected changes (V362I/T332S). An analysis of the V362I/T332S/Pr $R_{41}G$ substitutions, and their effects on MI compound susceptibility and viral growth, are described in the Table 1 below:

TABLE 1

Anti-Viral Sensitivity of Site Directed Mutants

| | | Virus titer, $TCID_{50}$ ($\times 10^5$/mL) | | | Fold wt | |
|---|---|---|---|---|---|---|
| | | | | | MI | BVM |
| Group | Genotype | CPE | Rluc | RT | Compound | (Bevirimat) |
| | Key substitutions Crosswise effects of T332S and Pr R41G on V362I | | | | | |
| 6 | V362I | 2.6 | 1.6 | 2.6 | 2.2 | 0.6 |
| | T332S | 2.6 | 6.6 | 0.4 | 1.9 | 23 |
| | HIV protease R41G | 2.6 | 2.6 | 1.0 | 1.5 | 1.9 |
| | T332S/V362I/ | 4.1 | 6.6 | 4.1 | 5.7 | 3.1 |

TABLE 1-continued

Anti-Viral Sensitivity of Site Directed Mutants

| Group | Genotype | Virus titer, $TCID_{50}$ ($\times 10^5$/mL) CPE | Rluc | RT | Fold wt MI Compound | Fold wt BVM (Bevirimat) |
|---|---|---|---|---|---|---|
| | T332S/prR41G | 0.6 | 1.0 | 0.4 | 6.1 | 4.2 |
| | V362I/prR41G | 0.6 | 1.6 | 0.6 | 9.3 | 3.9 |
| | T332S/V362I/Pr41G | 0.3 | 1.6 | 0.1 | 217 | 10 |

Viruses were constructed that contain T332S and HIV protease $R_{41}G$ combinations, with and without V362I.). Viruses with only a single change are only 2-fold less sensitive to the MI compound, while double combinations of these 3 substitutions are 5.7- to 9.3-fold less sensitive. The virus with the triple change is much less sensitive to the MI compound, suggesting that the $R_{41}G$ change in protease may 'crosstalk' with Gag changes to further reduce sensitivity to the MI compound, an unexpected finding. Thus, the T332S/V362I Site directed mutant (SDM) virus exhibits a fold change of only 5.7, but addition of the $R_{41}G$ protease change substantially increases the FC to 217.

[i] Johnson V A, Brun-Vezinet F, Clotet B, Gunthard H F, Kuritzkes D R, Pillay D, Schapiro J M, Richman D D. Update of the drug resistance mutations in HIV-1: December 2009. Top HIV Med. 2009 December; 17(5):138-45.

[ii] Dierynck, I, Van Markck, H, Van Ginderen, M, Jonckers, T H, Nalam, M N, Schiffer, C A, Raoof, A, Kraus, G, Picchio, G. TMC310911, a novel human immunodeficiency virus type 1 protease inhibitor, shows in vitro an improved resistance profile and higher genetic barrier to resistance compared

[iii] Stray K M, Callebaut C, Glass B, Tsai L, Xu L, Muller B, Krausslich H G, Cihlar T. Mutations in multiple domains of Gag drive the emergence of in vitro resistance to the phosphonate-containing HIV-1 protease inhibitor GS-8374. J Virol. 2013 87:454-63

All three recombinant viruses were used as described above in the HIV cell culture assay for the $NL_{4-3}$ virus. The $EC_{50}$ WT, $EC_{50}$ V370A/ΔT371, $EC_{50}$A364V and $EC_{50}$ T332s/V362I/Pr $R_{41}G$ data for the compounds is shown in Table 2.

Biological Data Key for $EC_{50S}$

| Compounds with $EC_{50} > 0.05$ μM | Compounds with $EC_{50} < 0.0.5$ μM |
|---|---|
| Group "B" | Group "A" |

TABLE 2

| Ex # | Structure | WT $EC_{50}$ (μM) | V370A/ ΔT371 $EC_{50}$ (μM) | A364V $EC_{50}$ (μM) | T332S/ V362I/ pr41G $EC_{50}$ (μM) |
|---|---|---|---|---|---|
| 1 | 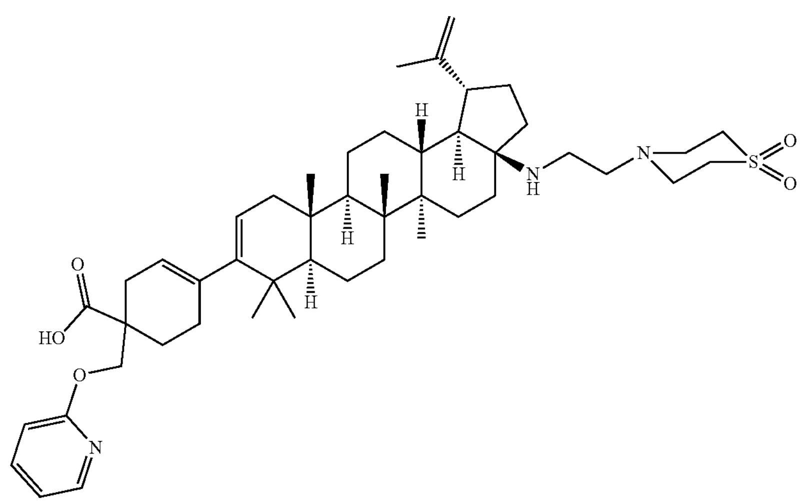 | 0.003 | 0.017 | 0.011 | 0.014 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
| --- | --- | --- | --- | --- | --- |
| 2 | 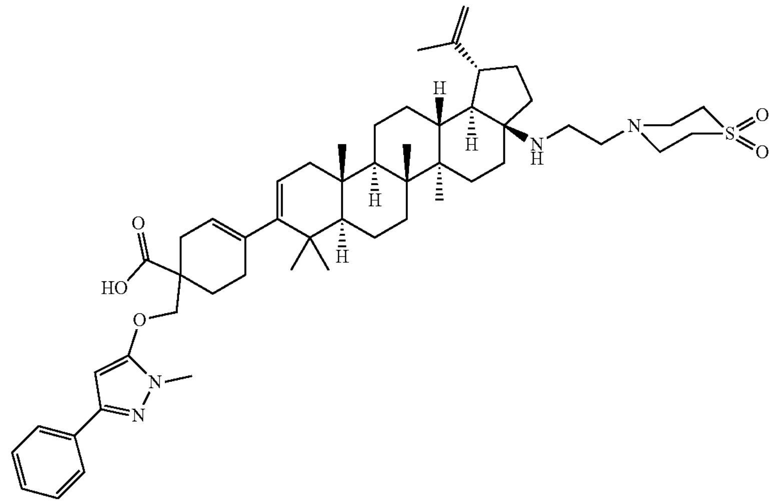 | 3.000 | — | 1.941 | 3.000 |
| 3 | 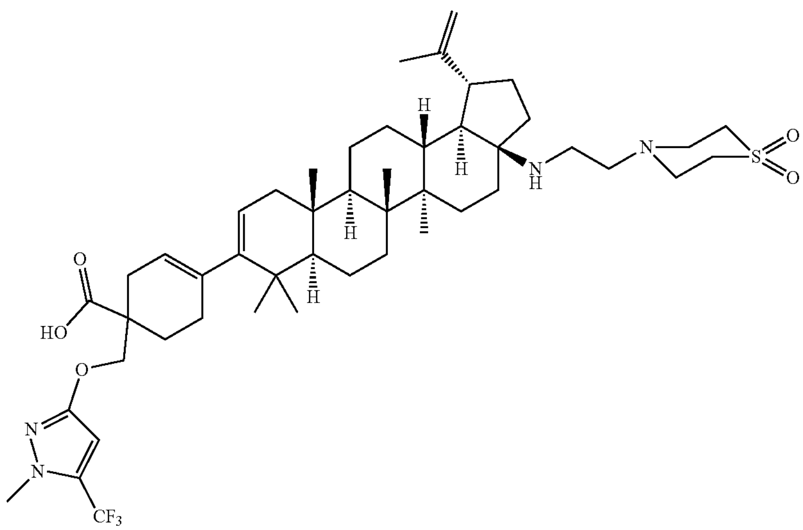 | 0.009 | — | 2.218 | 2.167 |
| 4 | 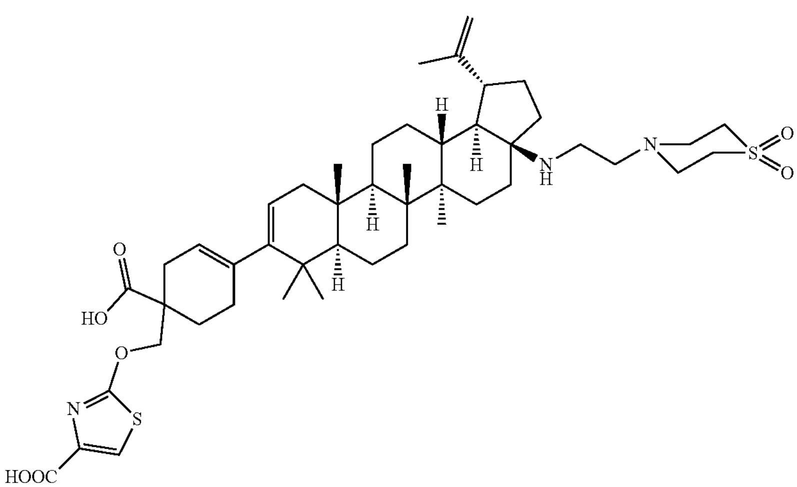 | B | B | B | B |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 5 | 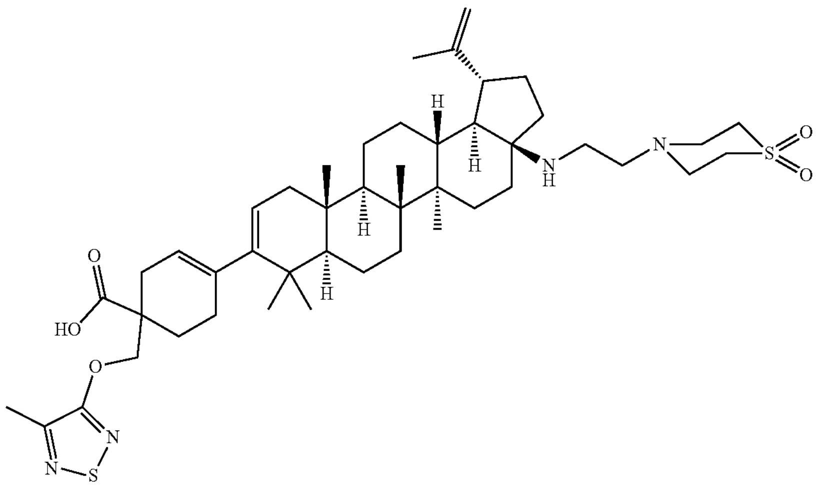 | 0.003 | 0.015 | 0.015 | 0.015 |
| 6 | 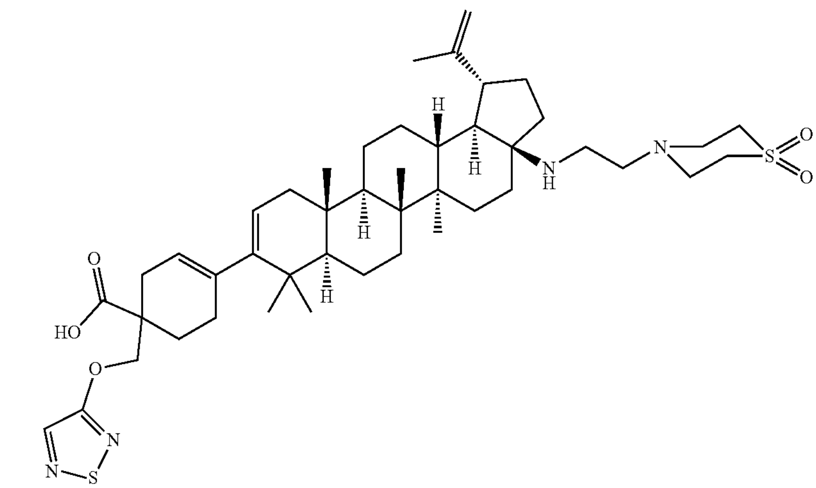 | A | A | B | A |
| 7 | 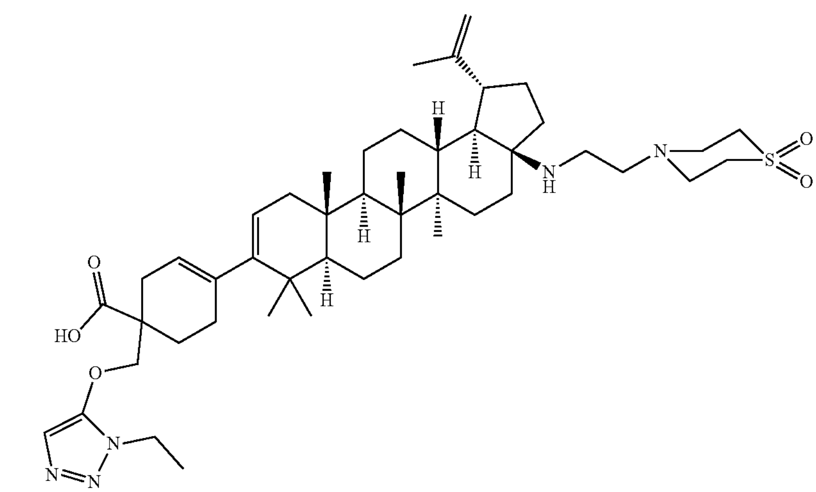 | 0.002 | 0.192 | 0.095 | 0.192 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 8 | 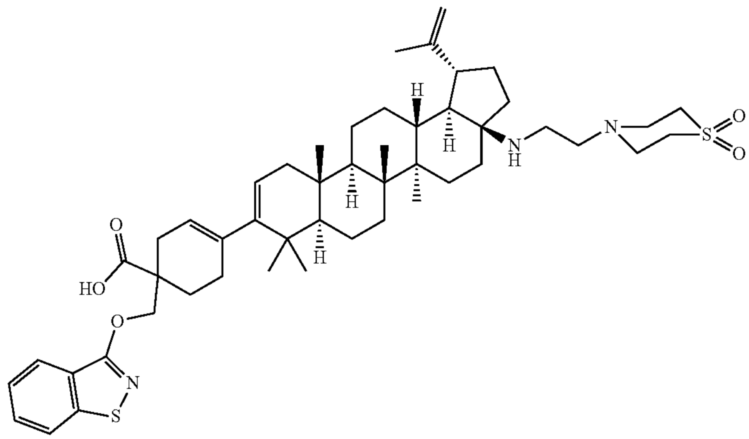 | A | A | A | A |
| 9 | 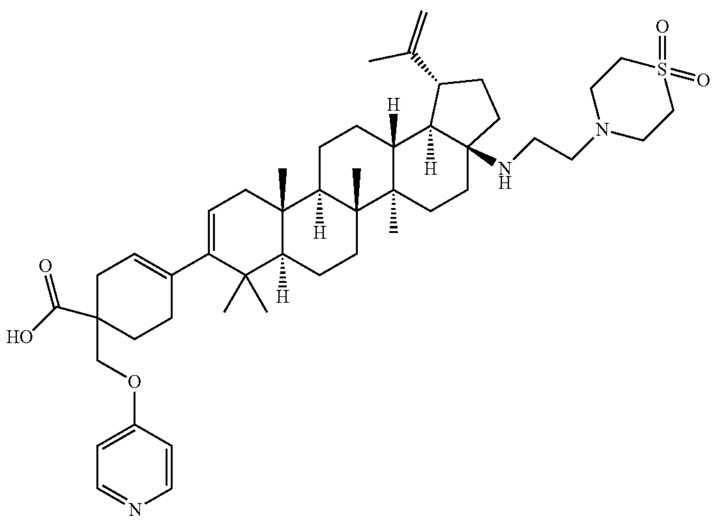 | 0.002 | — | 0.035 | 0.014 |
| 10 | 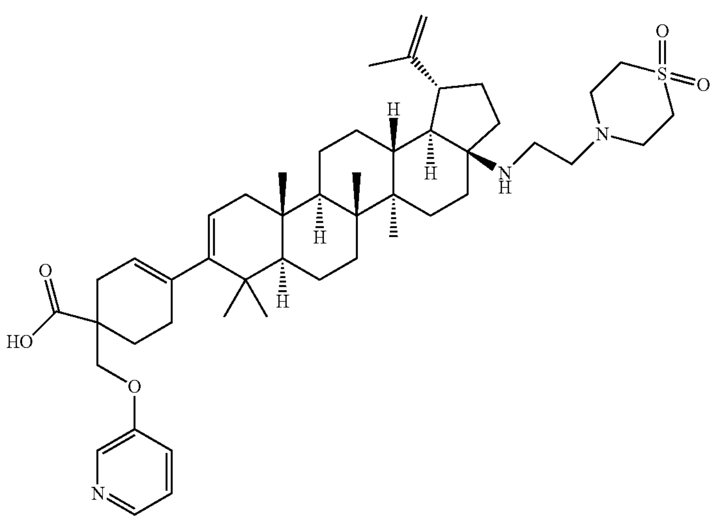 | 0.002 | — | 0.027 | 0.006 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 11 | 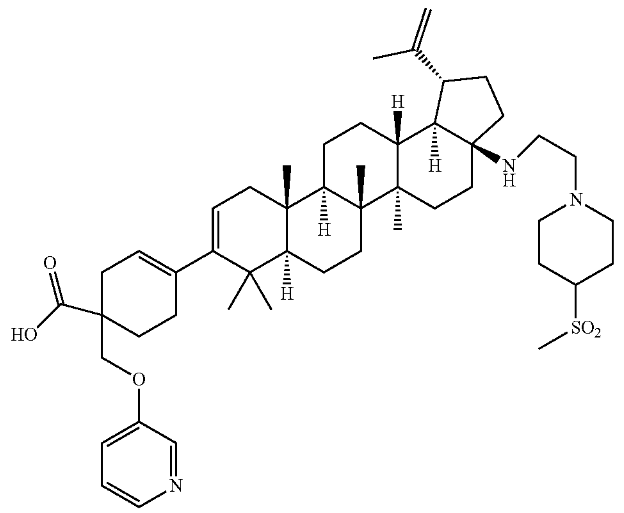 | 0.002 | — | 0.018 | 0.008 |
| 12 | 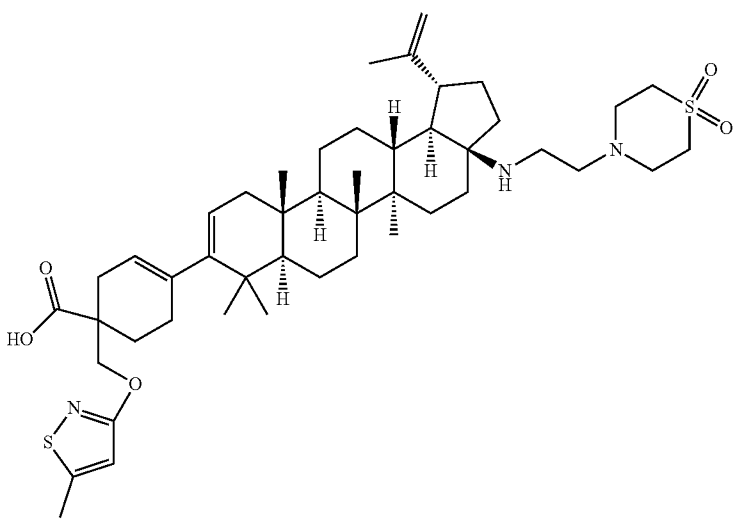 | A | A | A | A |
| 13 | 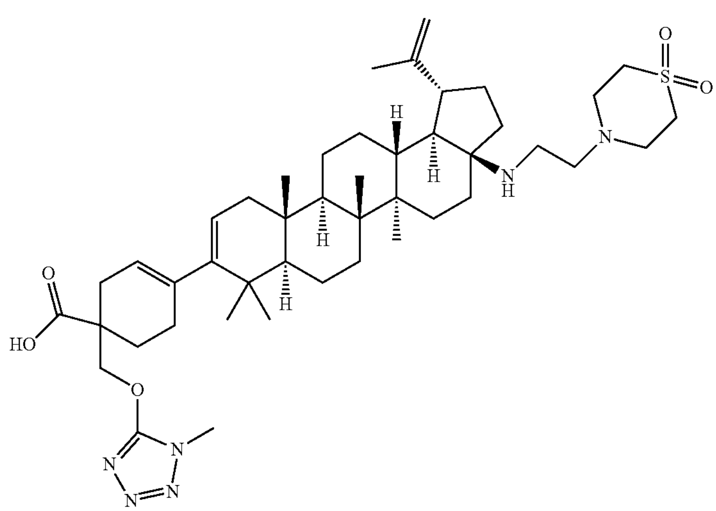 | 0.002 | 0.007 | 0.024 | 0.007 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
| --- | --- | --- | --- | --- | --- |
| 14 | 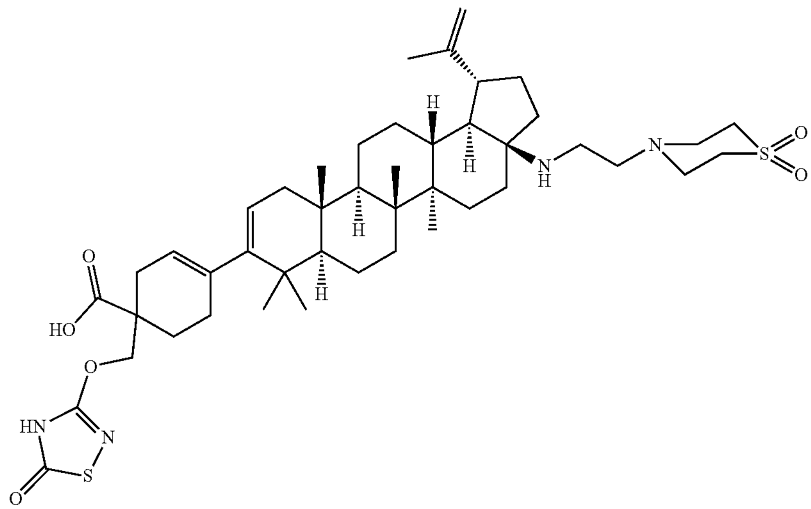 | 0.027 | B | B | B |
| 15 | 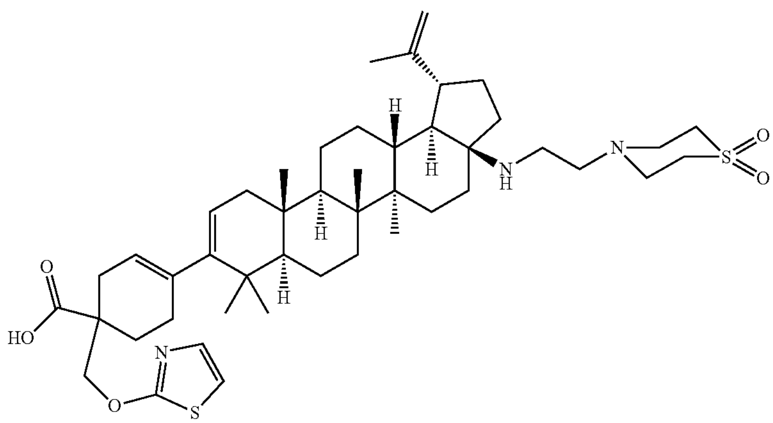 | 0.004 | 0.390 | 2.376 | 0.390 |
| 16 | 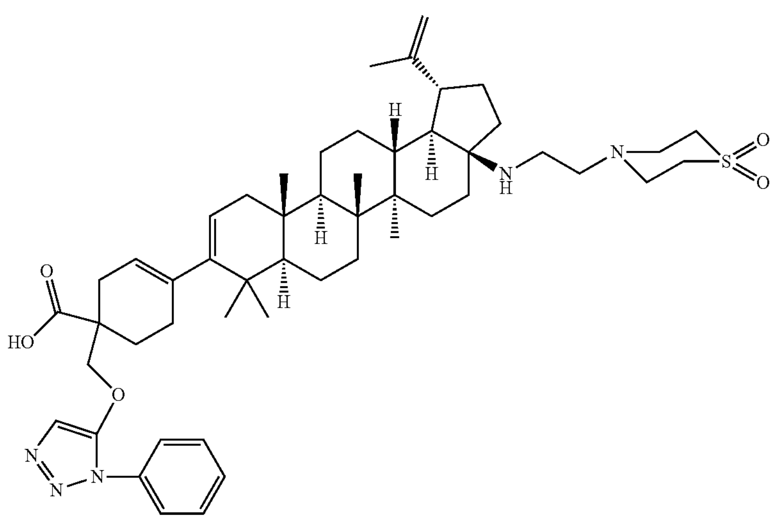 | 0.005 | 0.030 | 0.032 | 0.030 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
| --- | --- | --- | --- | --- | --- |
| 17 | 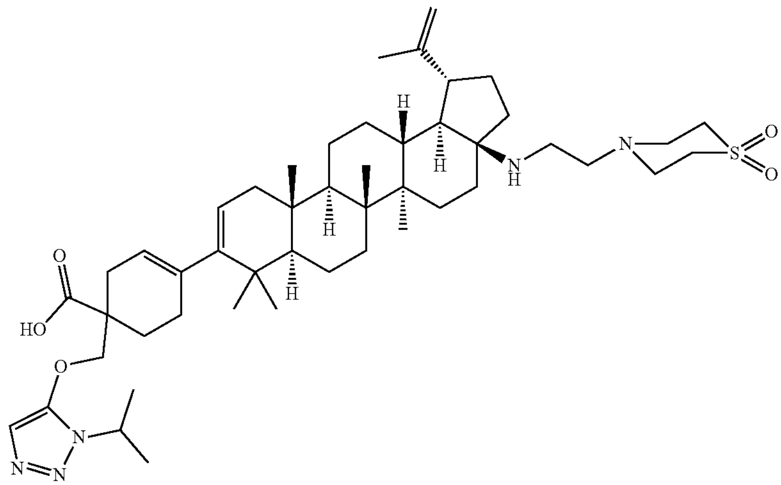 | 0.003 | 0.015 | B | 0.015 |
| 18 | 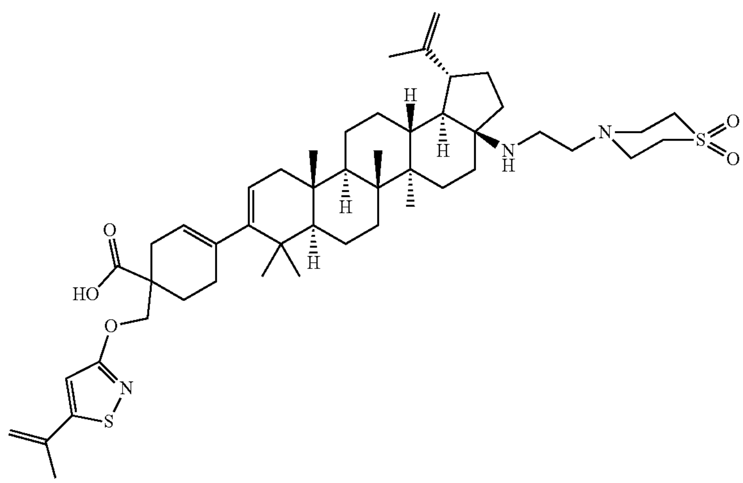 | 0.002 | A | 0.011 | 0.014 |
| 19 | 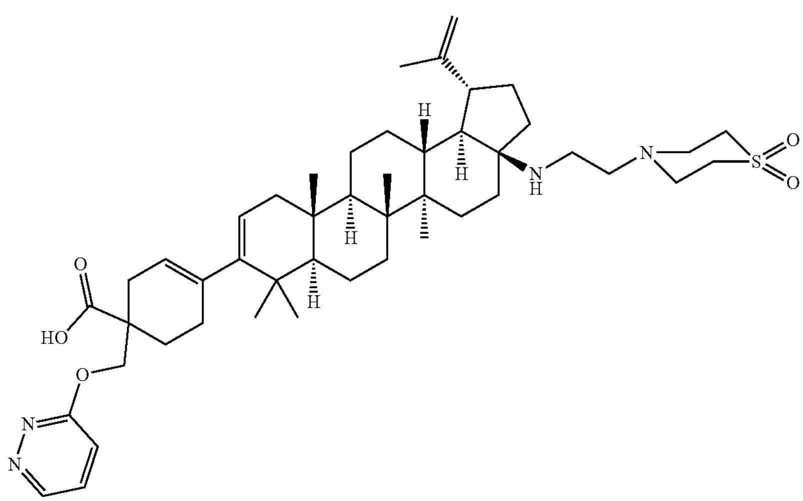 | 0.003 | 0.047 | 0.036 | 0.047 |

TABLE 2-continued
| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 20 | 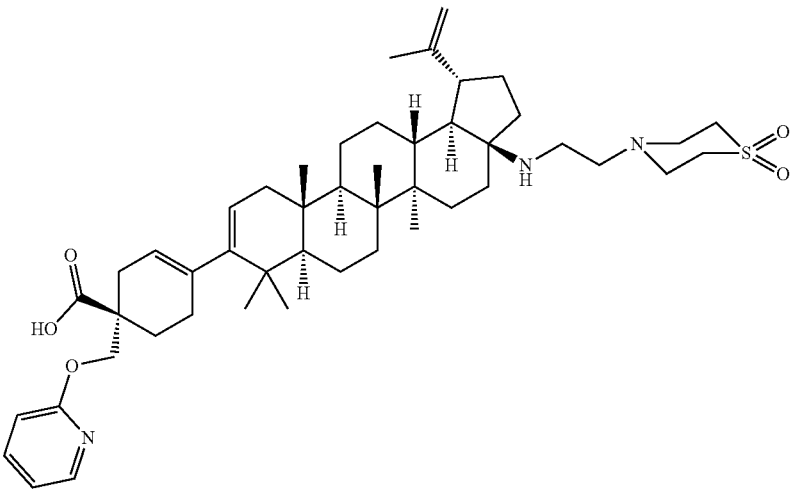 | A | A | A | A |
| 21 | 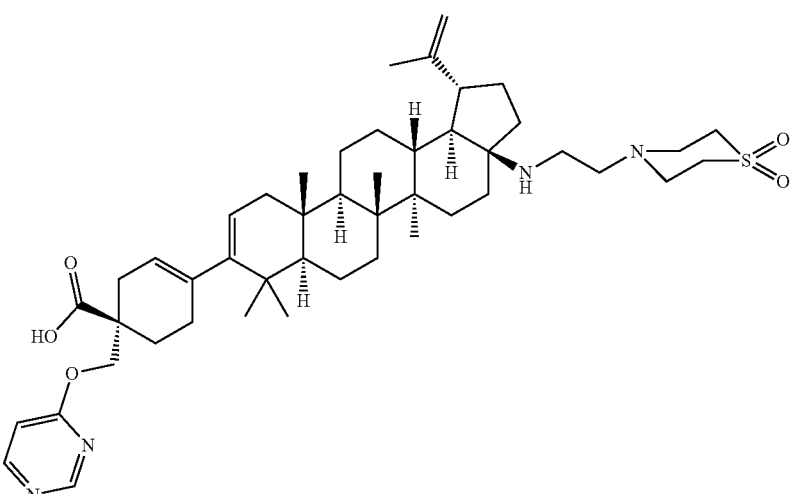 | A | B | A | B |
| 22 | 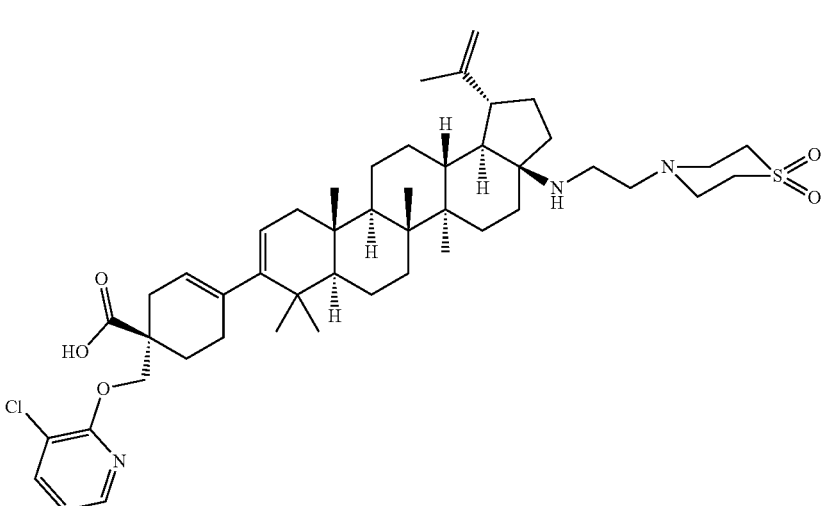 | 0.005 | 0.015 | 0.008 | 0.015 |

TABLE 2-continued
| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 23 | 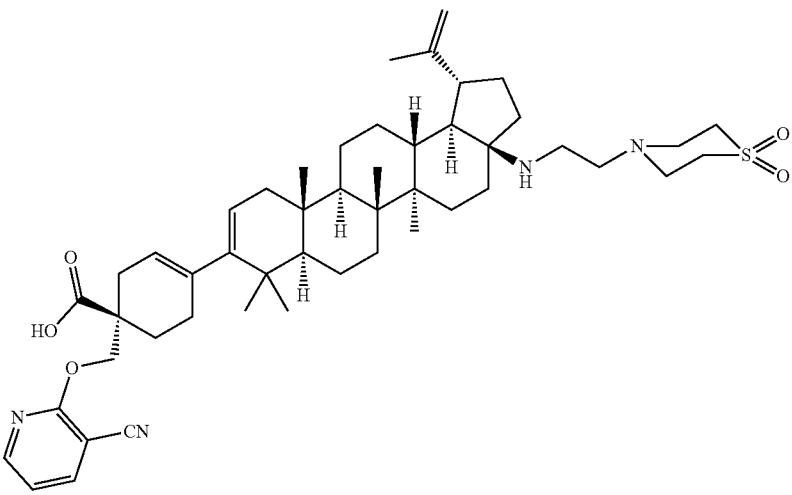 | 0.002 | A | B | 0.006 |
| 24 | 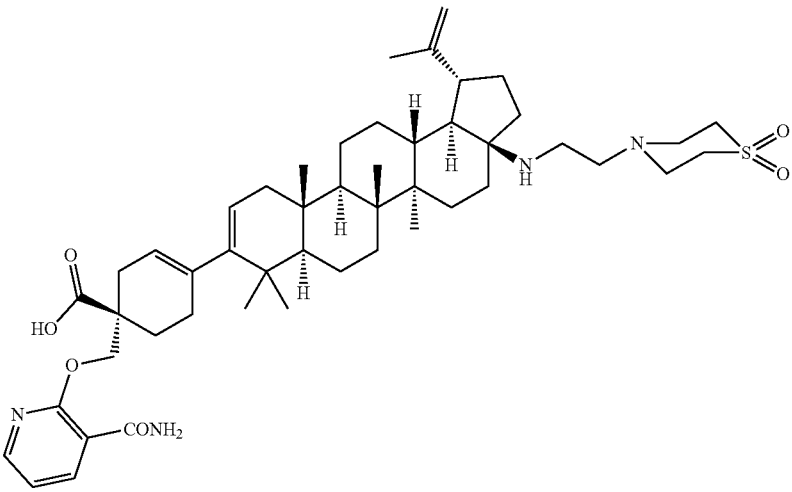 | 0.002 | 0.012 | 0.008 | 0.012 |
| 25 | 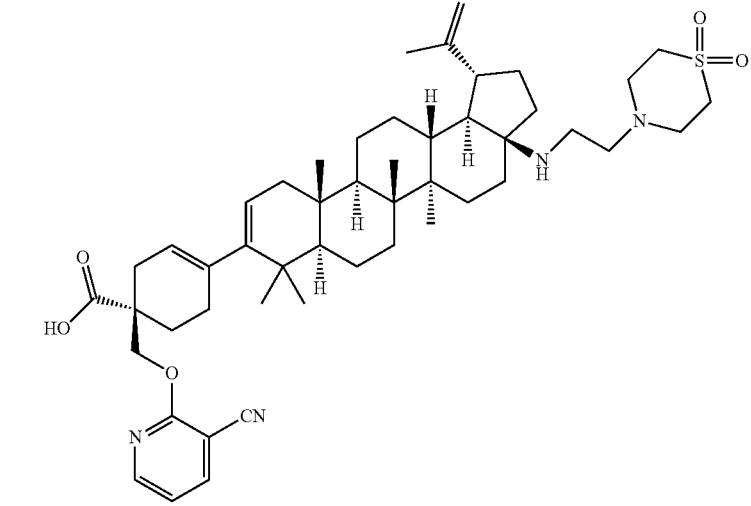 | 0.002 | 0.010 | 0.018 | 0.010 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 26 | 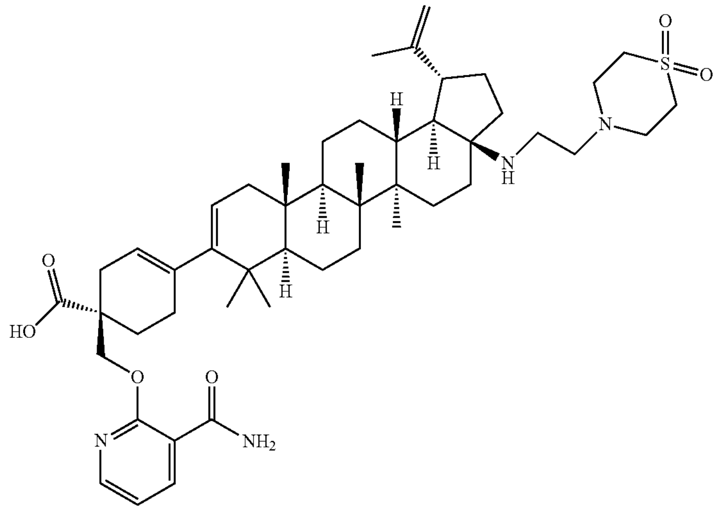 | 0.005 | 0.041 | 0.028 | 0.041 |
| 27 | 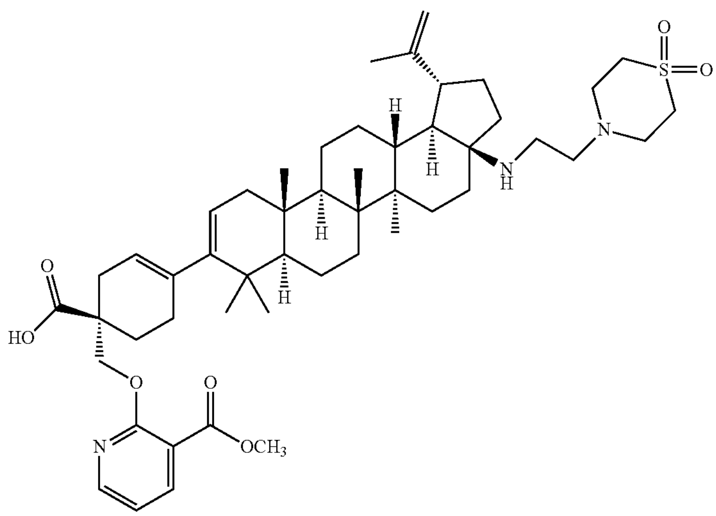 | A | A | A | A |
| 28 | 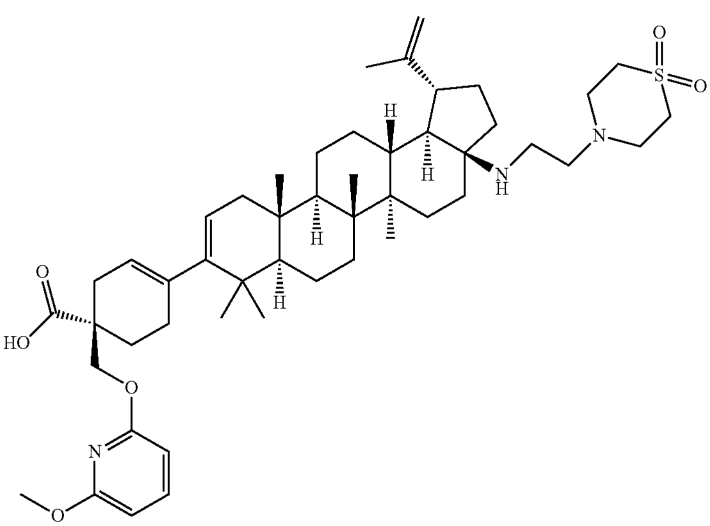 | 0.003 | 0.021 | 0.021 | 0.021 |

TABLE 2-continued
| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 29 | 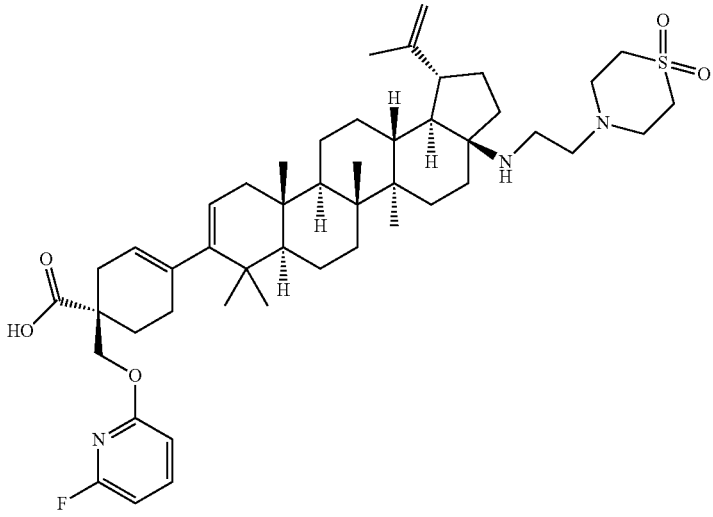 | 0.005 | 0.021 | 0.005 | 0.021 |
| 30 | 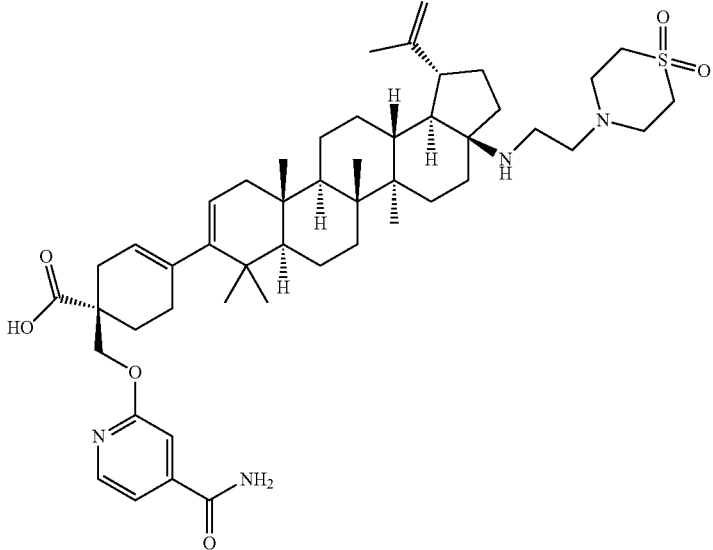 | A | A | A | A |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 31 | 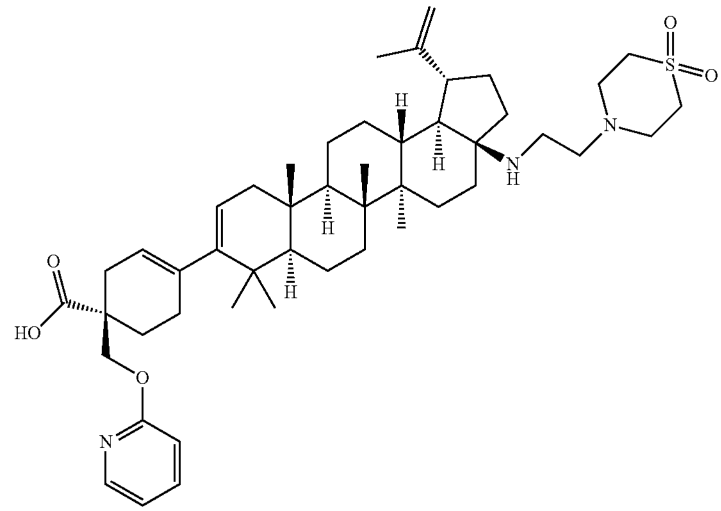 | 0.002 | 0.009 | 0.006 | 0.009 |
| 32 | 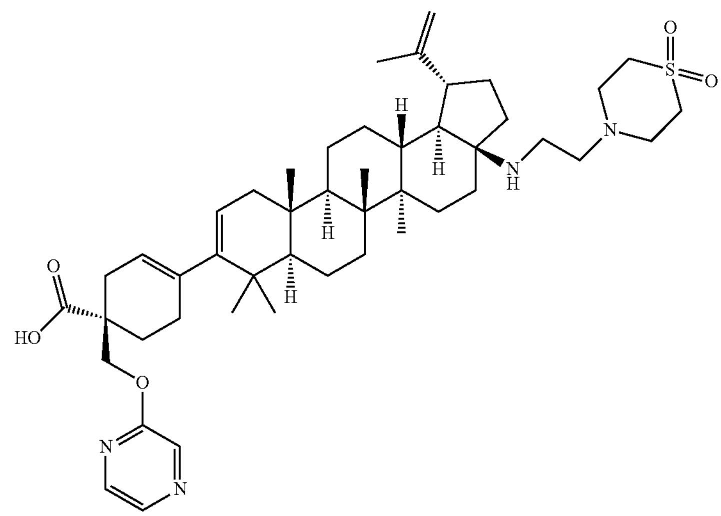 | A | A | A | A |
| 33 | 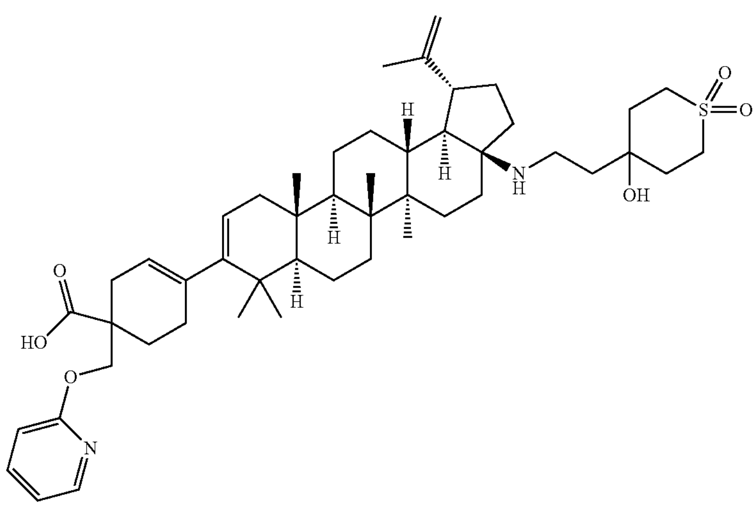 | 0.005 | A | 0.016 | A |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
| --- | --- | --- | --- | --- | --- |
| 34 | 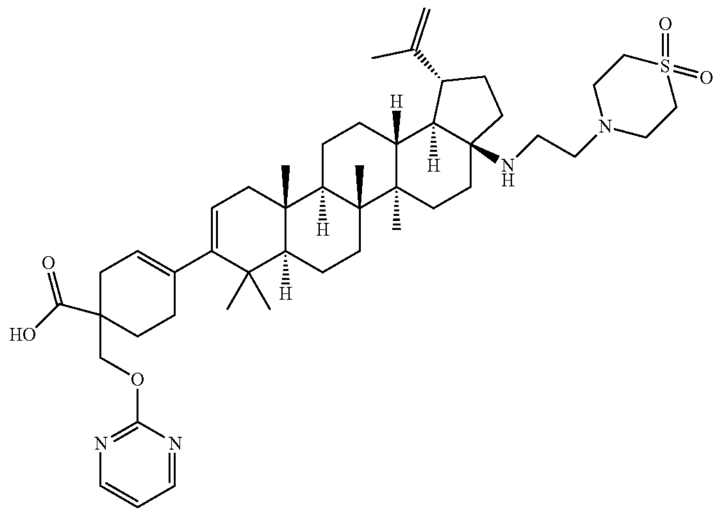 | 0.002 | 0.013 | A | 0.013 |
| 35 | 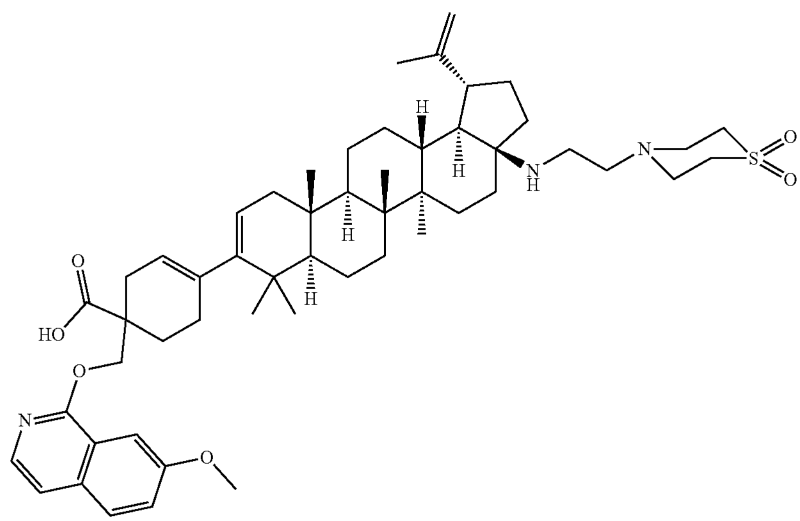 | 0.007 | B | 0.024 | B |
| 36 | 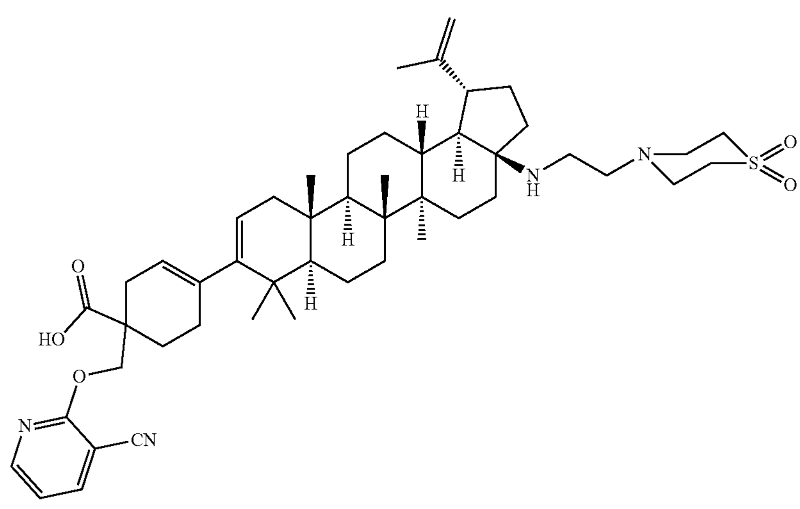 | 0.003 | 0.011 | 0.005 | 0.011 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 37 | 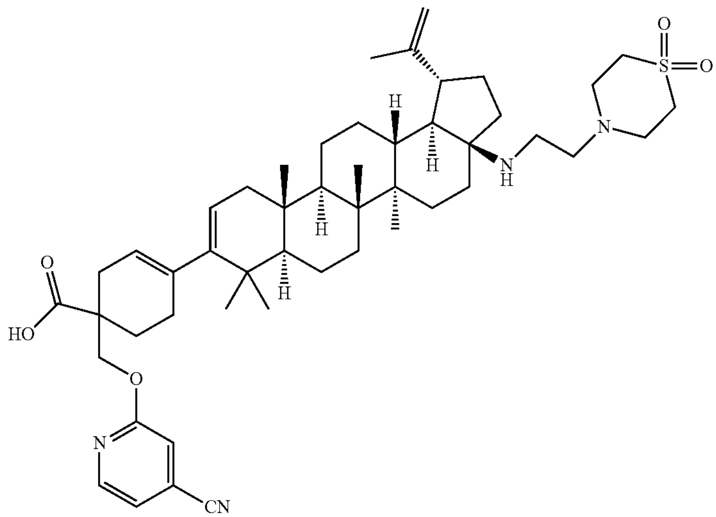 | A | B | B | B |
| 38 | 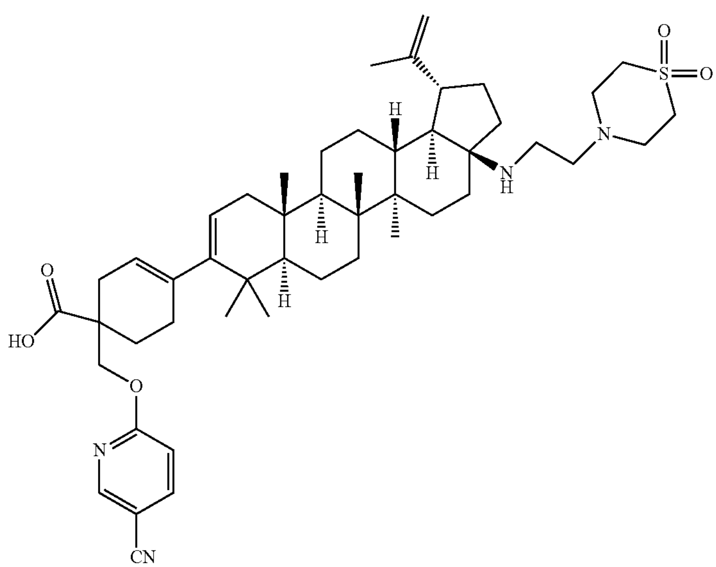 | 0.002 | 0.232 | 0.029 | 0.232 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| 39 | 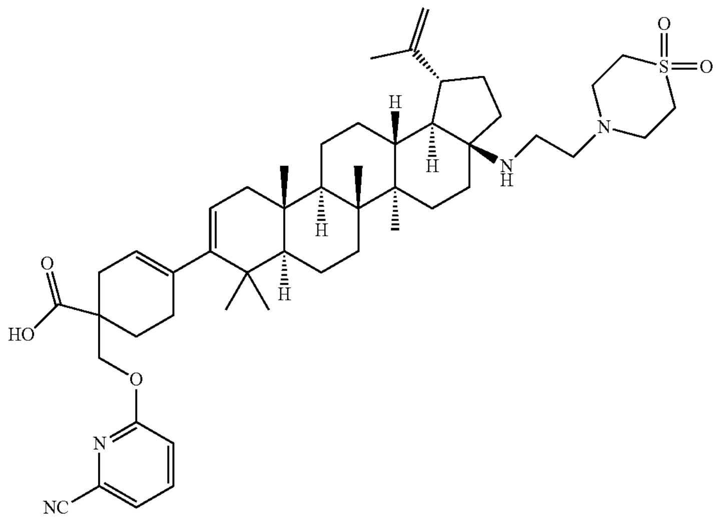 | 0.014 | B | A | B |
| 40 | 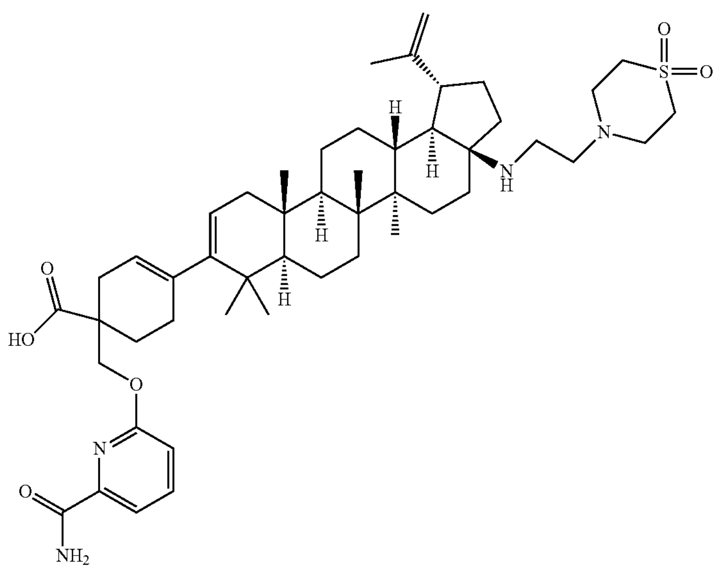 | 0.004 | 0.233 | 0.271 | 0.233 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
| --- | --- | --- | --- | --- | --- |
| A1 | 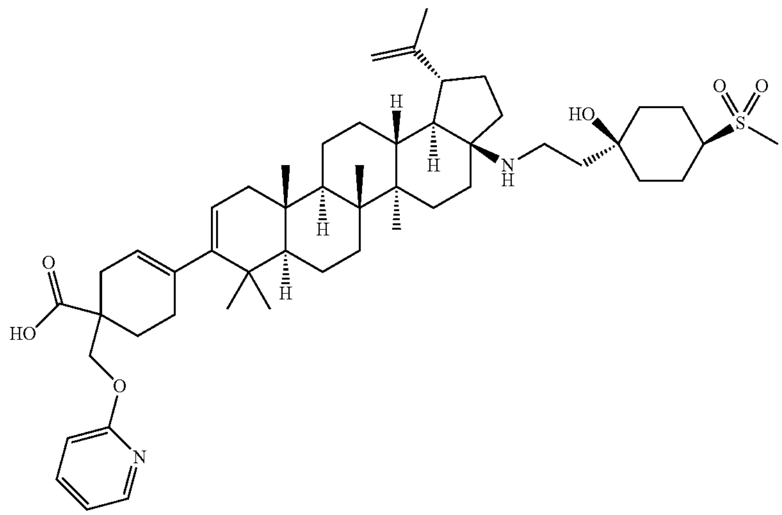 | 0.005 | 0.026 | 0.009 | 0.026 |
| A2 | 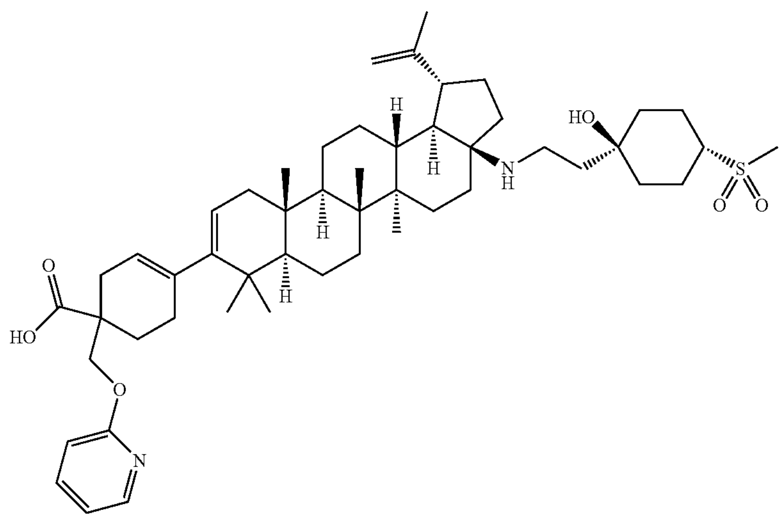 | 0.001 | 0.008 | 0.014 | 0.008 |
| A3 | 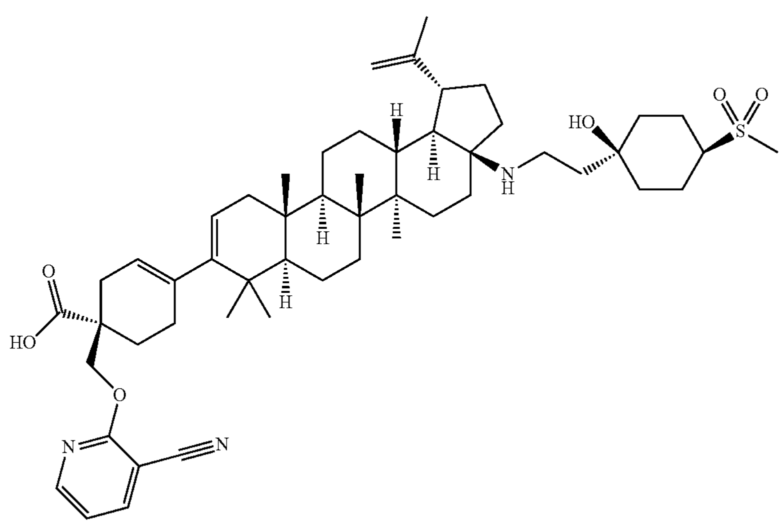 | 0.004 | 0.005 | 0.011 | 0.005 |

TABLE 2-continued

| Ex # | Structure | WT EC$_{50}$ (µM) | V370A/ ΔT371 EC$_{50}$ (µM) | A364V EC$_{50}$ (µM) | T332S/ V362I/ pr41G EC$_{50}$ (µM) |
|---|---|---|---|---|---|
| A4 | 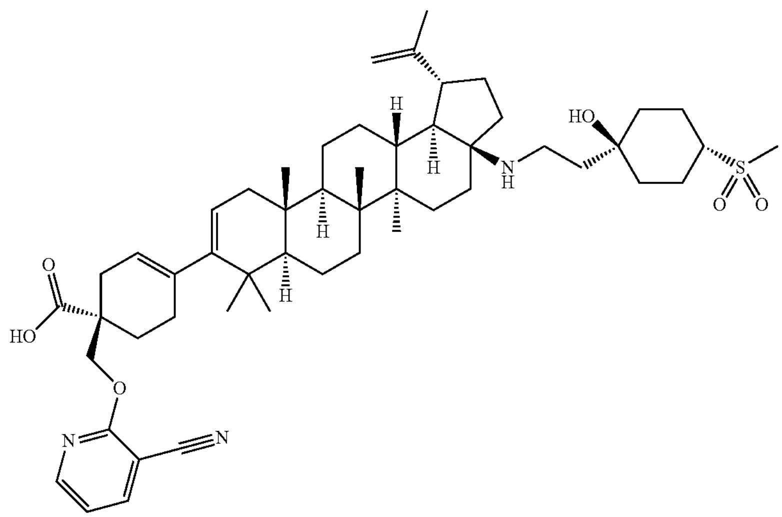 | 0.004 | 0.006 | 0.026 | 0.006 |
| A5 | 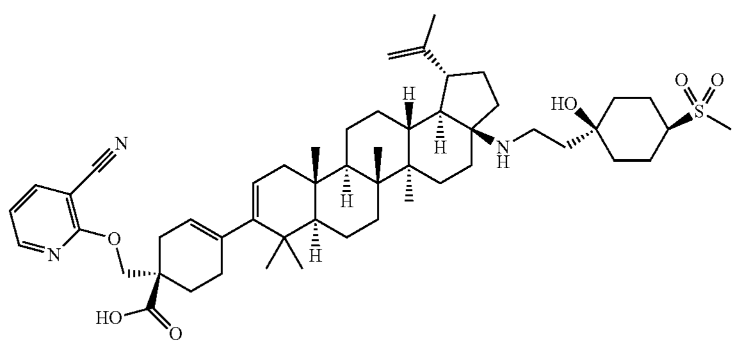 | 0.002 | 0.003 | 0.006 | 0.003 |
| A6 | 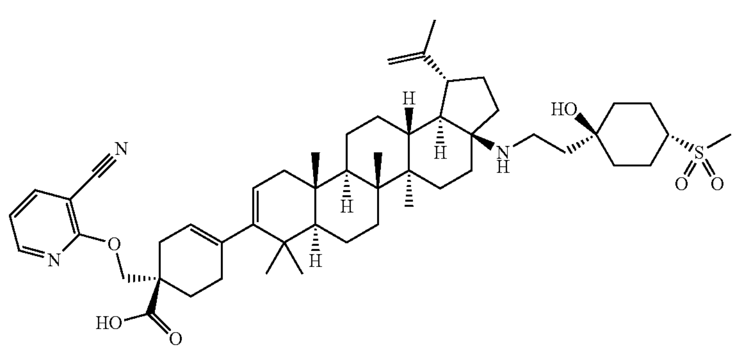 | 0.002 | 0.008 | 0.005 | 0.008 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A7 | 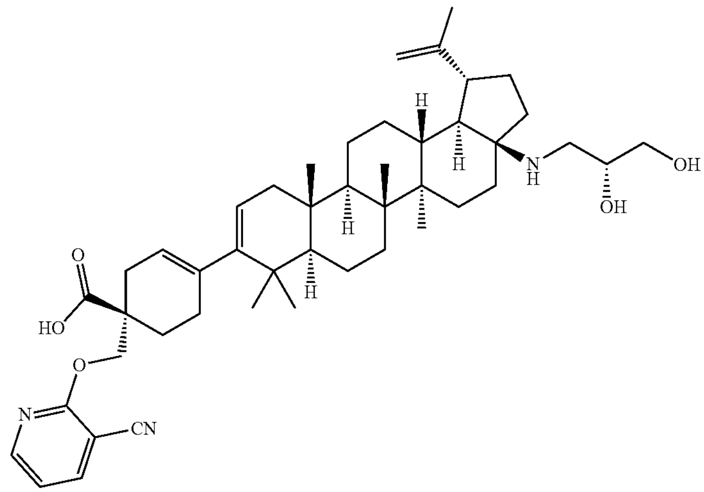 | 0.003 | 0.005 | 0.477 | 0.005 |
| A8 | 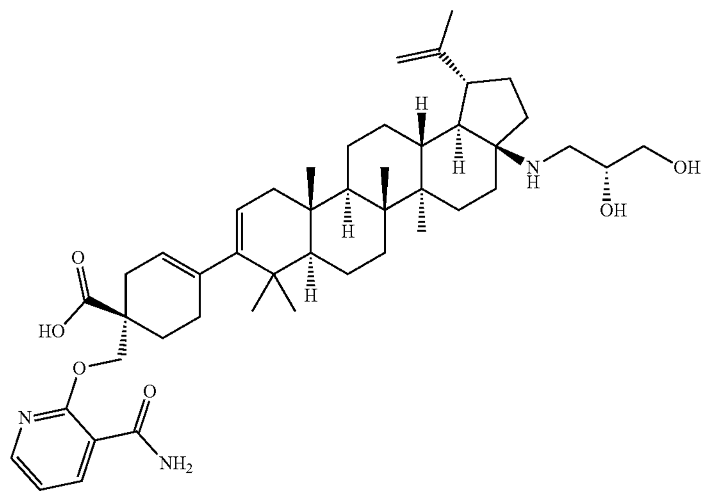 | 0.004 | 0.023 | 0.176 | 0.023 |
| A9 | 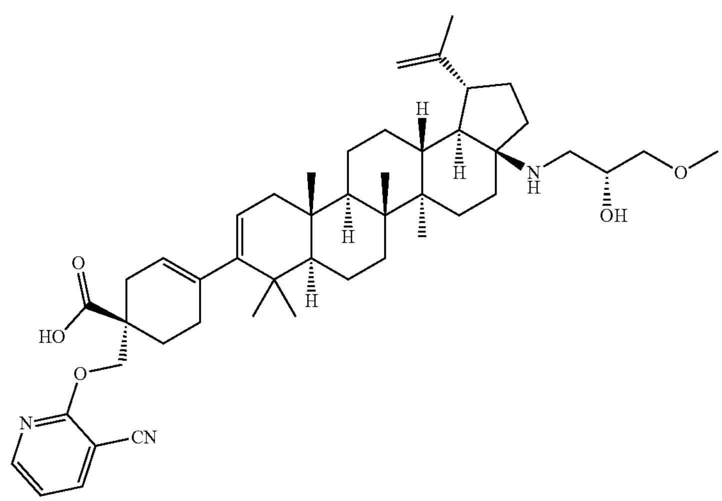 | 0.003 | 0.012 | 0.300 | 0.012 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A11 | 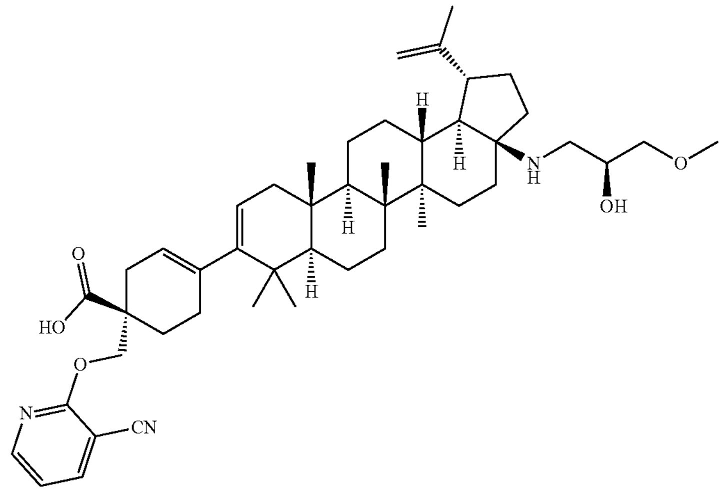 | 0.011 | 0.017 | 0.281 | 0.017 |
| A12 | 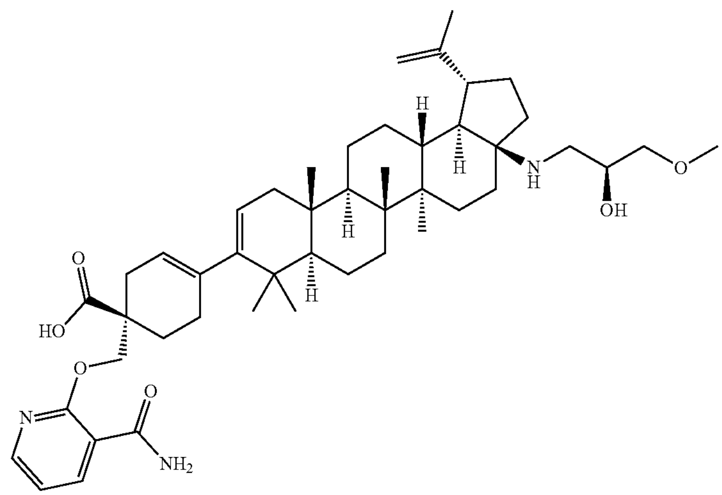 | 0.002 | 0.059 | 0.069 | 0.059 |
| A13 | 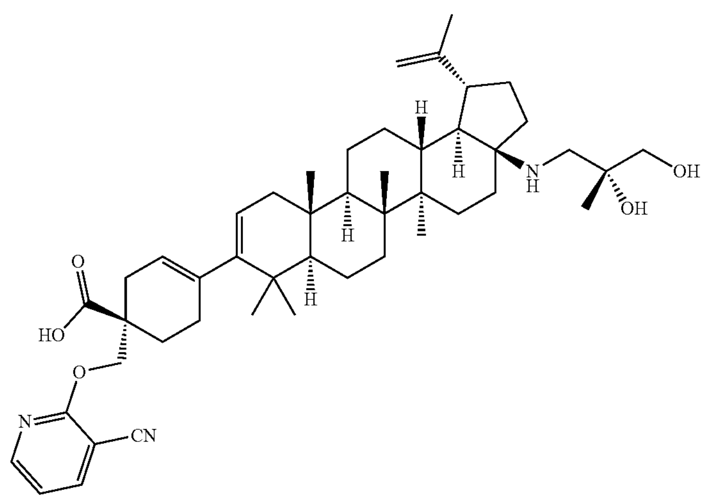 | 0.002 | 0.027 | 0.831 | 0.027 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
| --- | --- | --- | --- | --- | --- |
| A14 | 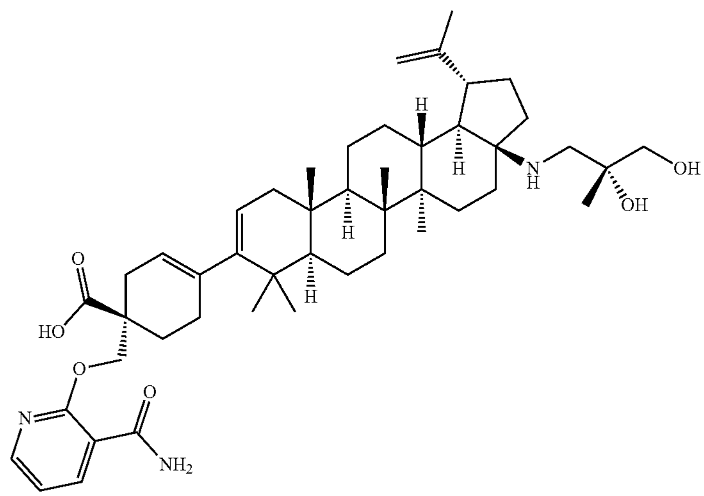 | 0.005 | 0.110 | 0.114 | 0.110 |
| A15 | 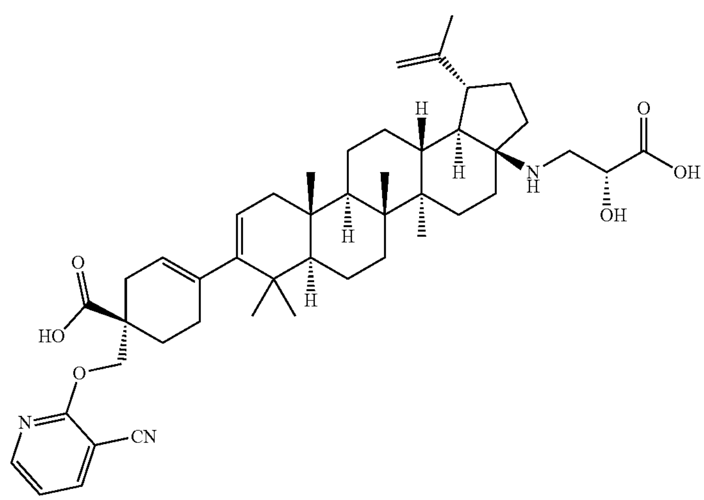 | 0.003 | 0.010 | 0.794 | 0.010 |
| A16 | 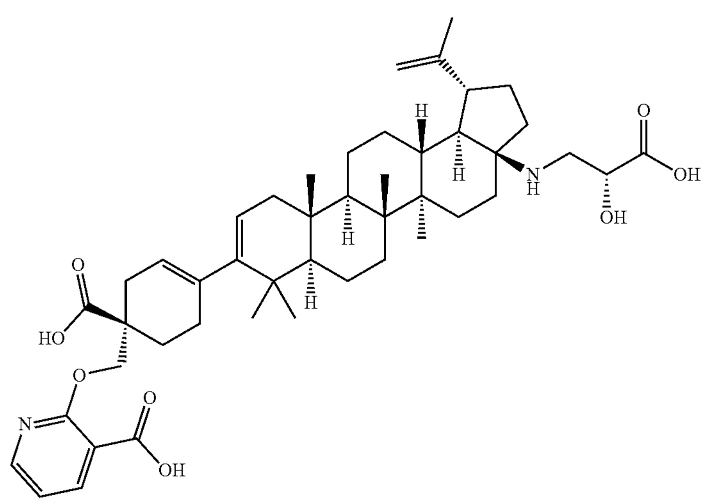 | 0.010 | 0.068 | 0.139 | 0.068 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A17 | 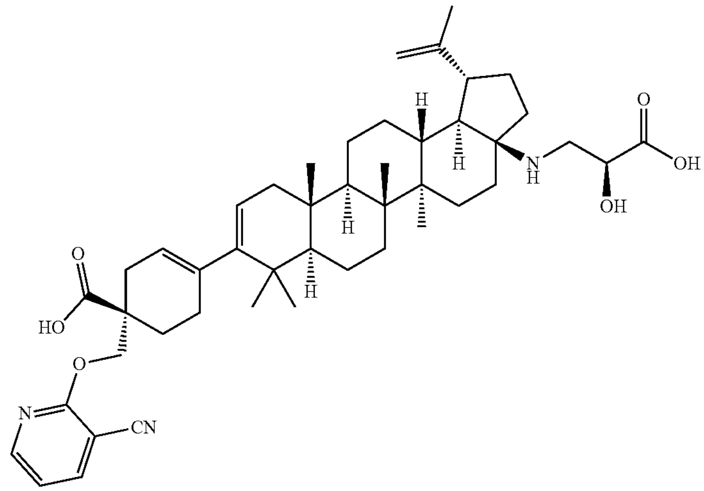 | 0.003 | 0.015 | 3.000 | 0.015 |
| A18 | 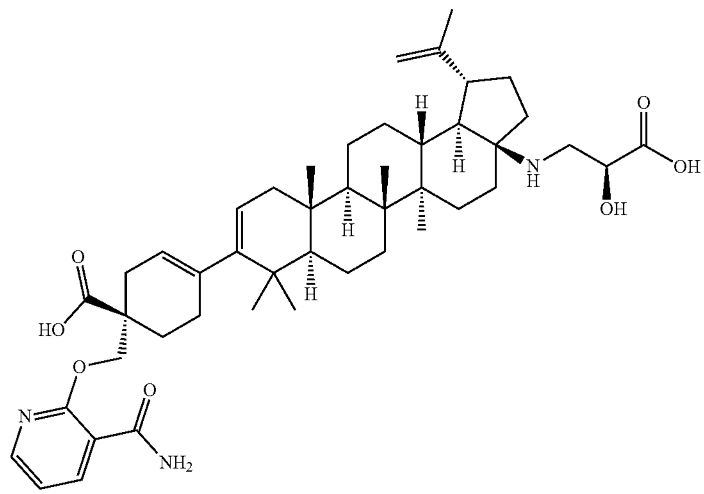 | 0.008 | 0.027 | 0.192 | 0.027 |
| A19 | 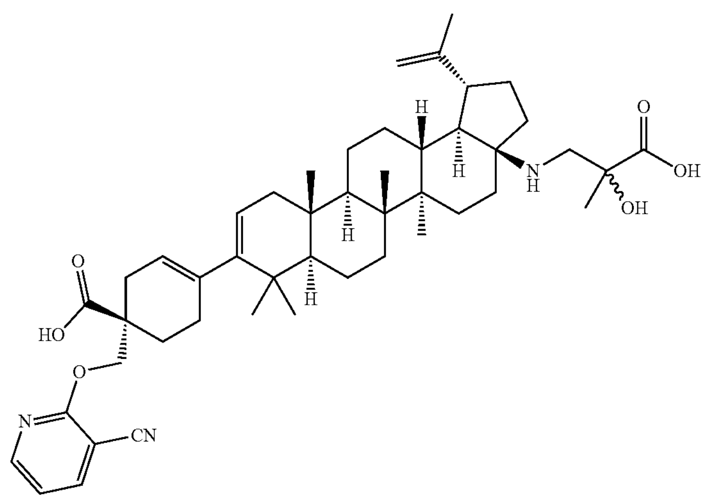 | 0.003 | 0.020 | B | 0.020 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A20 | 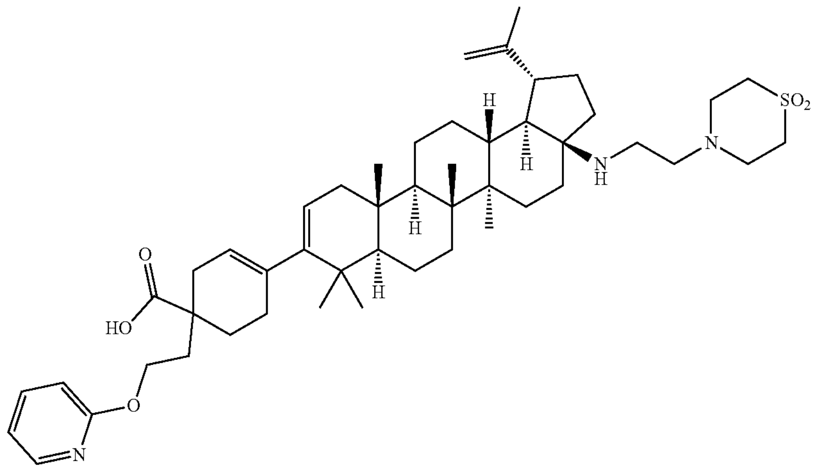 | A | A | A | A |
| A21 | 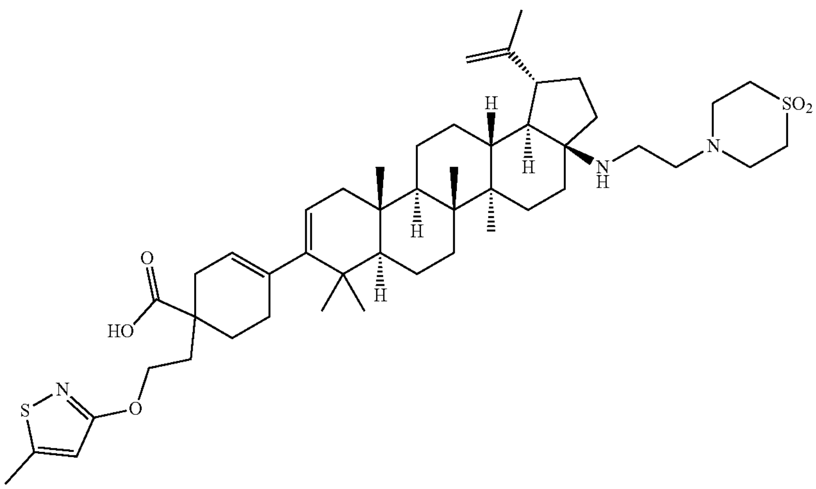 | 0.003 | 0.018 | 0.017 | 0.018 |
| A22 | 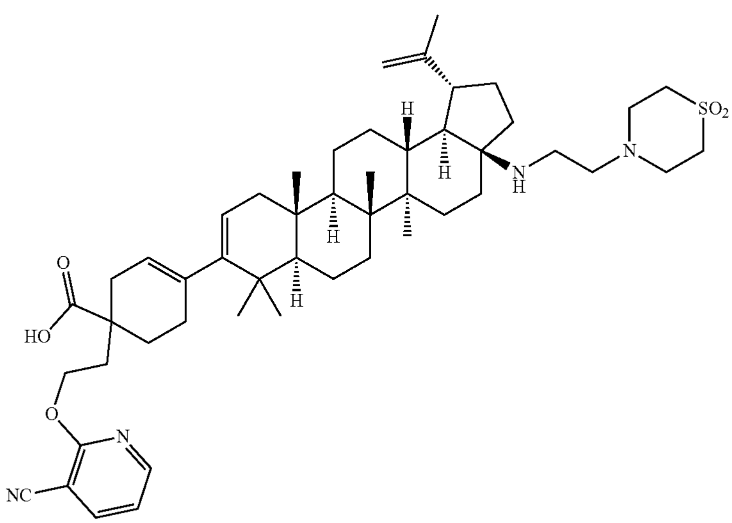 | 0.004 | 0.013 | 0.027 | 0.013 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A23 | 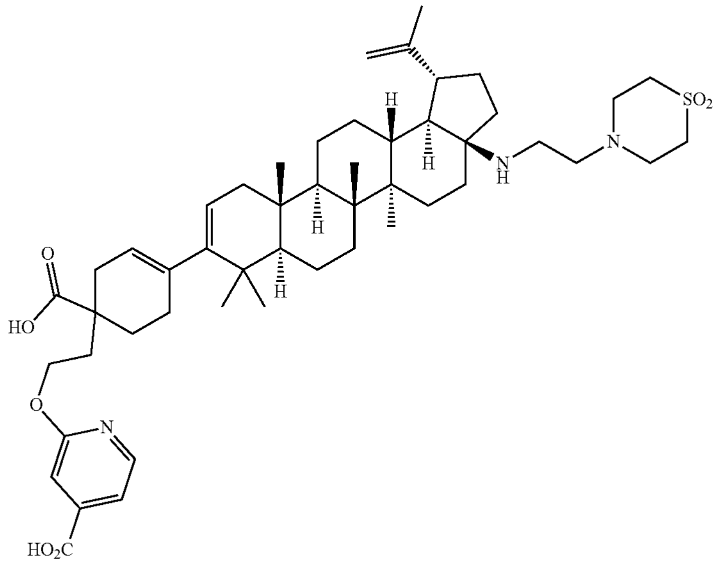 | 0.007 | B | 0.333 | 0.193 |
| A24 | 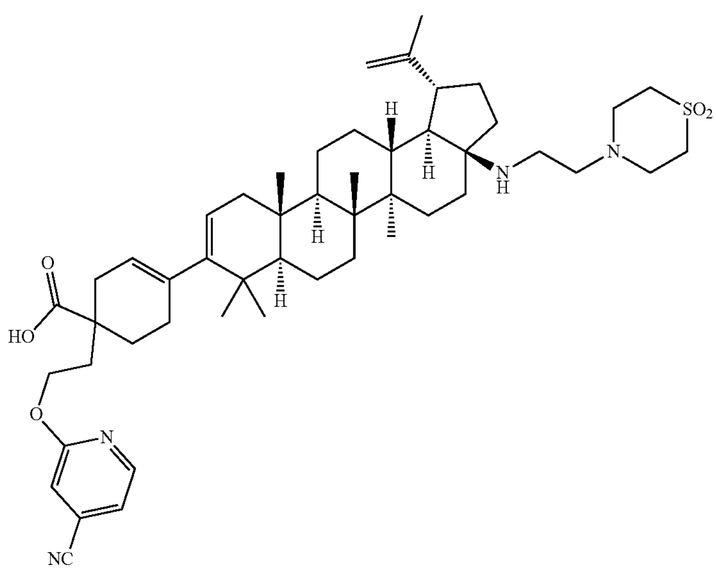 | 0.001 | 3.000 | 0.007 | 3.000 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A25 | 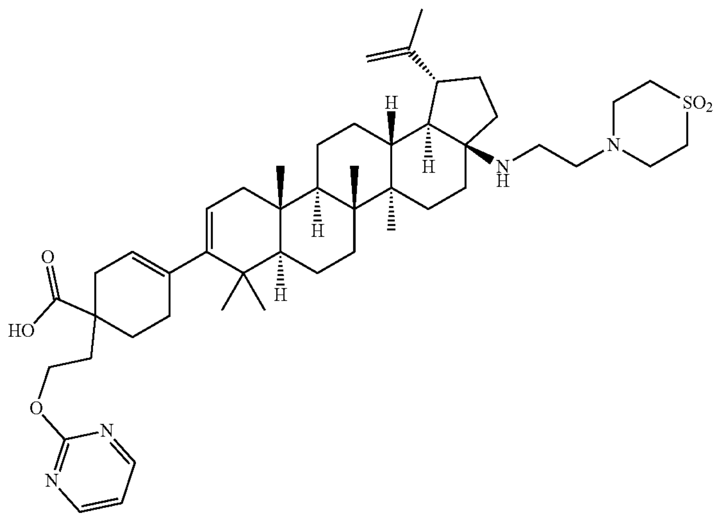 | A | A | A | A |
| A26 | 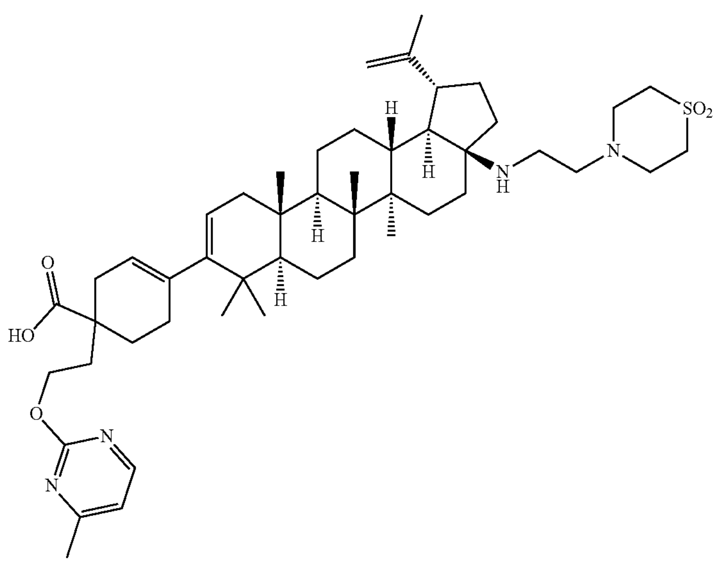 | 0.005 | B | B | B |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A27 | 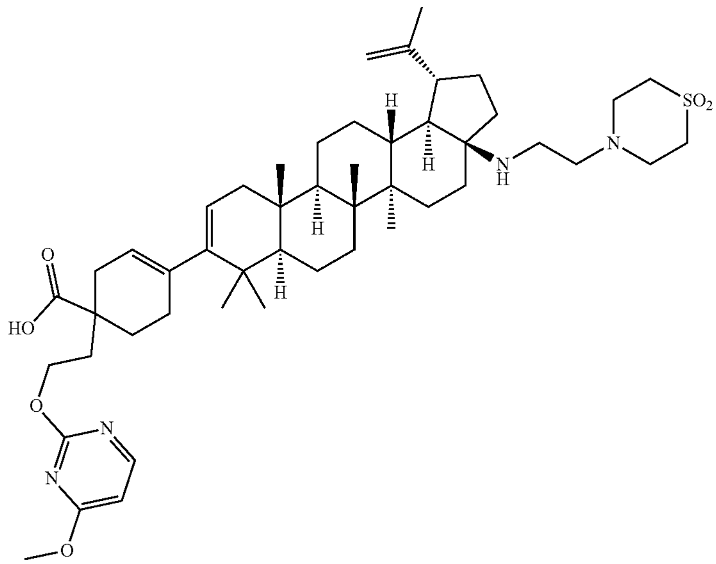 | 0.022 | B | B | 3.000 |
| A28 | 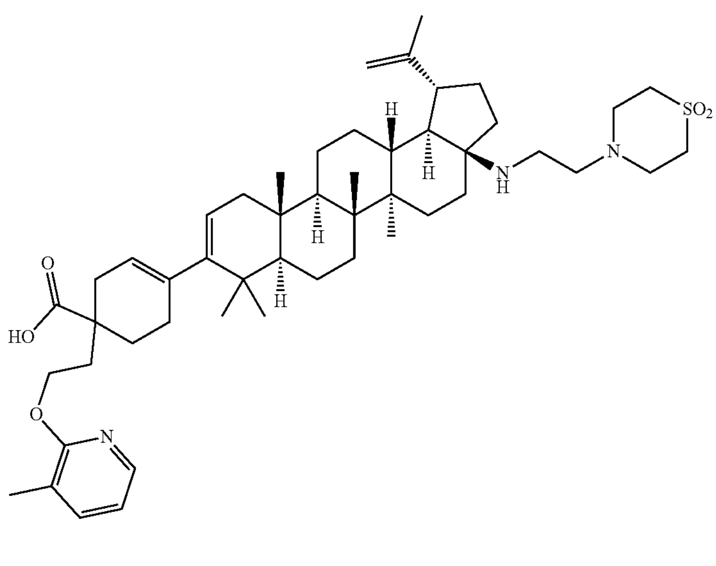 | A | 0.068 | B | 0.068 |

TABLE 2-continued
| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A29 | 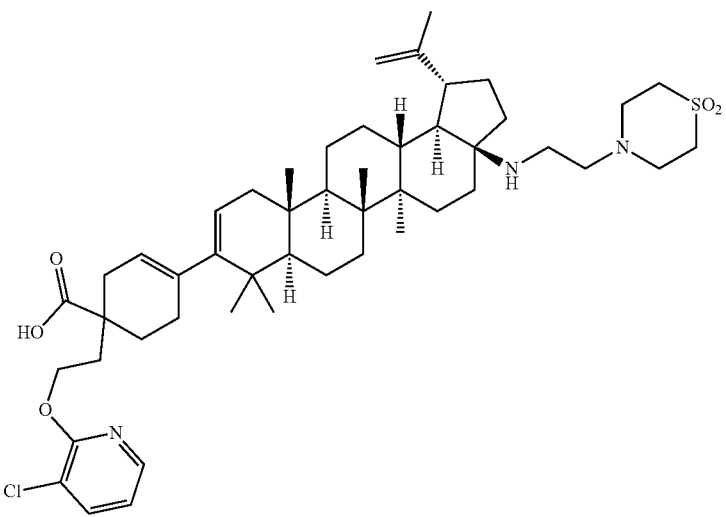 | 0.005 | 0.003 | 0.004 | 0.003 |
| A30 | 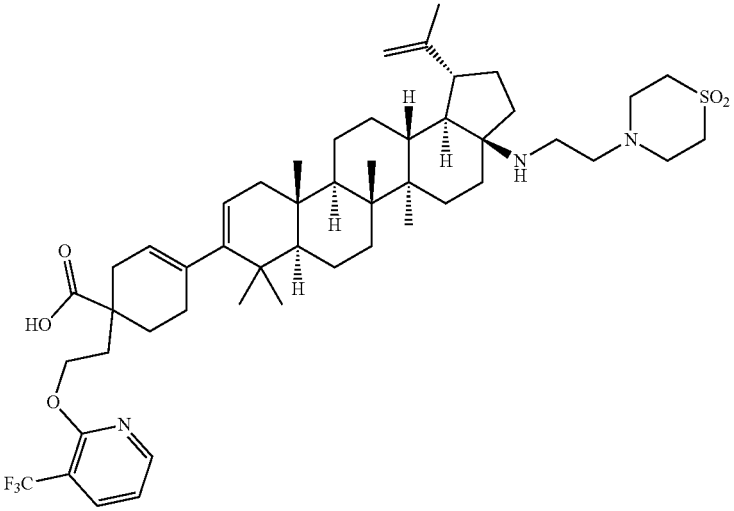 | 0.013 | 0.223 | 3.000 | 0.223 |

TABLE 2-continued
| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A31 | 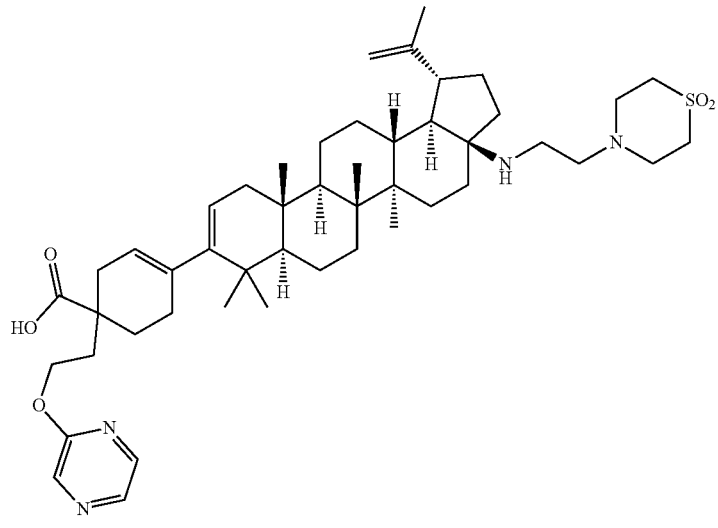 | 0.003 | B | 3.000 | B |
| A32 | 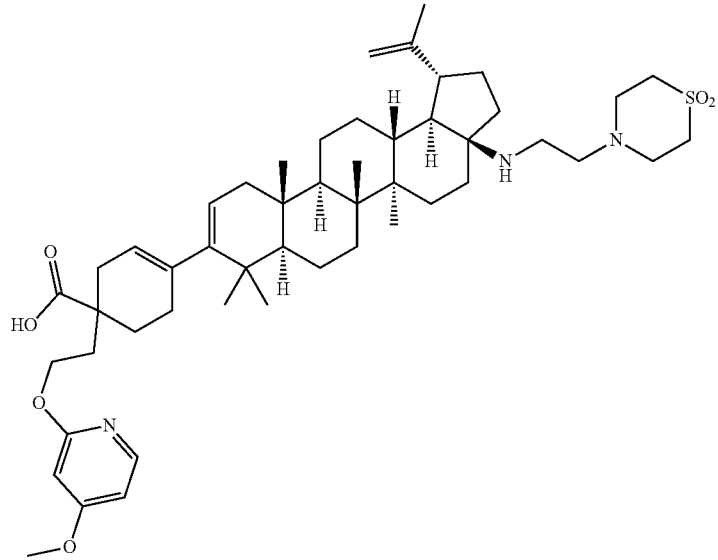 | 0.006 | B | B | 0.419 |

TABLE 2-continued
| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A33 | 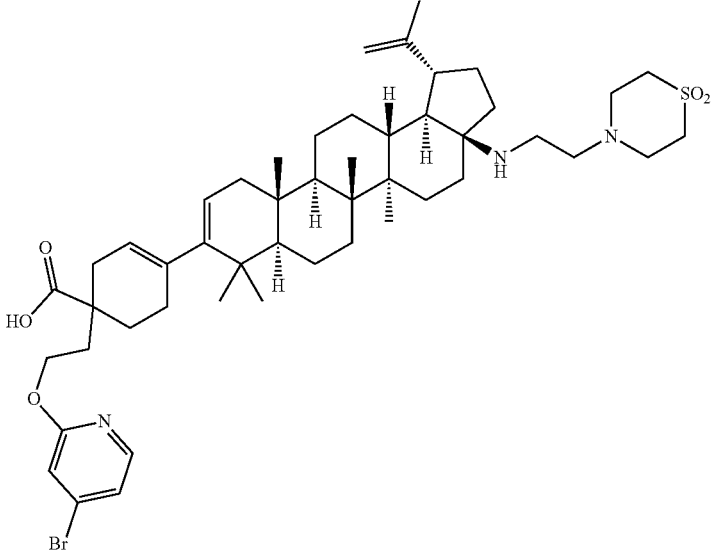 | 0.006 | B | 1.787 | 0.419 |
| A34 | 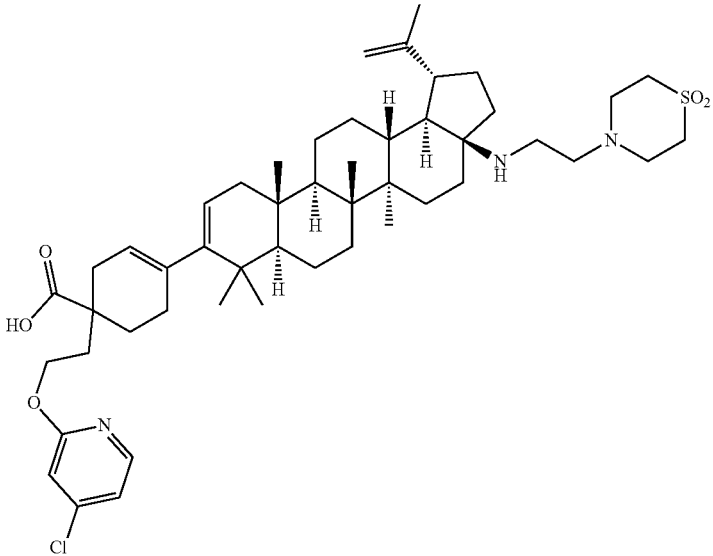 | 0.002 | B | 0.064 | 0.096 |

TABLE 2-continued

| Ex # | Structure | WT EC$_{50}$ (μM) | V370A/ ΔT371 EC$_{50}$ (μM) | A364V EC$_{50}$ (μM) | T332S/ V362I/ pr41G EC$_{50}$ (μM) |
|---|---|---|---|---|---|
| A35 | 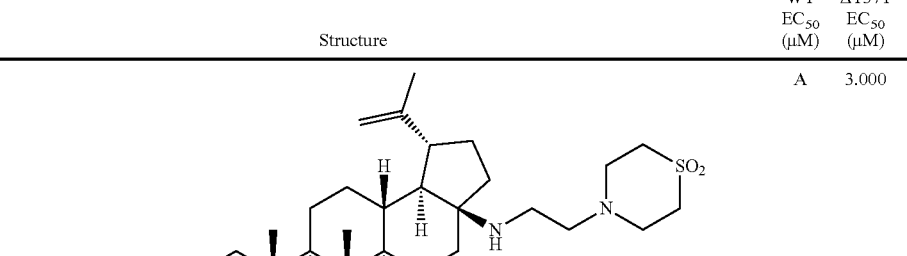 | A | 3.000 | 0.233 | B |

In Table 3 below, two compounds corresponding to two embodiments of the invention (Examples 25 and A3) were tested and compared with two other (comparative) compounds outside the scope thereof. Each compound was assessed for EC$_{50}$ (WT) or EC$_{90}$ values (see identified strains below, including the T332SN362I/pr R$_{41}$G triple mutant):

TABLE 3

| Ex | | WT EC$_{50}$ (uM) | delV370/ T371A EC$_{90}$ (uM) | A364V EC$_{90}$ (uM) | T332S/ V362I/ prR41G EC$_{90}$ (uM) |
|---|---|---|---|---|---|
| 25 | | 0.002 | 0.002 | 0.041 | 0.021 |

TABLE 3-continued

| Ex | | WT EC$_{50}$ (uM) | delV370/ T371A EC$_{90}$ (uM) | A364V EC$_{90}$ (uM) | T332S/ V362I/ prR41G EC$_{90}$ (uM) |
|---|---|---|---|---|---|
| A3 | | 0.004 | 0.015 | 0.166 | 0.017 |
| Comparative | | 0.003 | 2.418 | 0.228 | 2.418 |
| Comparative | | 0.002 | 1.464 | 0.340 | 1.464 |

As can be deduced from Table 3, the two identified compounds according to the invention had better $EC_{90}$ values versus the comparative compounds, when tested against the specified mutant strains identified above.

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound or salt selected from the group consisting of:

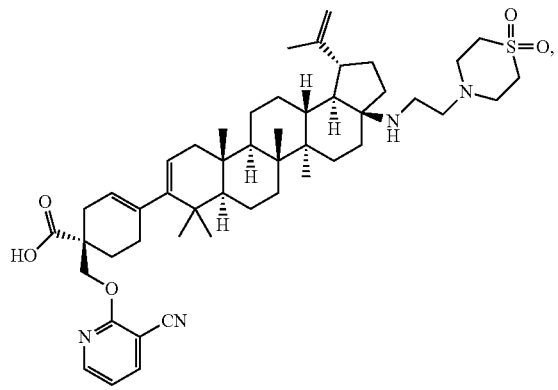

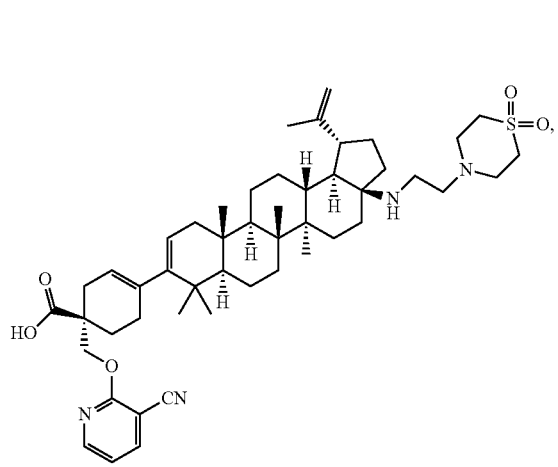

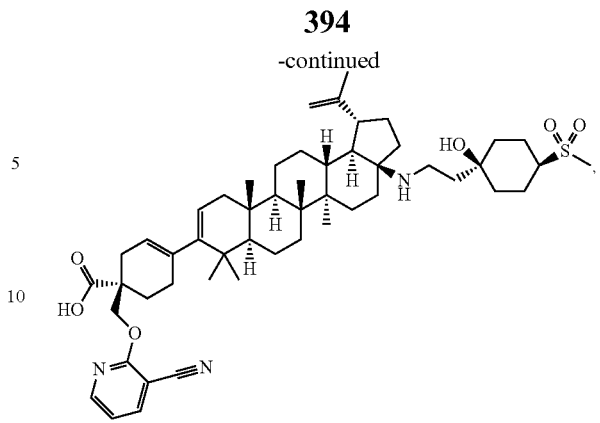

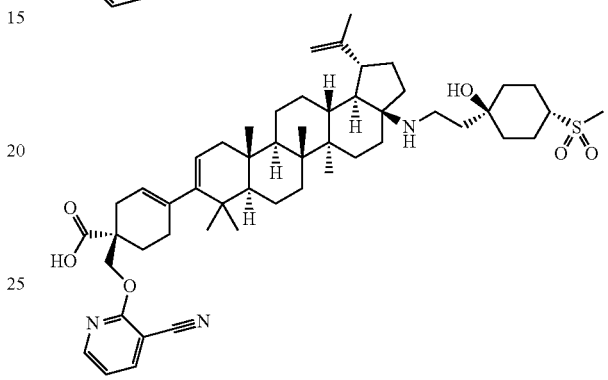

and pharmaceutically acceptable salts thereof.

2. A pharmaceutical composition comprising a compound or salt of claim 1.

3. A method for treating a mammal infected with the HIV virus comprising administering to said mammal a compound or salt of claim 1.

4. A compound or salt according to claim 1 wherein said compound or salt is the compound

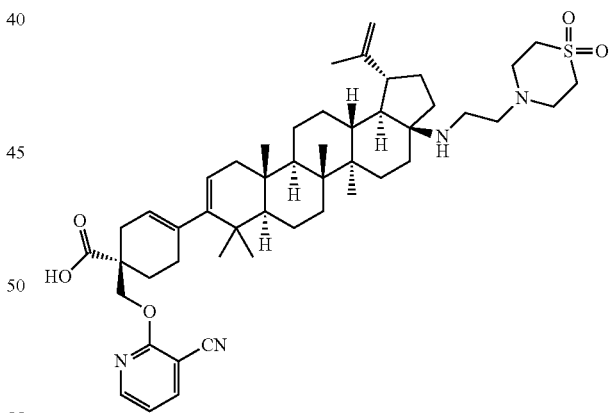

or a pharmaceutically acceptable salt thereof.

* * * * *